US008128938B1

(12) United States Patent
Luke et al.

(10) Patent No.: US 8,128,938 B1
(45) Date of Patent: *Mar. 6, 2012

(54) INFLUENZA VIRUS VACCINE COMPOSITION AND METHODS OF USE

(75) Inventors: Catherine J. Luke, Rockville, MD (US); Adrian Vilalta, San Diego, CA (US); Mary K. Wloch, San Diego, CA (US); Thomas G. Evans, San Diego, CA (US); Andrew J. Geall, San Marcos, CA (US); Gretchen S. Jimenez, San Diego, CA (US)

(73) Assignee: Vical Incorporated, San Diego, CA (US)

( * ) Notice: Subject to any disclaimer, the term of this patent is extended or adjusted under 35 U.S.C. 154(b) by 1203 days.

This patent is subject to a terminal disclaimer.

(21) Appl. No.: 11/892,016

(22) Filed: Aug. 17, 2007

Related U.S. Application Data

(62) Division of application No. 11/704,251, filed on Feb. 9, 2007, now Pat. No. 7,537,768, which is a division of application No. 11/131,479, filed on May 18, 2005, now abandoned.

(60) Provisional application No. 60/571,854, filed on May 18, 2004.

(51) Int. Cl.
*A61K 39/145* (2006.01)
*A61K 31/7088* (2006.01)
*C12N 15/44* (2006.01)
*C12N 15/36* (2006.01)

(52) U.S. Cl. ................ 424/209.1; 514/44 R; 536/23.72; 435/320.1

(58) Field of Classification Search ........................ None
See application file for complete search history.

(56) References Cited

U.S. PATENT DOCUMENTS

| | | | |
|---|---|---|---|
| 4,683,195 | A | 7/1987 | Mullis et al. |
| 4,816,567 | A | 3/1989 | Cabilly et al. |
| 4,818,527 | A | 4/1989 | Thornton et al. |
| 4,882,145 | A | 11/1989 | Thornton et al. |
| 5,143,726 | A | 9/1992 | Thornton et al. |
| 5,264,618 | A | 11/1993 | Felgner et al. |
| 5,561,064 | A | 10/1996 | Marquet et al. |
| 5,580,859 | A | 12/1996 | Felgner et al. |
| 5,591,631 | A | 1/1997 | Leppla et al. |
| 5,656,611 | A | 8/1997 | Kabanov et al. |
| 5,837,693 | A | 11/1998 | German et al. |
| 6,004,944 | A | 12/1999 | Rothman et al. |
| 6,207,646 | B1 | 3/2001 | Krieg et al. |
| 6,214,804 | B1 | 4/2001 | Felgner et al. |
| 6,231,864 | B1 | 5/2001 | Birkett |
| 6,406,705 | B1 | 6/2002 | Davis et al. |
| 6,429,199 | B1 | 8/2002 | Krieg et al. |
| 6,500,432 | B1 | 12/2002 | Dalemans et al. |
| 6,586,409 | B1 | 7/2003 | Wheeler et al. |
| 6,867,195 | B1 | 3/2005 | Felgner et al. |
| 6,875,748 | B2 | 4/2005 | Manthorpe et al. |
| 7,105,574 | B1 | 9/2006 | Wheeler |
| 7,250,404 | B2 | 7/2007 | Felgner et al. |
| 7,785,603 | B2 | 8/2010 | Luke et al. |
| 2002/0045594 | A1 | 4/2002 | Volkin et al. |
| 2002/0165172 | A1 | 11/2002 | Sallberg et al. |
| 2003/0032615 | A1 | 2/2003 | Felgner et al. |
| 2003/0191082 | A1 | 10/2003 | Wheeler |
| 2003/0202982 | A1 | 10/2003 | Birkett et al. |
| 2004/0023911 | A1 | 2/2004 | Felgner et al. |
| 2004/0157244 | A1 | 8/2004 | Budahazi et al. |
| 2004/0157789 | A1 | 8/2004 | Geall |
| 2004/0162256 | A1 | 8/2004 | Geall et al. |
| 2004/0171572 | A1 | 9/2004 | Wheeler |
| 2006/0024670 | A1 | 2/2006 | Luke et al. |
| 2007/0286869 | A1 | 12/2007 | Luke et al. |

FOREIGN PATENT DOCUMENTS

| | | | |
|---|---|---|---|
| CA | 2 025 598 | C | 3/1991 |
| EP | 0 173 494 | A2 | 3/1986 |
| EP | 0 171 496 | B1 | 5/1993 |
| EP | 0 385 610 | B1 | 3/1994 |
| EP | 0 421 635 | B1 | 7/1995 |
| WO | WO 86/01533 | A1 | 3/1986 |
| WO | WO 87/02671 | A1 | 5/1987 |
| WO | WO 94/21797 | A1 | 9/1994 |
| WO | WO96/10631 | | 4/1996 |
| WO | WO 99/40934 | A1 | 8/1999 |
| WO | WO 00/57917 | A2 | 10/2000 |
| WO | WO0183528 | A2 | 11/2001 |
| WO | WO 02/00844 | A2 | 1/2002 |
| WO | WO02/24876 | A2 | 3/2002 |

OTHER PUBLICATIONS

Aihara, H. and Miyazaki J.-I., "Gene transfer into muscle by electroporation in vivo," *Nat. Biotechnol.* 16:867-870, Nature America, Inc. (1998).

Attal, J., et al., "The RU5 ('R') region from human leukaemia viruses (HTLV-1) contains an internal ribosome entry site (IRES)-like sequence," *FEBS Letters* 392:220-224, Elsevier Science B.V. (1996).

(Continued)

*Primary Examiner* — Mary E Mosher
(74) *Attorney, Agent, or Firm* — Sughrue Mion, PLLC

(57) ABSTRACT

The present invention is directed to enhancing the immune response of a human in need of protection against IV infection by administering in vivo, into a tissue of the human, at least one polynucleotide comprising one or more regions of nucleic acid encoding an IV protein or a fragment, a variant, or a derivative thereof. The present invention is further directed to enhancing the immune response of a human in need of protection against IV infection by administering, in vivo, into a tissue of the human, at least one IV protein or a fragment, a variant, or derivative thereof. The IV protein can be, for example, in purified form or can be an inactivated IV, such as those present in inactivated IV vaccines. The polynucleotide is incorporated into the cells of the human in vivo, and an immunologically effective amount of an immunogenic epitope of an IV, or a fragment, variant, or derivative thereof is produced in vivo. The IV protein (in purified form or in the form of an inactivated IV vaccine) is also administered in an immunologically effective amount.

24 Claims, 19 Drawing Sheets

OTHER PUBLICATIONS

Berendt, R.F. and Hall, W.C., "Reaction of Squirrel Monkeys to Intratracheal Inoculation with Influenza/A/New Jersey/76 (Swine) Virus," *Infect. Immun.* 16:476-479, American Society for Microbiology (1977).

Billaut-Mulot, O., et al., "Interleukin-18 modulates immune responses induced by HIV-1 Nef DNA prime/protein boost vaccine," *Vaccine 19*:95-102, Elsevier Science Ltd. (2001).

Boulianne, G.L., et al., "Production of functional chimaeric mouse/human antibody," *Nature 312*:643-646, Macmillan Journals Ltd. (1984).

Chen, Z.-Y., et al., "Linear DNAs Concatemerize in Vivo and Result in Sustained Transgene Expression in Mouse Liver," *Mol. Ther.* 3:403-410, Academic Press (2001).

Cherng, J.-Y., et al., "Effect of DNA topology on the transfection efficiency of poly((2-dimethylamino)ethyl methacrylate)-plasmid complexes," *J. Control. Release 60*:343-353, Elsevier Science B.V. (1999).

Clarke, B.E., et al., "Improved immunogenicity of a peptide epitope after fusion to hepatitis B core protein," *Nature 330*:381-384, Macmillan Magazines Ltd. (1987).

Collins, P.L., et al., "Respiratory Syncytial Virus," in *Field's Virology, 4th Edition*, Knipe, D.M., et al., eds., Lipponcott Williams & Wilkins, Chapter 45, pp. 1464-1465 (2001).

Colucci, G., et al., "Identification of a Major Hepatitis B Core Antigen (HBcAg) Determinant by Using Synthetic Peptides and Monoclonal Antibodies," *J. Immunol.* 141:4376-4380, The American Association of Immunologists (1988).

Crasto, C.J. and Feng, J.-A., "LINKER: a program to generate linker sequences for fusion proteins," *Protein Eng.* 13:309-312, Oxford University Press (2000).

Darquet, A.-M., et al., "A new DNA vehicle for nonviral gene delivery: supercoiled minicircle," *Gene Therapy 4*:1341-1349, Stockton Press (1997).

Davis, H.L., et al., "Direct gene transfer in skeletal muscle: plasmid DNA-based immunization against the hepatitis B virus surface antigen," *Vaccine 12*:1503-1509, Butterworth-Heinemann Ltd. (1994).

Donnelly, J.J., et al., "DNA Vaccines," *Annu. Rev. Immunol.* 15:617-648, Annual Reviews Inc. (1997).

Felgner, P.L., et al., "Lipofection: A highly efficient, lipid-mediated DNA-transfection procedure," *Proc. Natl. Acad. Sci. USA 84*:7413-7417, The National Academy of Sciences (1987).

Fischer, W.B. and Sansom, M.S., "Viral ion channels: structure and function," *Biochim. Biophys. Acta 1561*:27-45, Elsevier Science B.V. (2002).

Galibert, F., et al., "Nucleotide sequence of the hepatitis B virus genome (subtype ayw) cloned in *E. coli,*" *Nature 281*:646-650, Macmillan Journals Ltd. (1979).

Gao, X. and Huang, L., "Potentiation of Cationic Liposome-Mediated Gene Delivery by Polycations," *Biochemistry 35*:1027-1036, American Chemical Society (1996).

Gilbert, S.C., et al., "Enhanced CD8 T cell immunogenicity and protective efficacy in a mouse malaria model using a recombinant adenoviral vaccine in heterologous prime-boost immunisation regimes," Vaccine 20:1039-1045, Elsevier Science Ltd. (2002).

Goff, S.P., "*Retroviridae*: The Retroviruses and Their Replication," in *Field's Virology, 4th Edition*, Knipe, D.M., et al., eds., Lipponcott Williams & Wilkins, Chapter 57, pp. 1871-1939 (2001).

Gonzalo, R.M., et al., "A heterologous prime-boost regime using DNA and recombinant vaccinia virus expressing the *Leishmania infantum* P36/LACK antigen protects BALB/c mice from *Cutaneous leishmaniasis,*" *Vaccine 20*:1226-1231, Elsevier Science Ltd. (2002).

Graham, F.L. and Van Der Eb, A.J., " A New Technique for the Assay of Infectivity of Human Adenovirus 5 DNA," *Virology 52*:456-467, Academic Press, Inc. (1973).

Gramzinski, R.A., et al., "Immune Response to a Hepatitis B DNA Vaccine in *Aotus* Monkeys: A Comparison of Vaccine Formulation, Route, and Method of Administration," *Mol. Med. 4*:109-118, The Picower Institute Press (1998).

National Research Council, *Guide for the Care and Use of Laboratory Animals*, National Academy Press, Washington, D.C. (1996).

Macken, C., et al., "The value of a database in surveillance and vaccine selection," in *Options for the Control of Influenza IV*, Osterhaus, A.D.M.E., et al., eds., Elsevier Science B.V., Amsterdam, pp. 103-106 (2001).

Hartikka, J., et al., "Vaxfectin enhances the humoral immune response to plasmid DNA-encoded antigens," *Vaccine 19*:1911-1923, Elsevier Science Ltd. (2001).

Hartikka, J., et al., "Electroporation-Facilitated Delivery of Plasmid DNA in Skeletal Muscle: Plasmid Dependence of Muscle Damage and Effect of Poloxamer 188," *Mol Ther 4*:407-415, Academic Press (2001).

Hartikka, J., et al., "An Improved Plasmid DNA Expression Vector for Direct Injection into Skeletal Muscle," *Hum. Gene Ther. 7*:1205-1217, Mary Ann Liebert, Inc. (1996).

Heinen, P.P., et al., "Vaccination of pigs with a DNA construct expressing an influenza virus M2-nucleoprotein fusion protein exacerbates disease after challenge with influenza A virus," *J. Gen. Virol.* 83:1851-1859, Society for General Microbiology (2002).

Horn, N.A., et al., "Cancer Gene Therapy Using Plasmid DNA: Purification of DNA for Human Clinical Trials," *Hum. Gene Ther.* 6:565-573, Mary Ann Liebert, Inc. (1995).

Ito, T., et al., "Evolutionary Analysis of the Influenza A Virus M Gene with Comparison of the M1 and M2 Proteins," *J. Virol.* 65:5491-5498, American Society for Microbiology (1991).

Jung, J., et al.,"Distinct Response of Human B cell Subpopulations in Recognition of an Innate Immune Signal, CpG DNA," *J. Immunol.* 169:2368-2373, The American Association of Immunologists, Inc. (2002).

Klinman, D.M., et al., "CpG motifs present in bacterial DNA rapidly induce lymphocytes to secrete interleukin 6, interleukin 12, and interferon γ," *Proc. Natl Acad. Sci. USA 93*:2879-2883, The National Academy of Sciences (1996).

Kodihalli, S., et al., "Strategies for inducing protection against avian influenza A virus subtypes with DNA vaccines," *Vaccine 18*:2592-2599, Elsevier Science Ltd. (2000).

Köhler, G., et al., "Fusion between immunoglobulin-secreting and nonsecreting myeloma cell lines," *Eur. J. Immunol.* 6:292-295, Verlag Chemie, GmbH and Academic Press Inc. (1976).

Köhler, G. and Milstein, C., "Derivation of specific antibody-producing tissue culture and tumor lines by cell fusion," *Eur. J. Immunol.* 6:511-519, Verlag Chemie, GmbH and Academic Press Inc. (1976).

Köhler, G. and Milstein, C., "Continuous cultures of fused cells secreting antibody of predefined specificity," *Nature 256*:495-497, Macmillan Journals Ltd. (1975).

Lamb, R.A. and Lai, C.-J., "Conservation of the Influenza Virus Membrane Protein (M1) Amino Acid Sequence and an Open Reading Frame of RNA Segment 7 Encoding a Second Protein (M2) in H1N1 and H3N2 Strains," *Virology 112*:746-751, Academic Press, Inc. (1981).

Lamb, R.A., et al., "Influenza Virus M2 Protein Is an Integral Membrane Protein Expressed on the Infected-Cell Surface," *Cell 40*:627-633, The MIT Press (1985).

Lindmayer, I., et al., "Development of New Jet Injector for Insulin Therapy," *Diabetes Care 9*:294-297, American Diabetes Association, Inc. (1986).

Manickan, E., et al., "DNA Vaccines—A Modern Gimmick or a Boon to Vaccinology?" *Crit. Rev. Immunol.* 17:139-154, Begell House, Inc. (1997).

Martins, J.K. and Roedl, E.A., "Medijector—A New Method of Corticosteroid-Anesthetic Delivery," *J. Occup. Med.* 21:821-824, Oxford University Press (1979).

Mathiesen, I., "Electropermeabilization of skeletal muscle enhances gene transfer in vivo," *Gene Ther.* 6:508-514, Stockton Press (1999).

Mir, L.M., et al., "High-efficiency gene transfer into skeletal muscle mediated by electric pulses," *Proc. Natl Acad. Sci. USA 96*:4262-4267, The National Academy of Sciences (1999).

Morrison, S.L., "Transfectomas Provide Novel Chimeric Antibodies," *Science 229*:1202-1207, American Association for the Advancement of Science (1985).

Nakamura, Y., et al., "Codon usage tabulated from international DNA sequence databases: status for the year 2000," *Nucl. Acids Res. 28*:292, Oxford University Press (2000).

Nassal, M., "Total chemical synthesis of a gene for hepatitis B virus core protein and its functional characterization," *Gene 66*:279-294, Elsevier Science Publishers B.V. (1988).
Neirynck, S., et al., "A universal influenza A vaccine based on the extracellular domain of the M2 protein," *Nat. Med.* 5:1157-1163, Nature America, Inc. (1999).
Neuberger, M.S., et al., "A hapten-specific chimaeric IgE antibody with human physiological effector function," *Nature 314*:268-270, Macmillan Journals Ltd. (1985).
Nossal, G., "Living up to the legacy," *Nat. Med. 4*(Vaccine Suppl.): 475-476, Nature America, Inc. (1998).
Oi, V.T. and Morrison, S.L., "Chimeric Antibodies," *BioTechniques 4*:214-221, Eaton Publishing Co. (1986).
Okuda, K., et al., "Protective immunity against influenza A virus induced by immunization with DNA plasmid containing influenza M gene," *Vaccine 19*:3681-3691, Elsevier Science Ltd. (2001).
Qin, Y.-J., et al., "Gene Suture—A Novel Method for Intramuscular Gene Transfer and Its Application in Hypertension Therapy," *Life Sciences 65*: 2193-2203, Elsevier Science Inc. (1999).
Rizzuto, G., et al., "Gene Electrotransfer Results in a High-Level Transduction of Rat Skeletal Muscle and Corrects Anemia of Renal Failure," *Hum. Gen. Ther. 11*:1891-1900, Mary Ann Liebert, Inc. (2000).
Robinson, H.L., "New Hope for an AIDS Vaccine," *Nat. Rev. Immunol. 2*:239-250, Nature Publishing Group (2002).
Salfeld, J., et al. "Antigenic Determinants and Functional Domains in Core Antigen and e Antigen from Hepatitis B Virus," *J. Virol. 63*:798-808, American Society for Microbiology (1989).
Sankar, V., et al., "Salivary gland delivery of pDNA-cationic lipoplexes elicits systemic immune responses," *Oral Diseases 8*:275-281, Blackwell Munksgaard (2002).
Schneider, J., et al., "Induction of CD8+ T cells using heterologous prime-boost immunisation strategies," *Immunol. Rev.* 170:29-38, Munksgaard Inetrnational Publishers Ltd. (1999).
Schrijver, R.S., et al., "Immunization of cattle with a BHV1 vector vaccine or a DNA vaccine both coding for the G protein of BRSV," *Vaccine 15*:1908-1916, Elsevier Science Ltd. (1997).
Shiver, J.W., et al., "Replication-incompetent adenoviral vaccine vector elicits effective anti-immunodeficiency-virus immunity," *Nature 415*:331-335, Nature Publishing Group (2002).
Shu, L.L., et al., "Analysis of the Evolution and Variation of the Human Influenza a Virus Nucleoprotein Gene from 1933 to 1990," *J. Virol*. 67:2723-2729, American Society for Microbiology (1993).
Sin, J.-I., et al., "DNA Priming-Protein Boosting Enhances Both Antigen-Specific Antibody and Th1-Type Cellular Immune Responses in a Murine Herpes Simplex Virus-2 gD Vaccine Model," *DNA Cell Biol*. 18:771-779, Mary Ann Liebert, Inc. (1999).
Slepushkin, V.A., et al., "Protection of mice against influenza A virus challenge by vaccination with baculovirus-expressed M2 protein," *Vaccine 13*:1399-1402, Elsevier Science Ltd. (1995).
Stahl, S.J. and Murray, K., "Immunogenicity of peptide fusions to hepatitis B virus core antigen," *Proc. Natl. Acad. Sci. USA*, 86:6283-6287, The National Academy of Sciences (1989).
Subbarao, K., "Influenza Vaccines: Present and Future," *Advances in Virus Research 54*:349-373, Academic Press (1999).
Sutcliffe, J.G., et al., "Antibodies That React with Predetermined Sites on Proteins," *Science 219*:660-666, American Association for the Advancement of Science (1983).
Takebe, Y., et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell Biol. 8*:466-472, American Society for Microbiology (1988).
Tanghe, A., "Improved Immunogenicity and Protective Efficacy of a Tuberculosis DNA Vaccine Encoding Ag85 by Protein Boosting," *Infect. Immun. 69*:3041-3047, American Society for Microbiology (2001).
Toncheva, V., et al., "Novel vectors for gene delivery formed by self-assembly of DNA with poly(L-lysine) grafted with hydrophilic polymers," *Biochim. Biophys. Acta 1380*:354-368, Elsevier Science B.V. (1998).
Treanor, J.J., et al., "Passively Transferred Monoclonal Antibody to the M2 Protein Inhibits Influenza A Virus Replication in Mice," *J. Virol. 64*:1375-1377, American Society for Microbiology (1990).
Trubetskoy, V.S., et al., "Cationic liposomes enhance targeted delivery and expression of exogenous DNA mediated by N-terminal modified poly(L-lysine)-antibody conjugate in mouse lung endothelial cells," *Biochem. Biophys. Acta 1131*:311-313, Elsevier Science Publishers B.V. (1992).
Ulmer, J.B., et al., "Protective $CD4^+$ and $CD8^+$ T cells against Influenza Virus Induced by Vaccination with Nucleoprotein DNA," *J Virol. 72*:5648-5653, American Society for Microbiology (1998).
Ulmer, J.B., et al., "Heterologous Protection Against Influenza by Injection of DNA Encoding a Viral Protein," *Science 259*:1745-1749, American Association for the Advancement of Science (1993).
Vahlsing, H.L., et al., "Immunization with plasmid DNA using a pneumatic gun," *J. Immunol. Methods 175*:11-22, Elsevier Science B.V. (1994).
Wagner, H., "Interactions between bacterial CpG-DNA and TLR9 bridge innate and adaptive immunity," *Curr. Opin. Microbiol*. 5:62-69, Elsevier Science Ltd. (2002).
Wands, J.R. and Zurawski, Jr., V.R., "High Affinity Monoclonal Antibodies to Hepatitis B Surface Antigen (HBsAg) Produced by Somatic Cell Hybrids," *Gastroenterology 80*:225-232, Elsevier North-Holland, Inc. (1981).
Watabe, S., et al., "Protection against influenza virus challenge by topical application of influenza DNA vaccine," *Vaccine 19*:4434-4444, Elsevier Science Ltd. (2001).
Wheeler, C.J., et al., "Converting an alcohol to an amine in a cationic lipid dramatically alters the co-lipid requirement, cellular transfection activity and the ultrastructure of DNA-cytofectin complexes," *Biochim. Biophys. Acta 1280*:1-11, Elsevier Science B.V. (1996).
Wheeler, C.J., et al., "A novel cationic lipid greatly enhances plasmid DNA delivery and expression in mouse lung," *Proc. Natl. Acad. Sci. USA 93*:11454-11459, The National Academy of Sciences (1996).
Widera, G., et al, "Increased DNA Vaccine Delivery and Immunogenicity by Electroporation in Vivo," *J. Immunol. 164*:4635-4640, The American Association of Immunologists (2000).
Yang, Z.-Y., et al. "Overcoming Immunity to a Viral Vaccine by DNA Priming before Vector Boosting," *J. Virol. 77*:799-803, American Society for Microbiology (2003).
Yanisch-Perron, C., et al. "Improved M13 phage cloning vectors and host strains: nucleotide sequences of the M13mp18 and pUC19 vectors," *Gene 33*:103-119, Elsevier Science Publishers (1985).
Zhong, Q., et al., "The M2 channel of influenza A virus: a molecular dynamics study," *FEBS Lett. 434*:265-271, Elsevier Science B.V. (1998).
NCBI Entrez, GenBank Report, Accession No. K01395 (Entry date 1993).
NCBI Entrez, GenBank Report, Accession No. AF046098 (Entry date 1998).
NCBI Entrez, GenBank Report, Accession No. AF116576 (Entry date 1999).
NCBI Entrez, GenBank Report, Accession No. AF202541 (Entry date 1999).
NCBI Entrez, GenBank Report, Accession No. AF389121 (Entry date 2002).
NCBI Entrez, GenBank Report, Accession No. AJ404626 (Entry date 2000).
NCBI Entrez, GenBank Report, Accession No. M38279 (Entry date 1993).
"Codon Usage Database" maintained by Kazusa DNA Research Institute, 1 page, available at http://www.kazusa.or.jp/codon/ (visited Jul. 9, 2002).
Mozdzanowska, K., et al., "Induction of influenza type A virus-specific resistance by immunization of mice with a synthetic multiple antigenic peptide vaccine that contains ectodomains of matrix protein 2," *Vaccine 21*:2616-2626, Elsevier Science (Jun. 2003).
Koide, Y., et al., "DNA vaccines," *Jpn. J. Pharmacol. 83*:167-174, Japanese Pharmacological Society (Jul. 2000).
NCBI Entrez, GenBank Report, Accession No. CAD30535, Gregory, V., et al. (first entered 2002, last updated Nov. 2006).

NCBI Entrez, GenBank Report, Accession No. AAA19192, Klimov,A.I., et al., (first entered 1992, last updated Jun. 2006).
Bender, B.S., et al., "Immunogenicity and efficacy of DNA vaccines encoding influenza A proteins in aged mice," *Vaccine 16*:1748-1755, Elsevier Science Ltd. (1998).
Bryder, K., et al., "Improved Immunogenicity of HIV-1 Epitopes in HbsAg Chimeric DNA Vaccine Plasmids by Structural Mutations of HbsAg," *DNA Cell Biol*. 18:219-225, Mary Ann Liebert, Inc. (1999).
Deml, L., et al., "Multiple Effects of Codon Usage Optimization on Expression and Immunogenicity of DNA Candidate Vaccines Encoding the Human Immunodeficiency Virus Type 1 Gag Protein," *J. Virol. 75*:10991-11001, American Society for Microbiology (2001).
Gaschen, B., et al., "Diversity Considerations in HIV-1 Vaccine Selection," *Science 296*:2354-2360, American Association for the Advancement of Science (2002).
Liu, W.J., et al., "Polynucleotide viral vaccines: codon optimisation and ubiquitin conjugation enhances prophylactic and therapeutic efficacy," *Vaccine 20*:862-869, Elsevier Science Ltd. (2002).
International Search Report for International Application No. PCT/US05/17157, mailed on Oct. 25, 2007, ISA/US, Alexandria, VA.
U.S. Appl. No. 11/715,973, inventors Luke et al., filed Mar. 9, 2007.
Liu, F, et al., "Independent but not synergistic enhancement to the immunogenicity of DNA vaccine expressing HIV-1 gp120 glycoprotein by codon optimization and C3d fusion in a mouse model" Vaccine, 22(13-14):1764-1772 (2004).
Uchijima, M., et al., "Opimization of codon usage of plasmid DNA vaccine is required for the effective MHC class I-restricted T cell responses agaisnt an intracellular bacterium," J. of Immunol. 161(10):5594-5599 (1998).
Garmony, H.S., et al., "DNA vaccines: improving expression of antigens" Genetic vaccines and therapy, 161(10):5594-5599 (2003).
Doria-Rose, N., et al.,"DNA vaccine strategies: candidates for immune modulation and immunization regimes" Methods: A companion to Methods in Enzymology 31(3):201-216 (2003).
Supplementary European Search Report issued for application No. EP 05 75 0540 on Oct. 26, 2009.
GenBank AAC63480, M2 Protein [influenza A virus H3N2] Oct. 9, 1998.
Epstein, et al., "DNA Vaccine expressing conserved influenza virus proteins protective against H5N1 challenge infection in mice" Emerging INfectious Diseases, 8(8):796-801 (2002).
Andre, et al., "Increased immune response elicited by DNA vaccination with a syntheic gp120 sequence with optimized codon usage" J. Virol. 72(2):1497-1503 (1998).
Liu, et al., "Codon Modified human papillomavirus type 16 E7 DNA vaccine enhanced cytotoxix T-lymphocyte induction and anti-tumor activity" Virology 301:43-52 (2002).
Ellenberger, D., et al., "Generation of a consensus sequence from prevalent and incident HIV-1 infections in west Africa to guide AIDS vaccine development" Virology 302:155-163 (2002).
Cachia, P., et al.,"The use of synthetic peptides in the design of a consensus sequence vaccine for *Pseudomonas aeruginosa*" J. Peptide. Res. 52:289-299 (1998).
Gammelin, M et al.,"Two subtypes of nucleoproteins (NP) of influenza A viruses" Virology 170:71-80 (1989).
Gorman, et al.,"Evolution of the nucleoprotein gene of influenze A virus" J. Virol. 64(4):1487-1497 (1990).
Office Action issued in copending Japanese application No. 2007-527348 on Dec. 3, 2010.
Lindstrom, S.E., et al., "Phylogenetic Analysis of the Entire Genome of Influenza A (H3N2) Viruses from Japan: Evidence for Genetic Reassortment of the Six Internal Genes," *J. Virol. 72*:8021-8031, American Society for Microbiology (1998).
NCBI Database, GenBank Report, Accession No. AAC63479, " M1 protein [Influenza A virus H3N2]," 2 pages (first available 1998).
NCBI Database, GenBank Report, Accession No. AAC63480, "M2 protein [Influenza A virus H3N2]," 2 pages (first available 1998).
NCBI Database, GenBank Report, Accession No. AF038271, "Influenza A virus H3N2 A/Niigata/137/96 matrix protein M1 and transmembrane ion channel M2 protein (M) gene, complete cds," 2 pages (first available 1998).
NCBI Database, GenBank Report, Accession No. Q38SQ6, "Matrix protein 1 (M1)," 3 pages (first available Jan. 2007).
NCBI Database, GenBank Report, Accession No. Q76V11, "Matrix protein 2 (Protein channel protein M2)," 3 pages (first available 1991).

```
                   1                                                50
Native NP          ATGGCGTCTC AAGGCACCAA ACGATCTTAC GAACAGATGG AGACTGATGG
Fully Optimized    ATGGCCTCTC AGGGGACAAA GCGGTCCTAC GAGCAGATGG AGACCGATGG

Consensus          ATGGCsTCTC ArGGsACmAA rCGrTCyTAC GArCAGATGG AGACyGATGG

                   51                                              100
Native NP          AGAACGCCAG AATGCCACTG AAATCAGAGC ATCCGTCGGA AAAATGATTG
Fully Optimized    AGAAAGGCAG AATGCTACCG AGATACGAGC CTCGGTGGGA AAGATGATAG

Consensus          AGAAmGsCAG AATGCyACyG ArATmmGAGC mTCsGTsGGA AArATGATwG

                   101                                             150
Native NP          GTGGAATTGG ACGATTCTAC ATCCAAATGT GCACCGAACT CAAACTCAGT
Fully Optimized    GCGGGATCGG TAGGTTTTAC ATTCAGATGT GCACTGAGCT TAAGCTGAGT

Consensus          GyGGrATyGG wmGrTTyTAC ATyCArATGT GCACyGArCT yAArCTsAGT

                   151                                              200
Native NP          GATTATGAGG GACGGTTGAT CCAAAACAGC TTAACAATAG AGAGAATGGT
Fully Optimized    GATTATGAAG GTAGACTGAT ACAGAATTCA CTCACCATCG AAAGAATGGT

Consensus          GATTATGArG GwmGryTGAT mCArAAywsm yTmACmATmG ArAGAATGGT

                   201                                             250
Native NP          GCTCTCTGCT TTTGACGAAA GGAGAAATAA ATACCTTGAA GAACATCCCA
Fully Optimized    GCTGAGTGCA TTCGACGAGC GCCGAAACAA ATACCTGGAG GAACATCCTT

Consensus          GCTswsTGCw TTyGACGArm GsmGAAAyAA ATACCTkGAr GAACATCCyw

                   251                                             300
Native NP          GTGCGGGGAA AGATCCTAAG AAAACTGGAG GACCTATATA CAGGAGAGTA
Fully Optimized    CAGCCGGCAA GGATCCCAAG AAAACTGGCG GACCCATCTA CCGGAGGGTG

Consensus          swGCsGGsAA rGATCCyAAG AAAACTGGmG GACCyATmTA CmGGAGrGTr

                   301                                             350
Native NP          AACGGAAAGT GGATGAGAGA ACTCATCCTT TATGACAAAG AAGAAATAAG
Fully Optimized    AACGGGAAAT GGATGCGCGA GCTGATTCTG TATGATAAAG AAGAAATCCG

Consensus          AACGGrAArT GGATGmGmGA rCTsATyCTk TATGAyAAAG AAGAAATmmG

                   351                                             400
Native NP          GCGAATCTGG CGCCAAGCTA ATAATGGTGA CGATGCAACG GCTGGTCTGA
Fully Optimized    GCGTATCTGG AGGCAAGCTA ACAACGGAGA TGATGCCACA GCCGGACTGA

Consensus          GCGwATCTGG mGsCAAGCTA AyAAyGGwGA yGATGCmACr GCyGGwCTGA
```

Figure 1A

```
                   401                                                450
Native NP          CTCACATGAT GATCTGGCAT TCCAATTTGA ATGATGCAAC TTATCAGAGG
Fully Optimized    CGCATATGAT GATTTGGCAC TCTAACCTTA ACGACGCGAC CTACCAGAGG

Consensus          CkCAyATGAT GATyTGGCAy TCyAAyyTkA AyGAyGCrAC yTAyCAGAGG

                   451                                                500
Native NP          ACAAGAGCTC TTGTTCGCAC CGGAATGGAT CCCAGGATGT GCTCTCTGAT
Fully Optimized    ACCCGGGCCC TCGTGAGAAC AGGCATGGAT CCACGAATGT GCTCACTTAT

Consensus          ACmmGrGCyC TyGTkmGmAC mGGmATGGAT CCmmGrATGT GCTCwCTkAT

                   501                                                550
Native NP          GCAAGGTTCA ACTCTCCCTA GGAGGTCTGG AGCCGCAGGT GCTGCAGTCA
Fully Optimized    GCAGGGGTCC ACCCTGCCAA GGAGGAGCGG GGCAGCTGGT GCCGCAGTCA

Consensus          GCArGGkTCm ACyCTsCCwA GGAGGwsyGG rGCmGCwGGT GCyGCAGTCA

                   551                                                600
Native NP          AAGGAGTTGG AACAATGGTG ATGGAATTGG TCAGAATGAT CAAACGTGGG
Fully Optimized    AAGGGGTGGG AACTATGGTG ATGGAGCTAG TGCGTATGAT TAAGCGCGGC

Consensus          AAGGrGTkGG AACwATGGTG ATGGAryTrG TsmGwATGAT yAArCGyGGs

                   601                                                650
Native NP          ATCAATGATC GGAACTTCTG GAGGGGTGAG AATGGACGAA AAACAAGAAT
Fully Optimized    ATAAATGACC GCAATTTCTG GCGGGGGGAA AACGGACGAA AGACACGCAT

Consensus          ATmAATGAyC GsAAyTTCTG GmGGGGkGAr AAyGGACGAA ArACAmGmAT

                   651                                                700
Native NP          TGCTTATGAA AGAATGTGCA ACATTCTCAA AGGGAAATTT CAAACTGCTG
Fully Optimized    TGCATATGAA CGCATGTGCA ATATTCTCAA GGGGAAATTC CAGACGGCTG

Consensus          TGCwTATGAA mGmATGTGCA AyATTCTCAA rGGGAAATTy CArACkGCTG

                   701                                                750
Native NP          CACAAAAAGC AATGATGGAT CAAGTGAGAG AGAGCCGGAA CCCAGGGAAT
Fully Optimized    CTCAAAAGGC CATGATGGAC CAGGTGAGGG AGTCAAGAAA CCCAGGCAAC

Consensus          CwCAAAArGC mATGATGGAy CArGTGAGrG AGwsmmGrAA CCCAGGsAAy
```

Figure 1B

```
                  751                                                    800
Native NP         GCTGAGTTCG AAGATCTCAC TTTTCTAGCA CGGTCTGCAC TCATATTGAG
Fully Optimized   GCCGAGTTTG AAGACCTGAC CTTCCTGGCA CGGTCTGCTC TAATCCTCAG

Consensus         GCyGAGTTyG AAGAyCTsAC yTTyCTrGCA CGGTCTGCwC TmATmyTsAG

                  801                                                    850
Native NP         AGGGTCGGTT GCTCACAAGT CCTGCCTGCC TGCCTGTGTG TATGGACCTG
Fully Optimized   AGGTAGTGTA GCACACAAGA GTTGTCTTCC GGCTTGTGTG TATGGACCAG
Consensus         AGGkwskGTw GCwCACAAGw syTGyCTkCC kGCyTGTGTG TATGGACCwG

                  851                                                    900
Native NP         CCGTAGCCAG TGGGTACGAC TTTGAAAGGG AGGGATACTC TCTAGTCGGA
Fully Optimized   CTGTTGCATC AGGGTATGAT TTCGAAAGGG AAGGCTACAG CCTAGTTGGT

Consensus         CyGTwGCmws wGGGTAyGAy TTyGAAAGGG ArGGmTACws yCTAGTyGGw

                  901                                                    950
Native NP         ATAGACCCTT TCAGACTGCT TCAAAACAGC CAAGTGTACA GCCTAATCAG
Fully Optimized   ATCGACCCGT TTAGACTCTT ACAGAATTCC CAAGTCTATT CCCTGATCAG

Consensus         ATmGACCCkT TyAGACTsyT wCArAAywsC CAAGTsTAyw sCCTrATCAG

                  951                                                   1000
Native NP         ACCAAATGAG AATCCAGCAC ACAAGAGTCA ACTGGTGTGG ATGGCATGCC
Fully Optimized   ACCCAACGAG AATCCTGCTC ACAAAAGCCA GTTGGTCTGG ATGGCCTGTC

Consensus         ACCmAAyGAG AATCCwGCwC ACAArAGyCA ryTGGTsTGG ATGGCmTGyC

                  1001                                                  1050
Native NP         ATTCTGCCGC ATTTGAAGAT CTAAGAGTAT TAAGCTTCAT CAAAGGGACG
Fully Optimized   ACTCCGCCGC CTTCGAGGAC CTCCGGGTCT TGTCCTTTAT CAAAGGCACT

Consensus         AyTCyGCCGC mTTyGArGAy CTmmGrGTmT TrwsCTTyAT CAAAGGsACk

                  1051                                                  1100
Native NP         AAGGTGCTCC CAAGAGGGAA GCTTTCCACT AGAGGAGTTC AAATTGCTTC
Fully Optimized   AAGGTTCTGC CCCGCGGCAA GTTAAGCACT AGGGGAGTTC AGATCGCAAG

Consensus         AAGGTkCTsC CmmGmGGsAA GyTwwsCACT AGrGGAGTTC ArATyGCwws

                  1101                                                  1150
Native NP         CAATGAAAAT ATGGAGACTA TGGAATCAAG TACACTTGAA CTGAGAAGCA
Fully Optimized   TAACGAGAAC ATGGAGACAA TGGAGTCTAG CACCTTGGAA TTGCGCTCCC

Consensus         yAAyGArAAy ATGGAGACwA TGGArTCwAG yACmyTkGAA yTGmGmwsCm
```

Figure 1C

```
                 1151                                              1200
Native NP        GGTACTGGGC CATAAGGACC AGAAGTGGAG GAAACACCAA TCAACAGAGG
Fully Optimized  GTTATTGGGC GATCCGGACA AGAAGCGGAG GTAACACGAA TCAGCAACGG

Consensus        GkTAyTGGGC sATmmGGACm AGAAGyGGAG GwAACACsAA TCArCArmGG

                 1201                                              1250
Native NP        GCATCTGCGG GCCAAATCAG CATACAACCT ACGTTCTCAG TACAGAGAAA
Fully Optimized  GCCAGCGCGG GCCAAATTTC GATACAGCCT ACTTTCAGCG TGCAGCGGAA

Consensus        GCmwsyGCGG GCCAAATyws sATACArCCT ACkTTCwsmG TrCAGmGrAA

                 1251                                              1300
Native NP        TCTCCCTTTT GACAGAACAA CCGTTATGGC AGCATTCAGT GGGAATACAG
Fully Optimized  TCTCCCCTTC GATCGCACCA CCGTAATGGC CGCGTTTAGT GGTAATACAG

Consensus        TCTCCCyTTy GAymGmACmA CCGTwATGGC mGCrTTyAGT GGkAATACAG

                 1301                                              1350
Native NP        AGGGGAGAAC ATCTGACATG AGGACCGAAA TCATAAGGAT GATGGAAAGT
Fully Optimized  AGGGCAGAAC TTCTGACATG CGAACAGAGA TTATCCGTAT GATGGAGAGC

Consensus        AGGGsAGAAC wTCTGACATG mGrACmGArA TyATmmGkAT GATGGArAGy

                 1351                                              1400
Native NP        GCAAGACCAG AAGATGTGTC TTTCCAGGGG CGGGGAGTCT TCGAGCTCTC
Fully Optimized  GCTCGACCTG AAGATGTGTC ATTTCAGGGC AGAGGCGTAT TTGAGCTGTC

Consensus        GCwmGACCwG AAGATGTGTC wTTyCAGGGs mGrGGmGTmT TyGAGCTsTC

                 1401                                              1450
Native NP        GGACGAAAAG GCAGCGAGCC CGATCGTGCC TTCCTTTGAC ATGAGTAATG
Fully Optimized  CGACGAGAAA GCAGCCTCTC CTATTGTCCC CTCTTTCGAC ATGTCCAACG

Consensus        sGACGArAAr GCAGCswsyC CkATyGTsCC yTCyTTyGAC ATGwsyAAyG

                 1451                                          1497
Native NP        AAGGATCTTA TTTCTTCGGA GACAATGCAG AGGAATACGA TAATTAA
Fully Optimized  AGGGGAGCTA CTTCTTTGGC GACAATGCCG AAGAATACGA CAAT...

Consensus        ArGGrwsyTA yTTCTTyGGm GACAATGCmG ArGAATACGA yAATnnn
```

Figure 1D

NP consensus vs. 1990-2000 strains

```
NP consensus      1 masqgtkrsyeqmetdgerqnateirasvgkmidgigrfyiqmctelklsdyegrliqns
2000trans is      1 .................d............r.............................
2000trans is      1 .................d............r.............................
1999trans ay      1 ------------..ig..............r.vg...k.............h.c......
1999trans af      1 ...............g..............r.vg......v..........q........
1999trans aj      1 ..t..............d..........................................
1998trans ab      1 .................d..........................................
1998trans AF      1 .................d...............g...............n..........
1998trans af      1 ...............g....d.........r..g..........................
1997trans AJ      1 ..............................r.............................
1997trans AF      1 ...............g..............r.vg.................q........
1997trans AF      1 ...............g..............r.vg.................q........
1997trans af      1 .................d..........................................
1997trans af      1 ...............g..............r.vg......v..........q........
1996trans af      1 ............................................................
1995trans AB      1 ............................................................
1995trans u7      1 ............................................................
1994trans u7      1 ............................................................
1993trans af      1 ............................................................
1991trans l2      1 ...............g....d.........r..g..........................
1991trans z5      1 .................................g..........................
1990trans l0      1 ............................................................
1990trans lo      1 ............................................................

NP consensus     61 ltiermvlsafderrnryleehpsagkdpkktggpiyrrvdgkwmrelvlydkeeirriw
2000trans is     61 ....k.......................................................
2000trans is     61 ....k.......................................................
1999trans ay     49 i......................................re.......i...........
1999trans af     61 i......................................r....v...i...........
1999trans aj     61 ....k...................................n.r.................
1998trans ab     61 ....k.....................................r.................
1998trans AF     61 ................k...........................v...............
1998trans af     61 i...............k...............................i.........v.
1997trans AJ     61 ....k...................t............k....r.................
1997trans AF     61 i......................................r....v...i...........
1997trans AF     61 i......................................r....v...i...........
1997trans af     61 ....k................................k....r.................
1997trans af     61 i......................................r....v...i...........
1996trans af     61 .....................................k....r.................
1995trans AB     61 .....................................k....r.................
1995trans u7     61 .....................................k....r.................
1994trans u7     61 ....k................................k....r.................
1993trans af     61 .....................................k....r.................
1991trans l2     61 i...............k...............................i.........v.
1991trans z5     61 ................k.......................n.......t...........
1990trans l0     61 ..v..................................k..g.r.................
1990trans lo     61 .....................................k....r.................

NP consensus    121 rqanngedataglthmmiwhsnlndttyqrtralvrtgmdprmcslmqgstlprrsgaag
2000trans is    121 ............................................................
2000trans is    121 ............................................................
1999trans ay    109 ...............l.........a..................................
1999trans af    121 .........................a..................................
1999trans aj    121 ......d.....................................................
1998trans ab    121 ............................................................
1998trans AF    121 ......d........i............................................
1998trans af    121 ...............i.........a..................................
1997trans AJ    121 ......d.....................................................
```

Figure 12A

NP consensus vs. 1990-2000 strains

```
1997trans AF     121 .........................a..................................
1997trans AF     121 .........................a..................................
1997trans af     121 ............................................................
1997trans af     121 .........................a..................................
1996trans af     121 ......d.....................................................
1995trans AB     121 ......d.....................................................
1995trans u7     121 ......d.....................................................
1994trans u7     121 ............................................................
1993trans af     121 ......d.....................................................
1991trans 12     121 ...............i.........a..................................
1991trans z5     121 ......d..................a..................................
1990trans 10     121 ......d...r.................................................
1990trans lo     121 ......d...r.................................................

NP consensus     181 aavkgigtmvmelirmikrgindrnfwrgengrktrsayermcnilkgkfqtaaqrammd
2000trans is     181 ................v..........................t..............v.
2000trans is     181 ................v.........................................v.
1999trans ay     169 ..i..............................r..i.....................v.
1999trans af     181 ..i..v.......................d...r..i.......................
1999trans aj     181 ................v.........................................v.
1998trans ab     181 ..........................................................v.
1998trans AF     181 .....v....l.........................i.......................
1998trans af     181 .....v..ia.......................r..i.......................
1997trans AJ     181 ................v...........................................
1997trans AF     181 ..i..v..................k........r..i..................k....
1997trans AF     181 ..i..v..................k........r..i..................k....
1997trans af     181 ................v.........................................v.
1997trans af     181 ..i..v.......v...............d...r..i.......................
1996trans af     181 ............................................................
1995trans AB     181 ............................................................
1995trans u7     181 ............................................................
1994trans u7     181 ................v...........................................
1993trans af     181 ............................................................
1991trans 12     181 .....v..ia.......................r..i.......................
1991trans z5     181 .....v.......v......................i..................k....
1990trans 10     181 ....................................i.......................
1990trans lo     181 ............................................................

NP consensus     241 qvresrnpgnaeiedliflarsalilrgsvahksclpacvygpavssgydfekegyslvg
2000trans is     241 ............................................................
2000trans is     241 ............................................................
1999trans ay     229 .......................................i..l..a......r.......
1999trans af     241 ..........................................l..a......r.......
1999trans aj     241 ............................................................
1998trans ab     241 ............................................................
1998trans AF     241 ............d...t............................a..............
1998trans af     241 ..........................................l..a..h...r.......
1997trans AJ     241 ............................................................
1997trans AF     241 ..........................................l..a......r.......
1997trans AF     241 .............................................a......r.......
1997trans af     241 ............................................................
1997trans af     241 ..........................................l..a......r.......
1996trans af     241 ..................s.........................................
1995trans AB     241 ..................s.........................................
1995trans u7     241 ..................s.........................................
1994trans u7     241 .................................................n..........
1993trans af     241 ..................s..............................n..........
1991trans 12     241 ..........................................l..a..h...r.......
1991trans z5     241 ............f...t.....t......................a......r.......
1990trans 10     241 ..................s.........................................
1990trans lo     241 ..................s.........................................

NP consensus     301 idpfkllqnsqvyslirpnenpahksqlvwmachsaafedlrllsfirgtkvsprgklst
2000trans is     301 ............................................................
2000trans is     301 ............................................................
1999trans ay     289 ....r.......f....s..........i.............vs......r.v...q...
```

Figure 12B

NP consensus vs. 1990-2000 strains

```
1999trans af     301 ....r.......f.............................vs......r.i...q...
1999trans aj     301 ............................................................
1998trans ab     301 ............................................................
1998trans AF     301 v.......t........................n........vs......r.l.......
1998trans af     301 ............f..........y..................vs.....k..i.......
1997trans AJ     301 ............................................................
1997trans AF     301 ....r.......f.....k.d........r............vs......r.i...q...
1997trans AF     301 ....r.......f.....k.......................vs......r.i...q...
1997trans af     301 ............................................................
1997trans af     301 ....r.......f.............................vs......r.i...q...
1996trans af     301 ............................................................
1995trans AB     301 ............................................................
1995trans u7     301 ............................................................
1994trans u7     301 ............................................................
1993trans af     301 ............................................................
1991trans 12     301 ............f.............................vs.....k..v.......
1991trans z5     301 ....r.....................................v....k....l.......
1990trans 10     301 ............................................................
1990trans lo     301 ............................................................

NP consensus     361 rgvqiasnenmdnmgsstlelrsrywairtrsggntnqqrasagqisvqptfsvqrnlpf
2000trans is     361 .......................g....................................
2000trans is     361 .......................g....................................
1999trans ay     349 ...........etvd.......................h.................s...
1999trans af     361 ..........vea.d.............................................
1999trans aj     361 .......................g........d...........................
1998trans ab     361 ..i....................g....................................
1998trans AF     361 ............aiv................................t............
1998trans af     361 ..........vea.d.n......................k....................
1997trans AJ     361 ..i....................g..........................a.........
1997trans AF     361 ..........vea.d..........................f........n......f..
1997trans AF     361 ..........vea.d.t...........................................
1997trans af     361 .......................g....................................
1997trans af     361 ..........vea.d.............................................
1996trans af     361 ..............e.............................................
1995trans AB     361 ..............e.............................................
1995trans u7     361 ..............e.............................................
1994trans u7     361 .......................g....................................
1993trans af     361 ..............e.............................................
1991trans 12     361 ..........vea.d........................k....................
1991trans z5     361 ...........et.e................................i............
1990trans 10     361 ..............e.............................................
1990trans lo     361 ..............e.............................................

NP consensus     421 ekstvmaaftgntegrtsdmr-aeiirmmegakpeevsfrgrgvfelsdekatnpivpsf
2000trans is     421 .....................-......................................
2000trans is     421 .....................-......................................
1999trans ay     409 .ra.i................-t.......s....d...q....................
1999trans af     421 .rp.i....k...........-t.......s.r..d...q....................
1999trans aj     421 .....................-......................................
1998trans ab     421 .....................-......................................
1998trans AF     421 ..t.i................r....k.-.s.r......q.........kr.........
1998trans af     421 .ra......s..n........-t.v.....s....tl..q.............s......
1997trans AJ     421 .....................-......................................
1997trans AF     421 .rv.i....k......r....-t.......s.r..d...q....................
1997trans AF     421 .rv.i....k...........-t.......s.r..d...q....................
1997trans af     421 .....................-......................................
1997trans af     421 .r..i....k...........-t.......s.r..d...q....................
1996trans af     421 .....................-.........t............................
1995trans AB     421 .....................-......................................
1995trans u7     421 .....................-.........t............................
1994trans u7     421 .....................-......................................
1993trans af     421 .....................-......................................
1991trans 12     421 .ra....v.s..n........-t.v.....s....dl..q....................
1991trans z5     421 drt.i....n...........-t.......s.r..d...q............as......
1990trans 10     421 .....................-......................................
```

Figure 12C

NP consensus vs. 1990-2000 strains

```
1990trans lo    421 .....................-..........k...........................

NP consensus    480 dmsnegsyffgdnaeeydn
2000trans is    480 e......------------
2000trans is    480 ei.....------------
1999trans ay    468 .------------------
1999trans af    480 ...................
1999trans aj    480 ...................
1998trans ab    480 ...................
1998trans AF    480 ...............d...
1998trans af    480 ...................
1997trans AJ    480 ...................
1997trans AF    480 ...................
1997trans AF    480 ...................
1997trans af    480 ...................
1997trans af    480 ...................
1996trans af    480 ...................
1995trans AB    480 ...................
1995trans u7    480 ...................
1994trans u7    480 ...................
1993trans af    480 ...................
1991trans 12    480 ...................
1991trans z5    480 ...................
1990trans 10    480 ...................
1990trans lo    480 ..............-----
```

Figure 12D

| Plasmid # | Gene Orientation | | | | | | | |
|---|---|---|---|---|---|---|---|---|
| VR4756 | > | CMV | Intron A | Seg 7 > | mRBG | | | |
| VR4759 | > | CMV | Intron A | NP > | mRBG | | | |
| VR4762 | > | CMV | Intron A | M2 > | mRBG | | | |
| VR4764 | > | RSV | | Seg 7 > | BGH | | | |
| VR4765 | > | RSV | | NP > | BGH | | | |
| VR4766 | > > | CMV | Intron A | NP > | mRBG | RSV | Seg 7 > | BGH |
| VR4767 | > < | CMV | Intron A | NP > | mRBG | BGH | < Seg 7 | RSV |
| VR4768 | > > | CMV | Intron A | Seg 7 > | mRBG | RSV | NP > | BGH |
| VR4769 | > < | CMV | Intron A | Seg 7 > | mRBG | BGH | < NP | RSV |
| VR4770 | > | RSV | R-H/C Intron | Seg 7 > | BGH | | | |
| VR4771 | > | RSV | R-H/C Intron | NP > | BGH | | | |
| VR4772 | > | RSV | R-H/C Intron | M2 > | BGH | | | |
| VR4773 | > > | CMV | Intron A | Seg 7 > | mRBG | RSV* | R-H/C Intron | NP > | BGH |
| VR4774 | > < | CMV | Intron A | Seg 7 > | mRBG | BGH | < NP | R-H/C Intron | RSV* |
| VR4775 | > > | CMV | Intron A | NP > | mRBG | RSV* | R-H/C Intron | Seg 7 > | BGH |
| VR4776 | > < | CMV | Intron A | NP > | mRBG | BGH | < Seg 7 | R-H/C Intron | RSV* |
| VR4777 | > > | CMV | Intron A | NP > | mRBG | RSV* | R-H/C Intron | M2 > | BGH |
| VR4778 | > < | CMV | Intron A | NP > | mRBG | BGH | < M2 | R-H/C Intron | RSV* |
| VR4779 | > > | CMV | Intron A | M2 > | mRBG | RSV* | R-H/C Intron | NP > | BGH |
| VR4780 | > < | CMV | Intron A | M2 > | mRBG | BGH | < NP | R-H/C Intron | RSV* |

| | |
|---|---|
| CMV | Human CMV promoter |
| RSV | RSV promoter from Allovectin, XbaI site (tctaga) near transcriptional start |
| RSV* | Modified RSV promoter (G. Hermanson changed XbaI to aataaa)) |
| Intron A | Intron A from human CMV immediate early |
| R-H/C Intron | R = 122bp from U5 region of HTLV-1, H/C= hybrid intron with HTLV-1 donor/ CMV-IE intron A acceptor |
| NP | NP- codon optimized, consensus |
| Seg 7 | Segment 7- consensus sequence encoding M1 and M2 |
| M2 | M2- codon-optimized, consensus |
| BGH | Bovine Growth Hormone terminator |
| mRBG | modified rabbit beta-globin terminator, Proudfoot |

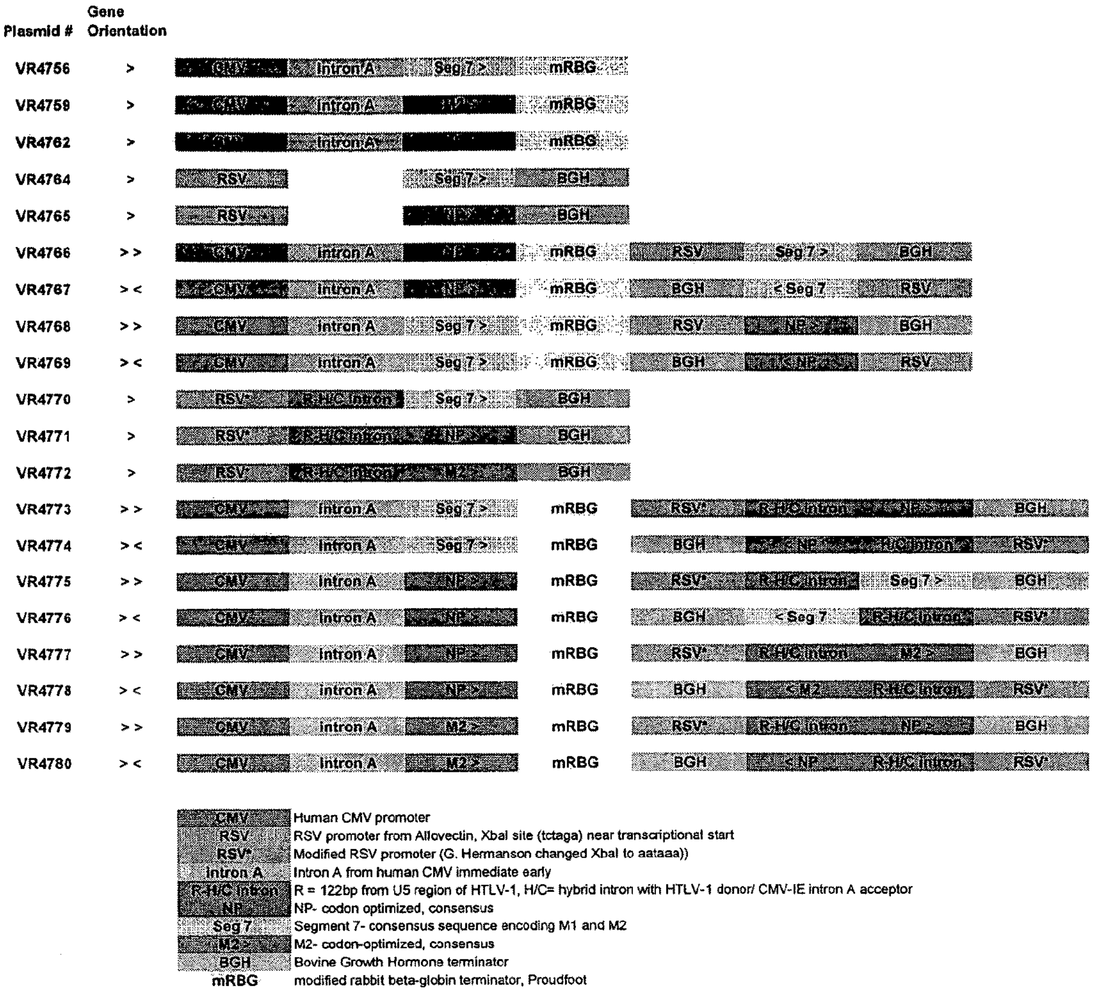

Figure 13

*Influenza A* Western blots:
M2 and NP expression in VM92 cells

SEQUENCE LISTING

<160> NUMBER OF SEQ ID NOS: 112

<210> SEQ ID NO 1
<211> LENGTH: 1565
<212> TYPE: DNA
<213> ORGANISM: Influenza A virus

<400> SEQUENCE: 1
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960

-continued

```
ctgcttcaaa acagccaagt gtacagccta atcagaccaa atgagaatcc agcacacaag   1020

agtcaactgg tgtggatggc atgccattct gccgcatttg aagatctaag agtattaagc   1080

ttcatcaaag ggacgaaggt gctcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccgtt   1320

atggcagcat tcagtgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggaa tacgataatt aaagaaaaat acccttgttt   1560

ctact                                                               1565
```

<210> SEQ ID NO 2
<211> LENGTH: 498
<212> TYPE: PRT
<213> ORGANISM: Influenza A virus

<400> SEQUENCE: 2

```
Met Ala Ser Gln Gly Thr Lys Arg Ser Thr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270
```

```
Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Ser Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 3
<211> LENGTH: 1027
<212> TYPE: DNA
<213> ORGANISM: Influenza A virus

<400> SEQUENCE: 3

agcgaaagca ggtagatatt gaaagatgag tcttctaacc gaggtcgaaa cgtacgtact      60

ctctatcatc ccgtcaggcc ccctcaaagc cgagatcgca cagagacttg aagatgtctt     120

tgcagggaag aacactgatc ttgaggttct catggaatgg ctaaagacaa gaccaatcct     180

gtcacctctg actaagggga ttttaggatt tgtgttcacg ctcaccgtgc ccagtgagcg     240

aggactgcag cgtagacgct ttgtccaaaa tgcccttaat gggaacgggg atccaaataa     300

catggacaaa gcagttaaac tgtataggaa gctcaagagg gagataacat tccatggggc     360

caaagaaatc tcactcagtt attctgctgg tgcacttgcc agttgtatgg gcctcatata     420

caacaggatg gggctgtga ccactgaagt ggcatttggc ctggtatgtg caacctgtga     480

acagattgct gactcccagc atcggtctca taggcaaatg gtgacaacaa ccaatccact     540

aatcagacat gagaacagaa tggttttagc cagcactaca gctaaggcta tggagcaaat     600

ggctggatcg agtgagcaag cagcagaggc catggaggtt gctagtcagg ctagacaaat     660

ggtgcaagcg atgagaacca ttgggactca tcctagctcc agtgctggtc tgaaaaatga     720

tcttcttgaa aatttgcagg cctatcagaa acgaatgggg gtgcagatgc aacggttcaa     780

gtgatcctct cgctattgcc gcaaatatca ttgggatctt gcacttgaca ttgtggattc     840
```

```
ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027


<210> SEQ ID NO 4
<211> LENGTH: 252
<212> TYPE: PRT
<213> ORGANISM: Influenza A virus

<400> SEQUENCE: 4

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 5
<211> LENGTH: 97
<212> TYPE: PRT
<213> ORGANISM: Influenza A virus

<400> SEQUENCE: 5

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Thr Leu Trp Ile Leu Asp Arg Leu Phe Phe
        35                  40                  45
```

```
Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu
```

<210> SEQ ID NO 6
<211> LENGTH: 1566
<212> TYPE: DNA
<213> ORGANISM: Artificial sequence
<220> FEATURE:
<223> OTHER INFORMATION: eM2NP fusion

<400> SEQUENCE: 6

```
atgagtcttc taaccgaggt cgaaacgcct atcagaaacg aatgggggtg cagatgcaac     60

ggttcaagtg atatggcgtc tcaaggcacc aaacgatctt acgaacagat ggagactgat    120

ggagaacgcc agaatgccac tgaaatcaga gcatccgtcg gaaaaatgat tggtggaatt    180

ggacgattct acatccaaat gtgcaccgaa ctcaaactca gtgattatga gggacggttg    240

atccaaaaca gcttaacaat agagagaatg gtgctctctg cttttgacga aaggagaaat    300

aaataccttg aagaacatcc cagtgcgggg aaagatccta agaaaactgg aggacctata    360

tacaggagag taaacggaaa gtggatgaga gaactcatcc tttatgacaa agaagaaata    420

aggcgaatct ggcgccaagc taataatggt gacgatgcaa cggctggtct gactcacatg    480

atgatctggc attccaattt gaatgatgca acttatcaga ggacaagagc tcttgttcgc    540

accggaatgg atcccaggat gtgctctctg atgcaaggtt caactctccc taggaggtct    600

ggagccgcag gtgctgcagt caaaggagtt ggaacaatgg tgatggaatt ggtcagaatg    660

atcaaacgtg ggatcaatga tcggaacttc tggagggggtg agaatggacg aaaaacaaga    720

attgcttatg aaagaatgtg caacattctc aaagggaaat ttcaaactgc tgcacaaaaa    780

gcaatgatgg atcaagtgag agagagccgg aacccaggga atgctgagtt cgaagatctc    840

acttttctag cacggtctgc actcatattg agagggtcgg ttgctcacaa gtcctgcctg    900

cctgcctgtg tgtatggacc tgccgtagcc agtgggtacg actttgaaag ggagggatac    960

tctctagtcg gaatagaccc tttcagactg cttcaaaaca gccaagtgta cagcctaatc   1020

agaccaaatg agaatccagc acacaagagt caactggtgt ggatggcatg ccattctgcc   1080

gcatttgaag atctaagagt attaagcttc atcaaaggga cgaaggtgct cccaagaggg   1140

aagctttcca ctagaggagt tcaaattgct tccaatgaaa atatggagac tatggaatca   1200

agtacacttg aactgagaag caggtactgg gccataagga ccagaagtgg aggaaacacc   1260

aatcaacaga gggcatctgc gggccaaatc agcatacaac ctacgttctc agtacagaga   1320

aatctccctt ttgacagaac aaccgttatg gcagcattca gtgggaatac agaggggaga   1380

acatctgaca tgaggaccga aatcataagg atgatggaaa gtgcaagacc agaagatgtg   1440

tctttccagg ggcggggagt cttcgagctc tcggacgaaa aggcagcgag cccgatcgtg   1500

ccttcctttg acatgagtaa tgaaggatct tatttcttcg gagacaatgc agaggaatac   1560

gataat                                                              1566
```

<210> SEQ ID NO 7
<211> LENGTH: 522
<212> TYPE: PRT
<213> ORGANISM: Artificial sequence
<220> FEATURE:
<223> OTHER INFORMATION: eM2NP fusion

<400> SEQUENCE: 7

```
Met Ser Leu Leu Thr Glu Val Glu Thr Pro Ile Arg Asn Glu Trp Gly
1               5                   10                  15

Cys Arg Cys Asn Gly Ser Ser Asp Met Ala Ser Gln Gly Thr Lys Arg
            20                  25                  30

Ser Tyr Glu Gln Met Glu Thr Asp Gly Glu Arg Gln Asn Ala Thr Glu
        35                  40                  45

Ile Arg Ala Ser Val Gly Lys Met Ile Gly Gly Ile Gly Arg Phe Tyr
    50                  55                  60

Ile Gln Met Cys Thr Glu Leu Lys Leu Ser Asp Tyr Glu Gly Arg Leu
65                  70                  75                  80

Ile Gln Asn Ser Leu Thr Ile Glu Arg Met Val Leu Ser Ala Phe Asp
                85                  90                  95

Glu Arg Arg Asn Lys Tyr Leu Glu Glu His Pro Ser Ala Gly Lys Asp
            100                 105                 110

Pro Lys Lys Thr Gly Gly Pro Ile Tyr Arg Arg Val Asn Gly Lys Trp
        115                 120                 125

Met Arg Glu Leu Ile Leu Tyr Asp Lys Glu Glu Ile Arg Arg Ile Trp
    130                 135                 140

Arg Gln Ala Asn Asn Gly Asp Asp Ala Thr Ala Gly Leu Thr His Met
145                 150                 155                 160

Met Ile Trp His Ser Asn Leu Asn Asp Ala Thr Tyr Gln Arg Thr Arg
                165                 170                 175

Ala Leu Val Arg Thr Gly Met Asp Pro Arg Met Cys Ser Leu Met Gln
            180                 185                 190

Gly Ser Thr Leu Pro Arg Arg Ser Gly Ala Ala Gly Ala Ala Val Lys
        195                 200                 205

Gly Val Gly Thr Met Val Met Glu Leu Val Arg Met Ile Lys Arg Gly
    210                 215                 220

Ile Asn Asp Arg Asn Phe Trp Arg Gly Glu Asn Gly Arg Lys Thr Arg
225                 230                 235                 240

Ile Ala Tyr Glu Arg Met Cys Asn Ile Leu Lys Gly Lys Phe Gln Thr
                245                 250                 255

Ala Ala Gln Lys Ala Met Met Asp Gln Val Arg Glu Ser Arg Asn Pro
            260                 265                 270

Gly Asn Ala Glu Phe Glu Asp Leu Thr Phe Leu Ala Arg Ser Ala Leu
        275                 280                 285

Ile Leu Arg Gly Ser Val Ala His Lys Ser Cys Leu Pro Ala Cys Val
    290                 295                 300

Tyr Gly Pro Ala Val Ala Ser Gly Tyr Asp Phe Glu Arg Glu Gly Tyr
305                 310                 315                 320

Ser Leu Val Gly Ile Asp Pro Phe Arg Leu Leu Gln Asn Ser Gln Val
                325                 330                 335

Tyr Ser Leu Ile Arg Pro Asn Glu Asn Pro Ala His Lys Ser Gln Leu
            340                 345                 350

Val Trp Met Ala Cys His Ser Ala Ala Phe Glu Asp Leu Arg Val Leu
        355                 360                 365

Ser Phe Ile Lys Gly Thr Lys Val Leu Pro Arg Gly Lys Leu Ser Thr
    370                 375                 380

Arg Gly Val Gln Ile Ala Ser Asn Glu Asn Met Glu Thr Met Glu Ser
385                 390                 395                 400
```

```
Ser Thr Leu Glu Leu Arg Ser Arg Tyr Trp Ala Ile Arg Thr Arg Ser
                405                 410                 415

Gly Gly Asn Thr Asn Gln Gln Arg Ala Ser Ala Gly Gln Ile Ser Ile
            420                 425                 430

Gln Pro Thr Phe Ser Val Gln Arg Asn Leu Pro Phe Asp Arg Thr Thr
        435                 440                 445

Val Met Ala Ala Phe Ser Gly Asn Thr Glu Gly Arg Thr Ser Asp Met
    450                 455                 460

Arg Thr Glu Ile Ile Arg Met Met Glu Ser Ala Arg Pro Glu Asp Val
465                 470                 475                 480

Ser Phe Gln Gly Arg Gly Val Phe Glu Leu Ser Asp Glu Lys Ala Ala
                485                 490                 495

Ser Pro Ile Val Pro Ser Phe Asp Met Ser Asn Glu Gly Ser Tyr Phe
            500                 505                 510

Phe Gly Asp Asn Ala Glu Glu Tyr Asp Asn
        515                 520
```

<210> SEQ ID NO 8
<211> LENGTH: 1566
<212> TYPE: DNA
<213> ORGANISM: Artificial sequence
<220> FEATURE:
<223> OTHER INFORMATION: NPeM2 Fusion Construct

<400> SEQUENCE: 8

```
atggcgtctc aaggcaccaa acgatcttac gaacagatgg agactgatgg agaacgccag     60

aatgccactg aaatcagagc atccgtcgga aaaatgattg gtggaattgg acgattctac    120

atccaaatgt gcaccgaact caaactcagt gattatgagg gacggttgat ccaaaacagc    180

ttaacaatag agagaatggt gctctctgct tttgacgaaa ggagaaataa ataccttgaa    240

gaacatccca gtgcggggaa agatcctaag aaaactggag gacctatata caggagagta    300

aacggaaagt ggatgagaga actcatcctt tatgacaaag aagaaataag gcgaatctgg    360

cgccaagcta ataatggtga cgatgcaacg gctggtctga ctcacatgat gatctggcat    420

tccaatttga atgatgcaac ttatcagagg acaagagctc ttgttcgcac cggaatggat    480

cccaggatgt gctctctgat gcaaggttca actctcccta ggaggtctgg agccgcaggt    540

gctgcagtca aggagttgg aacaatggtg atggaattgg tcagaatgat caaacgtggg    600

atcaatgatc ggaacttctg gaggggtgag aatggacgaa aaacaagaat tgcttatgaa    660

agaatgtgca acattctcaa agggaaattt caaactgctg cacaaaaagc aatgatggat    720

caagtgagag agagccggaa cccagggaat gctgagttcg aagatctcac ttttctagca    780

cggtctgcac tcatattgag agggtcggtt gctcacaagt cctgcctgcc tgcctgtgtg    840

tatggacctg ccgtagccag tgggtacgac tttgaaaggg agggatactc tctagtcgga    900

atagaccctt tcagactgct tcaaaacagc caagtgtaca gcctaatcag accaaatgag    960

aatccagcac acaagagtca actggtgtgg atggcatgcc attctgccgc atttgaagat   1020

ctaagagtat taagcttcat caaagggacg aaggtgctcc caagagggaa gctttccact   1080

agaggagttc aaattgcttc caatgaaaat atggagacta tggaatcaag tacacttgaa   1140

ctgagaagca ggtactgggc cataaggacc agaagtggag gaaacaccaa tcaacagagg   1200

gcatctgcgg gccaaatcag catacaacct acgttctcag tacagagaaa tctccctttt   1260

gacagaacaa ccgttatggc agcattcagt gggaatacag aggggagaac atctgacatg   1320

aggaccgaaa tcataaggat gatggaaagt gcaagaccag aagatgtgtc tttccagggg   1380
```

-continued

```
cggggagtct tcgagctctc ggacgaaaag gcagcgagcc cgatcgtgcc ttcctttgac   1440

atgagtaatg aaggatctta tttcttcgga gacaatgcag aggaatacga taatatgagt   1500

cttctaaccg aggtcgaaac gcctatcaga aacgaatggg ggtgcagatg caacggttca   1560

agtgat                                                               1566


<210> SEQ ID NO 9
<211> LENGTH: 522
<212> TYPE: PRT
<213> ORGANISM: Artificial sequence
<220> FEATURE:
<223> OTHER INFORMATION: NPeM2 Fusion Construct

<400> SEQUENCE: 9

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335
```

```
Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Ser Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn Met Ser Leu Leu Thr Glu Val Glu Thr Pro Ile Arg Asn Glu
            500                 505                 510

Trp Gly Cys Arg Cys Asn Gly Ser Ser Asp
        515                 520


<210> SEQ ID NO 10
<211> LENGTH: 6
<212> TYPE: PRT
<213> ORGANISM: Artificial sequence
<220> FEATURE:
<223> OTHER INFORMATION: Linker Peptide

<400> SEQUENCE: 10

Gly Tyr Ala Thr Arg Ala
1               5


<210> SEQ ID NO 11
<211> LENGTH: 6
<212> TYPE: PRT
<213> ORGANISM: Artificial sequence
<220> FEATURE:
<223> OTHER INFORMATION: Linker Peptide

<400> SEQUENCE: 11

Phe Gln Met Gly Glu Thr
1               5


<210> SEQ ID NO 12
<211> LENGTH: 8
<212> TYPE: PRT
<213> ORGANISM: Artificial sequence
<220> FEATURE:
<223> OTHER INFORMATION: Linker Peptide

<400> SEQUENCE: 12

Phe Asp Arg Val Lys His Leu Lys
1               5


<210> SEQ ID NO 13
<211> LENGTH: 9
<212> TYPE: PRT
<213> ORGANISM: Artificial sequence
```

<220> FEATURE:
<223> OTHER INFORMATION: Linker Peptide

<400> SEQUENCE: 13

Gly Arg Asn Thr Asn Gly Val Ile Thr
1 5

<210> SEQ ID NO 14
<211> LENGTH: 10
<212> TYPE: PRT
<213> ORGANISM: Artificial sequence
<220> FEATURE:
<223> OTHER INFORMATION: Linker Peptide

<400> SEQUENCE: 14

Val Asn Glu Lys Thr Ile Pro Asp His Asp
1 5 10

<210> SEQ ID NO 15
<211> LENGTH: 1683
<212> TYPE: DNA
<213> ORGANISM: Influenza B virus

<400> SEQUENCE: 15
atgtccaaca tggatattga cagtataaat accggaacaa tcgataaaac accagaagaa 60
ctgactcccg gaaccagtgg ggcaaccaga ccaatcatca agccagcaac ccttgctccg 120
ccaagcaaca aacgaacccg aaatccatct ccagaaagga caaccacaag cagtgaaacc 180
gatatcggaa ggaaaatcca aaagaaacaa accccaacag agataaagaa gagcgtctac 240
aaaatggtgg taaaactggg tgaattctac aaccagatga tggtcaaagc tggacttaat 300
gatgacatgg aaaggaatct aattcaaaat gcacaagctg tggagagaat cctattggct 360
gcaactgatg acaagaaaac tgaataccaa aagaaaagga atgccagaga tgtcaaagaa 420
gggaaggaag aaatagacca caacaagaca ggaggcacct tttataagat ggtaagagat 480
gataaaacca tctacttcag ccctataaaa attacctttt taaaagaaga ggtgaaaaca 540
atgtacaaga ccaccatggg gagtgatggt ttcagtggac taaatcacat tatgattgga 600
cattcacaga tgaacgatgt ctgtttccaa agatcaaagg gactgaaaag ggttggactt 660
gacccttcat taatcagtac ttttgccgga agcacactac ccagaagatc aggtacaact 720
ggtgttgcaa tcaaaggagg tggaacttta gtggatgaag ccatccgatt tataggaaga 780
gcaatggcag acagagggct actgagagac atcaaggcca agacggccta tgaaaagatt 840
cttctgaatc tgaaaaacaa gtgctctgcg ccgcaacaaa aggctctagt tgatcaagtg 900
atcggaagta ggaacccagg gattgcagac atagaagacc taactctgct tgccagaagc 960
atggtagttg tcagaccctc tgtagcgagc aaagtggtgc ttcccataag catttatgct 1020
aaaatacctc aactaggatt caataccgaa gaatactcta tggttgggta tgaagccatg 1080
gctctttata atatggcaac acctgtttcc atattaagaa tgggagatga cgcaaaagat 1140
aaatctcaac tattcttcat gtcgtgcttc ggagctgcct atgaagatct aagagtgtta 1200
tctgcactaa cgggcaccga atttaagcct agatcagcac taaaatgcaa gggtttccat 1260
gtcccggcta aggagcaagt agaaggaatg gggcagctc tgatgtccat caagcttcag 1320
ttctgggccc caatgaccag atctggaggg aatgaagtaa gtggagaagg agggtctggt 1380
caaataagtt gcagccctgt gtttgcagta gaaagaccta ttgctctaag caagcaagct 1440
gtaagaagaa tgctgtcaat gaacgttgaa ggacgtgatg cagatgtcaa aggaaatcta 1500
ctcaaaatga tgaatgattc aatggcaaag aaaaccagtg gaaatgcttt cattgggaag 1560

-continued

```
aaaatgtttc aaatatcaga caaaaacaaa gtcaatccca ttgagattcc aattaagcag   1620

accatcccca atttcttctt tgggagggac acagcagagg attatgatga cctcgattat   1680

taa                                                                 1683


<210> SEQ ID NO 16
<211> LENGTH: 560
<212> TYPE: PRT
<213> ORGANISM: Artificial sequence
<220> FEATURE:
<223> OTHER INFORMATION: Influenza B Virus

<400> SEQUENCE: 16

Met Ser Asn Met Asp Ile Asp Ser Ile Asn Thr Gly Thr Ile Asp Lys
1               5                   10                  15

Thr Pro Glu Glu Leu Thr Pro Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Thr Thr Thr Ser Ser Glu Thr Asp Ile Gly Arg
    50                  55                  60

Lys Ile Gln Lys Lys Gln Thr Pro Thr Glu Ile Lys Lys Ser Val Tyr
65                  70                  75                  80

Lys Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala Gln
            100                 105                 110

Ala Val Glu Arg Ile Leu Leu Ala Ala Thr Asp Asp Lys Lys Thr Glu
        115                 120                 125

Tyr Gln Lys Lys Arg Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Lys Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Gly Leu Lys Arg Val Gly Leu Asp Pro Ser Leu
    210                 215                 220

Ile Ser Thr Phe Ala Gly Ser Thr Leu Pro Arg Arg Ser Gly Thr Thr
225                 230                 235                 240

Gly Val Ala Ile Lys Gly Gly Gly Thr Leu Val Asp Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335
```

```
Ser Ile Tyr Ala Lys Ile Pro Gln Leu Gly Phe Asn Thr Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Ser Gly Glu Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Val Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Val Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 17
<211> LENGTH: 1220
<212> TYPE: DNA
<213> ORGANISM: Influenza A virus

<400> SEQUENCE: 17

atggaggcaa gactactggt cttgttatgt gcatttgcag ctacaaatgc agacacaata      60

tgtataggct accatgcgaa taactcaacc gacactgttg acacagtact cgaaaagaat     120

gtgaccgtga cacactctgt taacctgctc gaagacagcc acaacggaaa actatgtaaa     180

ttaaaaggaa tagccccatt acaattgggg aaatgtaata tcgccggatg gctcttggga     240

aacccggaat gcgatttact gctcacagcg agctcatggt cctatattgt agaaacatcg     300

aactcagaga atggaacatg ttacccagga gatttcatcg actatgaaga actgagggag     360

caattgagct cagtgtcatc gtttgaaaaa ttcgaaatat ttcccaagac aagctcgtgg     420

cccaatcatg aaacaaccaa aggtgtaacg gcagcatgct cctatgcggg agcaagcagt     480

ttttacagaa atttgctgtg gctgacaaag aagggaagct catacccaaa gcttagcaag     540

tcctatgtga acaataaagg gaaagaagtc cttgtactat ggggtgttca tcatccgcct     600

accggtactg atcaacagag tctctatcag aatgcagatg cttatgtctc tgtagggtca     660

tcaaaatata acaggagatt caccccggaa atagcagcga gacccaaagt aagaggtcaa     720

gctgggagga tgaactatta ctggacatta ctagaacccg gagacacaat aacatttgag     780

gcaactggaa atctaatagc accatggtat gctttcgcac tgaatagagg ttctggatcc     840

ggtatcatca cttcagacgc accagtgcat gattgtaaca cgaagtgtca aacaccccat     900
```

-continued

```
ggtgctataa acagcagtct ccctttccag aatatacatc cagtcacaat aggagagtgc     960

ccaaaatacg tcaggagtac caaattgagg atggctacag gactaagaaa cattccatct    1020

attcaatcca ggggtctatt tggagccatt gccggtttta ttgagggggg atggactgga    1080

atgatagatg gatggtatgg ttatcatcat cagaatgaac agggatcagg ctatgcagcg    1140

gatcaaaaaa gcacacaaaa tgccattgac gggattacaa acaaggtgaa ttctgttatc    1200

gagaaaatga acacccaatt                                                 1220


<210> SEQ ID NO 18
<211> LENGTH: 406
<212> TYPE: PRT
<213> ORGANISM: Influenza A virus

<400> SEQUENCE: 18

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320
```

-continued

```
Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln
                405


<210> SEQ ID NO 19
<211> LENGTH: 1741
<212> TYPE: DNA
<213> ORGANISM: Influenza A virus

<400> SEQUENCE: 19

ctgtcaaaat ggagaaaata gtgcttcttc ttgcaacagt cagtcttgtt aaaagtgatc     60

agatttgcat tggttaccat gcaaacaact cgacagagca ggttgacaca ataatggaaa    120

agaatgttac tgttacacat gcccaagaca tactggaaag gacacacaac gggaagctct    180

gcgatctaaa tggagtgaaa cctctcattt tgagggattg tagtgtagct ggatggctcc    240

tcggaaaccc tatgtgtgac gaattcatca atgtgccgga atggtcttac atagtggaga    300

aggccagtcc agccaatgac ctctgttatc cagggaattt caacgactat gaagaactga    360

aacacctatt gagcagaata aaccattttg agaaaattca gatcatcccc aaaagttctt    420

ggtccaatca tgatgcctca tcaggggtga gctcagcatg tccatacctt gggaggtcct    480

cctttttcag aaatgtggta tggcttatca aaaagaacag tgcataccca acaataaaga    540

ggagctacaa taataccaac caagaagatc ttttggtact gtgggggatt caccatccta    600

atgatgcggc agagcagaca aagctctatc aaaatccaac cacctacatt tccgttggaa    660

catcaacact gaaccagaga ttggttccag aaatagctac tagacccaaa gtaaacgggc    720

aaagtggaag aatggagttc ttctggacaa ttttaaagcc gaatgatgcc atcaatttcg    780

agagtaatgg aaatttcatt gccccagaat atgcatacaa aattgtcaag aaaggggact    840

caacaattat gaaaagtgaa ttggaatatg gtaactgcaa caccaagtgt caaactccaa    900

tgggggcgat aaactctagt atgccattcc acaacataca ccccctcacc atcggggaat    960

gccccaaata tgtgaaatca aacagattag ttcttgcgac tggactcaga aataccccctc  1020

aaagggagag aagaagaaaa aagagaggac tatttggagc tatagcaggt tttatagagg   1080

gaggatggca gggcatggta gatggttggt atgggtacca ccatagcaat gagcagggga   1140

gtggatacgc tgcagacaaa gaatccactc aaaaggcaat agatggagtc accaataagg   1200

tcaactcgat cattaacaaa atgaacactc agtttgaggc cgttggaagg gaatttaata   1260

acttagaaag gagaatagag aatttaaaca agaaaatgga agacggattc ctagatgtct   1320

ggacttacaa tgctgaactt ctggttctca tggaaaatga gagaactctc gactttcatg   1380

actcaaatgt caagaacctt tacgacaagg tccgactaca gcttagggat aatgcaaagg   1440

aactgggtaa tggttgtttc gaattctatc acaaatgtga taatgaatgt atggaaagtg   1500

taaaaaacgg aacgtatgac tacccgcagt attcagaaga agcaagacta aacagagagg   1560

aaataagtgg agtaaaattg gaatcaatgg gaacttacca aatactgtca atttattcaa   1620
```

-continued cagtggcgag ttccctagca ctggcaatca tggtagctgg tctatcttta tggatgtgct 1680
ccaatggatc gttacaatgc agaatttgca tttaaatttg tgagttcaga ttgtagttaa 1740
a 1741

<210> SEQ ID NO 20
<211> LENGTH: 568
<212> TYPE: PRT
<213> ORGANISM: Influenza A virus

<400> SEQUENCE: 20

Met Glu Lys Ile Val Leu Leu Leu Ala Thr Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Arg Thr His Asn Gly Lys Leu Cys Asp Leu Asn Gly Val Lys
50 55 60

Pro Leu Ile Leu Arg Asp Cys Ser Val Ala Gly Trp Leu Leu Gly Asn
65 70 75 80

Pro Met Cys Asp Glu Phe Ile Asn Val Pro Glu Trp Ser Tyr Ile Val
85 90 95

Glu Lys Ala Ser Pro Ala Asn Asp Leu Cys Tyr Pro Gly Asn Phe Asn
100 105 110

Asp Tyr Glu Glu Leu Lys His Leu Leu Ser Arg Ile Asn His Phe Glu
115 120 125

Lys Ile Gln Ile Ile Pro Lys Ser Ser Trp Ser Asn His Asp Ala Ser
130 135 140

Ser Gly Val Ser Ser Ala Cys Pro Tyr Leu Gly Arg Ser Ser Phe Phe
145 150 155 160

Arg Asn Val Val Trp Leu Ile Lys Lys Asn Ser Ala Tyr Pro Thr Ile
165 170 175

Lys Arg Ser Tyr Asn Asn Thr Asn Gln Glu Asp Leu Leu Val Leu Trp
180 185 190

Gly Ile His His Pro Asn Asp Ala Ala Glu Gln Thr Lys Leu Tyr Gln
195 200 205

Asn Pro Thr Thr Tyr Ile Ser Val Gly Thr Ser Thr Leu Asn Gln Arg
210 215 220

Leu Val Pro Glu Ile Ala Thr Arg Pro Lys Val Asn Gly Gln Ser Gly
225 230 235 240

Arg Met Glu Phe Phe Trp Thr Ile Leu Lys Pro Asn Asp Ala Ile Asn
245 250 255

Phe Glu Ser Asn Gly Asn Phe Ile Ala Pro Glu Tyr Ala Tyr Lys Ile
260 265 270

Val Lys Lys Gly Asp Ser Thr Ile Met Lys Ser Glu Leu Glu Tyr Gly
275 280 285

Asn Cys Asn Thr Lys Cys Gln Thr Pro Met Gly Ala Ile Asn Ser Ser
290 295 300

Met Pro Phe His Asn Ile His Pro Leu Thr Ile Gly Glu Cys Pro Lys
305 310 315 320

Tyr Val Lys Ser Asn Arg Leu Val Leu Ala Thr Gly Leu Arg Asn Thr
325 330 335

Pro Gln Arg Glu Arg Arg Arg Lys Lys Arg Gly Leu Phe Gly Ala Ile
340 345 350

-continued

```
Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asn Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Met Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565
```

<210> SEQ ID NO 21
<211> LENGTH: 1714
<212> TYPE: DNA
<213> ORGANISM: Influenza A virus

<400> SEQUENCE: 21

```
gcaaaagcag gggaattact taactagcaa aatggaaaca atatcactaa taactatact     60

actagtagta acagcaagca atgcagataa aatctgcatc ggccaccagt caacaaactc    120

cacagaaact gtggacacgc taacagaaac caatgttcct gtgacacatg ccaaagaatt    180

gctccacaca gagcataatg gaatgctgtg tgcaacaagc ctgggacatc ccctcattct    240

agacacatgc actattgaag gactagtcta tggcaaccct tcttgtgacc tgctgttggg    300

aggaagagaa tggtcctaca tcgtcgaaag atcatcagct gtaaatggaa cgtgttaccc    360

tgggaatgta gaaaacctag aggaactcag gacacttttt agttccgcta gttcctacca    420

aagaatccaa atcttcccag acacaacctg gaatgtgact tacactggaa caagcagagc    480

atgttcaggt tcattctaca ggagtatgag atggctgact caaaagagcg gtttttaccc    540

tgttcaagac gcccaataca caaataacag gggaaagagc attcttttcg tgtggggcat    600

acatcaccca cccacctata ccgagcaaac aaatttgtac ataagaaacg acacaacaac    660

aagcgtgaca acagaagatt tgaataggac cttcaaacca gtgatagggc caaggcccct    720

tgtcaatggt ctgcagggaa gaattgatta ttattggtcg gtactaaaac caggccaaac    780

attgcgagta cgatccaatg ggaatctaat tgctccatgg tatggacacg ttctttcagg    840

agggagccat ggaagaatcc tgaagactga tttaaaaggt ggtaattgtg tagtgcaatg    900
```

```
tcagactgaa aaaggtggct taaacagtac attgccattc cacaatatca gtaaatatgc    960

atttggaacc tgccccaaat atgtaagagt taatagtctc aaactggcag tcggtctgag   1020

gaacgtgcct gctagatcaa gtagaggact atttggagcc atagctggat tcatagaagg   1080

aggttggcca ggactagtcg ctggctggta tggtttccag cattcaaatg atcaaggggt   1140

tggtatggct gcagataggg attcaactca aaaggcaatt gataaaataa catccaaggt   1200

gaataatata gtcgacaaga tgaacaagca atatgaaata attgatcatg aattcagtga   1260

ggttgaaact agactcaata tgatcaataa taagattgat gaccaaatac aagacgtatg   1320

ggcatataat gcagaattgc tagtactact tgaaaatcaa aaaacactcg atgagcatga   1380

tgcgaacgtg aacaatctat ataacaaggt gaagagggca ctgggctcca atgctatgga   1440

agatgggaaa ggctgtttcg agctatacca taaatgtgat gatcagtgca tggaaacaat   1500

tcggaacggg acctataata ggagaaagta tagagaggaa tcaagactag aaaggcagaa   1560

aatagagggg gttaagctgg aatctgaggg aacttacaaa atcctcacca tttattcgac   1620

tgtcgcctca tctcttgtgc ttgcaatggg gtttgctgcc ttcctgttct gggccatgtc   1680

caatggatct tgcagatgca acatttgtat ataa                               1714
```

<210> SEQ ID NO 22
<211> LENGTH: 560
<212> TYPE: PRT
<213> ORGANISM: Influenza A virus

<400> SEQUENCE: 22

```
Met Glu Thr Ile Ser Leu Ile Thr Ile Leu Leu Val Val Thr Ala Ser
1               5                   10                  15

Asn Ala Asp Lys Ile Cys Ile Gly His Gln Ser Thr Asn Ser Thr Glu
            20                  25                  30

Thr Val Asp Thr Leu Thr Glu Thr Asn Val Pro Val Thr His Ala Lys
        35                  40                  45

Glu Leu Leu His Thr Glu His Asn Gly Met Leu Cys Ala Thr Ser Leu
    50                  55                  60

Gly His Pro Leu Ile Leu Asp Thr Cys Thr Ile Glu Gly Leu Val Tyr
65                  70                  75                  80

Gly Asn Pro Ser Cys Asp Leu Leu Leu Gly Gly Arg Glu Trp Ser Tyr
                85                  90                  95

Ile Val Glu Arg Ser Ser Ala Val Asn Gly Thr Cys Tyr Pro Gly Asn
            100                 105                 110

Val Glu Asn Leu Glu Glu Leu Arg Thr Leu Phe Ser Ser Ala Ser Ser
        115                 120                 125

Tyr Gln Arg Ile Gln Ile Phe Pro Asp Thr Thr Trp Asn Val Thr Tyr
    130                 135                 140

Thr Gly Thr Ser Arg Ala Cys Ser Gly Ser Phe Tyr Arg Ser Met Arg
145                 150                 155                 160

Trp Leu Thr Gln Lys Ser Gly Phe Tyr Pro Val Gln Asp Ala Gln Tyr
                165                 170                 175

Thr Asn Asn Arg Gly Lys Ser Ile Leu Phe Val Trp Gly Ile His His
            180                 185                 190

Pro Pro Thr Tyr Thr Glu Gln Thr Asn Leu Tyr Ile Arg Asn Asp Thr
        195                 200                 205

Thr Thr Ser Val Thr Thr Glu Asp Leu Asn Arg Thr Phe Lys Pro Val
    210                 215                 220

Ile Gly Pro Arg Pro Leu Val Asn Gly Leu Gln Gly Arg Ile Asp Tyr
225                 230                 235                 240
```

-continued

```
Tyr Trp Ser Val Leu Lys Pro Gly Gln Thr Leu Arg Val Arg Ser Asn
                245                 250                 255

Gly Asn Leu Ile Ala Pro Trp Tyr Gly His Val Leu Ser Gly Gly Ser
            260                 265                 270

His Gly Arg Ile Leu Lys Thr Asp Leu Lys Gly Gly Asn Cys Val Val
        275                 280                 285

Gln Cys Gln Thr Glu Lys Gly Gly Leu Asn Ser Thr Leu Pro Phe His
    290                 295                 300

Asn Ile Ser Lys Tyr Ala Phe Gly Thr Cys Pro Lys Tyr Val Arg Val
305                 310                 315                 320

Asn Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
    370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Val Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Met Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Arg Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
    530                 535                 540

Leu Phe Trp Ala Met Ser Asn Gly Ser Cys Arg Cys Asn Ile Cys Ile
545                 550                 555                 560
```

<210> SEQ ID NO 23
<211> LENGTH: 1494
<212> TYPE: DNA
<213> ORGANISM: Artificial sequence
<220> FEATURE:
<223> OTHER INFORMATION: Human Codon Optimized Influenza A Virus H1N1
      Nucleoprotein

<400> SEQUENCE: 23

```
atggcctctc aggggacaaa gcggtcctac gagcagatgg agaccgatgg agaaaggcag      60

aatgctaccg agatacgagc ctcggtggga aagatgatag gcgggatcgg taggttttac     120

attcagatgt gcactgagct taagctgagt gattatgaag gtagactgat acagaattca     180

ctcaccatcg aaagaatggt gctgagtgca ttcgacgagc gccgaaacaa atacctggag     240

gaacatcctt cagccggcaa ggatcccaag aaaactggcg gacccatcta ccggagggtg     300
```

-continued

```
aacgggaaat ggatgcgcga gctgattctg tatgataaag aagaaatccg gcgtatctgg    360
aggcaagcta acaacggaga tgatgccaca gccggactga cgcatatgat gatttggcac    420
tctaacctta acgacgcgac ctaccagagg acccgggccc tcgtgagaac aggcatggat    480
ccacgaatgt gctcacttat gcaggggtcc accctgccaa ggaggagcgg ggcagctggt    540
gccgcagtca aggggtggg aactatggtg atggagctag tgcgtatgat taagcgcggc    600
ataaatgacc gcaatttctg gcggggggaa aacggacgaa agacacgcat tgcatatgaa    660
cgcatgtgca atattctcaa ggggaaattc cagacggctg ctcaaaaggc catgatggac    720
caggtgaggg agtcaagaaa cccaggcaac gccgagtttg aagacctgac cttcctggca    780
cggtctgctc taatcctcag aggtagtgta gcacacaaga gttgtcttcc ggcttgtgtg    840
tatggaccag ctgttgcatc agggtatgat ttcgaaaggg aaggctacag cctagttggt    900
atcgacccgt ttagactctt acagaattcc caagtctatt ccctgatcag acccaacgag    960
aatcctgctc acaaaagcca gttggtctgg atggcctgtc actccgccgc cttcgaggac   1020
ctccgggtct tgtcctttat caaaggcact aaggttctgc cccgcggcaa gttaagcact   1080
aggggagttc agatcgcaag taacgagaac atggagacaa tggagtctag caccttggaa   1140
ttgcgctccc gttattgggc gatccggaca agaagcggag gtaacacgaa tcagcaacgg   1200
gccagcgcgg gccaaatttc gatacagcct actttcagcg tgcagcggaa tctccccttc   1260
gatcgcacca ccgtaatggc cgcgtttagt ggtaatacag agggcagaac ttctgacatg   1320
cgaacagaga ttatccgtat gatggagagc gctcgacctg aagatgtgtc atttcagggc   1380
agaggcgtat ttgagctgtc cgacgagaaa gcagcctctc ctattgtccc ctctttcgac   1440
atgtccaacg aggggagcta cttctttggc gacaatgccg aagaatacga caat         1494
```

<210> SEQ ID NO 24
<211> LENGTH: 1497
<212> TYPE: DNA
<213> ORGANISM: Artificial Sequence
<220> FEATURE:
<223> OTHER INFORMATION: Human Codon Optimized Influenza A Virus H1N1 Nucleoprotein

<400> SEQUENCE: 24

```
atggccagcc agggcaccaa gcggagctac gagcagatgg agaccgacgg cgagcggcag     60
aacgccaccg agatccgggc cagcgtgggc aagatgatcg gcggcatcgg ccggttctac    120
atccagatgt gcaccgagct gaagctgagc gactacgagg gccggctgat ccagaacagc    180
ctgaccatcg agcggatggt gctgagcgcc ttcgacgagc ggcggaacaa gtacctggag    240
gagcacccca gcgccggcaa ggaccccaag aagaccggcg gccccatcta ccggcgggtg    300
aacggcaagt ggatgcggga gctgatcctg tacgacaagg aggagatccg gcggatctgg    360
cggcaggcca acaacggcga cgacgccacc gccggcctga cccacatgat gatctggcac    420
agcaacctga acgacgccac ctaccagcgg acccgggccc tggtgcggac cggcatggac    480
ccccggatgt gcagcctgat gcagggcagc accctgcccc ggcggagcgg cgccgccggc    540
gccgccgtga agggcgtggg caccatggtg atggagctgg tgcggatgat caagcggggc    600
atcaacgacc ggaacttctg gcggggcgag aacggccgga agacccggat cgcctacgag    660
cggatgtgca acatcctgaa gggcaagttc cagaccgccg cccagaaggc catgatggac    720
caggtgcggg agagccggaa ccccggcaac gccgagttcg aggacctgac cttcctggcc    780
cggagcgccc tgatcctgcg gggcagcgtg gcccacaaga gctgcctgcc cgcctgcgtg    840
tacggccccg ccgtggccag cggctacgac ttcgagcggg agggctacag cctggtgggc    900
```

```
atcgacccct tccggctgct gcagaacagc caggtgtaca gcctgatccg gcccaacgag     960
aaccccgccc acaagagcca gctggtgtgg atggcctgcc acagcgccgc cttcgaggac    1020
ctgcgggtgc tgagcttcat caagggcacc aaggtgctgc ccggggcaa gctgagcacc    1080
cggggcgtgc agatcgccag caacgagaac atggagacca tggagagcag caccctggag    1140
ctgcggagcc ggtactgggc catccggacc cggagcggcg gcaacaccaa ccagcagcgg    1200
gccagcgccg gccagatcag catccagccc accttcagcg tgcagcggaa cctgcccttc    1260
gaccggacca ccgtgatggc cgccttcagc ggcaacaccg agggccggac cagcgacatg    1320
cggaccgaga tcatccggat gatggagagc gcccggcccg aggacgtgag cttccagggc    1380
cggggcgtgt tcgagctgag cgacgagaag gccgccagcc ccatcgtgcc cagcttcgac    1440
atgagcaacg agggcagcta cttcttcggc gacaacgccg aggagtacga caactga       1497
```

<210> SEQ ID NO 25
<211> LENGTH: 1497
<212> TYPE: DNA
<213> ORGANISM: Artificial sequence
<220> FEATURE:
<223> OTHER INFORMATION: Human Codon Optimized Influenza A Virus H1N1 Nucleoprotein

<400> SEQUENCE: 25

```
atggcctcac agggcaccaa gcggagttat gagcagatgg agaccgatgg cgagagacag      60
aacgccacag agatcagagc ctcagttggc aagatgatcg gcggcatcgg ccggttctat     120
atccagatgt gcacggagct gaagctgagc gactacgagg gcagactgat tcagaactct     180
ctgaccatcg agagaatggt cctgagtgcc ttcgatgaga gacgaaacaa gtatctggag     240
gagcatccct ccgccggcaa ggaccccaag aagacgggcg gccccatata tagaagagtt     300
aacggcaagt ggatgagaga gctgatcctg tacgataagg aggagatccg cagaatatgg     360
aggcaggcca acaacggcga cgatgccact gccggcctga cacatatgat gatatggcac     420
agtaacctga acgacgccac ctaccagaga acaagggccc tggttcgcac gggcatggat     480
cccagaatgt gttcactgat gcagggctct acactgccca gaaggtctgg cgccgccggc     540
gccgccgtca agggcgttgg cacaatggtg atggagctgg tgcggatgat caagagaggc     600
attaacgatc ggaacttttg gaggggcgag aacggcagaa agaccaggat agcctacgag     660
cgaatgtgca acattctgaa gggcaagttc cagactgccg cccagaaggc catgatggat     720
caggtgcggg agagcagaaa ccccggcaac gccgagttcg aggacctgac tttcctggcc     780
agatctgccc tgatactgag ggctctgta gcccacaagt cctgcctgcc cgcctgcgtg     840
tacggccccg ccgtggcctc cggctatgac ttcgagcgag agggctactc cctggtaggc     900
atcgatccct ttagactgct gcagaactct caggtctaca gtctgattag acccaacgag     960
aaccccgccc ataagagcca gctggtgtgg atggcctgcc acagtgccgc cttcgaggac    1020
ctgagggtgc tgtcttttat aaagggcaca aaggtgctgc ccgcggcaa gctgtctact    1080
aggggcgtcc agatagcctc caacgagaac atggagacaa tggagtctag tactctggag    1140
ctgaggtcta ggtactgggc catcaggact aggagcggcg gcaacaccaa ccagcagagg    1200
gccagcgccg gccagatcag cattcagccc accttcagtg tacagagaaa cctgcccttt    1260
gatagaacta ctgttatggc cgccttctct ggcaacactg agggcagaac tagtgacatg    1320
cgaacagaga tcataagaat gatggagtcg gcccgtcccg aggatgtgtc ctttcagggc    1380
aggggcgtct tcgagctgag cgacgagaag gccgccagcc ccatcgtacc ctctttcgat    1440
atgagtaacg agggctcgta ctttttggc gacaacgccg aggagtatga taactga       1497
```

<210> SEQ ID NO 26
<211> LENGTH: 756
<212> TYPE: DNA
<213> ORGANISM: Artificial sequence
<220> FEATURE:
<223> OTHER INFORMATION: Human Codon Optimized Influenza A Virus M1
Protein

<400> SEQUENCE: 26

```
atgagcttgc taacagaagt ggaaacctat gtcctcagta tcattcctag cggcccctta      60

aaagccgaaa tcgctcagcg gctcgaggat gtttttgccg gcaagaacac cgacctggag     120

gtattgatgg agtggctgaa aacgcgacct attctgagcc ccctgactaa gggaatactc     180

ggcttcgttt ttacattgac cgtgccctca gagaggggtc tccaaaggag gcgcttcgtg     240

cagaacgcct taaacgggaa cggggaccca aataatatgg ataaggcagt gaaactgtat     300

cgcaaattaa agcgggagat aaccttccat ggagccaagg agatctccct gtcttactct     360

gcaggtgctc tcgcgtcgtg tatgggactt atctacaacc gaatgggcgc cgtcacaaca     420

gaagtggctt tcgggctggt gtgcgcaact tgcgaacaga ttgctgacag tcagcaccgg     480

tcccaccgtc aaatggtcac caccaccaat ccgctgatta gacatgaaaa tcgcatggtt     540

ctagcatcaa ctacagccaa agcaatggaa caaatggccg gaagctccga gcaggctgcc     600

gaggcgatgg aggtggcgtc ccaggccaga cagatggtac aggctatgag aactatcggt     660

acgcacccaa gttcttcagc tgggctgaag aatgatcttc ttgagaacct gcaggcctac     720

caaaagcgga tgggcgtcca gatgcagaga tttaaa                               756
```

<210> SEQ ID NO 27
<211> LENGTH: 756
<212> TYPE: DNA
<213> ORGANISM: Artificial sequence
<220> FEATURE:
<223> OTHER INFORMATION: Human Codon Optimized Influenza A Virus M1
Protein

<400> SEQUENCE: 27

```
atgagcctgc tgaccgaggt ggagacctac gtgctgagca tcatccccag cggcccccctg      60

aaggccgaga tcgcccagag gctggaggac gtgttcgccg gcaagaacac cgacctggag     120

gtgctgatgg agtggctgaa gaccaggccc atcctgagcc ccctgaccaa gggcatcctg     180

ggcttcgtgt tcaccctgac cgtgcccagc gagaggggcc tgcagaggag gaggttcgtg     240

cagaacgccc tgaacggcaa cggcgacccc aacaacatgg acaaggccgt gaagctgtac     300

aggaagctga agagggagat caccttccac ggcgccaagg agatcagcct gagctacagc     360

gccggcgccc tggccagctg catgggcctg atctacaaca ggatgggcgc cgtgaccacc     420

gaggtggcct tcggcctggt gtgcgccacc tgcgagcaga tcgccgacag ccagcacagg     480

agccacaggc agatggtgac caccaccaac cccctgatca ggcacgagaa caggatggtg     540

ctggccagca ccaccgccaa ggccatggag cagatggccg gcagcagcga gcaggccgcc     600

gaggccatgg aggtggccag ccaggccagg cagatggtgc aggccatgag gaccatcggc     660

acccaccccca gcagcagcgc cggcctgaag aacgacctgc tggagaacct gcaggcctac     720

cagaagagga tgggcgtgca gatgcagagg ttcaag                               756
```

<210> SEQ ID NO 28
<211> LENGTH: 756
<212> TYPE: DNA
<213> ORGANISM: Artificial sequence -continued
<220> FEATURE:
<223> OTHER INFORMATION: Human Codon Optimized Influenza A Virus M1
      Protein

<400> SEQUENCE: 28

```
atgagtctgc tgacagaggt tgagacgtac gtgctgtcca tcattccctc aggccccctg     60

aaggccgaga ttgcccagag actggaggac gtcttcgccg gcaagaacac cgatctggag    120

gtgctgatgg agtggctgaa gactcgcccc atcctgtctc ccctgacaaa gggcatcctg    180

ggcttcgtat ttacactgac cgtcccctcc gagagaggcc tgcagcggag gaggttcgtt    240

cagaacgccc tgaacggcaa cggcgatccc aacaacatgg ataaggccgt gaagctgtat    300

agaaagctga agcgagagat cacatttcat ggcgccaagg agatatcgct gagctacagt    360

gccggcgccc tggcctcttg catgggcctg atatacaaca gaatgggcgc cgttactaca    420

gaggtagcct ttggcctggt ctgcgccact tgcgagcaga tcgccgactc tcagcataga    480

tctcacagac agatggtgac gactacaaac cccctgatac ggcacgagaa caggatggtg    540

ctggcctcta ctaccgccaa ggccatggag cagatggccg gcagcagtga gcaggccgcc    600

gaggccatgg aggtagcctc acaggccagg cagatggtgc aggccatgcg aaccatcggc    660

actcacccct ccagctctgc cggcctgaag aacgacctgc tggagaacct gcaggcctat    720

cagaagagaa tgggcgtaca gatgcagagg ttcaag                              756
```

<210> SEQ ID NO 29
<211> LENGTH: 294
<212> TYPE: DNA
<213> ORGANISM: Artificial sequence
<220> FEATURE:
<223> OTHER INFORMATION: Human Codon Optimized Influenza A Virus M2
      Protein

<400> SEQUENCE: 29

```
atgagtcttc taaccgaggt cgaaacgcct atcagaaacg aatgggggtg cagatgcaac     60

ggttcaagtg atcctctcgc tattgccgca aatatcattg ggatcttgca cttgacattg    120

tggattcttg atcgtctttt tttcaaatgc atttaccgtc gctttaaata cggactgaaa    180

ggagggcctt ctacggaagg agtgccaaag tctatgaggg aagaatatcg aaaggaacag    240

cagagtgctg tggatgctga cgatggtcat tttgtcagca tagagctgga gtaa          294
```

<210> SEQ ID NO 30
<211> LENGTH: 294
<212> TYPE: DNA
<213> ORGANISM: Artificial sequence
<220> FEATURE:
<223> OTHER INFORMATION: Human Codon Optimized Influenza A Virus M2
      Protein

<400> SEQUENCE: 30

```
atgagcctgc tgaccgaggt ggagaccccc atccggaacg agtggggctg ccggtgcaac     60

ggcagcagcg accccctggc catcgccgcc aacatcatcg gcatcctgca cctgaccctg    120

tggatcctgg accggctgtt cttcaagtgc atctaccggc ggttcaagta cggcctgaag    180

ggcggcccca gcaccgaggg cgtgcccaag agcatgcggg aggagtaccg gaaggagcag    240

cagagcgccg tggacgccga cgacggccac ttcgtgagca tcgagctgga gtga          294
```

<210> SEQ ID NO 31
<211> LENGTH: 294
<212> TYPE: DNA
<213> ORGANISM: Artificial sequence
<220> FEATURE:
<223> OTHER INFORMATION: Human Codon-Optimized Influenza A Virus M2
      Protein

<400> SEQUENCE: 31

```
atgtctctgc tgacagaggt ggagacaccc ataaggaacg agtggggctg caggtgcaac     60

ggctctagtg atcccctggc catcgccgcc aacatcattg gcatactgca tctgaccctg    120

tggatcctgg atagactgtt ctttaagtgc atttacagac gatttaagta tggcctgaag    180

ggcggcccct caactgaggg cgtgcccaag agtatgagag aggagtaccg gaaggagcag    240

cagagcgccg ttgacgccga tgacggccac ttcgtctcca tcgagctgga gtga          294
```

<210> SEQ ID NO 32
<211> LENGTH: 1566
<212> TYPE: DNA
<213> ORGANISM: Artificial sequence
<220> FEATURE:
<223> OTHER INFORMATION: Human Codon Optimized Coding Region Encoding
      eM2NP

<400> SEQUENCE: 32

```
atgagccttc tcacagaagt ggaaacacct atcagaaatg aatggggatg cagatgcaat     60

gggtcgagtg atatggcctc tcaaggtacg aaaagaagct acgagcaaat ggaaacggat    120

ggagaaagac aaaacgcgac cgaaatcaga gcatccgtcg ggaagatgat tggaggaatc    180

ggacgattct acatccagat gtgcacagag ctaaagctat cggattatga agggagacta    240

atacaaaata gcctaactat cgagagaatg gtgctgtctg catttgacga aaggagaaac    300

aaatacctgg aagaacaccc ctctgcaggg aaagacccaa aaaaaactgg aggtccgata    360

taccggagag tcaacggtaa atggatgaga gagctgatct tgtatgataa ggaagaaata    420

agacgcatct ggcggcaagc taataatgga gacgacgcta ctgcagggct cacgcatatg    480

atgatctggc actctaattt gaatgatgca acgtaccaaa gaacccgcgc acttgtgcgg    540

accggaatgg accctcgtat gtgcagcctt atgcaggggt ccacactgcc cagaaggtcc    600

ggagcagctg gagcagcagt aaagggggtt ggaaccatgg tgatggagct ggtgagaatg    660

attaagaggg ggatcaatga caggaacttc tggcgaggag aaaacgggag aaaaactagg    720

atagcatatg agaggatgtg taacatcctc aaaggaaaat tccaaaccgc tgctcagaaa    780

gcaatgatgg atcaagtacg cgaaagtaga aatcctggaa atgcagagtt tgaagatctc    840

actttcctcg cgcgaagcgc tctcatcctc agagggagtg tcgctcataa aagttgcctg    900

cctgcctgcg tatatggtcc tgccgtggca agtggatacg actttgagag agaggggtac    960

tctcttgttg gaatagatcc attcagatta cttcagaatt cccaggtgta cagtttaata   1020

aggccaaacg aaaatcctgc acacaaatca caacttgttt ggatggcatg ccatagtgcc   1080

gcattcgaag atctaagagt tctctctttc atcaaaggta caaaggtcct tccaagggga   1140

aaactctcta ccagaggggt acaaatagct tcaaatgaga acatggagac aatggaatct   1200

agcacattgg aattgagaag taggtattgg gccattagaa ccaggagtgg aggcaatact   1260

aatcaacagc gggcttctgc cggtcaaatt agcatacaac ctactttttc agtgcaacgg   1320

aatctccctt ttgataggac aactgtcatg gcggcattct ctggaaatac cgaaggaagg   1380

acttccgata tgaggactga gatcattagg atgatggaaa gtgcccgacc tgaagacgtc   1440

agttttcaag gaagaggtgt gttcgaactc tctgacgaaa aggcagctag cccaatcgtt   1500

ccttcttttg atatgtcaaa tgaaggatcc tacttcttcg gcgataatgc ggaggaatat   1560

gacaac                                                               1566
```

-continued

<210> SEQ ID NO 33
<211> LENGTH: 1566
<212> TYPE: DNA
<213> ORGANISM: Artificial sequence
<220> FEATURE:
<223> OTHER INFORMATION: Human Codon Optimized Coding Region Encoding eM2NP

<400> SEQUENCE: 33
atgagcctgc tgaccgaggt ggagaccccc atcaggaacg agtggggctg caggtgcaac 60
ggcagcagcg acatggccag ccagggcacc aagaggagct acgagcagat ggagaccgac 120
ggcgagaggc agaacgccac cgagatcagg gccagcgtgg gcaagatgat cggcggcatc 180
ggcaggttct acatccagat gtgcaccgag ctgaagctga gcgactacga gggcaggctg 240
atccagaaca gcctgaccat cgagaggatg gtgctgagcg ccttcgacga gaggaggaac 300
aagtacctgg aggagcaccc cagcgccggc aaggacccca agaagaccgg cggccccatc 360
tacaggaggg tgaacggcaa gtggatgagg gagctgatcc tgtacgacaa ggaggagatc 420
aggaggatct ggaggcaggc caacaacggc gacgacgcca ccgccggcct gacccacatg 480
atgatctggc acagcaacct gaacgacgcc acctaccaga ggaccagggc cctggtgagg 540
accggcatgg accccaggat gtgcagcctg atgcagggca gcaccctgcc caggaggagc 600
ggcgccgccg gcgccgccgt gaagggcgtg ggcaccatgg tgatggagct ggtgaggatg 660
atcaagaggg gcatcaacga caggaacttc tggaggggcg agaacggcag gaagaccagg 720
atcgcctacg agaggatgtg caacatcctg aagggcaagt tccagaccgc cgcccagaag 780
gccatgatgg accaggtgag ggagagcagg aaccccggca acgccgagtt cgaggacctg 840
accttcctgg ccaggagcgc cctgatcctg aggggcagcg tggcccacaa gagctgcctg 900
cccgcctgcg tgtacggccc cgccgtggcc agcggctacg acttcgagag ggagggctac 960
agcctggtgg gcatcgaccc cttcaggctg ctgcagaaca gccaggtgta cagcctgatc 1020
aggcccaacg agaaccccgc ccacaagagc cagctggtgt ggatggcctg ccacagcgcc 1080
gccttcgagg acctgagggt gctgagcttc atcaagggca ccaaggtgct gcccaggggc 1140
aagctgagca ccaggggcgt gcagatcgcc agcaacgaga acatggagac catggagagc 1200
agcaccctgg agctgaggag caggtactgg gccatcagga ccaggagcgg cggcaacacc 1260
aaccagcaga gggccagcgc cggccagatc agcatccagc ccaccttcag cgtgcagagg 1320
aacctgccct tcgacaggac caccgtgatg gccgccttca gcggcaacac cgagggcagg 1380
accagcgaca tgaggaccga gatcatcagg atgatggaga gcgccaggcc cgaggacgtg 1440
agcttccagg gcaggggcgt gttcgagctg agcgacgaga aggccgccag ccccatcgtg 1500
cccagcttcg acatgagcaa cgagggcagc tacttcttcg gcgacaacgc cgaggagtac 1560
gacaac 1566

<210> SEQ ID NO 34
<211> LENGTH: 1566
<212> TYPE: DNA
<213> ORGANISM: Artificial seequence
<220> FEATURE:
<223> OTHER INFORMATION: Human Codon Optimized Coding Region Encoding NPeM2

<400> SEQUENCE: 34
atggcaagcc agggcacaaa acgcagttac gagcagatgg agactgatgg tgagaggcag 60
aacgccaccg aaatccgggc ctccgtcggc aagatgattg gtggcatcgg aagattctat 120
atccagatgt gcacggagct taagctgtcc gattacgagg ggcgcttaat acagaactct 180

-continued

```
ctgactatcg agcgaatggt cttgagcgcc tttgatgagc ggcgtaataa gtatctcgaa    240

gagcaccctt ctgctggaaa agaccccaaa aagaccgggg gacctatcta ccgacgtgtg    300

aacggaaaat ggatgcgcga actgatactg tacgacaagg aggagatccg taggatctgg    360

agacaggcta ataacggaga tgatgccaca gctgggctga cccatatgat gatatggcat    420

agcaacctga acgacgcaac ctatcaacgc actagagcac tcgtgaggac cggtatggac    480

ccacgcatgt gctcattgat gcaaggtagc acattgcctc ggaggtcagg cgccgccggt    540

gccgccgtaa agggggtggg cacaatggtg atggaactgg tccgaatgat caaaagaggc    600

atcaatgaca ggaacttttg gcgcggagaa aacgggcgca agacccgcat tgcctacgag    660

cgcatgtgta acattttaaa aggcaaattc cagactgcag cccagaaagc aatgatggac    720

caagttagag aaagtagaaa tcccgggaat gccgagtttg aagacctgac tttcctggct    780

agaagcgcct tgatcctgcg gggctctgtc gcccacaaga gctgcctccc cgcttgcgtt    840

tacggccccg cggtcgcaag tggctacgat ttcgagaggg aggggtattc cctagttggg    900

atcgatccct tccggctcct acagaattct caggtgtata gtctgattag acccaacgaa    960

aacccggctc acaagagtca gcttgtttgg atggcatgtc actcagcagc tttcgaagac   1020

ctgcgggtac tcagctttat taaaggcacc aaggtcctgc caagaggaaa gctctccacg   1080

aggggagtac agatcgcctc aaacgagaac atggagacaa tggaaagctc caccccttgag   1140

cttaggtcgc ggtattgggc tattagaaca cgatctgggg ggaataccaa tcagcaacga   1200

gcgagtgctg gtcagatttc cattcagcct actttctctg tgcaacggaa tctaccattt   1260

gacaggacaa ctgtgatggc agcgttctcc ggcaatacag aaggacgaac atcagacatg   1320

aggaccgaaa ttatccggat gatggagagc gctcggccag aagatgtgtc gttccagggc   1380

cggggcgtgt ttgagctcag cgacgagaag gccgcgtctc caattgtgcc ttcctttgat   1440

atgagcaatg aggggtcata ctttttcgga gacaatgccg aagagtatga taatatgtct   1500

ctgcttaccg aggtggaaac gccgatacgc aacgaatggg gttgtcgttg taacggctcc   1560

agtgat                                                              1566
```

```
<210> SEQ ID NO 35
<211> LENGTH: 1566
<212> TYPE: DNA
<213> ORGANISM: Artificial sequence
<220> FEATURE:
<223> OTHER INFORMATION: Human Codon Optimized Coding Region Encoding
      NPeM2

<400> SEQUENCE: 35
```

```
atggccagcc agggcaccaa gaggagctac gagcagatgg agaccgacgg cgagaggcag     60

aacgccaccg agatcagggc cagcgtgggc aagatgatcg gcggcatcgg caggttctac    120

atccagatgt gcaccgagct gaagctgagc gactacgagg gcaggctgat ccagaacagc    180

ctgaccatcg agaggatggt gctgagcgcc ttcgacgaga ggaggaacaa gtacctggag    240

gagcacccca gcgccggcaa ggaccccaag aagaccggcg gccccatcta caggagggtg    300

aacggcaagt ggatgaggga gctgatcctg tacgacaagg aggagatcag gaggatctgg    360

aggcaggcca acaacggcga cgacgccacc gccggcctga cccacatgat gatctggcac    420

agcaacctga acgacgccac ctaccagagg accagggccc tggtgaggac cggcatggac    480

cccaggatgt gcagcctgat gcagggcagc accctgccca ggaggagcgg cgccgccggc    540

gccgccgtga agggcgtggg caccatggtg atggagctgg tgaggatgat caagaggggc    600

atcaacgaca ggaacttctg gaggggcgag aacggcagga agaccaggat cgcctacgag    660
```

-continued

```
aggatgtgca acatcctgaa gggcaagttc cagaccgccg cccagaaggc catgatggac     720
caggtgaggg agagcaggaa ccccggcaac gccgagttcg aggacctgac cttcctggcc     780
aggagcgccc tgatcctgag gggcagcgtg gcccacaaga gctgcctgcc cgcctgcgtg     840
tacggccccg ccgtggccag cggctacgac ttcgagaggg agggctacag cctggtgggc     900
atcgacccct tcaggctgct gcagaacagc caggtgtaca gcctgatcag gcccaacgag     960
aaccccgccc acaagagcca gctggtgtgg atggcctgcc acagcgccgc cttcgaggac    1020
ctgagggtgc tgagcttcat caagggcacc aaggtgctgc ccaggggcaa gctgagcacc    1080
aggggcgtgc agatcgccag caacgagaac atggagacca tggagagcag caccctggag    1140
ctgaggagca ggtactgggc catcaggacc aggagcggcg gcaacaccaa ccagcagagg    1200
gccagcgccg gccagatcag catccagccc accttcagcg tgcagaggaa cctgcccttc    1260
gacaggacca ccgtgatggc cgccttcagc ggcaacaccg agggcaggac cagcgacatg    1320
aggaccgaga tcatcaggat gatggagagc gccaggcccg aggacgtgag cttccagggc    1380
aggggcgtgt tcgagctgag cgacgagaag gccgccagcc ccatcgtgcc cagcttcgac    1440
atgagcaacg agggcagcta cttcttcggc gacaacgccg aggagtacga caacatgagc    1500
ctgctgaccg aggtggagac ccccatcagg aacgagtggg gctgcaggtg caacggcagc    1560
agcgac                                                               1566
```

<210> SEQ ID NO 36
<211> LENGTH: 1683
<212> TYPE: DNA
<213> ORGANISM: Artificial sequence
<220> FEATURE:
<223> OTHER INFORMATION: Human Codon Optimized Coding Region Encoding
      IBV NP Protein

<400> SEQUENCE: 36

```
atgtcgaaca tggacatcga cagcattaac acaggtacta ttgacaaaac ccccgaagaa      60
ctaacccctg gaacctcagg agcaacacgc ccaataatca aaccggccac cctcgcgccc     120
cctagcaata agaggacccg caatccaagt cctgagagaa ccactacttc atctgaaacg     180
gatatcggtc ggaaaattca aaaaaagcag acgcccacag agataaagaa gtctgtttac     240
aaaatggtgg taaagctcgg tgagttttat aaccagatga tggtcaaggc ggggcttaac     300
gacgatatgg aacgaaatct tatacagaat gcacaggcag tagagagaat actgctggcc     360
gctactgatg acaagaaaac ggagtaccaa aaaaaacgga atgctcgaga tgtgaaagaa     420
ggaaaagaag aaattgacca taacaaaact gggggggacat tctataagat ggtgcgggac     480
gataagacaa tctattttag cccgataaag attaccttcc tgaaggagga ggttaaaaca     540
atgtacaaga cgacgatggg cagcgatggg ttttccggac ttaatcatat aatgattggt     600
cactcgcaga tgaacgatgt atgtttccag cgctccaagg gcttaaagag ggtaggtctt     660
gacccgtctc taatatcaac tttcgcagga tccactttgc cgaggcgttc tggcacgaca     720
ggcgtggcta tcaagggcgg ggggacgctg gtcgatgagg ccattcgctt tattggtagg     780
gccatggccg atagagggct tctacgagac atcaaagcaa aaacagcata tgagaagata     840
ttattaaact taaagaacaa atgctccgct cctcagcaaa aagcgctcgt tgaccaagta     900
atcggttcga gaaatccagg cattgccgat atcgaagatc ttacactctt ggcgcgaagc     960
atggtcgttg tccgtcccag tgtcgctagt aaggtggtac taccaatctc gatttacgca    1020
aaaattccac aactcggctt taatacagag gaatattcta tggtaggtta tgaagccatg    1080
gcgttgtata atatggctac accagtctcc atattgcgta tgggagatga cgcaaaagat    1140
```

aagagtcaac tctttttcat gtcatgtttc ggcgcagcgt acgaagatct gagagtacta 1200
tccgccttga ctggaacgga atttaaacca cggtcagcct taaagtgtaa gggttttcac 1260
gtccctgcta aggagcaagt tgagggaatg ggcgcggcac tgatgagtat aaaattacaa 1320
ttttgggctc caatgacgcg ttcgggaggg aatgaagttt ctggtgaggg agggagtgga 1380
cagatatcat gctcgcccgt gttcgcggtt gaacgtccga ttgctttgag taagcaggcg 1440
gttaggcgga tgttaagtat gaatgtggag ggccgcgatg ccgacgtcaa aggcaactta 1500
ttaaaaatga tgaacgacag catggcaaag aagactagtg ggaatgcttt tatagggaaa 1560
aaaatgttcc aaataagtga caaaaacaaa gtgaacccca tcgaaatacc tatcaagcaa 1620
accatcccga atttcttttt cggtcgagac accgcggagg actacgatga cctagattac 1680
taa 1683

<210> SEQ ID NO 37
<211> LENGTH: 1683
<212> TYPE: DNA
<213> ORGANISM: Artificial sequence
<220> FEATURE:
<223> OTHER INFORMATION: Human Codon Optimized Coding Region Encoding
IBV NP Protein

<400> SEQUENCE: 37
atgagcaaca tggacatcga cagcatcaac accggcacca tcgacaagac ccccgaggag 60
ctgacccccg gcaccagcgg cgccacccgg cccatcatca agcccgccac cctggccccc 120
cccagcaaca agcggacccg gaaccccagc cccgagcgga ccaccaccag cagcgagacc 180
gacatcggcc ggaagatcca gaagaagcag acccccaccg agatcaagaa gagcgtgtac 240
aagatggtgg tgaagctggg cgagttctac aaccagatga tggtgaaggc cggcctgaac 300
gacgacatgg agcggaacct gatccagaac gcccaggccg tggagcggat cctgctggcc 360
gccaccgacg acaagaagac cgagtaccag aagaagcgga acgcccggga cgtgaaggag 420
ggcaaggagg agatcgacca caacaagacc ggcggcacct tctacaagat ggtgcgggac 480
gacaagacca tctacttcag ccccatcaag atcaccttcc tgaaggagga ggtgaagacc 540
atgtacaaga ccaccatggg cagcgacggc ttcagcggcc tgaaccacat catgatcggc 600
cacagccaga tgaacgacgt gtgcttccag cggagcaagg gcctgaagcg ggtgggcctg 660
gaccccagcc tgatcagcac cttcgccggc agcaccctgc cccggcggag cggcaccacc 720
ggcgtggcca tcaagggcgg cggcaccctg gtggacgagg ccatccggtt catcggccgg 780
gccatggccg accggggcct gctgcgggac atcaaggcca agaccgccta cgagaagatc 840
ctgctgaacc tgaagaacaa gtgcagcgcc ccccagcaga aggccctggt ggaccaggtg 900
atcggcagcc ggaaccccgg catcgccgac atcgaggacc tgaccctgct ggcccggagc 960
atggtggtgg tgcggcccag cgtggccagc aaggtggtgc tgcccatcag catctacgcc 1020
aagatccccc agctgggctt caacaccgag gagtacagca tggtgggcta cgaggccatg 1080
gccctgtaca acatggccac ccccgtgagc atcctgcgga tgggcgacga cgccaaggac 1140
aagagccagc tgttcttcat gagctgcttc ggcgccgcct acgaggacct gcgggtgctg 1200
agcgccctga ccggcaccga gttcaagccc cggagcgccc tgaagtgcaa gggcttccac 1260
gtgcccgcca aggagcaggt ggagggcatg ggcgccgccc tgatgagcat caagctgcag 1320
ttctgggccc ccatgacccg gagcggcggc aacgaggtga gcggcgaggg cggcagcggc 1380
cagatcagct gcagccccgt gttcgccgtg gagcggccca tcgccctgag caagcaggcc 1440
gtgcggcgga tgctgagcat gaacgtggag ggccgggacg ccgacgtgaa gggcaacctg 1500

```
ctgaagatga tgaacgacag catggccaag aagaccagcg gcaacgcctt catcggcaag   1560

aagatgttcc agatcagcga caagaacaag gtgaacccca tcgagatccc catcaagcag   1620

accatcccca acttcttctt cggccgggac accgccgagg actacgacga cctggactac   1680

tga                                                                  1683
```

```
<210> SEQ ID NO 38
<211> LENGTH: 1683
<212> TYPE: DNA
<213> ORGANISM: Artificial sequence
<220> FEATURE:
<223> OTHER INFORMATION: Human Codon Optimized Coding Region Encoding
      IBV NP Protein

<400> SEQUENCE: 38

atgtctaaca tggacatcga ctctataaac acaggcacga tcgataagac ccccgaggag     60

ctgacacccg gcacttcagg cgccaccaga cccataataa agcccgccac tctggccccc    120

ccctctaaca agaggacgag gaacccctct cccgagcgca ccacaacgag tagcgagacg    180

gacatcggca ggaagataca gaagaagcag actcccactg agattaagaa gtccgtgtat    240

aagatggtgg ttaagctggg cgagttttac aaccagatga tggtgaaggc cggcctgaac    300

gatgacatgg agaggaacct gatacagaac gcccaggccg tggagaggat tctgctggcc    360

gccaccgatg acaagaagac tgagtatcag aagaagagaa acgcccggga cgttaaggag    420

ggcaaggagg agatcgatca caacaagaca ggcggcactt tctataagat ggtccgtgat    480

gacaagacaa tctacttttc tcccatcaag atcacattcc tgaaggagga ggtaaagact    540

atgtacaaga caactatggg ctccgatggc ttcagtggcc tgaaccacat aatgataggc    600

catagtcaga tgaacgatgt gtgcttccag agaagcaagg gcctgaagag ggtcggcctg    660

gatccctcgc tgattagtac cttcgccggc agcactctgc ccagaagatc tggcactact    720

ggcgtagcca taaagggcgg cggcacactg gtagacgagg ccataaggtt tattggcaga    780

gccatggccg accgcggcct gctgagagat atcaaggcca agaccgccta cgagaagata    840

ctgctgaacc tgaagaacaa gtgctcagcc ccccagcaga aggccctggt ggatcaggtg    900

atcggcagta gaaaccccgg catcgccgac atcgaggatc tgactctgct ggccagaagc    960

atggtagtcg taagaccctc tgtggcctct aaggttgtgc tgcccatctc catctacgcc   1020

aagattcccc agctgggctt taacactgag gagtactcca tggtgggcta tgaggccatg   1080

gccctgtata acatggccac acccgtctct atcctgcgga tgggcgacga tgccaaggac   1140

aagtctcagc tgttttttat gagttgtttc ggcgccgcct atgaggatct gagagtcctg   1200

tcagccctga caggcactga gttcaagccc aggtccgccc tgaagtgcaa gggctttcat   1260

gtgcccgcca aggagcaggt ggagggcatg ggcgccgccc tgatgagcat caagctgcag   1320

ttctgggccc ccatgacccg gtctggcggc aacgaggtct cgggcgaggg cggcagtggc   1380

cagataagtt gcagccccgt ttttgccgtt gagagaccca tcgccctgtc taagcaggcc   1440

gttagacgaa tgctgagtat gaacgtcgag ggccgagacg ccgatgtgaa gggcaacctg   1500

ctgaagatga tgaacgattc catggccaag aagacaagcg gcaacgcctt cattggcaag   1560

aagatgttcc agataagcga taagaacaag gttaacccca tcgagattcc catcaagcag   1620

accatcccca acttcttctt cggcagggat accgccgagg attacgatga cctggactac   1680

tga                                                                  1683
```

<210> SEQ ID NO 39
<211> LENGTH: 552
<212> TYPE: DNA
<213> ORGANISM: Hepatitis B virus

<400> SEQUENCE: 39

```
atggacatcg acccttataa agaatttgga gctactgtgg agttactctc gtttttgcct     60

tctgacttct ttccttcagt acgagatctt ctagataccg cctcagctct gtatcgggaa    120

gccttagagt ctcctgagca ttgttcacct caccatactg cactcaggca agcaattctt    180

tgctgggggg aactaatgac tctagctacc tgggtgggtg ttaatttgga agatccagcg    240

tctagagacc tagtagtcag ttatgtcaac actaatatgg gcctaaagtt caggcaactc    300

ttgtggtttc acatttcttg tctcactttt ggaagagaaa cagttataga gtatttggtg    360

tctttcggag tgtggattcg cactcctcca gcttatagac caccaaatgc ccctatccta    420

tcaacacttc cggagactac tgttgttaga cgacgaggca ggtcccctag aagaagaact    480

ccctcgcctc gcagacgaag gtctcaatcg ccgcgtcgca gaagatctca atctcgggaa    540

tctcaatgtt ag                                                        552
```

<210> SEQ ID NO 40
<211> LENGTH: 183
<212> TYPE: PRT
<213> ORGANISM: Artificial sequence
<220> FEATURE:
<223> OTHER INFORMATION: Hepatitus B Virus

<400> SEQUENCE: 40

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 41
<211> LENGTH: 555
<212> TYPE: DNA
<213> ORGANISM: Artificial sequence
<220> FEATURE:
<223> OTHER INFORMATION: Synthetic HBcAg

<400> SEQUENCE: 41

```
atggatatcg atccttataa agaattcgga gctactgtgg agttactctc gtttctcccg     60
agtgacttct ttccttcagt acgagatctt ctggataccg ccagcgcgct gtatcgggaa    120
gccttggagt ctcctgagca ctgcagccct caccatactg ccctcaggca agcaattctt    180
tgctgggggg agctcatgac tctggccacg tgggtgggtg ttaacttgga agatccagct    240
agcagggacc tggtagtcag ttatgtcaac actaatatgg gtttaaagtt caggcaactc    300
ttgtggtttc acattagctg cctcactttc ggccgagaaa cagttctaga atatttggtg    360
tctttcggag tgtggatccg cactcctcca gcttataggc ctccgaatgc ccctatcctg    420
tcgacactcc cggagactac tgttgttaga cgtcgaggca ggtcacctag aagaagaact    480
ccttcgcctc gcaggcgaag gtctcaatcg ccgcggcgcc gaagatctca atctcgggaa    540
tctcaatgtt agtga                                                     555
```

<210> SEQ ID NO 42
<211> LENGTH: 183
<212> TYPE: PRT
<213> ORGANISM: Artificial sequence
<220> FEATURE:
<223> OTHER INFORMATION: Synthetic HBcAg

<400> SEQUENCE: 42

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 43
<211> LENGTH: 2043
<212> TYPE: DNA
<213> ORGANISM: Artificial sequence
<220> FEATURE:
<223> OTHER INFORMATION: Influenza A Virus NP Gene Fused to Synthetic
      HBcAg

<400> SEQUENCE: 43
atggcgtctc aaggcaccaa acgatcttac gaacagatgg agactgatgg agaacgccag 60
aatgccactg aaatcagagc atccgtcgga aaaatgattg gtggaattgg acgattctac 120
atccaaatgt gcaccgaact caaactcagt gattatgagg gacggttgat ccaaaacagc 180
ttaacaatag agagaatggt gctctctgct tttgacgaaa ggagaaataa ataccttgaa 240
gaacatccca gtgcggggaa agatcctaag aaaactggag gacctatata caggagagta 300
aacggaaagt ggatgagaga actcatcctt tatgacaaag aagaaataag gcgaatctgg 360
cgccaagcta ataatggtga cgatgcaacg gctggtctga ctcacatgat gatctggcat 420
tccaatttga atgatgcaac ttatcagagg acaagagctc ttgttcgcac cggaatggat 480
cccaggatgt gctctctgat gcaaggttca actctcccta ggaggtctgg agccgcaggt 540
gctgcagtca aggagttgg aacaatggtg atggaattgg tcagaatgat caaacgtggg 600
atcaatgatc ggaacttctg gaggggtgag aatggacgaa aaacaagaat tgcttatgaa 660
agaatgtgca acattctcaa agggaaattt caaactgctg cacaaaaagc aatgatggat 720
caagtgagag agagccggaa cccagggaat gctgagttcg aagatctcac ttttctagca 780
cggtctgcac tcatattgag agggtcggtt gctcacaagt cctgcctgcc tgcctgtgtg 840
tatggacctg ccgtagccag tgggtacgac tttgaaaggg agggatactc tctagtcgga 900
atagaccctt tcagactgct tcaaaacagc caagtgtaca gcctaatcag accaaatgag 960
aatccagcac acaagagtca actggtgtgg atggcatgcc attctgccgc atttgaagat 1020
ctaagagtat taagcttcat caaagggacg aaggtgctcc caagagggaa gctttccact 1080
agaggagttc aaattgcttc caatgaaaat atggagacta tggaatcaag tacacttgaa 1140
ctgagaagca ggtactgggc cataaggacc agaagtggag gaaacaccaa tcaacagagg 1200
gcatctgcgg gccaaatcag catacaacct acgttctcag tacagagaaa tctccctttt 1260
gacagaacaa ccgttatggc agcattcagt gggaatacag aggggagaac atctgacatg 1320
aggaccgaaa tcataaggat gatggaaagt gcaagaccag aagatgtgtc tttccagggg 1380
cggggagtct tcgagctctc ggacgaaaag gcagcgagcc cgatcgtgcc ttcctttgac 1440
atgagtaatg aaggatctta tttcttcgga gacaatgcag aggaatacga taatatggat 1500
atcgatcctt ataaagaatt cggagctact gtggagttac tctcgtttct cccgagtgac 1560
ttctttcctt cagtacgaga tcttctggat accgccagcg cgctgtatcg ggaagccttg 1620
gagtctcctg agcactgcag ccctcaccat actgccctca ggcaagcaat tctttgctgg 1680
ggggagctca tgactctggc cacgtgggtg ggtgttaact tggaagatcc agctagcagg 1740
gacctggtag tcagttatgt caacactaat atgggtttaa agttcaggca actcttgtgg 1800
tttcacatta gctgcctcac tttcggccga gaaacagttc tagaatattt ggtgtctttc 1860
ggagtgtgga tccgcactcc tccagcttat aggcctccga atgcccctat cctgtcgaca 1920
ctcccggaga ctactgttgt tagacgtcga ggcaggtcac ctagaagaag aactccttcg 1980
cctcgcaggc gaaggtctca atcgccgcgg cgccgaagat ctcaatctcg ggaatctcaa 2040
tgt 2043

<210> SEQ ID NO 44
<211> LENGTH: 2230
<212> TYPE: DNA
<213> ORGANISM: Artificial sequence
<220> FEATURE:
<223> OTHER INFORMATION: Influenza B Virus NP Gene Fused to Synthetic HBcAg -continued

<400> SEQUENCE: 44

```
atgtccaaca tggatattga cagtataaat accggaacaa tcgataaaac accagaagaa     60
ctgactcccg gaaccagtgg ggcaaccaga ccaatcatca agccagcaac ccttgctccg    120
ccaagcaaca aacgaacccg aaatccatct ccagaaagga caaccacaag cagtgaaacc    180
gatatcggaa ggaaaatcca aaagaaacaa accccaacag agataaagaa gagcgtctac    240
aaaatggtgg taaaactggg tgaattctac aaccagatga tggtcaaagc tggacttaat    300
gatgacatgg aaaggaatct aattcaaaat gcacaagctg tggagagaat cctattggct    360
gcaactgatg acaagaaaac tgaataccaa aagaaaagga atgccagaga tgtcaaagaa    420
gggaaggaag aaatagacca caacaagaca ggaggcacct tttataagat ggtaagagat    480
gataaaacca tctacttcag ccctataaaa attacctttt taaaagaaga ggtgaaaaca    540
atgtacaaga ccaccatggg gagtgatggt ttcagtggac taaatcacat tatgattgga    600
cattcacaga tgaacgatgt ctgtttccaa agatcaaagg gactgaaaag ggttggactt    660
gacccttcat taatcagtac ttttgccgga agcacactac ccagaagatc aggtacaact    720
ggtgttgcaa tcaaaggagg tggaacttta gtggatgaag ccatccgatt tataggaaga    780
gcaatggcag acagagggct actgagagac atcaaggcca agacggccta tgaaaagatt    840
cttctgaatc tgaaaaacaa gtgctctgcg ccgcaacaaa aggctctagt tgatcaagtg    900
atcggaagta ggaacccagg gattgcagac atagaagacc taactctgct tgccagaagc    960
atggtagttg tcagaccctc tgtagcgagc aaagtggtgc ttcccataag catttatgct   1020
aaaatacctc aactaggatt caataccgaa gaatactcta tggttgggta tgaagccatg   1080
gctctttata atatggcaac acctgtttcc atattaagaa tgggagatga cgcaaaagat   1140
aaatctcaac tattcttcat gtcgtgcttc ggagctgcct atgaagatct aagagtgtta   1200
tctgcactaa cgggcaccga atttaagcct agatcagcac taaaatgcaa gggtttccat   1260
gtcccggcta aggagcaagt agaaggaatg ggggcagctc tgatgtccat caagcttcag   1320
ttctgggccc caatgaccag atctggaggg aatgaagtaa gtggagaagg agggtctggt   1380
caaataagtt gcagccctgt gtttgcagta gaaagaccta ttgctctaag caagcaagct   1440
gtaagaagaa tgctgtcaat gaacgttgaa ggacgtgatg cagatgtcaa aggaaatcta   1500
ctcaaaatga tgaatgattc aatggcaaag aaaaccagtg gaaatgcttt cattgggaag   1560
aaaatgtttc aaatatcaga caaaaacaaa gtcaatccca ttgagattcc aattaagcag   1620
accatcccca atttcttctt tgggagggac acagcagagg attatgatga cctcgattat   1680
atggatatcg atccttataa agaattcgga gctactgtgg agttactctc gtttctcccg   1740
agtgacttct ttccttcagt acgagatctt ctggataccg ccagcgcgct gtatcgggaa   1800
gccttggagt ctcctgagca ctgcagccct caccatactg ccctcaggca agcaattctt   1860
tgctgggggg agctcatgac tctggccacg tgggtgggtg ttaacttgga agatccagct   1920
agcagggacc tggtagtcag ttatgtcaac actaatatgg gtttaaagtt caggcaactc   1980
ttgtggtttc acattagctg cctcactttc ggccgagaaa cagttctaga atatttggtg   2040
tctttcggag tgtggatccg cactcctcca gcttataggc ctccgaatgc ccctatcctg   2100
tcgacactcc cggagactac tgttgttaga cgtcgaggca ggtcacctag aagaagaact   2160
ccttcgcctc gcaggcgaag gtctcaatcg ccgcggcgcc gaagatctca atctcgggaa   2220
tctcaatgtt                                                          2230
```

<210> SEQ ID NO 45
<211> LENGTH: 1305
<212> TYPE: DNA
<213> ORGANISM: Artificial sequence
<220> FEATURE:
<223> OTHER INFORMATION: Influenza A Virus M1 Fused to Synthetic HBcAg

<400> SEQUENCE: 45
atgagtcttc taaccgaggt cgaaacgtac gtactctcta tcatcccgtc aggcccccte 60 aaagccgaga tcgcacagag acttgaagat gtctttgcag ggaagaacac tgatcttgag 120
gttctcatgg aatggctaaa gacaagacca atcctgtcac ctctgactaa ggggatttta 180
ggatttgtgt tcacgctcac cgtgcccagt gagcgaggac tgcagcgtag acgctttgtc 240
caaaatgccc ttaatgggaa cggggatcca aataacatgg acaaagcagt taaactgtat 300
aggaagctca agagggagat aacattccat ggggccaaag aaatctcact cagttattct 360
gctggtgcac ttgccagttg tatgggcctc atatacaaca ggatgggggc tgtgaccact 420
gaagtggcat ttggcctggt atgtgcaacc tgtgaacaga ttgctgactc ccagcatcgg 480
tctcataggc aaatggtgac aacaaccaat ccactaatca gacatgagaa cagaatggtt 540
ttagccagca ctacagctaa ggctatggag caaatggctg gatcgagtga gcaagcagca 600
gaggccatgg aggttgctag tcaggctaga caaatggtgc aagcgatgag aaccattggg 660
actcatccta gctccagtgc tggtctgaaa aatgatcttc ttgaaaattt gcaggcctat 720
cagaaacgaa tgggggtgca gatgcaacgg ttcaagatgg atatcgatcc ttataaagaa 780
ttcggagcta ctgtggagtt actctcgttt ctcccgagtg acttctttcc ttcagtacga 840
gatcttctgg ataccgccag cgcgctgtat cgggaagcct tggagtctcc tgagcactgc 900
agccctcacc atactgccct caggcaagca attctttgct gggggggagct catgactctg 960 gccacgtggg tgggtgttaa cttggaagat ccagctagca gggacctggt agtcagttat 1020
gtcaacacta atatgggttt aaagttcagg caactcttgt ggtttcacat tagctgcctc 1080
actttcggcc gagaaacagt tctagaatat ttggtgtctt tcggagtgtg gatccgcact 1140
cctccagctt ataggcctcc gaatgcccct atcctgtcga cactcccgga gactactgtt 1200
gttagacgtc gaggcaggtc acctagaaga agaactcctt cgcctcgcag gcgaaggtct 1260
caatcgccgc ggcgccgaag atctcaatct cgggaatctc aatgt 1305

<210> SEQ ID NO 46
<211> LENGTH: 1581
<212> TYPE: DNA
<213> ORGANISM: Artificial sequence
<220> FEATURE:
<223> OTHER INFORMATION: Open Reading Frame for TPANP from VR4700

<400> SEQUENCE: 46
atggatgcaa tgaagagagg gctctgctgt gtgctgctgc tgtgtggagc agtcttcgtt 60
tcgcccagcg ctagaggatc gggaatggcg tcccaaggca ccaaacggtc ttacgaacag 120
atggagactg atggagaacg ccagaatgcc actgaaatca gagcatccgt cggaaaaatg 180
attggtggaa ttggacgatt ctacatccaa atgtgcaccg aactcaaact cagtgattat 240
gagggacggt tgatccaaaa cagcttaaca atagagagaa tggtgctctc tgcttttgac 300
gaaaggagaa ataaatacct ggaagaacat cccagtgcgg ggaaagatcc taagaaaact 360
ggaggaccta tatacaggag agtaaacgga aagtggatga gagaactcat cctttatgac 420
aaagaagaaa taaggcgaat ctggcgccaa gctaataatg gtgacgatgc aacggctggt 480
ctgactcaca tgatgatctg gcattccaat ttgaatgatg caacttatca gaggacaaga 540

-continued

```
gctcttgttc gcaccggaat ggatcccagg atgtgctctc tgatgcaagg ttcaactctc    600

cctaggaggt ctggagccgc aggtgctgca gtcaaaggag ttggaacaat ggtgatggaa    660

ttggtcagga tgatcaaacg tgggatcaat gatcggaact tctggagggg tgagaatgga    720

cgaaaaacaa gaattgctta tgaaagaatg tgcaacattc tcaaagggaa atttcaaact    780

gctgcacaaa aagcaatgat ggatcaagtg agagagagcc ggaacccagg gaatgctgag    840

ttcgaagatc tcacttttct agcacggtct gcactcatat tgagagggtc ggttgctcac    900

aagtcctgcc tgcctgcctg tgtgtatgga cctgccgtag ccagtgggta cgactttgaa    960

agagagggat actctctagt cggaatagac cctttcagac tgcttcaaaa cagccaagtg   1020

tacagcctaa tcagaccaaa tgagaatcca gcacacaaga gtcaactggt gtggatggca   1080

tgccattctg ccgcatttga agatctaaga gtattaagct tcatcaaagg gacgaaggtg   1140

ctcccaagag ggaagctttc cactagagga gttcaaattg cttccaatga aaatatggag   1200

actatggaat caagtacact tgaactgaga agcaggtact gggccataag gaccagaagt   1260

ggaggaaaca ccaatcaaca gagggcatct gcgggccaaa tcagcataca acctacgttc   1320

tcagtacaga gaaatctccc ttttgacaga acaaccatta tggcagcatt caatgggaat   1380

acagagggaa gaacatctga catgaggacc gaaatcataa ggatgatgga aagtgcaaga   1440

ccagaagatg tgtctttcca ggggcgggga gtcttcgagc tctcggacga aaaggcagcg   1500

agcccgatcg tgccttcctt tgacatgagt aatgaaggat cttatttctt cggagacaat   1560

gcagatgagt acgacaatta a                                              1581
```

```
<210> SEQ ID NO 47
<211> LENGTH: 333
<212> TYPE: DNA
<213> ORGANISM: Artificial sequence
<220> FEATURE:
<223> OTHER INFORMATION: Open Reading Frame for TPAM2 DeltaTM from
      VR4707

<400> SEQUENCE: 47

atggatgcaa tgaagagagg gctctgctgt gtgctgctgc tgtgtggagc agtcttcgtt     60

tcgcccagcg ctagaggatc gggaatgagt cttctgaccg aggtcgaaac ccctatcaga    120

aacgaatggg ggtgcagatg caacgattca agtgatcctg gcggcggcga tcggcttttt    180

ttcaaatgca tttatcggcg ctttaaatac ggcttgaaaa gagggccttc taccgaagga    240

gtgccagagt ctatgaggga agaatatcgg aaggaacagc agaatgctgt ggatgttgac    300

gatagccatt ttgtcagcat cgagctggag taa                                 333
```

```
<210> SEQ ID NO 48
<211> LENGTH: 24
<212> TYPE: DNA
<213> ORGANISM: Artificial sequence
<220> FEATURE:
<223> OTHER INFORMATION: Primer Used to Amplify TPAM2 Fragment

<400> SEQUENCE: 48

gccgaatcca tggatgcaat gaag                                            24
```

```
<210> SEQ ID NO 49
<211> LENGTH: 36
<212> TYPE: DNA
<213> ORGANISM: Artificial sequence
<220> FEATURE:
<223> OTHER INFORMATION: Primer Used to Amplify TPAM2 Fragment
```

<400> SEQUENCE: 49
ggtgccttgg gacgccatat cacttgaatc gttgca 36

<210> SEQ ID NO 50
<211> LENGTH: 36
<212> TYPE: DNA
<213> ORGANISM: Artificial sequence
<220> FEATURE:
<223> OTHER INFORMATION: Primer Used to Amplify NP Gene

<400> SEQUENCE: 50
tgcaacgatt caagtgatat ggcgtcccaa ggcacc 36

<210> SEQ ID NO 51
<211> LENGTH: 24
<212> TYPE: DNA
<213> ORGANISM: Artificial sequence
<220> FEATURE:
<223> OTHER INFORMATION: Primer Used to Amplify NP Gene

<400> SEQUENCE: 51
gccgtcgact taattgtcgt actc 24

<210> SEQ ID NO 52
<211> LENGTH: 1653
<212> TYPE: DNA
<213> ORGANISM: Artificial sequence
<220> FEATURE:
<223> OTHER INFORMATION: Open Reading Frame for TPAM2NP from VR4710

<400> SEQUENCE: 52
atggatgcaa tgaagagagg gctctgctgt gtgctgctgc tgtgtggagc agtcttcgtt 60
tcgcccagcg ctagaggatc gggaatgagt cttctgaccg aggtcgaaac ccctatcaga 120
aacgaatggg ggtgcagatg caacgattca agtgatatgg cgtcccaagg caccaaacgg 180
tcttacgaac agatggagac tgatggagaa cgccagaatg ccactgaaat cagagcatcc 240
gtcggaaaaa tgattggtgg aattggacga ttctacatcc aaatgtgcac cgaactcaaa 300
ctcagtgatt atgagggacg gttgatccaa aacagcttaa caatagagag aatggtgctc 360
tctgcttttg acgaaaggag aaataaatac ctggaagaac atcccagtgc ggggaaagat 420
cctaagaaaa ctggaggacc tatatacagg agagtaaacg gaaagtggat gagagaactc 480
atcctttatg acaaagaaga aataaggcga atctggcgcc aagctaataa tggtgacgat 540
gcaacggctg gtctgactca catgatgatc tggcattcca atttgaatga tgcaacttat 600
cagaggacaa gagctcttgt tcgcaccgga atggatccca ggatgtgctc tctgatgcaa 660
ggttcaactc tccctaggag gtctggagcc gcaggtgctg cagtcaaagg agttggaaca 720
atggtgatgg aattggtcag gatgatcaaa cgtgggatca atgatcggaa cttctggagg 780
ggtgagaatg gacgaaaaac aagaattgct tatgaaagaa tgtgcaacat tctcaaaggg 840
aaatttcaaa ctgctgcaca aaaagcaatg atggatcaag tgagagagag ccggaaccca 900
gggaatgctg agttcgaaga tctcactttt ctagcacggt ctgcactcat attgagaggg 960
tcggttgctc acaagtcctg cctgcctgcc tgtgtgtatg gacctgccgt agccagtggg 1020
tacgactttg aaagagaggg atactctcta gtcggaatag accctttcag actgcttcaa 1080
aacagccaag tgtacagcct aatcagacca aatgagaatc cagcacacaa gagtcaactg 1140
gtgtggatgg catgccattc tgccgcattt gaagatctaa gagtattaag cttcatcaaa 1200
gggacgaagg tgctcccaag agggaagctt tccactagag gagttcaaat tgcttccaat 1260
gaaaatatgg agactatgga atcaagtaca cttgaactga gaagcaggta ctgggccata 1320
aggaccagaa gtggaggaaa caccaatcaa cagagggcat ctgcgggcca aatcagcata 1380
caacctacgt tctcagtaca gagaaatctc ccttttgaca gaacaaccat tatggcagca 1440
ttcaatggga atacagaggg aagaacatct gacatgagga ccgaaatcat aaggatgatg 1500
gaaagtgcaa gaccagaaga tgtgtctttc caggggcggg gagtcttcga gctctcggac 1560
gaaaaggcag cgagcccgat cgtgccttcc tttgacatga gtaatgaagg atcttatttc 1620
ttcggagaca atgcagatga gtacgacaat taa 1653

<210> SEQ ID NO 53
<211> LENGTH: 35
<212> TYPE: DNA
<213> ORGANISM: Artificial sequence
<220> FEATURE:
<223> OTHER INFORMATION: Primer Used to Amplify the HA Gene

<400> SEQUENCE: 53
gggctagcgc cgccaccatg aagaccatca ttgct 35

<210> SEQ ID NO 54
<211> LENGTH: 26
<212> TYPE: DNA
<213> ORGANISM: Artificial sequence
<220> FEATURE:
<223> OTHER INFORMATION: Primer Used to Amplify the HA Gene

<400> SEQUENCE: 54
ccgtcgactc aaatgcaaat gttgca 26

<210> SEQ ID NO 55
<211> LENGTH: 1701
<212> TYPE: DNA
<213> ORGANISM: Artificial sequence
<220> FEATURE:
<223> OTHER INFORMATION: Open Reading Frame for HA H3N2 from VR4750

<400> SEQUENCE: 55
atgaagacca tcattgcttt gagctacatt ttctgtctgg ctctcggcca agaccttcca 60
ggaaatgaca acaacacagc aacgctgtgc ctgggacatc atgcggtgcc aaacggaaca 120
ctagtgaaaa caatcacaga tgatcagatt gaagtgacta atgctactga gctagttcag 180
agctcctcaa cggggaaaat atgcaacaat cctcatcgaa tccttgatgg aatagactgc 240
acactgatag atgctctatt gggggaccct cattgtgatg tttttcaaaa tgagacatgg 300
gaccttttcg ttgaacgcag caaagctttc agcaactgtt acccttatga tgtgccagat 360
tatgcccccc ttaggtcact agttgcctcg tcaggcactc tggagtttat cactgagggt 420
ttcacttgga ctggggtcac tcagaatggg ggaagcagtg cttgcaaaag gggacctggt 480
agcggttttt tcagtagact gaactggttg accaaatcag gaagcacata tccagtgctg 540
aacgtgacta tgccaaacaa tgacaatttt gacaaactat acatttgggg ggttcaccac 600
ccgagcacga accaagaaca aaccagcctg tatgttcaag catcagggag agtcacagtc 660
tctaccagga gaagccagca aactataatc ccgaatatcg agtccagacc ctgggtaagg 720
ggtctgtcta gtagaataag catctattgg acaatagtta agccgggaga cgtactggta 780
attaatagta atgggaacct aatcgctcct cggggttatt tcaagatgcg cactgggaaa 840
agctcaataa tgaggtcaga tgcacctatt gatacctgta tttctgaatg catcactcca 900
aatggaagca ttcccaatga caagcccttt caaaacgtaa acaaaatcac gtatggagca 960
tgccccaagt atgttaagca aaacaccctg aagttggcaa cagggatgcg gaatgtacca 1020
gagaaacaaa ctagaggcct attcggcgca atagcaggtt tcatagaaaa tggttgggag 1080
ggaatgatag acggttggta cggtttcagg catcaaaatt ctgagggcac aggacaagca 1140
gcagatctta aaagcactca agcagccatc gaccaaatca atgggaaatt gaacaggata 1200
atcaagaaga cgaacgagaa attccatcaa atcgaaaagg aattctcaga agtagaaggg 1260
agaattcagg acctcgagaa atacgttgaa gacactaaaa tagatctctg gtcttacaat 1320
gcggagcttc ttgtcgctct ggagaatcaa catacaattg acctgactga ctcggaaatg 1380
aacaagctgt ttgaaaaaac aaggaggcaa ctgagggaaa atgctgaaga catgggcaat 1440
ggttgcttca aaatatacca caaatgtgac aacgcttgca tagagtcaat cagaactggg 1500
acttatgacc atgatgtata cagagacgaa gcattaaaca accggtttca gatcaaaggt 1560
gttgaactga agtctggata caaagactgg atcctgtgga tttcctttgc catatcatgc 1620
tttttgcttt gtgttgtttt gctggggttc atcatgtggg cctgccagaa aggcaacatt 1680
aggtgcaaca tttgcatttg a 1701

<210> SEQ ID NO 56
<211> LENGTH: 35
<212> TYPE: DNA
<213> ORGANISM: Artificial sequence
<220> FEATURE:
<223> OTHER INFORMATION: Primer Used to Amplify the HA Gene

<400> SEQUENCE: 56
gggctagcgc cgccaccatg aaggcaaacc tactg 35

<210> SEQ ID NO 57
<211> LENGTH: 26
<212> TYPE: DNA
<213> ORGANISM: Artificial sequence
<220> FEATURE:
<223> OTHER INFORMATION: Primer Used to Amplify the HA Gene

<400> SEQUENCE: 57
ccgtcgactc agatgcatat tctgca 26

<210> SEQ ID NO 58
<211> LENGTH: 1701
<212> TYPE: DNA
<213> ORGANISM: Artificial sequence
<220> FEATURE:
<223> OTHER INFORMATION: Open Reading Frame for HA H1N1 from VR4752

<400> SEQUENCE: 58
atgaaggcaa acctactggt cctgttatgt gcacttgcag ctgcagatgc agacacaata 60
tgtataggct accatgcgaa caattcaacc gacactgttg acacagtgct cgagaagaat 120
gtgacagtga cacactctgt taacctgctc gaagacagcc acaacggaaa actatgtaga 180
ttaaaaggaa tagccccact acaattgggg aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaccaa aggagtaacg gcagcatgct cccatgcggg gaaaagcagt 480
ttttacagaa atttgctatg gctgacggag aaggagggct catacccaaa gctgaaaaat 540
tcttatgtga acaagaaagg gaaagaagtc cttgtactgt ggggtattca tcacccgtct 600
aacagtaagg atcaacagaa tatctatcag aatgaaaatg cttatgtctc tgtagtgact 660
tcaaattata acaggagatt taccccggaa atagcagaaa gacccaaagt aagagatcaa 720
gctgggagga tgaactatta ctggaccttg ctaaaacccg gagacacaat aatatttgag 780
gcaaatggaa atctaatagc accaaggtat gctttcgcac tgagtagagg ctttgggtcc 840
ggcatcatca cctcaaacgc atcaatgcat gagtgtaaca cgaagtgtca aacacccctg 900
ggagctataa acagcagtct ccctttccag aatatacacc cagtcacaat aggagagtgc 960
ccaaaatacg tcaggagtgc caaattgagg atggttacag gactaaggaa cattccgtcc 1020
attcaatcca gaggtctatt tggagccatt gccggtttta ttgaaggggg atggactgga 1080
atgatagatg gatggtacgg ttatcatcat cagaatgaac agggatcagg ctatgcagcg 1140
gatcaaaaaa gcacacaaaa tgccattaac gggattacaa acaaggtgaa ctctgttatc 1200
gagaaaatga acattcaatt cacagctgtg ggtaaagaat tcaacaaatt agaaaaaagg 1260
atggaaaatt taaataaaaa agttgatgat ggatttctgg acatttggac atataatgca 1320
gaattgttag ttctactgga aaatgaaagg actctggatt tccatgactc aaatgtgaag 1380
aatctgtatg agaaagtaaa aagccaatta aagaataatg ccaaagaaat cggaaatgga 1440
tgttttgagt tctaccacaa gtgtgacaat gaatgcatgg aaagtgtaag aaatgggact 1500
tatgattatc ccaaatattc agaagagtca aagttgaaca gggaaaaggt agatggagtg 1560
aaattggaat caatggggat ctatcagatt ctggcgatct actcaactgt cgccagttca 1620
ctggtgcttt tggtctccct gggggcaatc agtttctgga tgtgttctaa tggatctttg 1680
cagtgcagaa tatgcatctg a 1701

<210> SEQ ID NO 59
<211> LENGTH: 1050
<212> TYPE: DNA
<213> ORGANISM: Artificial sequence
<220> FEATURE:
<223> OTHER INFORMATION: Open Reading Frame for the M2M1 Fusion from VR4755

<400> SEQUENCE: 59
atgagcctgc tgaccgaggt ggagaccccc atcagaaacg agtggggctg cagatgcaac 60
gacagcagcg accccctggt ggtggccgcc agcatcatcg gcatcctgca cctgatcctg 120
tggatcctgg acagactgtt cttcaagtgc atctacagac tgttcaagca cggcctgaag 180
agaggcccca gcaccgaggg cgtgcccgag agcatgagag aggagtacag aaaggagcag 240
cagaacgccg tggacgccga cgacagccac ttcgtgagca tcgagctgga gatgtccctg 300
ctgacagaag tggaaacata cgtgctgagc atcgtgccca gcggccccct gaaggccgag 360
atcgcccaga gactggagga cgtgttcgcc ggcaagaaca ccgacctgga ggccctgatg 420
gagtggctga agaccagacc catcctgagc cccctgacca agggcatcct gggcttcgtg 480
ttcaccctga ccgtgcccag cgagagaggc ctgcagagaa gaagattcgt gcagaacgcc 540
ctgaacggca acggcgaccc caacaacatg gaccgggccg tgaagctgta ccggaagctg 600
aagagagaga tcaccttcca cggcgccaag gagatcgccc tgagctacag cgccggcgcc 660
ctggccagct gcatgggcct gatctacaac agaatgggcg ccgtgaccac cgaggtggcc 720
ttcggcctgg tgtgcgccac ctgcgagcag atcgccgaca gccagcacag aagccacaga 780
cagatggtgg ccaccaccaa ccccctgatc agacacgaga acagaatggt gctggccagc 840
accaccgcca aggccatgga gcagatggcc ggcagcagcg agcaggccgc cgaggccatg 900
gagatcgcca gccaggccag acagatggtg caggccatga gagccatcgg cacccacccc 960
agcagcagcg ccggcctgaa ggacgacctg ctggagaacc tgcagaccta ccagaagaga 1020
atgggcgtgc agatgcagag attcaagtga 1050

<210> SEQ ID NO 60
<211> LENGTH: 982
<212> TYPE: DNA
<213> ORGANISM: Artificial sequence
<220> FEATURE:
<223> OTHER INFORMATION: Open Reading Frame for Fragment 7 from VR4756

<400> SEQUENCE: 60
atgagccttc taaccgaggt cgaaacgtat gttctctcta tcgttccatc aggcccccctc 60 aaagccgaaa tcgcgcagag acttgaagat gtctttgctg ggaaaaacac agatcttgag 120
gctctcatgg aatggctaaa gacaagacca atcctgtcac ctctgactaa ggggattttg 180
gggtttgtgt tcacgctcac cgtgcccagt gagcgaggac tgcagcgtag acgctttgtc 240
caaaatgccc tcaatgggaa tggggatcca aataacatgg acagagcagt taaactatat 300
agaaaactta agagggagat tacattccat ggggccaaag aaatagcact cagttattct 360
gctggtgcac ttgccagttg catgggcctc atatacaaca gaatgggggc tgtaaccact 420
gaagtggcct ttggcctggt atgtgcaaca tgtgaacaga ttgctgactc ccagcacagg 480
tctcataggc aaatggtggc aacaaccaat ccattaataa ggcatgagaa cagaatggtt 540
ttggccagca ctacagctaa ggctatggag caaatggctg gatcaagtga gcaggcagcg 600
gaggccatgg aaattgctag tcaggccagg caaatggtgc aggcaatgag agccattggg 660
actcatccta gctccagtgc tggtctaaaa gatgatcttc ttgaaaattt gcagacctat 720
cagaaacgaa tgggggtgca gatgcaacga ttcaagtgac ccgcttgttg ttgctgcgag 780
tatcattggg atcttgcact tgatattgtg gattcttgat cgtctttttt tcaaatgcat 840
ctatcgactc ttcaaacacg gtctgaaaag agggccttct acggaaggag tacctgagtc 900
tatgagggaa gaatatcgaa aggaacagca gaatgctgtg gatgctgacg acagtcattt 960
tgtcagcata gagctggagt aa 982

<210> SEQ ID NO 61
<211> LENGTH: 982
<212> TYPE: DNA
<213> ORGANISM: Artificial sequence
<220> FEATURE:
<223> OTHER INFORMATION: Codon Optimized Segment 7 from VR4763

<400> SEQUENCE: 61
atgagcctgc tgaccgaggt cgaaacgtat gttctctcta tcgtgcccag cggcccccctg 60 aaggccgaga tcgcccagag actggaggac gtgttcgccg gcaagaacac cgacctggag 120
gccctgatgg agtggctgaa gaccagaccc atcctgagcc ccctgaccaa gggcatcctg 180
ggcttcgtgt tcaccctgac cgtgcccagc gagagaggcc tgcagagaag aagattcgtg 240
cagaacgccc tgaacggcaa cggcgacccc aacaacatgg acagagccgt gaagctgtac 300
agaaagctga agagagagat caccttccac ggcgccaagg agatcgccct gagctacagc 360
gccggcgccc tggccagctg catgggcctg atctacaaca gaatgggcgc cgtgaccacc 420
gaggtggcct tcggcctggt gtgcgccacc tgcgagcaga tcgccgacag ccagcacaga 480
agccacagac agatggtggc caccaccaac cccctgatca gacacgagaa cagaatggtg 540
ctggccagca ccaccgccaa ggccatggag cagatggccg gcagcagcga gcaggccgcc 600
gaggccatgg agatcgccag ccaggccaga cagatggtgc aggccatgag agccatcggc 660

```
acccacccca gcagcagcgc cggcctgaaa gatgatcttc ttgaaaattt gcagacctat     720

cagaaacgaa tgggggtgca gatgcaacga ttcaagtgac cccctggtgg tggccgccag     780

catcatcggc atcctgcacc tgatcctgtg gatcctggac agactgttct tcaagtgcat     840

ctacagactg ttcaagcacg gcctgaagag aggccccagc accgagggcg tgcccgagag     900

catgagagag gagtacagaa aggagcagca gaacgccgtg gacgccgacg acagccactt     960

cgtgagcatc gagctggagt ga                                              982
```

<210> SEQ ID NO 62
<211> LENGTH: 1569
<212> TYPE: DNA
<213> ORGANISM: Artificial sequence
<220> FEATURE:
<223> OTHER INFORMATION: Open Reading Frame for eM2NP Codon Optimized by Contract

<400> SEQUENCE: 62

```
atgagcttgc tcactgaagt cgagacacca atcagaaacg aatggggatg tagatgcaac      60

gatagctcag acatggcctc ccagggaacc aaaagaagct atgaacagat ggagactgac     120

ggagagagac agaacgccac agagatcaga gctagtgtag gaaagatgat agacggtatc     180

gggcgatttt acattcaaat gtgtacggaa ttgaaactca gcgactatga aggcagactt     240

atccagaact cactcacaat tgagcgcatg gtactcagtg catttgatga aagaaggaat     300

aggtacctcg aagaacaccc cagcgccggc aaagatccca agaagactgg cggcccaatt     360

tacagaagag tggacggtaa gtggatgaga gagctggtat tgtacgataa agaagaaatt     420

agaagaatct ggaggcaagc aaacaatgga gaggatgcta cagctggcct gacccacatg     480

atgatttggc atagtaacct gaatgatacc acctaccagc ggacaagggc tctcgttcga     540

accgggatgg atccccgcat gtgctcattg atgcagggta gtacactccc gaggaggtca     600

ggcgcggccg gtgcagccgt gaaaggaatc ggcactatgg taatggaatt gataagaatg     660

attaaaaggg ggattaatga caggaacttt tggagaggag aaaatggacg caaaacaagg     720

agtgcgtatg aacggatgtg caatattttg aaaggaaaat tccaaactgc agcacagcgc     780

gccatgatgg atcaggtacg agaaagtcgc aacccaggta atgctgaaat agaggacctt     840

atatttctcg cccggagtgc tctcatactt agaggaagcg tggcccataa aagttgtctc     900

cccgcatgcg tatacggtcc cgctgtgtct tccggatacg attttgaaaa agagggatat     960

tcattggtgg gaatcgaccc ttttaagctg cttcagaact cacaggttta cagtttgatt    1020

agaccaaacg agaacccagc ccacaaatca caactcgtgt ggatggcatg ccactctgcc    1080

gctttcgaag atctgagact gctctcattt attagaggca ctaaagtgag cccgagggga    1140

aaactgagca cacgaggagt acagatagca tctaacgaaa atatggataa tatgggatct    1200

agcacactcg aattgaggtc acgatactgg gctattagaa cacggagcgg agggaacacc    1260

aaccagcaga gagcatccgc cggtcagata agcgttcagc ctacattttc agtacaacga    1320

aacctgccat ttgaaaagag tacagtgatg gccgcattta ctggcaacac cgagggacga    1380

acaagcgaca tgagagcaga gattattaga atgatggaag gagctaaacc agaggaggtt    1440

tcatttagag gaaggggagt cttcgaattg tccgatgaga aagccacaaa tcccatagta    1500

cctagcttcg acatgtccaa cgaaggctct tactttttgg gtgacaatgc cgaagagtac    1560

gacaattga                                                            1569
```

-continued

<210> SEQ ID NO 63
<211> LENGTH: 1569
<212> TYPE: DNA
<213> ORGANISM: Artificial sequence
<220> FEATURE:
<223> OTHER INFORMATION: Open Reading Frame for eM2NP Codon Optimized by Applicants

<400> SEQUENCE: 63
atgagcctgc tgaccgaggt ggagaccccc atcagaaacg agtggggctg cagatgcaac 60
gacagcagcg acatggccag ccagggcacc aagagaagct acgagcagat ggagaccgac 120
ggcgagagac agaacgccac cgagatcaga gccagcgtgg gcaagatgat cgacggcatc 180
ggcagattct acatccagat gtgcaccgag ctgaagctga gcgactacga gggcagactg 240
atccagaaca gcctgaccat cgagagaatg gtgctgagcg ccttcgacga gagaagaaac 300
agatacctgg aggagcaccc cagcgccggc aaggacccca agaagaccgg cggccccatc 360
tacagaagag tggacggcaa gtggatgaga gagctggtgc tgtacgacaa ggaggagatc 420
agaagaatct ggagacaggc caacaacggc gaggacgcca ccgccggcct gacccacatg 480
atgatctggc acagcaacct gaacgacacc acctaccaga gaaccagagc cctggtgcgg 540
accggcatgg accccagaat gtgcagcctg atgcagggca gcaccctgcc cagaagaagc 600
ggcgccgccg gcgccgccgt gaagggcatc ggcaccatgg tgatggagct gatcagaatg 660
atcaagagag gcatcaacga cagaaacttc tggagaggcg agaacggcag aaagaccaga 720
agcgcctacg agagaatgtg caacatcctg aagggcaagt tccagaccgc cgcccagaga 780
gccatgatgg accaggtccg ggagagcaga aacccccggca acgccgagat cgaggacctg 840
atcttcctgg ccagaagcgc cctgatcctg agaggcagcg tggcccacaa gagctgcctg 900
cccgcctgcg tgtacggccc cgccgtgagc agcggctacg acttcgagaa ggagggctac 960
agcctggtgg gcatcgaccc cttcaagctg ctgcagaaca gccaggtgta cagcctgatc 1020
agacccaacg agaaccccgc ccacaagagc cagctggtgt ggatggcctg ccacagcgcc 1080
gccttcgagg acctgagact gctgagcttc atcagaggca ccaaggtgtc ccccagaggc 1140
aagctgagca ccagaggcgt gcagatcgcc agcaacgaga acatggacaa catgggcagc 1200
agcaccctgg agctgagaag cagatactgg gccatcagaa ccagaagcgg cggcaacacc 1260
aaccagcaga gagccagcgc cggccagatc agcgtgcagc ccaccttcag cgtgcagaga 1320
aacctgccct tcgagaagag caccgtgatg gccgccttca ccggcaacac cgagggcaga 1380
accagcgaca tgagagccga gatcatcaga atgatggagg gcgccaagcc cgaggaggtg 1440
tccttcagag gcagaggcgt gttcgagctg agcgacgaga aggccaccaa ccccatcgtg 1500
cctagcttcg acatgagcaa cgagggcagc tacttcttcg gcgacaacgc cgaggagtac 1560
gacaactga 1569

<210> SEQ ID NO 64
<211> LENGTH: 30
<212> TYPE: DNA
<213> ORGANISM: Artificial sequence
<220> FEATURE:
<223> OTHER INFORMATION: Primer Used to Amplify the M2 Gene

<400> SEQUENCE: 64
gccgaattcg ccaccatgag cctgctgacc 30

<210> SEQ ID NO 65
<211> LENGTH: 33
<212> TYPE: DNA
<213> ORGANISM: Artificial sequence
<220> FEATURE:
<223> OTHER INFORMATION: Primer Used to Amplify the M2 Gene

<400> SEQUENCE: 65
gccgtcgact gatcactcca gctcgatgct cac 33

<210> SEQ ID NO 66
<211> LENGTH: 294
<212> TYPE: DNA
<213> ORGANISM: Artificial sequence
<220> FEATURE:
<223> OTHER INFORMATION: Open Reading Frame for M2 Gene from VR4759

<400> SEQUENCE: 66
atgagcctgc tgaccgaggt ggagaccccc atcagaaacg agtggggctg cagatgcaac 60
gacagcagcg accccctggt ggtggccgcc agcatcatcg gcatcctgca cctgatcctg 120
tggatcctgg acagactgtt cttcaagtgc atctacagac tgttcaagca cggcctgaag 180
agaggcccca gcaccgaggg cgtgcccgag agcatgagag aggagtacag aaaggagcag 240
cagaacgccg tggacgccga cgacagccac ttcgtgagca tcgagctgga gtga 294

<210> SEQ ID NO 67
<211> LENGTH: 36
<212> TYPE: DNA
<213> ORGANISM: Artificial sequence
<220> FEATURE:
<223> OTHER INFORMATION: Primer Used Amplify M1 Gene from VR4755

<400> SEQUENCE: 67
gccgaattcg ccaccatgtc cctgctgaca gaagtg 36

<210> SEQ ID NO 68
<211> LENGTH: 31
<212> TYPE: DNA
<213> ORGANISM: Artificial sequence
<220> FEATURE:
<223> OTHER INFORMATION: Primer Used to Amplify M1 Gene from VR4755

<400> SEQUENCE: 68
gccgtcgact gatcacttga atctctgcat c 31

<210> SEQ ID NO 69
<211> LENGTH: 759
<212> TYPE: DNA
<213> ORGANISM: Artificial sequence
<220> FEATURE:
<223> OTHER INFORMATION: Open Reading Frame for M1 Gene from VR4760

<400> SEQUENCE: 69
atgtccctgc tgacagaagt ggaaacatac gtgctgagca tcgtgcccag cggcccccctg 60 aaggccgaga tcgcccagag actggaggac gtgttcgccg gcaagaacac cgacctggag 120
gccctgatgg agtggctgaa gaccagaccc atcctgagcc ccctgaccaa gggcatcctg 180
ggcttcgtgt tcaccctgac cgtgcccagc gagagaggcc tgcagagaag aagattcgtg 240
cagaacgccc tgaacggcaa cggcgacccc aacaacatgg accgggccgt gaagctgtac 300
cggaagctga agagagagat caccttccac ggcgccaagg agatcgccct gagctacagc 360
gccggcgccc tggccagctg catgggcctg atctacaaca gaatgggcgc cgtgaccacc 420
gaggtggcct tcggcctggt gtgcgccacc tgcgagcaga tcgccgacag ccagcacaga 480
agccacagac agatggtggc caccaccaac cccctgatca gacacgagaa cagaatggtg 540
ctggccagca ccaccgccaa ggccatggag cagatggccg gcagcagcga gcaggccgcc 600
gaggccatgg agatcgccag ccaggccaga cagatggtgc aggccatgag agccatcggc 660
acccacccca gcagcagcgc cggcctgaag gacgacctgc tggagaacct gcagacctac 720
cagaagagaa tgggcgtgca gatgcagaga ttcaagtga 759

<210> SEQ ID NO 70
<211> LENGTH: 38
<212> TYPE: DNA
<213> ORGANISM: Artificial sequence
<220> FEATURE:
<223> OTHER INFORMATION: Primer Used to Amplify NP Gene from VR4757

<400> SEQUENCE: 70
gccgaattcg ccaccatggc ctcccaggga accaaaag 38

<210> SEQ ID NO 71
<211> LENGTH: 30
<212> TYPE: DNA
<213> ORGANISM: Artificial sequence
<220> FEATURE:
<223> OTHER INFORMATION: Primer Used to Amplify NP Gene from VR4757

<400> SEQUENCE: 71
gccgtcgact gatcaattgt cgtactcttc 30

<210> SEQ ID NO 72
<211> LENGTH: 1497
<212> TYPE: DNA
<213> ORGANISM: Artificial sequence
<220> FEATURE:
<223> OTHER INFORMATION: Open Reading Frame for NP Codon Optimized by
      Contract

<400> SEQUENCE: 72
atggcctccc agggaaccaa aagaagctat gaacagatgg agactgacgg agagagacag 60
aacgccacag agatcagagc tagtgtagga aagatgatag acggtatcgg gcgattttac 120
attcaaatgt gtacggaatt gaaactcagc gactatgaag gcagacttat ccagaactca 180
ctcacaattg agcgcatggt actcagtgca tttgatgaaa gaaggaatag gtacctcgaa 240
gaacacccca gcgccggcaa agatcccaag aagactggcg gcccaattta cagaagagtg 300
gacggtaagt ggatgagaga gctggtattg tacgataaag aagaaattag aagaatctgg 360
aggcaagcaa acaatggaga ggatgctaca gctggcctga cccacatgat gatttggcat 420
agtaacctga atgataccac ctaccagcgg acaagggctc tcgttcgaac cgggatggat 480
ccccgcatgt gctcattgat gcagggtagt acactcccga ggaggtcagg cgcggccggt 540
gcagccgtga aaggaatcgg cactatggta atggaattga taagaatgat taaaaggggg 600
attaatgaca ggaacttttg gagaggagaa aatggacgca aaacaaggag tgcgtatgaa 660
cggatgtgca atattttgaa aggaaaattc caaactgcag cacagcgcgc catgatggat 720
caggtacgag aaagtcgcaa cccaggtaat gctgaaatag aggaccttat atttctcgcc 780
cggagtgctc tcatacttag aggaagcgtg gcccataaaa gttgtctccc cgcatgcgta 840
tacggtcccg ctgtgtcttc cggatacgat tttgaaaaag agggatattc attggtggga 900
atcgaccctt ttaagctgct tcagaactca caggtttaca gtttgattag accaaacgag 960
aacccagccc acaaatcaca actcgtgtgg atggcatgcc actctgccgc tttcgaagat 1020
ctgagactgc tctcatttat tagaggcact aaagtgagcc cgaggggaaa actgagcaca 1080

```
cgaggagtac agatagcatc taacgaaaat atggataata tgggatctag cacactcgaa   1140

ttgaggtcac gatactgggc tattagaaca cggagcggag ggaacaccaa ccagcagaga   1200

gcatccgccg gtcagataag cgttcagcct acattttcag tacaacgaaa cctgccattt   1260

gaaaagagta cagtgatggc cgcatttact ggcaacaccg agggacgaac aagcgacatg   1320

agagcagaga ttattagaat gatggaagga gctaaaccag aggaggtttc atttagagga   1380

aggggagtct tcgaattgtc cgatgagaaa gccacaaatc ccatagtacc tagcttcgac   1440

atgtccaacg aaggctctta ctttttttggt gacaatgccg aagagtacga caattga      1497
```

<210> SEQ ID NO 73
<211> LENGTH: 36
<212> TYPE: DNA
<213> ORGANISM: Artificial sequence
<220> FEATURE:
<223> OTHER INFORMATION: Primer Used to Amplify NP Gene from VR4758

<400> SEQUENCE: 73

```
gccgaattcg ccaccatggc cagccagggc accaag                              36
```

<210> SEQ ID NO 74
<211> LENGTH: 28
<212> TYPE: DNA
<213> ORGANISM: Artificial sequence
<220> FEATURE:
<223> OTHER INFORMATION: Primer Used to Amplify NP Gene from VR4758

<400> SEQUENCE: 74

```
gccgtcgact gatcagttgt cgtactcc                                       28
```

<210> SEQ ID NO 75
<211> LENGTH: 1497
<212> TYPE: DNA
<213> ORGANISM: Artificial sequence
<220> FEATURE:
<223> OTHER INFORMATION: Open Reading Frame for NP Codon Optimized by
      Applicants from VR4762

<400> SEQUENCE: 75

```
atggccagcc agggcaccaa gagaagctac gagcagatgg agaccgacgg cgagagacag     60

aacgccaccg agatcagagc cagcgtgggc aagatgatcg acggcatcgg cagattctac    120

atccagatgt gcaccgagct gaagctgagc gactacgagg gcagactgat ccagaacagc    180

ctgaccatcg agagaatggt gctgagcgcc ttcgacgaga gaagaaacag atacctggag    240

gagcacccca gcgccggcaa ggaccccaag aagaccggcg gccccatcta cagaagagtg    300

gacggcaagt ggatgagaga gctggtgctg tacgacaagg aggagatcag aagaatctgg    360

agacaggcca acaacggcga ggacgccacc gccggcctga cccacatgat gatctggcac    420

agcaacctga acgacaccac ctaccagaga accagagccc tggtgcggac cggcatggac    480

cccagaatgt gcagcctgat gcagggcagc accctgccca gaagaagcgg cgccgccggc    540

gccgccgtga agggcatcgg caccatggtg atggagctga tcagaatgat caagagaggc    600

atcaacgaca gaaacttctg gagaggcgag aacggcagaa agaccagaag cgcctacgag    660

agaatgtgca acatcctgaa gggcaagttc cagaccgccg cccagagagc catgatggac    720

caggtccggg agagcagaaa ccccggcaac gccgagatcg aggacctgat cttcctggcc    780

agaagcgccc tgatcctgag aggcagcgtg gcccacaaga gctgcctgcc cgcctgcgtg    840

tacggccccg ccgtgagcag cggctacgac ttcgagaagg agggctacag cctggtgggc    900

atcgacccct tcaagctgct gcagaacagc caggtgtaca gcctgatcag acccaacgag    960
```

```
aaccccgccc acaagagcca gctggtgtgg atggcctgcc acagcgccgc cttcgaggac   1020

ctgagactgc tgagcttcat cagaggcacc aaggtgtccc ccagaggcaa gctgagcacc   1080

agaggcgtgc agatcgccag caacgagaac atggacaaca tgggcagcag caccctggag   1140

ctgagaagca gatactgggc catcagaacc agaagcggcg gcaacaccaa ccagcagaga   1200

gccagcgccg gccagatcag cgtgcagccc accttcagcg tgcagagaaa cctgcccttc   1260

gagaagagca ccgtgatggc cgccttcacc ggcaacaccg agggcagaac cagcgacatg   1320

agagccgaga tcatcagaat gatggagggc gccaagcccg aggaggtgtc cttcagaggc   1380

agaggcgtgt tcgagctgag cgacgagaag gccaccaacc ccatcgtgcc tagcttcgac   1440

atgagcaacg agggcagcta cttcttcggc gacaacgccg aggagtacga caactga      1497
```

```
<210> SEQ ID NO 76
<211> LENGTH: 498
<212> TYPE: PRT
<213> ORGANISM: Artificial sequence
<220> FEATURE:
<223> OTHER INFORMATION: NP Consensus Sequence

<400> SEQUENCE: 76

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270
```

```
Lys Ser Cys Leu Pro Ala Cys Val Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Lys Ser Thr Val Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 77
<211> LENGTH: 252
<212> TYPE: PRT
<213> ORGANISM: Influenza A Virus

<400> SEQUENCE: 77

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140
```

Gly Leu Val Cys Ala Thr Cys Glu Gln Ile Ala Asp Ser Gln His Arg
145 150 155 160

Ser His Arg Gln Met Val Ala Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Ile Ala Ser Gln
195 200 205

Ala Arg Gln Met Val Gln Ala Met Arg Ala Ile Gly Thr His Pro Ser
210 215 220

Ser Ser Ala Gly Leu Lys Asp Asp Leu Leu Glu Asn Leu Gln Thr Tyr
225 230 235 240

Gln Lys Arg Met Gly Val Gln Met Gln Arg Phe Lys
245 250

<210> SEQ ID NO 78
<211> LENGTH: 97
<212> TYPE: PRT
<213> ORGANISM: Influenza A Virus

<400> SEQUENCE: 78

Met Ser Leu Leu Thr Glu Val Glu Thr Pro Ile Arg Asn Glu Trp Gly
1 5 10 15

Cys Arg Cys Asn Asp Ser Ser Asp Pro Leu Val Val Ala Ala Ser Ile
20 25 30

Ile Gly Ile Leu His Leu Ile Leu Trp Ile Leu Asp Arg Leu Phe Phe
35 40 45

Lys Cys Ile Tyr Arg Leu Phe Lys His Gly Leu Lys Arg Gly Pro Ser
50 55 60

Thr Glu Gly Val Pro Glu Ser Met Arg Glu Glu Tyr Arg Lys Glu Gln
65 70 75 80

Gln Asn Ala Val Asp Ala Asp Asp Ser His Phe Val Ser Ile Glu Leu
85 90 95

Glu

<210> SEQ ID NO 79
<211> LENGTH: 759
<212> TYPE: DNA
<213> ORGANISM: Artificial sequence
<220> FEATURE:
<223> OTHER INFORMATION: Optimized M1 Coding Region

<400> SEQUENCE: 79
atgagcctgc tgaccgaggt cgaaacgtat gttctctcta tcgtgcccag cggcccccctg 60 aaggccgaga tcgcccagag actggaggac gtgttcgccg gcaagaacac cgacctggag 120
gccctgatgg agtggctgaa gaccagaccc atcctgagcc ccctgaccaa gggcatcctg 180
ggcttcgtgt tcaccctgac cgtgcccagc gagagaggcc tgcagagaag aagattcgtg 240
cagaacgccc tgaacggcaa cggcgacccc aacaacatgg acagagccgt gaagctgtac 300
agaaagctga agagagagat caccttccac ggcgccaagg agatcgccct gagctacagc 360
gccggcgccc tggccagctg catgggcctg atctacaaca gaatgggcgc cgtgaccacc 420
gaggtggcct tcggcctggt gtgcgccacc tgcgagcaga tcgccgacag ccagcacaga 480
agccacagac agatggtggc caccaccaac cccctgatca gacacgagaa cagaatggtg 540
ctggccagca ccaccgccaa ggccatggag cagatggccg gcagcagcga gcaggccgcc 600
gaggccatgg agatcgccag ccaggccaga cagatggtgc aggccatgag agccatcggc 660
acccacccca gcagcagcgc cggcctgaaa gatgatcttc ttgaaaattt gcagacctat 720
cagaaacgaa tgggggtgca gatgcaacga ttcaagtga 759

<210> SEQ ID NO 80
<211> LENGTH: 294
<212> TYPE: DNA
<213> ORGANISM: Artificial sequence
<220> FEATURE:
<223> OTHER INFORMATION: Optimized M2 Coding Region

<400> SEQUENCE: 80
atgagcctgc tgaccgaggt cgaaacacct atcagaaacg aatgggggtg cagatgcaac 60
gattcaagtg accccctggt ggtggccgcc agcatcatcg gcatcctgca cctgatcctg 120
tggatcctgg acagactgtt cttcaagtgc atctacagac tgttcaagca cggcctgaag 180
agaggcccca gcaccgaggg cgtgcccgag agcatgagag aggagtacag aaaggagcag 240
cagaacgccg tggacgccga cgacagccac ttcgtgagca tcgagctgga gtga 294

<210> SEQ ID NO 81
<211> LENGTH: 9
<212> TYPE: PRT
<213> ORGANISM: Artificial sequence
<220> FEATURE:
<223> OTHER INFORMATION: H2Kd Binding Peptide

<400> SEQUENCE: 81

Thr Tyr Gln Arg Thr Arg Ala Leu Val
1               5

<210> SEQ ID NO 82
<211> LENGTH: 11
<212> TYPE: DNA
<213> ORGANISM: Artificial sequence
<220> FEATURE:
<223> OTHER INFORMATION: RSV Promoter from Plasmid VCL1005

<400> SEQUENCE: 82
tactctagac g 11

<210> SEQ ID NO 83
<211> LENGTH: 11
<212> TYPE: DNA
<213> ORGANISM: Artificial sequence
<220> FEATURE:
<223> OTHER INFORMATION: Promoter RSV/R

<400> SEQUENCE: 83
tacaataaac g 11

<210> SEQ ID NO 84
<211> LENGTH: 27
<212> TYPE: DNA
<213> ORGANISM: Artificial Sequence
<220> FEATURE:
<223> OTHER INFORMATION: Primer RSVfor

<400> SEQUENCE: 84
catcagctgc tccctgcttg tgtgttg 27

<210> SEQ ID NO 85
<211> LENGTH: 19
<212> TYPE: DNA
<213> ORGANISM: Artificial sequence
<220> FEATURE:
<223> OTHER INFORMATION: Primer WNVpst rev

<400> SEQUENCE: 85
cgatatccga cgacggtga 19

<210> SEQ ID NO 86
<211> LENGTH: 39
<212> TYPE: DNA
<213> ORGANISM: Artificial sequence
<220> FEATURE:
<223> OTHER INFORMATION: Primer RSV HTLV5

<400> SEQUENCE: 86
caccacattg gtgtgcacct ccatcggctc gcatctctc 39

<210> SEQ ID NO 87
<211> LENGTH: 42
<212> TYPE: DNA
<213> ORGANISM: Artificial sequence
<220> FEATURE:
<223> OTHER INFORMATION: Primer HTLV RSVrev

<400> SEQUENCE: 87
aggtgcacac caatgtggtg aatggtcaaa tggcgtttat tg 42

<210> SEQ ID NO 88
<211> LENGTH: 44
<212> TYPE: DNA
<213> ORGANISM: Artificial sequence
<220> FEATURE:
<223> OTHER INFORMATION: Primer RSVrev

<400> SEQUENCE: 88
aatggtcaaa tggcgtttat tgtatcgagc taggcactta aata 44

<210> SEQ ID NO 89
<211> LENGTH: 6254
<212> TYPE: DNA
<213> ORGANISM: Artificial sequence
<220> FEATURE:
<223> OTHER INFORMATION: VR-6430, RSV RWNV

<400> SEQUENCE: 89
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggctg ctccctgctt gtgtgttgga ggtcgctgag tagtgcgcga gcaaaattta 300
agctacaaca aggcaaggct tgaccgacaa ttgcatgaag aatctgctta gggttaggcg 360
ttttgcgctg cttcgcgatg tacgggccag atatacgcgt atctgagggg actagggtgt 420
gtttaggcga aaagcggggc ttcggttgta cgcggttagg agtcccctca ggatatagta 480
gtttcgcttt tgcataggga gggggaaatg tagtcttatg caatactctt gtagtcttgc 540
aacatggtaa cgatgagtta gcaacatgcc ttacaaggag agaaaaagca ccgtgcatgc 600
cgattggtgg aagtaaggtg gtacgatcgt gccttattag gaaggcaaca gacgggtctg 660
acatggattg gacgaaccac tgaattccgc attgcagaga tattgtattt aagtgcctag 720
ctcgatacaa taaacgccat ttgaccattc accacattgg tgtgcacctc catcggctcg 780
catctctcct tcacgcgccc gccgccctac ctgaggccgc catccacgcc ggttgagtcg 840
cgttctgccg cctcccgcct gtggtgcctc ctgaactgcg tccgccgtct aggtaagttt 900

-continued

```
aaagctcagg tcgagaccgg gcctttgtcc ggcgctccct tggagcctac ctagactcag    960
ccggctctcc acgctttgcc tgaccctgct tgctcaactc tagttaacgg tggagggcag   1020
tgtagtctga gcagtactcg ttgctgccgc gcgcgccacc agacataata gctgacagac   1080
taacagactg ttcctttcca tgggtctttt ctgcagtcac cgtcgtcgga tatcgaattc   1140
gccgccacca tgggcaagcg gagcgctggc tcaatcatgt ggctcgcgag cttggcagtt   1200
gtcatagctt gtgcaggagc cgttaccctc tctaacttcc aagggaaggt gatgatgacg   1260
gtaaatgcta ctgacgtcac agatgtcatc acgattccaa cagctgctgg aaagaaccta   1320
tgcattgtca gagcaatgga tgtgggatac atgtgcgatg atactatcac ctatgaatgc   1380
ccagtgctgt cggctggtaa tgatccagaa gacatcgact gttggtgcac aaagtcagca   1440
gtctacgtca ggtatggaag atgcaccaag acacgccact caagacgcag tcggaggtca   1500
ctgacagtgc agacacacgg agaaagcact ctagcgaaca agaaggggc ttggatggac   1560
agcaccaagg ccacaaggta tttggtaaaa acagaatcat ggatcttgag gaaccctgga   1620
tatgccctgg tggcagccgt cattggttgg atgcttggga gcaacaccat gcagagagtt   1680
gtgtttgtcg tgctattgct tttggtggcc ccagcttaca gcttcaactg ccttggaatg   1740
agcaacagag acttcttgga aggagtgtct ggagcaacat gggtggattt ggttctcgaa   1800
ggcgatagct gcgtgactat catgtctaag gacaagccta ccatcgatgt gaagatgatg   1860
aatatggagg cggccaacct ggcagaggtc cgcagttatt gctatttggc taccgtcagc   1920
gatctctcca ccaaagctgc gtgcccgacc atgggggaag cccacaatga caaacgtgct   1980
gacccagctt ttgtgtgcag acaaggagtg gtggacaggg gctggggcaa cggctgcgga   2040
ctatttggca aaggaagcat tgacacatgc gccaaatttg cctgctctac caaggcaata   2100
ggaagaacca tcttgaaaga gaatatcaag tacgaagtgg ccatttttgt ccatggacca   2160
actactgtgg agtcgcacgg aaactactcc acacaggttg gagccactca ggcagggaga   2220
ttcagcatca ctcctgcggc gccttcatac acactaaagc ttggagaata tggagaggtg   2280
acagtggact gtgaaccacg gtcagggatt gacaccaatg catactacgt gatgactgtt   2340
ggaacaaaga cgttcttggt ccatcgtgag tggttcatgg acctcaacct cccttggagc   2400
agtgctggaa gtactgtgtg gaggaacaga gagacgttaa tggagtttga ggaaccacac   2460
gccacgaagc agtctgtgat agcattgggc tcacaagagg gagctctgca tcaagctttg   2520
gctggagcca ttcctgtgga attttcaagc aacactgtca agttgacgtc gggtcatttg   2580
aagtgtagag tgaagatgga aaaattgcag ttgaagggaa caacctatgg cgtctgttca   2640
aaggctttca agtttcttgg gactcccgca gacacaggtc acggcactgt ggtgttggaa   2700
ttgcagtaca ctggcacgga tggaccttgc aaagttccta tctcgtcagt ggcttcattg   2760
aacgacctaa cgccagtggg cagattggtc actgtcaacc cttttgtttc agtggccacg   2820
gccaacgcta aggtcctgat tgaattggaa ccacccttttg gagactcata catagtggtg   2880
ggcagaggag aacaacagat caatcaccat tggcacaagt ctggaagcag cattggcaaa   2940
gcctttacaa ccaccctcaa aggagcgcag agactagccg ctctaggaga cacagcttgg   3000
gactttggat cagttggagg ggtgttcacc tcagttggga aggctgtcca tcaagtgttc   3060
ggaggagcat tccgctcact gttcggaggc atgtcctgga taacgcaagg attgctgggg   3120
gctctcctgt tgtggatggg catcaatgct cgtgataggt ccatagctct cacgtttctc   3180
gcagttggag gagttctgct cttcctctcc gtgaacgtgc acgcttgagg atccagatct   3240
gctgtgcctt ctagttgcca gccatctgtt gtttgcccct cccccgtgcc ttccttgacc   3300
```

ctggaaggtg ccactcccac tgtcctttcc taataaaatg aggaaattgc atcgcattgt 3360
ctgagtaggt gtcattctat tctggggggt ggggtggggc aggacagcaa gggggaggat 3420
tgggaagaca atagcaggca tgctggggat gcggtgggct ctatgggtac ccaggtgctg 3480
aagaattgac ccggttcctc ctgggccaga aagaagcagg cacatcccct tctctgtgac 3540
acaccctgtc cacgcccctg gttcttagtt ccagccccac tcataggaca ctcatagctc 3600
aggagggctc cgccttcaat cccacccgct aaagtacttg gagcggtctc tccctccctc 3660
atcagcccac caaaccaaac ctagcctcca agagtgggaa gaaattaaag caagataggc 3720
tattaagtgc agagggagag aaaatgcctc caacatgtga ggaagtaatg agagaaatca 3780
tagaatttta aggccatgat ttaaggccat catggcctta atcttccgct tcctcgctca 3840
ctgactcgct gcgctcggtc gttcggctgc ggcgagcggt atcagctcac tcaaaggcgg 3900
taatacggtt atccacagaa tcaggggata acgcaggaaa gaacatgtga gcaaaaggcc 3960
agcaaaaggc caggaaccgt aaaaaggccg cgttgctggc gtttttccat aggctccgcc 4020
cccctgacga gcatcacaaa aatcgacgct caagtcagag gtggcgaaac ccgacaggac 4080
tataaagata ccaggcgttt ccccctggaa gctccctcgt gcgctctcct gttccgaccc 4140
tgccgcttac cggatacctg tccgcctttc tcccttcggg aagcgtggcg ctttctcata 4200
gctcacgctg taggtatctc agttcggtgt aggtcgttcg ctccaagctg ggctgtgtgc 4260
acgaaccccc cgttcagccc gaccgctgcg ccttatccgg taactatcgt cttgagtcca 4320
acccggtaag acacgactta tcgccactgg cagcagccac tggtaacagg attagcagag 4380
cgaggtatgt aggcggtgct acagagttct tgaagtggtg gcctaactac ggctacacta 4440
gaagaacagt atttggtatc tgcgctctgc tgaagccagt taccttcgga aaaagagttg 4500
gtagctcttg atccggcaaa caaaccaccg ctggtagcgg tggttttttt gtttgcaagc 4560
agcagattac gcgcagaaaa aaaggatctc aagaagatcc tttgatcttt tctacggggt 4620
ctgacgctca gtggaacgaa aactcacgtt aagggatttt ggtcatgaga ttatcaaaaa 4680
ggatcttcac ctagatcctt ttaaattaaa aatgaagttt taaatcaatc taaagtatat 4740
atgagtaaac ttggtctgac agttaccaat gcttaatcag tgaggcacct atctcagcga 4800
tctgtctatt tcgttcatcc atagttgcct gactcggggg gggggggcgc tgaggtctgc 4860
ctcgtgaaga aggtgttgct gactcatacc aggcctgaat cgccccatca tccagccaga 4920
aagtgaggga gccacggttg atgagagctt tgttgtaggt ggaccagttg gtgattttga 4980
acttttgctt tgccacggaa cggtctgcgt tgtcgggaag atgcgtgatc tgatccttca 5040
actcagcaaa agttcgattt attcaacaaa gccgccgtcc cgtcaagtca gcgtaatgct 5100
ctgccagtgt tacaaccaat taaccaattc tgattagaaa aactcatcga gcatcaaatg 5160
aaactgcaat ttattcatat caggattatc aataccatat ttttgaaaaa gccgtttctg 5220
taatgaagga gaaaactcac cgaggcagtt ccataggatg gcaagatcct ggtatcggtc 5280
tgcgattccg actcgtccaa catcaataca acctattaat ttcccctcgt caaaaataag 5340
gttatcaagt gagaaatcac catgagtgac gactgaatcc ggtgagaatg gcaaaagctt 5400
atgcatttct ttccagactt gttcaacagg ccagccatta cgctcgtcat caaaatcact 5460
cgcatcaacc aaaccgttat tcattcgtga ttgcgcctga gcgagacgaa atacgcgatc 5520
gctgttaaaa ggacaattac aaacaggaat cgaatgcaac cggcgcagga acactgccag 5580
cgcatcaaca atattttcac ctgaatcagg atattcttct aatacctgga atgctgtttt 5640
cccggggatc gcagtggtga gtaaccatgc atcatcagga gtacggataa aatgcttgat 5700

```
ggtcggaaga ggcataaatt ccgtcagcca gtttagtctg accatctcat ctgtaacatc   5760

attggcaacg ctacctttgc catgtttcag aaacaactct ggcgcatcgg gcttcccata   5820

caatcgatag attgtcgcac ctgattgccc gacattatcg cgagcccatt tatacccata   5880

taaatcagca tccatgttgg aatttaatcg cggcctcgag caagacgttt cccgttgaat   5940

atggctcata acaccccttg tattactgtt tatgtaagca gacagtttta ttgttcatga   6000

tgatatattt ttatcttgtg caatgtaaca tcagagattt tgagacacaa cgtggctttc   6060

cccccccccc cattattgaa gcatttatca gggttattgt ctcatgagcg gatacatatt   6120

tgaatgtatt tagaaaaata aacaaatagg ggttccgcgc acatttcccc gaaaagtgcc   6180

acctgacgtc taagaaacca ttattatcat gacattaacc tataaaaata ggcgtatcac   6240

gaggcccttt cgtc                                                     6254
```

```
<210> SEQ ID NO 90
<211> LENGTH: 6425
<212> TYPE: DNA
<213> ORGANISM: Artificial sequence
<220> FEATURE:
<223> OTHER INFORMATION: VR6307, Ligation of VCL6292 into VR6430

<400> SEQUENCE: 90
```

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggctg ctccctgctt gtgtgttgga ggtcgctgag tagtgcgcga gcaaaattta    300

agctacaaca aggcaaggct tgaccgacaa ttgcatgaag aatctgctta gggttaggcg    360

ttttgcgctg cttcgcgatg tacgggccag atatacgcgt atctgagggg actagggtgt    420

gtttaggcga aaagcggggc ttcggttgta cgcggttagg agtcccctca ggatatagta    480

gtttcgcttt tgcataggga gggggaaatg tagtcttatg caatactctt gtagtcttgc    540

aacatggtaa cgatgagtta gcaacatgcc ttacaaggag agaaaaagca ccgtgcatgc    600

cgattggtgg aagtaaggtg gtacgatcgt gccttattag gaaggcaaca gacgggtctg    660

acatggattg gacgaaccac tgaattccgc attgcagaga tattgtattt aagtgcctag    720

ctcgatacaa taaacgccat ttgaccattc accacattgg tgtgcacctc catcggctcg    780

catctctcct tcacgcgccc gccgccctac ctgaggccgc catccacgcc ggttgagtcg    840

cgttctgccg cctcccgcct gtggtgcctc ctgaactgcg tccgccgtct aggtaagttt    900

aaagctcagg tcgagaccgg gcctttgtcc ggcgctccct tggagcctac ctagactcag    960

ccggctctcc acgctttgcc tgaccctgct tgctcaactc tagttaacgg tggagggcag   1020

tgtagtctga gcagtactcg ttgctgccgc gcgcgccacc agacataata gctgacagac   1080

taacagactg ttcctttcca tgggtctttt ctgcagtcac cgtcgtcgga tatcgccacc   1140

atggatgcaa tgaagagagg gctctgctgt gtgctgctgc tgtgtggagc agtcttcgtt   1200

tcgcccagcg aagtgaagca agaaaatcga cttctgaacg agagcgaaag ttcatcacag   1260

ggtcttctcg gatactactt cagtgacttg aatttccaag caccaatggt ggtgactagt   1320

agcaccaccg gcgatttgag cattcccagc tctgagttgg agaacattcc cagcgaaaat   1380

cagtacttcc agtctgctat ctggtccgga ttcattaagg ttaaaaagtc cgacgaatat   1440
```

-continued

```
acatttgcta cctcggcgga taaccatgtg acaatgtggg tggacgacca ggaagtgatc   1500
aacaaggctt caaactctaa taaaatccgg ctcgagaagg ggaggctcta ccagatcaaa   1560
attcagtacc agcgggaaaa ccctacagaa aaaggactcg atttcaagct gtactggaca   1620
gatagccaaa acaagaaaga agttatcagc tcagacaatc tgcagttacc cgagctcaag   1680
cagaagagtt ctaatacaag cgctgggcca actgtgcccg acagagacaa tgatggaatc   1740
cctgatagtc tagaggttga gggatacacg gtagatgtca agaacaaaag gacttttctc   1800
tcgccttgga tctcaaatat ccatgagaag aaggggctta ccaagtacaa gtcctccccc   1860
gagaagtggt ctaccgcttc cgatccatat agcgatttcg agaaggtcac aggccggatc   1920
gataaaaatg tgtctccaga ggctagacac cccctggtag cagcctaccc gattgtacac   1980
gtggacatgg agaacatcat tctaagcaaa aacgaggacc agtccacaca aaacactgac   2040
tccgagaccc gcaccatatc taaaaacacc agtacttcaa ggacccacac ctctgaagtg   2100
cacggcaatg cggaagtcca tgcatcgttt ttcgatattg gtggctccgt gtcagccggc   2160
tttagcaata gcaactcctc gacggttgcc attgaccact cactgtcatt agcaggtgag   2220
aggacttggg ctgaaactat gggtctgaat accgccgata cggcccggct caacgcaaat   2280
attcggtacg tcaacacagg gactgctcct atatataacg tgctgcctac gacaagtctt   2340
gtcctgggca aaaatcagac cctcgcaacc attaaggcaa aggaaaatca gctgagccag   2400
atcctcgccc ctaacaacta ttatccatcc aaaaatttag cccccatagc cctgaacgcc   2460
caggacgact tttcctctac ccccataact atgaattaca atcagttcct ggagctggaa   2520
aagacgaagc agctgagact agacaccgat caggtgtatg gaaacatagc gacatataac   2580
tttgagaacg gccgcgtgcg cgtcgacact gggtcaaact ggtctgaagt tctgccgcaa   2640
attcaagaga caaccgccag aattatcttt aatgggaagg acttgaacct tgtcgaacgt   2700
agaattgccg ccgtgaaccc cagtgatcca ctcgagacga ctaaaccgga tatgacactg   2760
aaagaggctc tgaagattgc cttcggattc aacgaaccta atggcaattt gcagtatcag   2820
gggaaagaca tcacagagtt tgatttcaat ttcgatcagc agacttccca aaatatcaaa   2880
aatcagttgg cagagctgaa tgccaccaat atctacacgg ttctcgataa aatcaaactt   2940
aacgccaaga tgaacatatt gattcgagac aaacgcttcc actacgaccg caacaatata   3000
gccgtaggcg ctgatgagtc tgtcgtcaag gaggctcata gggaagttat caacagcagt   3060
actgaagggc tgttacttaa tatcgacaag gacattcgga agatcctgtc cgggtatatc   3120
gtggagatcg aggataccga gggcctgaag gaagtcatta acgaccgcta tgatatgctg   3180
aacatttcca gcttacgaca ggacggtaag acatttattg actttaaaaa gtataacgac   3240
aagctacccc tgtacatttc caacccaaat tacaaagtta atgtgtatgc tgtaaccaag   3300
gagaacacaa tcatcaatcc aagcgagaac ggcgatacca gcacaaatgg aatcaaaaag   3360
atccttatat ttagtaaaaa aggctacgag atcggttgag gatccagatc tgctgtgcct   3420
tctagttgcc agccatctgt tgtttgcccc tcccccgtgc cttccttgac cctggaaggt   3480
gccactccca ctgtcctttc ctaataaaat gaggaaattg catcgcattg tctgagtagg   3540
tgtcattcta ttctgggggg tggggtgggg caggacagca agggggagga ttgggaagac   3600
aatagcaggc atgctgggga tgcggtgggc tctatgggta cccaggtgct gaagaattga   3660
cccggttcct cctgggccag aaagaagcag gcacatcccc ttctctgtga cacaccctgt   3720
ccacgcccct ggttcttagt tccagcccca ctcataggac actcatagct caggagggct   3780
ccgccttcaa tcccacccgc taaagtactt ggagcggtct ctccctccct catcagccca   3840
```

-continued ccaaaccaaa cctagcctcc aagagtggga agaaattaaa gcaagatagg ctattaagtg 3900
cagagggaga gaaaatgcct ccaacatgtg aggaagtaat gagagaaatc atagaatttt 3960
aaggccatga tttaaggcca tcatggcctt aatcttccgc ttcctcgctc actgactcgc 4020
tgcgctcggt cgttcggctg cggcgagcgg tatcagctca ctcaaaggcg gtaatacggt 4080
tatccacaga atcaggggat aacgcaggaa agaacatgtg agcaaaaggc cagcaaaagg 4140
ccaggaaccg taaaaaggcc gcgttgctgg cgtttttcca taggctccgc ccccctgacg 4200
agcatcacaa aaatcgacgc tcaagtcaga ggtggcgaaa cccgacagga ctataaagat 4260
accaggcgtt tccccctgga agctccctcg tgcgctctcc tgttccgacc ctgccgctta 4320
ccggatacct gtccgccttt ctcccttcgg gaagcgtggc gctttctcat agctcacgct 4380
gtaggtatct cagttcggtg taggtcgttc gctccaagct gggctgtgtg cacgaacccc 4440
ccgttcagcc cgaccgctgc gccttatccg gtaactatcg tcttgagtcc aacccggtaa 4500
gacacgactt atcgccactg gcagcagcca ctggtaacag gattagcaga gcgaggtatg 4560
taggcggtgc tacagagttc ttgaagtggt ggcctaacta cggctacact agaagaacag 4620
tatttggtat ctgcgctctg ctgaagccag ttaccttcgg aaaaagagtt ggtagctctt 4680
gatccggcaa acaaaccacc gctggtagcg gtggtttttt tgtttgcaag cagcagatta 4740
cgcgcagaaa aaaaggatct caagaagatc ctttgatctt ttctacgggg tctgacgctc 4800
agtggaacga aaactcacgt taagggattt tggtcatgag attatcaaaa aggatcttca 4860
cctagatcct tttaaattaa aaatgaagtt ttaaatcaat ctaaagtata tatgagtaaa 4920
cttggtctga cagttaccaa tgcttaatca gtgaggcacc tatctcagcg atctgtctat 4980
ttcgttcatc catagttgcc tgactcgggg gggggggcg ctgaggtctg cctcgtgaag 5040
aaggtgttgc tgactcatac caggcctgaa tcgccccatc atccagccag aaagtgaggg 5100
agccacggtt gatgagagct ttgttgtagg tggaccagtt ggtgattttg aacttttgct 5160
ttgccacgga acggtctgcg ttgtcgggaa gatgcgtgat ctgatccttc aactcagcaa 5220
aagttcgatt tattcaacaa agccgccgtc ccgtcaagtc agcgtaatgc tctgccagtg 5280
ttacaaccaa ttaaccaatt ctgattagaa aaactcatcg agcatcaaat gaaactgcaa 5340
tttattcata tcaggattat caataccata tttttgaaaa agccgtttct gtaatgaagg 5400
agaaaactca ccgaggcagt tccataggat ggcaagatcc tggtatcggt ctgcgattcc 5460
gactcgtcca acatcaatac aacctattaa tttcccctcg tcaaaaataa ggttatcaag 5520
tgagaaatca ccatgagtga cgactgaatc cggtgagaat ggcaaaagct tatgcatttc 5580
tttccagact tgttcaacag gccagccatt acgctcgtca tcaaaatcac tcgcatcaac 5640
caaaccgtta ttcattcgtg attgcgcctg agcgagacga aatacgcgat cgctgttaaa 5700
aggacaatta caaacaggaa tcgaatgcaa ccggcgcagg aacactgcca gcgcatcaac 5760
aatattttca cctgaatcag gatattcttc taatacctgg aatgctgttt tcccggggat 5820
cgcagtggtg agtaaccatg catcatcagg agtacggata aaatgcttga tggtcggaag 5880
aggcataaat tccgtcagcc agtttagtct gaccatctca tctgtaacat cattggcaac 5940
gctacctttg ccatgtttca gaaacaactc tggcgcatcg ggcttcccat acaatcgata 6000
gattgtcgca cctgattgcc cgacattatc gcgagcccat ttatacccat ataaatcagc 6060
atccatgttg gaatttaatc gcggcctcga gcaagacgtt tcccgttgaa tatggctcat 6120
aacacccctt gtattactgt ttatgtaagc agacagtttt attgttcatg atgatatatt 6180
tttatcttgt gcaatgtaac atcagagatt ttgagacaca acgtggcttt cccccccccc 6240
ccattattga agcatttatc agggttattg tctcatgagc ggatacatat ttgaatgtat 6300
ttagaaaaat aaacaaatag gggttccgcg cacatttccc cgaaaagtgc cacctgacgt 6360
ctaagaaacc attattatca tgacattaac ctataaaaat aggcgtatca cgaggccctt 6420
tcgtc 6425

<210> SEQ ID NO 91
<211> LENGTH: 5398
<212> TYPE: DNA
<213> ORGANISM: Artificial sequence
<220> FEATURE:
<223> OTHER INFORMATION: VR4756, Ligation of Segment7 into VR10551

<400> SEQUENCE: 91
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960
ggtgacgata ctttccatta ctaatccata acatggctct ttgccacaac tatctctatt 1020
ggctatatgc caatactctg tccttcagag actgacacgg actctgtatt tttacaggat 1080
ggggtcccat ttattattta caaattcaca tatacaacaa cgccgtcccc cgtgcccgca 1140
gtttttatta aacatagcgt gggatctcca cgcgaatctc gggtacgtgt tccggacatg 1200
ggctcttctc cggtagcggc ggagcttcca catccgagcc ctggtcccat gcctccagcg 1260
gctcatggtc gctcggcagc tccttgctcc taacagtgga ggccagactt aggcacagca 1320
caatgcccac caccaccagt gtgccgcaca aggccgtggc ggtagggtat gtgtctgaaa 1380
atgagcgtgg agattgggct cgcacggctg acgcagatgg aagacttaag gcagcggcag 1440
aagaagatgc aggcagctga gttgttgtat tctgataaga gtcagaggta actcccgttg 1500
cggtgctgtt aacggtggag ggcagtgtag tctgagcagt actcgttgct gccgcgcgcg 1560
ccaccagaca taatagctga cagactaaca gactgttcct ttccatgggt cttttctgca 1620
gtcaccgtcg tcggatatcg aattcgccac catgagcctt ctaaccgagg tcgaaacgta 1680
tgttctctct atcgttccat caggccccct caaagccgaa atcgcgcaga gacttgaaga 1740
tgtctttgct gggaaaaaca cagatcttga ggctctcatg gaatggctaa agacaagacc 1800
aatcctgtca cctctgacta aggggatttt ggggtttgtg ttcacgctca ccgtgcccag 1860

-continued

```
tgagcgagga ctgcagcgta gacgctttgt ccaaaatgcc ctcaatggga atggggatcc   1920
aaataacatg gacagagcag ttaaactata tagaaaactt aagagggaga ttacattcca   1980
tggggccaaa gaaatagcac tcagttattc tgctggtgca cttgccagtt gcatgggcct   2040
catatacaac agaatggggg ctgtaaccac tgaagtggcc tttggcctgg tatgtgcaac   2100
atgtgaacag attgctgact cccagcacag gtctcatagg caaatggtgg caacaaccaa   2160
tccattaata aggcatgaga acagaatggt tttggccagc actacagcta aggctatgga   2220
gcaaatggct ggatcaagtg agcaggcagc ggaggccatg gaaattgcta gtcaggccag   2280
gcaaatggtg caggcaatga gagccattgg gactcatcct agctccagtg ctggtctaaa   2340
agatgatctt cttgaaaatt tgcagaccta tcagaaacga atgggggtgc agatgcaacg   2400
attcaagtga cccgcttgtt gttgctgcga gtatcattgg gatcttgcac ttgatattgt   2460
ggattcttga tcgtcttttt ttcaaatgca tctatcgact cttcaaacac ggtctgaaaa   2520
gagggccttc tacggaagga gtacctgagt ctatgaggga agaatatcga aaggaacagc   2580
agaatgctgt ggatgctgac gacagtcatt ttgtcagcat agagctggag taatcagtcg   2640
accacgtgtg atccagatct acttctggct aataaaagat cagagctcta gagatctgtg   2700
tgttggtttt ttgtgtggta ctcttccgct tcctcgctca ctgactcgct gcgctcggtc   2760
gttcggctgc ggcgagcggt atcagctcac tcaaaggcgg taatacggtt atccacagaa   2820
tcaggggata acgcaggaaa gaacatgtga gcaaaaggcc agcaaaaggc caggaaccgt   2880
aaaaaggccg cgttgctggc gtttttccat aggctccgcc cccctgacga gcatcacaaa   2940
aatcgacgct caagtcagag gtggcgaaac ccgacaggac tataaagata ccaggcgttt   3000
ccccctggaa gctccctcgt gcgctctcct gttccgaccc tgccgcttac cggatacctg   3060
tccgcctttc tcccttcggg aagcgtggcg ctttctcata gctcacgctg taggtatctc   3120
agttcggtgt aggtcgttcg ctccaagctg ggctgtgtgc acgaaccccc cgttcagccc   3180
gaccgctgcg ccttatccgg taactatcgt cttgagtcca acccggtaag acacgactta   3240
tcgccactgg cagcagccac tggtaacagg attagcagag cgaggtatgt aggcggtgct   3300
acagagttct tgaagtggtg gcctaactac ggctacacta gaagaacagt atttggtatc   3360
tgcgctctgc tgaagccagt taccttcgga aaaagagttg gtagctcttg atccggcaaa   3420
caaaccaccg ctggtagcgg tggttttttt gtttgcaagc agcagattac gcgcagaaaa   3480
aaaggatctc aagaagatcc tttgatcttt tctacggggt ctgacgctca gtggaacgaa   3540
aactcacgtt aagggatttt ggtcatgaga ttatcaaaaa ggatcttcac ctagatcctt   3600
ttaaattaaa aatgaagttt taaatcaatc taaagtatat atgagtaaac ttggtctgac   3660
agttaccaat gcttaatcag tgaggcacct atctcagcga tctgtctatt tcgttcatcc   3720
atagttgcct gactcggggg gggggggcgc tgaggtctgc ctcgtgaaga aggtgttgct   3780
gactcatacc aggcctgaat cgccccatca tccagccaga aagtgaggga gccacggttg   3840
atgagagctt tgttgtaggt ggaccagttg gtgattttga acttttgctt tgccacggaa   3900
cggtctgcgt tgtcgggaag atgcgtgatc tgatccttca actcagcaaa agttcgattt   3960
attcaacaaa gccgccgtcc cgtcaagtca gcgtaatgct ctgccagtgt tacaaccaat   4020
taaccaattc tgattagaaa aactcatcga gcatcaaatg aaactgcaat ttattcatat   4080
caggattatc aataccatat ttttgaaaaa gccgtttctg taatgaagga gaaaactcac   4140
cgaggcagtt ccataggatg gcaagatcct ggtatcggtc tgcgattccg actcgtccaa   4200
catcaataca acctattaat ttcccctcgt caaaaataag gttatcaagt gagaaatcac   4260
```

catgagtgac gactgaatcc ggtgagaatg gcaaaagctt atgcatttct ttccagactt 4320
gttcaacagg ccagccatta cgctcgtcat caaaatcact cgcatcaacc aaaccgttat 4380
tcattcgtga ttgcgcctga gcgagacgaa atacgcgatc gctgttaaaa ggacaattac 4440
aaacaggaat cgaatgcaac cggcgcagga acactgccag cgcatcaaca atattttcac 4500
ctgaatcagg atattcttct aatacctgga atgctgtttt cccggggatc gcagtggtga 4560
gtaaccatgc atcatcagga gtacggataa aatgcttgat ggtcggaaga ggcataaatt 4620
ccgtcagcca gtttagtctg accatctcat ctgtaacatc attggcaacg ctacctttgc 4680
catgtttcag aaacaactct ggcgcatcgg gcttcccata caatcgatag attgtcgcac 4740
ctgattgccc gacattatcg cgagcccatt tatacccata taaatcagca tccatgttgg 4800
aatttaatcg cggcctcgag caagacgttt cccgttgaat atggctcata acaccccttg 4860
tattactgtt tatgtaagca gacagtttta ttgttcatga tgatatattt ttatcttgtg 4920
caatgtaaca tcagagattt tgagacacaa cgtggctttc cccccccccc cattattgaa 4980
gcatttatca gggttattgt ctcatgagcg gatacatatt tgaatgtatt tagaaaaata 5040
aacaaatagg ggttccgcgc acatttcccc gaaaagtgcc acctgacgtc taagaaacca 5100
ttattatcat gacattaacc tataaaaata ggcgtatcac gaggcccttt cgtctcgcgc 5160
gtttcggtga tgacggtgaa aacctctgac acatgcagct cccggagacg gtcacagctt 5220
gtctgtaagc ggatgccggg agcagacaag cccgtcaggg cgcgtcagcg ggtgttggcg 5280
ggtgtcgggg ctggcttaac tatgcggcat cagagcagat tgtactgaga gtgcaccata 5340
tgcggtgtga aataccgcac agatgcgtaa ggagaaaata ccgcatcaga ttggctat 5398

<210> SEQ ID NO 92
<211> LENGTH: 4710
<212> TYPE: DNA
<213> ORGANISM: Artificial sequence
<220> FEATURE:
<223> OTHER INFORMATION: VR4759, Ligation of M2 into 10551

<400> SEQUENCE: 92
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960

-continued

```
ggtgacgata ctttccatta ctaatccata acatggctct ttgccacaac tatctctatt   1020
ggctatatgc caatactctg tccttcagag actgacacgg actctgtatt tttacaggat   1080
ggggtcccat ttattattta caaattcaca tatacaacaa cgccgtcccc cgtgcccgca   1140
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catgagcctg ctgaccgagg tggagacccc   1680
catcagaaac gagtggggct gcagatgcaa cgacagcagc gaccccctgg tggtggccgc   1740
cagcatcatc ggcatcctgc acctgatcct gtggatcctg gacagactgt tcttcaagtg   1800
catctacaga ctgttcaagc acggcctgaa gagaggcccc agcaccgagg gcgtgcccga   1860
gagcatgaga gaggagtaca gaaaggagca gcagaacgcc gtggacgccg acgacagcca   1920
cttcgtgagc atcgagctgg agtgatcagt cgaccacgtg tgatccagat ctacttctgg   1980
ctaataaaag atcagagctc tagagatctg tgtgttggtt ttttgtgtgg tactcttccg   2040
cttcctcgct cactgactcg ctgcgctcgg tcgttcggct gcggcgagcg gtatcagctc   2100
actcaaaggc ggtaatacgg ttatccacag aatcagggga taacgcagga aagaacatgt   2160
gagcaaaagg ccagcaaaag gccaggaacc gtaaaaaggc cgcgttgctg gcgtttttcc   2220
ataggctccg cccccctgac gagcatcaca aaaatcgacg ctcaagtcag aggtggcgaa   2280
acccgacagg actataaaga taccaggcgt ttccccctgg aagctccctc gtgcgctctc   2340
ctgttccgac cctgccgctt accggatacc tgtccgcctt tctcccttcg ggaagcgtgg   2400
cgctttctca tagctcacgc tgtaggtatc tcagttcggt gtaggtcgtt cgctccaagc   2460
tgggctgtgt gcacgaaccc cccgttcagc ccgaccgctg cgccttatcc ggtaactatc   2520
gtcttgagtc caacccggta agacacgact tatcgccact ggcagcagcc actggtaaca   2580
ggattagcag agcgaggtat gtaggcggtg ctacagagtt cttgaagtgg tggcctaact   2640
acggctacac tagaagaaca gtatttggta tctgcgctct gctgaagcca gttaccttcg   2700
gaaaaagagt tggtagctct tgatccggca aacaaaccac cgctggtagc ggtggttttt   2760
ttgtttgcaa gcagcagatt acgcgcagaa aaaaaggatc tcaagaagat cctttgatct   2820
tttctacggg gtctgacgct cagtggaacg aaaactcacg ttaagggatt ttggtcatga   2880
gattatcaaa aaggatcttc acctagatcc ttttaaatta aaaatgaagt tttaaatcaa   2940
tctaaagtat atatgagtaa acttggtctg acagttacca atgcttaatc agtgaggcac   3000
ctatctcagc gatctgtcta tttcgttcat ccatagttgc ctgactcggg gggggggggc   3060
gctgaggtct gcctcgtgaa gaaggtgttg ctgactcata ccaggcctga atcgccccat   3120
catccagcca gaaagtgagg gagccacggt tgatgagagc tttgttgtag gtggaccagt   3180
tggtgatttt gaacttttgc tttgccacgg aacggtctgc gttgtcggga agatgcgtga   3240
tctgatcctt caactcagca aaagttcgat ttattcaaca aagccgccgt cccgtcaagt   3300
cagcgtaatg ctctgccagt gttacaacca attaaccaat tctgattaga aaaactcatc   3360
```

```
gagcatcaaa tgaaactgca atttattcat atcaggatta tcaataccat atttttgaaa   3420

aagccgtttc tgtaatgaag gagaaaactc accgaggcag ttccatagga tggcaagatc   3480

ctggtatcgg tctgcgattc cgactcgtcc aacatcaata caacctatta atttcccctc   3540

gtcaaaaata aggttatcaa gtgagaaatc accatgagtg acgactgaat ccggtgagaa   3600

tggcaaaagc ttatgcattt ctttccagac ttgttcaaca ggccagccat tacgctcgtc   3660

atcaaaatca ctcgcatcaa ccaaaccgtt attcattcgt gattgcgcct gagcgagacg   3720

aaatacgcga tcgctgttaa aaggacaatt acaaacagga atcgaatgca accggcgcag   3780

gaacactgcc agcgcatcaa caatattttc acctgaatca ggatattctt ctaatacctg   3840

gaatgctgtt ttcccgggga tcgcagtggt gagtaaccat gcatcatcag gagtacggat   3900

aaaatgcttg atggtcggaa gaggcataaa ttccgtcagc cagtttagtc tgaccatctc   3960

atctgtaaca tcattggcaa cgctaccttt gccatgtttc agaaacaact ctggcgcatc   4020

gggcttccca tacaatcgat agattgtcgc acctgattgc ccgacattat cgcgagccca   4080

tttataccca tataaatcag catccatgtt ggaatttaat cgcggcctcg agcaagacgt   4140

ttcccgttga atatggctca taacacccct tgtattactg tttatgtaag cagacagttt   4200

tattgttcat gatgatatat ttttatcttg tgcaatgtaa catcagagat tttgagacac   4260

aacgtggctt tccccccccc cccattattg aagcatttat cagggttatt gtctcatgag   4320

cggatacata tttgaatgta tttagaaaaa taaacaaata ggggttccgc gcacatttcc   4380

ccgaaaagtg ccacctgacg tctaagaaac cattattatc atgacattaa cctataaaaa   4440

taggcgtatc acgaggccct ttcgtctcgc gcgtttcggt gatgacggtg aaaacctctg   4500

acacatgcag ctcccggaga cggtcacagc ttgtctgtaa gcggatgccg ggagcagaca   4560

agcccgtcag ggcgcgtcag cgggtgttgg cgggtgtcgg ggctggctta actatgcggc   4620

atcagagcag attgtactga gagtgcacca tatgcggtgt gaaataccgc acagatgcgt   4680

aaggagaaaa taccgcatca gattggctat                                    4710
```

<210> SEQ ID NO 93
<211> LENGTH: 5913
<212> TYPE: DNA
<213> ORGANISM: Artificial sequence
<220> FEATURE:
<223> OTHER INFORMATION: VR4762, Ligation of NP Consensus into 10551

<400> SEQUENCE: 93

```
tggccattgc atacgttgta tccatatcat aatatgtaca tttatattgg ctcatgtcca     60

acattaccgc catgttgaca ttgattattg actagttatt aatagtaatc aattacgggg    120

tcattagttc atagcccata tatggagttc cgcgttacat aacttacggt aaatggcccg    180

cctggctgac cgcccaacga cccccgccca ttgacgtcaa taatgacgta tgttcccata    240

gtaacgccaa tagggacttt ccattgacgt caatgggtgg agtatttacg gtaaactgcc    300

cacttggcag tacatcaagt gtatcatatg ccaagtacgc cccctattga cgtcaatgac    360

ggtaaatggc ccgcctggca ttatgcccag tacatgacct tatgggactt tcctacttgg    420

cagtacatct acgtattagt catcgctatt accatggtga tgcggttttg gcagtacatc    480

aatgggcgtg gatagcggtt tgactcacgg ggatttccaa gtctccaccc cattgacgtc    540

aatgggagtt tgttttggca ccaaaatcaa cgggactttc caaaatgtcg taacaactcc    600

gccccattga cgcaaatggg cggtaggcgt gtacggtggg aggtctatat aagcagagct    660

cgtttagtga accgtcagat cgcctggaga cgccatccac gctgttttga cctccataga    720
```

-continued

```
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctcccctatt    960
ggtgacgata ctttccatta ctaatccata acatggctct ttgccacaac tatctctatt   1020
ggctatatgc caatactctg tccttcagag actgacacgg actctgtatt tttacaggat   1080
ggggtcccat ttattattta caaattcaca tatacaacaa cgccgtcccc cgtgcccgca   1140
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catggccagc cagggcacca agagaagcta   1680
cgagcagatg gagaccgacg gcgagagaca gaacgccacc gagatcagag ccagcgtggg   1740
caagatgatc gacggcatcg gcagattcta catccagatg tgcaccgagc tgaagctgag   1800
cgactacgag ggcagactga tccagaacag cctgaccatc gagagaatgg tgctgagcgc   1860
cttcgacgag agaagaaaca gatacctgga ggagcacccc agcgccggca aggaccccaa   1920
gaagaccggc ggccccatct acagaagagt ggacggcaag tggatgagag agctggtgct   1980
gtacgacaag gaggagatca gaagaatctg gagacaggcc aacaacggcg aggacgccac   2040
cgccggcctg acccacatga tgatctggca cagcaacctg aacgacacca cctaccagag   2100
aaccagagcc ctggtgcgga ccggcatgga ccccagaatg tgcagcctga tgcagggcag   2160
caccctgccc agaagaagcg gcgccgccgg cgccgccgtg aagggcatcg gcaccatggt   2220
gatggagctg atcagaatga tcaagagagg catcaacgac agaaacttct ggagaggcga   2280
gaacggcaga aagaccagaa gcgcctacga gagaatgtgc aacatcctga agggcaagtt   2340
ccagaccgcc gcccagagag ccatgatgga ccaggtccgg gagagcagaa accccggcaa   2400
cgccgagatc gaggacctga tcttcctggc cagaagcgcc ctgatcctga gaggcagcgt   2460
ggcccacaag agctgcctgc ccgcctgcgt gtacggcccc gccgtgagca gcggctacga   2520
cttcgagaag gagggctaca gcctggtggg catcgacccc ttcaagctgc tgcagaacag   2580
ccaggtgtac agcctgatca gacccaacga gaaccccgcc cacaagagcc agctggtgtg   2640
gatggcctgc cacagcgccg ccttcgagga cctgagactg ctgagcttca tcagaggcac   2700
caaggtgtcc cccagaggca agctgagcac cagaggcgtg cagatcgcca gcaacgagaa   2760
catggacaac atgggcagca gcaccctgga gctgagaagc agatactggg ccatcagaac   2820
cagaagcggc ggcaacacca accagcagag agccagcgcc ggccagatca gcgtgcagcc   2880
caccttcagc gtgcagagaa acctgccctt cgagaagagc accgtgatgg ccgccttcac   2940
cggcaacacc gagggcagaa ccagcgacat gagagccgag atcatcagaa tgatggaggg   3000
cgccaagccc gaggaggtgt ccttcagagg cagaggcgtg ttcgagctga gcgacgagaa   3060
ggccaccaac cccatcgtgc ctagcttcga catgagcaac gagggcagct acttcttcgg   3120
```

-continued

```
cgacaacgcc gaggagtacg acaactgatc agtcgaccac gtgtgatcca gatctacttc   3180
tggctaataa aagatcagag ctctagagat ctgtgtgttg gtttttgtg tggtactctt   3240
ccgcttcctc gctcactgac tcgctgcgct cggtcgttcg gctgcggcga gcggtatcag   3300
ctcactcaaa ggcggtaata cggttatcca cagaatcagg ggataacgca ggaaagaaca   3360
tgtgagcaaa aggccagcaa aaggccagga accgtaaaaa ggccgcgttg ctggcgtttt   3420
tccataggct ccgcccccct gacgagcatc acaaaaatcg acgctcaagt cagaggtggc   3480
gaaacccgac aggactataa agataccagg cgtttccccc tggaagctcc ctcgtgcgct   3540
ctcctgttcc gaccctgccg cttaccggat acctgtccgc ctttctccct tcgggaagcg   3600
tggcgctttc tcatagctca cgctgtaggt atctcagttc ggtgtaggtc gttcgctcca   3660
agctgggctg tgtgcacgaa ccccccgttc agcccgaccg ctgcgcctta tccggtaact   3720
atcgtcttga gtccaacccg gtaagacacg acttatcgcc actggcagca gccactggta   3780
acaggattag cagagcgagg tatgtaggcg gtgctacaga gttcttgaag tggtggccta   3840
actacggcta cactagaaga acagtatttg gtatctgcgc tctgctgaag ccagttacct   3900
tcggaaaaag agttggtagc tcttgatccg gcaaacaaac caccgctggt agcggtggtt   3960
tttttgtttg caagcagcag attacgcgca gaaaaaaagg atctcaagaa gatcctttga   4020
tcttttctac ggggtctgac gctcagtgga acgaaaactc acgttaaggg attttggtca   4080
tgagattatc aaaaaggatc ttcacctaga tccttttaaa ttaaaaatga agttttaaat   4140
caatctaaag tatatatgag taaacttggt ctgacagtta ccaatgctta atcagtgagg   4200
cacctatctc agcgatctgt ctatttcgtt catccatagt tgcctgactc gggggggggg   4260
ggcgctgagg tctgcctcgt gaagaaggtg ttgctgactc ataccaggcc tgaatcgccc   4320
catcatccag ccagaaagtg agggagccac ggttgatgag agctttgttg taggtggacc   4380
agttggtgat tttgaacttt tgctttgcca cggaacggtc tgcgttgtcg ggaagatgcg   4440
tgatctgatc cttcaactca gcaaaagttc gatttattca acaaagccgc cgtcccgtca   4500
agtcagcgta atgctctgcc agtgttacaa ccaattaacc aattctgatt agaaaaactc   4560
atcgagcatc aaatgaaact gcaatttatt catatcagga ttatcaatac catatttttg   4620
aaaaagccgt ttctgtaatg aaggagaaaa ctcaccgagg cagttccata ggatggcaag   4680
atcctggtat cggtctgcga ttccgactcg tccaacatca atacaaccta ttaatttccc   4740
ctcgtcaaaa ataaggttat caagtgagaa atcaccatga gtgacgactg aatccggtga   4800
gaatggcaaa agcttatgca tttctttcca gacttgttca acaggccagc cattacgctc   4860
gtcatcaaaa tcactcgcat caaccaaacc gttattcatt cgtgattgcg cctgagcgag   4920
acgaaatacg cgatcgctgt taaaaggaca attacaaaca ggaatcgaat gcaaccggcg   4980
caggaacact gccagcgcat caacaatatt ttcacctgaa tcaggatatt cttctaatac   5040
ctggaatgct gttttcccgg ggatcgcagt ggtgagtaac catgcatcat caggagtacg   5100
gataaaatgc ttgatggtcg gaagaggcat aaattccgtc agccagttta gtctgaccat   5160
ctcatctgta acatcattgg caacgctacc tttgccatgt ttcagaaaca actctggcgc   5220
atcgggcttc ccatacaatc gatagattgt cgcacctgat tgcccgacat tatcgcgagc   5280
ccatttatac ccatataaat cagcatccat gttggaattt aatcgcggcc tcgagcaaga   5340
cgtttcccgt tgaatatggc tcataacacc ccttgtatta ctgtttatgt aagcagacag   5400
ttttattgtt catgatgata tatttttatc ttgtgcaatg taacatcaga gattttgaga   5460
cacaacgtgg ctttcccccc ccccccatta ttgaagcatt tatcagggtt attgtctcat   5520
```

-continued

```
gagcggatac atatttgaat gtatttagaa aaataaacaa ataggggttc cgcgcacatt   5580

tccccgaaaa gtgccacctg acgtctaaga aaccattatt atcatgacat taacctataa   5640

aaataggcgt atcacgaggc cctttcgtct cgcgcgtttc ggtgatgacg gtgaaaacct   5700

ctgacacatg cagctcccgg agacggtcac agcttgtctg taagcggatg ccgggagcag   5760

acaagcccgt cagggcgcgt cagcgggtgt tggcgggtgt cggggctggc ttaactatgc   5820

ggcatcagag cagattgtac tgagagtgca ccatatgcgg tgtgaaatac cgcacagatg   5880

cgtaaggaga aaataccgca tcagattggc tat                                5913
```

```
<210> SEQ ID NO 94
<211> LENGTH: 3817
<212> TYPE: DNA
<213> ORGANISM: Artificial sequence
<220> FEATURE:
<223> OTHER INFORMATION: VR10682

<400> SEQUENCE: 94

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatggt gcactctcag tacaatctgc tctgatgccg catagttaag ccagtatctg    240

ctccctgctt gtgtgttgga ggtcgctgag tagtgcgcga gcaaaattta agctacaaca    300

aggcaaggct tgaccgacaa ttgcatgaag aatctgctta gggttaggcg ttttgcgctg    360

cttcgcgatg tacgggccag atatacgcgt atctgagggg actagggtgt gtttaggcga    420

aaagcggggc ttcggttgta cgcggttagg agtcccctca ggatatagta gtttcgcttt    480

tgcataggga gggggaaatg tagtcttatg caatactctt gtagtcttgc aacatggtaa    540

cgatgagtta gcaacatgcc ttacaaggag agaaaaagca ccgtgcatgc cgattggtgg    600

aagtaaggtg gtacgatcgt gccttattag gaaggcaaca gacgggtctg acatggattg    660

gacgaaccac tgaattccgc attgcagaga tattgtattt aagtgcctag ctcgatactc    720

tagacgccat ttgaccattc accacattgg tgtgcacctc caagcttccg tcaccgtcgt    780

cgacacgtgt gatcagatat cgcggccgct ctagaccagg cgcctggatc cagatctgct    840

gtgccttcta gttgccagcc atctgttgtt tgcccctccc ccgtgccttc cttgaccctg    900

gaaggtgcca ctcccactgt cctttcctaa taaaatgagg aaattgcatc gcattgtctg    960

agtaggtgtc attctattct ggggggtggg gtggggcagg acagcaaggg ggaggattgg   1020

gaagacaata gcaggcatgc tggggatgcg gtgggctcta tgggtaccca ggtgctgaag   1080

aattgacccg gttcctcctg ggccagaaag aagcaggcac atccccttct ctgtgacaca   1140

ccctgtccac gcccctggtt cttagttcca gccccactca taggacactc atagctcagg   1200

agggctccgc cttcaatccc acccgctaaa gtacttggag cggtctctcc ctccctcatc   1260

agcccaccaa accaaaccta gcctccaaga gtgggaagaa attaaagcaa gataggctat   1320

taagtgcaga gggagagaaa atgcctccaa catgtgagga agtaatgaga gaaatcatag   1380

aatttcttcc gcttcctcgc tcactgactc gctgcgctcg gtcgttcggc tgcggcgagc   1440

ggtatcagct cactcaaagg cggtaatacg gttatccaca gaatcagggg ataacgcagg   1500

aaagaacatg tgagcaaaag gccagcaaaa ggccaggaac cgtaaaaagg ccgcgttgct   1560

ggcgtttttc cataggctcc gcccccctga cgagcatcac aaaaatcgac gctcaagtca   1620

gaggtggcga aacccgacag gactataaag ataccaggcg tttccccctg gaagctccct   1680
```

```
cgtgcgctct cctgttccga ccctgccgct taccggatac ctgtccgcct ttctcccttc   1740

gggaagcgtg gcgctttctc atagctcacg ctgtaggtat ctcagttcgg tgtaggtcgt   1800

tcgctccaag ctgggctgtg tgcacgaacc ccccgttcag cccgaccgct gcgccttatc   1860

cggtaactat cgtcttgagt ccaacccggt aagacacgac ttatcgccac tggcagcagc   1920

cactggtaac aggattagca gagcgaggta tgtaggcggt gctacagagt tcttgaagtg   1980

gtggcctaac tacggctaca ctagaagaac agtatttggt atctgcgctc tgctgaagcc   2040

agttaccttc ggaaaaagag ttggtagctc ttgatccggc aaacaaacca ccgctggtag   2100

cggtggtttt tttgtttgca agcagcagat tacgcgcaga aaaaaaggat ctcaagaaga   2160

tcctttgatc ttttctacgg ggtctgacgc tcagtggaac gaaaactcac gttaagggat   2220

tttggtcatg agattatcaa aaaggatctt cacctagatc cttttaaatt aaaaatgaag   2280

ttttaaatca atctaaagta tatatgagta aacttggtct gacagttacc aatgcttaat   2340

cagtgaggca cctatctcag cgatctgtct atttcgttca tccatagttg cctgactcgg   2400

gggggggggg cgctgaggtc tgcctcgtga agaaggtgtt gctgactcat accaggcctg   2460

aatcgcccca tcatccagcc agaaagtgag ggagccacgg ttgatgagag ctttgttgta   2520

ggtggaccag ttggtgattt tgaacttttg ctttgccacg gaacggtctg cgttgtcggg   2580

aagatgcgtg atctgatcct tcaactcagc aaaagttcga tttattcaac aaagccgccg   2640

tcccgtcaag tcagcgtaat gctctgccag tgttacaacc aattaaccaa ttctgattag   2700

aaaaactcat cgagcatcaa atgaaactgc aatttattca tatcaggatt atcaatacca   2760

tatttttgaa aaagccgttt ctgtaatgaa ggagaaaact caccgaggca gttccatagg   2820

atggcaagat cctggtatcg gtctgcgatt ccgactcgtc caacatcaat acaacctatt   2880

aatttcccct cgtcaaaaat aaggttatca agtgagaaat caccatgagt gacgactgaa   2940

tccggtgaga atggcaaaag cttatgcatt tctttccaga cttgttcaac aggccagcca   3000

ttacgctcgt catcaaaatc actcgcatca accaaaccgt tattcattcg tgattgcgcc   3060

tgagcgagac gaaatacgcg atcgctgtta aaaggacaat tacaaacagg aatcgaatgc   3120

aaccggcgca ggaacactgc cagcgcatca acaatatttt cacctgaatc aggatattct   3180

tctaatacct ggaatgctgt tttcccgggg atcgcagtgg tgagtaacca tgcatcatca   3240

ggagtacgga taaaatgctt gatggtcgga agaggcataa attccgtcag ccagtttagt   3300

ctgaccatct catctgtaac atcattggca acgctacctt tgccatgttt cagaaacaac   3360

tctggcgcat cgggcttccc atacaatcga tagattgtcg cacctgattg cccgacatta   3420

tcgcgagccc atttataccc atataaatca gcatccatgt tggaatttaa tcgcggcctc   3480

gagcaagacg tttcccgttg aatatggctc ataacacccc ttgtattact gtttatgtaa   3540

gcagacagtt ttattgttca tgatgatata tttttatctt gtgcaatgta acatcagaga   3600

ttttgagaca caacgtggct ttcccccccc ccccattatt gaagcattta tcagggttat   3660

tgtctcatga gcggatacat atttgaatgt atttagaaaa ataaacaaat aggggttccg   3720

cgcacatttc cccgaaaagt gccacctgac gtctaagaaa ccattattat catgacatta   3780

acctataaaa ataggcgtat cacgaggccc tttcgtc                            3817
```

<210> SEQ ID NO 95
<211> LENGTH: 4822
<212> TYPE: DNA
<213> ORGANISM: Artificial sequence
<220> FEATURE:
<223> OTHER INFORMATION: VR4764, Ligation of VR4756 RV-SalI into VR10682 RV -continued

<400> SEQUENCE: 95

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatggt gcactctcag tacaatctgc tctgatgccg catagttaag ccagtatctg    240
ctccctgctt gtgtgttgga ggtcgctgag tagtgcgcga gcaaaattta agctacaaca    300
aggcaaggct tgaccgacaa ttgcatgaag aatctgctta gggttaggcg ttttgcgctg    360
cttcgcgatg tacgggccag atatacgcgt atctgagggg actagggtgt gtttaggcga    420
aaagcggggc ttcggttgta cgcggttagg agtcccctca ggatatagta gtttcgcttt    480
tgcataggga gggggaaatg tagtcttatg caatactctt gtagtcttgc aacatggtaa    540
cgatgagtta gcaacatgcc ttacaaggag agaaaaagca ccgtgcatgc cgattggtgg    600
aagtaaggtg gtacgatcgt gccttattag gaaggcaaca gacgggtctg acatggattg    660
gacgaaccac tgaattccgc attgcagaga tattgtattt aagtgcctag ctcgatactc    720
tagacgccat ttgaccattc accacattgg tgtgcacctc caagcttccg tcaccgtcgt    780
cgacacgtgt gatcagatat cgaattcgcc accatgagcc ttctaaccga ggtcgaaacg    840
tatgttctct ctatcgttcc atcaggcccc ctcaaagccg aaatcgcgca gagacttgaa    900
gatgtctttg ctgggaaaaa cacagatctt gaggctctca tggaatggct aaagacaaga    960
ccaatcctgt cacctctgac taaggggatt ttggggtttg tgttcacgct caccgtgccc   1020
agtgagcgag gactgcagcg tagacgcttt gtccaaaatg ccctcaatgg gaatggggat   1080
ccaaataaca tggacagagc agttaaacta tatagaaaac ttaagaggga gattacattc   1140
catggggcca aagaaatagc actcagttat tctgctggtg cacttgccag ttgcatgggc   1200
ctcatataca acagaatggg ggctgtaacc actgaagtgg cctttggcct ggtatgtgca   1260
acatgtgaac agattgctga ctcccagcac aggtctcata ggcaaatggt ggcaacaacc   1320
aatccattaa taaggcatga gaacagaatg gttttggcca gcactacagc taaggctatg   1380
gagcaaatgg ctggatcaag tgagcaggca gcggaggcca tggaaattgc tagtcaggcc   1440
aggcaaatgg tgcaggcaat gagagccatt gggactcatc ctagctccag tgctggtcta   1500
aaagatgatc ttcttgaaaa tttgcagacc tatcagaaac gaatgggggt gcagatgcaa   1560
cgattcaagt gacccgcttg ttgttgctgc gagtatcatt gggatcttgc acttgatatt   1620
gtggattctt gatcgtcttt ttttcaaatg catctatcga ctcttcaaac acggtctgaa   1680
aagagggcct tctacggaag gagtacctga gtctatgagg gaagaatatc gaaaggaaca   1740
gcagaatgct gtggatgctg acgacagtca ttttgtcagc atagagctgg agtaatcagt   1800
cgaatcgcgg ccgctctaga ccaggcgcct ggatccagat ctgctgtgcc ttctagttgc   1860
cagccatctg ttgtttgccc ctcccccgtg ccttccttga ccctggaagg tgccactccc   1920
actgtccttt cctaataaaa tgaggaaatt gcatcgcatt gtctgagtag gtgtcattct   1980
attctggggg gtggggtggg gcaggacagc aagggggagg attgggaaga caatagcagg   2040
catgctgggg atgcggtggg ctctatgggt acccaggtgc tgaagaattg acccggttcc   2100
tcctgggcca gaaagaagca ggcacatccc cttctctgtg acacaccctg tccacgcccc   2160
tggttcttag ttccagcccc actcatagga cactcatagc tcaggagggc tccgccttca   2220
atcccacccg ctaaagtact tggagcggtc tctccctccc tcatcagccc accaaaccaa   2280
acctagcctc caagagtggg aagaaattaa agcaagatag gctattaagt gcagagggag   2340
```

-continued

```
agaaaatgcc tccaacatgt gaggaagtaa tgagagaaat catagaattt cttccgcttc   2400
ctcgctcact gactcgctgc gctcggtcgt tcggctgcgg cgagcggtat cagctcactc   2460
aaaggcggta atacggttat ccacagaatc aggggataac gcaggaaaga acatgtgagc   2520
aaaaggccag caaaaggcca ggaaccgtaa aaaggccgcg ttgctggcgt ttttccatag   2580
gctccgcccc cctgacgagc atcacaaaaa tcgacgctca agtcagaggt ggcgaaaccc   2640
gacaggacta taaagatacc aggcgtttcc ccctggaagc tccctcgtgc gctctcctgt   2700
tccgaccctg ccgcttaccg gatacctgtc cgcctttctc ccttcgggaa gcgtggcgct   2760
ttctcatagc tcacgctgta ggtatctcag ttcggtgtag gtcgttcgct ccaagctggg   2820
ctgtgtgcac gaaccccccg ttcagcccga ccgctgcgcc ttatccggta actatcgtct   2880
tgagtccaac ccggtaagac acgacttatc gccactggca gcagccactg gtaacaggat   2940
tagcagagcg aggtatgtag gcggtgctac agagttcttg aagtggtggc ctaactacgg   3000
ctacactaga agaacagtat ttggtatctg cgctctgctg aagccagtta ccttcggaaa   3060
aagagttggt agctcttgat ccggcaaaca aaccaccgct ggtagcggtg gtttttttgt   3120
ttgcaagcag cagattacgc gcagaaaaaa aggatctcaa gaagatcctt tgatcttttc   3180
tacggggtct gacgctcagt ggaacgaaaa ctcacgttaa gggattttgg tcatgagatt   3240
atcaaaaagg atcttcacct agatcctttt aaattaaaaa tgaagtttta aatcaatcta   3300
aagtatatat gagtaaactt ggtctgacag ttaccaatgc ttaatcagtg aggcacctat   3360
ctcagcgatc tgtctatttc gttcatccat agttgcctga ctcggggggg gggggcgctg   3420
aggtctgcct cgtgaagaag gtgttgctga ctcataccag gcctgaatcg ccccatcatc   3480
cagccagaaa gtgagggagc cacggttgat gagagctttg ttgtaggtgg accagttggt   3540
gattttgaac ttttgctttg ccacggaacg gtctgcgttg tcgggaagat gcgtgatctg   3600
atccttcaac tcagcaaaag ttcgatttat tcaacaaagc cgccgtcccg tcaagtcagc   3660
gtaatgctct gccagtgtta caaccaatta accaattctg attagaaaaa ctcatcgagc   3720
atcaaatgaa actgcaattt attcatatca ggattatcaa taccatattt ttgaaaaagc   3780
cgtttctgta atgaaggaga aaactcaccg aggcagttcc ataggatggc aagatcctgg   3840
tatcggtctg cgattccgac tcgtccaaca tcaatacaac ctattaattt cccctcgtca   3900
aaaataaggt tatcaagtga gaaatcacca tgagtgacga ctgaatccgg tgagaatggc   3960
aaaagcttat gcatttcttt ccagacttgt tcaacaggcc agccattacg ctcgtcatca   4020
aaatcactcg catcaaccaa accgttattc attcgtgatt gcgcctgagc gagacgaaat   4080
acgcgatcgc tgttaaaagg acaattacaa acaggaatcg aatgcaaccg gcgcaggaac   4140
actgccagcg catcaacaat attttcacct gaatcaggat attcttctaa tacctggaat   4200
gctgttttcc cggggatcgc agtggtgagt aaccatgcat catcaggagt acggataaaa   4260
tgcttgatgg tcggaagagg cataaattcc gtcagccagt ttagtctgac catctcatct   4320
gtaacatcat tggcaacgct acctttgcca tgtttcagaa acaactctgg cgcatcgggc   4380
ttcccataca atcgatagat tgtcgcacct gattgcccga cattatcgcg agcccattta   4440
tacccatata aatcagcatc catgttggaa tttaatcgcg gcctcgagca agacgtttcc   4500
cgttgaatat ggctcataac accccttgta ttactgttta tgtaagcaga cagttttatt   4560
gttcatgatg atatattttt atcttgtgca atgtaacatc agagattttg agacacaacg   4620
tggctttccc cccccccca ttattgaagc atttatcagg gttattgtct catgagcgga   4680
tacatatttg aatgtattta gaaaaataaa caaatagggg ttccgcgcac atttccccga   4740
```

-continued

```
aaagtgccac ctgacgtcta agaaaccatt attatcatga cattaaccta taaaaatagg   4800

cgtatcacga ggccctttcg tc                                            4822
```

<210> SEQ ID NO 96
<211> LENGTH: 5341
<212> TYPE: DNA
<213> ORGANISM: Artificial sequence
<220> FEATURE:
<223> OTHER INFORMATION: VR4765, Ligation of NP from 4762 into VR10682

<400> SEQUENCE: 96

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatggt gcactctcag tacaatctgc tctgatgccg catagttaag ccagtatctg    240

ctccctgctt gtgtgttgga ggtcgctgag tagtgcgcga gcaaaattta agctacaaca    300

aggcaaggct tgaccgacaa ttgcatgaag aatctgctta gggttaggcg ttttgcgctg    360

cttcgcgatg tacgggccag atatacgcgt atctgagggg actagggtgt gtttaggcga    420

aaagcggggc ttcggttgta cgcggttagg agtcccctca ggatatagta gtttcgcttt    480

tgcataggga gggggaaatg tagtcttatg caatactctt gtagtcttgc aacatggtaa    540

cgatgagtta gcaacatgcc ttacaaggag agaaaaagca ccgtgcatgc cgattggtgg    600

aagtaaggtg gtacgatcgt gccttattag gaaggcaaca gacgggtctg acatggattg    660

gacgaaccac tgaattccgc attgcagaga tattgtattt aagtgcctag ctcgatactc    720

tagacgccat ttgaccattc accacattgg tgtgcacctc caagcttccg tcaccgtcgt    780

cgacacgtgt gatcagatat cgaattcgcc accatggcca gccagggcac caagagaagc    840

tacgagcaga tggagaccga cggcgagaga cagaacgcca ccgagatcag agccagcgtg    900

ggcaagatga tcgacggcat cggcagattc tacatccaga tgtgcaccga gctgaagctg    960

agcgactacg agggcagact gatccagaac agcctgacca tcgagagaat ggtgctgagc   1020

gccttcgacg agagaagaaa cagatacctg gaggagcacc ccagcgccgg caaggacccc   1080

aagaagaccg gcggccccat ctacagaaga gtggacggca agtggatgag agagctggtg   1140

ctgtacgaca aggaggagat cagaagaatc tggagacagg ccaacaacgg cgaggacgcc   1200

accgccggcc tgacccacat gatgatctgg cacagcaacc tgaacgacac cacctaccag   1260

agaaccagag ccctggtgcg gaccggcatg gaccccagaa tgtgcagcct gatgcagggc   1320

agcaccctgc ccagaagaag cggcgccgcc ggcgccgccg tgaagggcat cggcaccatg   1380

gtgatggagc tgatcagaat gatcaagaga ggcatcaacg acagaaactt ctggagaggc   1440

gagaacggca gaaagaccag aagcgcctac gagagaatgt gcaacatcct gaagggcaag   1500

ttccagaccg ccgcccagag agccatgatg gaccaggtcc gggagagcag aaaccccggc   1560

aacgccgaga tcgaggacct gatcttcctg gccagaagcg ccctgatcct gagaggcagc   1620

gtggcccaca agagctgcct gcccgcctgc gtgtacggcc ccgccgtgag cagcggctac   1680

gacttcgaga aggagggcta cagcctggtg ggcatcgacc ccttcaagct gctgcagaac   1740

agccaggtgt acagcctgat cagacccaac gagaaccccg cccacaagag ccagctggtg   1800

tggatggcct gccacagcgc cgccttcgag gacctgagac tgctgagctt catcagaggc   1860

accaaggtgt cccccagagg caagctgagc accagaggcg tgcagatcgc cagcaacgag   1920

aacatggaca acatgggcag cagcaccctg gagctgagaa gcagatactg ggccatcaga   1980
```

-continued

```
accagaagcg gcggcaacac caaccagcag agagccagcg ccggccagat cagcgtgcag   2040
cccaccttca gcgtgcagag aaacctgccc ttcgagaaga gcaccgtgat ggccgccttc   2100
accggcaaca ccgagggcag aaccagcgac atgagagccg agatcatcag aatgatggag   2160
ggcgccaagc ccgaggaggt gtccttcaga ggcagaggcg tgttcgagct gagcgacgag   2220
aaggccacca accccatcgt gcctagcttc gacatgagca acgagggcag ctacttcttc   2280
ggcgacaacg ccgaggagta cgacaactga tcagtcgacc acatcgcggc cgctctagac   2340
caggcgcctg gatccagatc tgctgtgcct tctagttgcc agccatctgt tgtttgcccc   2400
tcccccgtgc cttccttgac cctggaaggt gccactccca ctgtcctttc ctaataaaat   2460
gaggaaattg catcgcattg tctgagtagg tgtcattcta ttctgggggg tggggtgggg   2520
caggacagca agggggagga ttgggaagac aatagcaggc atgctgggga tgcggtgggc   2580
tctatgggta cccaggtgct gaagaattga cccggttcct cctgggccag aaagaagcag   2640
gcacatcccc ttctctgtga cacaccctgt ccacgcccct ggttcttagt tccagcccca   2700
ctcataggac actcatagct caggagggct ccgccttcaa tcccacccgc taaagtactt   2760
ggagcggtct ctccctccct catcagccca ccaaaccaaa cctagcctcc aagagtggga   2820
agaaattaaa gcaagatagg ctattaagtg cagagggaga gaaaatgcct ccaacatgtg   2880
aggaagtaat gagagaaatc atagaatttc ttccgcttcc tcgctcactg actcgctgcg   2940
ctcggtcgtt cggctgcggc gagcggtatc agctcactca aaggcggtaa tacggttatc   3000
cacagaatca ggggataacg caggaaagaa catgtgagca aaaggccagc aaaaggccag   3060
gaaccgtaaa aaggccgcgt tgctggcgtt tttccatagg ctccgccccc ctgacgagca   3120
tcacaaaaat cgacgctcaa gtcagaggtg gcgaaacccg acaggactat aaagatacca   3180
ggcgtttccc cctggaagct ccctcgtgcg ctctcctgtt ccgaccctgc cgcttaccgg   3240
atacctgtcc gcctttctcc cttcgggaag cgtggcgctt tctcatagct cacgctgtag   3300
gtatctcagt tcggtgtagg tcgttcgctc caagctgggc tgtgtgcacg aaccccccgt   3360
tcagcccgac cgctgcgcct tatccggtaa ctatcgtctt gagtccaacc cggtaagaca   3420
cgacttatcg ccactggcag cagccactgg taacaggatt agcagagcga ggtatgtagg   3480
cggtgctaca gagttcttga agtggtggcc taactacggc tacactagaa gaacagtatt   3540
tggtatctgc gctctgctga agccagttac cttcggaaaa agagttggta gctcttgatc   3600
cggcaaacaa accaccgctg gtagcggtgg tttttttgtt tgcaagcagc agattacgcg   3660
cagaaaaaaa ggatctcaag aagatccttt gatcttttct acggggtctg acgctcagtg   3720
gaacgaaaac tcacgttaag ggattttggt catgagatta tcaaaaagga tcttcaccta   3780
gatcctttta aattaaaaat gaagttttaa atcaatctaa agtatatatg agtaaacttg   3840
gtctgacagt taccaatgct taatcagtga ggcacctatc tcagcgatct gtctatttcg   3900
ttcatccata gttgcctgac tcgggggggg ggggcgctga ggtctgcctc gtgaagaagg   3960
tgttgctgac tcataccagg cctgaatcgc cccatcatcc agccagaaag tgagggagcc   4020
acggttgatg agagctttgt tgtaggtgga ccagttggtg attttgaact tttgctttgc   4080
cacggaacgg tctgcgttgt cgggaagatg cgtgatctga tccttcaact cagcaaaagt   4140
tcgatttatt caacaaagcc gccgtcccgt caagtcagcg taatgctctg ccagtgttac   4200
aaccaattaa ccaattctga ttagaaaaac tcatcgagca tcaaatgaaa ctgcaattta   4260
ttcatatcag gattatcaat accatatttt tgaaaaagcc gtttctgtaa tgaaggagaa   4320
aactcaccga ggcagttcca taggatggca agatcctggt atcggtctgc gattccgact   4380
```

```
cgtccaacat caatacaacc tattaatttc ccctcgtcaa aaataaggtt atcaagtgag   4440

aaatcaccat gagtgacgac tgaatccggt gagaatggca aaagcttatg catttctttc   4500

cagacttgtt caacaggcca gccattacgc tcgtcatcaa aatcactcgc atcaaccaaa   4560

ccgttattca ttcgtgattg cgcctgagcg agacgaaata cgcgatcgct gttaaaagga   4620

caattacaaa caggaatcga atgcaaccgg cgcaggaaca ctgccagcgc atcaacaata   4680

ttttcacctg aatcaggata ttcttctaat acctggaatg ctgttttccc ggggatcgca   4740

gtggtgagta accatgcatc atcaggagta cggataaaat gcttgatggt cggaagaggc   4800

ataaattccg tcagccagtt tagtctgacc atctcatctg taacatcatt ggcaacgcta   4860

cctttgccat gtttcagaaa caactctggc gcatcgggct tcccatacaa tcgatagatt   4920

gtcgcacctg attgcccgac attatcgcga gcccatttat acccatataa atcagcatcc   4980

atgttggaat ttaatcgcgg cctcgagcaa gacgtttccc gttgaatatg gctcataaca   5040

ccccttgtat tactgtttat gtaagcagac agttttattg ttcatgatga tatattttta   5100

tcttgtgcaa tgtaacatca gagattttga gacacaacgt ggctttcccc cccccccccat  5160

tattgaagca tttatcaggg ttattgtctc atgagcggat acatatttga atgtatttag   5220

aaaaataaac aaataggggt tccgcgcaca tttccccgaa aagtgccacc tgacgtctaa   5280

gaaaccatta ttatcatgac attaacctat aaaaataggc gtatcacgag gccctttcgt   5340

c                                                                   5341
```

<210> SEQ ID NO 97
<211> LENGTH: 7798
<212> TYPE: DNA
<213> ORGANISM: Artificial sequence
<220> FEATURE:
<223> OTHER INFORMATION: VR4766, Ligation of Seg7 into VR4762

<400> SEQUENCE: 97

```
tggccattgc atacgttgta tccatatcat aatatgtaca tttatattgg ctcatgtcca     60

acattaccgc catgttgaca ttgattattg actagttatt aatagtaatc aattacgggg    120

tcattagttc atagcccata tatggagttc cgcgttacat aacttacggt aaatggcccg    180

cctggctgac cgcccaacga cccccgccca ttgacgtcaa taatgacgta tgttcccata    240

gtaacgccaa tagggacttt ccattgacgt caatgggtgg agtatttacg gtaaactgcc    300

cacttggcag tacatcaagt gtatcatatg ccaagtacgc cccctattga cgtcaatgac    360

ggtaaatggc ccgcctggca ttatgcccag tacatgacct tatgggactt tcctacttgg    420

cagtacatct acgtattagt catcgctatt accatggtga tgcggttttg gcagtacatc    480

aatgggcgtg gatagcggtt tgactcacgg ggatttccaa gtctccaccc cattgacgtc    540

aatgggagtt tgttttggca ccaaaatcaa cgggactttc caaaatgtcg taacaactcc    600

gccccattga cgcaaatggg cggtaggcgt gtacggtggg aggtctatat aagcagagct    660

cgtttagtga accgtcagat cgcctggaga cgccatccac gctgttttga cctccataga    720

agacaccggg accgatccag cctccgcggc cgggaacggt gcattggaac gcggattccc    780

cgtgccaaga gtgacgtaag taccgcctat agactctata ggcacacccc tttggctctt    840

atgcatgcta tactgttttt ggcttggggc ctatacaccc ccgcttcctt atgctatagg    900

tgatggtata gcttagccta taggtgtggg ttattgacca ttattgacca ctcccctatt    960

ggtgacgata ctttccatta ctaatccata acatggctct ttgccacaac tatctctatt   1020

ggctatatgc caatactctg tccttcagag actgacacgg actctgtatt tttacaggat   1080
```

-continued

```
ggggtcccat ttattattta caaattcaca tatacaacaa cgccgtcccc cgtgcccgca   1140
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catggccagc cagggcacca agagaagcta   1680
cgagcagatg gagaccgacg gcgagagaca gaacgccacc gagatcagag ccagcgtggg   1740
caagatgatc gacggcatcg gcagattcta catccagatg tgcaccgagc tgaagctgag   1800
cgactacgag ggcagactga tccagaacag cctgaccatc gagagaatgg tgctgagcgc   1860
cttcgacgag agaagaaaca gatacctgga ggagcacccc agcgccggca aggaccccaa   1920
gaagaccggc ggccccatct acagaagagt ggacggcaag tggatgagag agctggtgct   1980
gtacgacaag gaggagatca gaagaatctg gagacaggcc aacaacggcg aggacgccac   2040
cgccggcctg acccacatga tgatctggca cagcaacctg aacgacacca cctaccagag   2100
aaccagagcc ctggtgcgga ccggcatgga ccccagaatg tgcagcctga tgcagggcag   2160
caccctgccc agaagaagcg gcgccgccgg cgccgccgtg aagggcatcg gcaccatggt   2220
gatggagctg atcagaatga tcaagagagg catcaacgac agaaacttct ggagaggcga   2280
gaacggcaga aagaccagaa gcgcctacga gagaatgtgc aacatcctga agggcaagtt   2340
ccagaccgcc gcccagagag ccatgatgga ccaggtccgg gagagcagaa accccggcaa   2400
cgccgagatc gaggacctga tcttcctggc cagaagcgcc ctgatcctga gaggcagcgt   2460
ggcccacaag agctgcctgc ccgcctgcgt gtacggcccc gccgtgagca gcggctacga   2520
cttcgagaag gagggctaca gcctggtggg catcgacccc ttcaagctgc tgcagaacag   2580
ccaggtgtac agcctgatca gacccaacga gaaccccgcc cacaagagcc agctggtgtg   2640
gatggcctgc cacagcgccg ccttcgagga cctgagactg ctgagcttca tcagaggcac   2700
caaggtgtcc cccagaggca agctgagcac cagaggcgtg cagatcgcca gcaacgagaa   2760
catggacaac atgggcagca gcaccctgga gctgagaagc agatactggg ccatcagaac   2820
cagaagcggc ggcaacacca accagcagag agccagcgcc ggccagatca gcgtgcagcc   2880
caccttcagc gtgcagagaa acctgccctt cgagaagagc accgtgatgg ccgccttcac   2940
cggcaacacc gagggcagaa ccagcgacat gagagccgag atcatcagaa tgatggaggg   3000
cgccaagccc gaggaggtgt ccttcagagg cagaggcgtg ttcgagctga gcgacgagaa   3060
ggccaccaac cccatcgtgc ctagcttcga catgagcaac gagggcagct acttcttcgg   3120
cgacaacgcc gaggagtacg acaactgatc agtcgaccac gtgtgatcca gatctacttc   3180
tggctaataa aagatcagag ctctagagat ctgtgtgttg gttttttgtg tggtactctt   3240
ccgcttcctc gctcactgac tcgctgcgct cggtcgttcg gctgcggcga gcggtatcag   3300
ctcactcaaa ggcggtaata cggttatcca cagaatcagg ggataacgca ggaaagaaca   3360
tgtgagcaaa aggccagcaa aaggccagga accgtaaaaa ggccgcgttg ctggcgtttt   3420
tccataggct ccgcccccct gacgagcatc acaaaaatcg acgctcaagt cagaggtggc   3480
```

gaaacccgac aggactataa agataccagg cgtttccccc tggaagctcc ctcgtgcgct 3540
ctcctgttcc gaccctgccg cttaccggat acctgtccgc ctttctccct tcgggaagcg 3600
tggcgctttc tcatagctca cgctgtaggt atctcagttc ggtgtaggtc gttcgctcca 3660
agctgggctg tgtgcacgaa ccccccgttc agcccgaccg ctgcgcctta tccggtaact 3720
atcgtcttga gtccaacccg gtaagacacg acttatcgcc actggcagca gccactggta 3780
acaggattag cagagcgagg tatgtaggcg gtgctacaga gttcttgaag tggtggccta 3840
actacggcta cactagaaga acagtatttg gtatctgcgc tctgctgaag ccagttacct 3900
tcggaaaaag agttggtagc tcttgatccg gcaaacaaac caccgctggt agcggtggtt 3960
tttttgtttg caagcagcag attacgcgca gaaaaaaagg atctcaagaa gatcctttga 4020
tcttttctac ggggtctgac gctcagtgga acgaaaactc acgttaaggg attttggtca 4080
tgagattatc aaaaaggatc ttcacctaga tccttttaaa ttaaaaatga agttttaaat 4140
caatctaaag tatatatgag taaacttggt ctgacagtta ccaatgctta atcagtgagg 4200
cacctatctc agcgatctgt ctatttcgtt catccatagt tgcctgactc gggggggggg 4260
ggcgctgagg tctgcctcgt gaagaaggtg ttgctgactc ataccaggcc tgaatcgccc 4320
catcatccag ccagaaagtg agggagccac ggttgatgag agctttgttg taggtggacc 4380
agttggtgat tttgaacttt tgctttgcca cggaacggtc tgcgttgtcg ggaagatgcg 4440
tgatctgatc cttcaactca gcaaaagttc gatttattca acaaagccgc cgtcccgtca 4500
agtcagcgta atgctctgcc agtgttacaa ccaattaacc aattctgatt agaaaaactc 4560
atcgagcatc aaatgaaact gcaatttatt catatcagga ttatcaatac catatttttg 4620
aaaaagccgt ttctgtaatg aaggagaaaa ctcaccgagg cagttccata ggatggcaag 4680
atcctggtat cggtctgcga ttccgactcg tccaacatca atacaaccta ttaatttccc 4740
ctcgtcaaaa ataaggttat caagtgagaa atcaccatga gtgacgactg aatccggtga 4800
gaatggcaaa agcttatgca tttctttcca gacttgttca acaggccagc cattacgctc 4860
gtcatcaaaa tcactcgcat caaccaaacc gttattcatt cgtgattgcg cctgagcgag 4920
acgaaatacg cgatcgctgt taaaaggaca attacaaaca ggaatcgaat gcaaccggcg 4980
caggaacact gccagcgcat caacaatatt ttcacctgaa tcaggatatt cttctaatac 5040
ctggaatgct gttttcccgg ggatcgcagt ggtgagtaac catgcatcat caggagtacg 5100
gataaaatgc ttgatggtcg gaagaggcat aaattccgtc agccagttta gtctgaccat 5160
ctcatctgta acatcattgg caacgctacc tttgccatgt ttcagaaaca actctggcgc 5220
atcgggcttc ccatacaatc gatagattgt cgcacctgat tgcccgacat tatcgcgagc 5280
ccatttatac ccatataaat cagcatccat gttggaattt aatcgcggcc tcgagcaaga 5340
cgtttcccgt tgaatatggc tcataacacc ccttgtatta ctgtttatgt aagcagacag 5400
ttttattgtt catgatgata tatttttatc ttgtgcaatg taacatcaga gattttgaga 5460
cactatggtg cactctcagt acaatctgct ctgatgccgc atagttaagc cagtatctgc 5520
tccctgcttg tgtgttggag gtcgctgagt agtgcgcgag caaaatttaa gctacaacaa 5580
ggcaaggctt gaccgacaat tgcatgaaga atctgcttag ggttaggcgt tttgcgctgc 5640
ttcgcgatgt acgggccaga tatacgcgta tctgagggga ctagggtgtg tttaggcgaa 5700
aagcggggct tcggttgtac gcggttagga gtcccctcag gatatagtag tttcgctttt 5760
gcatagggag ggggaaatgt agtcttatgc aatactcttg tagtcttgca acatggtaac 5820
gatgagttag caacatgcct tacaaggaga gaaaaagcac cgtgcatgcc gattggtgga 5880
agtaaggtgg tacgatcgtg ccttattagg aaggcaacag acgggtctga catggattgg 5940
acgaaccact gaattccgca ttgcagagat attgtattta agtgcctagc tcgatactct 6000
agacgccatt tgaccattca ccacattggt gtgcacctcc aagcttccgt caccgtcgtc 6060
gacacgtgtg atcagatatc gaattcgcca ccatgagcct tctaaccgag gtcgaaacgt 6120
atgttctctc tatcgttcca tcaggccccc tcaaagccga aatcgcgcag agacttgaag 6180
atgtctttgc tgggaaaaac acagatcttg aggctctcat ggaatggcta aagacaagac 6240
caatcctgtc acctctgact aaggggattt tggggtttgt gttcacgctc accgtgccca 6300
gtgagcgagg actgcagcgt agacgctttg tccaaaatgc cctcaatggg aatggggatc 6360
caaataacat ggacagagca gttaaactat atagaaaact taagagggag attacattcc 6420
atggggccaa agaaatagca ctcagttatt ctgctggtgc acttgccagt tgcatgggcc 6480
tcatatacaa cagaatgggg gctgtaacca ctgaagtggc ctttggcctg gtatgtgcaa 6540
catgtgaaca gattgctgac tcccagcaca ggtctcatag gcaaatggtg gcaacaacca 6600
atccattaat aaggcatgag aacagaatgg ttttggccag cactacagct aaggctatgg 6660
agcaaatggc tggatcaagt gagcaggcag cggaggccat ggaaattgct agtcaggcca 6720
ggcaaatggt gcaggcaatg agagccattg ggactcatcc tagctccagt gctggtctaa 6780
aagatgatct tcttgaaaat ttgcagacct atcagaaacg aatgggggtg cagatgcaac 6840
gattcaagtg acccgcttgt tgttgctgcg agtatcattg ggatcttgca cttgatattg 6900
tggattcttg atcgtctttt tttcaaatgc atctatcgac tcttcaaaca cggtctgaaa 6960
agagggcctt ctacggaagg agtacctgag tctatgaggg aagaatatcg aaaggaacag 7020
cagaatgctg tggatgctga cgacagtcat tttgtcagca tagagctgga gtaatcagtc 7080
gaccacatcg cggccgctct agaccaggcg cctggatcca gatctgctgt gccttctagt 7140
tgccagccat ctgttgtttg cccctccccc gtgccttcct tgaccctgga aggtgccact 7200
cccactgtcc tttcctaata aaatgaggaa attgcatcgc attgtctgag taggtgtcat 7260
tctattctgg ggggtggggt ggggcaggac agcaaggggg aggattggga agacaatagc 7320
aggcatgctg gggatgcggt gggctctatg ggtggctttc cccccccccc cattattgaa 7380
gcatttatca gggttattgt ctcatgagcg gatacatatt tgaatgtatt tagaaaaata 7440
aacaaatagg ggttccgcgc acatttcccc gaaaagtgcc acctgacgtc taagaaacca 7500
ttattatcat gacattaacc tataaaaata ggcgtatcac gaggcccttt cgtctcgcgc 7560
gtttcggtga tgacggtgaa aacctctgac acatgcagct cccggagacg gtcacagctt 7620
gtctgtaagc ggatgccggg agcagacaag cccgtcaggg cgcgtcagcg ggtgttggcg 7680
ggtgtcgggg ctggcttaac tatgcggcat cagagcagat tgtactgaga gtgcaccata 7740
tgcggtgtga aataccgcac agatgcgtaa ggagaaaata ccgcatcaga ttggctat 7798

<210> SEQ ID NO 98
<211> LENGTH: 7798
<212> TYPE: DNA
<213> ORGANISM: Artificial sequence
<220> FEATURE:
<223> OTHER INFORMATION: VR4767, Ligation of Inverted RSVSeg7 into VR4762

<400> SEQUENCE: 98
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180

```
cctggctgac cgcccaacga cccccgccca ttgacgtcaa taatgacgta tgttcccata    240
gtaacgccaa tagggacttt ccattgacgt caatgggtgg agtatttacg gtaaactgcc    300
cacttggcag tacatcaagt gtatcatatg ccaagtacgc cccctattga cgtcaatgac    360
ggtaaatggc ccgcctggca ttatgcccag tacatgacct tatgggactt tcctacttgg    420
cagtacatct acgtattagt catcgctatt accatggtga tgcggttttg gcagtacatc    480
aatgggcgtg gatagcggtt tgactcacgg ggatttccaa gtctccaccc cattgacgtc    540
aatgggagtt tgttttggca ccaaaatcaa cgggactttc caaaatgtcg taacaactcc    600
gccccattga cgcaaatggg cggtaggcgt gtacggtggg aggtctatat aagcagagct    660
cgtttagtga accgtcagat cgcctggaga cgccatccac gctgttttga cctccataga    720
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctcccctatt    960
ggtgacgata ctttccatta ctaatccata acatggctct ttgccacaac tatctctatt   1020
ggctatatgc caatactctg tccttcagag actgacacgg actctgtatt tttacaggat   1080
ggggtcccat ttattattta caaattcaca tatacaacaa cgccgtcccc cgtgcccgca   1140
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catggccagc cagggcacca agagaagcta   1680
cgagcagatg gagaccgacg gcgagagaca gaacgccacc gagatcagag ccagcgtggg   1740
caagatgatc gacggcatcg gcagattcta catccagatg tgcaccgagc tgaagctgag   1800
cgactacgag ggcagactga tccagaacag cctgaccatc gagagaatgg tgctgagcgc   1860
cttcgacgag agaagaaaca gatacctgga ggagcacccc agcgccggca aggaccccaa   1920
gaagaccggc ggccccatct acagaagagt ggacggcaag tggatgagag agctggtgct   1980
gtacgacaag gaggagatca gaagaatctg gagacaggcc aacaacggcg aggacgccac   2040
cgccggcctg acccacatga tgatctggca cagcaacctg aacgacacca cctaccagag   2100
aaccagagcc ctggtgcgga ccggcatgga ccccagaatg tgcagcctga tgcagggcag   2160
caccctgccc agaagaagcg gcgccgccgg cgccgccgtg aagggcatcg gcaccatggt   2220
gatggagctg atcagaatga tcaagagagg catcaacgac agaaacttct ggagaggcga   2280
gaacggcaga aagaccagaa gcgcctacga gagaatgtgc aacatcctga agggcaagtt   2340
ccagaccgcc gcccagagag ccatgatgga ccaggtccgg gagagcagaa accccggcaa   2400
cgccgagatc gaggacctga tcttcctggc cagaagcgcc ctgatcctga gaggcagcgt   2460
ggcccacaag agctgcctgc ccgcctgcgt gtacggcccc gccgtgagca gcggctacga   2520
cttcgagaag gagggctaca gcctggtggg catcgacccc ttcaagctgc tgcagaacag   2580
```

-continued

```
ccaggtgtac agcctgatca gacccaacga gaaccccgcc cacaagagcc agctggtgtg   2640
gatggcctgc cacagcgccg ccttcgagga cctgagactg ctgagcttca tcagaggcac   2700
caaggtgtcc cccagaggca agctgagcac cagaggcgtg cagatcgcca gcaacgagaa   2760
catggacaac atgggcagca gcaccctgga gctgagaagc agatactggg ccatcagaac   2820
cagaagcggc ggcaacacca accagcagag agccagcgcc ggccagatca gcgtgcagcc   2880
caccttcagc gtgcagagaa acctgccctt cgagaagagc accgtgatgg ccgccttcac   2940
cggcaacacc gagggcagaa ccagcgacat gagagccgag atcatcagaa tgatggaggg   3000
cgccaagccc gaggaggtgt ccttcagagg cagaggcgtg ttcgagctga gcgacgagaa   3060
ggccaccaac cccatcgtgc ctagcttcga catgagcaac gagggcagct acttcttcgg   3120
cgacaacgcc gaggagtacg acaactgatc agtcgaccac gtgtgatcca gatctacttc   3180
tggctaataa aagatcagag ctctagagat ctgtgtgttg gtttttttgtg tggtactctt   3240
ccgcttcctc gctcactgac tcgctgcgct cggtcgttcg gctgcggcga gcggtatcag   3300
ctcactcaaa ggcggtaata cggttatcca cagaatcagg ggataacgca ggaaagaaca   3360
tgtgagcaaa aggccagcaa aaggccagga accgtaaaaa ggccgcgttg ctggcgtttt   3420
tccataggct ccgcccccct gacgagcatc acaaaaatcg acgctcaagt cagaggtggc   3480
gaaacccgac aggactataa agataccagg cgtttccccc tggaagctcc ctcgtgcgct   3540
ctcctgttcc gaccctgccg cttaccggat acctgtccgc ctttctccct tcgggaagcg   3600
tggcgctttc tcatagctca cgctgtaggt atctcagttc ggtgtaggtc gttcgctcca   3660
agctgggctg tgtgcacgaa ccccccgttc agcccgaccg ctgcgcctta tccggtaact   3720
atcgtcttga gtccaacccg gtaagacacg acttatcgcc actggcagca gccactggta   3780
acaggattag cagagcgagg tatgtaggcg gtgctacaga gttcttgaag tggtggccta   3840
actacggcta cactagaaga acagtatttg gtatctgcgc tctgctgaag ccagttacct   3900
tcggaaaaag agttggtagc tcttgatccg gcaaacaaac caccgctggt agcggtggtt   3960
tttttgtttg caagcagcag attacgcgca gaaaaaaagg atctcaagaa gatcctttga   4020
tcttttctac ggggtctgac gctcagtgga acgaaaactc acgttaaggg attttggtca   4080
tgagattatc aaaaaggatc ttcacctaga tccttttaaa ttaaaaatga agttttaaat   4140
caatctaaag tatatatgag taaacttggt ctgacagtta ccaatgctta atcagtgagg   4200
cacctatctc agcgatctgt ctatttcgtt catccatagt tgcctgactc gggggggggg   4260
ggcgctgagg tctgcctcgt gaagaaggtg ttgctgactc ataccaggcc tgaatcgccc   4320
catcatccag ccagaaagtg agggagccac ggttgatgag agctttgttg taggtggacc   4380
agttggtgat tttgaacttt tgctttgcca cggaacggtc tgcgttgtcg ggaagatgcg   4440
tgatctgatc cttcaactca gcaaaagttc gatttattca acaaagccgc cgtcccgtca   4500
agtcagcgta atgctctgcc agtgttacaa ccaattaacc aattctgatt agaaaaactc   4560
atcgagcatc aaatgaaact gcaatttatt catatcagga ttatcaatac catatttttg   4620
aaaaagccgt ttctgtaatg aaggagaaaa ctcaccgagg cagttccata ggatggcaag   4680
atcctggtat cggtctgcga ttccgactcg tccaacatca atacaaccta ttaatttccc   4740
ctcgtcaaaa ataaggttat caagtgagaa atcaccatga gtgacgactg aatccggtga   4800
gaatggcaaa agcttatgca tttctttcca gacttgttca acaggccagc cattacgctc   4860
gtcatcaaaa tcactcgcat caaccaaacc gttattcatt cgtgattgcg cctgagcgag   4920
acgaaatacg cgatcgctgt taaaaggaca attacaaaca ggaatcgaat gcaaccggcg   4980
```

-continued

```
caggaacact gccagcgcat caacaatatt ttcacctgaa tcaggatatt cttctaatac   5040
ctggaatgct gttttcccgg ggatcgcagt ggtgagtaac catgcatcat caggagtacg   5100
gataaaatgc ttgatggtcg gaagaggcat aaattccgtc agccagttta gtctgaccat   5160
ctcatctgta acatcattgg caacgctacc tttgccatgt ttcagaaaca actctggcgc   5220
atcgggcttc ccatacaatc gatagattgt cgcacctgat tgcccgacat tatcgcgagc   5280
ccatttatac ccatataaat cagcatccat gttggaattt aatcgcggcc tcgagcaaga   5340
cgtttcccgt tgaatatggc tcataacacc ccttgtatta ctgtttatgt aagcagacag   5400
ttttattgtt catgatgata tatttttatc ttgtgcaatg taacatcaga gattttgaga   5460
cacccataga gcccaccgca tccccagcat gcctgctatt gtcttcccaa tcctccccct   5520
tgctgtcctg ccccacccca ccccccagaa tagaatgaca cctactcaga caatgcgatg   5580
caatttcctc attttattag gaaaggacag tgggagtggc accttccagg gtcaaggaag   5640
gcacggggga ggggcaaaca acagatggct ggcaactaga aggcacagca gatctggatc   5700
caggcgcctg gtctagagcg gccgcgatgt ggtcgactga ttactccagc tctatgctga   5760
caaaatgact gtcgtcagca tccacagcat tctgctgttc ctttcgatat tcttccctca   5820
tagactcagg tactccttcc gtagaaggcc ctcttttcag accgtgtttg aagagtcgat   5880
agatgcattt gaaaaaaaga cgatcaagaa tccacaatat caagtgcaag atcccaatga   5940
tactcgcagc aacaacaagc gggtcacttg aatcgttgca tctgcacccc cattcgtttc   6000
tgataggtct gcaaattttc aagaagatca tcttttagac cagcactgga gctaggatga   6060
gtcccaatgg ctctcattgc ctgcaccatt tgcctggcct gactagcaat ttccatggcc   6120
tccgctgcct gctcacttga tccagccatt tgctccatag ccttagctgt agtgctggcc   6180
aaaaccattc tgttctcatg ccttattaat ggattggttg ttgccaccat ttgcctatga   6240
gacctgtgct gggagtcagc aatctgttca catgttgcac ataccaggcc aaaggccact   6300
tcagtggtta cagcccccat tctgttgtat atgaggccca tgcaactggc aagtgcacca   6360
gcagaataac tgagtgctat ttctttggcc ccatggaatg taatctccct cttaagtttt   6420
ctatatagtt taactgctct gtccatgtta tttggatccc cattcccatt gagggcattt   6480
tggacaaagc gtctacgctg cagtcctcgc tcactgggca cggtgagcgt gaacacaaac   6540
cccaaaatcc ccttagtcag aggtgacagg attggtcttg tctttagcca ttccatgaga   6600
gcctcaagat ctgtgttttt cccagcaaag acatcttcaa gtctctgcgc gatttcggct   6660
ttgagggggc ctgatggaac gatagagaga acatacgttt cgacctcggt tagaaggctc   6720
atggtggcga attcgatatc tgatcacacg tgtcgacgac ggtgacggaa gcttggaggt   6780
gcacaccaat gtggtgaatg gtcaaatggc gtctagagta tcgagctagg cacttaaata   6840
caatatctct gcaatgcgga attcagtggt tcgtccaatc catgtcagac ccgtctgttg   6900
ccttcctaat aaggcacgat cgtaccacct tacttccacc aatcggcatg cacggtgctt   6960
tttctctcct tgtaaggcat gttgctaact catcgttacc atgttgcaag actacaagag   7020
tattgcataa gactacattt ccccctccct atgcaaaagc gaaactacta tatcctgagg   7080
ggactcctaa ccgcgtacaa ccgaagcccc gcttttcgcc taaacacacc ctagtcccct   7140
cagatacgcg tatatctggc ccgtacatcg cgaagcagcg caaaacgcct aaccctaagc   7200
agattcttca tgcaattgtc ggtcaagcct tgccttgttg tagcttaaat tttgctcgcg   7260
cactactcag cgacctccaa cacacaagca gggagcagat actggcttaa ctatgcggca   7320
tcagagcaga ttgtactgag agtgcaccat agtggctttc cccccccccc cattattgaa   7380
```

gcatttatca gggttattgt ctcatgagcg gatacatatt tgaatgtatt tagaaaaata 7440
aacaaatagg ggttccgcgc acatttcccc gaaaagtgcc acctgacgtc taagaaacca 7500
ttattatcat gacattaacc tataaaaata ggcgtatcac gaggcccttt cgtctcgcgc 7560
gtttcggtga tgacggtgaa aacctctgac acatgcagct cccggagacg gtcacagctt 7620
gtctgtaagc ggatgccggg agcagacaag cccgtcaggg cgcgtcagcg ggtgttggcg 7680
ggtgtcgggg ctggcttaac tatgcggcat cagagcagat tgtactgaga gtgcaccata 7740
tgcggtgtga aataccgcac agatgcgtaa ggagaaaata ccgcatcaga ttggctat 7798

<210> SEQ ID NO 99
<211> LENGTH: 7798
<212> TYPE: DNA
<213> ORGANISM: Artificial sequence
<220> FEATURE:
<223> OTHER INFORMATION: VR4768, Ligation of RSVNP into VR4756

<400> SEQUENCE: 99
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960
ggtgacgata ctttccatta ctaatccata acatggctct ttgccacaac tatctctatt 1020
ggctatatgc caatactctg tccttcagag actgacacgg actctgtatt tttacaggat 1080
ggggtcccat ttattattta caaattcaca tatacaacaa cgccgtcccc cgtgcccgca 1140
gtttttatta aacatagcgt gggatctcca cgcgaatctc gggtacgtgt tccggacatg 1200
ggctcttctc cggtagcggc ggagcttcca catccgagcc ctggtcccat gcctccagcg 1260
gctcatggtc gctcggcagc tccttgctcc taacagtgga ggccagactt aggcacagca 1320
caatgcccac caccaccagt gtgccgcaca aggccgtggc ggtagggtat gtgtctgaaa 1380
atgagcgtgg agattgggct cgcacggctg acgcagatgg aagacttaag gcagcggcag 1440
aagaagatgc aggcagctga gttgttgtat tctgataaga gtcagaggta actcccgttg 1500
cggtgctgtt aacggtggag ggcagtgtag tctgagcagt actcgttgct gccgcgcgcg 1560
ccaccagaca taatagctga cagactaaca gactgttcct ttccatgggt cttttctgca 1620
gtcaccgtcg tcggatatcg aattcgccac catgagcctt ctaaccgagg tcgaaacgta 1680

-continued

```
tgttctctct atcgttccat caggcccccct caaagccgaa atcgcgcaga gacttgaaga   1740
tgtctttgct gggaaaaaca cagatcttga ggctctcatg gaatggctaa agacaagacc   1800
aatcctgtca cctctgacta aggggatttt ggggtttgtg ttcacgctca ccgtgcccag   1860
tgagcgagga ctgcagcgta gacgctttgt ccaaaatgcc ctcaatggga atggggatcc   1920
aaataacatg gacagagcag ttaaactata tagaaaactt aagagggaga ttacattcca   1980
tggggccaaa gaaatagcac tcagttattc tgctggtgca cttgccagtt gcatgggcct   2040
catatacaac agaatggggg ctgtaaccac tgaagtggcc tttggcctgg tatgtgcaac   2100
atgtgaacag attgctgact cccagcacag gtctcatagg caaatggtgg caacaaccaa   2160
tccattaata aggcatgaga acagaatggt tttggccagc actacagcta aggctatgga   2220
gcaaatggct ggatcaagtg agcaggcagc ggaggccatg gaaattgcta gtcaggccag   2280
gcaaatggtg caggcaatga gagccattgg gactcatcct agctccagtg ctggtctaaa   2340
agatgatctt cttgaaaatt tgcagaccta tcagaaacga atgggggtgc agatgcaacg   2400
attcaagtga cccgcttgtt gttgctgcga gtatcattgg gatcttgcac ttgatattgt   2460
ggattcttga tcgtcttttt ttcaaatgca tctatcgact cttcaaacac ggtctgaaaa   2520
gagggccttc tacggaagga gtacctgagt ctatgaggga agaatatcga aaggaacagc   2580
agaatgctgt ggatgctgac gacagtcatt ttgtcagcat agagctggag taatcagtcg   2640
accacgtgtg atccagatct acttctggct aataaaagat cagagctcta gagatctgtg   2700
tgttggtttt ttgtgtggta ctcttccgct tcctcgctca ctgactcgct gcgctcggtc   2760
gttcggctgc ggcgagcggt atcagctcac tcaaaggcgg taatacggtt atccacagaa   2820
tcaggggata acgcaggaaa gaacatgtga gcaaaaggcc agcaaaaggc caggaaccgt   2880
aaaaaggccg cgttgctggc gtttttccat aggctccgcc cccctgacga gcatcacaaa   2940
aatcgacgct caagtcagag gtggcgaaac ccgacaggac tataaagata ccaggcgttt   3000
ccccctggaa gctccctcgt gcgctctcct gttccgaccc tgccgcttac cggatacctg   3060
tccgcctttc tcccttcggg aagcgtggcg ctttctcata gctcacgctg taggtatctc   3120
agttcggtgt aggtcgttcg ctccaagctg ggctgtgtgc acgaaccccc cgttcagccc   3180
gaccgctgcg ccttatccgg taactatcgt cttgagtcca acccggtaag acacgactta   3240
tcgccactgg cagcagccac tggtaacagg attagcagag cgaggtatgt aggcggtgct   3300
acagagttct tgaagtggtg gcctaactac ggctacacta gaagaacagt atttggtatc   3360
tgcgctctgc tgaagccagt taccttcgga aaaagagttg gtagctcttg atccggcaaa   3420
caaaccaccg ctggtagcgg tggttttttt gtttgcaagc agcagattac gcgcagaaaa   3480
aaaggatctc aagaagatcc tttgatcttt tctacggggt ctgacgctca gtggaacgaa   3540
aactcacgtt aagggatttt ggtcatgaga ttatcaaaaa ggatcttcac ctagatcctt   3600
ttaaattaaa aatgaagttt taaatcaatc taaagtatat atgagtaaac ttggtctgac   3660
agttaccaat gcttaatcag tgaggcacct atctcagcga tctgtctatt tcgttcatcc   3720
atagttgcct gactcggggg gggggggcgc tgaggtctgc ctcgtgaaga aggtgttgct   3780
gactcatacc aggcctgaat cgccccatca tccagccaga aagtgaggga gccacggttg   3840
atgagagctt tgttgtaggt ggaccagttg gtgattttga acttttgctt tgccacggaa   3900
cggtctgcgt tgtcgggaag atgcgtgatc tgatccttca actcagcaaa agttcgattt   3960
attcaacaaa gccgccgtcc cgtcaagtca gcgtaatgct ctgccagtgt tacaaccaat   4020
taaccaattc tgattagaaa aactcatcga gcatcaaatg aaactgcaat ttattcatat   4080
```

-continued

```
caggattatc aataccatat ttttgaaaaa gccgtttctg taatgaagga gaaaactcac   4140
cgaggcagtt ccataggatg gcaagatcct ggtatcggtc tgcgattccg actcgtccaa   4200
catcaataca acctattaat ttcccctcgt caaaaataag gttatcaagt gagaaatcac   4260
catgagtgac gactgaatcc ggtgagaatg gcaaaagctt atgcatttct ttccagactt   4320
gttcaacagg ccagccatta cgctcgtcat caaaatcact cgcatcaacc aaaccgttat   4380
tcattcgtga ttgcgcctga gcgagacgaa atacgcgatc gctgttaaaa ggacaattac   4440
aaacaggaat cgaatgcaac cggcgcagga acactgccag cgcatcaaca atattttcac   4500
ctgaatcagg atattcttct aatacctgga atgctgtttt cccggggatc gcagtggtga   4560
gtaaccatgc atcatcagga gtacggataa aatgcttgat ggtcggaaga ggcataaatt   4620
ccgtcagcca gtttagtctg accatctcat ctgtaacatc attggcaacg ctacctttgc   4680
catgtttcag aaacaactct ggcgcatcgg gcttcccata caatcgatag attgtcgcac   4740
ctgattgccc gacattatcg cgagcccatt tatacccata taaatcagca tccatgttgg   4800
aatttaatcg cggcctcgag caagacgttt cccgttgaat atggctcata acaccccttg   4860
tattactgtt tatgtaagca gacagtttta ttgttcatga tgatatattt ttatcttgtg   4920
caatgtaaca tcagagattt tgagacacta tggtgcactc tcagtacaat ctgctctgat   4980
gccgcatagt taagccagta tctgctccct gcttgtgtgt tggaggtcgc tgagtagtgc   5040
gcgagcaaaa tttaagctac aacaaggcaa ggcttgaccg acaattgcat gaagaatctg   5100
cttagggtta ggcgttttgc gctgcttcgc gatgtacggg ccagatatac gcgtatctga   5160
ggggactagg gtgtgtttag gcgaaaagcg gggcttcggt tgtacgcggt taggagtccc   5220
ctcaggatat agtagtttcg cttttgcata gggagggga aatgtagtct tatgcaatac    5280
tcttgtagtc ttgcaacatg gtaacgatga gttagcaaca tgccttacaa ggagagaaaa   5340
agcaccgtgc atgccgattg gtggaagtaa ggtggtacga tcgtgcctta ttaggaaggc   5400
aacagacggg tctgacatgg attggacgaa ccactgaatt ccgcattgca gagatattgt   5460
atttaagtgc ctagctcgat actctagacg ccatttgacc attcaccaca ttggtgtgca   5520
cctccaagct tccgtcaccg tcgtcgacac gtgtgatcag atatcgaatt cgccaccatg   5580
gccagccagg gcaccaagag aagctacgag cagatggaga ccgacggcga gagacagaac   5640
gccaccgaga tcagagccag cgtgggcaag atgatcgacg gcatcggcag attctacatc   5700
cagatgtgca ccgagctgaa gctgagcgac tacgagggca gactgatcca gaacagcctg   5760
accatcgaga gaatggtgct gagcgccttc gacgagagaa gaaacagata cctggaggag   5820
caccccagcg ccggcaagga ccccaagaag accggcggcc ccatctacag aagagtggac   5880
ggcaagtgga tgagagagct ggtgctgtac gacaaggagg agatcagaag aatctggaga   5940
caggccaaca acggcgagga cgccaccgcc ggcctgaccc acatgatgat ctggcacagc   6000
aacctgaacg acaccaccta ccagagaacc agagccctgg tgcggaccgg catggacccc   6060
agaatgtgca gcctgatgca gggcagcacc ctgcccagaa gaagcggcgc cgccggcgcc   6120
gccgtgaagg gcatcggcac catggtgatg gagctgatca gaatgatcaa gagaggcatc   6180
aacgacagaa acttctggag aggcgagaac ggcagaaaga ccagaagcgc ctacgagaga   6240
atgtgcaaca tcctgaaggg caagttccag accgccgccc agagagccat gatggaccag   6300
gtccgggaga gcagaaaccc cggcaacgcc gagatcgagg acctgatctt cctggccaga   6360
agcgccctga tcctgagagg cagcgtggcc cacaagagct gcctgcccgc ctgcgtgtac   6420
ggccccgccg tgagcagcgg ctacgacttc gagaaggagg gctacagcct ggtgggcatc   6480
```

gaccccttca agctgctgca gaacagccag gtgtacagcc tgatcagacc caacgagaac 6540
cccgcccaca agagccagct ggtgtggatg gcctgccaca gcgccgcctt cgaggacctg 6600
agactgctga gcttcatcag aggcaccaag gtgtccccca gaggcaagct gagcaccaga 6660
ggcgtgcaga tcgccagcaa cgagaacatg gacaacatgg gcagcagcac cctggagctg 6720
agaagcagat actgggccat cagaaccaga agcggcggca acaccaacca gcagagagcc 6780
agcgccggcc agatcagcgt gcagcccacc ttcagcgtgc agagaaacct gcccttcgag 6840
aagagcaccg tgatggccgc cttcaccggc aacaccgagg gcagaaccag cgacatgaga 6900
gccgagatca tcagaatgat ggagggcgcc aagcccgagg aggtgtcctt cagaggcaga 6960
ggcgtgttcg agctgagcga cgagaaggcc accaacccca tcgtgcctag cttcgacatg 7020
agcaacgagg gcagctactt cttcggcgac aacgccgagg agtacgacaa ctgatcagtc 7080
gaccacatcg cggccgctct agaccaggcg cctggatcca gatctgctgt gccttctagt 7140
tgccagccat ctgttgtttg cccctccccc gtgccttcct tgaccctgga aggtgccact 7200
cccactgtcc tttcctaata aaatgaggaa attgcatcgc attgtctgag taggtgtcat 7260
tctattctgg ggggtggggt ggggcaggac agcaaggggg aggattggga agacaatagc 7320
aggcatgctg gggatgcggt gggctctatg ggtggctttc cccccccccc cattattgaa 7380
gcatttatca gggttattgt ctcatgagcg gatacatatt tgaatgtatt tagaaaaata 7440
aacaaatagg ggttccgcgc acatttcccc gaaaagtgcc acctgacgtc taagaaacca 7500
ttattatcat gacattaacc tataaaaata ggcgtatcac gaggcccttt cgtctcgcgc 7560
gtttcggtga tgacggtgaa aacctctgac acatgcagct cccggagacg gtcacagctt 7620
gtctgtaagc ggatgccggg agcagacaag cccgtcaggg cgcgtcagcg ggtgttggcg 7680
ggtgtcgggg ctggcttaac tatgcggcat cagagcagat tgtactgaga gtgcaccata 7740
tgcggtgtga aataccgcac agatgcgtaa ggagaaaata ccgcatcaga ttggctat 7798

<210> SEQ ID NO 100
<211> LENGTH: 7798
<212> TYPE: DNA
<213> ORGANISM: Artificial sequence
<220> FEATURE:
<223> OTHER INFORMATION: VR4769, Ligation of Inverted NP into VR4756

<400> SEQUENCE: 100
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780

-continued

```
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctcccctatt    960
ggtgacgata ctttccatta ctaatccata acatggctct ttgccacaac tatctctatt   1020
ggctatatgc caatactctg tccttcagag actgacacgg actctgtatt tttacaggat   1080
ggggtcccat ttattattta caaattcaca tatacaacaa cgccgtcccc cgtgcccgca   1140
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catgagcctt ctaaccgagg tcgaaacgta   1680
tgttctctct atcgttccat caggccccct caaagccgaa atcgcgcaga gacttgaaga   1740
tgtctttgct gggaaaaaca cagatcttga ggctctcatg gaatggctaa agacaagacc   1800
aatcctgtca cctctgacta aggggatttt ggggtttgtg ttcacgctca ccgtgcccag   1860
tgagcgagga ctgcagcgta gacgctttgt ccaaaatgcc ctcaatggga atggggatcc   1920
aaataacatg gacagagcag ttaaactata tagaaaactt aagagggaga ttacattcca   1980
tggggccaaa gaaatagcac tcagttattc tgctggtgca cttgccagtt gcatgggcct   2040
catatacaac agaatggggg ctgtaaccac tgaagtggcc tttggcctgg tatgtgcaac   2100
atgtgaacag attgctgact cccagcacag gtctcatagg caaatggtgg caacaaccaa   2160
tccattaata aggcatgaga acagaatggt tttggccagc actacagcta aggctatgga   2220
gcaaatggct ggatcaagtg agcaggcagc ggaggccatg gaaattgcta gtcaggccag   2280
gcaaatggtg caggcaatga gagccattgg gactcatcct agctccagtg ctggtctaaa   2340
agatgatctt cttgaaaatt tgcagaccta tcagaaacga atgggggtgc agatgcaacg   2400
attcaagtga cccgcttgtt gttgctgcga gtatcattgg gatcttgcac ttgatattgt   2460
ggattcttga tcgtcttttt ttcaaatgca tctatcgact cttcaaacac ggtctgaaaa   2520
gagggccttc tacggaagga gtacctgagt ctatgaggga agaatatcga aaggaacagc   2580
agaatgctgt ggatgctgac gacagtcatt ttgtcagcat agagctggag taatcagtcg   2640
accacgtgtg atccagatct acttctggct aataaaagat cagagctcta gagatctgtg   2700
tgttggtttt ttgtgtggta ctcttccgct tcctcgctca ctgactcgct gcgctcggtc   2760
gttcggctgc ggcgagcggt atcagctcac tcaaaggcgg taatacggtt atccacagaa   2820
tcaggggata acgcaggaaa gaacatgtga gcaaaaggcc agcaaaaggc caggaaccgt   2880
aaaaaggccg cgttgctggc gtttttccat aggctccgcc cccctgacga gcatcacaaa   2940
aatcgacgct caagtcagag gtggcgaaac ccgacaggac tataaagata ccaggcgttt   3000
ccccctggaa gctccctcgt gcgctctcct gttccgaccc tgccgcttac cggatacctg   3060
tccgcctttc tcccttcggg aagcgtggcg ctttctcata gctcacgctg taggtatctc   3120
agttcggtgt aggtcgttcg ctccaagctg ggctgtgtgc acgaaccccc cgttcagccc   3180
```

gaccgctgcg ccttatccgg taactatcgt cttgagtcca acccggtaag acacgactta 3240
tcgccactgg cagcagccac tggtaacagg attagcagag cgaggtatgt aggcggtgct 3300
acagagttct tgaagtggtg gcctaactac ggctacacta gaagaacagt atttggtatc 3360
tgcgctctgc tgaagccagt taccttcgga aaaagagttg gtagctcttg atccggcaaa 3420
caaaccaccg ctggtagcgg tggttttttt gtttgcaagc agcagattac gcgcagaaaa 3480
aaaggatctc aagaagatcc tttgatcttt tctacggggt ctgacgctca gtggaacgaa 3540
aactcacgtt aagggatttt ggtcatgaga ttatcaaaaa ggatcttcac ctagatcctt 3600
ttaaattaaa aatgaagttt taaatcaatc taaagtatat atgagtaaac ttggtctgac 3660
agttaccaat gcttaatcag tgaggcacct atctcagcga tctgtctatt tcgttcatcc 3720
atagttgcct gactcggggg gggggggcgc tgaggtctgc ctcgtgaaga aggtgttgct 3780
gactcatacc aggcctgaat cgccccatca tccagccaga aagtgaggga gccacggttg 3840
atgagagctt tgttgtaggt ggaccagttg gtgattttga acttttgctt tgccacggaa 3900
cggtctgcgt tgtcgggaag atgcgtgatc tgatccttca actcagcaaa agttcgattt 3960
attcaacaaa gccgccgtcc cgtcaagtca gcgtaatgct ctgccagtgt tacaaccaat 4020
taaccaattc tgattagaaa aactcatcga gcatcaaatg aaactgcaat ttattcatat 4080
caggattatc aataccatat ttttgaaaaa gccgtttctg taatgaagga gaaaactcac 4140
cgaggcagtt ccataggatg gcaagatcct ggtatcggtc tgcgattccg actcgtccaa 4200
catcaataca acctattaat ttcccctcgt caaaaataag gttatcaagt gagaaatcac 4260
catgagtgac gactgaatcc ggtgagaatg gcaaaagctt atgcatttct ttccagactt 4320
gttcaacagg ccagccatta cgctcgtcat caaaatcact cgcatcaacc aaaccgttat 4380
tcattcgtga ttgcgcctga gcgagacgaa atacgcgatc gctgttaaaa ggacaattac 4440
aaacaggaat cgaatgcaac cggcgcagga acactgccag cgcatcaaca atattttcac 4500
ctgaatcagg atattcttct aatacctgga atgctgtttt cccggggatc gcagtggtga 4560
gtaaccatgc atcatcagga gtacggataa aatgcttgat ggtcggaaga ggcataaatt 4620
ccgtcagcca gtttagtctg accatctcat ctgtaacatc attggcaacg ctacctttgc 4680
catgtttcag aaacaactct ggcgcatcgg gcttcccata caatcgatag attgtcgcac 4740
ctgattgccc gacattatcg cgagcccatt tatacccata taaatcagca tccatgttgg 4800
aatttaatcg cggcctcgag caagacgttt cccgttgaat atggctcata acaccccttg 4860
tattactgtt tatgtaagca gacagtttta ttgttcatga tgatatattt ttatcttgtg 4920
caatgtaaca tcagagattt tgagacaccc atagagccca ccgcatcccc agcatgcctg 4980
ctattgtctt cccaatcctc ccccttgctg tcctgcccca ccccaccccc cagaatagaa 5040
tgacacctac tcagacaatg cgatgcaatt tcctcatttt attaggaaag gacagtggga 5100
gtggcacctt ccagggtcaa ggaaggcacg ggggagggggc aaacaacaga tggctggcaa 5160
ctagaaggca cagcagatct ggatccaggc gcctggtcta gagcggccgc gatgtggtcg 5220
actgatcagt tgtcgtactc ctcggcgttg tcgccgaaga agtagctgcc ctcgttgctc 5280
atgtcgaagc taggcacgat ggggttggtg gccttctcgt cgctcagctc gaacacgcct 5340
ctgcctctga aggacacctc ctcgggcttg gcgccctcca tcattctgat gatctcggct 5400
ctcatgtcgc tggttctgcc ctcggtgttg ccggtgaagg cggccatcac ggtgctcttc 5460
tcgaagggca ggtttctctg cacgctgaag gtgggctgca cgctgatctg gccggcgctg 5520
gctctctgct ggttggtgtt gccgccgctt ctggttctga tggcccagta tctgcttctc 5580

-continued

```
agctccaggg tgctgctgcc catgttgtcc atgttctcgt tgctggcgat ctgcacgcct   5640
ctggtgctca gcttgcctct gggggacacc ttggtgcctc tgatgaagct cagcagtctc   5700
aggtcctcga aggcggcgct gtggcaggcc atccacacca gctggctctt gtgggcgggg   5760
ttctcgttgg gtctgatcag gctgtacacc tggctgttct gcagcagctt gaaggggtcg   5820
atgcccacca ggctgtagcc ctccttctcg aagtcgtagc cgctgctcac ggcggggccg   5880
tacacgcagg cgggcaggca gctcttgtgg gccacgctgc ctctcaggat cagggcgctt   5940
ctggccagga agatcaggtc ctcgatctcg gcgttgccgg ggtttctgct ctcccggacc   6000
tggtccatca tggctctctg ggcggcggtc tggaacttgc ccttcaggat gttgcacatt   6060
ctctcgtagg cgcttctggt ctttctgccg ttctcgcctc tccagaagtt tctgtcgttg   6120
atgcctctct tgatcattct gatcagctcc atcaccatgg tgccgatgcc cttcacggcg   6180
gcgccggcgg cgccgcttct tctgggcagg gtgctgccct gcatcaggct gcacattctg   6240
gggtccatgc cggtccgcac cagggctctg gttctctggt aggtggtgtc gttcaggttg   6300
ctgtgccaga tcatcatgtg ggtcaggccg gcggtggcgt cctcgccgtt gttggcctgt   6360
ctccagattc ttctgatctc ctccttgtcg tacagcacca gctctctcat ccacttgccg   6420
tccactcttc tgtagatggg gccgccggtc ttcttggggt ccttgccggc gctggggtgc   6480
tcctccaggt atctgtttct tctctcgtcg aaggcgctca gcaccattct ctcgatggtc   6540
aggctgttct ggatcagtct gccctcgtag tcgctcagct tcagctcggt gcacatctgg   6600
atgtagaatc tgccgatgcc gtcgatcatc ttgcccacgc tggctctgat ctcggtggcg   6660
ttctgtctct cgccgtcggt ctccatctgc tcgtagcttc tcttggtgcc ctggctggcc   6720
atggtggcga attcgatatc tgatcacacg tgtcgacgac ggtgacggaa gcttggaggt   6780
gcacaccaat gtggtgaatg gtcaaatggc gtctagagta tcgagctagg cacttaaata   6840
caatatctct gcaatgcgga attcagtggt tcgtccaatc catgtcagac ccgtctgttg   6900
ccttcctaat aaggcacgat cgtaccacct tacttccacc aatcggcatg cacggtgctt   6960
tttctctcct tgtaaggcat gttgctaact catcgttacc atgttgcaag actacaagag   7020
tattgcataa gactacattt ccccctccct atgcaaaagc gaaactacta tatcctgagg   7080
ggactcctaa ccgcgtacaa ccgaagcccc gcttttcgcc taaacacacc ctagtcccct   7140
cagatacgcg tatatctggc ccgtacatcg cgaagcagcg caaaacgcct aaccctaagc   7200
agattcttca tgcaattgtc ggtcaagcct tgccttgttg tagcttaaat tttgctcgcg   7260
cactactcag cgacctccaa cacacaagca gggagcagat actggcttaa ctatgcggca   7320
tcagagcaga ttgtactgag agtgcaccat agtggctttc cccccccccc cattattgaa   7380
gcatttatca gggttattgt ctcatgagcg gatacatatt tgaatgtatt tagaaaaata   7440
aacaaatagg ggttccgcgc acatttcccc gaaaagtgcc acctgacgtc taagaaacca   7500
ttattatcat gacattaacc tataaaaata ggcgtatcac gaggcccttt cgtctcgcgc   7560
gtttcggtga tgacggtgaa aacctctgac acatgcagct cccggagacg gtcacagctt   7620
gtctgtaagc ggatgccggg agcagacaag cccgtcaggg cgcgtcagcg ggtgttggcg   7680
ggtgtcgggg ctggcttaac tatgcggcat cagagcagat tgtactgaga gtgcaccata   7740
tgcggtgtga aataccgcac agatgcgtaa ggagaaaata ccgcatcaga ttggctat     7798
```

<210> SEQ ID NO 101
<211> LENGTH: 5161
<212> TYPE: DNA
<213> ORGANISM: Artificial sequence
<220> FEATURE:
<223> OTHER INFORMATION: VR4770, M2 Insert Replacing WNV Insert in
VR6430

<400> SEQUENCE: 101

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggctg ctccctgctt gtgtgttgga ggtcgctgag tagtgcgcga gcaaaattta    300
agctacaaca aggcaaggct tgaccgacaa ttgcatgaag aatctgctta gggttaggcg    360
ttttgcgctg cttcgcgatg tacgggccag atatacgcgt atctgagggg actagggtgt    420
gtttaggcga aaagcggggc ttcggttgta cgcggttagg agtcccctca ggatatagta    480
gtttcgcttt tgcataggga gggggaaatg tagtcttatg caatactctt gtagtcttgc    540
aacatggtaa cgatgagtta gcaacatgcc ttacaaggag agaaaaagca ccgtgcatgc    600
cgattggtgg aagtaaggtg gtacgatcgt gccttattag gaaggcaaca gacgggtctg    660
acatggattg gacgaaccac tgaattccgc attgcagaga tattgtattt aagtgcctag    720
ctcgatacaa taaacgccat ttgaccattc accacattgg tgtgcacctc catcggctcg    780
catctctcct tcacgcgccc gccgccctac ctgaggccgc catccacgcc ggttgagtcg    840
cgttctgccg cctcccgcct gtggtgcctc ctgaactgcg tccgccgtct aggtaagttt    900
aaagctcagg tcgagaccgg gcctttgtcc ggcgctccct tggagcctac ctagactcag    960
ccggctctcc acgctttgcc tgaccctgct tgctcaactc tagttaacgg tggagggcag   1020
tgtagtctga gcagtactcg ttgctgccgc gcgcgccacc agacataata gctgacagac   1080
taacagactg ttcctttcca tgggtctttt ctgcagtcac cgtcgtcgga tatcgaattc   1140
gccaccatga gccttctaac cgaggtcgaa acgtatgttc tctctatcgt tccatcaggc   1200
cccctcaaag ccgaaatcgc gcagagactt gaagatgtct ttgctgggaa aaacacagat   1260
cttgaggctc tcatggaatg gctaaagaca agaccaatcc tgtcacctct gactaagggg   1320
attttggggt ttgtgttcac gctcaccgtg cccagtgagc gaggactgca gcgtagacgc   1380
tttgtccaaa atgccctcaa tgggaatggg gatccaaata acatggacag agcagttaaa   1440
ctatatagaa aacttaagag ggagattaca ttccatgggg ccaaagaaat agcactcagt   1500
tattctgctg gtgcacttgc cagttgcatg ggcctcatat acaacagaat gggggctgta   1560
accactgaag tggcctttgg cctggtatgt gcaacatgtg aacagattgc tgactcccag   1620
cacaggtctc ataggcaaat ggtggcaaca accaatccat taataaggca tgagaacaga   1680
atggttttgg ccagcactac agctaaggct atggagcaaa tggctggatc aagtgagcag   1740
gcagcggagg ccatggaaat tgctagtcag gccaggcaaa tggtgcaggc aatgagagcc   1800
attgggactc atcctagctc cagtgctggt ctaaaagatg atcttcttga aaatttgcag   1860
acctatcaga aacgaatggg ggtgcagatg caacgattca agtgacccgc ttgttgttgc   1920
tgcgagtatc attgggatct tgcacttgat attgtggatt cttgatcgtc tttttttcaa   1980
atgcatctat cgactcttca aacacggtct gaaaagaggg ccttctacgg aaggagtacc   2040
tgagtctatg agggaagaat atcgaaagga acagcagaat gctgtggatg ctgacgacag   2100
tcattttgtc agcatagagc tggagtaatc agtcgagatc cagatctgct gtgccttcta   2160
gttgccagcc atctgttgtt tgcccctccc ccgtgccttc cttgaccctg gaaggtgcca   2220
```

-continued

```
ctcccactgt cctttcctaa taaaatgagg aaattgcatc gcattgtctg agtaggtgtc   2280
attctattct ggggggtggg gtggggcagg acagcaaggg ggaggattgg gaagacaata   2340
gcaggcatgc tggggatgcg gtgggctcta tgggtaccca ggtgctgaag aattgacccg   2400
gttcctcctg ggccagaaag aagcaggcac atccccttct ctgtgacaca ccctgtccac   2460
gcccctggtt cttagttcca gccccactca taggacactc atagctcagg agggctccgc   2520
cttcaatccc acccgctaaa gtacttggag cggtctctcc ctccctcatc agcccaccaa   2580
accaaaccta gcctccaaga gtgggaagaa attaaagcaa gataggctat taagtgcaga   2640
gggagagaaa atgcctccaa catgtgagga agtaatgaga gaaatcatag aattttaagg   2700
ccatgattta aggccatcat ggccttaatc ttccgcttcc tcgctcactg actcgctgcg   2760
ctcggtcgtt cggctgcggc gagcggtatc agctcactca aaggcggtaa tacggttatc   2820
cacagaatca ggggataacg caggaaagaa catgtgagca aaaggccagc aaaaggccag   2880
gaaccgtaaa aaggccgcgt tgctggcgtt tttccatagg ctccgccccc ctgacgagca   2940
tcacaaaaat cgacgctcaa gtcagaggtg gcgaaacccg acaggactat aaagatacca   3000
ggcgtttccc cctggaagct ccctcgtgcg ctctcctgtt ccgaccctgc cgcttaccgg   3060
atacctgtcc gcctttctcc cttcgggaag cgtggcgctt tctcatagct cacgctgtag   3120
gtatctcagt tcggtgtagg tcgttcgctc caagctgggc tgtgtgcacg aaccccccgt   3180
tcagcccgac cgctgcgcct tatccggtaa ctatcgtctt gagtccaacc cggtaagaca   3240
cgacttatcg ccactggcag cagccactgg taacaggatt agcagagcga ggtatgtagg   3300
cggtgctaca gagttcttga agtggtggcc taactacggc tacactagaa gaacagtatt   3360
tggtatctgc gctctgctga agccagttac cttcggaaaa agagttggta gctcttgatc   3420
cggcaaacaa accaccgctg gtagcggtgg tttttttgtt tgcaagcagc agattacgcg   3480
cagaaaaaaa ggatctcaag aagatccttt gatcttttct acggggtctg acgctcagtg   3540
gaacgaaaac tcacgttaag ggattttggt catgagatta tcaaaaagga tcttcaccta   3600
gatcctttta aattaaaaat gaagttttaa atcaatctaa agtatatatg agtaaacttg   3660
gtctgacagt taccaatgct taatcagtga ggcacctatc tcagcgatct gtctatttcg   3720
ttcatccata gttgcctgac tcgggggggg ggggcgctga ggtctgcctc gtgaagaagg   3780
tgttgctgac tcataccagg cctgaatcgc cccatcatcc agccagaaag tgagggagcc   3840
acggttgatg agagctttgt tgtaggtgga ccagttggtg attttgaact tttgctttgc   3900
cacggaacgg tctgcgttgt cgggaagatg cgtgatctga tccttcaact cagcaaaagt   3960
tcgatttatt caacaaagcc gccgtcccgt caagtcagcg taatgctctg ccagtgttac   4020
aaccaattaa ccaattctga ttagaaaaac tcatcgagca tcaaatgaaa ctgcaattta   4080
ttcatatcag gattatcaat accatatttt tgaaaaagcc gtttctgtaa tgaaggagaa   4140
aactcaccga ggcagttcca taggatggca agatcctggt atcggtctgc gattccgact   4200
cgtccaacat caatacaacc tattaatttc ccctcgtcaa aaataaggtt atcaagtgag   4260
aaatcaccat gagtgacgac tgaatccggt gagaatggca aaagcttatg catttctttc   4320
cagacttgtt caacaggcca gccattacgc tcgtcatcaa aatcactcgc atcaaccaaa   4380
ccgttattca ttcgtgattg cgcctgagcg agacgaaata cgcgatcgct gttaaaagga   4440
caattacaaa caggaatcga atgcaaccgg cgcaggaaca ctgccagcgc atcaacaata   4500
ttttcacctg aatcaggata ttcttctaat acctggaatg ctgttttccc ggggatcgca   4560
gtggtgagta accatgcatc atcaggagta cggataaaat gcttgatggt cggaagaggc   4620
```

-continued

```
ataaattccg tcagccagtt tagtctgacc atctcatctg taacatcatt ggcaacgcta   4680

cctttgccat gtttcagaaa caactctggc gcatcgggct tcccatacaa tcgatagatt   4740

gtcgcacctg attgcccgac attatcgcga gcccatttat acccatataa atcagcatcc   4800

atgttggaat ttaatcgcgg cctcgagcaa gacgtttccc gttgaatatg gctcataaca   4860

ccccttgtat tactgtttat gtaagcagac agttttattg ttcatgatga tatattttta   4920

tcttgtgcaa tgtaacatca gagattttga gacacaacgt ggctttcccc cccccccat    4980

tattgaagca tttatcaggg ttattgtctc atgagcggat acatatttga atgtatttag   5040

aaaaataaac aaataggggt tccgcgcaca tttccccgaa aagtgccacc tgacgtctaa   5100

gaaaccatta ttatcatgac attaacctat aaaaataggc gtatcacgag gccctttcgt   5160

c                                                                   5161
```

<210> SEQ ID NO 102
<211> LENGTH: 5684
<212> TYPE: DNA
<213> ORGANISM: Artificial sequence
<220> FEATURE:
<223> OTHER INFORMATION: VR4771, NP Insert Repacing WNV Insert in VR6430

<400> SEQUENCE: 102

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggctg ctccctgctt gtgtgttgga ggtcgctgag tagtgcgcga gcaaaattta    300

agctacaaca aggcaaggct tgaccgacaa ttgcatgaag aatctgctta gggttaggcg    360

ttttgcgctg cttcgcgatg tacgggccag atatacgcgt atctgagggg actagggtgt    420

gtttaggcga aaagcggggc ttcggttgta cgcggttagg agtcccctca ggatatagta    480

gtttcgcttt tgcataggga gggggaaatg tagtcttatg caatactctt gtagtcttgc    540

aacatggtaa cgatgagtta gcaacatgcc ttacaaggag agaaaaagca ccgtgcatgc    600

cgattggtgg aagtaaggtg gtacgatcgt gccttattag gaaggcaaca gacgggtctg    660

acatggattg gacgaaccac tgaattccgc attgcagaga tattgtattt aagtgcctag    720

ctcgatacaa taaacgccat ttgaccattc accacattgg tgtgcacctc catcggctcg    780

catctctcct tcacgcgccc gccgccctac ctgaggccgc catccacgcc ggttgagtcg    840

cgttctgccg cctcccgcct gtggtgcctc ctgaactgcg tccgccgtct aggtaagttt    900

aaagctcagg tcgagaccgg gcctttgtcc ggcgctccct tggagcctac ctagactcag    960

ccggctctcc acgctttgcc tgaccctgct tgctcaactc tagttaacgg tggagggcag   1020

tgtagtctga gcagtactcg ttgctgccgc gcgcgccacc agacataata gctgacagac   1080

taacagactg ttcctttcca tgggtctttt ctgcagtcac cgtcgtcgga tatcgaattc   1140

gccaccatgg ccagccaggg caccaagaga agctacgagc agatggagac cgacggcgag   1200

agacagaacg ccaccgagat cagagccagc gtgggcaaga tgatcgacgg catcggcaga   1260

ttctacatcc agatgtgcac cgagctgaag ctgagcgact acgagggcag actgatccag   1320

aacagcctga ccatcgagag aatggtgctg agcgccttcg acgagagaag aaacagatac   1380

ctggaggagc accccagcgc cggcaaggac cccaagaaga ccggcggccc catctacaga   1440

agagtggacg gcaagtggat gagagagctg gtgctgtacg acaaggagga gatcagaaga   1500
```

-continued

```
atctggagac aggccaacaa cggcgaggac gccaccgccg gcctgaccca catgatgatc   1560
tggcacagca acctgaacga caccacctac cagagaacca gagccctggt gcggaccggc   1620
atggacccca gaatgtgcag cctgatgcag ggcagcaccc tgcccagaag aagcggcgcc   1680
gccggcgccg ccgtgaaggg catcggcacc atggtgatgg agctgatcag aatgatcaag   1740
agaggcatca acgacagaaa cttctggaga ggcgagaacg gcagaaagac cagaagcgcc   1800
tacgagagaa tgtgcaacat cctgaagggc aagttccaga ccgccgccca gagagccatg   1860
atggaccagg tccgggagag cagaaacccc ggcaacgccg agatcgagga cctgatcttc   1920
ctggccagaa gcgccctgat cctgagaggc agcgtggccc acaagagctg cctgcccgcc   1980
tgcgtgtacg gccccgccgt gagcagcggc tacgacttcg agaaggaggg ctacagcctg   2040
gtgggcatcg accccttcaa gctgctgcag aacagccagg tgtacagcct gatcagaccc   2100
aacgagaacc ccgcccacaa gagccagctg gtgtggatgg cctgccacag cgccgccttc   2160
gaggacctga gactgctgag cttcatcaga ggcaccaagg tgtcccccag aggcaagctg   2220
agcaccagag gcgtgcagat cgccagcaac gagaacatgg acaacatggg cagcagcacc   2280
ctggagctga gaagcagata ctgggccatc agaaccagaa gcggcggcaa caccaaccag   2340
cagagagcca gcgccggcca gatcagcgtg cagcccacct tcagcgtgca gagaaacctg   2400
cccttcgaga agagcaccgt gatggccgcc ttcaccggca acaccgaggg cagaaccagc   2460
gacatgagag ccgagatcat cagaatgatg gagggcgcca agcccgagga ggtgtccttc   2520
agaggcagag gcgtgttcga gctgagcgac gagaaggcca ccaaccccat cgtgcctagc   2580
ttcgacatga gcaacgaggg cagctacttc ttcggcgaca acgccgagga gtacgacaac   2640
tgatcagtcg accacgtgtg atccagatct gctgtgcctt ctagttgcca gccatctgtt   2700
gtttgcccct cccccgtgcc ttccttgacc ctggaaggtg ccactcccac tgtcctttcc   2760
taataaaatg aggaaattgc atcgcattgt ctgagtaggt gtcattctat tctggggggt   2820
ggggtggggc aggacagcaa gggggaggat tgggaagaca atagcaggca tgctggggat   2880
gcggtgggct ctatgggtac ccaggtgctg aagaattgac ccggttcctc ctgggccaga   2940
aagaagcagg cacatcccct tctctgtgac acaccctgtc cacgcccctg gttcttagtt   3000
ccagccccac tcataggaca ctcatagctc aggagggctc cgccttcaat cccacccgct   3060
aaagtacttg gagcggtctc tccctccctc atcagcccac caaaccaaac ctagcctcca   3120
agagtgggaa gaaattaaag caagataggc tattaagtgc agagggagag aaaatgcctc   3180
caacatgtga ggaagtaatg agagaaatca tagaatttta aggccatgat ttaaggccat   3240
catggcctta atcttccgct tcctcgctca ctgactcgct gcgctcggtc gttcggctgc   3300
ggcgagcggt atcagctcac tcaaaggcgg taatacggtt atccacagaa tcaggggata   3360
acgcaggaaa gaacatgtga gcaaaaggcc agcaaaaggc caggaaccgt aaaaaggccg   3420
cgttgctggc gtttttccat aggctccgcc cccctgacga gcatcacaaa aatcgacgct   3480
caagtcagag gtggcgaaac ccgacaggac tataaagata ccaggcgttt ccccctggaa   3540
gctccctcgt gcgctctcct gttccgaccc tgccgcttac cggatacctg tccgcctttc   3600
tcccttcggg aagcgtggcg ctttctcata gctcacgctg taggtatctc agttcggtgt   3660
aggtcgttcg ctccaagctg ggctgtgtgc acgaaccccc cgttcagccc gaccgctgcg   3720
ccttatccgg taactatcgt cttgagtcca acccggtaag acacgactta tcgccactgg   3780
cagcagccac tggtaacagg attagcagag cgaggtatgt aggcggtgct acagagttct   3840
tgaagtggtg gcctaactac ggctacacta gaagaacagt atttggtatc tgcgctctgc   3900
```

```
tgaagccagt taccttcgga aaaagagttg gtagctcttg atccggcaaa caaaccaccg   3960

ctggtagcgg tggttttttt gtttgcaagc agcagattac gcgcagaaaa aaaggatctc   4020

aagaagatcc tttgatcttt tctacggggt ctgacgctca gtggaacgaa aactcacgtt   4080

aagggatttt ggtcatgaga ttatcaaaaa ggatcttcac ctagatcctt ttaaattaaa   4140

aatgaagttt taaatcaatc taaagtatat atgagtaaac ttggtctgac agttaccaat   4200

gcttaatcag tgaggcacct atctcagcga tctgtctatt tcgttcatcc atagttgcct   4260

gactcggggg gggggggcgc tgaggtctgc ctcgtgaaga aggtgttgct gactcatacc   4320

aggcctgaat cgccccatca tccagccaga aagtgaggga gccacggttg atgagagctt   4380

tgttgtaggt ggaccagttg gtgattttga acttttgctt tgccacggaa cggtctgcgt   4440

tgtcgggaag atgcgtgatc tgatccttca actcagcaaa agttcgattt attcaacaaa   4500

gccgccgtcc cgtcaagtca gcgtaatgct ctgccagtgt tacaaccaat taaccaattc   4560

tgattagaaa aactcatcga gcatcaaatg aaactgcaat ttattcatat caggattatc   4620

aataccatat ttttgaaaaa gccgtttctg taatgaagga gaaaactcac cgaggcagtt   4680

ccataggatg gcaagatcct ggtatcggtc tgcgattccg actcgtccaa catcaataca   4740

acctattaat ttcccctcgt caaaaataag gttatcaagt gagaaatcac catgagtgac   4800

gactgaatcc ggtgagaatg gcaaaagctt atgcatttct ttccagactt gttcaacagg   4860

ccagccatta cgctcgtcat caaaatcact cgcatcaacc aaaccgttat tcattcgtga   4920

ttgcgcctga gcgagacgaa atacgcgatc gctgttaaaa ggacaattac aaacaggaat   4980

cgaatgcaac cggcgcagga acactgccag cgcatcaaca atattttcac ctgaatcagg   5040

atattcttct aatacctgga atgctgtttt cccggggatc gcagtggtga gtaaccatgc   5100

atcatcagga gtacggataa aatgcttgat ggtcggaaga ggcataaatt ccgtcagcca   5160

gtttagtctg accatctcat ctgtaacatc attggcaacg ctacctttgc catgtttcag   5220

aaacaactct ggcgcatcgg gcttcccata caatcgatag attgtcgcac ctgattgccc   5280

gacattatcg cgagcccatt tatacccata taaatcagca tccatgttgg aatttaatcg   5340

cggcctcgag caagacgttt cccgttgaat atggctcata acaccccttg tattactgtt   5400

tatgtaagca gacagtttta ttgttcatga tgatatattt ttatcttgtg caatgtaaca   5460

tcagagattt tgagacacaa cgtggctttc cccccccccc cattattgaa gcatttatca   5520

gggttattgt ctcatgagcg gatacatatt tgaatgtatt tagaaaaata aacaaatagg   5580

ggttccgcgc acatttcccc gaaaagtgcc acctgacgtc taagaaacca ttattatcat   5640

gacattaacc tataaaaata ggcgtatcac gaggcccttt cgtc                     5684
```

<210> SEQ ID NO 103
<211> LENGTH: 4473
<212> TYPE: DNA
<213> ORGANISM: Artificial sequence
<220> FEATURE:
<223> OTHER INFORMATION: VR4772, M2 Insert Replacing WNV Insert from
VR6430

<400> SEQUENCE: 103

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggctg ctccctgctt gtgtgttgga ggtcgctgag tagtgcgcga gcaaaattta    300
```

-continued

```
agctacaaca aggcaaggct tgaccgacaa ttgcatgaag aatctgctta gggttaggcg    360
ttttgcgctg cttcgcgatg tacgggccag atatacgcgt atctgagggg actagggtgt    420
gtttaggcga aaagcggggc ttcggttgta cgcggttagg agtcccctca ggatatagta    480
gtttcgcttt tgcataggga gggggaaatg tagtcttatg caatactctt gtagtcttgc    540
aacatggtaa cgatgagtta gcaacatgcc ttacaaggag agaaaaagca ccgtgcatgc    600
cgattggtgg aagtaaggtg gtacgatcgt gccttattag gaaggcaaca gacgggtctg    660
acatggattg gacgaaccac tgaattccgc attgcagaga tattgtattt aagtgcctag    720
ctcgatacaa taaacgccat ttgaccattc accacattgg tgtgcacctc catcggctcg    780
catctctcct tcacgcgccc gccgccctac ctgaggccgc catccacgcc ggttgagtcg    840
cgttctgccg cctcccgcct gtggtgcctc ctgaactgcg tccgccgtct aggtaagttt    900
aaagctcagg tcgagaccgg gcctttgtcc ggcgctccct tggagcctac ctagactcag    960
ccggctctcc acgctttgcc tgaccctgct tgctcaactc tagttaacgg tggagggcag   1020
tgtagtctga gcagtactcg ttgctgccgc gcgcgccacc agacataata gctgacagac   1080
taacagactg ttcctttcca tgggtctttt ctgcagtcac cgtcgtcgga tatcgaattc   1140
gccaccatga gcctgctgac cgaggtggag acccccatca gaaacgagtg gggctgcaga   1200
tgcaacgaca gcagcgaccc cctggtggtg gccgccagca tcatcggcat cctgcacctg   1260
atcctgtgga tcctggacag actgttcttc aagtgcatct acagactgtt caagcacggc   1320
ctgaagagag gccccagcac cgagggcgtg cccgagagca tgagagagga gtacagaaag   1380
gagcagcaga acgccgtgga cgccgacgac agccacttcg tgagcatcga gctggagtga   1440
tcagtcgaga tccagatctg ctgtgccttc tagttgccag ccatctgttg tttgcccctc   1500
ccccgtgcct tccttgaccc tggaaggtgc cactcccact gtcctttcct aataaaatga   1560
ggaaattgca tcgcattgtc tgagtaggtg tcattctatt ctggggggtg gggtggggca   1620
ggacagcaag ggggaggatt gggaagacaa tagcaggcat gctggggatg cggtgggctc   1680
tatgggtacc caggtgctga agaattgacc cggttcctcc tgggccagaa agaagcaggc   1740
acatcccctt ctctgtgaca caccctgtcc acgcccctgg ttcttagttc cagccccact   1800
cataggacac tcatagctca ggagggctcc gccttcaatc ccacccgcta aagtacttgg   1860
agcggtctct ccctccctca tcagcccacc aaaccaaacc tagcctccaa gagtgggaag   1920
aaattaaagc aagataggct attaagtgca gagggagaga aaatgcctcc aacatgtgag   1980
gaagtaatga gagaaatcat agaattttaa ggccatgatt taaggccatc atggccttaa   2040
tcttccgctt cctcgctcac tgactcgctg cgctcggtcg ttcggctgcg gcgagcggta   2100
tcagctcact caaaggcggt aatacggtta tccacagaat caggggataa cgcaggaaag   2160
aacatgtgag caaaaggcca gcaaaaggcc aggaaccgta aaaaggccgc gttgctggcg   2220
tttttccata ggctccgccc ccctgacgag catcacaaaa atcgacgctc aagtcagagg   2280
tggcgaaacc cgacaggact ataaagatac caggcgtttc cccctggaag ctccctcgtg   2340
cgctctcctg ttccgaccct gccgcttacc ggatacctgt ccgcctttct cccttcggga   2400
agcgtggcgc tttctcatag ctcacgctgt aggtatctca gttcggtgta ggtcgttcgc   2460
tccaagctgg gctgtgtgca cgaacccccc gttcagcccg accgctgcgc cttatccggt   2520
aactatcgtc ttgagtccaa cccggtaaga cacgacttat cgccactggc agcagccact   2580
ggtaacagga ttagcagagc gaggtatgta ggcggtgcta cagagttctt gaagtggtgg   2640
cctaactacg gctacactag aagaacagta tttggtatct gcgctctgct gaagccagtt   2700
```

accttcggaa aaagagttgg tagctcttga tccggcaaac aaaccaccgc tggtagcggt 2760
ggtttttttg tttgcaagca gcagattacg cgcagaaaaa aaggatctca agaagatcct 2820
ttgatctttt ctacggggtc tgacgctcag tggaacgaaa actcacgtta agggattttg 2880
gtcatgagat tatcaaaaag gatcttcacc tagatccttt taaattaaaa atgaagtttt 2940
aaatcaatct aaagtatata tgagtaaact tggtctgaca gttaccaatg cttaatcagt 3000
gaggcaccta tctcagcgat ctgtctattt cgttcatcca tagttgcctg actcgggggg 3060
ggggggcgct gaggtctgcc tcgtgaagaa ggtgttgctg actcatacca ggcctgaatc 3120
gccccatcat ccagccagaa agtgagggag ccacggttga tgagagcttt gttgtaggtg 3180
gaccagttgg tgattttgaa cttttgcttt gccacggaac ggtctgcgtt gtcgggaaga 3240
tgcgtgatct gatccttcaa ctcagcaaaa gttcgattta ttcaacaaag ccgccgtccc 3300
gtcaagtcag cgtaatgctc tgccagtgtt acaaccaatt aaccaattct gattagaaaa 3360
actcatcgag catcaaatga aactgcaatt tattcatatc aggattatca ataccatatt 3420
tttgaaaaag ccgtttctgt aatgaaggag aaaactcacc gaggcagttc cataggatgg 3480
caagatcctg gtatcggtct gcgattccga ctcgtccaac atcaatacaa cctattaatt 3540
tcccctcgtc aaaaataagg ttatcaagtg agaaatcacc atgagtgacg actgaatccg 3600
gtgagaatgg caaaagctta tgcatttctt tccagacttg ttcaacaggc cagccattac 3660
gctcgtcatc aaaatcactc gcatcaacca aaccgttatt cattcgtgat tgcgcctgag 3720
cgagacgaaa tacgcgatcg ctgttaaaag gacaattaca aacaggaatc gaatgcaacc 3780
ggcgcaggaa cactgccagc gcatcaacaa tattttcacc tgaatcagga tattcttcta 3840
atacctggaa tgctgttttc ccggggatcg cagtggtgag taaccatgca tcatcaggag 3900
tacggataaa atgcttgatg gtcggaagag gcataaattc cgtcagccag tttagtctga 3960
ccatctcatc tgtaacatca ttggcaacgc tacctttgcc atgtttcaga aacaactctg 4020
gcgcatcggg cttcccatac aatcgataga ttgtcgcacc tgattgcccg acattatcgc 4080
gagcccattt atacccatat aaatcagcat ccatgttgga atttaatcgc ggcctcgagc 4140
aagacgtttc ccgttgaata tggctcataa cacccttgt attactgttt atgtaagcag 4200
acagttttat tgttcatgat gatatatttt tatcttgtgc aatgtaacat cagagatttt 4260
gagacacaac gtggctttcc cccccccccc attattgaag catttatcag ggttattgtc 4320
tcatgagcgg atacatattt gaatgtattt agaaaaataa acaaataggg gttccgcgca 4380
catttccccg aaaagtgcca cctgacgtct aagaaaccat tattatcatg acattaacct 4440
ataaaaatag gcgtatcacg aggccctttc gtc 4473

<210> SEQ ID NO 104
<211> LENGTH: 8450
<212> TYPE: DNA
<213> ORGANISM: Artificial sequence
<220> FEATURE:
<223> OTHER INFORMATION: VR4773, Ligation of RSV RNP into VR4756

<400> SEQUENCE: 104
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300

-continued cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960
ggtgacgata ctttccatta ctaatccata acatggctct ttgccacaac tatctctatt 1020
ggctatatgc caatactctg tccttcagag actgacacgg actctgtatt tttacaggat 1080
ggggtcccat ttattattta caaattcaca tatacaacaa cgccgtcccc cgtgcccgca 1140
gtttttatta aacatagcgt gggatctcca cgcgaatctc gggtacgtgt tccggacatg 1200
ggctcttctc cggtagcggc ggagcttcca catccgagcc ctggtcccat gcctccagcg 1260
gctcatggtc gctcggcagc tccttgctcc taacagtgga ggccagactt aggcacagca 1320
caatgcccac caccaccagt gtgccgcaca aggccgtggc ggtagggtat gtgtctgaaa 1380
atgagcgtgg agattgggct cgcacggctg acgcagatgg aagacttaag gcagcggcag 1440
aagaagatgc aggcagctga gttgttgtat tctgataaga gtcagaggta actcccgttg 1500
cggtgctgtt aacggtggag ggcagtgtag tctgagcagt actcgttgct gccgcgcgcg 1560
ccaccagaca taatagctga cagactaaca gactgttcct ttccatgggt cttttctgca 1620
gtcaccgtcg tcggatatcg aattcgccac catgagcctt ctaaccgagg tcgaaacgta 1680
tgttctctct atcgttccat caggcccct caaagccgaa atcgcgcaga gacttgaaga 1740
tgtctttgct gggaaaaaca cagatcttga ggctctcatg gaatggctaa agacaagacc 1800
aatcctgtca cctctgacta aggggatttt ggggtttgtg ttcacgctca ccgtgcccag 1860
tgagcgagga ctgcagcgta gacgctttgt ccaaaatgcc ctcaatggga atggggatcc 1920
aaataacatg gacagagcag ttaaactata tagaaaactt aagagggaga ttacattcca 1980
tggggccaaa gaaatagcac tcagttattc tgctggtgca cttgccagtt gcatgggcct 2040
catatacaac agaatggggg ctgtaaccac tgaagtggcc tttggcctgg tatgtgcaac 2100
atgtgaacag attgctgact cccagcacag gtctcatagg caaatggtgg caacaaccaa 2160
tccattaata aggcatgaga acagaatggt tttggccagc actacagcta aggctatgga 2220
gcaaatggct ggatcaagtg agcaggcagc ggaggccatg gaaattgcta gtcaggccag 2280
gcaaatggtg caggcaatga gagccattgg gactcatcct agctccagtg ctggtctaaa 2340
agatgatctt cttgaaaatt tgcagaccta tcagaaacga atgggggtgc agatgcaacg 2400
attcaagtga cccgcttgtt gttgctgcga gtatcattgg gatcttgcac ttgatattgt 2460
ggattcttga tcgtcttttt ttcaaatgca tctatcgact cttcaaacac ggtctgaaaa 2520
gagggccttc tacggaagga gtacctgagt ctatgaggga agaatatcga aaggaacagc 2580
agaatgctgt ggatgctgac gacagtcatt ttgtcagcat agagctggag taatcagtcg 2640
accacgtgtg atccagatct acttctggct aataaaagat cagagctcta gagatctgtg 2700

-continued

```
tgttggtttt ttgtgtggta ctcttccgct tcctcgctca ctgactcgct gcgctcggtc   2760
gttcggctgc ggcgagcggt atcagctcac tcaaaggcgg taatacggtt atccacagaa   2820
tcaggggata acgcaggaaa gaacatgtga gcaaaaggcc agcaaaaggc caggaaccgt   2880
aaaaaggccg cgttgctggc gtttttccat aggctccgcc cccctgacga gcatcacaaa   2940
aatcgacgct caagtcagag gtggcgaaac ccgacaggac tataaagata ccaggcgttt   3000
ccccctggaa gctccctcgt gcgctctcct gttccgaccc tgccgcttac cggatacctg   3060
tccgcctttc tcccttcggg aagcgtggcg ctttctcata gctcacgctg taggtatctc   3120
agttcggtgt aggtcgttcg ctccaagctg ggctgtgtgc acgaaccccc cgttcagccc   3180
gaccgctgcg ccttatccgg taactatcgt cttgagtcca acccggtaag acacgactta   3240
tcgccactgg cagcagccac tggtaacagg attagcagag cgaggtatgt aggcggtgct   3300
acagagttct tgaagtggtg gcctaactac ggctacacta gaagaacagt atttggtatc   3360
tgcgctctgc tgaagccagt taccttcgga aaaagagttg gtagctcttg atccggcaaa   3420
caaaccaccg ctggtagcgg tggttttttt gtttgcaagc agcagattac gcgcagaaaa   3480
aaaggatctc aagaagatcc tttgatcttt tctacggggt ctgacgctca gtggaacgaa   3540
aactcacgtt aagggatttt ggtcatgaga ttatcaaaaa ggatcttcac ctagatcctt   3600
ttaaattaaa aatgaagttt taaatcaatc taaagtatat atgagtaaac ttggtctgac   3660
agttaccaat gcttaatcag tgaggcacct atctcagcga tctgtctatt tcgttcatcc   3720
atagttgcct gactcggggg gggggggcgc tgaggtctgc ctcgtgaaga aggtgttgct   3780
gactcatacc aggcctgaat cgccccatca tccagccaga aagtgaggga gccacggttg   3840
atgagagctt tgttgtaggt ggaccagttg gtgattttga acttttgctt tgccacggaa   3900
cggtctgcgt tgtcgggaag atgcgtgatc tgatccttca actcagcaaa agttcgattt   3960
attcaacaaa gccgccgtcc cgtcaagtca gcgtaatgct ctgccagtgt tacaaccaat   4020
taaccaattc tgattagaaa aactcatcga gcatcaaatg aaactgcaat ttattcatat   4080
caggattatc aataccatat ttttgaaaaa gccgtttctg taatgaagga gaaaactcac   4140
cgaggcagtt ccataggatg gcaagatcct ggtatcggtc tgcgattccg actcgtccaa   4200
catcaataca acctattaat ttcccctcgt caaaaataag gttatcaagt gagaaatcac   4260
catgagtgac gactgaatcc ggtgagaatg gcaaaagctt atgcatttct ttccagactt   4320
gttcaacagg ccagccatta cgctcgtcat caaaatcact cgcatcaacc aaaccgttat   4380
tcattcgtga ttgcgcctga gcgagacgaa atacgcgatc gctgttaaaa ggacaattac   4440
aaacaggaat cgaatgcaac cggcgcagga acactgccag cgcatcaaca atattttcac   4500
ctgaatcagg atattcttct aatacctgga atgctgtttt cccggggatc gcagtggtga   4560
gtaaccatgc atcatcagga gtacggataa aatgcttgat ggtcggaaga ggcataaatt   4620
ccgtcagcca gtttagtctg accatctcat ctgtaacatc attggcaacg ctacctttgc   4680
catgtttcag aaacaactct ggcgcatcgg gcttcccata caatcgatag attgtcgcac   4740
ctgattgccc gacattatcg cgagcccatt tatacccata taaatcagca tccatgttgg   4800
aatttaatcg cggcctcgag caagacgttt cccgttgaat atggctcata acaccccttg   4860
tattactgtt tatgtaagca gacagtttta ttgttcatga tgatatattt ttatcttgtg   4920
caatgtaaca tcagagattt tgagacacta tgcggtgtga aataccgcac agatgcgtaa   4980
ggagaaaata ccgcatcaga ttggctattg gctgctccct gcttgtgtgt tggaggtcgc   5040
tgagtagtgc gcgagcaaaa tttaagctac aacaaggcaa ggcttgaccg acaattgcat   5100
```

gaagaatctg cttagggtta ggcgttttgc gctgcttcgc gatgtacggg ccagatatac 5160
gcgtatctga ggggactagg gtgtgtttag gcgaaaagcg gggcttcggt tgtacgcggt 5220
taggagtccc ctcaggatat agtagtttcg cttttgcata gggaggggga aatgtagtct 5280
tatgcaatac tcttgtagtc ttgcaacatg gtaacgatga gttagcaaca tgccttacaa 5340
ggagagaaaa agcaccgtgc atgccgattg gtggaagtaa ggtggtacga tcgtgcctta 5400
ttaggaaggc aacagacggg tctgacatgg attggacgaa ccactgaatt ccgcattgca 5460
gagatattgt atttaagtgc ctagctcgat acaataaacg ccatttgacc attcaccaca 5520
ttggtgtgca cctccatcgg ctcgcatctc tccttcacgc gcccgccgcc ctacctgagg 5580
ccgccatcca cgccggttga gtcgcgttct gccgcctccc gcctgtggtg cctcctgaac 5640
tgcgtccgcc gtctaggtaa gtttaaagct caggtcgaga ccgggccttt gtccggcgct 5700
cccttggagc ctacctagac tcagccggct ctccacgctt tgcctgaccc tgcttgctca 5760
actctagtta acggtggagg gcagtgtagt ctgagcagta ctcgttgctg ccgcgcgcgc 5820
caccagacat aatagctgac agactaacag actgttcctt tccatgggtc ttttctgcag 5880
tcaccgtcgt cggatatcga attcgccacc atggccagcc agggcaccaa gagaagctac 5940
gagcagatgg agaccgacgg cgagagacag aacgccaccg agatcagagc cagcgtgggc 6000
aagatgatcg acggcatcgg cagattctac atccagatgt gcaccgagct gaagctgagc 6060
gactacgagg gcagactgat ccagaacagc ctgaccatcg agagaatggt gctgagcgcc 6120
ttcgacgaga gaagaaacag atacctggag gagcacccca gcgccggcaa ggacccccaag 6180
aagaccggcg gccccatcta cagaagagtg gacggcaagt ggatgagaga gctggtgctg 6240
tacgacaagg aggagatcag aagaatctgg agacaggcca acaacggcga ggacgccacc 6300
gccggcctga cccacatgat gatctggcac agcaacctga acgacaccac ctaccagaga 6360
accagagccc tggtgcggac cggcatggac cccagaatgt gcagcctgat gcagggcagc 6420
accctgccca gaagaagcgg cgccgccggc gccgccgtga agggcatcgg caccatggtg 6480
atggagctga tcagaatgat caagagaggc atcaacgaca gaaacttctg gagaggcgag 6540
aacggcagaa agaccagaag cgcctacgag agaatgtgca acatcctgaa gggcaagttc 6600
cagaccgccg cccagagagc catgatggac caggtccggg agagcagaaa ccccggcaac 6660
gccgagatcg aggacctgat cttcctggcc agaagcgccc tgatcctgag aggcagcgtg 6720
gcccacaaga gctgcctgcc cgcctgcgtg tacggccccg ccgtgagcag cggctacgac 6780
ttcgagaagg agggctacag cctggtgggc atcgacccct tcaagctgct gcagaacagc 6840
caggtgtaca gcctgatcag acccaacgag aaccccgccc acaagagcca gctggtgtgg 6900
atggcctgcc acagcgccgc cttcgaggac ctgagactgc tgagcttcat cagaggcacc 6960
aaggtgtccc ccagaggcaa gctgagcacc agaggcgtgc agatcgccag caacgagaac 7020
atggacaaca tgggcagcag caccctggag ctgagaagca gatactgggc catcagaacc 7080
agaagcggcg gcaacaccaa ccagcagaga gccagcgccg gccagatcag cgtgcagccc 7140
accttcagcg tgcagagaaa cctgcccttc gagaagagca ccgtgatggc cgccttcacc 7200
ggcaacaccg agggcagaac cagcgacatg agagccgaga tcatcagaat gatggagggc 7260
gccaagcccg aggaggtgtc cttcagaggc agaggcgtgt tcgagctgag cgacgagaag 7320
gccaccaacc ccatcgtgcc tagcttcgac atgagcaacg agggcagcta cttcttcggc 7380
gacaacgccg aggagtacga caactgatca gtcgaccacg tgtgatccag atctgctgtg 7440
ccttctagtt gccagccatc tgttgtttgc ccctcccccg tgccttcctt gaccctggaa 7500
ggtgccactc ccactgtcct ttcctaataa aatgaggaaa ttgcatcgca ttgtctgagt 7560
aggtgtcatt ctattctggg gggtggggtg gggcaggaca gcaaggggga ggattgggaa 7620
gacaatagca ggcatgctgg ggatgcggtg ggctctatgg gtacccaggt gctgaagaat 7680
tgacccggtt cctcctgggc cagaaagaag caggcacatc cccttctctg tgacacaccc 7740
tgtccacgcc cctggttctt agttccagcc ccactcatag gacactcata gctcaggagg 7800
gctccgcctt caatcccacc cgctaaagta cttggagcgg tctctccctc cctcatcagc 7860
ccaccaaacc aaacctagcc tccaagagtg ggaagaaatt aaagcaagat aggctattaa 7920
gtgcagaggg agagaaaatg cctccaacat gtgaggaagt aatgagagaa atcatagaat 7980
tttaaggcca tgatttaagg ccagtggctt tccccccccc cccattattg aagcatttat 8040
cagggttatt gtctcatgag cggatacata tttgaatgta tttagaaaaa taaacaaata 8100
ggggttccgc gcacatttcc ccgaaaagtg ccacctgacg tctaagaaac cattattatc 8160
atgacattaa cctataaaaa taggcgtatc acgaggccct ttcgtctcgc gcgtttcggt 8220
gatgacggtg aaaacctctg acacatgcag ctcccggaga cggtcacagc ttgtctgtaa 8280
gcggatgccg ggagcagaca agcccgtcag ggcgcgtcag cgggtgttgg cgggtgtcgg 8340
ggctggctta actatgcggc atcagagcag attgtactga gagtgcacca tatgcggtgt 8400
gaaataccgc acagatgcgt aaggagaaaa taccgcatca gattggctat 8450

<210> SEQ ID NO 105
<211> LENGTH: 8450
<212> TYPE: DNA
<213> ORGANISM: Artificial sequence
<220> FEATURE:
<223> OTHER INFORMATION: VR4774, Ligation of Inverted RSV RNP into VR4756

<400> SEQUENCE: 105
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960
ggtgacgata ctttccatta ctaatccata acatggctct ttgccacaac tatctctatt 1020
ggctatatgc caatactctg tccttcagag actgacacgg actctgtatt tttacaggat 1080
ggggtcccat ttattattta caaattcaca tatacaacaa cgccgtcccc cgtgcccgca 1140

-continued

```
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catgagcctt ctaaccgagg tcgaaacgta   1680
tgttctctct atcgttccat caggcccct caaagccgaa atcgcgcaga gacttgaaga   1740
tgtctttgct gggaaaaaca cagatcttga ggctctcatg gaatggctaa agacaagacc   1800
aatcctgtca cctctgacta aggggatttt ggggtttgtg ttcacgctca ccgtgcccag   1860
tgagcgagga ctgcagcgta gacgctttgt ccaaaatgcc ctcaatggga atggggatcc   1920
aaataacatg gacagagcag ttaaactata tagaaaactt aagagggaga ttacattcca   1980
tggggccaaa gaaatagcac tcagttattc tgctggtgca cttgccagtt gcatgggcct   2040
catatacaac agaatggggg ctgtaaccac tgaagtggcc tttggcctgg tatgtgcaac   2100
atgtgaacag attgctgact cccagcacag gtctcatagg caaatggtgg caacaaccaa   2160
tccattaata aggcatgaga acagaatggt tttggccagc actacagcta aggctatgga   2220
gcaaatggct ggatcaagtg agcaggcagc ggaggccatg gaaattgcta gtcaggccag   2280
gcaaatggtg caggcaatga gagccattgg gactcatcct agctccagtg ctggtctaaa   2340
agatgatctt cttgaaaatt tgcagaccta tcagaaacga atgggggtgc agatgcaacg   2400
attcaagtga cccgcttgtt gttgctgcga gtatcattgg gatcttgcac ttgatattgt   2460
ggattcttga tcgtcttttt ttcaaatgca tctatcgact cttcaaacac ggtctgaaaa   2520
gagggccttc tacggaagga gtacctgagt ctatgaggga agaatatcga aaggaacagc   2580
agaatgctgt ggatgctgac gacagtcatt ttgtcagcat agagctggag taatcagtcg   2640
accacgtgtg atccagatct acttctggct aataaaagat cagagctcta gagatctgtg   2700
tgttggtttt ttgtgtggta ctcttccgct tcctcgctca ctgactcgct gcgctcggtc   2760
gttcggctgc ggcgagcggt atcagctcac tcaaaggcgg taatacggtt atccacagaa   2820
tcaggggata acgcaggaaa gaacatgtga gcaaaaggcc agcaaaaggc caggaaccgt   2880
aaaaaggccg cgttgctggc gtttttccat aggctccgcc cccctgacga gcatcacaaa   2940
aatcgacgct caagtcagag gtggcgaaac ccgacaggac tataaagata ccaggcgttt   3000
ccccctggaa gctccctcgt gcgctctcct gttccgaccc tgccgcttac cggatacctg   3060
tccgcctttc tcccttcggg aagcgtggcg ctttctcata gctcacgctg taggtatctc   3120
agttcggtgt aggtcgttcg ctccaagctg ggctgtgtgc acgaaccccc cgttcagccc   3180
gaccgctgcg ccttatccgg taactatcgt cttgagtcca acccggtaag acacgactta   3240
tcgccactgg cagcagccac tggtaacagg attagcagag cgaggtatgt aggcggtgct   3300
acagagttct tgaagtggtg gcctaactac ggctacacta gaagaacagt atttggtatc   3360
tgcgctctgc tgaagccagt taccttcgga aaaagagttg gtagctcttg atccggcaaa   3420
caaaccaccg ctggtagcgg tggttttttt gtttgcaagc agcagattac gcgcagaaaa   3480
aaaggatctc aagaagatcc tttgatcttt tctacggggt ctgacgctca gtggaacgaa   3540
```

-continued

```
aactcacgtt aagggatttt ggtcatgaga ttatcaaaaa ggatcttcac ctagatcctt   3600
ttaaattaaa aatgaagttt taaatcaatc taaagtatat atgagtaaac ttggtctgac   3660
agttaccaat gcttaatcag tgaggcacct atctcagcga tctgtctatt tcgttcatcc   3720
atagttgcct gactcggggg gggggggcgc tgaggtctgc ctcgtgaaga aggtgttgct   3780
gactcatacc aggcctgaat cgccccatca tccagccaga aagtgaggga gccacggttg   3840
atgagagctt tgttgtaggt ggaccagttg gtgattttga acttttgctt tgccacggaa   3900
cggtctgcgt tgtcgggaag atgcgtgatc tgatccttca actcagcaaa agttcgattt   3960
attcaacaaa gccgccgtcc cgtcaagtca gcgtaatgct ctgccagtgt tacaaccaat   4020
taaccaattc tgattagaaa aactcatcga gcatcaaatg aaactgcaat ttattcatat   4080
caggattatc aataccatat ttttgaaaaa gccgtttctg taatgaagga gaaaactcac   4140
cgaggcagtt ccataggatg gcaagatcct ggtatcggtc tgcgattccg actcgtccaa   4200
catcaataca acctattaat ttcccctcgt caaaaataag gttatcaagt gagaaatcac   4260
catgagtgac gactgaatcc ggtgagaatg gcaaaagctt atgcatttct ttccagactt   4320
gttcaacagg ccagccatta cgctcgtcat caaaatcact cgcatcaacc aaaccgttat   4380
tcattcgtga ttgcgcctga gcgagacgaa atacgcgatc gctgttaaaa ggacaattac   4440
aaacaggaat cgaatgcaac cggcgcagga acactgccag cgcatcaaca atattttcac   4500
ctgaatcagg atattcttct aatacctgga atgctgtttt cccggggatc gcagtggtga   4560
gtaaccatgc atcatcagga gtacggataa aatgcttgat ggtcggaaga ggcataaatt   4620
ccgtcagcca gtttagtctg accatctcat ctgtaacatc attggcaacg ctacctttgc   4680
catgtttcag aaacaactct ggcgcatcgg gcttcccata caatcgatag attgtcgcac   4740
ctgattgccc gacattatcg cgagcccatt tatacccata taaatcagca tccatgttgg   4800
aatttaatcg cggcctcgag caagacgttt cccgttgaat atggctcata acaccccttg   4860
tattactgtt tatgtaagca gacagtttta ttgttcatga tgatatattt ttatcttgtg   4920
caatgtaaca tcagagattt tgagacactg gccttaaatc atggccttaa aattctatga   4980
tttctctcat tacttcctca catgttggag gcattttctc tccctctgca cttaatagcc   5040
tatcttgctt taatttcttc ccactcttgg aggctaggtt tggtttggtg ggctgatgag   5100
ggagggagag accgctccaa gtactttagc gggtgggatt gaaggcggag ccctcctgag   5160
ctatgagtgt cctatgagtg ggctggaac taagaaccag gggcgtggac agggtgtgtc   5220
acagagaagg ggatgtgcct gcttctttct ggcccaggag gaaccgggtc aattcttcag   5280
cacctgggta cccatagagc ccaccgcatc cccagcatgc ctgctattgt cttcccaatc   5340
ctcccccttg ctgtcctgcc ccaccccacc ccccagaata gaatgacacc tactcagaca   5400
atgcgatgca atttcctcat tttattagga aaggacagtg ggagtggcac cttccagggt   5460
caaggaaggc acgggggagg ggcaaacaac agatggctgg caactagaag gcacagcaga   5520
tctggatcac acgtggtcga ctgatcagtt gtcgtactcc tcggcgttgt cgccgaagaa   5580
gtagctgccc tcgttgctca tgtcgaagct aggcacgatg gggttggtgg ccttctcgtc   5640
gctcagctcg aacacgcctc tgcctctgaa ggacacctcc tcgggcttgg cgccctccat   5700
cattctgatg atctcggctc tcatgtcgct ggttctgccc tcggtgttgc cggtgaaggc   5760
ggccatcacg gtgctcttct cgaagggcag gtttctctgc acgctgaagg tgggctgcac   5820
gctgatctgg ccggcgctgg ctctctgctg gttggtgttg ccgccgcttc tggttctgat   5880
ggcccagtat ctgcttctca gctccagggt gctgctgccc atgttgtcca tgttctcgtt   5940
```

| | |
|---|---|
| gctggcgatc tgcacgcctc tggtgctcag cttgcctctg ggggacacct tggtgcctct | 6000 |
| gatgaagctc agcagtctca ggtcctcgaa ggcggcgctg tggcaggcca tccacaccag | 6060 |
| ctggctcttg tgggcggggt tctcgttggg tctgatcagg ctgtacacct ggctgttctg | 6120 |
| cagcagcttg aaggggtcga tgcccaccag gctgtagccc tccttctcga agtcgtagcc | 6180 |
| gctgctcacg gcggggccgt acacgcaggc gggcaggcag ctcttgtggg ccacgctgcc | 6240 |
| tctcaggatc agggcgcttc tggccaggaa gatcaggtcc tcgatctcgg cgttgccggg | 6300 |
| gtttctgctc tcccggacct ggtccatcat ggctctctgg gcggcggtct ggaacttgcc | 6360 |
| cttcaggatg ttgcacattc tctcgtaggc gcttctggtc tttctgccgt tctcgcctct | 6420 |
| ccagaagttt ctgtcgttga tgcctctctt gatcattctg atcagctcca tcaccatggt | 6480 |
| gccgatgccc ttcacggcgg cgccggcggc gccgcttctt ctgggcaggg tgctgccctg | 6540 |
| catcaggctg cacattctgg ggtccatgcc ggtccgcacc agggctctgg ttctctggta | 6600 |
| ggtggtgtcg ttcaggttgc tgtgccagat catcatgtgg gtcaggccgg cggtggcgtc | 6660 |
| ctcgccgttg ttggcctgtc tccagattct tctgatctcc tccttgtcgt acagcaccag | 6720 |
| ctctctcatc cacttgccgt ccactcttct gtagatgggg ccgccggtct tcttggggtc | 6780 |
| cttgccggcg ctggggtgct cctccaggta tctgtttctt ctctcgtcga aggcgctcag | 6840 |
| caccattctc tcgatggtca ggctgttctg gatcagtctg ccctcgtagt cgctcagctt | 6900 |
| cagctcggtg cacatctgga tgtagaatct gccgatgccg tcgatcatct tgcccacgct | 6960 |
| ggctctgatc tcggtggcgt tctgtctctc gccgtcggtc tccatctgct cgtagcttct | 7020 |
| cttggtgccc tggctggcca tggtggcgaa ttcgatatcc gacgacggtg actgcagaaa | 7080 |
| agacccatgg aaaggaacag tctgttagtc tgtcagctat tatgtctggt ggcgcgcgcg | 7140 |
| gcagcaacga gtactgctca gactacactg ccctccaccg ttaactagag ttgagcaagc | 7200 |
| agggtcaggc aaagcgtgga gagccggctg agtctaggta ggctccaagg gagcgccgga | 7260 |
| caaaggcccg gtctcgacct gagctttaaa cttacctaga cggcggacgc agttcaggag | 7320 |
| gcaccacagg cgggaggcgg cagaacgcga ctcaaccggc gtggatggcg gcctcaggta | 7380 |
| gggcggcggg cgcgtgaagg agagatgcga gccgatggag gtgcacacca atgtggtgaa | 7440 |
| tggtcaaatg gcgtttattg tatcgagcta ggcacttaaa tacaatatct ctgcaatgcg | 7500 |
| gaattcagtg gttcgtccaa tccatgtcag acccgtctgt tgccttccta ataaggcacg | 7560 |
| atcgtaccac cttacttcca ccaatcggca tgcacggtgc ttttctctc cttgtaaggc | 7620 |
| atgttgctaa ctcatcgtta ccatgttgca agactacaag agtattgcat aagactacat | 7680 |
| ttccccctcc ctatgcaaaa gcgaaactac tatatcctga ggggactcct aaccgcgtac | 7740 |
| aaccgaagcc ccgcttttcg cctaaacaca ccctagtccc ctcagatacg cgtatatctg | 7800 |
| gcccgtacat cgcgaagcag cgcaaaacgc ctaaccctaa gcagattctt catgcaattg | 7860 |
| tcggtcaagc cttgccttgt tgtagcttaa attttgctcg cgcactactc agcgacctcc | 7920 |
| aacacacaag cagggagcag ccaatagcca atctgatgcg gtattttctc cttacgcatc | 7980 |
| tgtgcggtat ttcacaccgc atagtggctt tccccccccc cccattattg aagcatttat | 8040 |
| cagggttatt gtctcatgag cggatacata tttgaatgta tttagaaaaa taaacaaata | 8100 |
| ggggttccgc gcacatttcc ccgaaaagtg ccacctgacg tctaagaaac cattattatc | 8160 |
| atgacattaa cctataaaaa taggcgtatc acgaggccct ttcgtctcgc gcgtttcggt | 8220 |
| gatgacggtg aaaacctctg acacatgcag ctcccggaga cggtcacagc ttgtctgtaa | 8280 |
| gcggatgccg ggagcagaca agcccgtcag gcgcgtcag cgggtgttgg cgggtgtcgg | 8340 |

ggctggctta actatgcggc atcagagcag attgtactga gagtgcacca tatgcggtgt 8400
gaaataccgc acagatgcgt aaggagaaaa taccgcatca gattggctat 8450

<210> SEQ ID NO 106
<211> LENGTH: 8442
<212> TYPE: DNA
<213> ORGANISM: Artificial sequence
<220> FEATURE:
<223> OTHER INFORMATION: VR4775, Ligation of RSV RSeg7 into VR4762

<400> SEQUENCE: 106
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960
ggtgacgata ctttccatta ctaatccata acatggctct ttgccacaac tatctctatt 1020
ggctatatgc caatactctg tccttcagag actgacacgg actctgtatt tttacaggat 1080
ggggtcccat ttattattta caaattcaca tatacaacaa cgccgtcccc cgtgcccgca 1140
gtttttatta aacatagcgt gggatctcca cgcgaatctc gggtacgtgt tccggacatg 1200
ggctcttctc cggtagcggc ggagcttcca catccgagcc ctggtcccat gcctccagcg 1260
gctcatggtc gctcggcagc tccttgctcc taacagtgga ggccagactt aggcacagca 1320
caatgcccac caccaccagt gtgccgcaca aggccgtggc ggtagggtat gtgtctgaaa 1380
atgagcgtgg agattgggct cgcacggctg acgcagatgg aagacttaag gcagcggcag 1440
aagaagatgc aggcagctga gttgttgtat tctgataaga gtcagaggta actcccgttg 1500
cggtgctgtt aacggtggag ggcagtgtag tctgagcagt actcgttgct gccgcgcgcg 1560
ccaccagaca taatagctga cagactaaca gactgttcct ttccatgggt cttttctgca 1620
gtcaccgtcg tcggatatcg aattcgccac catggccagc cagggcacca agagaagcta 1680
cgagcagatg gagaccgacg gcgagagaca gaacgccacc gagatcagag ccagcgtggg 1740
caagatgatc gacggcatcg gcagattcta catccagatg tgcaccgagc tgaagctgag 1800
cgactacgag ggcagactga tccagaacag cctgaccatc gagagaatgg tgctgagcgc 1860
cttcgacgag agaagaaaca gatacctgga ggagcacccc agcgccggca aggaccccaa 1920
gaagaccggc ggccccatct acagaagagt ggacggcaag tggatgagag agctggtgct 1980

-continued

```
gtacgacaag gaggagatca gaagaatctg gagacaggcc aacaacggcg aggacgccac   2040
cgccggcctg acccacatga tgatctggca cagcaacctg aacgacacca cctaccagag   2100
aaccagagcc ctggtgcgga ccggcatgga ccccagaatg tgcagcctga tgcagggcag   2160
caccctgccc agaagaagcg gcgccgccgg cgccgccgtg aagggcatcg gcaccatggt   2220
gatggagctg atcagaatga tcaagagagg catcaacgac agaaacttct ggagaggcga   2280
gaacggcaga aagaccagaa gcgcctacga gagaatgtgc aacatcctga agggcaagtt   2340
ccagaccgcc gcccagagag ccatgatgga ccaggtccgg gagagcagaa accccggcaa   2400
cgccgagatc gaggacctga tcttcctggc cagaagcgcc ctgatcctga gaggcagcgt   2460
ggcccacaag agctgcctgc ccgcctgcgt gtacggcccc gccgtgagca gcggctacga   2520
cttcgagaag gagggctaca gcctggtggg catcgacccc ttcaagctgc tgcagaacag   2580
ccaggtgtac agcctgatca gacccaacga gaaccccgcc cacaagagcc agctggtgtg   2640
gatggcctgc cacagcgccg ccttcgagga cctgagactg ctgagcttca tcagaggcac   2700
caaggtgtcc cccagaggca agctgagcac cagaggcgtg cagatcgcca gcaacgagaa   2760
catggacaac atgggcagca gcaccctgga gctgagaagc agatactggg ccatcagaac   2820
cagaagcggc ggcaacacca accagcagag agccagcgcc ggccagatca gcgtgcagcc   2880
caccttcagc gtgcagagaa acctgccctt cgagaagagc accgtgatgg ccgccttcac   2940
cggcaacacc gagggcagaa ccagcgacat gagagccgag atcatcagaa tgatggaggg   3000
cgccaagccc gaggaggtgt ccttcagagg cagaggcgtg ttcgagctga gcgacgagaa   3060
ggccaccaac cccatcgtgc ctagcttcga catgagcaac gagggcagct acttcttcgg   3120
cgacaacgcc gaggagtacg acaactgatc agtcgaccac gtgtgatcca gatctacttc   3180
tggctaataa aagatcagag ctctagagat ctgtgtgttg gttttttgtg tggtactctt   3240
ccgcttcctc gctcactgac tcgctgcgct cggtcgttcg gctgcggcga gcggtatcag   3300
ctcactcaaa ggcggtaata cggttatcca cagaatcagg ggataacgca ggaaagaaca   3360
tgtgagcaaa aggccagcaa aaggccagga accgtaaaaa ggccgcgttg ctggcgtttt   3420
tccataggct ccgcccccct gacgagcatc acaaaaatcg acgctcaagt cagaggtggc   3480
gaaacccgac aggactataa agataccagg cgtttccccc tggaagctcc ctcgtgcgct   3540
ctcctgttcc gaccctgccg cttaccggat acctgtccgc ctttctccct tcgggaagcg   3600
tggcgctttc tcatagctca cgctgtaggt atctcagttc ggtgtaggtc gttcgctcca   3660
agctgggctg tgtgcacgaa ccccccgttc agcccgaccg ctgcgcctta tccggtaact   3720
atcgtcttga gtccaacccg gtaagacacg acttatcgcc actggcagca gccactggta   3780
acaggattag cagagcgagg tatgtaggcg gtgctacaga gttcttgaag tggtggccta   3840
actacggcta cactagaaga acagtatttg gtatctgcgc tctgctgaag ccagttacct   3900
tcggaaaaag agttggtagc tcttgatccg gcaaacaaac caccgctggt agcggtggtt   3960
tttttgtttg caagcagcag attacgcgca gaaaaaaagg atctcaagaa gatcctttga   4020
tcttttctac ggggtctgac gctcagtgga acgaaaactc acgttaaggg attttggtca   4080
tgagattatc aaaaaggatc ttcacctaga tccttttaaa ttaaaaatga agttttaaat   4140
caatctaaag tatatatgag taaacttggt ctgacagtta ccaatgctta atcagtgagg   4200
cacctatctc agcgatctgt ctatttcgtt catccatagt tgcctgactc gggggggggg   4260
ggcgctgagg tctgcctcgt gaagaaggtg ttgctgactc ataccaggcc tgaatcgccc   4320
catcatccag ccagaaagtg agggagccac ggttgatgag agctttgttg taggtggacc   4380
```

-continued

```
agttggtgat tttgaacttt tgctttgcca cggaacggtc tgcgttgtcg ggaagatgcg   4440
tgatctgatc cttcaactca gcaaaagttc gatttattca acaaagccgc cgtcccgtca   4500
agtcagcgta atgctctgcc agtgttacaa ccaattaacc aattctgatt agaaaaactc   4560
atcgagcatc aaatgaaact gcaatttatt catatcagga ttatcaatac catatttttg   4620
aaaaagccgt ttctgtaatg aaggagaaaa ctcaccgagg cagttccata ggatggcaag   4680
atcctggtat cggtctgcga ttccgactcg tccaacatca atacaaccta ttaatttccc   4740
ctcgtcaaaa ataaggttat caagtgagaa atcaccatga gtgacgactg aatccggtga   4800
gaatggcaaa agcttatgca tttctttcca gacttgttca acaggccagc cattacgctc   4860
gtcatcaaaa tcactcgcat caaccaaacc gttattcatt cgtgattgcg cctgagcgag   4920
acgaaatacg cgatcgctgt taaaaggaca attacaaaca ggaatcgaat gcaaccggcg   4980
caggaacact gccagcgcat caacaatatt ttcacctgaa tcaggatatt cttctaatac   5040
ctggaatgct gttttcccgg ggatcgcagt ggtgagtaac catgcatcat caggagtacg   5100
gataaaatgc ttgatggtcg gaagaggcat aaattccgtc agccagttta gtctgaccat   5160
ctcatctgta acatcattgg caacgctacc tttgccatgt ttcagaaaca actctggcgc   5220
atcgggcttc ccatacaatc gatagattgt cgcacctgat tgcccgacat tatcgcgagc   5280
ccatttatac ccatataaat cagcatccat gttggaattt aatcgcggcc tcgagcaaga   5340
cgtttcccgt tgaatatggc tcataacacc ccttgtatta ctgtttatgt aagcagacag   5400
ttttattgtt catgatgata tatttttatc ttgtgcaatg taacatcaga gattttgaga   5460
cactatgcgg tgtgaaatac cgcacagatg cgtaaggaga aaataccgca tcagattggc   5520
tattggctgc tccctgcttg tgtgttggag gtcgctgagt agtgcgcgag caaaatttaa   5580
gctacaacaa ggcaaggctt gaccgacaat tgcatgaaga atctgcttag ggttaggcgt   5640
tttgcgctgc ttcgcgatgt acgggccaga tatacgcgta tctgagggga ctagggtgtg   5700
tttaggcgaa aagcggggct tcggttgtac gcggttagga gtcccctcag gatatagtag   5760
tttcgctttt gcatagggag ggggaaatgt agtcttatgc aatactcttg tagtcttgca   5820
acatggtaac gatgagttag caacatgcct tacaaggaga gaaaaagcac cgtgcatgcc   5880
gattggtgga agtaaggtgg tacgatcgtg ccttattagg aaggcaacag acgggtctga   5940
catggattgg acgaaccact gaattccgca ttgcagagat attgtattta agtgcctagc   6000
tcgatacaat aaacgccatt tgaccattca ccacattggt gtgcacctcc atcggctcgc   6060
atctctcctt cacgcgcccg ccgccctacc tgaggccgcc atccacgccg gttgagtcgc   6120
gttctgccgc ctcccgcctg tggtgcctcc tgaactgcgt ccgccgtcta ggtaagttta   6180
aagctcaggt cgagaccggg cctttgtccg gcgctccctt ggagcctacc tagactcagc   6240
cggctctcca cgctttgcct gaccctgctt gctcaactct agttaacggt ggagggcagt   6300
gtagtctgag cagtactcgt tgctgccgcg cgcgccacca gacataatag ctgacagact   6360
aacagactgt tcctttccat gggtcttttc tgcagtcacc gtcgtcggat atcgaattcg   6420
ccaccatgag ccttctaacc gaggtcgaaa cgtatgttct ctctatcgtt ccatcaggcc   6480
ccctcaaagc cgaaatcgcg cagagacttg aagatgtctt tgctgggaaa aacacagatc   6540
ttgaggctct catggaatgg ctaaagacaa gaccaatcct gtcacctctg actaagggga   6600
ttttggggtt tgtgttcacg ctcaccgtgc ccagtgagcg aggactgcag cgtagacgct   6660
ttgtccaaaa tgccctcaat gggaatgggg atccaaataa catggacaga gcagttaaac   6720
tatatagaaa acttaagagg gagattacat tccatggggc caaagaaata gcactcagtt   6780
```

```
attctgctgg tgcacttgcc agttgcatgg gcctcatata caacagaatg ggggctgtaa   6840
ccactgaagt ggcctttggc ctggtatgtg caacatgtga acagattgct gactcccagc   6900
acaggtctca taggcaaatg gtggcaacaa ccaatccatt aataaggcat gagaacagaa   6960
tggttttggc cagcactaca gctaaggcta tggagcaaat ggctggatca agtgagcagg   7020
cagcggaggc catggaaatt gctagtcagg ccaggcaaat ggtgcaggca atgagagcca   7080
ttgggactca tcctagctcc agtgctggtc taaaagatga tcttcttgaa aatttgcaga   7140
cctatcagaa acgaatgggg gtgcagatgc aacgattcaa gtgacccgct tgttgttgct   7200
gcgagtatca ttgggatctt gcacttgata ttgtggattc ttgatcgtct ttttttcaaa   7260
tgcatctatc gactcttcaa acacggtctg aaaagagggc cttctacgga aggagtacct   7320
gagtctatga gggaagaata tcgaaaggaa cagcagaatg ctgtggatgc tgacgacagt   7380
cattttgtca gcatagagct ggagtaatca gtcgagatcc agatctgctg tgccttctag   7440
ttgccagcca tctgttgttt gcccctcccc cgtgccttcc ttgaccctgg aaggtgccac   7500
tcccactgtc ctttcctaat aaaatgagga aattgcatcg cattgtctga gtaggtgtca   7560
ttctattctg gggggtgggg tggggcagga cagcaagggg gaggattggg aagacaatag   7620
caggcatgct ggggatgcgg tgggctctat gggtacccag gtgctgaaga attgacccgg   7680
ttcctcctgg gccagaaaga agcaggcaca tccccttctc tgtgacacac cctgtccacg   7740
cccctggttc ttagttccag ccccactcat aggacactca tagctcagga gggctccgcc   7800
ttcaatccca cccgctaaag tacttggagc ggtctctccc tccctcatca gcccaccaaa   7860
ccaaacctag cctccaagag tgggaagaaa ttaaagcaag ataggctatt aagtgcagag   7920
ggagagaaaa tgcctccaac atgtgaggaa gtaatgagag aaatcataga attttaaggc   7980
catgatttaa ggccagtggc tttccccccc cccccattat tgaagcattt atcagggtta   8040
ttgtctcatg agcggataca tatttgaatg tatttagaaa aataaacaaa taggggttcc   8100
gcgcacattt ccccgaaaag tgccacctga cgtctaagaa accattatta tcatgacatt   8160
aacctataaa aataggcgta tcacgaggcc ctttcgtctc gcgcgtttcg gtgatgacgg   8220
tgaaaacctc tgacacatgc agctcccgga gacggtcaca gcttgtctgt aagcggatgc   8280
cgggagcaga caagcccgtc agggcgcgtc agcgggtgtt ggcgggtgtc ggggctggct   8340
taactatgcg gcatcagagc agattgtact gagagtgcac catatgcggt gtgaaatacc   8400
gcacagatgc gtaaggagaa aataccgcat cagattggct at                      8442
```

<210> SEQ ID NO 107
<211> LENGTH: 8442
<212> TYPE: DNA
<213> ORGANISM: Artificial sequence
<220> FEATURE:
<223> OTHER INFORMATION: VR4776, Ligation of Inverted RSV R Seg7 into VR4762

<400> SEQUENCE: 107

```
tggccattgc atacgttgta tccatatcat aatatgtaca tttatattgg ctcatgtcca     60
acattaccgc catgttgaca ttgattattg actagttatt aatagtaatc aattacgggg    120
tcattagttc atagcccata tatggagttc cgcgttacat aacttacggt aaatggcccg    180
cctggctgac cgcccaacga cccccgccca ttgacgtcaa taatgacgta tgttcccata    240
gtaacgccaa tagggacttt ccattgacgt caatgggtgg agtatttacg gtaaactgcc    300
cacttggcag tacatcaagt gtatcatatg ccaagtacgc cccctattga cgtcaatgac    360
ggtaaatggc ccgcctggca ttatgcccag tacatgacct tatgggactt tcctacttgg    420
```

-continued

```
cagtacatct acgtattagt catcgctatt accatggtga tgcggttttg gcagtacatc    480

aatgggcgtg gatagcggtt tgactcacgg ggatttccaa gtctccaccc cattgacgtc    540

aatgggagtt tgttttggca ccaaaatcaa cgggactttc caaaatgtcg taacaactcc    600

gccccattga cgcaaatggg cggtaggcgt gtacggtggg aggtctatat aagcagagct    660

cgtttagtga accgtcagat cgcctggaga cgccatccac gctgttttga cctccataga    720

agacaccggg accgatccag cctccgcggc cgggaacggt gcattggaac gcggattccc    780

cgtgccaaga gtgacgtaag taccgcctat agactctata ggcacacccc tttggctctt    840

atgcatgcta tactgttttt ggcttggggc ctatacaccc ccgcttcctt atgctatagg    900

tgatggtata gcttagccta taggtgtggg ttattgacca ttattgacca ctcccctatt    960

ggtgacgata ctttccatta ctaatccata acatggctct ttgccacaac tatctctatt   1020

ggctatatgc caatactctg tccttcagag actgacacgg actctgtatt tttacaggat   1080

ggggtcccat ttattattta caaattcaca tatacaacaa cgccgtcccc cgtgcccgca   1140

gtttttatta aacatagcgt gggatctcca cgcgaatctc gggtacgtgt tccggacatg   1200

ggctcttctc cggtagcggc ggagcttcca catccgagcc ctggtcccat gcctccagcg   1260

gctcatggtc gctcggcagc tccttgctcc taacagtgga ggccagactt aggcacagca   1320

caatgcccac caccaccagt gtgccgcaca aggccgtggc ggtagggtat gtgtctgaaa   1380

atgagcgtgg agattgggct cgcacggctg acgcagatgg aagacttaag gcagcggcag   1440

aagaagatgc aggcagctga gttgttgtat tctgataaga gtcagaggta actcccgttg   1500

cggtgctgtt aacggtggag ggcagtgtag tctgagcagt actcgttgct gccgcgcgcg   1560

ccaccagaca taatagctga cagactaaca gactgttcct ttccatgggt cttttctgca   1620

gtcaccgtcg tcggatatcg aattcgccac catggccagc cagggcacca agagaagcta   1680

cgagcagatg gagaccgacg gcgagagaca gaacgccacc gagatcagag ccagcgtggg   1740

caagatgatc gacggcatcg gcagattcta catccagatg tgcaccgagc tgaagctgag   1800

cgactacgag ggcagactga tccagaacag cctgaccatc gagagaatgg tgctgagcgc   1860

cttcgacgag agaagaaaca gatacctgga ggagcacccc agcgccggca aggaccccaa   1920

gaagaccggc ggccccatct acagaagagt ggacggcaag tggatgagag agctggtgct   1980

gtacgacaag gaggagatca gaagaatctg gagacaggcc aacaacggcg aggacgccac   2040

cgccggcctg acccacatga tgatctggca cagcaacctg aacgacacca cctaccagag   2100

aaccagagcc ctggtgcgga ccggcatgga ccccagaatg tgcagcctga tgcagggcag   2160

caccctgccc agaagaagcg gcgccgccgg cgccgccgtg aagggcatcg gcaccatggt   2220

gatggagctg atcagaatga tcaagagagg catcaacgac agaaacttct ggagaggcga   2280

gaacggcaga aagaccagaa gcgcctacga gagaatgtgc aacatcctga agggcaagtt   2340

ccagaccgcc gcccagagag ccatgatgga ccaggtccgg gagagcagaa accccggcaa   2400

cgccgagatc gaggacctga tcttcctggc cagaagcgcc ctgatcctga gaggcagcgt   2460

ggcccacaag agctgcctgc ccgcctgcgt gtacggcccc gccgtgagca gcggctacga   2520

cttcgagaag gagggctaca gcctggtggg catcgacccc ttcaagctgc tgcagaacag   2580

ccaggtgtac agcctgatca gacccaacga gaaccccgcc cacaagagcc agctggtgtg   2640

gatggcctgc cacagcgccg ccttcgagga cctgagactg ctgagcttca tcagaggcac   2700

caaggtgtcc cccagaggca agctgagcac cagaggcgtg cagatcgcca gcaacgagaa   2760

catggacaac atgggcagca gcaccctgga gctgagaagc agatactggg ccatcagaac   2820
```

-continued

```
cagaagcggc ggcaacacca accagcagag agccagcgcc ggccagatca gcgtgcagcc   2880
caccttcagc gtgcagagaa acctgccctt cgagaagagc accgtgatgg ccgccttcac   2940
cggcaacacc gagggcagaa ccagcgacat gagagccgag atcatcagaa tgatggaggg   3000
cgccaagccc gaggaggtgt ccttcagagg cagaggcgtg ttcgagctga gcgacgagaa   3060
ggccaccaac cccatcgtgc ctagcttcga catgagcaac gagggcagct acttcttcgg   3120
cgacaacgcc gaggagtacg acaactgatc agtcgaccac gtgtgatcca gatctacttc   3180
tggctaataa aagatcagag ctctagagat ctgtgtgttg gttttttgtg tggtactctt   3240
ccgcttcctc gctcactgac tcgctgcgct cggtcgttcg gctgcggcga gcggtatcag   3300
ctcactcaaa ggcggtaata cggttatcca cagaatcagg ggataacgca ggaaagaaca   3360
tgtgagcaaa aggccagcaa aaggccagga accgtaaaaa ggccgcgttg ctggcgtttt   3420
tccataggct ccgcccccct gacgagcatc acaaaaatcg acgctcaagt cagaggtggc   3480
gaaacccgac aggactataa agataccagg cgtttccccc tggaagctcc ctcgtgcgct   3540
ctcctgttcc gaccctgccg cttaccggat acctgtccgc ctttctccct tcgggaagcg   3600
tggcgctttc tcatagctca cgctgtaggt atctcagttc ggtgtaggtc gttcgctcca   3660
agctgggctg tgtgcacgaa ccccccgttc agcccgaccg ctgcgcctta tccggtaact   3720
atcgtcttga gtccaacccg gtaagacacg acttatcgcc actggcagca gccactggta   3780
acaggattag cagagcgagg tatgtaggcg gtgctacaga gttcttgaag tggtggccta   3840
actacggcta cactagaaga acagtatttg gtatctgcgc tctgctgaag ccagttacct   3900
tcggaaaaag agttggtagc tcttgatccg gcaaacaaac caccgctggt agcggtggtt   3960
tttttgtttg caagcagcag attacgcgca gaaaaaaagg atctcaagaa gatcctttga   4020
tcttttctac ggggtctgac gctcagtgga acgaaaactc acgttaaggg attttggtca   4080
tgagattatc aaaaaggatc ttcacctaga tccttttaaa ttaaaaatga agttttaaat   4140
caatctaaag tatatatgag taaacttggt ctgacagtta ccaatgctta atcagtgagg   4200
cacctatctc agcgatctgt ctatttcgtt catccatagt tgcctgactc gggggggggg   4260
ggcgctgagg tctgcctcgt gaagaaggtg ttgctgactc ataccaggcc tgaatcgccc   4320
catcatccag ccagaaagtg agggagccac ggttgatgag agctttgttg taggtggacc   4380
agttggtgat tttgaacttt tgctttgcca cggaacggtc tgcgttgtcg ggaagatgcg   4440
tgatctgatc cttcaactca gcaaaagttc gatttattca acaaagccgc cgtcccgtca   4500
agtcagcgta atgctctgcc agtgttacaa ccaattaacc aattctgatt agaaaaactc   4560
atcgagcatc aaatgaaact gcaatttatt catatcagga ttatcaatac catatttttg   4620
aaaaagccgt ttctgtaatg aaggagaaaa ctcaccgagg cagttccata ggatggcaag   4680
atcctggtat cggtctgcga ttccgactcg tccaacatca atacaaccta ttaatttccc   4740
ctcgtcaaaa ataaggttat caagtgagaa atcaccatga gtgacgactg aatccggtga   4800
gaatggcaaa agcttatgca tttctttcca gacttgttca acaggccagc cattacgctc   4860
gtcatcaaaa tcactcgcat caaccaaacc gttattcatt cgtgattgcg cctgagcgag   4920
acgaaatacg cgatcgctgt taaaaggaca attacaaaca ggaatcgaat gcaaccggcg   4980
caggaacact gccagcgcat caacaatatt ttcacctgaa tcaggatatt cttctaatac   5040
ctggaatgct gttttcccgg ggatcgcagt ggtgagtaac catgcatcat caggagtacg   5100
gataaaatgc ttgatggtcg gaagaggcat aaattccgtc agccagttta gtctgaccat   5160
ctcatctgta acatcattgg caacgctacc tttgccatgt ttcagaaaca actctggcgc   5220
```

-continued

```
atcgggcttc ccatacaatc gatagattgt cgcacctgat tgcccgacat tatcgcgagc   5280
ccatttatac ccatataaat cagcatccat gttggaattt aatcgcggcc tcgagcaaga   5340
cgtttcccgt tgaatatggc tcataacacc ccttgtatta ctgtttatgt aagcagacag   5400
ttttattgtt catgatgata tatttttatc ttgtgcaatg taacatcaga gattttgaga   5460
cactggcctt aaatcatggc cttaaaattc tatgatttct ctcattactt cctcacatgt   5520
tggaggcatt ttctctccct ctgcacttaa tagcctatct tgctttaatt tcttcccact   5580
cttggaggct aggtttggtt tggtgggctg atgagggagg gagagaccgc tccaagtact   5640
ttagcgggtg ggattgaagg cggagccctc ctgagctatg agtgtcctat gagtggggct   5700
ggaactaaga accaggggcg tggacagggt gtgtcacaga gaaggggatg tgcctgcttc   5760
tttctggccc aggaggaacc gggtcaattc ttcagcacct gggtacccat agagcccacc   5820
gcatccccag catgcctgct attgtcttcc caatcctccc ccttgctgtc ctgccccacc   5880
ccaccccccca gaatagaatg acacctactc agacaatgcg atgcaatttc ctcattttat   5940
taggaaagga cagtgggagt ggcaccttcc agggtcaagg aaggcacggg ggaggggcaa   6000
acaacagatg gctggcaact agaaggcaca gcagatctgg atctcgactg attactccag   6060
ctctatgctg acaaaatgac tgtcgtcagc atccacagca ttctgctgtt cctttcgata   6120
ttcttccctc atagactcag gtactccttc cgtagaaggc cctcttttca gaccgtgttt   6180
gaagagtcga tagatgcatt tgaaaaaaag acgatcaaga atccacaata tcaagtgcaa   6240
gatcccaatg atactcgcag caacaacaag cgggtcactt gaatcgttgc atctgcaccc   6300
ccattcgttt ctgataggtc tgcaaatttt caagaagatc atcttttaga ccagcactgg   6360
agctaggatg agtcccaatg gctctcattg cctgcaccat ttgcctggcc tgactagcaa   6420
tttccatggc ctccgctgcc tgctcacttg atccagccat ttgctccata gccttagctg   6480
tagtgctggc caaaaccatt ctgttctcat gccttattaa tggattggtt gttgccacca   6540
tttgcctatg agacctgtgc tgggagtcag caatctgttc acatgttgca cataccaggc   6600
caaaggccac ttcagtggtt acagccccca ttctgttgta tatgaggccc atgcaactgg   6660
caagtgcacc agcagaataa ctgagtgcta tttctttggc cccatggaat gtaatctccc   6720
tcttaagttt tctatatagt ttaactgctc tgtccatgtt atttggatcc ccattcccat   6780
tgagggcatt ttggacaaag cgtctacgct gcagtcctcg ctcactgggc acggtgagcg   6840
tgaacacaaa ccccaaaatc cccttagtca gaggtgacag gattggtctt gtctttagcc   6900
attccatgag agcctcaaga tctgtgtttt tcccagcaaa gacatcttca agtctctgcg   6960
cgatttcggc tttgaggggg cctgatggaa cgatagagag aacatacgtt tcgacctcgg   7020
ttagaaggct catggtggcg aattcgatat ccgacgacgg tgactgcaga aaagacccat   7080
ggaaaggaac agtctgttag tctgtcagct attatgtctg gtggcgcgcg cggcagcaac   7140
gagtactgct cagactacac tgccctccac cgttaactag agttgagcaa gcagggtcag   7200
gcaaagcgtg gagagccggc tgagtctagg taggctccaa gggagcgccg gacaaaggcc   7260
cggtctcgac ctgagcttta aacttaccta gacggcggac gcagttcagg aggcaccaca   7320
ggcgggaggc ggcagaacgc gactcaaccg gcgtggatgg cggcctcagg tagggcggcg   7380
ggcgcgtgaa ggagagatgc gagccgatgg aggtgcacac caatgtggtg aatggtcaaa   7440
tggcgtttat tgtatcgagc taggcactta aatacaatat ctctgcaatg cggaattcag   7500
tggttcgtcc aatccatgtc agacccgtct gttgccttcc taataaggca cgatcgtacc   7560
accttacttc caccaatcgg catgcacggt gcttttctc tccttgtaag gcatgttgct   7620
```

aactcatcgt taccatgttg caagactaca agagtattgc ataagactac atttccccct 7680
ccctatgcaa aagcgaaact actatatcct gaggggactc ctaaccgcgt acaaccgaag 7740
ccccgctttt cgcctaaaca caccctagtc ccctcagata cgcgtatatc tggcccgtac 7800
atcgcgaagc agcgcaaaac gcctaaccct aagcagattc ttcatgcaat tgtcggtcaa 7860
gccttgcctt gttgtagctt aaattttgct cgcgcactac tcagcgacct ccaacacaca 7920
agcagggagc agccaatagc caatctgatg cggtattttc tccttacgca tctgtgcggt 7980
atttcacacc gcatagtggc tttccccccc cccccattat tgaagcattt atcagggtta 8040
ttgtctcatg agcggataca tatttgaatg tatttagaaa aataaacaaa taggggttcc 8100
gcgcacattt ccccgaaaag tgccacctga cgtctaagaa accattatta tcatgacatt 8160
aacctataaa aataggcgta tcacgaggcc ctttcgtctc gcgcgtttcg gtgatgacgg 8220
tgaaaacctc tgacacatgc agctcccgga gacggtcaca gcttgtctgt aagcggatgc 8280
cgggagcaga caagcccgtc agggcgcgtc agcgggtgtt ggcgggtgtc ggggctggct 8340
taactatgcg gcatcagagc agattgtact gagagtgcac catatgcggt gtgaaatacc 8400
gcacagatgc gtaaggagaa aataccgcat cagattggct at 8442

<210> SEQ ID NO 108
<211> LENGTH: 7754
<212> TYPE: DNA
<213> ORGANISM: Artificial sequence
<220> FEATURE:
<223> OTHER INFORMATION: VR4777, Ligation of RSVRM2 into VR4762

<400> SEQUENCE: 108
tggccattgc atacgttgta tccatatcat aatatgtaca tttatattgg ctcatgtcca 60
acattaccgc catgttgaca ttgattattg actagttatt aatagtaatc aattacgggg 120
tcattagttc atagcccata tatggagttc cgcgttacat aacttacggt aaatggcccg 180
cctggctgac cgcccaacga cccccgccca ttgacgtcaa taatgacgta tgttcccata 240
gtaacgccaa tagggacttt ccattgacgt caatgggtgg agtatttacg gtaaactgcc 300
cacttggcag tacatcaagt gtatcatatg ccaagtacgc cccctattga cgtcaatgac 360
ggtaaatggc ccgcctggca ttatgcccag tacatgacct tatgggactt tcctacttgg 420
cagtacatct acgtattagt catcgctatt accatggtga tgcggttttg gcagtacatc 480
aatgggcgtg gatagcggtt tgactcacgg ggatttccaa gtctccaccc cattgacgtc 540
aatgggagtt tgttttggca ccaaaatcaa cgggactttc caaaatgtcg taacaactcc 600
gccccattga cgcaaatggg cggtaggcgt gtacggtggg aggtctatat aagcagagct 660
cgtttagtga accgtcagat cgcctggaga cgccatccac gctgttttga cctccataga 720
agacaccggg accgatccag cctccgcggc cgggaacggt gcattggaac gcggattccc 780
cgtgccaaga gtgacgtaag taccgcctat agactctata ggcacacccc tttggctctt 840
atgcatgcta tactgttttt ggcttggggc ctatacaccc ccgcttcctt atgctatagg 900
tgatggtata gcttagccta taggtgtggg ttattgacca ttattgacca ctcccctatt 960
ggtgacgata ctttccatta ctaatccata acatggctct ttgccacaac tatctctatt 1020
ggctatatgc caatactctg tccttcagag actgacacgg actctgtatt tttacaggat 1080
ggggtcccat ttattattta caaattcaca tatacaacaa cgccgtcccc cgtgcccgca 1140
gtttttatta aacatagcgt gggatctcca cgcgaatctc gggtacgtgt tccggacatg 1200
ggctcttctc cggtagcggc ggagcttcca catccgagcc ctggtcccat gcctccagcg 1260

-continued

```
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catggccagc cagggcacca agagaagcta   1680
cgagcagatg gagaccgacg gcgagagaca gaacgccacc gagatcagag ccagcgtggg   1740
caagatgatc gacggcatcg gcagattcta catccagatg tgcaccgagc tgaagctgag   1800
cgactacgag ggcagactga tccagaacag cctgaccatc gagagaatgg tgctgagcgc   1860
cttcgacgag agaagaaaca gatacctgga ggagcacccc agcgccggca aggaccccaa   1920
gaagaccggc ggccccatct acagaagagt ggacggcaag tggatgagag agctggtgct   1980
gtacgacaag gaggagatca gaagaatctg gagacaggcc aacaacggcg aggacgccac   2040
cgccggcctg acccacatga tgatctggca cagcaacctg aacgacacca cctaccagag   2100
aaccagagcc ctggtgcgga ccggcatgga ccccagaatg tgcagcctga tgcagggcag   2160
caccctgccc agaagaagcg gcgccgccgg cgccgccgtg aagggcatcg gcaccatggt   2220
gatggagctg atcagaatga tcaagagagg catcaacgac agaaacttct ggagaggcga   2280
gaacggcaga aagaccagaa gcgcctacga gagaatgtgc aacatcctga agggcaagtt   2340
ccagaccgcc gcccagagag ccatgatgga ccaggtccgg gagagcagaa accccggcaa   2400
cgccgagatc gaggacctga tcttcctggc cagaagcgcc ctgatcctga gaggcagcgt   2460
ggcccacaag agctgcctgc ccgcctgcgt gtacggcccc gccgtgagca gcggctacga   2520
cttcgagaag gagggctaca gcctggtggg catcgacccc ttcaagctgc tgcagaacag   2580
ccaggtgtac agcctgatca gacccaacga gaaccccgcc cacaagagcc agctggtgtg   2640
gatggcctgc cacagcgccg ccttcgagga cctgagactg ctgagcttca tcagaggcac   2700
caaggtgtcc cccagaggca agctgagcac cagaggcgtg cagatcgcca gcaacgagaa   2760
catggacaac atgggcagca gcaccctgga gctgagaagc agatactggg ccatcagaac   2820
cagaagcggc ggcaacacca accagcagag agccagcgcc ggccagatca gcgtgcagcc   2880
caccttcagc gtgcagagaa acctgccctt cgagaagagc accgtgatgg ccgccttcac   2940
cggcaacacc gagggcagaa ccagcgacat gagagccgag atcatcagaa tgatggaggg   3000
cgccaagccc gaggaggtgt ccttcagagg cagaggcgtg ttcgagctga gcgacgagaa   3060
ggccaccaac cccatcgtgc ctagcttcga catgagcaac gagggcagct acttcttcgg   3120
cgacaacgcc gaggagtacg acaactgatc agtcgaccac gtgtgatcca gatctacttc   3180
tggctaataa aagatcagag ctctagagat ctgtgtgttg gtttttgtg tggtactctt   3240
ccgcttcctc gctcactgac tcgctgcgct cggtcgttcg gctgcggcga gcggtatcag   3300
ctcactcaaa ggcggtaata cggttatcca cagaatcagg ggataacgca ggaaagaaca   3360
tgtgagcaaa aggccagcaa aaggccagga accgtaaaaa ggccgcgttg ctggcgtttt   3420
tccataggct ccgcccccct gacgagcatc acaaaaatcg acgctcaagt cagaggtggc   3480
gaaacccgac aggactataa agataccagg cgtttccccc tggaagctcc ctcgtgcgct   3540
ctcctgttcc gaccctgccg cttaccggat acctgtccgc ctttctccct tcgggaagcg   3600
tggcgctttc tcatagctca cgctgtaggt atctcagttc ggtgtaggtc gttcgctcca   3660
```

-continued agctgggctg tgtgcacgaa ccccccgttc agcccgaccg ctgcgcctta tccggtaact 3720
atcgtcttga gtccaacccg gtaagacacg acttatcgcc actggcagca gccactggta 3780
acaggattag cagagcgagg tatgtaggcg gtgctacaga gttcttgaag tggtggccta 3840
actacggcta cactagaaga acagtatttg gtatctgcgc tctgctgaag ccagttacct 3900
tcggaaaaag agttggtagc tcttgatccg gcaaacaaac caccgctggt agcggtggtt 3960
tttttgtttg caagcagcag attacgcgca gaaaaaaagg atctcaagaa gatcctttga 4020
tcttttctac ggggtctgac gctcagtgga acgaaaactc acgttaaggg attttggtca 4080
tgagattatc aaaaaggatc ttcacctaga tccttttaaa ttaaaaatga agttttaaat 4140
caatctaaag tatatatgag taaacttggt ctgacagtta ccaatgctta atcagtgagg 4200
cacctatctc agcgatctgt ctatttcgtt catccatagt tgcctgactc gggggggggg 4260
ggcgctgagg tctgcctcgt gaagaaggtg ttgctgactc ataccaggcc tgaatcgccc 4320
catcatccag ccagaaagtg agggagccac ggttgatgag agctttgttg taggtggacc 4380
agttggtgat tttgaacttt tgctttgcca cggaacggtc tgcgttgtcg ggaagatgcg 4440
tgatctgatc cttcaactca gcaaaagttc gatttattca acaaagccgc cgtcccgtca 4500
agtcagcgta atgctctgcc agtgttacaa ccaattaacc aattctgatt agaaaaactc 4560
atcgagcatc aaatgaaact gcaatttatt catatcagga ttatcaatac catatttttg 4620
aaaaagccgt ttctgtaatg aaggagaaaa ctcaccgagg cagttccata ggatggcaag 4680
atcctggtat cggtctgcga ttccgactcg tccaacatca atacaaccta ttaatttccc 4740
ctcgtcaaaa ataaggttat caagtgagaa atcaccatga gtgacgactg aatccggtga 4800
gaatggcaaa agcttatgca tttctttcca gacttgttca acaggccagc cattacgctc 4860
gtcatcaaaa tcactcgcat caaccaaacc gttattcatt cgtgattgcg cctgagcgag 4920
acgaaatacg cgatcgctgt taaaaggaca attacaaaca ggaatcgaat gcaaccggcg 4980
caggaacact gccagcgcat caacaatatt ttcacctgaa tcaggatatt cttctaatac 5040
ctggaatgct gttttcccgg ggatcgcagt ggtgagtaac catgcatcat caggagtacg 5100
gataaaatgc ttgatggtcg gaagaggcat aaattccgtc agccagttta gtctgaccat 5160
ctcatctgta acatcattgg caacgctacc tttgccatgt ttcagaaaca actctggcgc 5220
atcgggcttc ccatacaatc gatagattgt cgcacctgat tgcccgacat tatcgcgagc 5280
ccatttatac ccatataaat cagcatccat gttggaattt aatcgcggcc tcgagcaaga 5340
cgtttcccgt tgaatatggc tcataacacc ccttgtatta ctgtttatgt aagcagacag 5400
ttttattgtt catgatgata tatttttatc ttgtgcaatg taacatcaga gattttgaga 5460
cactatgcgg tgtgaaatac cgcacagatg cgtaaggaga aaataccgca tcagattggc 5520
tattggctgc tccctgcttg tgtgttggag gtcgctgagt agtgcgcgag caaaatttaa 5580
gctacaacaa ggcaaggctt gaccgacaat tgcatgaaga atctgcttag ggttaggcgt 5640
tttgcgctgc ttcgcgatgt acgggccaga tatacgcgta tctgagggga ctagggtgtg 5700
tttaggcgaa aagcggggct tcggttgtac gcggttagga gtcccctcag gatatagtag 5760
tttcgctttt gcatagggag ggggaaatgt agtcttatgc aatactcttg tagtcttgca 5820
acatggtaac gatgagttag caacatgcct tacaaggaga gaaaaagcac cgtgcatgcc 5880
gattggtgga agtaaggtgg tacgatcgtg ccttattagg aaggcaacag acgggtctga 5940
catggattgg acgaaccact gaattccgca ttgcagagat attgtattta agtgcctagc 6000
tcgatacaat aaacgccatt tgaccattca ccacattggt gtgcacctcc atcggctcgc 6060

```
atctctcctt cacgcgcccg ccgccctacc tgaggccgcc atccacgccg gttgagtcgc   6120

gttctgccgc ctcccgcctg tggtgcctcc tgaactgcgt ccgccgtcta ggtaagttta   6180

aagctcaggt cgagaccggg cctttgtccg gcgctccctt ggagcctacc tagactcagc   6240

cggctctcca cgctttgcct gaccctgctt gctcaactct agttaacggt ggagggcagt   6300

gtagtctgag cagtactcgt tgctgccgcg cgcgccacca gacataatag ctgacagact   6360

aacagactgt tcctttccat gggtcttttc tgcagtcacc gtcgtcggat atcgaattcg   6420

ccaccatgag cctgctgacc gaggtggaga cccccatcag aaacgagtgg ggctgcagat   6480

gcaacgacag cagcgacccc ctggtggtgg ccgccagcat catcggcatc ctgcacctga   6540

tcctgtggat cctggacaga ctgttcttca agtgcatcta cagactgttc aagcacggcc   6600

tgaagagagg ccccagcacc gagggcgtgc ccgagagcat gagagaggag tacagaaagg   6660

agcagcagaa cgccgtggac gccgacgaca gccacttcgt gagcatcgag ctggagtgat   6720

cagtcgagat ccagatctgc tgtgccttct agttgccagc catctgttgt ttgcccctcc   6780

cccgtgcctt ccttgaccct ggaaggtgcc actcccactg tcctttccta ataaaatgag   6840

gaaattgcat cgcattgtct gagtaggtgt cattctattc tggggggtgg ggtggggcag   6900

gacagcaagg gggaggattg ggaagacaat agcaggcatg ctggggatgc ggtgggctct   6960

atgggtaccc aggtgctgaa gaattgaccc ggttcctcct gggccagaaa gaagcaggca   7020

catccccttc tctgtgacac accctgtcca cgcccctggt tcttagttcc agccccactc   7080

ataggacact catagctcag gagggctccg ccttcaatcc cacccgctaa agtacttgga   7140

gcggtctctc cctccctcat cagcccacca aaccaaacct agcctccaag agtgggaaga   7200

aattaaagca agataggcta ttaagtgcag agggagagaa aatgcctcca acatgtgagg   7260

aagtaatgag agaaatcata gaattttaag gccatgattt aaggccagtg gctttccccc   7320

ccccccatt attgaagcat ttatcagggt tattgtctca tgagcggata catatttgaa   7380

tgtatttaga aaaataaaca aataggggtt ccgcgcacat ttccccgaaa agtgccacct   7440

gacgtctaag aaaccattat tatcatgaca ttaacctata aaaataggcg tatcacgagg   7500

ccctttcgtc tcgcgcgttt cggtgatgac ggtgaaaacc tctgacacat gcagctcccg   7560

gagacggtca cagcttgtct gtaagcggat gccgggagca gacaagcccg tcagggcgcg   7620

tcagcgggtg ttggcgggtg tcggggctgg cttaactatg cggcatcaga gcagattgta   7680

ctgagagtgc accatatgcg gtgtgaaata ccgcacagat gcgtaaggag aaaataccgc   7740

atcagattgg ctat                                                    7754
```

<210> SEQ ID NO 109
<211> LENGTH: 7754
<212> TYPE: DNA
<213> ORGANISM: Artificial sequence
<220> FEATURE:
<223> OTHER INFORMATION: VR4778, Ligation of Inverted RSV RM2 into VR4762

<400> SEQUENCE: 109

```
tggccattgc atacgttgta tccatatcat aatatgtaca tttatattgg ctcatgtcca     60

acattaccgc catgttgaca ttgattattg actagttatt aatagtaatc aattacgggg    120

tcattagttc atagcccata tatggagttc cgcgttacat aacttacggt aaatggcccg    180

cctggctgac cgcccaacga cccccgccca ttgacgtcaa taatgacgta tgttcccata    240

gtaacgccaa tagggacttt ccattgacgt caatgggtgg agtatttacg gtaaactgcc    300

cacttggcag tacatcaagt gtatcatatg ccaagtacgc cccctattga cgtcaatgac    360
```

-continued

```
ggtaaatggc ccgcctggca ttatgcccag tacatgacct tatgggactt tcctacttgg    420
cagtacatct acgtattagt catcgctatt accatggtga tgcggttttg gcagtacatc    480
aatgggcgtg gatagcggtt tgactcacgg ggatttccaa gtctccaccc cattgacgtc    540
aatgggagtt tgttttggca ccaaaatcaa cgggactttc caaaatgtcg taacaactcc    600
gccccattga cgcaaatggg cggtaggcgt gtacggtggg aggtctatat aagcagagct    660
cgtttagtga accgtcagat cgcctggaga cgccatccac gctgttttga cctccataga    720
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctcccctatt    960
ggtgacgata ctttccatta ctaatccata acatggctct ttgccacaac tatctctatt   1020
ggctatatgc caatactctg tccttcagag actgacacgg actctgtatt tttacaggat   1080
ggggtcccat ttattattta caaattcaca tatacaacaa cgccgtcccc cgtgcccgca   1140
gtttttatta aacatagcgt gggatctcca cgcgaatctc gggtacgtgt tccggacatg   1200
ggctcttctc cggtagcggc ggagcttcca catccgagcc ctggtcccat gcctccagcg   1260
gctcatggtc gctcggcagc tccttgctcc taacagtgga ggccagactt aggcacagca   1320
caatgcccac caccaccagt gtgccgcaca aggccgtggc ggtagggtat gtgtctgaaa   1380
atgagcgtgg agattgggct cgcacggctg acgcagatgg aagacttaag gcagcggcag   1440
aagaagatgc aggcagctga gttgttgtat tctgataaga gtcagaggta actcccgttg   1500
cggtgctgtt aacggtggag ggcagtgtag tctgagcagt actcgttgct gccgcgcgcg   1560
ccaccagaca taatagctga cagactaaca gactgttcct ttccatgggt cttttctgca   1620
gtcaccgtcg tcggatatcg aattcgccac catggccagc cagggcacca agagaagcta   1680
cgagcagatg gagaccgacg gcgagagaca gaacgccacc gagatcagag ccagcgtggg   1740
caagatgatc gacggcatcg gcagattcta catccagatg tgcaccgagc tgaagctgag   1800
cgactacgag ggcagactga tccagaacag cctgaccatc gagagaatgg tgctgagcgc   1860
cttcgacgag agaagaaaca gatacctgga ggagcacccc agcgccggca aggaccccaa   1920
gaagaccggc ggccccatct acagaagagt ggacggcaag tggatgagag agctggtgct   1980
gtacgacaag gaggagatca gaagaatctg gagacaggcc aacaacggcg aggacgccac   2040
cgccggcctg acccacatga tgatctggca cagcaacctg aacgacacca cctaccagag   2100
aaccagagcc ctggtgcgga ccggcatgga ccccagaatg tgcagcctga tgcagggcag   2160
caccctgccc agaagaagcg gcgccgccgg cgccgccgtg aagggcatcg gcaccatggt   2220
gatggagctg atcagaatga tcaagagagg catcaacgac agaaacttct ggagaggcga   2280
gaacggcaga aagaccagaa gcgcctacga gagaatgtgc aacatcctga agggcaagtt   2340
ccagaccgcc gcccagagag ccatgatgga ccaggtccgg gagagcagaa accccggcaa   2400
cgccgagatc gaggacctga tcttcctggc cagaagcgcc ctgatcctga gaggcagcgt   2460
ggcccacaag agctgcctgc ccgcctgcgt gtacggcccc gccgtgagca gcggctacga   2520
cttcgagaag gagggctaca gcctggtggg catcgacccc ttcaagctgc tgcagaacag   2580
ccaggtgtac agcctgatca gacccaacga gaaccccgcc cacaagagcc agctggtgtg   2640
gatggcctgc cacagcgccg ccttcgagga cctgagactg ctgagcttca tcagaggcac   2700
caaggtgtcc cccagaggca agctgagcac cagaggcgtg cagatcgcca gcaacgagaa   2760
```

-continued

```
catggacaac atgggcagca gcaccctgga gctgagaagc agatactggg ccatcagaac   2820

cagaagcggc ggcaacacca accagcagag agccagcgcc ggccagatca gcgtgcagcc   2880

caccttcagc gtgcagagaa acctgccctt cgagaagagc accgtgatgg ccgccttcac   2940

cggcaacacc gagggcagaa ccagcgacat gagagccgag atcatcagaa tgatggaggg   3000

cgccaagccc gaggaggtgt ccttcagagg cagaggcgtg ttcgagctga gcgacgagaa   3060

ggccaccaac cccatcgtgc ctagcttcga catgagcaac gagggcagct acttcttcgg   3120

cgacaacgcc gaggagtacg acaactgatc agtcgaccac gtgtgatcca gatctacttc   3180

tggctaataa aagatcagag ctctagagat ctgtgtgttg gtttttttgtg tggtactctt   3240

ccgcttcctc gctcactgac tcgctgcgct cggtcgttcg gctgcggcga gcggtatcag   3300

ctcactcaaa ggcggtaata cggttatcca cagaatcagg ggataacgca ggaaagaaca   3360

tgtgagcaaa aggccagcaa aaggccagga accgtaaaaa ggccgcgttg ctggcgtttt   3420

tccataggct ccgcccccct gacgagcatc acaaaaatcg acgctcaagt cagaggtggc   3480

gaaacccgac aggactataa agataccagg cgtttccccc tggaagctcc ctcgtgcgct   3540

ctcctgttcc gaccctgccg cttaccggat acctgtccgc ctttctccct tcgggaagcg   3600

tggcgctttc tcatagctca cgctgtaggt atctcagttc ggtgtaggtc gttcgctcca   3660

agctgggctg tgtgcacgaa ccccccgttc agcccgaccg ctgcgcctta tccggtaact   3720

atcgtcttga gtccaacccg gtaagacacg acttatcgcc actggcagca gccactggta   3780

acaggattag cagagcgagg tatgtaggcg gtgctacaga gttcttgaag tggtggccta   3840

actacggcta cactagaaga acagtatttg gtatctgcgc tctgctgaag ccagttacct   3900

tcggaaaaag agttggtagc tcttgatccg gcaaacaaac caccgctggt agcggtggtt   3960

tttttgtttg caagcagcag attacgcgca gaaaaaaagg atctcaagaa gatcctttga   4020

tcttttctac ggggtctgac gctcagtgga acgaaaactc acgttaaggg attttggtca   4080

tgagattatc aaaaaggatc ttcacctaga tccttttaaa ttaaaaatga agttttaaat   4140

caatctaaag tatatatgag taaacttggt ctgacagtta ccaatgctta atcagtgagg   4200

cacctatctc agcgatctgt ctatttcgtt catccatagt tgcctgactc gggggggggg   4260

ggcgctgagg tctgcctcgt gaagaaggtg ttgctgactc ataccaggcc tgaatcgccc   4320

catcatccag ccagaaagtg agggagccac ggttgatgag agctttgttg taggtggacc   4380

agttggtgat tttgaacttt tgctttgcca cggaacggtc tgcgttgtcg ggaagatgcg   4440

tgatctgatc cttcaactca gcaaaagttc gatttattca acaaagccgc cgtcccgtca   4500

agtcagcgta atgctctgcc agtgttacaa ccaattaacc aattctgatt agaaaaactc   4560

atcgagcatc aaatgaaact gcaatttatt catatcagga ttatcaatac catatttttg   4620

aaaaagccgt ttctgtaatg aaggagaaaa ctcaccgagg cagttccata ggatggcaag   4680

atcctggtat cggtctgcga ttccgactcg tccaacatca atacaaccta ttaatttccc   4740

ctcgtcaaaa ataaggttat caagtgagaa atcaccatga gtgacgactg aatccggtga   4800

gaatggcaaa agcttatgca tttctttcca gacttgttca acaggccagc cattacgctc   4860

gtcatcaaaa tcactcgcat caaccaaacc gttattcatt cgtgattgcg cctgagcgag   4920

acgaaatacg cgatcgctgt taaaaggaca attacaaaca ggaatcgaat gcaaccggcg   4980

caggaacact gccagcgcat caacaatatt ttcacctgaa tcaggatatt cttctaatac   5040

ctggaatgct gttttcccgg ggatcgcagt ggtgagtaac catgcatcat caggagtacg   5100

gataaaatgc ttgatggtcg gaagaggcat aaattccgtc agccagttta gtctgaccat   5160
```

-continued

```
ctcatctgta acatcattgg caacgctacc tttgccatgt ttcagaaaca actctggcgc   5220
atcgggcttc ccatacaatc gatagattgt cgcacctgat tgcccgacat tatcgcgagc   5280
ccatttatac ccatataaat cagcatccat gttggaattt aatcgcggcc tcgagcaaga   5340
cgtttcccgt tgaatatggc tcataacacc ccttgtatta ctgtttatgt aagcagacag   5400
ttttattgtt catgatgata tatttttatc ttgtgcaatg taacatcaga gattttgaga   5460
cactggcctt aaatcatggc cttaaaattc tatgatttct ctcattactt cctcacatgt   5520
tggaggcatt ttctctccct ctgcacttaa tagcctatct tgctttaatt tcttcccact   5580
cttggaggct aggtttggtt tggtgggctg atgagggagg gagagaccgc tccaagtact   5640
ttagcgggtg ggattgaagg cggagccctc ctgagctatg agtgtcctat gagtggggct   5700
ggaactaaga accaggggcg tggacagggt gtgtcacaga gaaggggatg tgcctgcttc   5760
tttctggccc aggaggaacc gggtcaattc ttcagcacct gggtacccat agagcccacc   5820
gcatccccag catgcctgct attgtcttcc caatcctccc ccttgctgtc ctgccccacc   5880
ccacccccca gaatagaatg acacctactc agacaatgcg atgcaatttc ctcattttat   5940
taggaaagga cagtgggagt ggcaccttcc agggtcaagg aaggcacggg ggaggggcaa   6000
acaacagatg gctggcaact agaaggcaca gcagatctgg atctcgactg atcactccag   6060
ctcgatgctc acgaagtggc tgtcgtcggc gtccacggcg ttctgctgct cctttctgta   6120
ctcctctctc atgctctcgg gcacgccctc ggtgctgggg cctctcttca ggccgtgctt   6180
gaacagtctg tagatgcact tgaagaacag tctgtccagg atccacagga tcaggtgcag   6240
gatgccgatg atgctggcgg ccaccaccag ggggtcgctg ctgtcgttgc atctgcagcc   6300
ccactcgttt ctgatggggg tctccacctc ggtcagcagg ctcatggtgg cgaattcgat   6360
atccgacgac ggtgactgca gaaaagaccc atggaaagga acagtctgtt agtctgtcag   6420
ctattatgtc tggtggcgcg cgcggcagca acgagtactg ctcagactac actgccctcc   6480
accgttaact agagttgagc aagcagggtc aggcaaagcg tggagagccg gctgagtcta   6540
ggtaggctcc aagggagcgc cggacaaagg cccggtctcg acctgagctt taaacttacc   6600
tagacggcgg acgcagttca ggaggcacca caggcgggag gcggcagaac gcgactcaac   6660
cggcgtggat ggcggcctca ggtagggcgg cgggcgcgtg aaggagagat gcgagccgat   6720
ggaggtgcac accaatgtgg tgaatggtca aatggcgttt attgtatcga gctaggcact   6780
taaatacaat atctctgcaa tgcggaattc agtggttcgt ccaatccatg tcagacccgt   6840
ctgttgcctt cctaataagg cacgatcgta ccaccttact tccaccaatc ggcatgcacg   6900
gtgctttttc tctccttgta aggcatgttg ctaactcatc gttaccatgt tgcaagacta   6960
caagagtatt gcataagact acatttcccc ctccctatgc aaaagcgaaa ctactatatc   7020
ctgaggggac tcctaaccgc gtacaaccga agccccgctt ttcgcctaaa cacaccctag   7080
tcccctcaga tacgcgtata tctggcccgt acatcgcgaa gcagcgcaaa acgcctaacc   7140
ctaagcagat tcttcatgca attgtcggtc aagccttgcc ttgttgtagc ttaaattttg   7200
ctcgcgcact actcagcgac ctccaacaca caagcaggga gcagccaata gccaatctga   7260
tgcggtattt tctccttacg catctgtgcg gtatttcaca ccgcatagtg gctttccccc   7320
ccccccccatt attgaagcat ttatcagggt tattgtctca tgagcggata catatttgaa   7380
tgtatttaga aaaataaaca aataggggtt ccgcgcacat ttccccgaaa agtgccacct   7440
gacgtctaag aaaccattat tatcatgaca ttaacctata aaaataggcg tatcacgagg   7500
ccctttcgtc tcgcgcgttt cggtgatgac ggtgaaaacc tctgacacat gcagctcccg   7560
```

-continued gagacggtca cagcttgtct gtaagcggat gccgggagca gacaagcccg tcagggcgcg 7620
tcagcgggtg ttggcgggtg tcggggctgg cttaactatg cggcatcaga gcagattgta 7680
ctgagagtgc accatatgcg gtgtgaaata ccgcacagat gcgtaaggag aaaataccgc 7740
atcagattgg ctat 7754

<210> SEQ ID NO 110
<211> LENGTH: 7765
<212> TYPE: DNA
<213> ORGANISM: Artificial sequence
<220> FEATURE:
<223> OTHER INFORMATION: VR4779, 7765 bps DNA Circular

<400> SEQUENCE: 110
tggtatgcgg tgtgaaatac cgcacagatg cgtaaggaga aaataccgca tcagattggc 60
tattggctgc tccctgcttg tgtgttggag gtcgctgagt agtgcgcgag caaaatttaa 120
gctacaacaa ggcaaggctt gaccgacaat tgcatgaaga atctgcttag ggttaggcgt 180
tttgcgctgc ttcgcgatgt acgggccaga tatacgcgta tctgagggga ctagggtgtg 240
tttaggcgaa aagcggggct tcggttgtac gcggttagga gtcccctcag gatatagtag 300
tttcgctttt gcatagggag ggggaaatgt agtcttatgc aatactcttg tagtcttgca 360
acatggtaac gatgagttag caacatgcct tacaaggaga gaaaaagcac cgtgcatgcc 420
gattggtgga agtaaggtgg tacgatcgtg ccttattagg aaggcaacag acgggtctga 480
catggattgg acgaaccact gaattccgca ttgcagagat attgtattta agtgcctagc 540
tcgatacaat aaacgccatt tgaccattca ccacattggt gtgcacctcc atcggctcgc 600
atctctcctt cacgcgcccg ccgccctacc tgaggccgcc atccacgccg gttgagtcgc 660
gttctgccgc ctcccgcctg tggtgcctcc tgaactgcgt ccgccgtcta ggtaagttta 720
aagctcaggt cgagaccggg cctttgtccg gcgctccctt ggagcctacc tagactcagc 780
cggctctcca cgctttgcct gaccctgctt gctcaactct agttaacggt ggagggcagt 840
gtagtctgag cagtactcgt tgctgccgcg cgcgccacca gacataatag ctgacagact 900
aacagactgt tcctttccat gggtcttttc tgcagtcacc gtcgtcggat atcgaattcg 960
ccaccatggc cagccagggc accaagagaa gctacgagca gatggagacc gacggcgaga 1020
gacagaacgc caccgagatc agagccagcg tgggcaagat gatcgacggc atcggcagat 1080
tctacatcca gatgtgcacc gagctgaagc tgagcgacta cgagggcaga ctgatccaga 1140
acagcctgac catcgagaga atggtgctga gcgccttcga cgagagaaga aacagatacc 1200
tggaggagca ccccagcgcc ggcaaggacc ccaagaagac cggcggcccc atctacagaa 1260
gagtggacgg caagtggatg agagagctgg tgctgtacga caaggaggag atcagaagaa 1320
tctggagaca ggccaacaac ggcgaggacg ccaccgccgg cctgacccac atgatgatct 1380
ggcacagcaa cctgaacgac accacctacc agagaaccag agccctggtg cggaccggca 1440
tggaccccag aatgtgcagc ctgatgcagg gcagcaccct gcccagaaga agcggcgccg 1500
ccggcgccgc cgtgaagggc atcggcacca tggtgatgga gctgatcaga atgatcaaga 1560
gaggcatcaa cgacagaaac ttctggagag gcgagaacgg cagaaagacc agaagcgcct 1620
acgagagaat gtgcaacatc ctgaagggca agttccagac cgccgcccag agagccatga 1680
tggaccaggt ccgggagagc agaaaccccg gcaacgccga gatcgaggac ctgatcttcc 1740
tggccagaag cgccctgatc ctgagaggca gcgtggccca caagagctgc ctgcccgcct 1800
gcgtgtacgg ccccgccgtg agcagcggct acgacttcga gaaggagggc tacagcctgg 1860

-continued

```
tgggcatcga ccccttcaag ctgctgcaga acagccaggt gtacagcctg atcagaccca   1920
acgagaaccc cgcccacaag agccagctgg tgtggatggc ctgccacagc gccgccttcg   1980
aggacctgag actgctgagc ttcatcagag gcaccaaggt gtcccccaga ggcaagctga   2040
gcaccagagg cgtgcagatc gccagcaacg agaacatgga caacatgggc agcagcaccc   2100
tggagctgag aagcagatac tggccatca gaaccagaag cggcggcaac accaaccagc   2160
agagagccag cgccggccag atcagcgtgc agcccacctt cagcgtgcag agaaacctgc   2220
ccttcgagaa gagcaccgtg atggccgcct tcaccggcaa caccgagggc agaaccagcg   2280
acatgagagc cgagatcatc agaatgatgg agggcgccaa gcccgaggag gtgtccttca   2340
gaggcagagg cgtgttcgag ctgagcgacg agaaggccac caaccccatc gtgcctagct   2400
tcgacatgag caacgagggc agctacttct tcggcgacaa cgccgaggag tacgacaact   2460
gatcagtcga ccacgtgtga tccagatctg ctgtgccttc tagttgccag ccatctgttg   2520
tttgcccctc ccccgtgcct tccttgaccc tggaaggtgc cactcccact gtcctttcct   2580
aataaaatga ggaaattgca tcgcattgtc tgagtaggtg tcattctatt ctggggggtg   2640
gggtggggca ggacagcaag ggggaggatt gggaagacaa tagcaggcat gctggggatg   2700
cggtgggctc tatgggtacc caggtgctga agaattgacc cggttcctcc tgggccagaa   2760
agaagcaggc acatcccctt ctctgtgaca caccctgtcc acgcccctgg ttcttagttc   2820
cagccccact cataggacac tcatagctca ggagggctcc gccttcaatc ccacccgcta   2880
aagtacttgg agcggtctct ccctccctca tcagcccacc aaaccaaacc tagcctccaa   2940
gagtgggaag aaattaaagc aagataggct attaagtgca gagggagaga aaatgcctcc   3000
aacatgtgag gaagtaatga gagaaatcat agaattttaa ggccatgatt taaggccacc   3060
attgcatacg ttgtatccat atcataatat gtacatttat attggctcat gtccaacatt   3120
accgccatgt tgacattgat tattgactag ttattaatag taatcaatta cggggtcatt   3180
agttcatagc ccatatatgg agttccgcgt tacataactt acggtaaatg gcccgcctgg   3240
ctgaccgccc aacgaccccc gcccattgac gtcaataatg acgtatgttc ccatagtaac   3300
gccaataggg actttccatt gacgtcaatg ggtggagtat ttacggtaaa ctgcccactt   3360
ggcagtacat caagtgtatc atatgccaag tacgccccct attgacgtca atgacggtaa   3420
atggcccgcc tggcattatg cccagtacat gaccttatgg gactttccta cttggcagta   3480
catctacgta ttagtcatcg ctattaccat ggtgatgcgg ttttggcagt acatcaatgg   3540
gcgtggatag cggtttgact cacggggatt tccaagtctc caccccattg acgtcaatgg   3600
gagtttgttt tggcaccaaa atcaacggga ctttccaaaa tgtcgtaaca actccgcccc   3660
attgacgcaa atgggcggta ggcgtgtacg gtgggaggtc tatataagca gagctcgttt   3720
agtgaaccgt cagatcgcct ggagacgcca tccacgctgt tttgacctcc atagaagaca   3780
ccgggaccga tccagcctcc gcggccggga acggtgcatt ggaacgcgga ttccccgtgc   3840
caagagtgac gtaagtaccg cctatagact ctataggcac acccctttgg ctcttatgca   3900
tgctatactg tttttggctt ggggcctata cacccccgct tccttatgct ataggtgatg   3960
gtatagctta gcctataggt gtgggttatt gaccattatt gaccactccc ctattggtga   4020
cgatactttc cattactaat ccataacatg gctctttgcc acaactatct ctattggcta   4080
tatgccaata ctctgtcctt cagagactga cacggactct gtatttttac aggatggggt   4140
cccatttatt atttacaaat tcacatatac aacaacgccg tcccccgtgc ccgcagtttt   4200
tattaaacat agcgtgggat ctccacgcga atctcgggta cgtgttccgg acatgggctc   4260
```

-continued

```
ttctccggta gcggcggagc ttccacatcc gagccctggt cccatgcctc cagcggctca   4320
tggtcgctcg gcagctcctt gctcctaaca gtggaggcca gacttaggca cagcacaatg   4380
cccaccacca ccagtgtgcc gcacaaggcc gtggcggtag ggtatgtgtc tgaaaatgag   4440
cgtggagatt gggctcgcac ggctgacgca gatggaagac ttaaggcagc ggcagaagaa   4500
gatgcaggca gctgagttgt tgtattctga taagagtcag aggtaactcc cgttgcggtg   4560
ctgttaacgg tggagggcag tgtagtctga gcagtactcg ttgctgccgc gcgcgccacc   4620
agacataata gctgacagac taacagactg ttcctttcca tgggtctttt ctgcagtcac   4680
cgtcgtcgga tatcgaattc gccaccatga gcctgctgac cgaggtggag acccccatca   4740
gaaacgagtg gggctgcaga tgcaacgaca gcagcgaccc cctggtggtg gccgccagca   4800
tcatcggcat cctgcacctg atcctgtgga tcctggacag actgttcttc aagtgcatct   4860
acagactgtt caagcacggc ctgaagagag gccccagcac cgagggcgtg cccgagagca   4920
tgagagagga gtacagaaag gagcagcaga acgccgtgga cgccgacgac agccacttcg   4980
tgagcatcga gctggagtga tcagtcgacc acgtgtgatc cagatctact tctggctaat   5040
aaaagatcag agctctagag atctgtgtgt tggttttttg tgtggtactc ttccgcttcc   5100
tcgctcactg actcgctgcg ctcggtcgtt cggctgcggc gagcggtatc agctcactca   5160
aaggcggtaa tacggttatc cacagaatca ggggataacg caggaaagaa catgtgagca   5220
aaaggccagc aaaaggccag gaaccgtaaa aaggccgcgt tgctggcgtt tttccatagg   5280
ctccgccccc ctgacgagca tcacaaaaat cgacgctcaa gtcagaggtg gcgaaacccg   5340
acaggactat aaagatacca ggcgtttccc cctggaagct ccctcgtgcg ctctcctgtt   5400
ccgaccctgc cgcttaccgg atacctgtcc gcctttctcc cttcgggaag cgtggcgctt   5460
tctcatagct cacgctgtag gtatctcagt tcggtgtagg tcgttcgctc caagctgggc   5520
tgtgtgcacg aaccccccgt tcagcccgac cgctgcgcct tatccggtaa ctatcgtctt   5580
gagtccaacc cggtaagaca cgacttatcg ccactggcag cagccactgg taacaggatt   5640
agcagagcga ggtatgtagg cggtgctaca gagttcttga agtggtggcc taactacggc   5700
tacactagaa gaacagtatt tggtatctgc gctctgctga agccagttac cttcggaaaa   5760
agagttggta gctcttgatc cggcaaacaa accaccgctg gtagcggtgg tttttttgtt   5820
tgcaagcagc agattacgcg cagaaaaaaa ggatctcaag aagatccttt gatcttttct   5880
acggggtctg acgctcagtg gaacgaaaac tcacgttaag ggattttggt catgagatta   5940
tcaaaaagga tcttcaccta gatcctttta aattaaaaat gaagttttaa atcaatctaa   6000
agtatatatg agtaaacttg gtctgacagt taccaatgct taatcagtga ggcacctatc   6060
tcagcgatct gtctatttcg ttcatccata gttgcctgac tcgggggggg ggggcgctga   6120
ggtctgcctc gtgaagaagg tgttgctgac tcataccagg cctgaatcgc cccatcatcc   6180
agccagaaag tgagggagcc acggttgatg agagctttgt tgtaggtgga ccagttggtg   6240
attttgaact tttgctttgc cacggaacgg tctgcgttgt cgggaagatg cgtgatctga   6300
tccttcaact cagcaaaagt tcgatttatt caacaaagcc gccgtcccgt caagtcagcg   6360
taatgctctg ccagtgttac aaccaattaa ccaattctga ttagaaaaac tcatcgagca   6420
tcaaatgaaa ctgcaattta ttcatatcag gattatcaat accatatttt tgaaaaagcc   6480
gtttctgtaa tgaaggagaa aactcaccga ggcagttcca taggatggca agatcctggt   6540
atcggtctgc gattccgact cgtccaacat caatacaacc tattaatttc ccctcgtcaa   6600
aaataaggtt atcaagtgag aaatcaccat gagtgacgac tgaatccggt gagaatggca   6660
```

```
aaagcttatg catttctttc cagacttgtt caacaggcca gccattacgc tcgtcatcaa   6720
aatcactcgc atcaaccaaa ccgttattca ttcgtgattg cgcctgagcg agacgaaata   6780
cgcgatcgct gttaaaagga caattacaaa caggaatcga atgcaaccgg cgcaggaaca   6840
ctgccagcgc atcaacaata ttttcacctg aatcaggata ttcttctaat acctggaatg   6900
ctgttttccc ggggatcgca gtggtgagta accatgcatc atcaggagta cggataaaat   6960
gcttgatggt cggaagaggc ataaattccg tcagccagtt tagtctgacc atctcatctg   7020
taacatcatt ggcaacgcta cctttgccat gtttcagaaa caactctggc gcatcgggct   7080
tcccatacaa tcgatagatt gtcgcacctg attgcccgac attatcgcga gcccatttat   7140
acccatataa atcagcatcc atgttggaat ttaatcgcgg cctcgagcaa gacgtttccc   7200
gttgaatatg gctcataaca ccccttgtat tactgtttat gtaagcagac agttttattg   7260
ttcatgatga tatattttta tcttgtgcaa tgtaacatca gagattttga gacacaacgt   7320
ggctttcccc cccccccat tattgaagca tttatcaggg ttattgtctc atgagcggat   7380
acatatttga atgtatttag aaaaataaac aaataggggt tccgcgcaca tttccccgaa   7440
aagtgccacc tgacgtctaa gaaaccatta ttatcatgac attaacctat aaaaataggc   7500
gtatcacgag gccctttcgt ctcgcgcgtt tcggtgatga cggtgaaaac ctctgacaca   7560
tgcagctccc ggagacggtc acagcttgtc tgtaagcgga tgccgggagc agacaagccc   7620
gtcagggcgc gtcagcgggt gttggcgggt gtcggggctg gcttaactat gcggcatcag   7680
agcagattgt actgagagtg caccatatgc ggtgtgaaat accgcacaga tgcgtaagga   7740
gaaaataccg catcagattg gctat                                         7765
```

<210> SEQ ID NO 111
<211> LENGTH: 7765
<212> TYPE: DNA
<213> ORGANISM: Artificial sequence
<220> FEATURE:
<223> OTHER INFORMATION: VR4780, 7765 bps DNA Circular

<400> SEQUENCE: 111

```
tggtggcctt aaatcatggc cttaaaattc tatgatttct ctcattactt cctcacatgt     60
tggaggcatt ttctctccct ctgcacttaa tagcctatct tgctttaatt tcttcccact    120
cttggaggct aggtttggtt tggtgggctg atgagggagg gagagaccgc tccaagtact    180
ttagcgggtg ggattgaagg cggagccctc ctgagctatg agtgtcctat gagtggggct    240
ggaactaaga accaggggcg tggacagggt gtgtcacaga gaaggggatg tgcctgcttc    300
tttctggccc aggaggaacc gggtcaattc ttcagcacct gggtacccat agagcccacc    360
gcatccccag catgcctgct attgtcttcc caatcctccc ccttgctgtc ctgccccacc    420
ccacccccca gaatagaatg acacctactc agacaatgcg atgcaatttc ctcattttat    480
taggaaagga cagtgggagt ggcaccttcc agggtcaagg aaggcacggg ggaggggcaa    540
acaacagatg gctggcaact agaaggcaca gcagatctgg atcacacgtg gtcgactgat    600
cagttgtcgt actcctcggc gttgtcgccg aagaagtagc tgccctcgtt gctcatgtcg    660
aagctaggca cgatggggtt ggtggccttc tcgtcgctca gctcgaacac gcctctgcct    720
ctgaaggaca cctcctcggg cttggcgccc tccatcattc tgatgatctc ggctctcatg    780
tcgctggttc tgccctcggt gttgccggtg aaggcggcca tcacggtgct cttctcgaag    840
ggcaggtttc tctgcacgct gaaggtgggc tgcacgctga tctggccggc gctggctctc    900
tgctggttgg tgttgccgcc gcttctggtt ctgatggccc agtatctgct tctcagctcc    960
```

-continued

```
agggtgctgc tgcccatgtt gtccatgttc tcgttgctgg cgatctgcac gcctctggtg   1020
ctcagcttgc ctctgggga caccttggtg cctctgatga agctcagcag tctcaggtcc    1080
tcgaaggcgg cgctgtggca ggccatccac accagctggc tcttgtgggc ggggttctcg   1140
ttgggtctga tcaggctgta cacctggctg ttctgcagca gcttgaaggg gtcgatgccc   1200
accaggctgt agccctcctt ctcgaagtcg tagccgctgc tcacggcggg gccgtacacg   1260
caggcgggca ggcagctctt gtgggccacg ctgcctctca ggatcagggc gcttctggcc   1320
aggaagatca ggtcctcgat ctcggcgttg ccggggtttc tgctctcccg gacctggtcc   1380
atcatggctc tctgggcggc ggtctggaac ttgcccttca ggatgttgca cattctctcg   1440
taggcgcttc tggtctttct gccgttctcg cctctccaga agtttctgtc gttgatgcct   1500
ctcttgatca ttctgatcag ctccatcacc atggtgccga tgcccttcac ggcggcgccg   1560
gcggcgccgc ttcttctggg cagggtgctg ccctgcatca ggctgcacat tctggggtcc   1620
atgccggtcc gcaccagggc tctggttctc tggtaggtgg tgtcgttcag gttgctgtgc   1680
cagatcatca tgtgggtcag gccggcggtg gcgtcctcgc cgttgttggc ctgtctccag   1740
attcttctga tctcctcctt gtcgtacagc accagctctc tcatccactt gccgtccact   1800
cttctgtaga tggggccgcc ggtcttcttg gggtccttgc cggcgctggg gtgctcctcc   1860
aggtatctgt ttcttctctc gtcgaaggcg ctcagcacca ttctctcgat ggtcaggctg   1920
ttctggatca gtctgccctc gtagtcgctc agcttcagct cggtgcacat ctggatgtag   1980
aatctgccga tgccgtcgat catcttgccc acgctggctc tgatctcggt ggcgttctgt   2040
ctctcgccgt cggtctccat ctgctcgtag cttctcttgg tgccctggct ggccatggtg   2100
gcgaattcga tatccgacga cggtgactgc agaaaagacc catggaaagg aacagtctgt   2160
tagtctgtca gctattatgt ctggtggcgc gcgcggcagc aacgagtact gctcagacta   2220
cactgccctc caccgttaac tagagttgag caagcagggt caggcaaagc gtggagagcc   2280
ggctgagtct aggtaggctc caagggagcg ccggacaaag gcccggtctc gacctgagct   2340
ttaaacttac ctagacggcg gacgcagttc aggaggcacc acaggcggga ggcggcagaa   2400
cgcgactcaa ccggcgtgga tggcggcctc aggtagggcg gcgggcgcgt gaaggagaga   2460
tgcgagccga tggaggtgca caccaatgtg gtgaatggtc aaatggcgtt tattgtatcg   2520
agctaggcac ttaaatacaa tatctctgca atgcggaatt cagtggttcg tccaatccat   2580
gtcagacccg tctgttgcct tcctaataag gcacgatcgt accaccttac ttccaccaat   2640
cggcatgcac ggtgcttttt ctctccttgt aaggcatgtt gctaactcat cgttaccatg   2700
ttgcaagact acaagagtat tgcataagac tacatttccc cctccctatg caaaagcgaa   2760
actactatat cctgagggga ctcctaaccg cgtacaaccg aagccccgct tttcgcctaa   2820
acacacccta gtcccctcag atacgcgtat atctggcccg tacatcgcga agcagcgcaa   2880
aacgcctaac cctaagcaga ttcttcatgc aattgtcggt caagccttgc cttgttgtag   2940
cttaaatttt gctcgcgcac tactcagcga cctccaacac acaagcaggg agcagccaat   3000
agccaatctg atgcggtatt ttctccttac gcatctgtgc ggtatttcac accgcatacc   3060
attgcatacg ttgtatccat atcataatat gtacatttat attggctcat gtccaacatt   3120
accgccatgt tgacattgat tattgactag ttattaatag taatcaatta cggggtcatt   3180
agttcatagc ccatatatgg agttccgcgt tacataactt acggtaaatg gcccgcctgg   3240
ctgaccgccc aacgaccccc gcccattgac gtcaataatg acgtatgttc ccatagtaac   3300
gccaataggg actttccatt gacgtcaatg ggtggagtat ttacggtaaa ctgcccactt   3360
```

-continued

```
ggcagtacat caagtgtatc atatgccaag tacgccccct attgacgtca atgacggtaa   3420
atggcccgcc tggcattatg cccagtacat gaccttatgg gactttccta cttggcagta   3480
catctacgta ttagtcatcg ctattaccat ggtgatgcgg ttttggcagt acatcaatgg   3540
gcgtggatag cggtttgact cacggggatt tccaagtctc caccccattg acgtcaatgg   3600
gagtttgttt tggcaccaaa atcaacggga ctttccaaaa tgtcgtaaca actccgcccc   3660
attgacgcaa atgggcggta ggcgtgtacg gtgggaggtc tatataagca gagctcgttt   3720
agtgaaccgt cagatcgcct ggagacgcca tccacgctgt tttgacctcc atagaagaca   3780
ccgggaccga tccagcctcc gcggccggga acggtgcatt ggaacgcgga ttccccgtgc   3840
caagagtgac gtaagtaccg cctatagact ctataggcac acccctttgg ctcttatgca   3900
tgctatactg tttttggctt ggggcctata cacccccgct tccttatgct ataggtgatg   3960
gtatagctta gcctataggt gtgggttatt gaccattatt gaccactccc ctattggtga   4020
cgatactttc cattactaat ccataacatg gctctttgcc acaactatct ctattggcta   4080
tatgccaata ctctgtcctt cagagactga cacggactct gtatttttac aggatggggt   4140
cccatttatt atttacaaat tcacatatac aacaacgccg tcccccgtgc ccgcagtttt   4200
tattaaacat agcgtgggat ctccacgcga atctcgggta cgtgttccgg acatgggctc   4260
ttctccggta gcggcggagc ttccacatcc gagccctggt cccatgcctc cagcggctca   4320
tggtcgctcg gcagctcctt gctcctaaca gtggaggcca gacttaggca cagcacaatg   4380
cccaccacca ccagtgtgcc gcacaaggcc gtggcggtag ggtatgtgtc tgaaaatgag   4440
cgtggagatt gggctcgcac ggctgacgca gatggaagac ttaaggcagc ggcagaagaa   4500
gatgcaggca gctgagttgt tgtattctga taagagtcag aggtaactcc cgttgcggtg   4560
ctgttaacgg tggagggcag tgtagtctga gcagtactcg ttgctgccgc gcgcgccacc   4620
agacataata gctgacagac taacagactg ttcctttcca tgggtctttt ctgcagtcac   4680
cgtcgtcgga tatcgaattc gccaccatga gcctgctgac cgaggtggag acccccatca   4740
gaaacgagtg gggctgcaga tgcaacgaca gcagcgaccc cctggtggtg gccgccagca   4800
tcatcggcat cctgcacctg atcctgtgga tcctggacag actgttcttc aagtgcatct   4860
acagactgtt caagcacggc ctgaagagag gccccagcac cgagggcgtg cccgagagca   4920
tgagagagga gtacagaaag gagcagcaga acgccgtgga cgccgacgac agccacttcg   4980
tgagcatcga gctggagtga tcagtcgacc acgtgtgatc cagatctact tctggctaat   5040
aaaagatcag agctctagag atctgtgtgt tggttttttg tgtggtactc ttccgcttcc   5100
tcgctcactg actcgctgcg ctcggtcgtt cggctgcggc gagcggtatc agctcactca   5160
aaggcggtaa tacggttatc cacagaatca ggggataacg caggaaagaa catgtgagca   5220
aaaggccagc aaaaggccag gaaccgtaaa aaggccgcgt tgctggcgtt tttccatagg   5280
ctccgccccc ctgacgagca tcacaaaaat cgacgctcaa gtcagaggtg gcgaaacccg   5340
acaggactat aaagatacca ggcgtttccc cctggaagct ccctcgtgcg ctctcctgtt   5400
ccgaccctgc cgcttaccgg atacctgtcc gcctttctcc cttcgggaag cgtggcgctt   5460
tctcatagct cacgctgtag gtatctcagt tcggtgtagg tcgttcgctc caagctgggc   5520
tgtgtgcacg aaccccccgt tcagcccgac cgctgcgcct tatccggtaa ctatcgtctt   5580
gagtccaacc cggtaagaca cgacttatcg ccactggcag cagccactgg taacaggatt   5640
agcagagcga ggtatgtagg cggtgctaca gagttcttga agtggtggcc taactacggc   5700
tacactagaa gaacagtatt tggtatctgc gctctgctga agccagttac cttcggaaaa   5760
```

agagttggta gctcttgatc cggcaaacaa accaccgctg gtagcggtgg tttttttgtt 5820
tgcaagcagc agattacgcg cagaaaaaaa ggatctcaag aagatccttt gatcttttct 5880
acggggtctg acgctcagtg gaacgaaaac tcacgttaag ggattttggt catgagatta 5940
tcaaaaagga tcttcaccta gatcctttta aattaaaaat gaagttttaa atcaatctaa 6000
agtatatatg agtaaacttg gtctgacagt taccaatgct taatcagtga ggcacctatc 6060
tcagcgatct gtctatttcg ttcatccata gttgcctgac tcgggggggg ggggcgctga 6120
ggtctgcctc gtgaagaagg tgttgctgac tcataccagg cctgaatcgc cccatcatcc 6180
agccagaaag tgagggagcc acggttgatg agagctttgt tgtaggtgga ccagttggtg 6240
attttgaact tttgctttgc cacggaacgg tctgcgttgt cgggaagatg cgtgatctga 6300
tccttcaact cagcaaaagt tcgatttatt caacaaagcc gccgtcccgt caagtcagcg 6360
taatgctctg ccagtgttac aaccaattaa ccaattctga ttagaaaaac tcatcgagca 6420
tcaaatgaaa ctgcaattta ttcatatcag gattatcaat accatatttt tgaaaaagcc 6480
gtttctgtaa tgaaggagaa aactcaccga ggcagttcca taggatggca agatcctggt 6540
atcggtctgc gattccgact cgtccaacat caatacaacc tattaatttc ccctcgtcaa 6600
aaataaggtt atcaagtgag aaatcaccat gagtgacgac tgaatccggt gagaatggca 6660
aaagcttatg catttctttc cagacttgtt caacaggcca gccattacgc tcgtcatcaa 6720
aatcactcgc atcaaccaaa ccgttattca ttcgtgattg cgcctgagcg agacgaaata 6780
cgcgatcgct gttaaaagga caattacaaa caggaatcga atgcaaccgg cgcaggaaca 6840
ctgccagcgc atcaacaata ttttcacctg aatcaggata ttcttctaat acctggaatg 6900
ctgttttccc ggggatcgca gtggtgagta accatgcatc atcaggagta cggataaaat 6960
gcttgatggt cggaagaggc ataaattccg tcagccagtt tagtctgacc atctcatctg 7020
taacatcatt ggcaacgcta cctttgccat gtttcagaaa caactctggc gcatcgggct 7080
tcccatacaa tcgatagatt gtcgcacctg attgcccgac attatcgcga gcccatttat 7140
acccatataa atcagcatcc atgttggaat ttaatcgcgg cctcgagcaa gacgtttccc 7200
gttgaatatg gctcataaca ccccttgtat tactgtttat gtaagcagac agttttattg 7260
ttcatgatga tatattttta tcttgtgcaa tgtaacatca gagattttga gacacaacgt 7320
ggctttcccc cccccccat tattgaagca tttatcaggg ttattgtctc atgagcggat 7380
acatatttga atgtatttag aaaaataaac aaataggggt tccgcgcaca tttccccgaa 7440
aagtgccacc tgacgtctaa gaaaccatta ttatcatgac attaacctat aaaaataggc 7500
gtatcacgag gccctttcgt ctcgcgcgtt tcggtgatga cggtgaaaac ctctgacaca 7560
tgcagctccc ggagacggtc acagcttgtc tgtaagcgga tgccgggagc agacaagccc 7620
gtcagggcgc gtcagcgggt gttggcgggt gtcggggctg gcttaactat gcggcatcag 7680
agcagattgt actgagagtg caccatatgc ggtgtgaaat accgcacaga tgcgtaagga 7740
gaaaataccg catcagattg gctat 7765

<210> SEQ ID NO 112
<211> LENGTH: 4196
<212> TYPE: DNA
<213> ORGANISM: Artificial sequence
<220> FEATURE:
<223> OTHER INFORMATION: VR10686, 4196 bps DNA Circular

<400> SEQUENCE: 112

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggctg ctccctgctt gtgtgttgga ggtcgctgag tagtgcgcga gcaaaattta    300
agctacaaca aggcaaggct tgaccgacaa ttgcatgaag aatctgctta gggttaggcg    360
ttttgcgctg cttcgcgatg tacgggccag atatacgcgt atctgagggg actagggtgt    420
gtttaggcga aaagcggggc ttcggttgta cgcggttagg agtcccctca ggatatagta    480
gtttcgcttt tgcataggga gggggaaatg tagtcttatg caatactctt gtagtcttgc    540
aacatggtaa cgatgagtta gcaacatgcc ttacaaggag agaaaaagca ccgtgcatgc    600
cgattggtgg aagtaaggtg gtacgatcgt gccttattag gaaggcaaca gacgggtctg    660
acatggattg gacgaaccac tgaattccgc attgcagaga tattgtattt aagtgcctag    720
ctcgatacaa taaacgccat ttgaccattc accacattgg tgtgcacctc catcggctcg    780
catctctcct tcacgcgccc gccgccctac ctgaggccgc catccacgcc ggttgagtcg    840
cgttctgccg cctcccgcct gtggtgcctc ctgaactgcg tccgccgtct aggtaagttt    900
aaagctcagg tcgagaccgg gcctttgtcc ggcgctccct tggagcctac ctagactcag    960
ccggctctcc acgctttgcc tgaccctgct tgctcaactc tagttaacgg tggagggcag   1020
tgtagtctga gcagtactcg ttgctgccgc gcgcgccacc agacataata gctgacagac   1080
taacagactg ttcctttcca tgggtctttt ctgcagtcac cgtcgtcgac acgtgtgatc   1140
agatatcgcg gccgctctag accaggccct ggatccagat ctgctgtgcc ttctagttgc   1200
cagccatctg ttgtttgccc ctcccccgtg ccttccttga ccctggaagg tgccactccc   1260
actgtccttt cctaataaaa tgaggaaatt gcatcgcatt gtctgagtag gtgtcattct   1320
attctggggg gtggggtggg gcaggacagc aagggggagg attgggaaga caatagcagg   1380
catgctgggg atgcggtggg ctctatgggt acccaggtgc tgaagaattg acccggttcc   1440
tcctgggcca gaaagaagca ggcacatccc cttctctgtg acacaccctg tccacgcccc   1500
tggttcttag ttccagcccc actcatagga cactcatagc tcaggagggc tccgccttca   1560
atcccacccg ctaaagtact tggagcggtc tctccctccc tcatcagccc accaaaccaa   1620
acctagcctc caagagtggg aagaaattaa agcaagatag gctattaagt gcagagggag   1680
agaaaatgcc tccaacatgt gaggaagtaa tgagagaaat catagaattt taaggccatg   1740
atttaaggcc atcatggcct taatcttccg cttcctcgct cactgactcg ctgcgctcgg   1800
tcgttcggct gcggcgagcg gtatcagctc actcaaaggc ggtaatacgg ttatccacag   1860
aatcagggga taacgcagga aagaacatgt gagcaaaagg ccagcaaaag gccaggaacc   1920
gtaaaaaggc cgcgttgctg gcgtttttcc ataggctccg cccccctgac gagcatcaca   1980
aaaatcgacg ctcaagtcag aggtggcgaa acccgacagg actataaaga taccaggcgt   2040
ttccccctgg aagctccctc gtgcgctctc ctgttccgac cctgccgctt accggatacc   2100
tgtccgcctt tctcccttcg ggaagcgtgg cgctttctca tagctcacgc tgtaggtatc   2160
tcagttcggt gtaggtcgtt cgctccaagc tgggctgtgt gcacgaaccc cccgttcagc   2220
ccgaccgctg cgccttatcc ggtaactatc gtcttgagtc caacccggta agacacgact   2280
tatcgccact ggcagcagcc actggtaaca ggattagcag agcgaggtat gtaggcggtg   2340
```

-continued

```
ctacagagtt cttgaagtgg tggcctaact acggctacac tagaagaaca gtatttggta   2400
tctgcgctct gctgaagcca gttaccttcg gaaaaagagt tggtagctct tgatccggca   2460
aacaaaccac cgctggtagc ggtggttttt ttgtttgcaa gcagcagatt acgcgcagaa   2520
aaaaaggatc tcaagaagat cctttgatct tttctacggg gtctgacgct cagtggaacg   2580
aaaactcacg ttaagggatt ttggtcatga gattatcaaa aaggatcttc acctagatcc   2640
ttttaaatta aaaatgaagt tttaaatcaa tctaaagtat atatgagtaa acttggtctg   2700
acagttacca atgcttaatc agtgaggcac ctatctcagc gatctgtcta tttcgttcat   2760
ccatagttgc ctgactcggg gggggggggc gctgaggtct gcctcgtgaa gaaggtgttg   2820
ctgactcata ccaggcctga atcgccccat catccagcca gaaagtgagg gagccacggt   2880
tgatgagagc tttgttgtag gtggaccagt tggtgatttt gaacttttgc tttgccacgg   2940
aacggtctgc gttgtcggga agatgcgtga tctgatcctt caactcagca aaagttcgat   3000
ttattcaaca aagccgccgt cccgtcaagt cagcgtaatg ctctgccagt gttacaacca   3060
attaaccaat tctgattaga aaaactcatc gagcatcaaa tgaaactgca atttattcat   3120
atcaggatta tcaataccat atttttgaaa aagccgtttc tgtaatgaag gagaaaactc   3180
accgaggcag ttccatagga tggcaagatc ctggtatcgg tctgcgattc cgactcgtcc   3240
aacatcaata caacctatta atttcccctc gtcaaaaata aggttatcaa gtgagaaatc   3300
accatgagtg acgactgaat ccggtgagaa tggcaaaagc ttatgcattt ctttccagac   3360
ttgttcaaca ggccagccat tacgctcgtc atcaaaatca ctcgcatcaa ccaaaccgtt   3420
attcattcgt gattgcgcct gagcgagacg aaatacgcga tcgctgttaa aaggacaatt   3480
acaaacagga atcgaatgca accggcgcag gaacactgcc agcgcatcaa caatattttc   3540
acctgaatca ggatattctt ctaatacctg gaatgctgtt ttcccgggga tcgcagtggt   3600
gagtaaccat gcatcatcag gagtacggat aaaatgcttg atggtcggaa gaggcataaa   3660
ttccgtcagc cagtttagtc tgaccatctc atctgtaaca tcattggcaa cgctaccttt   3720
gccatgtttc agaaacaact ctggcgcatc gggcttccca tacaatcgat agattgtcgc   3780
acctgattgc ccgacattat cgcgagccca tttataccca tataaatcag catccatgtt   3840
ggaatttaat cgcggcctcg agcaagacgt ttcccgttga atatggctca taacacccct   3900
tgtattactg tttatgtaag cagacagttt tattgttcat gatgatatat ttttatcttg   3960
tgcaatgtaa catcagagat tttgagacac aacgtggctt tccccccccc cccattattg   4020
aagcatttat cagggttatt gtctcatgag cggatacata tttgaatgta tttagaaaaa   4080
taaacaaata ggggttccgc gcacatttcc ccgaaaagtg ccacctgacg tctaagaaac   4140
cattattatc atgacattaa cctataaaaa taggcgtatc acgaggccct ttcgtc       4196
```

INFLUENZA VIRUS VACCINE COMPOSITION AND METHODS OF USE

CROSS-REFERENCE TO RELATED APPLICATIONS

The present application is a divisional application of U.S. application Ser. No. 11/704,251, filed Feb. 9, 2007, now pending, which is a divisional application of U.S. application Ser. No. 11/131,479, filed May 18, 2005, now pending, which claims the benefit of the filing date of U.S. Provisional Application No. 60/571,854, filed May 18, 2004, all applications are incorporated herein by reference in its entirety.

REFERENCE TO A SEQUENCE LISTING SUBMITTED ELECTRONICALLY VIA EFS-WEB

This application includes a "Sequence Listing," which is provided as an "SequenceListing.txt", 334,996 bytes, created on Jun. 25, 2008, and updated on Aug. 15, 2008, and submitted electronically via EFS-Web which is hereby incorporated by reference in its entirety.

BACKGROUND OF THE INVENTION

The present invention relates to influenza virus vaccine compositions and methods of treating or preventing influenza infection and disease in mammals. Influenza is an acute febrile illness caused by infection of the respiratory tract. There are three types of influenza viruses: A, B, and C "IAV," "IBV" or "IAC," respectively, or generally "IV". Type A, which includes several subtypes, causes widespread epidemics and global pandemics such as those that occurred in 1918, 1957 and 1968. Type B causes regional epidemics. Type C causes sporadic cases and minor, local outbreaks. These virus types are distinguished in part on the basis of differences in two structural proteins, the nucleoprotein, found in the center of the virus, and the matrix protein, which forms the viral shell.

The disease can cause significant systemic symptoms, severe illness requiring hospitalization (such as viral pneumonia), and complications such as secondary bacterial pneumonia. More than 20 million people died during the pandemic flu season of 1918/1919, the largest pandemic of the $20^{th}$ century. Recent epidemics in the United States are believed to have resulted in greater than 10,000 (up to 40,000) excess deaths per year and 5,000-10,000 deaths per year in non-epidemic years.

The best strategy for prevention of morbidity and mortality associated with influenza is vaccination. Vaccination is especially recommended for people in high-risk groups, such as residents of nursing or residential homes, as well as for diabetes, chronic renal failure, or chronic respiratory conditions.

Traditional methods of producing influenza vaccines involve growth of an isolated strain in embryonated hens' eggs. Initially, the virus is recovered from a throat swab or similar source and isolated in eggs. The initial isolation in egg is difficult, but the virus adapts to its egg host and subsequent propagation in eggs takes place relatively easily. It is widely recognized, however, that the egg-derived production of IV for vaccine purposes has several disadvantages. One disadvantage is that such production process is rather vulnerable due to the varying (micro)biological quality of the eggs. Another disadvantage is that the process completely lacks flexibility if demand suddenly increases, i.e., in case of a serious epidemic or pandemic, because of the logistical problems due to the non-availability of large quantities of suitable eggs. Also, vaccines thus produced are contra-indicated for persons with a known hypersensitivity to chicken and/or egg proteins.

The influenza vaccines currently in use are designated whole virus (WV) vaccine or subvirion (SV) (also called "split" or "purified surface antigen"). The WV vaccine contains intact, inactivated virus, whereas the SV vaccine contains purified virus disrupted with detergents that solubilize the lipid-containing viral envelope, followed by chemical inactivation of residual virus. Attenuated viral vaccines against influenza are also in development. A discussion of methods of preparing conventional vaccine may be found in Wright, P. F. & Webster, R. G., FIELDS VIROLOGY, 4d Ed. (Knipe, D. M. et al. Ed.), 1464-65 (2001), for example.

Virus Structures

An IV is roughly spherical, but it can also be elongated or irregularly shaped. Inside the virus, eight segments of single-stranded RNA contain the genetic instructions for making the virus. The most striking feature of the virus is a layer of spikes projecting outward over its surface. There are two different types of spikes: one is composed of the molecule hemagglutinin (HA), the other of neuraminidase (NA). The HA molecule allows the virus to "stick" to a cell, initiating infection. The NA molecule allows newly formed viruses to exit their host cell without sticking to the cell surface or to each other. The viral capsid is comprised of viral ribonucleic acid and several so called "internal" proteins (polymerases (PB1, PB2, and PM, matrix protein (M1) and nucleoprotein (NP)). Because antibodies against HA and NA have traditionally proved the most effective in fighting infection, much research has focused on the structure, function, and genetic variation of those molecules. Researchers are also interested in a two non-structural proteins M2 and NS1; both molecules play important roles in viral infection.

Type A subtypes are described by a nomenclature system that includes the geographic site of discovery, a lab identification number, the year of discovery, and in parentheses the type of HA and NA it possesses, for example, A/Hong Kong/156/97 (H5N1). If the virus infects non-humans, the host species is included before the geographical site, as in A/Chicken/Hong Kong/G9/97 ($H_9N_2$).

Virions contain 7 segments (influenza C virus) to 8 segments (influenza A and B virus) of linear negative-sense single stranded RNA. Most of the segments of the virus genome code for a single protein. For many influenza viruses, the whole genome is now known. Genetic reassortment of the virus results from intermixing of the parental gene segments in the progeny of the viruses when a cell is co-infected by two different viruses of a given type. This phenomenon is facilitated by the segmental nature of the genome of influenza virus. Genetic reassortment is manifested as sudden changes in the viral surface antigens.

Antigenic changes in HA and NA allow the influenza virus to have tremendous variability. Antigenic drift is the term used to indicate minor antigenic variations in HA and NA of the influenza virus from the original parent virus, while major changes in HA and NA which make the new virions significantly different, are called Antigenic shift. The difference between the two phenomena is a matter of degree.

Antigenic drift (minor changes) occurs due to accumulation of point mutations in the gene which results in changes in the amino acids in the proteins. Changes which are extreme, and drastic (too drastic to be explained by mutation alone) result in antigenic shift of the virus. The segmented genomes of the influenza viruses reassort readily in double infected cells. Genetic reassortment between human and non-human influenza virus has been suggested as a mechanism for antigenic shift. Influenza is a zoonotic disease, and an important pathogen in a number of animal species, including swine, horses, and birds, both wild and domestic. Influenza viruses are transferred to humans from other species.

Because of antigenic shift and antigenic drift, immunity to an IV carrying a particular HA and/or NA protein does not necessarily confer protective immunity against IV strains carrying variant, or different HA and/or NA proteins. Because antibodies against HA and NA have traditionally proved the most effective in fighting IV infection, much research has focused on the structure, function and genetic variation of those molecules.

Recent IV Vaccine Candidates

During the past few years, there has been substantial interest in testing DNA-based vaccines for a number of infectious diseases where the need for a vaccine, or an improved vaccine, exists. Several well-recognized advantages of DNA-based vaccines include the speed, ease and cost of manufacture, the versatility of developing and testing multivalent vaccines, the finding that DNA vaccines can produce a robust cellular response in a wide variety of animal models as well as in humans, and the proven safety of using plasmid DNA as a delivery vector (Donnelly, J. J., et al., *Annu. Rev. Immunol.* 15:617-648 (1997); Manickan, E., et al., *Crit. Rev. Immunol.* 17(2):139-154 (1997); U.S. Pat. No. 6,214,804). DNA vaccines represent the next generation in the development of vaccines (Nossal, G., *Nat. Med.* 4(5 Supple):475-476 (1998)) and numerous DNA vaccines are in clinical trials. The above references are herein incorporated by reference in their entireties.

Studies have already been performed using DNA-based vaccines in animals. Ulmer, J. B. et al., *Science* 259:1745-9 (1993) revealed that mice could be protected by an IV nucleoprotein DNA vaccine alone against severe disease and death resulting from either a homologous or a heterologous IV challenge. Further studies have substantiated this model, and comparative studies of live influenza vaccines versus DNA influenza vaccines show them to be relatively equivalent in immune induction and protection in the murine model.

WO 94/21797, incorporated herein by reference in its entirety, discloses IV vaccine compositions comprising DNA constructs encoding NP, HA, M1, PB1 and NS1. WO 94/21797 also discloses methods of protecting against IV infection comprising immunization with a prophylactically effective amount of these DNA vaccine compositions.

The IV nucleoprotein is relatively conserved (see Shu, L. L. et al., *J. Virol.* 67:2723-9 (1993)), but just as conserved are the M1 matrix protein (which is a major T-cell target), and the M2 protein, which are encoded by separate reading frames of RNA segment 7. See Neirynck, S. et al., *Nat. Med.* 5:1157-63 (1999); Lamb, R. A. & Lai, C. J., *Virology* 112:746-51 (1981); Ito, T. et al., *J. Virol.* 65:5491-8 (1991). Animal DNA vaccine trials have been performed with DNA constructs encoding these genes alone or in combination, usually with success. See Okuda, K., et al., *Vaccine* 19:3681-91 (2001); Watabe, S. et al., Vaccine 19:4434-44 (2001). Of interest, the M2 protein is involved as part of an ion channel, is critical in resistance to the antiviral agents amantadine and rimantadine, and approximately 24 amino acids are extracellular (eM2). See Fischer, W. B., *Biochim Biophys Acta* 1561:27-45 (2002); Zhong, Q., *FEBS Lett* 434:265-71 (1998). Antibodies to this extracellular, highly conserved protein (eM2), which is highly expressed in infected cells (Lamb, R. A., et al., *Cell* 40:627-33 (1985)), have been shown to be involved in animal models. Treanor, J. J., *J. Virol.* 64:1375-7 (1990); Slepushkin, V. A. et al., *Vaccine* 13:1399-402 (1995). An approach using a conjugate hepatitis B core-eM2 protein has been evaluated in an animal model and proposed as a pandemic influenza vaccine. Neirynck, S. et al., *Nat. Med.* 5:1157-63 (1999). However, in one study vaccination of pigs with a DNA construct expressing eM2-NP fusion protein exacerbated disease after challenge with influenza A virus. Heinen, P. P., *J. Gen. Virol.* 83:1851-59 (2002). All of the above references are herein incorporated by reference in their entireties Heterologous "prime boost" strategies have been effective for enhancing immune responses and protection against numerous pathogens. Schneider et al., *Immunol. Rev.* 170:29-38 (1999); Robinson, H. L., *Nat. Rev. Immunol.* 2:239-50 (2002); Gonzalo, R. M. et al., *Vaccine* 20:1226-31 (2002); Tanghe, A., *Infect. Immun.* 69:3041-7 (2001). Providing antigen in different forms in the prime and the boost injections appears to maximize the immune response to the antigen. DNA vaccine priming followed by boosting with protein in adjuvant or by viral vector delivery of DNA encoding antigen appears to be the most effective way of improving antigen specific antibody and CD4+ T-cell responses or CD8+ T-cell responses respectively. Shiver J. W. et al., *Nature* 415: 331-5 (2002); Gilbert, S. C. et al., *Vaccine* 20:1039-45 (2002); Billaut-Mulot, O. et al., *Vaccine* 19:95-102 (2000); Sin, J. I. et al., DNA Cell Biol. 18:771-9 (1999). Recent data from monkey vaccination studies suggests that adding CRL1005 poloxamer (12 kDa, 5% POE), to DNA encoding the HIV gag antigen enhances T-cell responses when monkeys are vaccinated with an HIV gag DNA prime followed by a boost with an adenoviral vector expressing HIV gag (Ad5-gag). The cellular immune responses for a DNA/poloxamer prime followed by an Ad5-gag boost were greater than the responses induced with a DNA (without poloxamer) prime followed by Ad5-gag boost or for Ad5-gag only. Shiver, J. W. et al. *Nature* 415:331-5 (2002). U.S. Patent Appl. Publication No. US 2002/0165172 A1 describes simultaneous administration of a vector construct encoding an immunogenic portion of an antigen and a protein comprising the immunogenic portion of an antigen such that an immune response is generated. The document is limited to hepatitis B antigens and HIV antigens. Moreover, U.S. Pat. No. 6,500,432 is directed to methods of enhancing an immune response of nucleic acid vaccination by simultaneous administration of a polynucleotide and polypeptide of interest. According to the patent, simultaneous administration means administration of the polynucleotide and the polypeptide during the same immune response, preferably within 0-10 or 3-7 days of each other. The antigens contemplated by the patent include, among others, those of Hepatitis (all forms), HSV, HIV, CMV, EBV, RSV, VZV, HPV, polio, influenza, parasites (e.g., from the genus *Plasmodium*), and pathogenic bacteria (including but not limited to *M. tuberculosis, M. leprae, Chlamydia, Shigella, B. burgdorferi*, enterotoxigenic *E. coli, S. typhosa, H. pylori, V. cholerae, B. pertussis*, etc.). All of the above references are herein incorporated by reference in their entireties.

SUMMARY OF THE INVENTION

The present invention is directed to enhancing the immune response of a vertebrate in need of protection against IV infection by administering in vivo, into a tissue of the vertebrate, at least one polynucleotide, wherein the polynucleotide comprises one or more nucleic acid fragments, where the one or more nucleic acid fragments are optionally fragments of codon-optimized coding regions operably encoding one or more IV polypeptides, or fragments, variants, or derivatives thereof. The present invention is further directed to enhancing the immune response of a vertebrate in need of protection against IV infection by administering, in vivo, into a tissue of the vertebrate, a polynucleotide described above plus at least one isolated IV polypeptide or a fragment, a variant, or derivative thereof. The isolated IV polypeptide can be, for example, a purified subunit, a recombinant protein, a viral vector expressing an isolated IV polypeptide, or can be an inactivated or attentuated IV, such as those present in conventional IV vaccines. According to either method, the polynucleotide is incorporated into the cells of the vertebrate in vivo, and an immunologically effective amount of an immunogenic epitope of the encoded IV polypeptide, or a fragment, variant, or derivative thereof, is produced in vivo. When utilized, an isolated IV polypeptide or a fragment, variant, or derivative thereof is also administered in an immunologically effective amount.

According to the present invention, the polynucleotide can be administered either prior to, at the same time (simultaneously), or subsequent to the administration of the isolated IV polypeptide. The IV polypeptide or fragment, variant, or derivative thereof encoded by the polynucleotide comprises at least one immunogenic epitope capable of eliciting an immune response to influenza virus in a vertebrate. In addition, an isolated IV polypeptide or fragment, variant, or derivative thereof, when used, comprises at least one immunogenic epitope capable of eliciting an immune response in a vertebrate. The IV polypeptide or fragment, variant, or derivative thereof encoded by the polynucleotide can, but need not, be the same protein or fragment, variant, or derivative thereof as the isolated IV polypeptide which can be administered according to the method.

The polynucleotide of the invention can comprise a nucleic acid fragment, where the nucleic acid fragment is a fragment of a codon-optimized coding region operably encoding any IV polypeptide or fragment, variant, or derivative thereof, including, but not limited to, HA, NA, NP, M1 or M2 proteins or fragments (e.g., eM2), variants or derivatives thereof. A polynucleotide of the invention can also encode a derivative fusion protein, wherein two or more nucleic acid fragments, at least one of which encodes an IV polypeptide or fragment, variant, or derivative thereof, are joined in frame to encode a single polypeptide, e.g., NP fused to eM2. Additionally, a polynucleotide of the invention can further comprise a heterologous nucleic acid or nucleic acid fragment. Such heterologous nucleic acid or nucleic acid fragment may encode a heterologous polypeptide fused in frame with the polynucleotide encoding the IV polypeptide, e.g., a hepatitis B core protein or a secretory signal peptide. Preferably, the polynucleotide encodes an IV polypeptide or fragment, variant, or derivative thereof comprising at least one immunogenic epitope of IV, wherein the epitope elicits a B-cell (antibody) response, a T-cell (e.g., CTL) response, or both.

Similarly, the isolated IV polypeptide or fragment, variant, or derivative thereof to be delivered (either a recombinant protein, a purified subunit, or viral vector expressing an isolated IV polypeptide, or in the form of an inactivated IV vaccine) can be any isolated IV polypeptide or fragment, variant, or derivative thereof, including but not limited to the HA, NA, NP, M1 or M2 proteins or fragments (e.g., eM2), variants or derivatives thereof. In certain embodiments, a derivative protein can be a fusion protein, e.g., NP-eM2. In other embodiments, the isolated IV polypeptide or fragment, variant, or derivative thereof can be fused to a heterologous protein, e.g., a secretory signal peptide or the hepatitis B virus core protein. Preferably, the isolated N polypeptide or fragment, variant, or derivative thereof comprises at least one immunogenic epitope of IV, wherein the antigen elicits a B-cell antibody response, a T-cell antibody response, or both.

Nucleic acids and fragments thereof of the present invention can be altered from their native state in one or more of the following ways. First, a nucleic acid or fragment thereof which encodes an IV polypeptide or fragment, variant, or derivative thereof can be part or all of a codon-optimized coding region, optimized according to codon usage in the animal in which the vaccine is to be delivered. In addition, a nucleic acid or fragment thereof which encodes an IV polypeptide can be a fragment which encodes only a portion of a full-length polypeptide, and/or can be mutated so as to, for example, remove from the encoded polypeptide non-desired protein motifs present in the encoded polypeptide or virulence factors associated with the encoded polypeptide. For example, the nucleic acid sequence could be mutated so as not to encode a membrane anchoring region that would prevent release of the polypeptide from the cell as with, e.g., eM2. Upon delivery, the polynucleotide of the invention is incorporated into the cells of the vertebrate in vivo, and a prophylactically or therapeutically effective amount of an immunologic epitope of an IV is produced in vivo.

Similarly, the proteins of the invention can be a fragment of a full-length N polypeptide and/or can be altered so as to, for example, remove from the polypeptide non-desired protein motifs present in the polypeptide or virulence factors associated with the polypeptide. For example, the polypeptide could be altered so as not to encode a membrane anchoring region that would prevent release of the polypeptide from the cell.

The invention further provides immunogenic compositions comprising at least one polynucleotide, wherein the polynucleotide comprises one or more nucleic acid fragments, where each nucleic acid fragment is a fragment of a codon-optimized coding region encoding an IV polypeptide or a fragment, a variant, or a derivative thereof; and immunogenic compositions comprising a polynucleotide as described above and at least one isolated IV polypeptide or a fragment, a variant, or derivative thereof. Such compositions can further comprise, for example, carriers, excipients, transfection facilitating agents, and/or adjuvants as described herein.

The immunogenic compositions comprising a polynucleotide and an isolated IV polypeptide or fragment, variant, or derivative thereof as described above can be provided so that the polynucleotide and protein formulation are administered separately, for example, when the polynucleotide portion of the composition is administered prior (or subsequent) to the isolated IV polypeptide portion of the composition. Alternatively, immunogenic compositions comprising the polynucleotide and the isolated IV polypeptide or fragment, variant, or derivative thereof can be provided as a single formulation, comprising both the polynucleotide and the protein, for example, when the polynucleotide and the protein are administered simultaneously. In another alternative, the polynucleotide portion of the composition and the isolated IV polypeptide portion of the composition can be provided simultaneously, but in separate formulations.

Compositions comprising at least one polynucleotide comprising one or more nucleic acid fragments, where each nucleic acid fragment is optionally a fragment of a codon-optimized coding region operably encoding an N polypeptide or fragment, variant, or derivative thereof together with and one or more isolated IV polypeptides or fragments, variants or derivatives thereof (as either a recombinant protein, a purified subunit, a viral vector expressing the protein, or in the form of an inactivated or attenuated IV vaccine) will be referred to herein as "combinatorial polynucleotide (e.g., DNA) vaccine compositions" or "single formulation heterologous prime-boost vaccine compositions."

The compositions of the invention can be univalent, bivalent, trivalent or mulitvalent. A univalent composition will comprise only one polynucleotide comprising a nucleic acid fragment, where the nucleic acid fragment is optionally a fragment of a codon-optimized coding region encoding an IV polypeptide or a fragment, variant, or derivative thereof, and optionally the same IV polypeptide or a fragment, variant, or derivative thereof in isolated form. In a single formulation heterologous prime-boost vaccine composition, a univalent composition can include a polynucleotide comprising a nucleic acid fragment, where the nucleic acid fragment is optionally a fragment of a codon-optimized coding region encoding an IV polypeptide or a fragment, variant, or derivative thereof and an isolated polypeptide having the same antigenic region as the polynucleotide. A bivalent composition will comprise, either in polynucleotide or protein form, two different IV polypeptides or fragments, variants, or derivatives thereof, each capable of eliciting an immune response. The polynucleotide(s) of the composition can encode two IV polypeptides or alternatively, the polynucleotide can encode only one IV polypeptide and the second IV polypeptide would be provided by an isolated IV polypeptide of the invention as in, for example, a single formulation heterologous prime-boost vaccine composition. In the case where both IV polypeptides of a bivalent composition are delivered in polynucleotide form, the nucleic acid fragments operably encoding those IV polypeptides need not be on the same polynucleotide, but can be on two different polynucleotides. A trivalent or further multivalent composition will comprise three IV polypeptides or fragments, variants or derivatives thereof, either in isolated form or encoded by one or more polynucleotides of the invention.

The present invention further provides plasmids and other polynucleotide constructs for delivery of nucleic acid fragments of the invention to a vertebrate, e.g., a human, which provide expression of IV polypeptides, or fragments, variants, or derivatives thereof. The present invention further provides carriers, excipients, transfection-facilitating agents, immunogenicity-enhancing agents, e.g., adjuvants, or other agent or agents to enhance the transfection, expression or efficacy of the administered gene and its gene product.

In one embodiment, a mulitvalent composition comprises a single polynucleotide, e.g., plasmid, comprising one or more nucleic acid regions operably encoding IV polypeptides or fragments, variants, or derivatives thereof. Reducing the number of polynucleotides, e.g., plasmids in the compositions of the invention can have significant impacts on the manufacture and release of product, thereby reducing the costs associated with manufacturing the compositions. There are a number of approaches to include more than one expressed antigen coding sequence on a single plasmid. These include, for example, the use of Internal Ribosome Entry Site (IRES) sequences, dual promoters/expression cassettes, and fusion proteins.

The invention also provides methods for enhancing the immune response of a vertebrate to IV infection by administering to the tissues of a vertebrate one or more polynucleotides each comprising one or more nucleic acid fragments, where each nucleic acid fragment is optionally a fragment of a codon-optimized coding region encoding an IV polypeptide or fragment, variant, or derivative thereof; and optionally administering to the tissues of the vertebrate one or more isolated IV polypeptides, or fragments, variants, or derivatives thereof. The isolated IV polypeptide can be administered prior to, at the same time (simultaneously), or subsequent to administration of the polynucleotides encoding IV polypeptides.

In addition, the invention provides consensus amino acid sequences for IV polypeptides, or fragments, variants or derivatives thereof, including, but not limited to the HA, NA, NP, M1 or M2 proteins or fragments (e.g. eM2), variants or derivatives thereof. Polynucleotides which encode the consensus polypeptides or fragments, variants or derivatives thereof, are also embodied in this invention. Such polynucleotides can be obtained by known methods, for example by backtranslation of the amino acid sequence and PCR synthesis of the corresponding polynucleotide as described below.

BRIEF DESCRIPTION OF THE FIGURES

FIG. 1 shows an alignment of nucleotides 46-1542 of SEQ ID NO:1 (native NP coding region) with a coding region fully codon-optimized for human usage (SEQ ID NO:23).

FIGS. 12A-12D show the influenza A NP protein consensus amino acid sequence (SEQ ID: 76) aligned with 22 full length NP sequences. A dotted line indicates the same amino acid and a dashed line indicates that no sequence was available. Twenty-two NP full-length, or nearly full-length sequences were available for comparison on the World Wide Web at the URL flu.lan1.gov. The amino acid chosen for the consensus sequence was based on the majority of the 22 sequences examined. In instances of a tie, the amino acid found in strain 2000 was favored.

FIG. 13 is a schematic diagram of various vectors encoding influenza proteins described herein.

DETAILED DESCRIPTION OF THE INVENTION

Figure 2:
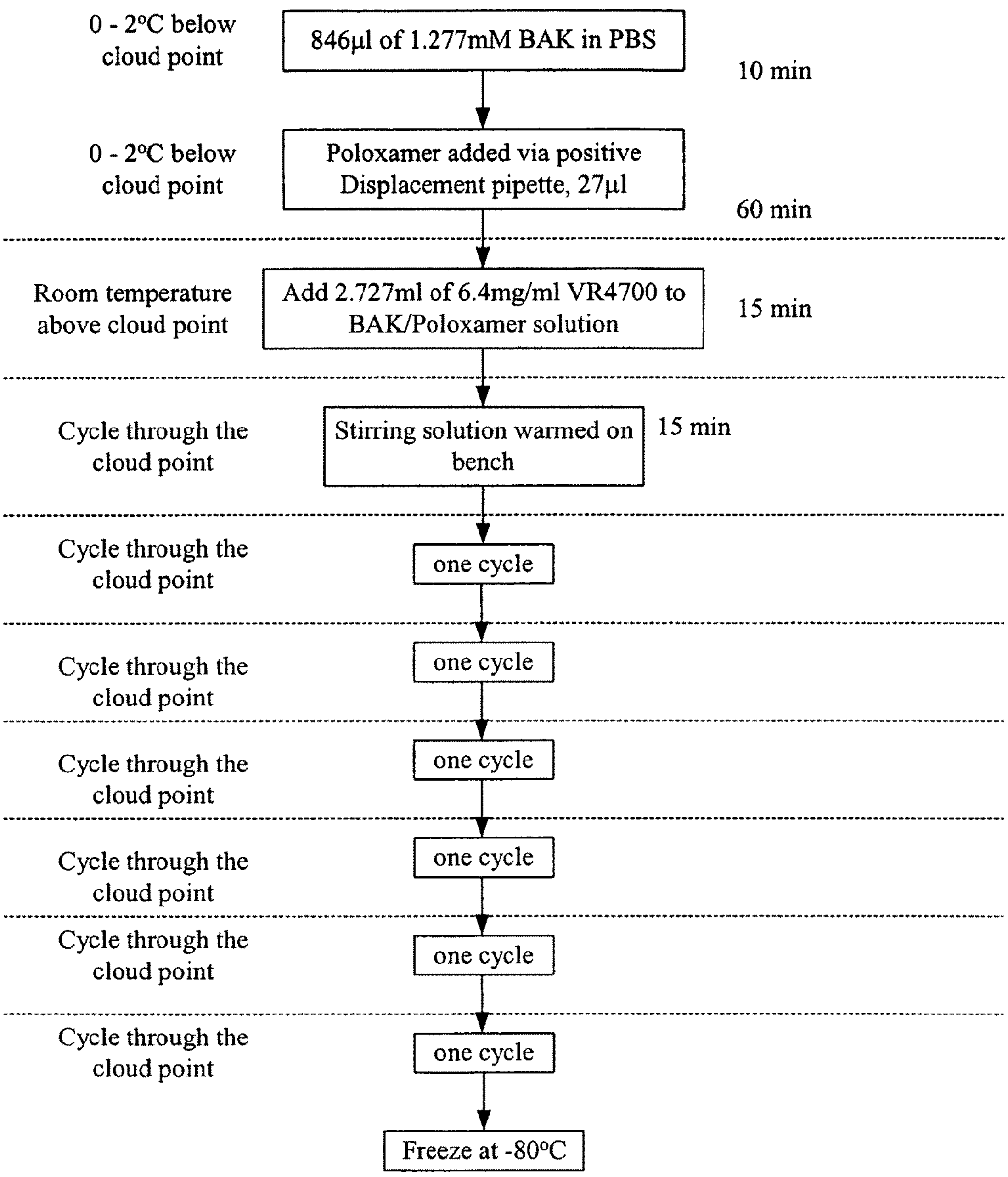
FIG. 2 shows the protocol for the preparation of a formulation comprising 0.3 mM BAK, 7.5 mg/ml CRL 1005 and 5 mg/ml of DNA in a final volume of 3.6 ml, through the use of thermal cycling.

The present invention is directed to compositions and methods for enhancing the immune response of a vertebrate in need of protection against IV infection by administering in vivo, into a tissue of a vertebrate, at least one polynucleotide comprising one or more nucleic acid fragments, where each nucleic acid fragment is optionally a fragment of a codon-optimized coding region operably encoding an IV polypeptide, or a fragment, variant, or derivative thereof in cells of the vertebrate in need of protection. The present invention is also directed to administering in vivo, into a tissue of the vertebrate the above described polynucleotide and at least one isolated IV polypeptide, or a fragment, variant, or derivative thereof. The isolated IV polypeptide or fragment, variant, or derivative thereof can be, for example, a recombinant protein, a purified subunit protein, a protein expressed and carried by a heterologous live or inactivated or attentuated viral vector expressing the protein, or can be an inactivated IV, such as those present in conventional, commercially available, inactivated IV vaccines. According to either method, the polynucleotide is incorporated into the cells of the vertebrate in vivo, and an immunologically effective amount of the influenza protein, or fragment or variant encoded by the polynucleotide is produced in vivo. The isolated protein or fragment, variant, or derivative thereof is also administered in an immunologically effective amount. The polynucleotide can be administered to the vertebrate in need thereof either prior to, at the same time (simultaneously), or subsequent to the administration of the isolated IV polypeptide or fragment, variant, or derivative thereof.

Non-limiting examples of IV polypeptides within the scope of the invention include, but are not limited to, NP, HA, NA, M1 and M2 polypeptides, and fragments, e.g., eM2, derivatives, e.g., an NP-eM2 fusion, and variants thereof. Nucleotide and amino acid sequences of IV polypeptides from a wide variety of IV types and subtypes are known in the art. The nucleotide sequences set out below are the wild-type sequences. For example, the nucleotide sequence of the NP protein of Influenza A/PR/8/34 (H1N1) is available as GenBank Accession Number M38279.1, and has the following sequence, referred to herein as SEQ ID NO:1:

```
AGCAAAAGCAGGGTAGATAATCACTCACTGAGTGACATCAAAATCATGGCG

TCTCAAGGCACCAAACGATCTTACGAACAGATGGAGACTGATGGAGAACGC

TCAGAATGCCACTGAAATCAGAGCACCGTCGGAAAAATGATTGGTGGAATT

GGACGATTCTACATCCAAATGTGCACCGAACTCAAACTCAGTGATTATGAG

GGACGGTTGATCCAAAACAGCTTAACAATAGAGAGAATGGTGCTCTCTGCT

TTTGACGAAAGGAGAAATAAATACCTTGAAGAACATCCCAGTGCGGGGAAA

GATCCTAAGAAAACTGGAGGACCTATATACAGGAGAGTAAACGGAAAGTGG

ATGAGAGAACTCATCCTTTATGACAAAGAAGAAATAAGGCGAATCTGGCGC

CAAGCTAATAATGGTGACGATGCAACGGCTGGTCTGACTCACATGATGATC

TGGCATTCCAATTTGAATGATGCAACTTATCAGAGGACAAGAGCTCTTGTT

CGCACCGGAATGGATCCCAGGATGTGCTCTCTGATGCAAGGTTCAACTCTC

CCTAGGAGGTCTGGAGCCGCAGGTGCTGCAGTCAAAGGAGTTGGAACAATG
```

-continued

```
GTGATGGAATTGGTCAGAATGATCAAACGTGGGATCAATGATCGGAACTTC

TGGAGGGGTGAGAATGGACGAAAAACAAGAATTGCTTATGAAAGAATGTGC

AACATTCTCAAAGGGAAATTTCAAACTGCTGCACAAAAAGCAATGATGGAT

CAAGTGAGAGAGAGCCGGAACCCAGGGAATGCTGAGTTCGAAGATCTCACT

CTTTTAGCACGGTCTGCACTCATATTGAGAGGGTCGGTTGCTCACAAGTCC

TGCCTGCCTGCCTGTGTGTATGGACCTGCCGTAGCCAGTGGGTACGACTTT

GAAAGGGAGGGATACTCTCTAGTCGGAATAGACCCTTTCAGACTGCTTCAA

AACAGCCAAGTGTACAGCCTAATCAGACCAAATGAGAATCCAGCACACAAG

AGTCAACTGGTGTGGATGGCATGCCATTCTGCCGCATTTGAAGATCTAAGA

GTATTAAGCTTCATCAAAGGGACGAAGGTGCTCCCAAGAGGGAAGCTTTCC

ACTAGAGGAGTTCAAATTGCTTCCAATGAAAATATGGAGACTATGGAATCA

AGTACACTTGAACTGAGAAGCAGGTACTGGGCCATAAGGACCAGAAGTGGA

GGAAACACCAATCAACAGAGGGCATCTGCGGGCCAAATCAGCATACAACCT

ACGTTCTCAGTACAGAGAAATCTCCCTTTTGACAGAACAACCGTTATGGCA

GCATTCAGTGGGAATACAGAGGGGAGAACATCTGACATGAGGACCGAAATC

ATAAGGATGATGGAAAGTGCAAGACCAGAAGATGTGTCTTTCCAGGGGCGG

GGAGTCTTCGAGCTCTCGGACGAAAAGGCAGCGAGCCCGATCGTGCCTTCC

TTTGACATGAGTAATGAAGGATCTTATTTCTTCGGAGACAATGCAGAGGAA

TACGATAATTAAAGAAAAATACCCTTGTTTCTACT
```

The amino acid sequence of the NP protein of Influenza A/PR/8/34 (H1N1), encoded by nucleotides 46-1494 of SEQ ID NO:1 is as follows, referred to herein as SEQ ID NO:2:

```
MASQGTKRSYEQMETDGERQNATEIRASVGKMIGGIGRFYIQMCTELKL

SDYEGRLIQNSLTIERMVLSAFDERRNKYLEEHPSAGKDPKKTGGPIYR

RVNGKWMRELILYDKEEIRRIWRQANNGDDATAGLTHMMIWHSNLNDAT

YQRTRALVRTGMDPRMCSLMQGSTLPRRSGAAGAAVKGVGTMVMELVRM

IKRGINDRNFWRGENGRKTRIAYERMCNILKGKFQTAAQKAMMDQVRES

RNPGNAEFEDLTFLARSALILRGSVAHKSCLPACVYGPAVASGYDFERE

GYSLVGIDPFRLLQNSQVYSLIRPNENPAHKSQLVWMACHSAAFEDLRV

LSFIKGTKVLPRGKLSTRGVQIASNENMETMESSTLELRSRYWAIRTRS

GGNTNQQRASAGQISIQPTFSVQRNLPFDRTTVMAAFSGNTEGRTSDMR

TEIIRMMESARPEDVSFQGRGVFELSDEKAASPIVPSFDMSNEGSYFFG

DNAEEYDN
```

Segment 7 of the JAY genome encodes both M1 and M2. Segment 7 of Influenza A virus (A/Puerto Rico/8/34/Mount Sinai (H1N1)), is available as GenBank Accession No. AF389121.1, and has the following sequence, referred to herein as SEQ ID NO:3:

```
AGCGAAAGCAGGTAGATATTGAAAGATGAGTCTTCTAACCGAGGTCGAA

ACGTACGTACTCTCTATCATCCCGTCAGGCCCCCTCAAAGCCGAGATCG

CACAGAGACTTGAAGATGTCTTTGCAGGGAAGAACACTGATCTTGAGGT
```

-continued

```
TCTCATGGAATGGCTAAAGACAAGACCAATCCTGTCACCTCTGACTAAG
GGGATTTTAGGATTTGTGTTCACGCTCACCGTGCCCAGTGAGCGAGGAC
TGCAGCGTAGACGCTTTGTCCAAAATGCCCTTAATGGGAACGGGGATCC
AAATAACATGGACAAAGCAGTTAAACTGTATAGGAAGCTCAAGAGGGAG
ATAACATTCCATGGGGCCAAAGAAATCTCACTCAGTTATTCTGCTGGTG
CACTTGCCAGTTGTATGGGCCTCATATACAACAGGATGGGGGCTGTGAC
CACTGAAGTGGCATTTGGCCTGGTATGTGCAACCTGTGAACAGATTGCT
GACTCCCAGCATCGGTCTCATAGGCAAATGGTGACAACAACCAATCCAC
TAATCAGACATGAGAACAGAATGGTTTTAGCCAGCACTACAGCTAAGGC
TATGGAGCAAATGGCTGGATCGAGTGAGCAAGCAGCAGAGGCCATGGAG
GTTGCTAGTCAGGCTAGACAAATGGTGCAAGCGATGAGAACCATTGGGA
CTCATCCTAGCTCCAGTGCTGGTCTGAAAAATGATCTTCTTGAAAATTT
GCAGGCCTATCAGAAACGAATGGGGGTGCAGATGCAACGGTTCAAGTGA
TCCTCTCGCTATTGCCGCAAATATCATTGGGATCTTGCACTTGACATTG
TGGATTCTTGATCGTCTTTTTTTCAAATGCATTTACCGTCGCTTTAAAT
ACGGACTGAAAGGAGGGCCTTCTACGGAAGGAGTGCCAAAGTCTATGAG
GGAAGAATATCGAAAGGAACAGCAGAGTGCTGTGGATGCTGACGATGGT
CATTTTGTCAGCATAGAGCTGGAGTAAAAAACTACCTTGTTTCTACT
```

The amino acid sequence of the M1 protein of Influenza A/Puerto Rico/8/34/Mount Sinai(H1N1), encoded by nucleotides 26 to 784 of SEQ ID NO:3 is as follows, referred to herein as SEQ ID NO:4:

```
MSLLTEVETYVLSIIPSGPLKAEIAQRLEDVFAGKNTDLEVLMEWLKTR
PILSPLTKGILGFVFTLTVPSERGLQRRRFVQNALNGNGDPNNMDKAVK
LYRKLKREITFHGAKEISLSYSAGALASCMGLIYNRMGAVTTEVAFGLV
CATCEQIADSQHRSHRQMVTTTNPLIRHENRMVLASTTAKAMEQMAGSS
EQAAEAMEVASQARQMVQAMRTIGTHPSSSAGLKNDLLENLQAYQKRMG
VQMQRFK
```

The amino acid sequence of the M2 protein of Influenza A/Puerto Rico/8/34/Mount Sinai ($H_1N_1$), encoded (in spliced form) by nucleotides 26 to 51 and 740 to 1007 of SEQ ID NO:3 is as follows, referred to herein as SEQ ID NO:5:

```
MSLLTEVETPIRNEWGCRCNGSSDPLAIAANIIGILHLTLWILDRLFFK
CIYRRFKYGLKGGPSTEGVPKSMREEYRKEQQSAVDADDGHFVSIELE
```

The Extracellular region of the M2 protein (eM2) corresponds to the first 24 amino acids of the N-terminal end of the protein, and is underlined above. See Fischer, W. B. et al., *Biochim. Biophys. Acta.* 1561:27-45 (2002); Zhong, Q. et al., *FEBS Lett.* 434:265-71 (1998).

A derivative of NP and eM2 described herein is encoded by a construct which encodes the first 24 amino acids of M2 and all or a portion of NP. The fusion constructs may be constructed with the eM2 sequences followed by the NP sequences, or with the NP sequences followed by the eM2 sequences. Exemplary fusion constructs using the NP and M2 sequences from Influenza A/PR/8/34 (H1N1) are set out below. A sequence, using the original influenza virus nucleotide sequences, which encodes the first 24 amino acids of M2 fused at its 3' end to a sequence which encodes NP in its entirety eM2-NP is referred to herein as SEQ ID NO:6:

```
   1  ATGAGTCTTC TAACCGAGGT CGAAACGCCT ATCAGAAACG AATGGGGGTG CAGATGCAAC
  61  GGTTCAAGTG ATATGGCGTC TCAAGGCACC AAACGATCTT ACGAACAGAT GGAGACTGAT
 121  GGAGAACGCC AGAATGCCAC TGAAATCAGA GCATCCGTCG GAAAAATGAT TGGTGGAATT
 181  GGACGATTCT ACATCCAAAT GTGCACCGAA CTCAAACTCA GTGATTATGA GGGACGGTTG
 241  ATCCAAAACA GCTTAACAAT AGAGAGAATG GTGCTCTCTG CTTTTGACGA AAGGAGAAAT
 301  AAATACCTTG AAGAACATCC CAGTGCGGGG AAAGATCCTA AGAAAACTGG AGGACCTATA
 361  TACAGGAGAG TAAACGGAAA GTGGATGAGA GAACTCATCC TTTATGACAA AGAAGAAATA
 421  AGGCGAATCT GGCGCCAAGC TAATAATGGT GACGATGCAA CGGCTGGTCT GACTCACATG
 481  ATGATCTGGC ATTCCAATTT GAATGATGCA ACTTATCAGA GGACAAGAGC TCTTGTTCGC
 541  ACCGGAATGG ATCCCAGGAT GTGCTCTCTG ATGCAAGGTT CAACTCTCCC TAGGAGGTCT
 601  GGAGCCGCAG GTGCTGCAGT CAAAGGAGTT GGAACAATGG TGATGGAATT GGTCAGAATG
 661  ATCAAACGTG GGATCAATGA TCGGAACTTC TGGAGGGGTG AGAATGGACG AAAAACAAGA
 721  ATTGCTTATG AAAGAATGTG CAACATTCTC AAAGGGAAAT TTCAAACTGC TGCACAAAAA
 781  GCAATGATGG ATCAAGTGAG AGAGAGCCGG AACCCAGGGA ATGCTGAGTT CGAAGATCTC
 841  ACTTTTCTAG CACGGTCTGC ACTCATATTG AGAGGGTCGG TTGCTCACAA GTCCTGCCTG
 901  CCTGCCTGTG TGTATGGACC TGCCGTAGCC AGTGGGTACG ACTTTGAAAG GGAGGGATAC
 961  TCTCTAGTCG GAATAGACCC TTTCAGACTG CTTCAAAACA GCCAAGTGTA CAGCCTAATC
1021  AGACCAAATG AGAATCCAGC ACACAAGAGT CAACTGGTGT GGATGGCATG CCATTCTGCC
```

-continued

```
1081 GCATTTGAAG ATCTAAGAGT ATTAAGCTTC ATCAAAGGGA CGAAGGTGCT CCCAAGAGGG

1141 AAGCTTTCCA CTAGAGGAGT TCAAATTGCT TCCAATGAAA ATATGGAGAC TATGGAATCA

1201 AGTACACTTG AACTGAGAAG CAGGTACTGG GCCATAAGGA CCAGAAGTGG AGGAAACACC

1261 AATCAACAGA GGGCATCTGC GGGCCAAATC AGCATACAAC CTACGTTCTC AGTACAGAGA

1321 AATCTCCCTT TTGACAGAAC AACCGTTATG GCAGCATTCA GTGGGAATAC AGAGGGGAGA

1381 ACATCTGACA TGAGGACCGA AATCATAAGG ATGATGGAAA GTGCAAGACC AGAAGATGTG

1441 TCTTTCCAGG GGCGGGGAGT CTTCGAGCTC TCGGACGAAA AGGCAGCGAG CCCGATCGTG

1501 CCTTCCTTTG ACATGAGTAA TGAAGGATCT TATTTCTTCG GAGACAATGC AGAGGAATAC

1561 GATAAT
```

The amino acid sequence of the eM2-NP fusion protein of Influenza A/PR/8/34/(H1N1), encoded by nucleotides 1 to 1566 SEQ ID NO:6 is as follows, referred to herein as SEQ ID NO:7 (eM2 amino acid sequence underlined):

```
MSLLTEVETPIRNEWGCRCNGSSDMASQGTKRSYEQMETDGERQNATE

IRASVGKMIGGIGRFYIQMCTELKLSDYEGRLIQNSLTIERMVLSAFD

ERRNKYLEEHPSAGKDPKKTGGPIYRRVNGKWMRELILYDKEEIRRIW

RQANNGDDATAGLTHMMIWHSNLNDATYQRTRALVRTGMDPRMCSLMQ

GSTLPRRSGAAGAAVKGVGTMVMELVRMIKRGINDRNFWRGENGRKTR

IAYERMCNILKGKFQTAAQKAMMDQVRESRNPGNAEFEDLTFLARSAL

ILRGSVAHKSCLPACVYGPAVASGYDFEREGYSLVGIDPFRLLQNSQV

YSLIRPNENPAHKSQLVWMACHSAAFEDLRVLSFIKGTKVLPRGKLST

RGVQIASNENMETMESSTLELRSRYWAIRTRSGGNTNQQRASAGQISI

QPTFSVQRNLPFDRTTVMAAFSGNTEGRTSDMRTEIIRMMESARPEDV

SFQGRGVFELSDEKAASPIVPSFDMSNEGSYFFGDNAEEYDN
```

A sequence, using the original influenza virus nucleotide sequences, which encodes NP in its entirety fused at its 3' end to the first 24 amino acids of M2 fused to a sequence which encodes NP in its entirety is referred to herein as SEQ ID NO:8:

```
ATGGCGTCTCAAGGCACCAAACGATCTTACGAACAGATGGAGACTGAT

GGAGAACGCCAGAATGCCACTGAAATCAGAGCATCCGTCGGAAAAATG

ATTGGTGGAATTGGACGATTCTACATCCAAATGTGCACCGAACTCAAA

CTCAGTGATTATGAGGGACGGTTGATCCAAAACAGCTTAACAATAGAG

AGAATGGTGCTCTCTGCTTTTGACGAAAGGAGAAATAAATACCTTGAA

GAACATCCCAGTGCGGGGAAAGATCCTAAGAAAACTGGAGGACCTATA

TACAGGAGAGTAAACGGAAAGTGGATGAGAGAACTCATCCTTTATGAC

AAAGAAGAAATAAGGCGAATCTGGCGCCAAGCTAATAATGGTGACGAT

GCAACGGCTGGTCTGACTCACATGATGATCTGGCATTCCAATTTGAAT

GATGCAACTTATCAGAGGACAAGAGCTCTTGTTCGCACCGGAATGGAT

CCCAGGATGTGCTCTCTGATGCAAGGTTCAACTCTCCCTAGGAGGTCT

GGAGCCGCAGGTGCTGCAGTCAAAGGAGTTGGAACAATGGTGATGGAA
```

-continued

```
TTGGTCAGAATGATCAAACGTGGGATCAATGATCGGAACTTCTGGAGG

GGTGAGAATGGACGAAAAACAAGAATTGCTTATGAAAGAATGTGCAAC

ATTCTCAAAGGGAAATTTCAAACTGCTGCACAAAAAGCAATGATGGAT

CAAGTGAGAGAGAGCCGGAACCCAGGGAATGCTGAGTTCGAAGATCTC

ACTTTTCTAGCACGGTCTGCACTCATATTGAGAGGGTCGGTTGCTCAC

AAGTCCTGCCTGCCTGCCTGTGTGTATGGACCTGCCGTAGCCAGTGGG

TACGACTTTGAAAGGGAGGGATACTCTCTAGTCGGAATAGACCCTTTC

AGACTGCTTCAAAACAGCCAAGTGTACAGCCTAATCAGACCAAATGAG

AATCCAGCACACAAGAGTCAACTGGTGTGGATGGCATGCCATTCTGCC

GCATTTGAAGATCTAAGAGTATTAAGCTTCATCAAAGGGACGAAGGTG

CTCCCAAGAGGGAAGCTTTCCACTAGAGGAGTTCAAATTGCTTCCAAT

GAAAATATGGAGACTATGGAATCAAGTACACTTGAACTGAGAAGCAGG

TACTGGGCCATAAGGACCAGAAGTGGAGGAAACACCAATCAACAGAGG

GCATCTGCGGGCCAAATCAGCATACAACCTACGTTCTCAGTACAGAGA

AATCTCCCTTTTGACAGAACAACCGTTATGGCAGCATTCAGTGGGAAT

ACAGAGGGGAGAACATCTGACATGAGGACCGAAATCATAAGGATGATG

GAAAGTGCAAGACCAGAAGATGTGTCTTTCCAGGGGCGGGGAGTCTTC

GAGCTCTCGGACGAAAAGGCAGCGAGCCCGATCGTGCCTTCCTTTGAC

ATGAGTAATGAAGGATCTTATTTCTTCGGAGACAATGCAGAGGAATAC

GATAATATGAGTCTTCTAACCGAGGTCGAAACGCCTATCAGAAACGAA

TGGGGGTGCAGATGCAACGGTTCAAGTGAT
```

The amino acid sequence of the NP-eM2 fusion protein of Influenza A/PR/8/34/(H1N1), encoded by nucleotides 1 to 1566 of SEQ ID NO:8 is as follows, referred to herein as SEQ ID NO:9 (eM2 amino acid sequence underlined):

```
MASQGTKRSYEQMETDGERQNATEIRASVGKMIGGIGRFYIQMCTELK

LSDYEGRLIQNSLTIERMVLSAFDERRNKYLEEHPSAGKDPKKTGGPI

YRRVNGKWMRELILYDKEEIRRIWRQANNGDDATAGLTHMMIWHSNLN

DATYQRTRALVRTGMDPRMCSLMQGSTLPRRSGAAGAAVKGVGTMVME

LVRMIKRGINDRNFWRGENGRKTRIAYERMCNILKGKFQTAAQKAMMD

QVRESRNPGNAEFEDLTFLARSALILRGSVAHKSCLPACVYGPAVASG
```

-continued

```
YDFEREGYSLVGIDPFRLLQNSQVYSLIRPNENPAHKSQLVWMACHSA

AFEDLRVLSFIKGTKVLPRGKLSTRGVQIASNENMETMESSTLELRSR

YWAIRTRSGGNTNQQRASAGQISIQPTFSVQRNLPFDRTTVMAAFSGN

TEGRTSDMRTEIIRMMESARPEDVSFQGRGVFELSDEKAASPIVPSFD

MSNEGSYFFGDNAEEYDNMSLLTEVETPIRNEWGCRCNGSSD
```

The construction of functional fusion proteins often requires a linker sequence between the two fused fragments, in order to adopt an extended conformation to allow maximal flexibility. We used program LINKER (Chiquita J. Crasto C. J. and Feng, *J. Protein Engineering* 13:309-312 (2000), program publicly available at chutney.med.yale.edu/linker/linker.html (visited Apr. 16, 2003)), that can automatically generate a set of linker sequences, which are known to adopt extended conformations as determined by X-ray crystallography and NMR. Examples of suitable linkers to use in various eM2-NP or NP-eM2 fusion proteins are as follows:

```
GYNTRA          (SEQ ID NO: 10)

FQMGET          (SEQ ID NO: 11)

FDRVKHLK        (SEQ ID NO: 12)

GRNTNGVIT       (SEQ ID NO: 13)

VNEKTIPDHD      (SEQ ID NO: 14)
```

The nucleotide sequence of the NP protein of Influenza B/LEE/40 is available as GenBank Accession Number K01395, and has the following sequence, referred to herein as SEQ ID NO:15:

```
   1  ATGTCCAACA TGGATATTGA CAGTATAAAT ACCGGAACAA TCGATAAAAC ACCAGAAGAA

  61  CTGACTCCCG GAACCAGTGG GGCAACCAGA CCAATCATCA AGCCAGCAAC CCTTGCTCCG

 121  CCAAGCAACA AACGAACCCG AAATCCATCT CCAGAAAGGA CAACCACAAG CAGTGAAACC

 181  GATATCGGAA GGAAAATCCA AAAGAAACAA ACCCCAACAG AGATAAAGAA GAGCGTCTAC

 241  AAAATGGTGG TAAAACTGGG TGAATTCTAC AACCAGATGA TGGTCAAAGC TGGACTTAAT

 301  GATGACATGG AAAGGAATCT AATTCAAAAT GCACAAGCTG TGGAGAGAAT CCTATTGGCT

 361  GCAACTGATG ACAAGAAAAC TGAATACCAA AAGAAAAGGA ATGCCAGAGA TGTCAAAGAA

 421  GGGAAGGAAG AAATAGACCA CAACAAGACA GGAGGCACCT TTTATAAGAT GGTAAGAGAT

 481  GATAAAACCA TCTACTTCAG CCCTATAAAA ATTACCTTTT TAAAAGAAGA GGTGAAAACA

 541  ATGTACAAGA CCACCATGGG GAGTGATGGT TTCAGTGGAC TAAATCACAT TATGATTGGA

 601  CATTCACAGA TGAACGATGT CTGTTTCCAA AGATCAAAGG GACTGAAAAG GGTTGGACTT

 661  GACCCTTCAT TAATCAGTAC TTTTGCCGGA AGCACACTAC CCAGAAGATC AGGTACAACT

 721  GGTGTTGCAA TCAAAGGAGG TGGAACTTTA GTGGATGAAG CCATCCGATT TATAGGAAGA

 781  GCAATGGCAG ACAGAGGGCT ACTGAGAGAC ATCAAGGCCA AGACGGCCTA TGAAAAGATT

 841  CTTCTGAATC TGAAAAACAA GTGCTCTGCG CCGCAACAAA AGGCTCTAGT TGATCAAGTG

 901  ATCGGAAGTA GGAACCCAGG GATTGCAGAC ATAGAAGACC TAACTCTGCT TGCCAGAAGC

 961  ATGGTAGTTG TCAGACCCTC TGTAGCGAGC AAAGTGGTGC TTCCCATAAG CATTTATGCT

1021  AAAATACCTC AACTAGGATT CAATACCGAA GAATACTCTA TGGTTGGGTA TGAAGCCATG

1081  GCTCTTTATA ATATGGCAAC ACCTGTTTCC ATATTAAGAA TGGGAGATGA CGCAAAAGAT

1141  AAATCTCAAC TATTCTTCAT GTCGTGCTTC GGAGCTGCCT ATGAAGATCT AAGAGTGTTA

1201  TCTGCACTAA CGGGCACCGA ATTTAAGCCT AGATCAGCAC TAAAATGCAA GGGTTTCCAT

1261  GTCCCGGCTA AGGAGCAAGT AGAAGGAATG GGGGCAGCTC TGATGTCCAT CAAGCTTCAG

1321  TTCTGGGCCC CAATGACCAG ATCTGGAGGG AATGAAGTAA GTGGAGAAGG AGGGTCTGGT

1381  CAAATAAGTT GCAGCCCTGT GTTTGCAGTA GAAAGACCTA TTGCTCTAAG CAAGCAAGCT

1441  GTAAGAAGAA TGCTGTCAAT GAACGTTGAA GGACGTGATG CAGATGTCAA AGGAAATCTA

1501  CTCAAAATGA TGAATGATTC AATGGCAAAG AAAACCAGTG GAAATGCTTT CATTGGGAAG

1561  AAAATGTTTC AAATATCAGA CAAAAACAAA GTCAATCCCA TTGAGATTCC AATTAAGCAG

1621  ACCATCCCCA ATTTCTTCTT TGGGAGGGAC ACAGCAGAGG ATTATGATGA CCTCGATTAT

1681  TAA
```

The amino acid sequence of the NP protein of IBV B/LEE/40, encoded by nucleotides 1-1680 of SEQ ID NO: 15 is as follows, referred to herein as SEQ ID

MSNMDIDSINTGTIDKTPEELTPGTSGATRPIIKPATLAPPSNKRTRNPS

PERTTTSSETDIGRKIQKKQTPTEIKKSVYKMVVKLGEFYNQMMVKAGLN

-continued

DDMERNLIQNAQAVERILLAATDDKKTEYQKKRNARDVKEGKEEIDHNKT

GGTFYKMVRDDKTIYFSP1KITFLKEEVKTMYKTTMGSDGFSGLNHIMIG

HSQMNDVCFQRSKGLKRVGLDPSLISTFAGSTLPRRSGTTGVAIKGGGTL

VDEAIRFIGRAMADRGLLRDIKAKTAYEKILLNLKNKCSAPQQKALVDQV

IGSRNPGIADIEDLTLLARSMVVVRPSVASKVVLPISIYAKIPQLGFNTE

EYSMVGYEAMALYNMATPVSILRMGDDAKDKSQLFFMSCFGAAYEDLRVL

SALTGTEFKPRSALKCKGFHVPAKEQVEGMGAALMSIKLQFWAPMTRSGG

NEVSGEGGSGQISCSPVFAVERPIALSKQAVRRMLSMNVEGRDADVKGNL

LKMMNDSMAKKTSGNAFIGKKMFQISDKNKVNPIEIPIKQTIPNFFFGRD

TAEDYDDLDY

Non limiting examples of nucleotide sequences encoding the IAV hemagglutinin (HA) are as follows. It should be noted that HA sequences vary significantly between IV subtypes. Virtually any nucleotide sequence encoding an IV HA is suitable for the present invention. In fact, HA sequences included in vaccines and therapeutic formulations of the present invention (discussed in more detail below) might change from year to year depending on the prevalent strain or strains of IV.

The partial nucleotide sequence of the HA protein of IAV A/New_York/1/18(H1N1) is available as GenBank Accession Number AF116576, and has the following sequence, referred to herein as SEQ ID NO:17:

```
   1 atggaggcaa gactactggt cttgttatgt gcatttgcag ctacaaatgc agacacaata
  61 tgtataggct accatgcgaa taactcaacc gacactgttg acacagtact cgaaaagaat
 121 gtgaccgtga cacactctgt taacctgctc gaagacagcc acaacggaaa actatgtaaa
 181 ttaaaaggaa tagccccatt acaattgggg aaatgtaata tcgccggatg gctcttggga
 241 aacccggaat gcgatttact gctcacagcg agctcatggt cctatattgt agaaacatcg
 301 aactcagaga atggaacatg ttacccagga gatttcatcg actatgaaga actgagggag
 361 caattgagct cagtgtcatc gtttgaaaaa ttcgaaatat ttcccaagac aagctcgtgg
 421 cccaatcatg aaacaaccaa aggtgtaacg gcagcatgct cctatgcggg agcaagcagt
 481 ttttacagaa atttgctgtg gctgacaaag aagggaagct catacccaaa gcttagcaag
 541 tcctatgtga acaataaagg gaaagaagtc cttgtactat ggggtgttca tcatccgcct
 601 accggtactg atcaacagag tctctatcag aatgcagatg cttatgtctc tgtagggtca
 661 tcaaaatata acaggagatt caccccggaa atagcagcga gacccaaagt aagaggtcaa
 721 gctgggagga tgaactatta ctggacatta ctagaacccg gagacacaat aacatttgag
 781 gcaactggaa atctaatagc accatggtat gctttcgcac tgaatagagg ttctggatcc
 841 ggtatcatca cttcagacgc accagtgcat gattgtaaca cgaagtgtca aacaccccat
 901 ggtgctataa acagcagtct ccctttccag aatatacatc cagtcacaat aggagagtgc
 961 ccaaaatacg tcaggagtac caaattgagg atggctacag gactaagaaa cattccatct
1021 attcaatcca ggggtctatt tggagccatt gccggtttta ttgagggggg atggactgga
1081 atgatagatg gatggtatgg ttatcatcat cagaatgaac agggatcagg ctatgcagcg
1141 gatcaaaaaa gcacacaaaa tgccattgac gggattacaa acaaggtgaa ttctgttatc
1201 gagaaaatga acacccaatt
```

The amino acid sequence of the partial HA protein of IAV A/New_York/1/18(H1N1), encoded by nucleotides 1 to 1218 of SEQ ID NO:17 is as follows, referred to herein as SEQ ID NO:18:

MEARLLVLLCAFAATNADTICIGYHANNSTDTVDTVLEKNVTVTHSV

NLLEDSHNGKLCKLKGIAPLQLGKCNIAGWLLGNPECDLLLTASSWS

YIVETSNSENGTCYPGDFIDYEELREQLSSVSSFEKFEIFPKTSSWP

NHETTKGVTAACSYAGASSFYRNLLWLTKKGSSYPKLSKSYVNNKGK

EVLVLWGVHHPPTGTDQQSLYQNADAYVSVGSSKYNRRFTPEIAARP

KVRGQAGRMNYYWTLLEPGDTITFEATGNLIAPWYAFALNRGSGSGI

ITSDAPVHDCNTKCQTPHGAINSSLPFQNIHPVTIGECPKYVRSTKL

RMATGLRNIPSIQSRGLFGAIAGFIEGGWTGMIDGWYGYHHQNEQGS

GYAADQKSTQNAIDGITNKVNSVIEKMNTQ

The nucleotide sequence of the IAV A/Hong Kong/482/97 hemagglutinin (H5) is available as GenBank Accession Number AF046098, and has the following sequence, referred to herein as SEQ ID NO:19:

```
   1 ctgtcaaaat ggagaaaata gtgcttcttc ttgcaacagt cagtcttgtt aaaagtgatc
  61 agatttgcat tggttaccat gcaaacaact cgacagagca ggttgacaca ataatggaaa
 121 agaatgttac tgttacacat gcccaagaca tactggaaag gacacacaac gggaagctct
 181 gcgatctaaa tggagtgaaa cctctcattt tgagggattg tagtgtagct ggatggctcc
 241 tcggaaaccc tatgtgtgac gaattcatca atgtgccgga atggtcttac atagtggaga
 301 aggccagtcc agccaatgac ctctgttatc cagggaattt caacgactat gaagaactga
 361 aacacctatt gagcagaata aaccattttg agaaaattca gatcatcccc aaaagttctt
 421 ggtccaatca tgatgcctca tcaggggtga gctcagcatg tccatacctt gggaggtcct
 481 ccttttttcag aaatgtggta tggcttatca aaaagaacag tgcataccca acaataaaga
 541 ggagctacaa taataccaac caagaagatc ttttggtact gtgggggatt caccatccta
 601 atgatgcggc agagcagaca aagctctatc aaaatccaac cacctacatt tccgttggaa
 661 catcaacact gaaccagaga ttggttccag aaatagctac tagacccaaa gtaaacgggc
 721 aaagtggaag aatggagttc ttctggacaa ttttaaagcc gaatgatgcc atcaatttcg
 781 agagtaatgg aaatttcatt gccccagaat atgcatacaa aattgtcaag aaaggggact
 841 caacaattat gaaaagtgaa ttggaatatg gtaactgcaa caccaagtgt caaactccaa
 901 tgggggcgat aaactctagt atgccattcc acaacataca ccccctcacc atcggggaat
 961 gccccaaata tgtgaaatca aacagattag ttcttgcgac tggactcaga aatacccctc
1021 aaagggagag aagaagaaaa aagagaggac tatttggagc tatagcaggt tttatagagg
1081 gaggatggca gggcatggta gatggttggt atgggtacca ccatagcaat gagcagggga
1141 gtggatacgc tgcagacaaa gaatccactc aaaaggcaat agatggagtc accaataagg
1201 tcaactcgat cattaacaaa atgaacactc agtttgaggc cgttggaagg gaatttaata
1261 acttagaaag gagaatagag aatttaaaca agaaaatgga agacggattc ctagatgtct
1321 ggacttacaa tgctgaactt ctggttctca tggaaaatga gagaactctc gactttcatg
1381 actcaaatgt caagaacctt tacgacaagg tccgactaca gcttagggat aatgcaaagg
1441 aactgggtaa tggttgtttc gaattctatc acaaatgtga taatgaatgt atggaaagtg
1501 taaaaaacgg aacgtatgac tacccgcagt attcagaaga agcaagacta aacagagagg
1561 aaataagtgg agtaaaattg gaatcaatgg gaacttacca aatactgtca atttattcaa
1621 cagtggcgag ttccctagca ctggcaatca tggtagctgg tctatcttta tggatgtgct
1681 ccaatggatc gttacaatgc agaatttgca tttaaatttg tgagttcaga ttgtagttaa
1741 a
```

The amino acid sequence of the HA protein of IAV A/Hong Kong/482/97 (H5), encoded by nucleotides 9 to 1715 of SEQ ID NO:19 is as follows, referred to herein as SEQ ID NO:20:

```
MEKIVLLLATVSLVKSDQICIGYHANNSTEQVDTIMEKNVTVTHAQD
ILERTHNGKLCDLNGVKPLILRDCSVAGWLLGNPMCDEFINVPEWSY
IVEKASPANDLCYPGNFNDYEELKHLLSRINHFEKIQIIPKSSWSNH
DASSGVSSACPYLGRSSFFRNVVWLIKKNSAYPTIKRSYNNTNQEDL
LVLWGIHHPNDAAEQTKLYQNPTTYISVGTSTLNQRLVPEIATRPKV
```

-continued

NGQSGRMEFFWTILKPNDAINFESNGNFIAPEYAYKIVKKGDSTIMK

SELEYGNCNTKCQTPMGAINSSMPFHNIHPLTIGECPKYVKSNRLVL

ATGLRNTPQRERRRKKRGLFGAIAGFIEGGWQGMVDGWYGYHHSNEQ

GSGYAADKESTQKAIDGVTNKVNSIINKMNTQFEAVGREFNNLERRI

ENLNKKMEDGFLDVWTYNAELLVLMENERTLDFHDSNVKNLYDKVRL

-continued

QLRDNAKELGNGCFEFYHKCDNECMESVKNGTYDYPQYSEEARLNRE

EISGVKLESMGTYQILSIYSTVASSLALAIMVAGLSLWMCSNGSLQC

RICI

The nucleotide sequence of the IAV A/Hong Kong/1073/99(H9N2) is available as GenBank Accession Number INA404626, and has the following sequence, referred to herein as SEQ ID NO:21:

```
   1  gcaaaagcag gggaattact taactagcaa aatggaaaca atatcactaa taactatact
  61  actagtagta acagcaagca atgcagataa aatctgcatc ggccaccagt caacaaactc
 121  cacagaaact gtggacacgc taacagaaac caatgttcct gtgacacatg ccaaagaatt
 181  gctccacaca gagcataatg gaatgctgtg tgcaacaagc ctgggacatc ccctcattct
 241  agacacatgc actattgaag gactagtcta tggcaaccct tcttgtgacc tgctgttggg
 301  aggaagagaa tggtcctaca tcgtcgaaag atcatcagct gtaaatggaa cgtgttaccc
 361  tgggaatgta gaaaacctag aggaactcag gacacttttt agttccgcta gttcctacca
 421  aagaatccaa atcttcccag acacaacctg gaatgtgact tacactggaa caagcagagc
 481  atgttcaggt tcattctaca ggagtatgag atggctgact caaaagagcg gtttttaccc
 541  tgttcaagac gcccaataca caaataacag gggaaagagc attcttttcg tgtggggcat
 601  acatcaccca cccacctata ccgagcaaac aaatttgtac ataagaaacg acacaacaac
 661  aagcgtgaca acagaagatt tgaataggac cttcaaacca gtgatagggc caaggcccct
 721  tgtcaatggt ctgcagggaa gaattgatta ttattggtcg gtactaaaac caggccaaac
 781  attgcgagta cgatccaatg ggaatctaat tgctccatgg tatggacacg ttctttcagg
 841  agggagccat ggaagaatcc tgaagactga tttaaaaggt ggtaattgtg tagtgcaatg
 901  tcagactgaa aaaggtggct taaacagtac attgccattc cacaatatca gtaaatatgc
 961  atttggaacc tgccccaaat atgtaagagt taatagtctc aaactggcag tcggtctgag
1021  gaacgtgcct gctagatcaa gtagaggact atttggagcc atagctggat tcatagaagg
1081  aggttggcca ggactagtcg ctggctggta tggtttccag cattcaaatg atcaaggggt
1141  tggtatggct gcagataggg attcaactca aaaggcaatt gataaaataa catccaaggt
1201  gaataatata gtcgacaaga tgaacaagca atatgaaata attgatcatg aattcagtga
1261  ggttgaaact agactcaata tgatcaataa taagattgat gaccaaatac aagacgtatg
1321  ggcatataat gcagaattgc tagtactact tgaaaatcaa aaaacactcg atgagcatga
1381  tgcgaacgtg aacaatctat ataacaaggt gaagagggca ctgggctcca atgctatgga
1441  agatgggaaa ggctgtttcg agctatacca taaatgtgat gatcagtgca tggaaacaat
1501  tcggaacggg acctataata ggagaaagta tagagaggaa tcaagactag aaaggcagaa
1561  aatagagggg gttaagctgg aatctgaggg aacttacaaa atcctcacca tttattcgac
1621  tgtcgcctca tctcttgtgc ttgcaatggg gtttgctgcc ttcctgttct gggccatgtc
1681  caatggatct tgcagatgca acatttgtat ataa
```

The amino acid sequence of the HA protein of IAV A/Hong Kong/1073/99 (H9N2), encoded by nucleotides 32 to 1711 of SEQ ID NO:21 is as follows, referred to herein as SEQ ID NO:22:

```
METISLITILLVVTASNADKICIGHQSTNSTETVDTLTETNVPVTHAK
ELLHTEHNGMLCATSLGHPLILDTCTIEGLVYGNPSCDLLLGGREWSY
IVERSSAVNGTCYPGNVENLEELRTLFSSASSYQRIQIFPDTTWNVTY
TGTSRACSGSFYRSMRWLTQKSGFYPVQDAQYTNNRGKSILFVWGIHH
PPTYTEQTNLYIRNDTTTSVTTEDLNRTFKPVIGPRPLVNGLQGRIDY
YWSVLKPGQTLRVRSNGNLIAPWYGHVLSGGSHGRILKTDLKGGNCVV
QCQTEKGGLNSTLPFHNISKYAFGTCPKYVRVNSLKLAVGLRNVPARS
SRGLFGAIAGFIEGGWPGLVAGWYGFQHSNDQGVGMAADRDSTQKAID
KITSKVNNIVDKNINKQYEIIDHEFSEVETRLNMINNKIDDQIQDVWA
YNAELLVLLENQKTLDEHDANVNNLYNKVKRALGSNAMEDGKGCFELY
HKCDDQCMETIRNGTYNRRKYREESRLERQKIEGVKLESEGTYKILTI
YSTVASSLVLAMGFAAFLFWAMSNGSCRCNICI
```

The present invention also provides vaccine compositions and methods for delivery of IV coding sequences to a vertebrate with optimal expression and safety conferred through codon optimization and/or other manipulations. These vaccine compositions are prepared and administered in such a manner that the encoded gene products are optimally expressed in the vertebrate of interest. As a result, these compositions and methods are useful in stimulating an immune response against IV infection. Also included in the invention are expression systems, delivery systems, and codon-optimized IV coding regions.

In a specific embodiment, the invention provides combinatorial polynucleotide (e.g., DNA) vaccines which combine both a polynucleotide vaccine and polypeptide (e.g., either a recombinant protein, a purified subunit protein, a viral vector expressing an isolated IV polypeptide, or in the form of an inactivated or attenuated IV vaccine) vaccine in a single formulation. The single formulation comprises an IV polypeptide-encoding polynucleotide vaccine as described herein, and optionally, an effective amount of a desired isolated IV polypeptide or fragment, variant, or derivative thereof. The polypeptide may exist in any form, for example, a recombinant protein, a purified subunit protein, a viral vector expressing an isolated IV polypeptide, or in the form of an inactivated or attenuated IV vaccine. The IV polypeptide or fragment, variant, or derivative thereof encoded by the polynucleotide vaccine may be identical to the isolated IV polypeptide or fragment, variant, or derivative thereof. Alternatively, the IV polypeptide or fragment, variant, or derivative thereof encoded by the polynucleotide may be different from the isolated IV polypeptide or fragment, variant, or derivative thereof.

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (parquet, A-M et al., *Gene Therapy* 4:1341-1349 (1997)) comprising a polynucleotide. A polynucleotide may comprise a conventional phosphodiester bond or a non-conventional bond (e.g., an amide bond, such as found in peptide nucleic acids (PNA)).

The terms "nucleic acid" or "nucleic acid fragment" refer to any one or more nucleic acid segments, e.g., DNA or RNA fragments, present in a polynucleotide or construct. A nucleic acid or fragment thereof may be provided in linear (e.g., mRNA) or circular (e.g., plasmid) form as well as double-stranded or single-stranded forms. By "isolated" nucleic acid or polynucleotide is intended a nucleic acid molecule, DNA or RNA, which has been removed from its native environment. For example, a recombinant polynucleotide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the polynucleotides of the present invention. Isolated polynucleotides or nucleic acids according to the present invention further include such molecules produced synthetically.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate (different) plasmids. Furthermore, any nucleic acid or nucleic acid fragment may encode a single IV polypeptide or fragment, derivative, or variant thereof, e.g., or may encode more than one polypeptide, e.g., a nucleic acid may encode two or more polypeptides. In addition, a nucleic acid may include a regulatory element such as a promoter, ribosome binding site, or a transcription terminator, or may encode heterologous coding regions fused to the IV coding region, e.g., specialized elements or motifs, such as a secretory signal peptide or a heterologous functional domain.

The terms "fragment," "variant," "derivative" and "analog" when referring to IV polypeptides of the present invention include any polypeptides which retain at least some of the immunogenicity or antigenicity of the corresponding native polypeptide. Fragments of IV polypeptides of the present invention include proteolytic fragments, deletion fragments and in particular, fragments of IV polypeptides which exhibit increased secretion from the cell or higher immunogenicity or reduced pathogenicity when delivered to an animal. Polypeptide fragments further include any portion of the polypeptide which comprises an antigenic or immunogenic epitope of the native polypeptide, including linear as well as three-dimensional epitopes. Variants of IV polypeptides of the present invention include fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome or genome of an organism or virus. Genes II, Lewin, B., ed., John Wiley & Sons, New York (1985), which is incorporated herein by reference. For example, as used herein, variations in a given gene product is a "variant". When referring to IV NA or HA proteins, each such protein is a "variant," in that native IV strains are distinguished by the type of NA and HA proteins encoded by the virus. However, within a single HA or NA variant type, further naturally or non-naturally occurring variations such as amino acid deletions, insertions or substitutions may occur. Non-naturally occurring variants may be produced using art-known mutagenesis techniques. Variant polypeptides may comprise conservative or non-conservative amino acid substitutions, deletions or additions. Derivatives of IV polypeptides of the present invention, are polypeptides which have been altered so as to exhibit additional features not found on the native polypeptide. Examples include fusion proteins. An analog is another form of an IV polypeptide of the present invention. An example is a proprotein which can be activated by cleavage of the proprotein to produce an active mature polypeptide.

The terms "infectious polynucleotide" or "infectious nucleic acid" are intended to encompass isolated viral polynucleotides and/or nucleic acids which are solely sufficient to mediate the synthesis of complete infectious virus particles upon uptake by permissive cells. Thus, "infectious nucleic acids" do not require pre-synthesized copies of any of the polypeptides it encodes, e.g., viral replicases, in order to initiate its replication cycle in a permissive host cell.

The terms "non-infectious polynucleotide" or "non-infectious nucleic acid" as defined herein are polynucleotides or nucleic acids which cannot, without additional added materials, e.g, polypeptides, mediate the synthesis of complete infectious virus particles upon uptake by permissive cells. An infectious polynucleotide or nucleic acid is not made "non-infectious" simply because it is taken up by a non-permissive cell. For example, an infectious viral polynucleotide from a virus with limited host range is infectious if it is capable of mediating the synthesis of complete infectious virus particles when taken up by cells derived from a permissive host (i.e., a host permissive for the virus itself). The fact that uptake by cells derived from a non-permissive host does not result in the synthesis of complete infectious virus particles does not make the nucleic acid "non-infectious." In other words, the term is not qualified by the nature of the host cell, the tissue type, or the species taking up the polynucleotide or nucleic acid fragment.

In some cases, an isolated infectious polynucleotide or nucleic acid may produce fully-infectious virus particles in a host cell population which lacks receptors for the virus particles, i.e., is non-permissive for virus entry. Thus viruses produced will not infect surrounding cells. However, if the supernatant containing the virus particles is transferred to cells which are permissive for the virus, infection will take place.

The terms "replicating polynucleotide" or "replicating nucleic acid" are meant to encompass those polynucleotides and/or nucleic acids which, upon being taken up by a permissive host cell, are capable of producing multiple, e.g., one or more copies of the same polynucleotide or nucleic acid. Infectious polynucleotides and nucleic acids are a subset of replicating polynucleotides and nucleic acids; the terms are not synonymous. For example, a defective virus genome lacking the genes for virus coat proteins may replicate, e.g., produce multiple copies of itself, but is NOT infectious because it is incapable of mediating the synthesis of complete infectious virus particles unless the coat proteins, or another nucleic acid encoding the coat proteins, are exogenously provided.

In certain embodiments, the polynucleotide, nucleic acid, or nucleic acid fragment is DNA. In the case of DNA, a polynucleotide comprising a nucleic acid which encodes a polypeptide normally also comprises a promoter and/or other transcription or translation control elements operably associated with the polypeptide-encoding nucleic acid fragment. An operable association is when a nucleic acid fragment encoding a gene product, e.g., a polypeptide, is associated with one or more regulatory sequences in such a way as to place expression of the gene product under the influence or control of the regulatory sequence(s). Two DNA fragments (such as a polypeptide-encoding nucleic acid fragment and a promoter associated with the 5' end of the nucleic acid fragment) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a nucleic acid fragment encoding a polypeptide if the promoter was capable of effecting transcription of that nucleic acid fragment. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, elements from picornaviruses (particularly an internal ribosome entry site, or IRES, also referred to as a CITE sequence).

A DNA polynucleotide of the present invention may be a circular or linearized plasmid or vector, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Cherng, J. Y., et al., *J. Control. Release* 60:343-53 (1999), and Chen, Z. Y., et al. *Mol. Ther.* 3:403-10 (2001), both of which are incorporated herein by reference. As used herein, the terms plasmid and vector can be used interchangeably Alternatively, DNA virus genomes may be used to administer DNA polynucleotides into vertebrate cells. In certain embodiments, a DNA virus genome of the present invention is nonreplicative, noninfectious, and/or nonintegrating. Suitable DNA virus genomes include without limitation, herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

In other embodiments, a polynucleotide of the present invention is RNA, for example, in the form of messenger RNA (mRNA). Methods for introducing RNA sequences into vertebrate cells are described in U.S. Pat. No. 5,580,859, the disclosure of which is incorporated herein by reference in its entirety.

Polynucleotides, nucleic acids, and nucleic acid fragments of the present invention may be associated with additional nucleic acids which encode secretory or signal peptides, which direct the secretion of a polypeptide encoded by a nucleic acid fragment or polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native leader sequence is used, or a functional derivative of that sequence that retains the ability to direct the secretion of the polypeptide that is operably associated with it. Alternatively, a heterologous mammalian leader sequence, or a functional derivative thereof, may be used. For example, the wild-type leader sequence may be substituted with the leader sequence of human tissue plasminogen activator (TPA) or mouse β-glucuronidase.

In accordance with one aspect of the present invention, there is provided a polynucleotide construct, for example, a plasmid, comprising a nucleic acid fragment, where the nucleic acid fragment is a fragment of a codon-optimized coding region operably encoding an IV-derived polypeptide, where the coding region is optimized for expression in vertebrate cells, of a desired vertebrate species, e.g., humans, to be delivered to a vertebrate to be treated or immunized. Suitable IV polypeptides, or fragments, variants, or derivatives thereof may be derived from, but are not limited to, the IV HA, NA, NP, M1, or M2 proteins. Additional IV-derived coding sequences, e.g., coding for HA, NA, NP, M1, M2 or eM2, may also be included on the plasmid, or on a separate plasmid, and expressed, either using native IV codons or codons optimized for expression in the vertebrate to be treated or immunized. When such a plasmid encoding one or more optimized influenza sequences is delivered, in vivo to a tissue of the vertebrate to be treated or immunized, one or more of the encoded gene products will be expressed, i.e., transcribed and translated. The level of expression of the gene product(s) will depend to a significant extent on the strength of the associated promoter and the presence and activation of an associated enhancer element, as well as the degree of optimization of the coding region.

As used herein, the term "plasmid" refers to a construct made up of genetic material (i.e., nucleic acids). Typically a plasmid contains an origin of replication which is functional in bacterial host cells, e.g., *Escherichia coli*, and selectable markers for detecting bacterial host cells comprising the plasmid. Plasmids of the present invention may include genetic elements as described herein arranged such that an inserted coding sequence can be transcribed and translated in eukaryotic cells. Also, the plasmid may include a sequence from a viral nucleic acid. However, such viral sequences normally are not sufficient to direct or allow the incorporation of the plasmid into a viral particle, and the plasmid is therefore a non-viral vector. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to IV polypeptides, which are used to prevent or treat, i.e., cure, ameliorate, lessen the severity of, or prevent or reduce contagion of infectious disease caused by the IV.

As used herein, an "antigenic polypeptide" or an "immunogenic polypeptide" is a polypeptide which, when introduced into a vertebrate, reacts with the vertebrate's immune system molecules, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, e.g., HA or fragments or variants thereof, e.g. NP, or fragments thereof, e.g., PB1, or fragments or variants thereof, e.g., NS1 or fragments or variants thereof, e.g., M1 or fragments or variants thereof, and e.g. M2 or fragments or variants thereof including the extracellular fragment of M2 (eM2), or e.g., any of the foregoing polypeptides or fragments fused to a heterologous polypeptide, for example, a hepatitis B core antigen. Isolated antigenic and immunogenic polypeptides of the present invention in addition to those encoded by polynucleotides of the invention, may be provided as a recombinant protein, a purified subunit, a viral vector expressing the protein, or may be provided in the form of an inactivated IV vaccine, e.g., a live-attenuated virus vaccine, a heat-killed virus vaccine, etc.

By an "isolated" IV polypeptide or a fragment, variant, or derivative thereof is intended an IV polypeptide or protein that is not in its natural form. No particular level of purification is required. For example, an isolated IV polypeptide can be removed from its native or natural environment. Recombinantly produced IV polypeptides and proteins expressed in host cells are considered isolated for purposed of the invention, as are native or recombinant IV polypeptides which have been separated, fractionated, or partially or substantially purified by any suitable technique, including the separation of IV virions from eggs or culture cells in which they have been propagated. In addition, an isolated IV polypeptide or protein can be provided as a live or inactivated viral vector expressing an isolated IV polypeptide and can include those found in inactivated IV vaccine compositions. Thus, isolated IV polypeptides and proteins can be provided as, for example, recombinant IV polypeptides, a purified subunit of IV, a viral vector expressing an isolated IV polypeptide, or in the form of an inactivated or attenuated IV vaccine.

The term "epitopes," as used herein, refers to portions of a polypeptide having antigenic or immunogenic activity in a vertebrate, for example a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind as determined by any method well known in the art. Immunospecific binding excludes non-specific binding but does not exclude cross-reactivity with other antigens. Where all immunogenic epitopes are antigenic, antigenic epitopes need not be immunogenic.

The term "immunogenic carrier" as used herein refers to a first polypeptide or fragment, variant, or derivative thereof which enhances the immunogenicity of a second polypeptide or fragment, variant, or derivative thereof. Typically, an "immunogenic carrier" is fused to or conjugated to the desired polypeptide or fragment thereof. An example of an "immunogenic carrier" is a recombinant hepatitis B core antigen expressing, as a surface epitope, an immunogenic epitope of interest. See, e.g., European Patent No. EP 0385610 B1, which is incorporated herein by reference in its entirety.

In the present invention, antigenic epitopes preferably contain a sequence of at least 4, at least 5, at least 6, at least 7, at least 8, at least 9, at least 10, at least 15, at least 20, at least 25, or between about 8 to about 30 amino acids contained within the amino acid sequence of an IV polypeptide of the invention, e.g., an NP polypeptide, an M1 polypeptide or an M2 polypeptide. Certain polypeptides comprising immunogenic or antigenic epitopes are at least 5, 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., *Science* 219:660-666 (1983), which is herein incorporated by reference.

Peptides capable of eliciting an immunogenic response are frequently represented in the primary sequence of a protein, can be characterized by a set of simple chemical rules, and are confined neither to immunodominant regions of intact proteins nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661. For instance, 18 of 20 peptides designed according to these guidelines, containing 8-39 residues covering 75% of the sequence of the IV hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Codon Optimization

"Codon optimization" is defined as modifying a nucleic acid sequence for enhanced expression in the cells of the vertebrate of interest, e.g. human, by replacing at least one, more than one, or a significant number, of codons of the native sequence with codons that are more frequently or most frequently used in the genes of that vertebrate. Various species exhibit particular bias for certain codons of a particular amino acid.

In one aspect, the present invention relates to polynucleotides comprising nucleic acid fragments of codon-optimized coding regions which encode IV polypeptides, or fragments, variants, or derivatives thereof, with the codon usage adapted for optimized expression in the cells of a given vertebrate, e.g., humans. These polynucleotides are prepared by incorporating codons preferred for use in the genes of the vertebrate of interest into the DNA sequence. Also provided are polynucleotide expression constructs, vectors, and host cells comprising nucleic acid fragments of codon-optimized coding regions which encode IV polypeptides, and fragments, variants, or derivatives thereof, and various methods of using the polynucleotide expression constructs, vectors, host cells to treat or prevent influenza disease in a vertebrate.

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |

TABLE 1-continued

| The Standard Genetic Code | | | | |
|---|---|---|---|---|
| | T | C | A | G |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at www.kazusa.or.jp/codon/ (visited Jul. 9, 2002), and these tables can be adapted in a number of ways. See Nakamura, Y., et al. "Codon usage tabulated from the international DNA sequence databases: status for the year 2000" *Nucl. Acids Res.* 28:292 (2000), which is incorporated by reference. As examples, the codon usage tables for human, mouse, domestic cat, and cow, calculated from GenBank Release 128.0 (15 Feb. 2002), are reproduced below as Tables 2-5. These Tables use mRNA nomenclature, and so instead of thymine (T) which is found in DNA, the Tables use uracil (U) which is found in RNA. The Tables have been adapted so that frequencies are calculated for each amino acid, rather than for all 64 codons.

TABLE 2

Codon Usage Table for Human Genes (*Homo sapiens*)

| Amino Acid | Codon | Number | Frequency |
|---|---|---|---|
| Phe | UUU | 326146 | 0.4525 |
| Phe | UUC | 394680 | 0.5475 |
| Total | | 720826 | |
| Leu | UUA | 139249 | 0.0728 |
| Leu | UUG | 242151 | 0.1266 |
| Leu | CUU | 246206 | 0.1287 |
| Leu | CUC | 374262 | 0.1956 |
| Leu | CUA | 133980 | 0.0700 |
| Leu | CUG | 777077 | 0.4062 |
| Total | | 1912925 | |
| Ile | AUU | 303721 | 0.3554 |
| Ile | AUC | 414483 | 0.4850 |
| Ile | AUA | 136399 | 0.1596 |
| Total | | 854603 | |
| Met | AUG | 430946 | 1.0000 |
| Total | | 430946 | |

TABLE 2-continued

Codon Usage Table for Human Genes (*Homo sapiens*)

| Amino Acid | Codon | Number | Frequency |
|---|---|---|---|
| Val | GUU | 210423 | 0.1773 |
| Val | GUC | 282445 | 0.2380 |
| Val | GUA | 134991 | 0.1137 |
| Val | GUG | 559044 | 0.4710 |
| Total | | 1186903 | |
| Ser | UCU | 282407 | 0.1840 |
| Ser | UCC | 336349 | 0.2191 |
| Ser | UCA | 225963 | 0.1472 |
| Ser | UCG | 86761 | 0.0565 |
| Ser | AGU | 230047 | 0.1499 |
| Ser | AGC | 373362 | 0.2433 |
| Total | | 1534889 | |
| Pro | CCU | 333705 | 0.2834 |
| Pro | CCC | 386462 | 0.3281 |
| Pro | CCA | 322220 | 0.2736 |
| Pro | CCG | 135317 | 0.1149 |
| Total | | 1177704 | |
| Thr | ACU | 247913 | 0.2419 |
| Thr | ACC | 371420 | 0.3624 |
| Thr | ACA | 285655 | 0.2787 |
| Thr | ACG | 120022 | 0.1171 |
| Total | | 1025010 | |
| Ala | GCU | 360146 | 0.2637 |
| Ala | GCC | 551452 | 0.4037 |
| Ala | GCA | 308034 | 0.2255 |
| Ala | GCG | 146233 | 0.1071 |
| Total | | 1365865 | |
| Tyr | UAU | 232240 | 0.4347 |
| Tyr | UAC | 301978 | 0.5653 |
| Total | | 534218 | |
| His | CAU | 201389 | 0.4113 |
| His | CAC | 288200 | 0.5887 |
| Total | | 489589 | |
| Gln | CAA | 227742 | 0.2541 |
| Gln | CAG | 668391 | 0.7459 |
| Total | | 896133 | |
| Asn | AAU | 322271 | 0.4614 |
| Asn | AAC | 376210 | 0.5386 |
| Total | | 698481 | |
| Lys | AAA | 462660 | 0.4212 |
| Lys | AAG | 635755 | 0.5788 |
| Total | | 1098415 | |
| Asp | GAU | 430744 | 0.4613 |
| Asp | GAC | 502940 | 0.5387 |
| Total | | 933684 | |
| Glu | GAA | 561277 | 0.4161 |
| Glu | GAG | 787712 | 0.5839 |
| Total | | 1348989 | |
| Cys | UGU | 190962 | 0.4468 |
| Cys | UGC | 236400 | 0.5532 |
| Total | | 427362 | |
| Trp | UGG | 248083 | 1.0000 |
| Total | | 248083 | |
| Arg | CGU | 90899 | 0.0830 |
| Arg | CGC | 210931 | 0.1927 |
| Arg | CGA | 122555 | 0.1120 |
| Arg | CGG | 228970 | 0.2092 |
| Arg | AGA | 221221 | 0.2021 |
| Arg | AGG | 220119 | 0.2011 |
| Total | | 1094695 | |

TABLE 2-continued

Codon Usage Table for Human Genes (*Homo sapiens*)

| Amino Acid | Codon | Number | Frequency |
|---|---|---|---|
| Gly | GGU | 209450 | 0.1632 |
| Gly | GGC | 441320 | 0.3438 |
| Gly | GGA | 315726 | 0.2459 |
| Gly | GGG | 317263 | 0.2471 |
| Total | | 1283759 | |
| Stop | UAA | 13963 | |
| Stop | UAG | 10631 | |
| Stop | UGA | 24607 | |

TABLE 3

Codon Usage Table for Mouse Genes (*Mus musculus*)

| Amino Acid | Codon | Number | Frequency |
|---|---|---|---|
| Phe | UUU | 150467 | 0.4321 |
| Phe | UUC | 197795 | 0.5679 |
| Total | | 348262 | |
| Leu | UUA | 55635 | 0.0625 |
| Leu | UUG | 116210 | 0.1306 |
| Leu | CUU | 114699 | 0.1289 |
| Leu | CUC | 179248 | 0.2015 |
| Leu | CUA | 69237 | 0.0778 |
| Leu | CUG | 354743 | 0.3987 |
| Total | | 889772 | |
| Ile | AUU | 137513 | 0.3367 |
| Ile | AUC | 208533 | 0.5106 |
| Ile | AUA | 62349 | 0.1527 |
| Total | | 408395 | |
| Met | AUG | 204546 | 1.0000 |
| Total | | 204546 | |
| Val | GUU | 93754 | 0.1673 |
| Val | GUC | 140762 | 0.2513 |
| Val | GUA | 64417 | 0.1150 |
| Val | GUG | 261308 | 0.4664 |
| Total | | 560241 | |
| Ser | UCU | 139576 | 0.1936 |
| Ser | UCC | 160313 | 0.2224 |
| Ser | UCA | 100524 | 0.1394 |
| Ser | UCG | 38632 | 0.0536 |
| Ser | AGU | 108413 | 0.1504 |
| Ser | AGC | 173518 | 0.2407 |
| Total | | 720976 | |
| Pro | CCU | 162613 | 0.3036 |
| Pro | CCC | 164796 | 0.3077 |
| Pro | CCA | 151091 | 0.2821 |
| Pro | CCG | 57032 | 0.1065 |
| Total | | 535532 | |
| Thr | ACU | 119832 | 0.2472 |
| Thr | ACC | 172415 | 0.3556 |
| Thr | ACA | 140420 | 0.2896 |
| Thr | ACG | 52142 | 0.1076 |
| Total | | 484809 | |
| Ala | GCU | 178593 | 0.2905 |
| Ala | GCC | 236018 | 0.3839 |
| Ala | GCA | 139697 | 0.2272 |
| Ala | GCG | 60444 | 0.0983 |
| Total | | 614752 | |
| Tyr | UAU | 108556 | 0.4219 |
| Tyr | UAC | 148772 | 0.5781 |
| Total | | 257328 | |

TABLE 3-continued

Codon Usage Table for Mouse Genes (*Mus musculus*)

| Amino Acid | Codon | Number | Frequency |
|---|---|---|---|
| His | CAU | 88786 | 0.3973 |
| His | CAC | 134705 | 0.6027 |
| Total | | 223491 | |
| Gln | CAA | 101783 | 0.2520 |
| Gln | CAG | 302064 | 0.7480 |
| Total | | 403847 | |
| Asn | AAU | 138868 | 0.4254 |
| Asn | AAC | 187541 | 0.5746 |
| Total | | 326409 | |
| Lys | AAA | 188707 | 0.3839 |
| Lys | AAG | 302799 | 0.6161 |
| Total | | 491506 | |
| Asp | GAU | 189372 | 0.4414 |
| Asp | GAC | 239670 | 0.5586 |
| Total | | 429042 | |
| Glu | GAA | 235842 | 0.4015 |
| Glu | GAG | 351582 | 0.5985 |
| Total | | 587424 | |
| Cys | UGU | 97385 | 0.4716 |
| Cys | UGC | 109130 | 0.5284 |
| Total | | 206515 | |
| Trp | UGG | 112588 | 1.0000 |
| Total | | 112588 | |
| Arg | CGU | 41703 | 0.0863 |
| Arg | CGC | 86351 | 0.1787 |
| Arg | CGA | 58928 | 0.1220 |
| Arg | CGG | 92277 | 0.1910 |
| Arg | AGA | 101029 | 0.2091 |
| Arg | AGG | 102859 | 0.2129 |
| Total | | 483147 | |
| Gly | GGU | 103673 | 0.1750 |
| Gly | GGC | 198604 | 0.3352 |
| Gly | GGA | 151497 | 0.2557 |
| Gly | GGG | 138700 | 0.2341 |
| Total | | 592474 | |
| Stop | UAA | 5499 | |
| Stop | UAG | 4661 | |
| Stop | UGA | 10356 | |

TABLE 4

Codon Usage Table for Domestic Cat Genes (*Felis cattus*)

| Amino Acid | Codon | Number | Frequency of usage |
|---|---|---|---|
| Phe | UUU | 1204.00 | 0.4039 |
| Phe | UUC | 1777.00 | 0.5961 |
| Total | | 2981 | |
| Leu | UUA | 404.00 | 0.0570 |
| Leu | UUG | 857.00 | 0.1209 |
| Leu | CUU | 791.00 | 0.1116 |
| Leu | CUC | 1513.00 | 0.2135 |
| Leu | CUA | 488.00 | 0.0688 |
| Leu | CUG | 3035.00 | 0.4282 |
| Total | | 7088 | |
| Ile | AUU | 1018.00 | 0.2984 |
| Ile | AUC | 1835.00 | 0.5380 |
| Ile | AUA | 558.00 | 0.1636 |
| Total | | 3411 | |

TABLE 4-continued

| Codon Usage Table for Domestic Cat Genes (*Felis cattus*) | | | |
|---|---|---|---|
| Amino Acid | Codon | Number | Frequency of usage |
| Met | AUG | 1553.00 | 0.0036 |
| Total | | 1553 | |
| Val | GUU | 696.00 | 0.1512 |
| Val | GUC | 1279.00 | 0.2779 |
| Val | GUA | 463.00 | 0.1006 |
| Val | GUG | 2164.00 | 0.4702 |
| Total | | 4602 | |
| Ser | UCU | 940.00 | 0.1875 |
| Ser | UCC | 1260.00 | 0.2513 |
| Ser | UCA | 608.00 | 0.1213 |
| Ser | UCG | 332.00 | 0.0662 |
| Ser | AGU | 672.00 | 0.1340 |
| Ser | AGC | 1202.00 | 0.2397 |
| Total | | 5014 | |
| Pro | CCU | 958.00 | 0.2626 |
| Pro | CCC | 1375.00 | 0.3769 |
| Pro | CCA | 850.00 | 0.2330 |
| Pro | CCG | 465.00 | 0.1275 |
| Total | | 3648 | |
| Thr | ACU | 822.00 | 0.2127 |
| Thr | ACC | 1574.00 | 0.4072 |
| Thr | ACA | 903.00 | 0.2336 |
| Thr | ACG | 566.00 | 0.1464 |
| Total | | 3865 | |
| Ala | GCU | 1129.00 | 0.2496 |
| Ala | GCC | 1951.00 | 0.4313 |
| Ala | GCA | 883.00 | 0.1952 |
| Ala | GCG | 561.00 | 0.1240 |
| Total | | 4524 | |
| Tyr | UAU | 837.00 | 0.3779 |
| Tyr | UAC | 1378.00 | 0.6221 |
| Total | | 2215 | |
| His | CAU | 594.00 | 0.3738 |
| His | CAC | 995.00 | 0.6262 |
| Total | | 1589 | |
| Gln | CAA | 747.00 | 0.2783 |
| Gln | CAG | 1937.00 | 0.7217 |
| Total | | 2684 | |
| Asn | AAU | 1109.00 | 0.3949 |
| Asn | AAC | 1699.00 | 0.6051 |
| Total | | 2808 | |
| Lys | AAA | 1445.00 | 0.4088 |
| Lys | AAG | 2090.00 | 0.5912 |
| Total | | 3535 | |
| Asp | GAU | 1255.00 | 0.4055 |
| Asp | GAC | 1840.00 | 0.5945 |
| Total | | 3095 | |
| Glu | GAA | 1637.00 | 0.4164 |
| Glu | GAG | 2294.00 | 0.5836 |
| Total | | 3931 | |
| Cys | UGU | 719.00 | 0.4425 |
| Cys | UGC | 906.00 | 0.5575 |
| Total | | 1625 | |
| Trp | UGG | 1073.00 | 1.0000 |
| Total | | 1073 | |
| Arg | CGU | 236.00 | 0.0700 |
| Arg | CGC | 629.00 | 0.1865 |
| Arg | CGA | 354.00 | 0.1050 |
| Arg | CGG | 662.00 | 0.1963 |

TABLE 4-continued

| Codon Usage Table for Domestic Cat Genes (*Felis cattus*) | | | |
|---|---|---|---|
| Amino Acid | Codon | Number | Frequency of usage |
| Arg | AGA | 712.00 | 0.2112 |
| Arg | AGG | 779.00 | 0.2310 |
| Total | | 3372 | |
| Gly | GGU | 648.00 | 0.1498 |
| Gly | GGC | 1536.00 | 0.3551 |
| Gly | GGA | 1065.00 | 0.2462 |
| Gly | GGG | 1077.00 | 0.2490 |
| Total | | 4326 | |
| Stop | UAA | 55 | |
| Stop | UAG | 36 | |
| Stop | UGA | 110 | |

TABLE 5

| Codon Usage Table for Cow Genes (*Bos taurus*) | | | |
|---|---|---|---|
| Amino Acid | Codon | Number | Frequency of usage |
| Phe | UUU | 13002 | 0.4112 |
| Phe | UUC | 18614 | 0.5888 |
| Total | | 31616 | |
| Leu | UUA | 4467 | 0.0590 |
| Leu | UUG | 9024 | 0.1192 |
| Leu | CUU | 9069 | 0.1198 |
| Leu | CUC | 16003 | 0.2114 |
| Leu | CUA | 4608 | 0.0609 |
| Leu | CUG | 32536 | 0.4298 |
| Total | | 75707 | |
| Ile | AUU | 12474 | 0.3313 |
| Ile | AUC | 19800 | 0.5258 |
| Ile | AUA | 5381 | 0.1429 |
| Total | | 37655 | |
| Met | AUG | 17770 | 1.0000 |
| Total | | 17770 | |
| Val | GUU | 8212 | 0.1635 |
| Val | GUC | 12846 | 0.2558 |
| Val | GUA | 4932 | 0.0982 |
| Val | GUG | 24222 | 0.4824 |
| Total | | 50212 | |
| Ser | UCU | 10287 | 0.1804 |
| Ser | UCC | 13258 | 0.2325 |
| Ser | UCA | 7678 | 0.1347 |
| Ser | UCG | 3470 | 0.0609 |
| Ser | AGU | 8040 | 0.1410 |
| Ser | AGC | 14279 | 0.2505 |
| Total | | 57012 | |
| Pro | CCU | 11695 | 0.2684 |
| Pro | CCC | 15221 | 0.3493 |
| Pro | CCA | 11039 | 0.2533 |
| Pro | CCG | 5621 | 0.1290 |
| Total | | 43576 | |
| Thr | ACU | 9372 | 0.2203 |
| Thr | ACC | 16574 | 0.3895 |
| Thr | ACA | 10892 | 0.2560 |
| Thr | ACG | 5712 | 0.1342 |
| Total | | 42550 | |
| Ala | GCU | 13923 | 0.2592 |
| Ala | GCC | 23073 | 0.4295 |
| Ala | GCA | 10704 | 0.1992 |
| Ala | GCG | 6025 | 0.1121 |
| Total | | 53725 | |

TABLE 5-continued

Codon Usage Table for Cow Genes (*Bos taurus*)

| Amino Acid | Codon | Number | Frequency of usage |
|---|---|---|---|
| Tyr | UAU | 9441 | 0.3882 |
| Tyr | UAC | 14882 | 0.6118 |
| Total | | 24323 | |
| His | CAU | 6528 | 0.3649 |
| His | CAC | 11363 | 0.6351 |
| Total | | 17891 | |
| Gln | CAA | 8060 | 0.2430 |
| Gln | CAG | 25108 | 0.7570 |
| Total | | 33168 | |
| Asn | AAU | 12491 | 0.4088 |
| Asn | AAC | 18063 | 0.5912 |
| Total | | 30554 | |
| Lys | AAA | 17244 | 0.3897 |
| Lys | AAG | 27000 | 0.6103 |
| Total | | 44244 | |
| Asp | GAU | 16615 | 0.4239 |
| Asp | GAC | 22580 | 0.5761 |
| Total | | 39195 | |
| Glu | GAA | 21102 | 0.4007 |
| Glu | GAG | 31555 | 0.5993 |
| Total | | 52657 | |
| Cys | UGU | 7556 | 0.4200 |
| Cys | UGC | 10436 | 0.5800 |
| Total | | 17992 | |
| Trp | UGG | 10706 | 1.0000 |
| Total | | 10706 | |
| Arg | CGU | 3391 | 0.0824 |
| Arg | CGC | 7998 | 0.1943 |
| Arg | CGA | 4558 | 0.1108 |
| Arg | CGG | 8300 | 0.2017 |
| Arg | AGA | 8237 | 0.2001 |
| Arg | AGG | 8671 | 0.2107 |
| Total | | 41155 | |
| Gly | GGU | 8508 | 0.1616 |
| Gly | GGC | 18517 | 0.3518 |
| Gly | GGA | 12838 | 0.2439 |
| Gly | GGG | 12772 | 0.2427 |
| Total | | 52635 | |
| Stop | UAA | 555 | |
| Stop | UAG | 394 | |
| Stop | UGA | 392 | |

By utilizing these or similar tables, one of ordinary skill in the art can apply the frequencies to any given polypeptide sequence, and produce a nucleic acid fragment of a codon-optimized coding region which encodes the polypeptide, but which uses codons more optimal for a given species. Codon-optimized coding regions can be designed by various different methods.

In one method, termed "uniform optimization," a codon usage table is used to find the single most frequent codon used for any given amino acid, and that codon is used each time that particular amino acid appears in the polypeptide sequence. For example, referring to Table 2 above, for leucine, the most frequent codon in humans is CUG, which is used 41% of the time. Thus all the leucine residues in a given amino acid sequence would be assigned the codon CUG. A coding region for IAV NP (SEQ ID NO:2) optimized by the "uniform optimization" method is presented herein as SEQ ID NO:24:

```
   1 ATGGCCAGCC AGGGCACCAA GCGGAGCTAC GAGCAGATGG AGACCGACGG CGAGCGGCAG
  61 AACGCCACCG AGATCCGGGC CAGCGTGGGC AAGATGATCG GCGGCATCGG CCGGTTCTAC
 121 ATCCAGATGT GCACCGAGCT GAAGCTGAGC GACTACGAGG GCCGGCTGAT CCAGAACAGC
 181 CTGACCATCG AGCGGATGGT GCTGAGCGCC TTCGACGAGC GGCGGAACAA GTACCTGGAG
 241 GAGCACCCCA GCGCCGGCAA GGACCCCAAG AAGACCGGCG GCCCCATCTA CCGGCGGGTG
 301 AACGGCAAGT GGATGCGGGA GCTGATCCTG TACGACAAGG AGGAGATCCG GCGGATCTGG
 361 CGGCAGGCCA ACAACGGCGA CGACGCCACC GCCGGCCTGA CCCACATGAT GATCTGGCAC
 421 AGCAACCTGA ACGACGCCAC CTACCAGCGG ACCCGGGCCC TGGTGCGGAC CGGCATGGAC
 481 CCCCGGATGT GCAGCCTGAT GCAGGGCAGC ACCCTGCCCC GGCGGAGCGG CGCCGCCGGC
 541 GCCGCCGTGA AGGGCGTGGG CACCATGGTG ATGGAGCTGG TGCGGATGAT CAAGCGGGGC
 601 ATCAACGACC GGAACTTCTG GCGGGGCGAG AACGGCCGGA AGACCCGGAT CGCCTACGAG
 661 CGGATGTGCA ACATCCTGAA GGGCAAGTTC CAGACCGCCG CCCAGAAGGC CATGATGGAC
 721 CAGGTGCGGG AGAGCCGGAA CCCCGGCAAC GCCGAGTTCG AGGACCTGAC CTTCCTGGCC
 781 CGGAGCGCCC TGATCCTGCG GGGCAGCGTG GCCCACAAGA GCTGCCTGCC CGCCTGCGTG
 841 TACGGCCCCG CCGTGGCCAG CGGCTACGAC TTCGAGCGGG AGGGCTACAG CCTGGTGGGC
 901 ATCGACCCCT TCCGGCTGCT GCAGAACAGC CAGGTGTACA GCCTGATCCG GCCCAACGAG
 961 AACCCCGCCC ACAAGAGCCA GCTGGTGTGG ATGGCCTGCC ACAGCGCCGC CTTCGAGGAC
1021 CTGCGGGTGC TGAGCTTCAT CAAGGGCACC AAGGTGCTGC CCCGGGGCAA GCTGAGCACC
```

-continued

```
1081 CGGGGCGTGC AGATCGCCAG CAACGAGAAC ATGGAGACCA TGGAGAGCAG CACCCTGGAG

1141 CTGCGGAGCC GGTACTGGGC CATCCGGACC CGGAGCGGCG GCAACACCAA CCAGCAGCGG

1201 GCCAGCGCCG GCCAGATCAG CATCCAGCCC ACCTTCAGCG TGCAGCGGAA CCTGCCCTTC

1261 GACCGGACCA CCGTGATGGC CGCCTTCAGC GGCAACACCG AGGGCCGGAC CAGCGACATG

1321 CGGACCGAGA TCATCCGGAT GATGGAGAGC GCCCGGCCCG AGGACGTGAG CTTCCAGGGC

1381 CGGGGCGTGT TCGAGCTGAG CGACGAGAAG GCCGCCAGCC CCATCGTGCC CAGCTTCGAC

1441 ATGAGCAACG AGGGCAGCTA CTTCTTCGGC GACAACGCCG AGGAGTACGA CAACTGA
```

In another method, termed "full-optimization," the actual frequencies of the codons are distributed randomly throughout the coding region. Thus, using this method for optimization, if a hypothetical polypeptide sequence had 100 leucine residues, referring to Table 2 for frequency of usage in humans, about 7, or 7% of the leucine codons would be UUA, about 13, or 13% of the leucine codons would be UUG, about 13, or 13% of the leucine codons would be CUU, about 20, or 20% of the leucine codons would be CUC, about 7, or 7% of the leucine codons would be CUA, and about 41, or 41% of the leucine codons would be CUG. These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

As an example, a nucleotide sequence for NP (SEQ ID NO:2) fully optimized for human codon usage, is shown as SEQ ID NO:23. An alignment of nucleotides 46-1542 of SEQ ID NO:1 (native NP coding region) with the codon-optimized coding region (SEQ ID NO:23) is presented in FIG. 1.

In using the "full-optimization" method, an entire polypeptide sequence may be codon-optimized as described above. With respect to various desired fragments, variants or derivatives of the complete polypeptide, the fragment variant, or derivative may first be designed, and is then codon-optimized individually. Alternatively, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The disadvantage of this approach is that synthesizing codon-optimized nucleic acid fragments encoding each fragment, variant, and derivative of a given polypeptide, although routine, would be time consuming and would result in significant expense.

When using the "full-optimization" method, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

In a third method termed "minimal optimization," coding regions are only partially optimized. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95% or 100% of the codon positions have been codon-optimized for a given species. That is, they contain a codon that is preferentially used in the genes of a desired species, e.g., a vertebrate species, e.g., humans, in place of a codon that is normally used in the native nucleic acid sequence. Codons that are rarely found in the genes of the vertebrate of interest are changed to codons more commonly utilized in the coding regions of the vertebrate of interest.

Thus, those codons which are used more frequently in the IV gene of interest than in genes of the vertebrate of interest are substituted with more frequently-used codons. The difference in frequency at which the IV codons are substituted may vary based on a number factors as discussed below. For example, codons used at least twice more per thousand in IV genes as compared to genes of the vertebrate of interest are substituted with the most frequently used codon for that amino acid in the vertebrate of interest. This ratio may be adjusted higher or lower depending on various factors such as those discussed below. Accordingly, a codon in an IV native coding region would be substituted with a codon used more frequently for that amino acid in coding regions of the vertebrate of interest if the codon is used 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.1 times, 3.2 times, 3.3 times, 3.4 times, 3.5 times, 3.6 times. 3.7 times, 3.8 times, 3.9 times, 4.0 times, 4.1 times, 4.2 times, 4.3 times, 4.4 times, 4.5 times, 4.6 times, 4.7 times, 4.8 times, 4.9 times, 5.0 times, 5.5 times, 6.0 times, 6.5 times, 7.0 times, 7.5 times, 8.0 times, 8.5 times, 9.0 times, 9.5 times, 10.0 times, 10.5 times, 11.0 times, 11.5 times, 12.0 times, 12.5 times, 13.0 times, 13.5 times, 14.0 times, 14.5 times, 15.0 times, 15.5 times, 16.0 times, 16.5 times, 17.0 times, 17.5 times, 18.0 times, 18.5 times, 19.0 times, 19.5 times, 20 times, 21 times, 22 times, 23 times, 24 times, 25 times, or greater more frequently in IV coding regions than in coding regions of the vertebrate of interest.

This minimal human codon optimization for highly variant codons has several advantages, which include but are not limited to the following examples. Since fewer changes are made to the nucleotide sequence of the gene of interest, fewer manipulations are required, which leads to reduced risk of introducing unwanted mutations and lower cost, as well as allowing the use of commercially available site-directed mutagenesis kits, and reducing the need for expensive oligonucleotide synthesis. Further, decreasing the number of changes in the nucleotide sequence decreases the potential of altering the secondary structure of the sequence, which can have a significant impact on gene expression in certain host cells. The introduction of undesirable restriction sites is also reduced, facilitating the subcloning of the genes of interest into the plasmid expression vector.

The present invention also provides isolated polynucleotides comprising coding regions of IV polypeptides, e.g., NP, M1, M2, HA, NA, PB1, PB2, PA, NS1 or NS2, or fragments, variants, or derivatives thereof. The isolated polynucleotides can also be codon-optimized.

In certain embodiments described herein, a codon-optimized coding region encoding SEQ ID NO:2 is optimized according to codon usage in humans (*Homo sapiens*). Alternatively, a codon-optimized coding region encoding SEQ ID NO:2 may be optimized according to codon usage in any plant, animal, or microbial species. Codon-optimized coding regions encoding SEQ ID NO:2, optimized according to codon usage in humans are designed as follows. The amino acid composition of SEQ ID NO:2 is shown in Table 6.

TABLE 6

| AMINO ACID | | Number in SEQ ID NO:2 |
|---|---|---|
| A | Ala | 39 |
| R | Arg | 49 |
| C | Cys | 6 |
| G | Gly | 41 |
| H | His | 6 |
| I | Ile | 26 |
| L | Leu | 33 |
| K | Lys | 21 |
| M | Met | 25 |
| F | Phe | 18 |
| P | Pro | 17 |
| S | Ser | 40 |
| T | Thr | 28 |
| W | Trp | 6 |
| Y | Tyr | 15 |
| V | Val | 23 |
| N | Asn | 26 |
| D | Asp | 22 |
| Q | Gln | 21 |
| E | Glu | 36 |

Using the amino acid composition shown in Table 6, a human codon-optimized coding region which encodes SEQ ID NO:2 can be designed by any of the methods discussed herein. For "uniform" optimization, each amino acid is assigned the most frequent codon used in the human genome for that amino acid. According to this method, codons are assigned to the coding region encoding SEQ ID NO:2 as follows: the 18 phenylalanine codons are TTC, the 33 leucine codons are CTG, the 26 isoleucine codons are ATC, the 25 methionine codons are ATG, the 23 valine codons are GTG, the 40 serine codons are AGC, the 17 proline codons are CCC, the 28 threonine codons are ACC, the 39 alanine codons are GCC, the 15 tyrosine codons are TAC, the 6 histidine codons are CAC, the 21 glutamine codons are CAG, the 26 asparagine codons are AAC, the 21 lysine codons are AAG, the 22 aspartic acid codons are GAC, the 36 glutamic acid codons are GAG, the 6 tryptophan codons are TGG, the 49 arginine codons are CGG, AGA, or AGG (the frequencies of usage of these three codons in the human genome are not significantly different), and the 41 glycine codons are GGC.

Alternatively, a human codon-optimized coding region which encodes SEQ ID NO:2 can be designed by the "full optimization" method, where each amino acid is assigned codons based on the frequency of usage in the human genome. These frequencies are shown in Table 7 below. Using this latter method, codons are assigned to the coding region encoding SEQ ID NO:2 as follows: about 8 of the 18 phenylalanine codons are TTT, and about 10 of the phenylalanine codons are TTC; about 2 of the 33 leucine codons are TTA, about 4 of the leucine codons are TTG, about 4 of the leucine codons are CTT, about 6 of the leucine codons are CTC, about 2 of the leucine codons are CTA, and about 13 of the leucine codons are CTG; about 9 of the 26 isoleucine codons are ATT, about 13 of the isoleucine codons are ATC, and about 4 of the isoleucine codons are ATA; the 25 methionine codons are ATG; about 4 of the 23 valine codons are GTT, about 5 of the valine codons are GTG, about 3 of the valine codons are GTA, and about 11 of the valine codons are GTG; about 7 of the 40 serine codons are TCT, about 9 of the serine codons are TCC, about 6 of the serine codons are TCA, about 2 of the serine codons are TCG, about 6 of the serine codons are AGT, and about 10 of the serine codons are AGC; about 5 of the 17 proline codons are CCT, about 6 of the proline codons are CCC, about 5 of the proline codons are CCA, and about 2 of the proline codons are CCG; about 7 of the 28 threonine codons are ACT, about 10 of the threonine codons are ACC, about 8 of the threonine codons are ACA, and about 3 of the threonine codons are ACG; about 10 of the 39 alanine codons are GCT, about 16 of the alanine codons are GCC, about 9 of the alanine codons are GCA, and about 4 of the alanine codons are GCG; about 7 of the 15 tyrosine codons are TAT and about 8 of the tyrosine codons are TAC; about 2 of the 6 histidine codons are CAT and about 4 of the histidine codons are CAC; about 5 of the 21 glutamine codons are CAA and about 16 of the glutamine codons are CAG; about 12 of the 26 asparagine codons are AAT and about 14 of the asparagine codons are AAC; about 9 of the 21 lysine codons are AAA and about 12 of the lysine codons are AAG; about 10 of the 22 aspartic acid codons are GAT and about 12 of the aspartic acid codons are GAC; about 11 of the 26 glutamic acid codons are GAA and about 15 of the glutamic acid codons are GAG; about 3 of the 6 cysteine codons are TGT and about 3 of the cysteine codons are TGC; the 6 tryptophan codons are TGG; about 4 of the 49 arginine codons are CGT, about 9 of the arginine codons are CGC, about 5 of the arginine codons are CGA, about 10 of the arginine codons are CGG, about 10 of the arginine codons are AGA, and about 10 of the arginine codons are AGG; and about 7 of the 41 glycine codons are GGT, about 14 of the glycine codons are GGC, about 10 of the glycine codons are GGA, and about 10 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:2, optimized according to codon usage in humans is presented herein as SEQ ID NO:23.

Additionally, a minimally codon-optimized nucleotide sequence encoding SEQ ID NO:2 can be designed by changing only certain codons found more frequently in IV genes than in human genes, as shown in Table 7. For example, if it is desired to substitute more frequently used codons in humans for those codons that occur at least 2 times more frequently in IV genes (designated with an asterisk in Table 7), Arg AGA, which occurs 2.3 times more frequently in IV genes than in human genes, is changed to, e.g., CGG; Asn AAT, which occurs 2.0 times more frequently in IV genes than in human genes, is changed to, e.g., AAC; Ile ATA, which occurs 3.6 times more frequently in IV genes than in human genes, is changed to, e.g., ATC; and Leu CTA, which occurs 2.0 times more frequently in IV genes than is human, is changed to, e.g., CTG.

TABLE 7

Codon Usage Table for Human Genes and IV Genes

| Amino Acid | | Codon | Human | IV |
|---|---|---|---|---|
| Ala | A | GCA | 16 | 25 |
| | | GCG | 8 | 5 |
| | | GCC | 19 | 11 |
| | | GCT | 19 | 15 |
| Arg | R | AGA | 12 | 28* |
| | | AGG | 11 | 14 |
| | | CGA | 6 | 7 |
| | | CGG | 12 | 4 |
| | | CGC | 11 | 3 |
| | | CGT | 5 | 3 |
| Asn | N | AAC | 20 | 27 |
| | | AAT | 17 | 34* |
| Asp | D | GAC | 26 | 20 |
| | | GAT | 22 | 25 |
| Cys | C | TGC | 12 | 13 |
| | | TGT | 10 | 12 |
| Gln | Q | CAA | 12 | 18 |
| | | CAG | 35 | 20 |
| Glu | E | GAA | 30 | 39 |
| | | GAG | 40 | 28 |
| Gly | G | GGA | 16 | 30 |
| | | GGG | 16 | 19 |
| | | GGC | 23 | 9 |
| | | GGT | 11 | 13 |
| His | H | CAC | 15 | 13 |
| | | CAT | 11 | 7 |
| Ile | I | ATA | 7 | 25* |
| | | ATC | 22 | 18 |
| | | ATT | 16 | 23 |

TABLE 7-continued

Codon Usage Table for Human Genes and IV Genes

| Amino Acid | | Codon | Human | IV |
|---|---|---|---|---|
| Leu | L | CTA | 7 | 14* |
| | | CTG | 40 | 17 |
| | | CTC | 20 | 14 |
| | | CTT | 13 | 14 |
| | | TTA | 7 | 8 |
| | | TTG | 13 | 14 |
| Lys | K | AAA | 24 | 35 |
| | | AAG | 33 | 20 |
| Met | M | ATG | 22 | 30 |
| Phe | F | TTC | 21 | 17 |
| | | TTT | 17 | 19 |
| Pro | P | CCA | 17 | 12 |
| | | CCG | 7 | 4 |
| | | CCC | 20 | 8 |
| | | CCT | 17 | 13 |
| Ser | S | AGC | 19 | 14 |
| | | AGT | 12 | 16 |
| | | TCA | 12 | 23 |
| | | TCG | 5 | 4 |
| | | TCC | 18 | 12 |
| | | TCT | 15 | 15 |
| Thr | T | ACA | 15 | 24 |
| | | ACG | 6 | 4 |
| | | ACC | 19 | 13 |
| | | ACT | 13 | 19 |
| Trp | W | TGG | 13 | 18 |
| Tyr | Y | TAC | 16 | 12 |
| | | TAT | 12 | 19 |
| Val | V | GTA | 7 | 13 |
| | | GTG | 29 | 20 |
| | | GTC | 15 | 12 |
| | | GTT | 11 | 15 |
| Term | | TAA | 1 | 2 |
| | | TAG | 0.5 | 0.4 |
| | | TGA | 1 | 1 |

In another form of minimal optimization, a Codon Usage Table (CUT) for the specific IV sequence in question is generated and compared to CUT for human genomic DNA (see Table 7, supra). Amino acids are identified for which there is a difference of at least 10 percentage points in codon usage between human and IV DNA (either more or less). Then the wild type IV codon is modified to conform to predominant human codon for each such amino acid. Furthermore, the remainder of codons for that amino acid are also modified such that they conform to the predominant human codon for each such amino acid.

A representative "minimally optimized" codon-optimized coding region encoding SEQ ID NO:2, minimally optimized according to codon usage in humans by this latter method, is presented herein as SEQ ID NO:25:

```
  1 ATGGCCTCAC AGGGCACCAA GCGGAGTTAT GAGCAGATGG AGACCGATGG CGAGAGACAG

 61 AACGCCACAG AGATCAGAGC CTCAGTTGGC AAGATGATCG GCGGCATCGG CCGGTTCTAT

121 ATCCAGATGT GCACGGAGCT GAAGCTGAGC GACTACGAGG GCAGACTGAT TCAGAACTCT

181 CTGACCATCG AGAGAATGGT CCTGAGTGCC TTCGATGAGA GACGAAACAA GTATCTGGAG

241 GAGCATCCCT CCGCCGGCAA GGACCCCAAG AAGACGGGCG GCCCCATATA TAGAAGAGTT

301 AACGGCAAGT GGATGAGAGA GCTGATCCTG TACGATAAGG AGGAGATCCG CAGAATATGG

361 AGGCAGGCCA ACAACGGCGA CGATGCCACT GCCGGCCTGA CACATATGAT GATATGGCAC

421 AGTAACCTGA ACGACGCCAC CTACCAGAGA ACAAGGGCCC TGGTTCGCAC GGGCATGGAT

481 CCCAGAATGT GTTCACTGAT GCAGGGCTCT ACACTGCCCA GAAGGTCTGG CGCCGCCGGC

541 GCCGCCGTCA AGGGCGTTGG CACAATGGTG ATGGAGCTGG TGCGGATGAT CAAGAGAGGC
```

-continued

```
601 ATTAACGATC GGAACTTTTG GAGGGGCGAG AACGGCAGAA AGACCAGGAT AGCCTACGAG

661 CGAATGTGCA ACATTCTGAA GGGCAAGTTC CAGACTGCCG CCCAGAAGGC CATGATGGAT

721 CAGGTGCGGG AGAGCAGAAA CCCCGGCAAC GCCGAGTTCG AGGACCTGAC TTTCCTGGCC

781 AGATCTGCCC TGATACTGAG GGGCTCTGTA GCCCACAAGT CCTGCCTGCC CGCCTGCGTG

841 TACGGCCCCG CCGTGGCCTC CGGCTATGAC TTCGAGCGAG AGGGCTACTC CCTGGTAGGC

901 ATCGATCCCT TTAGACTGCT GCAGAACTCT CAGGTCTACA GTCTGATTAG ACCCAACGAG

961 AACCCCGCCC ATAAGAGCCA GCTGGTGTGG ATGGCCTGCC ACAGTGCCGC CTTCGAGGAC

1021 CTGAGGGTGC TGTCTTTTAT AAAGGGCACA AAGGTGCTGC CCCGCGGCAA GCTGTCTACT

1081 AGGGGCGTCC AGATAGCCTC CAACGAGAAC ATGGAGACAA TGGAGTCTAG TACTCTGGAG

1141 CTGAGGTCTA GGTACTGGGC CATCAGGACT AGGAGCGGCG GCAACACCAA CCAGCAGAGG

1201 GCCAGCGCCG GCCAGATCAG CATTCAGCCC ACCTTCAGTG TACAGAGAAA CCTGCCCTTT

1261 GATAGAACTA CTGTTATGGC CGCCTTCTCT GGCAACACTG AGGGCAGAAC TAGTGACATG

1321 CGAACAGAGA TCATAAGAAT GATGGAGTCG GCCCGTCCCG AGGATGTGTC CTTTCAGGGC

1381 AGGGGCGTCT TCGAGCTGAG CGACGAGAAG GCCGCCAGCC CCATCGTACC CTCTTTCGAT

1441 ATGAGTAACG AGGGCTCGTA CTTTTTTGGC GACAACGCCG AGGAGTATGA TAACTGA
```

In certain embodiments described herein, a codon-optimized coding region encoding SEQ ID NO:4 is optimized according to codon usage in humans (*Homo sapiens*). Alternatively, a codon-optimized coding region encoding SEQ ID NO:4 may be optimized according to codon usage in any plant, animal, or microbial species. Codon-optimized coding regions encoding SEQ ID NO:4, optimized according to codon usage in humans are designed as follows. The amino acid composition of SEQ ID NO:4 is shown in Table 8.

TABLE 8

| AMINO ACID | | Number in SEQ ID NO:4 |
|---|---|---|
| A | Ala | 25 |
| R | Arg | 17 |
| C | Cys | 3 |
| G | Gly | 16 |
| H | His | 5 |
| I | Ile | 11 |
| L | Leu | 26 |
| K | Lys | 13 |
| M | Met | 14 |
| F | Phe | 7 |
| P | Pro | 8 |
| S | Ser | 18 |
| T | Thr | 18 |
| W | Trp | 1 |
| Y | Tyr | 5 |
| V | Val | 16 |
| N | Asn | 11 |
| D | Asp | 6 |
| Q | Gln | 15 |
| E | Glu | 17 |

Using the amino acid composition shown in Table 8, a human codon-optimized coding region which encodes SEQ ID NO:4 can be designed by any of the methods discussed herein. For "uniform" optimization, each amino acid is assigned the most frequent codon used in the human genome for that amino acid. According to this method, codons are assigned to the coding region encoding SEQ ID NO:4 as follows: the 7 phenylalanine codons are TTC, the 26 leucine codons are CTG, the 11 isoleucine codons are ATC, the 14 methionine codons are ATG, the 16 valine codons are GTG, the 18 serine codons are AGC, the 8 proline codons are CCC, the 18 threonine codons are ACC, the 25 alanine codons are GCC, the 5 tyrosine codons are TAC, the 5 histidine codons are CAC, the 15 glutamine codons are CAG, the 11 asparagine codons are AAC, the 13 lysine codons are AAG, the 6 aspartic acid codons are GAC, the 17 glutamic acid codons are GAG, the 1 tryptophan codon is TGG, the 17 arginine codons are CGG, AGA, or AGG (the frequencies of usage of these three codons in the human genome are not significantly different), and the 16 glycine codons are GGC. The codon-optimized coding region designed by this method is presented herein as SEQ ID NO:27:

```
ATGAGCCTGCTGACCGAGGTGGAGACCTACGTGCTGAGCATCATCCCCAGC

GGCCCCCTGAAGGCCGAGATCGCCCAGAGGCTGGAGGACGTGTTCGCCGGC

AAGAACACCGACCTGGAGGTGCTGATGGAGTGGCTGAAGACCAGGCCCATC

CTGAGCCCCCTGACCAAGGGCATCCTGGGCTTCGTGTTCACCCTGACCGTG

CCCAGCGAGAGGGGCCTGCAGAGGAGGAGGTTCGTGCAGAACGCCCTGAAC

GGCAACGGCGACCCCAACAACATGGACAAGGCCGTGAAGCTGTACAGGAAG

CTGAAGAGGGAGATCACCTTCCACGGCGCCAAGGAGATCAGCCTGAGCTAC

AGCGCCGGCGCCCTGGCCAGCTGCATGGGCCTGATCTACAACAGGATGGGC

GCCGTGACCACCGAGGTGGCCTTCGGCCTGGTGTGCGCCACCTGCGAGCAG

ATCGCCGACAGCCAGCACAGGAGCCACAGGCAGATGGTGACCACCACCAAC

CCCCTGATCAGGCACGAGAACAGGATGGTGCTGGCCAGCACCACCGCCAAG

GCCATGGAGCAGATGGCCGGCAGCAGCGAGCAGGCCGCCGAGGCCATGGAG

GTGGCCAGCCAGGCCAGGCAGATGGTGCAGGCCATGAGGACCATCGGCACC

CACCCCAGCAGCAGCGCCGGCCTGAAGAACGACCTGCTGGAGAACCTGCAG

GCCTACCAGAAGAGGATGGGCGTGCAGATGCAGAGGTTCAAG
```

Alternatively, a human codon-optimized coding region which encodes SEQ ID NO:4 can be designed by the "full optimization" method, where each amino acid is assigned codons based on the frequency of usage in the human genome. These frequencies are shown in Table 8 above. Using this latter method, codons are assigned to the coding region encoding SEQ ID NO:4 as follows: about 3 of the 7 phenylalanine codons are TTT, and about 4 of the phenylalanine codons are TTC; about 2 of the 26 leucine codons are TTA, about 3 of the leucine codons are TTG, about 3 of the leucine codons are CTT, about 5 of the leucine codons are CTC, about 2 of the leucine codons are CTA, and about 11 of the leucine codons are CTG; about 4 of the 11 isoleucine codons are ATT, about 5 of the isoleucine codons are ATC, and about 2 of the isoleucine codons are ATA; the 14 methionine codons are ATG; about 3 of the 16 valine codons are GTT, about 4 of the valine codons are GTG, about 2 of the valine codons are GTA, and about 8 of the valine codons are GTG; about 3 of the 18 serine codons are TCT, about 4 of the serine codons are TCC, about 3 of the serine codons are TCA, about 1 of the serine codons is TCG, about 3 of the serine codons are AGT, and about 4 of the serine codons are AGC; about 2 of the 8 proline codons are CCT, about 3 of the proline codons are CCC, about 2 of the proline codons are CCA, and about 1 of the proline codons is CCG; about 4 of the 18 threonine codons are ACT, about 7 of the threonine codons are ACC, about 5 of the threonine codons are ACA, and about 2 of the threonine codons are ACG; about 7 of the alanine codons are GCT, about 10 of the alanine codons are GCC, about 6 of the alanine codons are GCA, and about 3 of the alanine codons are GCG; about 2 of the 5 tyrosine codons are TAT and about 3 of the tyrosine codons are TAC; about 2 of the 5 histidine codons are CAT and about 3 of the histidine codons are CAC; about 4 of the 15 glutamine codons are CAA and about 11 of the glutamine codons are CAG; about 5 of the 11 asparagine codons are AAT and about 6 of the asparagine codons are AAC; about 5 of the 13 lysine codons are AAA and about 8 of the lysine codons are AAG; about 3 of the 6 aspartic acid codons are GAT and about 3 of the aspartic acid codons are GAC; about 7 of the 17 glutamic acid codons are GAA and about 10 of the glutamic acid codons are GAG; about 1 of the 3 cysteine codons is TGT and about 2 of the cysteine codons are TGC; the 1 tryptophan codons is TGG; about 1 of the 17 arginine codons are CGT, about 3 of the arginine codons are CGC, about 2 of the arginine codons are CGA, about 4 of the arginine codons are CGG, about 3 of the arginine codons are AGA, and about 3 of the arginine codons are AGG; and about 3 of the 16 glycine codons are GGT, about 6 of the glycine codons are GGC, about 4 of the glycine codons are GGA, and about 4 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:4, optimized according to codon usage in humans is presented herein as SEQ ID NO:26:

```
ATGAGCTTGCTAACAGAAGTGGAAACCTATGTCCTCAGTATCATTCCTAGC
GGCCCCTTAAAAGCCGAAATCGCTCAGCGGCTCGAGGATGTTTTTGCCGGC
AAGAACACCGACCTGGAGGTATTGATGGAGTGGCTGAAAACGCGACCTATT
CTGAGCCCCCTGACTAAGGGAATACTCGGCTTCGTTTTTACATTGACCGTG
```

-continued

```
CCCTCAGAGAGGGGTCTCCAAAGGAGGCGCTTCGTGCAGAACGCCTTAAAC
GGGAACGGGGACCCAAATAATATGGATAAGGCAGTGAAACTGTATCGCAAA
TTAAAGCGGGAGATAACCTTCCATGGAGCCAAGGAGATCTCCCTGTCTTAC
TCTGCAGGTGCTCTCGCGTCGTGTATGGGACTTATCTACAACCGAATGGGC
GCCGTCACAACAGAAGTGGCTTTCGGGCTGGTGTGCGCAACTTGCGAACAG
ATTGCTGACAGTCAGCACCGGTCCCACCGTCAAATGGTCACCACCACCAAT
CCGCTGATTAGACATGAAAATCGCATGGTTCTAGCATCAACTACAGCCAAA
GCAATGGAACAAATGGCCGGAAGCTCCGAGCAGGCTGCCGAGGCGATGGAG
GTGGCGTCCCAGGCCAGACAGATGGTACAGGCTATGAGAACTATCGGTACG
CACCCAAGTTCTTCAGCTGGGCTGAAGAATGATCTTCTTGAGAACCTGCAG
GCCTACCAAAAGCGGATGGGCGTCCAGATGCAGAGATTTAAA
```

Additionally, a minimally codon-optimized nucleotide sequence encoding SEQ ID NO:4 can be designed by changing only certain codons found more frequently in IV genes than in human genes, as shown in Table 7. For example, if it is desired to substitute more frequently used codons in humans for those codons that occur at least 2 times more frequently in IV genes (designated with an asterisk in Table 7), Arg AGA, which occurs 2.3 times more frequently in IV genes than in human genes, is changed to, e.g., CGG; Asn AAT, which occurs 2.0 times more frequently in IV genes than in human genes, is changed to, e.g., AAC; Ile ATA, which occurs 3.6 times more frequently in IV genes than in human genes, is changed to, e.g., ATC; and Leu CTA, which occurs 2.0 times more frequently in IV genes than in 4s human, is changed to, e.g., CTG.

In another form of minimal optimization, a Codon Usage Table (CUT) for the specific IV sequence in question is generated and compared to CUT for human genomic DNA (see Table 7, supra). Amino acids are identified for which there is a difference of at least 10 percentage points in codon usage between human and IV DNA (either more or less). Then the wild type IV codon is modified to conform to predominant human codon for each such amino acid. Furthermore, the remainder of codons for that amino acid are also modified such that they conform to the predominant human codon for each such amino acid.

A representative "minimally optimized" codon-optimized coding region encoding SEQ ID NO:4, minimally optimized according to codon usage in humans by this latter method, is presented herein as SEQ ID NO:28:

```
ATGAGTCTGCTGACAGAGGTTGAGACGTACGTGCTGTCCATCATTCCCTCA
GGCCCCCTGAAGGCCGAGATTGCCCAGAGACTGGAGGACGTCTTCGCCGGC
AAGAACACCGATCTGGAGGTGCTGATGGAGTGGCTGAAGACTCGCCCCATC
CTGTCTCCCCTGACAAAGGGCATCCTGGGCTTCGTATTTACACTGACCGTC
CCCTCCGAGAGAGGCCTGCAGCGGAGGAGGTTCGTTCAGAACGCCCTGAAC
GGCAACGGCGATCCCAACAACATGGATAAGGCCGTGAAGCTGTATAGAAAG
CTGAAGCGAGAGATCACATTTCATGGCGCCAAGGAGATATCGCTGAGCTAC
AGTGCCGGCGCCCTGGCCTCTTGCATGGGCCTGATATACAACAGAATGGGC
GCCGTTACTACAGAGGTAGCCTTTGGCCTGGTCTGCGCCACTTGCGAGCAG
ATCGCCGACTCTCAGCATAGATCTCACAGACAGATGGTGACGACTACAAAC
```

-continued

CCCCTGATACGGCACGAGAACAGGATGGTGCTGGCCTCTACTACCGCCAAG

GCCATGGAGCAGATGGCCGGCAGCAGTGAGCAGGCCGCCGAGGCCATGGAG

GTAGCCTCACAGGCCAGGCAGATGGTGCAGGCCATGCGAACCATCGGCACT

-continued

CACCCCTCCAGCTCTGCCGGCCTGAAGAACGACCTGCTGGAGAACCTGCAG

GCCTATCAGAAGAGAATGGGCGTACAGATGCAGAGGTTCAAG

In certain embodiments described herein, a codon-optimized coding region encoding SEQ ID NO:5 is optimized according to codon usage in humans (*Homo sapiens*). Alternatively, a codon-optimized coding region encoding SEQ ID NO:5 may be optimized according to codon usage in any plant, animal, or microbial species. Codon-optimized coding regions encoding SEQ ID NO:5, optimized according to codon usage in humans are designed as follows. The amino acid composition of SEQ ID NO:5 is shown in Table 9.

TABLE 9

| AMINO ACID | | Number in SEQ ID NO:5 |
|---|---|---|
| A | Ala | 5 |
| R | Arg | 7 |
| C | Cys | 3 |
| G | Gly | 8 |
| H | His | 2 |
| I | Ile | 8 |
| L | Leu | 10 |
| K | Lys | 5 |
| M | Met | 2 |
| F | Phe | 4 |
| P | Pro | 4 |
| S | Ser | 7 |
| T | Thr | 4 |
| W | Trp | 2 |
| Y | Tyr | 3 |
| V | Val | 4 |
| N | Asn | 3 |
| D | Asp | 5 |
| Q | Gln | 2 |
| E | Glu | 9 |

Using the amino acid composition shown in Table 9, a human codon-optimized coding region which encodes SEQ ID NO:5 can be designed by any of the methods discussed herein. For "uniform" optimization, each amino acid is assigned the most frequent codon used in the human genome for that amino acid. According to this method, codons are assigned to the coding region encoding SEQ ID NO:5 as follows: the 4 phenylalanine codons are TTC, the leucine codons are CTG, the 8 isoleucine codons are ATC, the 2 methionine codons are ATG, the 4 valine codons are GTG, the 7 serine codons are AGC, the 4 proline codons are CCC, the 4 threonine codons are ACC, the 5 alanine codons are GCC, the 3 tyrosine codons are TAC, the 2 histidine codons are CAC, the 2 glutamine codons are CAG, the 3 asparagine codons are AAC, the 5 lysine codons are AAG, the 5 aspartic acid codons are GAC, the 9 glutamic acid codons are GAG, the 2 tryptophan codons are TGG, the 7 arginine codons are CGG, AGA, or AGG (the frequencies of usage of these three codons in the human genome are not significantly different), and the 8 glycine codons are GGC. The codon-optimized PA coding region designed by this method is presented herein as SEQ ID NO:30:

```
  1 ATGAGCCTGC TGACCGAGGT GGAGACCCCC ATCCGGAACG AGTGGGGCTG CCGGTGCAAC
 61 GGCAGCAGCG ACCCCCTGGC CATCGCCGCC AACATCATCG GCATCCTGCA CCTGACCCTG
121 TGGATCCTGG ACCGGCTGTT CTTCAAGTGC ATCTACCGGC GGTTCAAGTA CGGCCTGAAG
181 GGCGGCCCCA GCACCGAGGG CGTGCCCAAG AGCATGCGGG AGGAGTACCG GAAGGAGCAG
241 CAGAGCGCCG TGGACGCCGA CGACGGCCAC TTCGTGAGCA TCGAGCTGGA GTGA
```

Alternatively, a human codon-optimized coding region which encodes SEQ ID NO:5 can be designed by the "full optimization" method, where each amino acid is assigned codons based on the frequency of usage in the human genome. These frequencies are shown in Table 9 above. Using this latter method, codons are assigned to the coding region encoding SEQ ID NO:5 as follows: about 2 of the 4 phenylalanine codons are TTT, and about 2 of the phenylalanine codons are TTC; about 1 of the 10 leucine codons are TTA, about 1 of the leucine codons are TTG, about 1 of the leucine codons are CTT, about 2 of the leucine codons are CTC, about 1 of the leucine codons are CTA, and about 4 of the leucine codons are CTG; about 3 of the 8 isoleucine codons are ATT, about 4 of the isoleucine codons are ATC, and about 1 of the isoleucine codons are ATA; the 2 methionine codons are ATG; about 1 of the 4 valine codons are GTT, about 1 of the valine codons are GTG, about 0 of the valine codons are GTA, and about 2 of the valine codons are GTG; about 1 of the 7 serine codons are TCT, about 2 of the serine codons are TCC, about 1 of the serine codons are TCA, about 0 of the serine codons are TCG, about 1 of the serine codons are AGT, and about 2 of the serine codons are AGC; about 1 of the 4 proline codons are CCT, about 1 of the proline codons are CCC, about 2 of the proline codons are CCA, and about 0 of the proline codons are CCG; about 1 of the 4 threonine codons are ACT, about 1 of the threonine codons are ACC, about 1 of the threonine codons are ACA, and about 0 of the threonine codons are ACG; about 1 of the 5 alanine codons are GGT, about 2 of the alanine codons are GCC, about 1 of the alanine codons are GCA, and about 1 of the alanine codons are GCG; about 1 of the 3 tyrosine codons are TAT and about 2 of the tyrosine codons are TAC; about 1 of the 2 histidine codons are CAT and about 1 of the histidine codons are CAC; about 1 of the 2 glutamine codons are CAA and about 1 of the glutamine codons are CAG; about 1 of the 3 asparagine codons are AAT and about 2 of the asparagine codons are AAC; about 2 of the 5 lysine codons are AAA and about 3 of the lysine codons are AAG; about 2 of the 5 aspartic acid codons are GAT and about 3 of the aspartic acid codons are GAC; about 4 of the 9 glutamic acid codons are GAA and about 5 of the glutamic acid codons are GAG; about 1 of the 3 cysteine codons are TGT and about 2 of the cysteine codons are TGC; the 2 tryptophan codons are TGG; about 1 of the 7 arginine codons are CGT, about 1 of the arginine codons are CGC, about 1 of the arginine codons are CGA, about 1 of the arginine codons are CGG, about 1 of the arginine codons are AGA, and about 1 of the arginine codons are AGG; and about 1 of the 8 glycine codons are GGT, about 3 of the glycine codons are GGC, about 2 of the glycine codons are GGA, and about 2 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:5, optimized according to codon usage in humans is presented herein as SEQ ID NO:29:

```
  1 ATGAGTCTTC TAACCGAGGT CGAAACGCCT ATCAGAAACG AATGGGGGTG CAGATGCAAC

 61 GGTTCAAGTG ATCCTCTCGC TATTGCCGCA AATATCATTG GGATCTTGCA CTTGACATTG

121 TGGATTCTTG ATCGTCTTTT TTTCAAATGC ATTTACCGTC GCTTTAAATA CGGACTGAAA

181 GGAGGGCCTT CTACGGAAGG AGTGCCAAAG TCTATGAGGG AAGAATATCG AAAGGAACAG

241 CAGAGTGCTG TGGATGCTGA CGATGGTCAT TTTGTCAGCA TAGAGCTGGA GTAA
```

Additionally, a minimally codon-optimized nucleotide sequence encoding SEQ ID NO:5 can be designed by changing only certain codons found more frequently in IV genes than in human genes, as shown in Table 7. For example, if it is desired to substitute more frequently used codons in humans for those codons that occur at least 2 times more frequently in IV genes (designated with an asterisk in Table 7), Arg AGA, which occurs 2.3 times more frequently in IV genes than in human genes, is changed to, e.g., CGG; Asn AAT, which occurs 2.0 times more frequently in IV genes than in human genes, is changed to, e.g., AAC; Ile ATA, which occurs 3.6 times more frequently in IV genes than in human genes, is changed to, e.g., ATC; and Leu CTA, which occurs 2.0 times more frequently in IV genes than in human, is changed to, e.g., CTG.

In another form of minimal optimization, a Codon Usage Table (CUT) for the specific IV sequence in question is generated and compared to CUT for human genomic DNA (see Table 7, supra). Amino acids are identified for which there is a difference of at least 10 percentage points in codon usage between human and IV DNA (either more or less). Then the wild type IV codon is modified to conform to predominant human codon for each such amino acid. Furthermore, the remainder of codons for that amino acid are also modified such that they conform to the predominant human codon for each such amino acid.

A representative "minimally optimized" codon-optimized coding region encoding SEQ ID NO:5, minimally optimized according to codon usage in humans by this latter method, is presented herein as SEQ ID NO:31:

```
  1 ATGTCTCTGC TGACAGAGGT GGAGACACCC ATAAGGAACG AGTGGGGCTG CAGGTGCAAC

 61 GGCTCTAGTG ATCCCCTGGC CATCGCCGCC AACATCATTG GCATACTGCA TCTGACCCTG

121 TGGATCCTGG ATAGACTGTT CTTTAAGTGC ATTTACAGAC GATTTAAGTA TGGCCTGAAG

181 GGCGGCCCCT CAACTGAGGG CGTGCCCAAG AGTATGAGAG AGGAGTACCG GAAGGAGCAG

241 CAGAGCGCCG TTGACGCCGA TGACGGCCAC TTCGTCTCCA TCGAGCTGGA GTGA
```

In certain embodiments described herein, a codon-optimized coding region encoding SEQ ID NO:7 is optimized according to codon usage in humans (*Homo sapiens*). Alternatively, a codon-optimized coding region encoding SEQ ID NO:7 may be optimized according to codon usage in any plant, animal, or microbial species. Codon-optimized coding regions encoding SEQ ID NO:7, optimized according to codon usage in humans are designed as follows. The amino acid composition of SEQ ID NO:7 is shown in Table 10.

TABLE 10

| AMINO ACID | | Number in SEQ ID NO:7 |
|---|---|---|
| A | Ala | 39 |
| R | Arg | 51 |
| C | Cys | 8 |
| G | Gly | 43 |
| H | His | 6 |
| I | Ile | 27 |
| L | Leu | 35 |
| K | Lys | 21 |
| M | Met | 26 |
| F | Phe | 18 |
| P | Pro | 18 |
| S | Ser | 43 |
| T | Thr | 30 |
| W | Trp | 7 |
| Y | Tyr | 15 |
| V | Val | 24 |
| N | Asn | 28 |
| D | Asp | 23 |
| Q | Gln | 21 |
| E | Glu | 39 |

Using the amino acid composition shown in Table 10, a human codon-optimized coding region which encodes SEQ ID NO:7 can be designed by any of the methods discussed herein. For "uniform" optimization, each amino acid is assigned the most frequent codon used in the human genome for that amino acid. According to this method, codons are assigned to the coding region encoding SEQ ID NO:7 as follows: the 18 phenylalanine codons are TTC, the leucine codons are CTG, the 27 isoleucine codons are ATC, the 26 methionine codons are ATG, the 24 valine codons are GTG, the 43 serine codons are AGC, the 18 proline codons are CCC, the 30 threonine codons are ACC, the 39 alanine codons are GCC, the 15 tyrosine codons are TAC, the 6 histidine codons are CAC, the 21 glutamine codons are CAG, the 28 asparagine codons are AAC, the 21 lysine codons are AAG, the 23 aspartic acid codons are GAC, the 39 glutamic acid codons are GAG, the 7 tryptophan codons are TGG, the 51 arginine codons are CGG, AGA, or AGG (the frequencies of usage of these three codons in the human genome are not significantly different), and the 43 glycine codons are GGC. The codon-optimized PA coding region designed by this method is presented herein as SEQ ID NO:33:

```
ATGAGCCTGCTGACCGAGGTGGAGACCCCCATCAGGAACGAGTGGGGCTGC
AGGTGCAACGGCAGCAGCGACATGGCCAGCCAGGGCACCAAGAGGAGCTAC
GAGCAGATGGAGACCGACGGCGAGAGGCAGAACGCCACCGAGATCAGGGCC
AGCGTGGGCAAGATGATCGGCGGCATCGGCAGGTTCTACATCCAGATGTGC
ACCGAGCTGAAGCTGAGCGACTACGAGGGCAGGCTGATCCAGAACAGCCTG
ACCATCGAGAGGATGGTGCTGAGCGCCTTCGACGAGAGGAGGAACAAGTAC
CTGGAGGAGCACCCCAGCGCCGGCAAGGACCCCAAGAAGACCGGCGGCCCC
ATCTACAGGAGGGTGAACGGCAAGTGGATGAGGGAGCTGATCCTGTACGAC
AAGGAGGAGATCAGGAGGATCTGGAGGCAGGCCAACAACGGCGACGACGCC
ACCGCCGGCCTGACCCACATGATGATCTGGCACAGCAACCTGAACGACGCC
ACCTACCAGAGGACCAGGGCCCTGGTGAGGACCGGCATGGACCCCAGGATG
TGCAGCCTGATGCAGGGCAGCACCCTGCCCAGGAGGAGCGGCGCCGCCGGC
GCCGCCGTGAAGGGCGTGGGCACCATGGTGATGGAGCTGGTGAGGATGATC
AAGAGGGGCATCAACGACAGGAACTTCTGGAGGGGCGAGAACGGCAGGAAG
ACCAGGATCGCCTACGAGAGGATGTGCAACATCCTGAAGGGCAAGTTCCAG
ACCGCCGCCCAGAAGGCCATGATGGACCAGGTGAGGGAGAGCAGGAACCCC
GGCAACGCCGAGTTCGAGGACCTGACCTTCCTGGCCAGGAGCGCCCTGATC
CTGAGGGGCAGCGTGGCCCACAAGAGCTGCCTGCCCGCCTGCGTGTACGGC
CCCGCCGTGGCCAGCGGCTACGACTTCGAGAGGGAGGGCTACAGCCTGGTG
GGCATCGACCCCTTCAGGCTGCTGCAGAACAGCCAGGTGTACAGCCTGATC
AGGCCCAACGAGAACCCCGCCCACAAGAGCCAGCTGGTGTGGATGGCCTGC
CACAGCGCCGCCTTCGAGGACCTGAGGGTGCTGAGCTTCATCAAGGGCACC
AAGGTGCTGCCCAGGGGCAAGCTGAGCACCAGGGGCGTGCAGATCGCCAGC
AACGAGAACATGGAGACCATGGAGAGCAGCACCCTGGAGCTGAGGAGCAGG
TACTGGGCCATCAGGACCAGGAGCGGCGGCAACACCAACCAGCAGAGGGCC
AGCGCCGGCCAGATCAGCATCCAGCCCACCTTCAGCGTGCAGAGGAACCTG
CCCTTCGACAGGACCACCGTGATGGCCGCCTTCAGCGGCAACACCGAGGGC
AGGACCAGCGACATGAGGACCGAGATCATCAGGATGATGGAGAGCGCCAGG
CCCGAGGACGTGAGCTTCCAGGGCAGGGGCGTGTTCGAGCTGAGCGACGAG
AAGGCCGCCAGCCCCATCGTGCCCAGCTTCGACATGAGCAACGAGGGCAGC
TACTTCTTCGGCGACAACGCCGAGGAGTACGACAAC
```

Alternatively, a human codon-optimized coding region which encodes SEQ ID NO:7 can be designed by the "full optimization" method, where each amino acid is assigned codons based on the frequency of usage in the human genome. These frequencies are shown in Table 10 above. Using this latter method, codons are assigned to the coding region encoding SEQ ID NO:7 as follows: about 8 of the 18 phenylalanine codons are TTT, and about 10 of the phenylalanine codons are TTC; about 3 of the 35 leucine codons are TTA, about 4 of the leucine codons are TTG, about 5 of the leucine codons are CTT, about 7 of the leucine codons are CTC, about 2 of the leucine codons are CTA, and about 14 of the leucine codons are CTG; about 10 of the 27 isoleucine codons are ATT, about 13 of the isoleucine codons are ATC, and about 4 of the isoleucine codons are ATA; the 26 methionine codons are ATG; about 4 of the 24 valine codons are GTT, about 6 of the valine codons are GTG, about 3 of the valine codons are GTA, and about 11 of the valine codons are GTG; about 8 of the 43 serine codons are TCT, about 9 of the serine codons are TCC, about 6 of the serine codons are TCA, about 2 of the serine codons are TCG, about 6 of the serine codons are AGT, and about 10 of the serine codons are AGC; about 5 of the 18 proline codons are CCT, about 6 of the proline codons are CCC, about 5 of the proline codons are CCA, and about 2 of the proline codons are CCG; about 7 of the 30 threonine codons are ACT, about 11 of the threonine codons are ACC, about 8 of the threonine codons are ACA, and about 4 of the threonine codons are ACG; about 10 of the 39 alanine codons are GCT, about 16 of the alanine codons are GCC, about 9 of the alanine codons are GCA, and about 4 of the alanine codons are GCG; about 7 of the 15 tyrosine codons are TAT and about 8 of the tyrosine codons are TAC; about 2 of the 6 histidine codons are CAT and about 4 of the histidine codons are CAC; about 5 of the 21 glutamine codons are CAA and about 16 of the glutamine codons are CAG; about 13 of the 28 asparagine codons are AAT and about 15 of the asparagine codons are AAC; about 9 of the 21 lysine codons are AAA and about 12 of the lysine codons are AAG; about 11 of the 23 aspartic acid codons are GAT and about 12 of the aspartic acid codons are GAC; about 16 of the 39 glutamic acid codons are GAA and about 23 of the glutamic acid codons are GAG; about 4 of the 8 cysteine codons are TGT and about 4 of the cysteine codons are TGC; the 7 tryptophan codons are TGG; about 4 of the 51 arginine codons are CGT, about 10 of the arginine codons are CGC, about 6 of the arginine codons are CGA, about 11 of the arginine codons are CGG, about 10 of the arginine codons are AGA, and about 10 of the arginine codons are AGG; and about 7 of the 43 glycine codons are GGT, about 15 of the glycine codons are GGC, about 11 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:7, optimized according to codon usage in humans is presented herein as SEQ ID NO:32:

```
ATGAGCCTTCTCACAGAAGTGGAAACACCTATCAGAAATGAATGGGGATGC
AGATGCAATGGGTCGAGTGATATGGCCTCTCAAGGTACGAAAAGAAGCTAC
GAGCAAATGGAAACGGATGGAGAAAGACAAAACGCGACCGAAATCAGAGCA
TCCGTCGGGAAGATGATTGGAGGAATCGGACGATTCTACATCCAGATGTGC
ACAGAGCTAAAGCTATCGGATTATGAAGGGAGACTAATACAAAATAGCCTA
ACTATCGAGAGAATGGTGCTGTCTGCATTTGACGAAAGGAGAAACAAATAC
```

-continued

```
CTGGAAGAACACCCCTCTGCAGGGAAAGACCCAAAAAAAACTGGAGGTCCG

ATATACCGGAGAGTCAACGGTAAATGGATGAGAGAGCTGATCTTGTATGAT

AAGGAAGAAATAAGACGCATCTGGCGGCAAGCTAATAATGGAGACGACGCT

ACTGCAGGGCTCACGCATATGATGATCTGGCACTCTAATTTGAATGATGCA

ACGTACCAAAGAACCCGCGCACTTGTGCGGACCGGAATGGACCCTCGTATG

TGCAGCCTTATGCAGGGGTCCACACTGCCCAGAAGGTCCGGAGCAGCTGGA

GCAGCAGTAAAGGGGGTTGGAACCATGGTGATGGAGCTGGTGAGAATGATT

AAGAGGGGGATCAATGACAGGAACTTCTGGCGAGGAGAAAACGGGAGAAAA

ACTAGGATAGCATATGAGAGGATGTGTAACATCCTCAAAGGAAAATTCCAA

ACCGCTGCTCAGAAAGCAATGATGGATCAAGTACGCGAAAGTAGAAATCCT

GGAAATGCAGAGTTTGAAGATCTCACTTTCCTCGCGCGAAGCGCTCTCATC

CTCAGAGGGAGTGTCGCTCATAAAAGTTGCCTGCCTGCCTGCGTATATGGT

CCTGCCGTGGCAAGTGGATACGACTTTGAGAGAGAGGGGTACTCTCTTGTT

GGAATAGATCCATTCAGATTACTTCAGAATTCCCAGGTGTACAGTTTAATA

AGGCCAAACGAAAATCCTGCACACAAATCACAACTTGTTTGGATGGCATGC

CATAGTGCCGCATTCGAAGATCTAAGAGTTCTCTCTTTCATCAAAGGTACA

AAGGTCCTTCCAAGGGGAAAACTCTCTACCAGAGGGGTACAAATAGCTTCA

AATGAGAACATGGAGACAATGGAATCTAGCACATTGGAATTGAGAAGTAGG

TATTGGGCCATTAGAACCAGGAGTGGAGGCAATACTAATCAACAGCGGGCT

TCTGCCGGTCAAATTAGCATACAACCTACTTTTTCAGTGCAACGGAATCTC

CCTTTTGATAGGACAACTGTCATGGCGGCATTCTCTGGAAATACCGAAGGA

AGGACTTCCGATATGAGGACTGAGATCATTAGGATGATGGAAAGTGCCCGA

CCTGAAGACGTCAGTTTTCAAGGAAGAGGTGTGTTCGAACTCTCTGACGAA

AAGGCAGCTAGCCCAATCGTTCCTTCTTTTGATATGTCAAATGAAGGATCC

TACTTCTTCGGCGATAATGCGGAGGAATATGACAAC
```

In certain embodiments described herein, a codon-optimized coding region encoding SEQ ID NO:9 is optimized according to codon usage in humans (*Homo sapiens*). Alternatively, a codon-optimized coding region encoding SEQ ID NO:9 may be optimized according to codon usage in any plant, animal, or microbial species. Codon-optimized coding regions encoding SEQ ID NO:9, optimized according to codon usage in humans are designed as follows. The amino acid composition of SEQ ID NO:9 is shown in Table 11.

TABLE 11

| AMINO ACID | | Number in SEQ ID NO:9 |
|---|---|---|
| A | Ala | 39 |
| R | Arg | 51 |
| C | Cys | 8 |
| G | Gly | 43 |
| H | His | 6 |
| I | Ile | 27 |
| L | Leu | 35 |
| K | Lys | 21 |
| M | Met | 26 |
| F | Phe | 18 |
| P | Pro | 18 |
| S | Ser | 43 |
| T | Thr | 30 |
| W | Trp | 7 |
| Y | Tyr | 15 |
| V | Val | 24 |
| N | Asn | 28 |
| D | Asp | 23 |
| Q | Gln | 21 |
| E | Glu | 39 |

Using the amino acid composition shown in Table 11, a human codon-optimized coding region which encodes SEQ ID NO:9 can be designed by any of the methods discussed herein. For "uniform" optimization, each amino acid is assigned the most frequent codon used in the human genome for that amino acid. According to this method, codons are assigned to the coding region encoding SEQ ID NO:9 as follows: the 18 phenylalanine codons are TTC, the leucine codons are CTG, the 27 isoleucine codons are ATC, the 26 methionine codons are ATG, the 24 valine codons are GTG, the 43 serine codons are AGC, the 18 proline codons are CCC, the 30 threonine codons are ACC, the 39 alanine codons are GCC, the 15 tyrosine codons are TAC, the 6 histidine codons are CAC, the 21 glutamine codons are CAG, the 28 asparagine codons are AAC, the 21 lysine codons are AAG, the 23 aspartic acid codons are GAC, the 39 glutamic acid codons are GAG, the 7 tryptophan codons are TGG, the 51 arginine codons are CGG, AGA, or AGG (the frequencies of usage of these three codons in the human genome are not significantly different), and the 43 glycine codons are GGC. The codon-optimized PA coding region designed by this method is presented herein as SEQ ID NO:35:

```
ATGGCCAGCCAGGGCACCAAGAGGAGCTACGAGCAGATGGAGACCGACGGC

GAGAGGCAGAACGCCACCGAGATCAGGGCCAGCGTGGGCAAGATGATCGGC

GGCATCGGCAGGTTCTACATCCAGATGTGCACCGAGCTGAAGCTGAGCGAC

TACGAGGGCAGGCTGATCCAGAACAGCCTGACCATCGAGAGGATGGTGCTG

AGCGCCTTCGACGAGAGGAGGAACAAGTACCTGGAGGAGCACCCCAGCGCC

GGCAAGGACCCCAAGAAGACCGGCGGCCCCATCTACAGGAGGGTGAACGGC

AAGTGGATGAGGGAGCTGATCCTGTACGACAAGGAGGAGATCAGGAGGATC

TGGAGGCAGGCCAACAACGGCGACGACGCCACCGCCGGCCTGACCCACATG

ATGATCTGGCACAGCAACCTGAACGACGCCACCTACCAGAGGACCAGGGCC

CTGGTGAGGACCGGCATGGACCCCAGGATGTGCAGCCTGATGCAGGGCAGC

ACCCTGCCCAGGAGGAGCGGCGCCGCCGGCGCCGCCGTGAAGGGCGTGGGC

ACCATGGTGATGGAGCTGGTGAGGATGATCAAGAGGGGCATCAACGACAGG

AACTTCTGGAGGGGCGAGAACGGCAGGAAGACCAGGATCGCCTACGAGAGG

ATGTGCAACATCCTGAAGGGCAAGTTCCAGACCGCCGCCCAGAAGGCCATG

ATGGACCAGGTGAGGGAGAGCAGGAACCCCGGCAACGCCGAGTTCGAGGAC

CTGACCTTCCTGGCCAGGAGCGCCCTGATCCTGAGGGGCAGCGTGGCCCAC

AAGAGCTGCCTGCCCGCCTGCGTGTACGGCCCCGCCGTGGCCAGCGGCTAC

GACTTCGAGAGGGAGGGCTACAGCCTGGTGGGCATCGACCCCTTCAGGCTG

CTGCAGAACAGCCAGGTGTACAGCCTGATCAGGCCCAACGAGAACCCCGCC

CACAAGAGCCAGCTGGTGTGGATGGCCTGCCACAGCGCCGCCTTCGAGGAC
```

-continued
```
CTGAGGGTGCTGAGCTTCATCAAGGGCACCAAGGTGCTGCCCAGGGGCAAG

CTGAGCACCAGGGGCGTGCAGATCGCCAGCAACGAGAACATGGAGACCATG

GAGAGCAGCACCCTGGAGCTGAGGAGCAGGTACTGGGCCATCAGGACCAGG

AGCGGCGGCAACACCAACCAGCAGAGGGCCAGCGCCGGCCAGATCAGCATC

CAGCCCACCTTCAGCGTGCAGAGGAACCTGCCCTTCGACAGGACCACCGTG

ATGGCCGCCTTCAGCGGCAACACCGAGGGCAGGACCAGCGACATGAGGACC

GAGATCATCAGGATGATGGAGAGCGCCAGGCCCGAGGACGTGAGCTTCCAG

GGCAGGGGCGTGTTCGAGCTGAGCGACGAGAAGGCCGCCAGCCCCATCGTG

CCCAGCTTCGACATGAGCAACGAGGGCAGCTACTTCTTCGGCGACAACGCC

GAGGAGTACGACAACATGAGCCTGCTGACCGAGGTGGAGACCCCCATCAGG

AACGAGTGGGGCTGCAGGTGCAACGGCAGCAGCGAC
```

Alternatively, a human codon-optimized coding region which encodes SEQ ID NO:9 can be designed by the "full optimization" method, where each amino acid is assigned codons based on the frequency of usage in the human genome. These frequencies are shown in Table 11 above. Using this latter method, codons are assigned to the coding region encoding SEQ ID NO:9 as follows: about 8 of the 18 phenylalanine codons are TTT, and about 10 of the phenylalanine codons are TTC; about 3 of the 35 leucine codons are TTA, about 4 of the leucine codons are TTG, about 5 of the leucine codons are CTT, about 7 of the leucine codons are CTC, about 2 of the leucine codons are CTA, and about 14 of the leucine codons are CTG; about 10 of the 27 isoleucine codons are ATT, about 13 of the isoleucine codons are ATC, and about 4 of the isoleucine codons are ATA; the 26 methionine codons are ATG; about 4 of the 24 valine codons are GTT, about 6 of the valine codons are GTG, about 3 of the valine codons are GTA, and about 11 of the valine codons are GTG; about 8 of the 43 serine codons are TCT, about 9 of the serine codons are TCC, about 6 of the serine codons are TCA, about 2 of the serine codons are TCG, about 6 of the serine codons are AGT, and about 10 of the serine codons are AGC; about 5 of the 18 proline codons are CCT, about 6 of the proline codons are CCC, about 5 of the proline codons are CCA, and about 2 of the proline codons are CCG; about 7 of the 30 threonine codons are ACT, about 11 of the threonine codons are ACC, about 8 of the threonine codons are ACA, and about 4 of the threonine codons are ACG; about 10 of the 39 alanine codons are GGT, about 16 of the alanine codons are GCC, about 9 of the alanine codons are GCA, and about 4 of the alanine codons are GCG; about 7 of the 15 tyrosine codons are TAT and about 8 of the tyrosine codons are TAC; about 2 of the 6 histidine codons are CAT and about 4 of the histidine codons are CAC; about 5 of the 21 glutamine codons are CAA and about 16 of the glutamine codons are CAG; about 13 of the 28 asparagine codons are AAT and about 15 of the asparagine codons are AAC; about 9 of the 21 lysine codons are AAA and about 12 of the lysine codons are AAG; about 11 of the 23 aspartic acid codons are GAT and about 12 of the aspartic acid codons are GAC; about 16 of the 39 glutamic acid codons are GAA and about 23 of the glutamic acid codons are GAG; about 4 of the 8 cysteine codons are TGT and about 4 of the cysteine codons are TGC; the 7 tryptophan codons are TGG; about 4 of the 51 arginine codons are CGT, about 10 of the arginine codons are CGC, about 6 of the arginine codons are CGA, about 11 of the arginine codons are CGG, about 10 of the arginine codons are AGA, and about 10 of the arginine codons are AGG; about 7 of the 43 glycine codons are GGT, about 15 of the glycine codons are GGC, about 11 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:9, optimized according to codon usage in humans is presented herein as SEQ ID NO:34:

```
ATGGCAAGCCAGGGCACAAAACGCAGTTACGAGCAGATGGAGACTGATGGT

GAGAGGCAGAACGCCACCGAAATCCGGGCCTCCGTCGGCAAGATGATTGGT

GGCATCGGAAGATTCTATATCCAGATGTGCACGGAGCTTAAGCTGTCCGAT

TACGAGGGGCGCTTAATACAGAACTCTCTGACTATCGAGCGAATGGTCTTG

AGCGCCTTTGATGAGCGGCGTAATAAGTATCTCGAAGAGCACCCTTCTGCT

GGAAAAGACCCCAAAAAGACCGGGGGACCTATCTACCGACGTGTGAACGGA

AAATGGATGCGCGAACTGATACTGTACGACAAGGAGGAGATCCGTAGGATC

TGGAGACAGGCTAATAACGGAGATGATGCCACAGCTGGGCTGACCCATATG

ATGATATGGCATAGCAACCTGAACGACGCAACCTATCAACGCACTAGAGCA

CTCGTGAGGACCGGTATGGACCCACGCATGTGCTCATTGATGCAAGGTAGC

ACATTGCCTCGGAGGTCAGGCGCCGCCGGTGCCGCCGTAAAGGGGGTGGGC

ACAATGGTGATGGAACTGGTCCGAATGATCAAAAGAGGCATCAATGACAGG

AACTTTTGGCGCGGAGAAAACGGGCGCAAGACCCGCATTGCCTACGAGCGC

ATGTGTAACATTTTAAAAGGCAAATTCCAGACTGCAGCCCAGAAAGCAATG

ATGGACCAAGTTAGAGAAAGTAGAAATCCCGGGAATGCCGAGTTTGAAGAC

CTGACTTTCCTGGCTAGAAGCGCCTTGATCCTGCGGGGCTCTGTCGCCCAC

AAGAGCTGCCTCCCCGCTTGCGTTTACGGCCCCGCGGTCGCAAGTGGCTAC

GATTTCGAGAGGGAGGGGTATTCCCTAGTTGGGATCGATCCCTTCCGGCTC

CTACAGAATTCTCAGGTGTATAGTCTGATTAGACCCAACGAAAACCCGGCT

CACAAGAGTCAGCTTGTTTGGATGGCATGTCACTCAGCAGCTTTCGAAGAC

CTGCGGGTACTCAGCTTTATTAAAGGCACCAAGGTCCTGCCAAGAGGAAAG

CTCTCCACGAGGGGAGTACAGATCGCCTCAAACGAGAACATGGAGACAATG

GAAAGCTCCACCCTTGAGCTTAGGTCGCGGTATTGGGCTATTAGAACACGA

TCTGGGGGGAATACCAATCAGCAACGAGCGAGTGCTGGTCAGATTTCCATT

CAGCCTACTTTCTCTGTGCAACGGAATCTACCATTTGACAGGACAACTGTG

ATGGCAGCGTTCTCCGGCAATACAGAAGGACGAACATCAGACATGAGGACC

GAAATTATCCGGATGATGGAGAGCGCTCGGCCAGAAGATGTGTCGTTCCAG

GGCCGGGGCGTGTTTGAGCTCAGCGACGAGAAGGCCGCGTCTCCAATTGTG

CCTTCCTTTGATATGAGCAATGAGGGGTCATACTTTTTCGGAGACAATGCC

GAAGAGTATGATAATATGTCTCTGCTTACCGAGGTGGAAACGCCGATACGC

AACGAATGGGGTTGTCGTTGTAACGGCTCCAGTGAT
```

In certain embodiments described herein, a codon-optimized coding region encoding SEQ ID NO:16 is optimized according to codon usage in humans (*Homo sapiens*). Alternatively, a codon-optimized coding region encoding SEQ ID NO:16 may be optimized according to codon usage in any plant, animal, or microbial species. Codon-optimized coding regions encoding SEQ ID NO:16, optimized according to codon usage in humans are designed as follows. The amino acid composition of SEQ ID NO:16 is shown in Table 12.

TABLE 12

| AMINO ACID | | Number in SEQ ID NO:16 |
|---|---|---|
| A | Ala | 41 |
| R | Arg | 30 |
| C | Cys | 5 |
| G | Gly | 44 |
| H | His | 4 |
| I | He | 38 |
| L | Leu | 39 |
| K | Lys | 52 |
| M | Met | 27 |
| F | Phe | 21 |
| P | Pro | 26 |
| S | Ser | 40 |
| T | Thr | 38 |
| W | Trp | 1 |
| Y | Tyr | 14 |
| V | Val | 32 |
| N | Asn | 25 |
| D | Asp | 34 |
| Q | Gln | 19 |
| E | Glu | 30 |

Using the amino acid composition shown in Table 12, a human codon-optimized coding region which encodes SEQ ID NO:16 can be designed by any of the methods discussed herein. For "uniform" optimization, each amino acid is assigned the most frequent codon used in the human genome for that amino acid. According to this method, codons are assigned to the coding region encoding SEQ ID NO:16 as follows: the 21 phenylalanine codons are TTC, the 39 leucine codons are CTG, the 38 isoleucine codons are ATC, the 27 methionine codons are ATG, the 32 valine codons are GTG, the 40 serine codons are AGC, the 26 proline codons are CCC, the 38 threonine codons are ACC, the 41 alanine codons are GCC, the 14 tyrosine codons are TAC, the 4 histidine codons are CAC, the 19 glutamine codons are CAG, the 25 asparagine codons are AAC, the 52 lysine codons are AAG, the 34 aspartic acid codons are GAC, the 30 glutamic acid codons are GAG, the 1 tryptophan codon is TGG, the 30 arginine codons are CGG, AGA, or AGG (the frequencies of usage of these three codons in the human genome are not significantly different), and the 44 glycine codons are GGC. The codon-optimized PA coding region designed by this method is presented herein as SEQ ID NO:37:

```
ATGAGCAACATGGACATCGACAGCATCAACACCGGCACCATCGACAAGACC
CCCGAGGAGCTGACCCCCGGCACCAGCGGCGCCACCCGGCCCATCATCAAG
CCCGCCACCCTGGCCCCCCCCAGCAACAAGCGGACCCGGAACCCCAGCCCC
GAGCGGACCACCACCAGCAGCGAGACCGACATCGGCCGGAAGATCCAGAAG
AAGCAGACCCCCACCGAGATCAAGAAGAGCGTGTACAAGATGGTGGTGAAG
CTGGGCGAGTTCTACAACCAGATGATGGTGAAGGCCGGCCTGAACGACGAC
ATGGAGCGGAACCTGATCCAGAACGCCCAGGCCGTGGAGCGGATCCTGCTG
GCCGCCACCGACGACAAGAAGACCGAGTACCAGAAGAAGCGGAACGCCCGG
```

-continued

```
GACGTGAAGGAGGGCAAGGAGGAGATCGACCACAACAAGACCGGCGGCACC
TTCTACAAGATGGTGCGGGACGACAAGACCATCTACTTCAGCCCCATCAAG
ATCACCTTCCTGAAGGAGGAGGTGAAGACCATGTACAAGACCACCATGGGC
AGCGACGGCTTCAGCGGCCTGAACCACATCATGATCGGCCACAGCCAGATG
AACGACGTGTGCTTCCAGCGGAGCAAGGGCCTGAAGCGGGTGGGCCTGGAC
CCCAGCCTGATCAGCACCTTCGCCGGCAGCACCCTGCCCCGGCGGAGCGGC
ACCACCGGCGTGGCCATCAAGGGCGGCGGCACCCTGGTGGACGAGGCCATC
CGGTTCATCGGCCGGGCCATGGCCGACCGGGGCCTGCTGCGGGACATCAAG
GCCAAGACCGCCTACGAGAAGATCCTGCTGAACCTGAAGAACAAGTGCAGC
GCCCCCCAGCAGAAGGCCCTGGTGGACCAGGTGATCGGCAGCCGGAACCCC
GGCATCGCCGACATCGAGGACCTGACCCTGCTGGCCCGGAGCATGGTGGTG
GTGCGGCCCAGCGTGGCCAGCAAGGTGGTGCTGCCCATCAGCATCTACGCC
AAGATCCCCCAGCTGGGCTTCAACACCGAGGAGTACAGCATGGTGGGCTAC
GAGGCCATGGCCCTGTACAACATGGCCACCCCCGTGAGCATCCTGCGGATG
GGCGACGACGCCAAGGACAAGAGCCAGCTGTTCTTCATGAGCTGCTTCGGC
GCCGCCTACGAGGACCTGCGGGTGCTGAGCGCCCTGACCGGCACCGAGTTC
AAGCCCCGGAGCGCCCTGAAGTGCAAGGGCTTCCACGTGCCCGCCAAGGAG
CAGGTGGAGGGCATGGGCGCCGCCCTGATGAGCATCAAGCTGCAGTTCTGG
GCCCCCATGACCCGGAGCGGCGGCAACGAGGTGAGCGGCGAGGGCGGCAGC
GGCCAGATCAGCTGCAGCCCCGTGTTCGCCGTGGAGCGGCCCATCGCCCTG
AGCAAGCAGGCCGTGCGGCGGATGCTGAGCATGAACGTGGAGGGCCGGGAC
GCCGACGTGAAGGGCAACCTGCTGAAGATGATGAACGACAGCATGGCCAAG
AAGACCAGCGGCAACGCCTTCATCGGCAAGAAGATGTTCCAGATCAGCGAC
AAGAACAAGGTGAACCCCATCGAGATCCCCATCAAGCAGACCATCCCCAAC
TTCTTCTTCGGCCGGGACACCGCCGAGGACTACGACGACCTGGACTACTGA
```

Alternatively, a human codon-optimized coding region which encodes SEQ ID NO:16 can be designed by the "full optimization" method, where each amino acid is assigned codons based on the frequency of usage in the human genome. These frequencies are shown in Table 12 above. Using this latter method, codons are assigned to the coding region encoding SEQ ID NO:16 as follows: about 10 of the 21 phenylalanine codons are TTT, and about 12 of the phenylalanine codons are TTC; about 3 of the 39 leucine codons are TTA, about 5 of the leucine codons are TTG, about 5 of the leucine codons are CTT, about 8 of the leucine codons are CTC, about 3 of the leucine codons are CTA, and about 16 of the leucine codons are CTG; about 14 of the 38 isoleucine codons are ATT, about 18 of the isoleucine codons are ATC, and about 6 of the isoleucine codons are ATA; the 27 methionine codons are ATG; about 6 of the 32 valine codons are GTT, about 8 of the valine codons are GTG, about 4 of the valine codons are GTA, and about 15 of the valine codons are GTG; about 7 of the 40 serine codons are TCT, about 9 of the serine codons are TCC, about 6 of the serine codons are TCA, about 2 of the serine codons are TCG, about 6 of the serine codons are AGT, and about 10 of the serine codons are AGC; about 7 of the 26 proline codons are CCT, about 9 of the proline codons are CCC, about 7 of the proline codons are CCA, and about 3 of the proline codons are CCG; about 9 of the 38 threonine codons are ACT, about 14 of the threonine codons are ACC, about 11 of the threonine codons are ACA, and about 4 of the threonine codons are ACG; about 11 of the 41 alanine codons are GGT, about 17 of the alanine codons are GCC, about 9 of the alanine codons are GCA, and about 4 of the alanine codons are GCG; about 6 of the 14 tyrosine codons are TAT and about 8 of the tyrosine codons are TAC; about 2 of the 4 histidine codons are CAT and about 2 of the histidine codons are CAC; about 5 of the 19 glutamine codons are CAA and about 14 of the glutamine codons are CAG; about 12 of the 25 asparagine codons are AAT and about 13 of the asparagine codons are AAC; about 22 of the 52 lysine codons are AAA and about 30 of the lysine codons are AAG; about 16 of the 34 aspartic acid codons are GAT and about 18 of the aspartic acid codons are GAC; about 12 of the 30 glutamic acid codons are GAA and about 18 of the glutamic acid codons are GAG; about 2 of the 5 cysteine codons are TGT and about 3 of the cysteine codons are TGC; the single tryptophan codon is TGG; about 2 of the 30 arginine codons are CGT, about 6 of the arginine codons are CGC, about 3 of the arginine codons are CGA, about 6 of the arginine codons are CGG, about 6 of the arginine codons are AGA, and about 6 of the arginine codons are AGG; and about 7 of the 44 glycine codons are GGT, about 15 of the glycine codons are GGC, about 11 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:16, optimized according to codon usage in humans is presented herein as SEQ ID NO:36:

```
ATGTCGAACATGGACATCGACAGCATTAACACAGGTACTATTGACAAAACC
CCCGAAGAACTAACCCCTGGAACCTCAGGAGCAACACGCCCAATAATCAAA
CCGGCCACCCTCGCGCCCCCTAGCAATAAGAGGACCCGCAATCCAAGTCCT
GAGAGAACCACTACTTCATCTGAAACGGATATCGGTCGGAAAATTCAAAAA
AAGCAGACGCCCACAGAGATAAAGAAGTCTGTTTACAAAATGGTGGTAAAG
CTCGGTGAGTTTTATAACCAGATGATGGTCAAGGCGGGGCTTAACGACGAT
ATGGAACGAAATCTTATACAGAATGCACAGGCAGTAGAGAGAATACTGCTG
GCCGCTACTGATGACAAGAAAACGGAGTACCAAAAAAAACGGAATGCTCGA
GATGTGAAAGAAGGAAAAGAAGAAATTGACCATAACAAAACTGGGGGGACA
TTCTATAAGATGGTGCGGGACGATAAGACAATCTATTTTAGCCCGATAAAG
ATTACCTTCCTGAAGGAGGAGGTTAAAACAATGTACAAGACGACGATGGGC
AGCGATGGGTTTTCCGGACTTAATCATATAATGATTGGTCACTCGCAGATG
AACGATGTATGTTTCCAGCGCTCCAAGGGCTTAAAGAGGGTAGGTCTTGAC
CCGTCTCTAATATCAACTTTCGCAGGATCCACTTTGCCGAGGCGTTCTGGC
ACGACAGGCGTGGCTATCAAGGGCGGGGGACGCTGGTCGATGAGGCCATT
CGCTTTATTGGTAGGGCCATGGCCGATAGAGGGCTTCTACGAGACATCAAA
GCAAAAACAGCATATGAGAAGATATTATTAAACTTAAAGAACAAATGCTCC
GCTCCTCAGCAAAAAGCGCTCGTTGACCAAGTAATCGGTTCGAGAAATCCA
```

-continued

```
GGCATTGCCGATATCGAAGATCTTACACTCTTGGCGCGAAGCATGGTCGTT
GTCCGTCCCAGTGTCGCTAGTAAGGTGGTACTACCAATCTCGATTTACGCA
AAAATTCCACAACTCGGCTTTAATACAGAGGAATATTCTATGGTAGGTTAT
GAAGCCATGGCGTTGTATAATATGGCTACACCAGTCTCCATATTGCGTATG
GGAGATGACGCAAAAGATAAGAGTCAACTCTTTTTCATGTCATGTTTCGGC
GCAGCGTACGAAGATCTGAGAGTACTATCCGCCTTGACTGGAACGGAATTT
AAACCACGGTCAGCCTTAAAGTGTAAGGGTTTTCACGTCCCTGCTAAGGAG
CAAGTTGAGGGAATGGGCGCGGCACTGATGAGTATAAAATTACAATTTTGG
GCTCCAATGACGCGTTCGGGAGGGAATGAAGTTTCTGGTGAGGGAGGGAGT
GGACAGATATCATGCTCGCCCGTGTTCGCGGTTGAACGTCCGATTGCTTTG
AGTAAGCAGGCGGTTAGGCGGATGTTAAGTATGAATGTGGAGGGCCGCGAT
GCCGACGTCAAAGGCAACTTATTAAAAATGATGAACGACAGCATGGCAAAG
AAGACTAGTGGGAATGCTTTTATAGGGAAAAAAATGTTCCAAATAAGTGAC
AAAAACAAAGTGAACCCCATCGAAATACCTATCAAGCAAACCATCCCGAAT
TTCTTTTTCGGTCGAGACACCGCGGAGGACTACGATGACCTAGATTACTAA
```

Additionally, a minimally codon-optimized nucleotide sequence encoding SEQ ID NO:16 can be designed by changing only certain codons found more frequently in IV genes than in human genes, as shown in Table 7. For example, if it is desired to substitute more frequently used codons in humans for those codons that occur at least 2 times more frequently in N genes (designated with an asterisk in Table 7), Arg AGA, which occurs 2.3 times more frequently in IV genes than in human genes, is changed to, e.g., CGG; Asn AAT, which occurs 2.0 times more frequently in IV genes than in human genes, is changed to, e.g., AAC; Ile ATA, which occurs 3.6 times more frequently in IV genes than in human genes, is changed to, e.g., ATC; and Leu CTA, which occurs 2.0 times more frequently in IV genes than is human, is changed to, e.g., CTG.

In another form of minimal optimization, a Codon Usage Table (CUT) for the specific IV sequence in question is generated and compared to CUT for human genomic DNA (see Table 7, supra). Amino acids are identified for which there is a difference of at least 10 percentage points in codon usage between human and IV DNA (either more or less). Then the wild type IV codon is modified to conform to predominant human codon for each such amino acid. Furthermore, the remainder of codons for that amino acid are also modified such that they conform to the predominant human codon for each such amino acid.

A representative "minimally optimized" codon-optimized coding region encoding SEQ ID NO:16, minimally optimized according to codon usage in humans by this latter method, is presented herein as SEQ ID NO:38:

```
ATGTCTAACATGGACATCGACTCTATAAACACAGGCACGATCGATAAGACC
CCCGAGGAGCTGACACCCGGCACTTCAGGCGCCACCAGACCCATAATAAAG
CCCGCCACTCTGGCCCCCCCCTCTAACAAGAGGACGAGGAACCCCTCTCCC
GAGCGCACCACAACGAGTAGCGAGACGGACATCGGCAGGAAGATACAGAAG
AAGCAGACTCCCACTGAGATTAAGAAGTCCGTGTATAAGATGGTGGTTAAG
CTGGGCGAGMTACAACCAGATGATGGTGAAGGCCGGCCTGAACGATGACAT
```

-continued

```
GGAGAGGAACCTGATACAGAACGCCCAGGCCGTGGAGAGGATTCTGCTGGC

CGCCACCGATGACAAGAAGACTGAGTATCAGAAGAAGAGAAACGCCCGGGA

CGTTAAGGAGGGCAAGGAGGAGATCGATCACAACAAGACAGGCGGCACTTT

CTATAAGATGGTCCGTGATGACAAGACAATCTACTTTTCTCCCATCAAGAT

CACATTCCTGAAGGAGGAGGTAAAGACTATGTACAAGACAACTATGGGCTC

CGATGGCTTCAGTGGCCTGAACCACATAATGATAGGCCATAGTCAGATGAA

CGATGTGTGCTTCCAGAGAAGCAAGGGCCTGAAGAGGGTCGGCCTGGATCC

CTCGCTGATTAGTACCTTCGCCGGCAGCACTCTGCCCAGAAGATCTGGCAC

TACTGGCGTAGCCATAAAGGGCGGCGGCACACTGGTAGACGAGGCCATAAG

GTTTATTGGCAGAGCCATGGCCGACCGCGGCCTGCTGAGAGATATCAAGGC

CAAGACCGCCTACGAGAAGATACTGCTGAACCTGAAGAACAAGTGCTCAGC

CCCCCAGCAGAAGGCCCTGGTGGATCAGGTGATCGGCAGTAGAAACCCCGG

CATCGCCGACATCGAGGATCTGACTCTGCTGGCCAGAAGCATGGTAGTCGT

AAGACCCTCTGTGGCCTCTAAGG1TGTGCTGCCCATCTCCATCTACGCCAA

GATTCCCCAGCTGGGCTTTAACACTGAGGAGTACTCCATGGTGGGCTATGA

GGCCATGGCCCTGTATAACATGGCCACACCCGTCTCTATCCTGCGGATGGG

CGACGATGCCAAGGACAAGTCTCAGCTGTTTTTATGAGTTGTTTCGGCGC

CGCCTATGAGGATCTGAGAGTCCTGTCAGCCCTGACAGGCACTGAGTTCAA

GCCCAGGTCCGCCCTGAAGTGCAAGGGCTTTCATGTGCCCGCCAAGGAGCA

GGTGGAGGGCATGGGCGCCGCCCTGATGAGCATCAAGCTGCAGTTCTGGGC

CCCCATGACCCGGTCTGGCGGCAACGAGGTCTCGGGCGAGGGCGGCAGTGG

CCAGATAAGTTGCAGCCCCGTTTTTGCCGTTGAGAGACCCATCGCCCTGTC

TAAGCAGGCCGTTAGACGAATGCTGAGTATGAACGTCGAGGGCCGAGACGC

CGATGTGAAGGGCAACCTGCTGAAGATGATGAACGATTCCATGGCCAAGAA

GACAAGCGGCAACGCCTTCATTGGCAAGAAGATGTTCCAGATAAGCGATAA

GAACAAGGTTAACCCCATCGAOATTCCCATCAAGCAGACCATCCCCAACTT

CTTCTTCGGCAGGGATACCGCCGAGGATTACGATGACCTGGACTACTGA
```

Randomly assigning codons at an optimized frequency to encode a given polypeptide sequence using the "full-optimization" or "minimal optimization" methods, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences. For example, the "backtranslation" function found at www.entelechon.com/eng/backtranslation.html (visited Jul. 9, 2002), and the "backtranseq" function available at bioinfo.pbi.nrc.ca:8090/EMBOSS/index.html (visited Oct. 15, 2002). Constructing a rudimentary algorithm to assign codons based on a given frequency can also easily be accomplished with basic mathematical functions by one of ordinary skill in the art.

A number of options are available for synthesizing codon-optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The codon-optimized coding regions can be versions encoding any gene products from any strain, derivative, or variant of IV, or fragments, variants, or derivatives of such gene products. For example, nucleic acid fragments of codon-optimized coding regions encoding the NP, M1 and M2 polypeptides, or fragments, variants or derivatives thereof. Codon-optimized coding regions encoding other IV polypeptides or fragments, variants, or derivatives thereof (e.g. HA, NA, PB1, PB2, PA, NS1 or NS2), are included within the present invention. Additional, non-codon-optimized polynucleotides encoding IV polypeptides or other polypeptides are included as well.

Consensus Sequences

The present invention is further directed to specific consensus sequences of influenza virus proteins, and fragments, derivatives and variants thereof. A "consensus sequence" is, e.g., an idealized sequence that represents the amino acids most often present at each position of two or more sequences which have been compared to each other. A consensus sequence is a theoretical representative amino acid sequence in which each amino acid is the one which occurs most frequently at that site in the different sequences which occur in nature. The term also refers to an actual sequence which approximates the theoretical consensus. A consensus sequence can be derived from sequences which have, e.g., shared functional or structural purposes. It can be defined by aligning as many known examples of a particular structural or functional domain as possible to maximize the homology. A sequence is generally accepted as a consensus when each particular amino acid is reasonably predominant at its position, and most of the sequences which form the basis of the comparison are related to the consensus by rather few substitutions, e.g., from 0 to about 100 substitutions. In general, the wild-type comparison sequences are at least about 50%, 75%, 80%, 90%, 95%, 96%, 97%, 98% or 99% identical to the consensus sequence. Accordingly, polypeptides of the invention are about 50%, 75%, 80%, 85%, 90%, 91%, 92%, 93%, 94%, 95%, 96%, 97%, 98%, 99% or 100% identical to the consensus sequence. Consensus amino acid sequences can be prepared for any of the influenza antigens. By analyzing amino acid sequences from influenza A strains sequenced since 1990, consensus amino acid sequences were derived for the influenza A NP (SEQ ID NO: 76), M1 (SEQ ID NO:77) and M2 (SEQ ID NO:78) proteins (Example 3). The consensus sequences for M1 (SEQ ID NO:77) and M2 (SEQ ID NO:78) are identical to the M1 and M2 amino acid sequences derived from the influenza virus strain A/Niigata/137/96.

A "consensus amino acid" is an amino acid chosen to occupy a given position in the consensus protein. A system which is organized to select consensus amino acids can be a computer program, or a combination of one or more computer programs with "by hand" analysis and calculation. When a consensus amino acid is obtained for each position of the aligned amino acid sequences, then these consensus amino acids are "lined up" to obtain the amino acid sequence of the consensus protein.

Another embodiment of this invention is directed to a process for the preparation of a consensus protein comprising a process to calculate an amino acid residue for nearly all positions of a so-called consensus protein and to synthesize a complete gene from this sequence that could be expressed in a prokaryotic or eukaryotic expression system.

Polynucleotides which encode the consensus influenza polypeptides, or fragments, variants or derivatives thereof, are also part of this invention. Such polynucleotides can be obtained by known methods, for example by backtranslation of the amino acid sequence and PCR synthesis of the corresponding polynucleotide.

Compositions and Methods

In certain embodiments, the present invention is directed to compositions and methods of enhancing the immune response of a vertebrate in need of protection against IV infection by administering in vivo, into a tissue of a vertebrate, one or more polynucleotides comprising at least one codon-optimized coding region encoding an IV polypeptide, or a fragment, variant, or derivative thereof. In addition, the present invention is directed to compositions and methods of enhancing the immune response of a vertebrate in need of protection against IV infection by administering to the vertebrate a composition comprising one or more polynucleotides as described herein, and at least one isolated IV polypeptide, or a fragment, variant, or derivative thereof. The polynucleotide may be administered either prior to, at the same time (simultaneously), or subsequent to the administration of the isolated polypeptide.

The coding regions encoding IV polypeptides or fragments, variants, or derivatives thereof may be codon optimized for a particular vertebrate. Codon optimization is carried out by the methods described herein, for example, in certain embodiments codon-optimized coding regions encoding polypeptides of IV, or nucleic acid fragments of such coding regions encoding fragments, variants, or derivatives thereof are optimized according to the codon usage of the particular vertebrate. The polynucleotides of the invention are incorporated into the cells of the vertebrate in vivo, and an immunologically effective amount of an IV polypeptide or a fragment, variant, or derivative thereof is produced in vivo. The coding regions encoding an IV polypeptide or a fragment, variant, or derivative thereof may be codon optimized for mammals, e.g., humans, apes, monkeys (e.g., owl, squirrel, cebus, rhesus, African green, patas, cynomolgus, and cercopithecus), orangutans, baboons, gibbons, and chimpanzees, dogs, wolves, cats, lions, and tigers, horses, donkeys, zebras, cows, pigs, sheep, deer, giraffes, bears, rabbits, mice, ferrets, seals, whales; birds, e.g., ducks, geese, terns, shearwaters, gulls, turkeys, chickens, quail, pheasants, geese, starlings and budgerigars, or other vertebrates.

In one embodiment, the present invention relates to codon-optimized coding regions encoding polypeptides of IV, or nucleic acid fragments of such coding regions fragments, variants, or derivatives thereof which have been optimized according to human codon usage. For example, human codon-optimized coding regions encoding polypeptides of IV, or fragments, variants, or derivatives thereof are prepared by substituting one or more codons preferred for use in human genes for the codons naturally used in the DNA sequence encoding the IV polypeptide or a fragment, variant, or derivative thereof. Also provided are polynucleotides, vectors, and other expression constructs comprising codon-optimized coding regions encoding polypeptides of IV, or nucleic acid fragments of such coding regions encoding fragments, variants, or derivatives thereof; pharmaceutical compositions comprising polynucleotides, vectors, and other expression constructs comprising codon-optimized coding regions encoding polypeptides of IV, or nucleic acid fragments of such coding regions encoding fragments, variants, or derivatives thereof; and various methods of using such polynucleotides, vectors and other expression constructs. Coding regions encoding IV polypeptides can be uniformly optimized, fully optimized, minimally optimized, codon-optimized by region and/or not codon-optimized, as described herein.

The present invention is further directed towards polynucleotides comprising codon-optimized coding regions encoding polypeptides of IV antigens, for example, HA, NA, NP, M1 and M2, optionally in conjunction with other antigens. The invention is also directed to polynucleotides comprising codon-optimized nucleic acid fragments encoding fragments, variants and derivatives of these polypeptides, e.g., an eM2 or a fusion of NP and eM2.

In certain embodiments, the present invention provides an isolated polynucleotide comprising a nucleic acid fragment, where the nucleic acid fragment is a fragment of a codon-optimized coding region encoding a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to an N polypeptide, e.g., HA, NA, NP, M1 or M2, and where the nucleic acid fragment is a variant of a codon-optimized coding region encoding an IV polypeptide, e.g., HA, NA, NP, M1 or M2. The human codon-optimized coding region can be optimized for any vertebrate species and by any of the methods described herein.

Isolated IV Polypeptides

The present invention is further drawn to compositions which include at least one polynucleotide comprising one or more nucleic acid fragments, where each nucleic acid fragment is optionally a fragment of a codon-optimized coding region operably encoding an IV polypeptide or fragment, variant, or derivative thereof; together with one or more isolated IV component or isolated polypeptide. The IV component may be inactivated virus, attenuated virus, a viral vector expressing an isolated influenza virus polypeptide, or an influenza virus protein, fragment, variant or derivative thereof.

The polypeptides or fragments, variants or derivatives thereof, in combination with the codon-optimized nucleic acid compositions may be referred to as "combinatorial polynucleotide vaccine compositions" or "single formulation heterologous prime-boost vaccine compositions."

The isolated IV polypeptides of the invention may be in any form, and are generated using techniques well known in the art. Examples include isolated IV proteins produced recombinantly, isolated IV proteins directly purified from their natural milieu, recombinant (non-IV) virus vectors expressing an isolated IV protein, or proteins delivered in the form of an inactivated IV vaccine, such as conventional vaccines When utilized, an isolated IV polypeptide or fragment, variant or derivative thereof is administered in an immunologically effective amount. Conventional IV vaccines have been standardized to micrograms of viral antigens HA and NA. See Subbarao, K., *Advances in Viral Research* 54:349-373 (1999), incorporated herein by reference in its entirety. The recommended dose for these vaccines is 15 ug of each HA per 0.5 ml. Id. The effective amount of conventional IV vaccines is determinable by one of ordinary skill in the art based upon several factors, including the antigen being expressed, the age and weight of the subject, and the precise condition requiring treatment and its severity, and route of administration.

In the instant invention, the combination of conventional antigen vaccine compositions with the codon-optimized nucleic acid compositions provides for therapeutically beneficial effects at dose sparing concentrations. For example, immunological responses sufficient for a therapeutically beneficial effect in patients predetermined for an approved commercial product, such as for the conventional product described above, can be attained by using less of the approved commercial product when supplemented or enhanced with the appropriate amount of codon-optimized nucleic acid. Thus, dose sparing is contemplated by administration of conventional IV vaccines administered in combination with the codon-optimized nucleic acids of the invention In particular, the dose of conventional vaccine may be reduced by at least 5%, at least 10%, at least 20%, at least 30%, at least 40%, at least 50%, at least 60% or at least 70% when administered in combination with the codon-optimized nucleic acid compositions of the invention.

Similarly, a desirable level of an immunological response afforded by a DNA based pharmaceutical alone may be attained with less DNA by including an aliquot of a conventional vaccine. Further, using a combination of conventional and DNA based pharmaceuticals may allow both materials to be used in lesser amounts while still affording the desired level of immune response arising from administration of either component alone in higher amounts (e.g. one may use less of either immunological product when they are used in combination). This may be manifest not only by using lower amounts of materials being delivered at any time, but also to reducing the number of administrations points in a vaccination regime (e.g. 2 versus 3 or 4 injections), and/or to reducing the kinetics of the immunological response (e.g. desired response levels are attained in 3 weeks in stead of 6 after immunization).

In particular, the dose of DNA based pharmaceuticals, may be reduced by at least 5%, at least 10%, at least 20%, at least 30%, at least 40%, at least 50%, at least 60% or at least 70% when administered in combination with conventional IV vaccines.

Determining the precise amounts of DNA based pharmaceutical and conventional antigen is based on a number of factors as described above, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional vaccine; adding a conventional vaccine to a DNA pharmaceutical to enhance humoral response; using a combination that induces additional epitopes (both humoral and/or cellular) to be recognized and/or more desirably responded to (epitope broadening); employing a DNA-conventional vaccine combination designed for a particular desired spectrum of immunological responses; obtaining a desirable spectrum by using higher amounts of either component. The broadened immune response is measurable by one of ordinary skill in the art by standard immunological assay specific for the desirable response spectrum.

Both broadening and dose sparing can be obtained simultaneously.

The isolated IV polypeptide or fragment, variant, or derivative thereof to be delivered (either a recombinant protein, a purified subunit, or viral vector expressing an isolated IV polypeptide, or in the form of an inactivated N vaccine) can be any isolated IV polypeptide or fragment, variant, or derivative thereof, including but not limited to the HA, NA, NP, M1, or M2 proteins or fragments, variants or derivatives thereof. Fragments include, but are not limited to, the eM2 protein. In certain embodiments, a derivative protein can be a fusion protein, e.g., NP-eM2. It should be noted that any isolated N polypeptide or fragment, variant, or derivative thereof described herein can be combined in a composition with any polynucleotide comprising a nucleic acid fragment, where the nucleic acid fragment is optionally a fragment of a codon-optimized coding region operably encoding an IV polypeptide or fragment, variant, or derivative thereof. The proteins can be different, the same, or can be combined in any combination of one or more isolated IV proteins and one or more polynucleotides.

In certain embodiments, the isolated IV polypeptides, or fragments, derivatives or variants thereof can be fused to or conjugated to a second isolated IV polypeptide, or fragment, derivative or variant thereof, or can be fused to other heterologous proteins, including for example, hepatitis B proteins including, but not limited to the hepatitis B core antigen (HBcAg), or those derived from diphtheria or tetanus. The second isolated IV polypeptide or other heterologous protein can act as a "carrier" that potentiates the immunogenicity of the IV polypeptide or a fragment, variant, or derivative thereof to which it is attached. Hepatitis B virus proteins and fragments and variants thereof useful as carriers within the scope of the invention are disclosed in U.S. Pat. Nos. 6,231,864 and 5,143,726, which are incorporated by reference in their entireties. Polynucleotides comprising coding regions encoding said fused or conjugated proteins are also within the scope of the invention.

The use of recombinant particles comprising hepatitis B. core antigen ("HBcAg") and heterologous protein sequences as potent immunogenic moieties is well documented. For example, addition of heterologous sequences to the amino terminus of a recombinant HBcAg results in the spontaneous assembly of particulate structures which express the heterologous epitope on their surface, and which are highly immunogenic when inoculated into experimental animals. See Clarke et al., *Nature* 330:381-384 (1987). Heterologous epitopes can also be inserted into HBcAg particles by replacing approximately 40 amino acids of the carboxy terminus of the protein with the heterologous sequences. These recombinant HBcAg proteins also spontaneously form immunogenic particles. See Stahl and Murray, *Proc. Natl. Acad. Sci. USA*, 86:6283-6287 (1989). Additionally, chimeric HBcAg particles may be constructed where the heterologous epitope is inserted in or replaces all or part of the sequence of amino acid residues in a more central region of the HBcAg protein, in an immunodominant loop, thereby allowing the heterologous epitope to be displayed on the surface of the resulting particles. See EP Patent No. 0421635 B1. Shown below are the DNA and amino acid sequences of the human hepatitis B core protein (HBc), subtype ayw (SEQ ID NOs 39 and 40), as described in Galibert, F., et al., *Nature* 281:646-650 (1979); see also U.S. Pat. Nos. 4,818,527, 4,882,145 and 5,143,726. All of the above references are incorporated herein by reference in their entireties. The nucleotide and amino acid sequences are presented herein as SEQ ID NO 39:

ATGGACATCGACCCTTATAAAGAATTTGGAGCTACTGTGGAGTTACT

CTCGTTTTTGCCTTCTGACTTCTTTCCTTCAGTACGAGATCTTCTAG

ATACCGCCTCAGCTCTGTATCGGGAAGCCTTAGAGTCTCCTGAGCAT

TGTTCACCTCACCATACTGCACTCAGGCAAGCAATTCTTTGCTGGGG

GGAATCTAATGACTCTAGCTACCTGGGTGGGTGTTAATTTGGAAGAT

CCAGCGTCTAGAGACCTAGTAGTCAGTTATGTCAACACTAATATGGG

CCTAAAGTTCAGGCAACTCTTGTGGTTTCACATTTCTTGTCTCACTT

TTGGAAGAGAAACAGTTATAGAGTATTTGGTGTCTTTCGGAGTGTGG

ATTCGCACTCCTCCAGCTTATAGACCACCAAATGCCCCTATCCTATC

AACACTTCCGGAGACTACTGTTGTTAGACGACGAGGCAGGTCCCCTA

GAAGAAGAACTCCCTCGCCTCGCAGACGAAGGTCTCAATCGCCGCGT

CGCAGAAGATCTCAATCTCGGGAATCTCAATGTTAG and SEQ ID NO:40:

MDIDPYKEFGATVELLSFLPSDFFPSVRDLLDTASALYREALESPEH

CSPHHTALRQAILCWGELMTLATWVGVNLEDPASRDLVVSYVNTNMG

LKFRQLLWFHISCLTFGRETVIEYLVSFGVWIRTPPAYRPPNAPILS

TLPETTVVRRRGRSPRRRTPSPRRRRSQSPRRRRSQSRESQC

A completely synthetic HBcAg has been synthesized as well. See Nassal, M. Gene 66:279-294 (1988). The nucleotide and amino acid sequences are presented herein as SEQ ID NO 41:

ATGGATATCGATCCTTATAAAGAATTCGGAGCTACTGGGAGTTACTC

TCGTTTCTCCCGAGTGACTTCTTTCCTTCAGTACGAGATCTTCTGGA

TACCGCCAGCGCGCTGTATCGGGAAGCCTTGGAGTCTCCTGAGCACT

GCAGCCCTCACCATACTGCCCTCAGGCAAGCAATTCTTTGCTGGGGG

GAGCTCATGACTCTGGCCACGTGGGTGGGTGTTAACTTGGAAGATCC

AGCTAGCAGGGACCTGGTAGTCAGTTATGTCAACACTAATATGGGTT

TAAAGTTCAGGCAACTCTTGTGGTTTCACATTAGCTGCCTCACTTTC

GGCCGAGAAACAGTTCTAGAATATTTGGTGTCTTTCGGAGTGTGGAT

CCGCACTCCTCCAGCTTATAGGCCTCCGAATGCCCCTATCCTGTCGA

-continued

CACTCCCGGAGACTACTGTTGTTAGACGTCGAGGCAGGTCACCTAGA

AGAAGAACTCCTTCGCCTCGCAGGCGAAGGTCTCAATCGCCGCGGCG

CCGAAGATCTCAATCTCGGGAATCTCAATGTTAGTGA and SEQ ID NO:42:

MDIDPYICEFGATVELLSFLPSDFFPSVRDLLDTASALYREALESPE

HCSPHHTALRQAILCWGELMTLATWVGVNLEDPASRDLVVSYVNTNM

GLICFRQLLWFHISCLTFGRETVLEYLVSFGVWIRTPPAYRPPNAPI

LSTLPETTVVRRRGRSPRRRTPSPRRRRSQSPRRRRSQSRESQC

Chimaeric HBcAg particles comprising isolated IV proteins or variants, fragments or derivatives thereof are prepared by recombinant techniques well known to those of ordinary skill in the art. A polynucleotide, e.g., a plasmid, which carries the coding region for the HBcAg operably associated with a promoter is constructed. Convenient restrictions sites are engineered into the coding region encoding the N-terminal, central, and/or C-terminal portions of the HBcAg, such that heterologous sequences may be inserted. A construct which expresses a HBcAg/IV fusion protein is prepared by inserting a DNA sequence encoding an IV protein or variant, fragment or derivative thereof, in frame, into a desired restriction site in the coding region of the HBcAg. The resulting construct is then inserted into a suitable host cell, e.g., *E. coli*, under conditions where the chimeric HBcAg will be expressed. The chimaeric HBcAg self-assembles into particles when expressed, and can then be isolated, e.g., by ultracentrifugation. The particles formed resemble the natural 27 nm HBcAg particles isolated from a hepatitis B virus, except that an isolated IV protein or fragment, variant, or derivative thereof is contained in the particle, preferably exposed on the outer particle surface.

The IV protein or fragment, variant, or derivative thereof expressed in a chimaeric HBcAg particle may be of any size which allows suitable particles of the chimeric HBcAg to self-assemble. As discussed above, even small antigenic epitopes may be immunogenic when expressed in the context of an immunogenic carrier, e.g., a HBcAg. Thus, HBcAg particles of the invention may comprise at least 4, at least 5, at least 6, at least 7, at least 8, at least 9, at least 10, at least 15, at least 20, at least 25, or between about 15 to about 30 amino acids of an IV protein fragment of interest inserted therein. HBcAg particles of the invention may further comprise immunogenic or antigenic epitopes of at least 5, 10, 15, 20, 25, 30, 35, 40, 45, 50, 55, 60, 65, 70, 75, 80, 85, 90, 95, or 100 amino acid residues of an IV protein fragment of interest inserted therein.

The immunodominant loop region of HBcAg was mapped to about amino acid residues 75 to 83, to about amino acids 75 to 85 or to about amino acids 130 to 140. See Colucci et al., *J. Immunol.* 141:4376-4380 (1988), and Salfeld et al. *J. Virol.* 63:798 (1989), which are incorporated by reference. A chimeric HBcAg is still often able to form core particles when foreign epitopes are cloned into the immunodominant loop. Thus, for example, amino acids of the IV protein fragment may be inserted into the sequence of HBcAg amino acids at various positions, for example, at the N-terminus, from about amino acid 75 to about amino acid 85, from about amino acid 75 to about amino acid 83, from about amino acid 130 to about amino acid 140, or at the C-terminus. Where amino acids of the IV protein fragment replace all or part of the native core protein sequence, the inserted IV sequence is generally not shorter, but may be longer, than the HBcAg sequence it replaces.

Alternatively, if particle formation is not desired, full-length IV coding sequences can be fused to the coding region for the HBcAg. The HBcAg sequences can be fused either at the N- or C-terminus of any of the Influenza antigens described herein, including the eM2-NP constructs. Fusions could include flexible protein linkers as described for NP-eM2 fusions above. Examples of IV coding sequences fused to the HBcAg coding sequence of SEQ ID NO:41 include an IAV NP-HBcAg fusion (SEQ ID NO:43),

```
ATGGCGTCTCAAGGCACCAAACGATCTTACGAACAGATGGAGACTGA
TGGAGAACGCCAGAATGCCACTGAAATCAGAGCATCCGTCGGAAAAA
TGATTGGTGGAATTGGACGATTCTACATCCAAATGTGCACCGAACTC
AAACTCAGTGATTATGAGGGACGGTTGATCCAAAACAGCTTAACAAT
AGAGAGAATGGTGCTCTCTGCTTTTGACGAAAGGAGAAATAAATACC
TTGAAGAACATCCCAGTGCGGGGAAAGATCCTAAGAAAACTGGAGGA
CCTATATACAGGAGAGTAAACGGAAAGTGGATGAGAGAACTCATCCT
TTATGACAAAGAAGAAATAAGGCGAATCTGGCGCCAAGCTAATAATG
GTGACGATGCAACGGCTGGTCTGACTCACATGATGATCTGGCATTCC
AATTTGAATGATGCAACTTATCAGAGGACAAGAGCTCTTGTTCGCAC
CGGAATGGATCCCAGGATGTGCTCTCTGATGCAAGGTTCAACTCTCC
CTAGGAGGTCTGGAGCCGCAGGTGCTGCAGTCAAAGGAGTTGGAACA
ATGGTGATGGAATTGGTCAGAATGATCAAACGTGGGATCAATGATCG
GAACTTCTGGAGGGGTGAGAATGGACGAAAAACAAGAATTGCTTATG
AAAGAATGTGCAACATTCTCAAAGGGAAATTTCAAACTGCTGCACAA
AAAGCAATGATGGATCAAGTGAGAGAGAGCCGGAACCCAGGGAATGC
TGAGTTCGAAGATCTCACTTTTCTAGCACGGTCTGCACTCATATTGA
GAGGGTCGGTTGCTCACAAGTCCTGCCTGCCTGCCTGTGTGTATGGA
CCTGCCGTAGCCAGTGGGTACGACTTTGAAAGGGAGGGATACTCTCT
AGTCGGAATAGACCCTTTCAGACTGCTTCAAAACAGCCAAGTGTACA
GCCTAATCAGACCAAATGAGAATCCAGCACACAAGAGTCAACTGGTG
TGGATGGCATGCCATTCTGCCGCATTTGAAGATCTAAGAGTATTAAG
CTTCATCAAAGGGACGAAGGTGCTCCCAAGAGGGAAGCTTTCCACTA
GAGGAGTTCAAATTGCTTCCAATGAAAATATGGAGACTATGGAATCA
AGTACACTTGAACTGAGAAGCAGGTACTGGGCCATAAGGACCAGAAG
TGGAGGAAACACCAATCAACAGAGGGCATCTGCGGGCCAAATCAGCA
TACAACCTACGTTCTCAGTACAGAGAAATCTCCCTTTTGACAGAACA
ACCGTTATGGCAGCATTCAGTGGGAATACAGAGGGGAGATGGCGTCT
CAAGGCACCAAACGATCTTACGAACAGATGGAGACTGATGGAGAACG
CCAGAATGCCACTGAAATCAGAGCATCCGTCGGAAAAATGATTGGTG
GAATTGGACGATTCTACATCCAAATGTGCACCGAACTCAAACTCAGT
GATTATGAGGGACGGTTGATCCAAAACAGCTTAACAATAGAGAGAAT
```

-continued

```
GGTGCTCTCTGCTTTTGACGAAAGGAGAAATAAATACCTTGAAGAAC
ATCCCAGTGCGGGGAAAGATCCTAAGAAAACTGGAGGACCTATATAC
AGGAGAGTAAACGGAAAGTGGATGAGAGAACTCATCCTTTATGACAA
AGAAGAAATAAGGCGAATCTGGCGCCAAGCTAATAATGGTGACGATG
CAACGGCTGGTCTGACTCACATGATGATCTGGCATTCCAATTTGAAT
GATGCAACTTATCAGAGGACAAGAGCTCTTGTTCGCACCGGAATGGA
TCCCAGGATGTGCTCTCTGATGCAAGGTTCAACTCTCCCTAGGAGGT
CTGGAGCCGCAGGTGCTGCAGTCAAAGGAGTTGGAACAATGGTGATG
GAATTGGTCAGAATGATCAAACGTGGGATCAATGATCGGAACTTCTG
GAGGGGTGAGAATGGACGAAAAACAAGAATTGCTTATGAAAGAATGT
GCAACATTCTCAAAGGGAAATTTCAAACTGCTGCACAAAAAGCAATG
ATGGATCAAGTGAGAGAGAGCCGGAACCCAGGGAATGCTGAGTTCGA
AGATCTCACTTTTCTAGCACGGTCTGCACTCATATTGAGAGGGTCGG
TTGCTCACAAGTCCTGCCTGCCTGCCTGTGTGTATGGACCTGCCGTA
GCCAGTGGGTACGACTTTGAAAGGGAGGGATACTCTCTAGTCGGAAT
AGACCCTTTCAGACTGCTTCAAAACAGCCAAGTGTACAGCCTAATCA
GACCAAATGAGAATCCAGCACACAAGAGTCAACTGGTGTGGATGGCA
TGCCATTCTGCCGCATTTGAAGATCTAAGAGTATTAAGCTTCATCAA
AGGGACGAAGGTGCTCCCAAGAGGGAAGCTTTCCACTAGAGGAGTTC
AAATTGCTTCCAATGAAAATATGGAGACTATGGAATCAAGTACACTT
GAACTGAGAAGCAGGTACTGGGCCATAAGGACCAGAAGTGGAGGAAA
CACCAATCAACAGAGGGCATCTGCGGGCCAAATCAGCATACAACCTA
CGTTCTCAGTACAGAGAAATCTCCCTTTTTGACAGAACAACCGTTAT
GGCAGCATTCAGTGGGAATACAGAGGGGAGAACATCTGACATGAGGA
CCGAAATCATAAGGATGATGGAAAGTGCAAGACCAGAAGATGTGTCT
TTCCAGGGGCGGGGAGTCTTCGAGCTCTCGGACGAAAAGGCAGCGAG
CCCGATCGTGCCTTCCTTTGACATGAGTAATGAAGGATCTTATTTCT
TCGGAGACAATGCAGAGGAATACGATAATATGGATATCGATCCTTAT
AAAGAATTCGGAGCTACTGTGGAGTTACTCTCGTTTCTCCCGAGTGA
CTTCTTTCCTTCAGTACGAGATCTTCTGGATACCGCCAGCGCGCTGT
ATCGGGAAGCCTTGGAGTCTCCTGAGCACTGCAGCCCTCACCATACT
GCCCTCAGGCAAGCAATTCTTTGCTGGGGGGAGCTCATGACTCTGGC
CACGTGGGTGGGTGTTAACTTGGAAGATCCAGCTAGCAGGGACCTGG
TAGTCAGTTATGTCAACACTAATATGGGTTTAAAGTTCAGGCAACTC
TTGTGGTTTCACATTAGCTGCCTCACTTTCGGCCGAGAAACAGTTCT
AGAATATTTGGTGTCTTTCGGAGTGTGGATCCGCACTCCTCCAGCTT
ATAGGCCTCCGAATGCCCCTATCCTGTCGACACTCCCGGAGACTACT
GTTGTTAGACGTCGAGGCAGGTCACCTAGAAGAAGAACTCCTTCGCC
TCGCAGGCGAAGGTCTCAATCGCCGCGGCGCCGAAGATCTCAATCTC
GGGAATCTCAATGT
```

an IBV NP-HBcAg fusion (SEQ ID NO:44),

```
ATGTCCAACATGGATATTGACAGTATAAATACCGGAACAATCGATAA
AACACCAGAAGAACTGACTCCCGGAACCAGTGGGGCAACCAGACCAA
TCATCAAGCCAGCAACCCTTGCTCCGCCAAGCAACAAACGAACCCGA
AATCCATCTCCAGAAAGGACAACCACAAGCAGTGAAACCGATATCGG
AAGGAAAATCCAAAAGAAACAAACCCCAACAGAGATAAAGAAGAGCG
TCTACAAAATGGTGGTAAAACTGGGTGAATTCTACAACCAGATGATG
GTCAAAGCTGGACTTAATGATGACATGGAAAGGAATCTAATTCAAAA
TGCACAAGCTGTGGAGAGAATCCTATTGGCTGCAACTGATGACAAGA
AAACTGAATACCAAAAGAAAAGGAATGCCAGAGATGTCAAAGAAGGG
AAGGAAGAAATAGACCACAACAAGACAGGAGGCACCTTTTATAAGAT
GGTAAGAGATGATAAAACCATCTACTTCAGCCCTATAAAAATTACCT
TTTTAAAAGAAGAGGTGAAAACAATGTACAAGACCACCATGGGGAGT
GATGGTTTCAGTGGACTAAATCACATTATGATTGGACATTCACAGAT
GAACGATGTCTGTTTCCAAAGATCAAAGGGACTGAAAAGGGTTGGAC
TTGACCCTTCATTAATCAGTACTTTTGCCGGAAGCACACTACCCAGA
AGATCAGGTACAACTGGTGTTGCAATCAAAGGAGGTGGAACTTTAGT
GGATGAAGCCATCCGATTTATAGGAAGAGCAATGGCAGACAGAGGGC
TACTGAGAGACATCAAGGCCAAGACGGCCTATGAAAAGATTCTTCTG
AATCTGAAAAACAAGTGCTCTGCGCCGCAACAAAAGGCTCTAGTTGA
TCAAGTGATCGGAAGTAGGAACCCAGGGATTGCAGACATAGAAGACC
TAACTCTGCTTGCCAGAAGCATGGTAGTTGTCAGACCCTCTGTAGCG
AGCAAAGTGGTGCTTCCCATAAGCATTTATGCTAAAATACCTCAACT
AGGATTCAATACCGAAGAATACTCTATGGTTGGGTATGAAGCCATGG
CTCTTTATAATATGGCAACACCTGTTTCCATATTAAGAATGGGAGAT
GACGCAAAAGATAAATCTCAACTATTCTTCATGTCGTGCTTCGGAGC
TGCCTATGAAGATCTAAGAGTGTTATCTGCACTAACGGGCACCGAAT
TTAAGCCTAGATCAGCACTAAAATGCAAGGGTTTCCATGTCCCGGCT
AAGGAGCAAGTAGAAGGAATGGGGGCAGCTCTGATGTCCATCAAGCT
TCAGTTCTGGGCCCCAATGACCAGATCTGGAGGGAATGAAGTAAGTG
GAGAAGGAGGGTCTGGTCAAATAAGTTGCAGCCCTGTGTTTGCAGTA
GAAAGACCTATTGCTCTAAGCAAGCAAGCTGTAAGAAGAATGCTGTC
AATGAACGTTGAAGGACGTGATGCAGATGTCAAAGGAAATCTACTCA
AAATGATGAATGATTCAATGGCAAAGAAAACCAGTGGAAATGCTTTC
ATTGGGAAGAAAATGTTTCAAATATCAGACAAAAACAAAGTCAATCC
CATTGAGATTCCAATTAAGCAGACCATCCCCAATTTCTTCTTTGGGA
GGGACACAGCAGAGGATTATGATGACCTCGATTATATGGATATCGAT
CCTTATAAAGAATTCGGAGCTACTGTGGAGTTACTCTCGTTTCTCCC
GAGTGACTTCTTTCCTTCAGTACGAGATCTTCTGGATACCGCCAGCG
CGCTGTATCGGGAAGCCTTGGAGTCTCCTGAGCACTGCAGCCCTCAC
```

-continued

```
CATACTGCCCTCAGGCAAGCAATTCTTTGCTGGGGGGAGCTCATGAC
TCTGGCCACGTGGGTGGGTGTTAACTTGGAAGATCCAGCTAGCAGGG
ACCTGGTAGTCAGTTATGTCAACACTAATATGGGTTTAAAGTTCAGG
CAACTCTTGTGGTTTCACATTAGCTGCCTCACTTTCGGCCGAGAAAC
AGTTCTAGAATATTTGGTGTCTTTCGGAGTGTGGATCCGCACTCCTC
CAGCTTATAGGCCTCCGAATGCCCCTATCCTGTCGACACTCCCGGAG
ACTACTGTTGTTAGACGTCGAGGCAGGTCACCTAGAAGAAGAACTCC
TTCGCCTCGCAGGCGAAGGTCTCAATCGCCGCGGCGCCGAAGATCTC
AATCTCGGGAATCTCAATGTT
```

or an IAV M1-HBcAg fusion (SEQ ID NO:45),

```
ATGAGTCTTCTAACCGAGGTCGAAACGTACGTACTCTCTATCATCCC
GTCAGGCCCCCTCAAAGCCGAGATCGCACAGAGACTTGAAGATGTCT
TTGCAGGGAAGAACACTGATCTTGAGGTTCTCATGGAATGGCTAAAG
ACAAGACCAATCCTGTCACCTCTGACTAAGGGGATTTTAGGATTTGT
GTTCACGCTCACCGTGCCCAGTGAGCGAGGACTGCAGCGTAGACGCT
TTGTCCAAAATGCCCTTAATGGGAACGGGGATCCAAATAACATGGAC
AAAGCAGTTAAACTGTATAGGAAGCTCAAGAGGGAGATAACATTCCA
TGGGGCCAAAGAAATCTCACTCAGTTATTCTGCTGGTGCACTTGCCA
GTTGTATGGGCCTCATATACAACAGGATGGGGGCTGTGACCACTGAA
GTGGCATTTGGCCTGGTATGTGCAACCTGTGAACAGATTGCTGACTC
CCAGCATCGGTCTCATAGGCAAATGGTGACAACAACCAATCCACTAA
TCAGACATGAGAACAGAATGGTTTTAGCCAGCACTACAGCTAAGGCT
ATGGAGCAAATGGCTGGATCGAGTGAGCAAGCAGCAGAGGCCATGGA
GGTTGCTAGTCAGGCTAGACAAATGGTGCAAGCGATGAGAACCATTG
GGACTCATCCTAGCTCCAGTGCTGGTCTGAAAAATGATCTTCTTGAA
AATTTGCAGGCCTATCAGAAACGAATGGGGGTGCAGATGCAACGGTT
CAAGATGGATATCGATCCTTATAAAGAATTCGGAGCTACTGTGGAGT
TACTCTCGTTTCTCCCGAGTGACTTCTTTCCTTCAGTACGAGATCTT
CTGGATACCGCCAGCGCGCTGTATCGGGAAGCCTTGGAGTCTCCTGA
GCACTGCAGCCCTCACCATACTGCCCTCAGGCAAGCAATTCTTTGCT
GGGGGGAGCTCATGACTCTGGCCACGTGGGTGGGTGTTAACTTGGAA
GATCCAGCTAGCAGGGACCTGGTAGTCAGTTATGTCAACACTAATAT
GGGTTTAAAGTTCAGGCAACTCTTGTGGTTTCACATTAGCTGCCTCA
CTTTCGGCCGAGAAACAGTTCTAGAATATTTGGTGTCTTTCGGAGTG
TGGATCCGCACTCCTCCAGCTTATAGGCCTCCGAATGCCCCTATCCT
GTCGACACTCCCGGAGACTACTGTTGTTAGACGTCGAGGCAGGTCAC
CTAGAAGAAGAACTCCTTCGCCTCGCAGGCGAAGGTCTCAATCGCCG
CGGCGCCGAAGATCTCAATCTCGGGAATCTCAATGT
```

These fusion constructs could be codon optimized by any of the methods described.

The chimeric HBcAg can be used in the present invention in conjunction with a polynucleotide comprising a nucleic acid fragment, where each nucleic acid fragment is optionally a fragment of a codon-optimized coding region operably encoding an IV polypeptide, or a fragment, variant, or derivative thereof, as an influenza vaccine for a vertebrate.

Methods and Administration

The present invention also provides methods for delivering an N polypeptide or a fragment, variant, or derivative thereof to a human, which comprise administering to a human one or more of the compositions described herein; such that upon administration of compositions such as those described herein, an IV polypeptide or a fragment, variant, or derivative thereof is expressed in human cells, in an amount sufficient to generate an immune response to the IV or administering the IV polypeptide or a fragment, variant, or derivative thereof itself to the human in an amount sufficient to generate an immune response.

The present invention further provides methods for delivering an N polypeptide or a fragment, variant, or derivative thereof to a human, which comprise administering to a vertebrate one or more of the compositions described herein; such that upon administration of compositions such as those described herein, an immune response is generated in the vertebrate.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The present invention further provides a method for generating, enhancing or modulating an immune response to an IV comprising administering to a vertebrate one or more of the compositions described herein. In this method, the compositions may include one or more isolated polynucleotides comprising at least one nucleic acid fragment where the nucleic acid fragment is optionally a fragment of a codon-optimized coding region encoding an IV polypeptide, or a fragment, variant, or derivative thereof. In another embodiment, the compositions may include both a polynucleotide as described above, and also an isolated IV polypeptide, or a fragment, variant, or derivative thereof, wherein the protein is provided as a recombinant protein, in particular, a fusion protein, a purified subunit, viral vector expressing the protein, or in the form of an inactivated IV vaccine. Thus, the latter compositions include both a polynucleotide encoding an IV polypeptide or a fragment, variant, or derivative thereof and an isolated IV polypeptide or a fragment, variant, or derivative thereof. The IV polypeptide or a fragment, variant, or derivative thereof encoded by the polynucleotide of the compositions need not be the same as the isolated IV polypeptide or a fragment, variant, or derivative thereof of the compositions. Compositions to be used according to this method may be univalent, bivalent, trivalent or multivalent.

The polynucleotides of the compositions may comprise a fragment of a human (or other vertebrate) codon-optimized coding region encoding a protein of the IV, or a fragment, variant, or derivative thereof. The polynucleotides are incorporated into the cells of the vertebrate in vivo, and an antigenic amount of the IV polypeptide, or fragment, variant, or derivative thereof, is produced in vivo. Upon administration of the composition according to this method, the IV polypeptide or a fragment, variant, or derivative thereof is expressed in the vertebrate in an amount sufficient to elicit an immune response. Such an immune response might be used, for example, to generate antibodies to the IV for use in diagnostic assays or as laboratory reagents, or as therapeutic or preventative vaccines as described herein.

The present invention further provides a method for generating, enhancing, or modulating a protective and/or therapeutic immune response to IV in a vertebrate, comprising administering to a vertebrate in need of therapeutic and/or preventative immunity one or more of the compositions described herein. In this method, the compositions include one or more polynucleotides comprising at least one nucleic acid fragment, where the nucleic acid fragment is optionally a fragment of a codon-optimized coding region encoding an IV polypeptide, or a fragment, variant, or derivative thereof. In a further embodiment, the composition used in this method includes both an isolated polynucleotide comprising at least one nucleic acid fragment, where the nucleic acid fragment is optionally a fragment of a codon-optimized coding region encoding an IV polypeptide, or a fragment, variant, or derivative thereof; and at least one isolated IV polypeptide, or a fragment, variant, or derivative thereof. Thus, the latter composition includes both an isolated polynucleotide encoding an IV polypeptide or a fragment, variant, or derivative thereof and an isolated IV polypeptide or a fragment, variant, or derivative thereof, for example, a recombinant protein, a purified subunit, viral vector expressing the protein, or an inactivated virus vaccine. Upon administration of the composition according to this method, the IV polypeptide or a fragment, variant, or derivative thereof is expressed in the human in a therapeutically or prophylactically effective amount.

As used herein, an "immune response" refers to the ability of a vertebrate to elicit an immune reaction to a composition delivered to that vertebrate. Examples of immune responses include an antibody response or a cellular, e.g., cytotoxic T-cell, response. One or more compositions of the present invention may be used to prevent influenza infection in vertebrates, e.g., as a prophylactic vaccine, to establish or enhance immunity to IV in a healthy individual prior to exposure to influenza or contraction of influenza disease, thus preventing the disease or reducing the severity of disease symptoms.

As mentioned above, compositions of the present invention can be used both to prevent IV infection, and also to therapeutically treat IV infection. In individuals already exposed to influenza, or already suffering from influenza disease, the present invention is used to further stimulate the immune system of the vertebrate, thus reducing or eliminating the symptoms associated with that disease or disorder. As defined herein, "treatment" refers to the use of one or more compositions of the present invention to prevent, cure, retard, or reduce the severity of influenza disease symptoms in a vertebrate, and/or result in no worsening of influenza disease over a specified period of time in a vertebrate which has already been exposed to IV and is thus in need of therapy. The term "prevention" refers to the use of one or more compositions of the present invention to generate immunity in a vertebrate which has not yet been exposed to a particular strain of IV, thereby preventing or reducing disease symptoms if the vertebrate is later exposed to the particular strain of N. The methods of the present invention therefore may be referred to as therapeutic vaccination or preventative or prophylactic vaccination. It is not required that any composition of the present invention provide total immunity to influenza or totally cure or eliminate all influenza disease symptoms. As used herein, a "vertebrate in need of therapeutic and/or preventative immunity" refers to an individual for whom it is desirable to treat, i.e., to prevent, cure, retard, or reduce the severity of influenza disease symptoms, and/or result in no worsening of influenza disease over a specified period of time. Vertebrates to treat and/or vaccinate include humans, apes, monkeys (e.g., owl, squirrel, cebus, rhesus, African green, patas, cynomolgus, and cercopithecus), orangutans, baboons, gibbons, and chimpanzees, dogs, wolves, cats, lions, and tigers, horses, donkeys, zebras, cows, pigs, sheep, deer, giraffes, bears, rabbits, mice, ferrets, seals, whales, ducks, geese, terns, shearwaters, gulls, turkeys, chickens, quail, pheasants, geese, starlings and budgerigars.

One or more compositions of the present invention are utilized in a "prime boost" regimen. An example of a "prime boost" regimen may be found in Yang, Z. et al. *J. Viral.* 77:799-803 (2002), which is incorporated herein by reference in its entirety. In these embodiments, one or more polynucleotide vaccine compositions of the present invention are delivered to a vertebrate, thereby priming the immune response of the vertebrate to an IV, and then a second immunogenic composition is utilized as a boost vaccination. One or more compositions of the present invention are used to prime immunity, and then a second immunogenic composition, e.g., a recombinant viral vaccine or vaccines, a different polynucleotide vaccine, or one or more purified subunit isolated IV polypeptides or fragments, variants or derivatives thereof is used to boost the anti-IV immune response.

In one embodiment, a priming composition and a boosting composition are combined in a single composition or single formulation. For example, a single composition may comprise an isolated IV polypeptide or a fragment, variant, or derivative thereof as the priming component and a polynucleotide encoding an influenza protein as the boosting component. In this embodiment, the compositions may be contained in a single vial where the priming component and boosting component are mixed together. In general, because the peak levels of expression of protein from the polynucleotide does not occur until later (e.g., 7-10 days) after administration, the polynucleotide component may provide a boost to the isolated protein component. Compositions comprising both a priming component and a boosting component are referred to herein as "combinatorial vaccine compositions" or "single formulation heterologous prime-boost vaccine compositions." In addition, the priming composition may be administered before the boosting composition, or even after the boosting composition, if the boosting composition is expected to take longer to act.

In another embodiment, the priming composition may be administered simultaneously with the boosting composition, but in separate formulations where the priming component and the boosting component are separated.

The terms "priming" or "primary" and "boost" or "boosting" as used herein may refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

In certain embodiments, one or more compositions of the present invention are delivered to a vertebrate by methods described herein, thereby achieving an effective therapeutic and/or an effective preventative immune response. More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the vertebrate from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944, both of which are incorporated herein by reference in their entireties.

In certain embodiments, the compositions are administered into embryonated chicken eggs or by intra-muscular injection into the defeathered breast area of chicks as described in Kodihalli S. et al., *Vaccine* 18:2592-9 (2000), which is incorporated herein by reference in its entirety.

In certain embodiments, the compositions are administered to muscle, either skeletal muscle or cardiac muscle, or to lung tissue. Specific, but non-limiting modes for administration to lung tissue are disclosed in Wheeler, C. J., et al., *Proc. Natl. Acad. Sci. USA* 93:11454-11459 (1996), which is incorporated herein by reference in its entirety.

According to the disclosed methods, compositions of the present invention can be administered by intramuscular (i.m.), subcutaneous (s.c.), or intrapulmonary routes. Other suitable routes of administration include, but are not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), inraatrial (i.e., into the heart atrium) and sub arachnoid (i.e., into the sub arachnoid spaces of the brain) administration.

Any mode of administration can be used so long as the mode results in the expression of the desired peptide or protein, in the desired tissue, in an amount sufficient to generate an immune response to IV and/or to generate a prophylactically or therapeutically effective immune response to IV in a human in need of such response. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15: 1908-1916 (1997)), Biojector (Davis, H., et al., *Vaccine* 12: 1503-1509 (1994); Gramzinski, R., et al., *Mol. Med.* 4: 109-118 (1998)), AdvantaJet (Linmayer, I., et al., *Diabetes Care* 9:294-297 (1986)), Medijector (Martins, J., and Roedl, E. J. *Occup. Med.* 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., *Life Sciences* 65: 2193-2203 (1999)) or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M. et al., *Proc. Natl. Acad. Sci. USA* 96:4262-7 (1999); Hartikka, J. et al., *Mol. Ther.* 4:407-15 (2001); Mathiesen, I., *Gene Ther.* 6:508-14 (1999); Rizzuto G. et al., *Hum. Gen. Ther.* 11:1891-900 (2000). Each of the references cited in this paragraph is incorporated herein by reference in its entirety.

Determining an effective amount of one or more compositions of the present invention depends upon a number of factors including, for example, the antigen being expressed or administered directly, e.g., HA, NA, NP, M1 or M2, or fragments, e.g., eM2, variants, or derivatives thereof, the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

Compositions of the present invention may include various salts, excipients, delivery vehicles and/or auxiliary agents as are disclosed, e.g., in U.S. Patent Application Publication No. 2002/0019358, published Feb. 14, 2002, which is incorporated herein by reference in its entirety.

Furthermore, compositions of the present invention may include one or more transfection facilitating compounds that facilitate delivery of polynucleotides to the interior of a cell, and/or to a desired location within a cell. As used herein, the terms "transfection facilitating compound," "transfection facilitating agent," and "transfection facilitating material" are synonymous, and may be used interchangeably. It should be noted that certain transfection facilitating compounds may also be "adjuvants" as described infra, i.e., in addition to facilitating delivery of polynucleotides to the interior of a cell, the compound acts to alter or increase the immune response to the antigen encoded by that polynucleotide. Examples of the transfection facilitating compounds include, but are not limited to inorganic materials such as calcium phosphate, alum (aluminum sulfate), and gold particles (e.g., "powder" type delivery vehicles); peptides that are, for example, cationic, intercell targeting (for selective delivery to certain cell types), intracell targeting (for nuclear localization or endosomal escape), and amphipathic (helix forming or pore forming); proteins that are, for example, basic (e.g., positively charged) such as histones, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); and polymers such as dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), poloxamers (e.g., CRL 1005) and polyethylene glycol (PEG). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., *Biochim. Biophys. Acta* 1380(3):354-368 (1988)), mechanical mixing (e.g., free moving materials in liquid or solid phase such as "polylysine+cationic lipids") (Gao and Huang, Biochemistry 35:1027-1036 (1996); Trubetskoy, et al., *Biochem. Biophys. Acta* 1131:311-313 (1992)), and aggregation (e.g., co-precipitation, gel forming such as in cationic lipids+poly-lactide, and polylysine+gelatin). Each of the references cited in this paragraph is incorporated herein by reference in its entirety.

One category of transfection facilitating materials is cationic lipids. Examples of cationic lipids are 5-carboxyspermylglycine dioctadecylamide (DOGS) and dipalmitoyl-phosphatidylethanolamine-5-carboxyspermylamide (DPPES). Cationic cholesterol derivatives are also useful, including {3β-[N-N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino)propyl-ammonium bromide (PA-TELO), and N1-(3-aminopropyl)((2-dodecyloxy)ethyl)-N2-(2-dodecyloxy)ethyl-1-piperazinaminium bromide (GA-LOE-BP) can also be employed in the present invention.

Non-diether cationic lipids, such as DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. In some embodiments, cationic lipids comprise groups attached via a heteroatom attached to the quaternary ammonium moiety in the head group. A glycyl spacer can connect the linker to the hydroxyl group.

Specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Other specific but non-limiting cationic surfactants for use in certain embodiments of the present invention include Bn-DMRIE, DhxRIE, DhxRIE-OAc, DhxRIE-OBz and Pr-DOctRIE-OAc. These lipids are disclosed in copending U.S. patent application Ser. No. 10/725,015. In another aspect of the present invention, the cationic surfactant is Pr-DOctRIE-OAc.

Other cationic lipids include (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., *Biochim. Biophys. Acta* 1280:1-11 (1996), and (±)-N-(3-aminopropyl)-N,N-dimethyl-2,3-bis (dodecyloxy)-1-propaniminium bromide (GAP-DLRIE) (Wheeler, et al., *Proc. Natl. Acad. Sci. USA* 93:11454-11459 (1996)), which have been developed from DMRIE. Both of the references cited in this paragraph are incorporated herein by reference in their entirety.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N-((N''-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

In the embodiments where the immunogenic composition comprises a cationic lipid, the cationic lipid may be mixed with one or more co-lipids. For purposes of definition, the term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. One non-limiting class of co-lipids are the zwitterionic phospholipids, which include the phosphatidylethanolamines and the phosphatidylcholines. Examples of phosphatidylethanolamines, include DOPE, DMPE and DPyPE. In certain embodiments, the co-lipid is DPyPE, which comprises two phytanoyl substituents incorporated into the diacylphosphatidylethanolamine skeleton. In other embodiments, the co-lipid is DOPE, CAS name 1,2-diolyeoyl-sn-glycero-3-phosphoethanolamine.

When a composition of the present invention comprises a cationic lipid and co-lipid, the cationic lipid:co-lipid molar ratio may be from about 9:1 to about 1:9, from about 4:1 to about 1:4, from about 2:1 to about 1:2, or about 1:1.

In order to maximize homogeneity, the cationic lipid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, a codon-optimized polynucleotide of the present invention, according to methods known to those skilled in the art. For example, the sonication of a lipid solution is described in Feigner et al., *Proc. Natl. Acad. Sci. USA* 8: 7413-7417 (1987) and in U.S. Pat. No. 5,264,618, the disclosures of which are incorporated herein by reference.

In those embodiments where the composition includes a cationic lipid, polynucleotides of the present invention are complexed with lipids by mixing, for example, a plasmid in aqueous solution and a solution of cationic lipid:co-lipid as prepared herein are mixed. The concentration of each of the constituent solutions can be adjusted prior to mixing such that the desired final plasmid/cationic lipid:co-lipid ratio and the desired plasmid final concentration will be obtained upon mixing the two solutions. The cationic lipid:co-lipid mixtures are suitably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in compositions of the present invention. In such compositions, these additives may be included in an amount between about 0.1 mol % and about 99.9 mol % (relative to total lipid), about 1-50 mol %, or about 2-25 mol %.

Additional embodiments of the present invention are drawn to compositions comprising an auxiliary agent which is administered before, after, or concurrently with the polynucleotide. As used herein, an "auxiliary agent" is a substance included in a composition for its ability to enhance, relative to is composition which is identical except for the inclusion of the auxiliary agent, the entry of polynucleotides into vertebrate cells in vivo, and/or the in vivo expression of polypeptides encoded by such polynucleotides. Certain auxiliary agents may, in addition to enhancing entry of polynucleotides into cells, enhance an immune response to an immunogen encoded by the polynucleotide. Auxiliary agents of the present invention include nonionic, anionic, cationic, or zwitterionic surfactants or detergents, with nonionic surfactants or detergents being preferred, chelators, DNase inhibitors, poloxamers, agents that aggregate or condense nucleic acids, emulsifying or solubilizing agents, wetting agents, gel-forming agents, and buffers.

Auxiliary agents for use in compositions of the present invention include, but are not limited to non-ionic detergents and surfactants IGEPAL CA 630®, NONIDET NP-40, Nonidet® P40, Tween-20TH, Tween-80TH, Pluronic® F68 (ave. MW: 8400; approx. MW of hydrophobe, 1800; approx. wt. % of hydrophile, 80%), Pluronic F77® (ave. MW: 6600; approx. MW of hydrophobe, 2100; approx. wt. % of hydrophile, 70%), Pluronic P65® (ave. MW: 3400; approx. MW of hydrophobe, 1800; approx. wt. % of hydrophile, 50%), Triton X100™, and Triton X-114™; the anionic detergent sodium dodecyl sulfate (SDS); the sugar stachyose; the condensing agent DMSO; and the chelator/DNAse inhibitor EDTA, CRL 1005 (12 kDa, 5% POE), and BAK (Benzalkonium chloride 50% solution, available from Ruger Chemical Co. Inc.). In certain specific embodiments, the auxiliary agent is DMSO, Nonidet P40, Pluronic F68® (ave. MW: 8400; approx. MW of hydrophobe, 1800; approx. wt. % of hydrophile, 80%), Pluronic F77® (ave. MW: 6600; approx. MW of hydrophobe, 2100; approx. wt. % of hydrophile, 70%), Pluronic P650 (ave. MW: 3400; approx. MW of hydrophobe, 1800; approx. wt. % of hydrophile, 50%), Pluronic L64® (ave. MW: 2900; approx. MW of hydrophobe, 1800; approx. wt. % of hydrophile, 40%), and Pluronic F108® (ave. MW: 14600; approx. MW of hydrophobe, 3000; approx. wt. % of hydrophile, 80%). See, e.g., U.S. Patent Application Publication No. 2002/0019358, published Feb. 14, 2002, which is incorporated herein by reference in its entirety.

Certain compositions of the present invention can further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," can be a transfection facilitating material. Similarly, certain "transfection facilitating materials" described supra, may also be an "adjuvant." An adjuvant may be used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: inert carriers, such as alum, bentonite, latex, and acrylic particles; pluronic block polymers, such as TiterMax® (block copolymer CRL-8941, squalene (a metabolizable oil) and a microparticulate silica stabilizer); depot formers, such as Freunds adjuvant, surface active materials, such as saponin, lysolecithin, retinal, Quil A, liposomes, and pluronic polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly(oxypropylene) tri-block copolymers. Also included as adjuvants are transfection-facilitating materials, such as those described above.

Poloxamers which may be screened for their ability to enhance the immune response according to the present invention include, but are not limited to, commercially available poloxamers such as Pluronic® surfactants, which are block copolymers of propylene oxide and ethylene oxide in which the propylene oxide block is sandwiched between two ethylene oxide blocks. Examples of Pluronic® surfactants include Pluronic® L121 (ave. MW: 4400; approx. MW of hydrophobe, 3600; approx. wt. % of hydrophile, 10%), Pluronic® L101 (ave. MW: 3800; approx. MW of hydrophobe, 3000; approx. wt. % of hydrophile, 10%), Pluronic® L81 (ave. MW: 2750; approx. MW of hydrophobe, 2400; approx. wt. % of hydrophile, 10%), Pluronic® L61 (ave. MW: 2000; approx. MW of hydrophobe, 1800; approx. wt. % of hydrophile, 10%), Pluronic® L31 (ave. MW: 1100; approx. MW of hydrophobe, 900; approx. wt. % of hydrophile, 10%), Pluronic® L122 (ave. MW: 5000; approx. MW of hydrophobe, 3600; approx. wt. % of hydrophile, 20%), Pluronic® L92 (ave. MW: 3650; approx. MW of hydrophobe, 2700; approx. wt. % of hydrophile, 20%), Pluronic® L72 (ave. MW: 2750; approx. MW of hydrophobe, 2100; approx. wt. % of hydrophile, 20%), Pluronic® L62 (ave. MW: 2500; approx. MW of hydrophobe, 1800; approx. wt. % of hydrophile, 20%), Pluronic® L42 (ave. MW: 1630; approx. MW of hydrophobe, 1200; approx. wt. % of hydrophile, 20%), Pluronic® L63 (ave. MW: 2650; approx. MW of hydrophobe, 1800; approx. wt. % of hydrophile, 30%), Pluronic® L43 (ave. MW: 1850; approx. MW of hydrophobe, 1200; approx. wt. % of hydrophile, 30%), Pluronic® L64 (ave. MW: 2900; approx. MW of hydrophobe, 1800; approx. wt. % of hydrophile, 40%), Pluronic® L44 (ave. MW: 2200; approx. MW of hydrophobe, 1200; approx. wt. % of hydrophile, 40%), Pluronic® L35 (ave. MW: 1900; approx. MW of hydrophobe, 900; approx. wt. % of hydrophile, 50%), Pluronic® P123 (ave. MW: 5750; approx. MW of hydrophobe, 3600; approx. wt. % of hydrophile, 30%), Pluronic® P103 (ave. MW: 4950; approx. MW of hydrophobe, 3000; approx. wt. % of hydrophile, 30%), Pluronic® P104 (ave. MW: 5900; approx. MW of hydrophobe, 3000; approx. wt. % of hydrophile, 40%), Pluronic® P84 (ave. MW: 4200; approx. MW of hydrophobe, 2400; approx. wt. % of hydrophile, 40%), Pluronic® P105 (ave. MW: 6500; approx. MW of hydrophobe, 3000; approx. wt. % of hydrophile, 50%), Pluronic® P85 (ave. MW: 4600; approx. MW of hydrophobe, 2400; approx. wt. % of hydrophile, 50%), Pluronic® P75 (ave. MW: 4150; approx. MW of hydrophobe, 2100; approx. wt. % of hydrophile, 50%), Pluronic® P65 (ave. MW: 3400; approx. MW of hydrophobe, 1800; approx. wt. % of hydrophile, 50%), Pluronic® F127 (ave. MW: 12600; approx. MW of hydrophobe, 3600; approx. wt. % of hydrophile, 70%), Pluronic® F98 (ave. MW: 13000; approx. MW of hydrophobe, 2700; approx. wt. % of hydrophile, 80%), Pluronic® F87 (ave. MW: 7700; approx. MW of hydrophobe, 2400; approx. wt. % of hydrophile, 70%), Pluronic® F77 (ave. MW: 6600; approx. MW of hydrophobe, 2100; approx. wt. % of hydrophile, 70%), Pluronic® F108 (ave. MW: 14600; approx. MW of hydrophobe, 3000; approx. wt. % of hydrophile, 80%), Pluronic® F98 (ave. MW: 13000; approx. MW of hydrophobe, 2700; approx. wt. % of hydrophile, 80%), Pluronic® F88 (ave. MW: 11400; approx. MW of hydrophobe, 2400; approx. wt. % of hydrophile, 80%), Pluronic® F68 (ave. MW: 8400; approx. MW of hydrophobe, 1800; approx. wt. % of hydrophile, 80%), Pluronic® F38 (ave. MW: 4700; approx. MW of hydrophobe, 900; approx. wt. % of hydrophile, 80%).

Reverse poloxamers which may be screened for their ability to enhance the immune response according to the present invention include, but are not limited to Pluronic® R 31R1 (ave. MW: 3250; approx. MW of hydrophobe, 3100; approx. wt. % of hydrophile, 10%), Pluronic® R 25R1 (ave. MW: 2700; approx. MW of hydrophobe, 2500; approx. wt. % of hydrophile, 10%), Pluronic® R 17R1 (ave. MW: 1900; approx. MW of hydrophobe, 1700; approx. wt. % of hydrophile, 10%), Pluronic® R 31R2 (ave. MW: 3300; approx. MW of hydrophobe, 3100; approx. wt. % of hydrophile, 20%), Pluronic® R 25R2 (ave. MW: 3100; approx. MW of hydrophobe, 2500; approx. wt. % of hydrophile, 20%), Pluronic® R 17R2 (ave. MW: 2150; approx. MW of hydrophobe, 1700; approx. wt. % of hydrophile, 20%), Pluronic® R 12R3 (ave. MW: 1800; approx. MW of hydrophobe, 1200; approx. wt. % of hydrophile, 30%), Pluronic® R 31R4 (ave. MW: 4150; approx. MW of hydrophobe, 3100; approx. wt. % of hydrophile, 40%), Pluronic® R 25R4 (ave. MW: 3600; approx. MW of hydrophobe, 2500; approx. wt. % of hydrophile, 40%), Pluronic® R 22R4 (ave. MW: 3350; approx. MW of hydrophobe, 2200; approx. wt. % of hydrophile, 40%), Pluronic® R 17R4 (ave. MW: 3650; approx. MW of hydrophobe, 1700; approx. wt. % of hydrophile, 40%), Pluronic® R 25R5 (ave. MW: 4320; approx. MW of hydrophobe, 2500; approx. wt. % of hydrophile, 50%), Pluronic® R 10R5 (ave. MW: 1950; approx. MW of hydrophobe, 1000; approx. wt. % of hydrophile, 50%), Pluronic® R 25R8 (ave. MW: 8550; approx. MW of hydrophobe, 2500; approx. wt. % of hydrophile, 80%), Pluronic® R 17R8 (ave. MW: 7000;

approx. MW of hydrophobe, 1700; approx. wt. % of hydrophile, 80%), and Pluronic® R 10R8 (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as Synperonic® L121 (ave. MW: 4400), Synperonic® L122 (ave. MW: 5000), Synperonic® P104 (ave. MW: 5850), Synperonic® P105 (ave. MW: 6500), Synperonic® P123 (ave. MW: 5750), Synperonic® P85 (ave. MW: 4600) and Synperonic® P94 (ave. MW: 4600), in which L indicates that the surfactants are liquids, P that they are pastes, the first digit is a measure of the molecular weight of the polypropylene portion of the surfactant and the last digit of the number, multiplied by 10, gives the percent ethylene oxide content of the surfactant; and compounds that are nonylphenyl polyethylene glycol such as Synperonic® NP10 (nonylphenol ethoxylated surfactant −10% solution), Synperonic® NP30 (condensate of 1 mole of nonylphenol with 30 moles of ethylene oxide) and Synperonic® NP5 (condensate of 1 mole of nonylphenol with 5.5 moles of naphthalene oxide).

Other poloxamers which may be screened for their ability to enhance the immune response according to the present invention include: (a) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—$R^0$, wherein $R^0$ is a straight chain aliphatic group of 2 to 6 carbon atoms, which may be substituted, wherein said polyether segments comprise at least one of an A-type of B-type segment. See U.S. Pat. No. 5,656,611, by Kabonov, et al., which is incorporated herein by reference in its entirety. Other poloxamers of interest include CRL1005 (12 kDa, 5% POE), CRL8300 (11 kDa, 5% POE), CRL2690 (12 kDa, 10% POE), CRL4505 (15 kDa, 5% POE) and CRL1415 (9 kDa, 10% POE).

Other auxiliary agents which may be screened for their ability to enhance the immune response according to the present invention include, but are not limited to *Acacia* (gum arabic); the poloxyethylene ether R—O—$(C_2H_4O)_x$—H (BRIJ®), e.g., polyethylene glycol dodecyl ether (BRIJ® 35, x=23), polyethylene glycol dodecyl ether (BRU® 30, x=4), polyethylene glycol hexadecyl ether (BRU® 52 x=2), polyethylene glycol hexadecyl ether (BRIJ® 56, x=10), polyethylene glycol hexadecyl ether (BRIJ® 58P, x=20), polyethylene glycol octadecyl ether (BRIJ® 72, x=2), polyethylene glycol octadecyl ether (BRIJ® 76, x=10), polyethylene glycol octadecyl ether (BRIJ® 78P, x=20), polyethylene glycol oleyl ether (BRIJ® 92V, x=2), and polyoxyl 10 oleyl ether (BRIJ® 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40®); octylphenoxypolyethoxyethanol (NONIDET NP-40 from Amresco); ethyl phenol poly (ethylene glycol ether)", n=11 (Nonidet® P40 from Roche); octyl phenol ethylene oxide condensate with about 9 ethylene oxide units (nonidet P40); IGEPAL CA 630® ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20®; polyoxyethylene sorbitan monooleate (polysorbate 80, or TWEEN-80®); propylene glycol diacetate; propylene glycol monstearate; protamine sulfate; proteolytic enzymes; sodium dodecyl sulfate (SDS); sodium monolaurate; sodium stearate; sorbitan derivatives (SPAN®), e.g., sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85); 2,6,10,15,19,23-hexamethyl-2,6,10,14,18,22-tetracosa-hexaene (squalene); stachyose; stearic acid; sucrose; surfactin (lipopeptide antibiotic from *Bacillus subtilis*); dodecylpoly$(ethyleneglycolether)_9$ (Thesit®) MW 582.9; octyl phenol ethylene oxide condensate with about 9-10 ethylene oxide units (Triton X-100™); octyl phenol ethylene oxide condensate with about 7-8 ethylene oxide units (Triton X-114™); tris(2-hydroxyethyl) amine (trolamine); and emulsifying wax.

In certain adjuvant compostions, the adjuvant is a cytokine. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFN$\alpha$), interferon beta (IFN$\beta$), interferon gamma (IFN$\gamma$), interferon omega (IFN$\omega$), interferon tau (IFN$\tau$), interferon gamma inducing factor I (IGIF), transforming growth factor beta (TGF-$\beta$), RANTES (regulated upon activation, normal T-cell expressed and presumably secreted), macrophage inflammatory proteins (e.g., MIP-1 alpha and MIP-1 beta), *Leishmania* elongation initiating factor (LEIF), and Flt-3 ligand.

In certain compositions of the present invention, the polynucleotide construct may be complexed with an adjuvant composition comprising (±)-N-(3-aminopropyl)-N,N-dimethyl-2,3-bis(syn-9-tetradeceneyloxy)-1-p-ropanaminium bromide (GAP-DMORIE). The composition may also comprise one or more co-lipids, e.g., 1,2-dioleoyl-sn-glycero-3-phosphoethanolamine (DOPE),1,2-diphytanoyl-sn-glycero-3-phosphoethanolamine (DPyPE), and/or 1,2-dimyristoyl-glycero-3-phosphoethanolamine (DMPE). An adjuvant composition comprising GAP-DMORIE and DPyPE at a 1:1 molar ratio is referred to herein as Vaxfectin™. See, e.g., PCT Publication No. WO 00/57917, which is incorporated herein by reference in its entirety.

In other embodiments, the polynucleotide itself may function as an adjuvant as is the case when the polynucleotides of the invention are derived, in whole or in part, from bacterial DNA. Bacterial DNA containing motifs of unmethylated CpG-dinucleotides (CpG-DNA) triggers innate immune cells in vertebrates through a pattern recognition receptor (including toll receptors such as TLR 9) and thus possesses potent immunostimulatory effects on macrophages, dendritic cells and B-lymphocytes. See, e.g., Wagner, H., *Curr. Opin. Microbiol.* 5:62-69 (2002); Jung, J. et al., *J. Immunol.* 169: 2368-73 (2002); see also Klinman, D. M. et al., *Proc. Natl Acad. Sci. U.S.A.* 93:2879-83 (1996). Methods of using unmethylated CpG-dinucleotides as adjuvants are described in, for example, U.S. Pat. Nos. 6,207,646, 6,406,705 and 6,429,199, the disclosures of which are herein incorporated by reference.

The ability of an adjuvant to increase the immune response to an antigen is typically manifested by a significant increase in immune-mediated protection. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or $Th_2$ response into a primarily cellular, or $Th_1$ response.

Nucleic acid molecules and/or polynucleotides of the present invention, e.g., plasmid DNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995), both of which are incorporated herein by reference in their entireties. Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims. All references cited in the Examples are incorporated herein by reference in their entireties.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual,* 2nd Ed., Sambrook et al., ed., Cold Spring Harbor Laboratory Press: (1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R: I. Freshney, Alan R. Liss, Inc., 1987); *Immobilized Cells And Enzymes* (IRL Press, 1986); B. Perbal, A Practical *Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); and in Ausubel et al., *Current Protocols in Molecular Biology*, John Wiley and Sons, Baltimore, Md. (1989). Each of the references cited in this paragraph is incorporated herein by reference in its entirety.

Gene Construction

Constructs of the present invention are constructed based on the sequence information provided herein or in the art utilizing standard molecular biology techniques, including, but not limited to the following. First, a series complementary oligonucleotide pairs of 80-90 nucleotides each in length and spanning the length of the construct are synthesized by standard methods. These oligonucleotide pairs are synthesized such that upon annealing, they form double stranded fragments of 80-90 base pairs, containing cohesive ends. The single-stranded ends of each pair of oligonucleotides are designed to anneal with a single-stranded end of an adjacent oligonucleotide duplex. Several adjacent oligonucleotide pairs prepared in this manner are allowed to anneal, and approximately five to six adjacent oligonucleotide duplex fragments are then allowed to anneal together via the cohesive single stranded ends. This series of annealed oligonucleotide duplex fragments is then ligated together and cloned into a suitable plasmid, such as the TOPO® vector available from Invitrogen Corporation, Carlsbad, Calif. The construct is then sequenced by standard methods. Constructs prepared in this manner, comprising 5 to 6 adjacent 80 to 90 base pair fragments ligated together, i.e., fragments of about 500 base pairs, are prepared, such that the entire desired sequence of the construct is represented in a series of plasmid constructs. The inserts of these plasmids are then cut with appropriate restriction enzymes and ligated together to form the final construct. The final construct is then cloned into a standard bacterial cloning vector, and sequenced. The oligonucleotides and primers referred to herein can easily be designed by a person of skill in the art based on the sequence information provided herein and in the art, and such can be synthesized by any of a number of commercial nucleotide providers, for example Retrogen, San Diego, Calif., and GENEART, Regensburg, Germany.

Plasmid Vectors

Constructs of the present invention can be inserted, for example, into eukaryotic expression vectors VR1012 or VR10551. These vectors are built on a modified pUC18 background (see Yanisch-Perron, C., et al. *Gene* 33:103-119 (1985)), and contain a kanamycin resistance gene, the human cytomegalovirus immediate early promoter/enhancer and intron A, and the bovine growth hormone transcription termination signal, and a polylinker for inserting foreign genes. See Hartikka, J., et al., *Hum. Gene Ther.* 7:1205-1217 (1996). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6N5-His, pVAX1, and pZeoSV2 (available from Invitrogen, San Diego, Calif.), and plasmid pCI (available from Promega, Madison, Wis.).

An optimized backbone plasmid, termed VR10551, has minor changes from the VR1012 backbone described above. The VR10551 vector is derived from and similar to VR1012 in that it uses the human cytomegalovirus immediate early (hCMV-IE) gene enhancer/promoter and 5' untranslated region (UTR), including the hCMV-IE Intron A. The changes from the VR1012 to the VR10551 include some modifications to the multiple cloning site, and a modified rabbit β globin 3' untranslated region/polyadenylation signal sequence/transcriptional terminator has been substituted for the same functional domain derived from the bovine growth hormone gene.

Additionally, constructs of the present invention can be inserted into other eukaryotic expression vector backbones such as VR10682 or VR10686. The VR10682 expression vector backbone (SEQ ID NO:94) contains a modified rous sarcoma virus (RSV) promoter from expression plasmid VCL1005, the bovine growth hormone (BGH) poly-adenylation site and a polylinker for inserting foreign genes and a kanamycin resistance gene. The RSV promoter in VCL1005 and VR10682 contains a XbaI endonuclease restriction site near the transcription start site in the sequence TAC TCT AGA CG (SEQ ID NO:82). The modified RSV promoter contained in plasmid VR10682. Expression plasmid VCL1005 is described in U.S. Pat. No. 5,561,064 and is incorporated herein by reference.

The VR10686 expression vector backbone (SEQ ID NO:112) was created by replacing the West Nile Virus (WNV) antigen insert in VR6430 (SEQ ID NO:89) with the multiple cloning site from the VR1012 vector. The VR10686 and VR6430 expression vector backbones contain the RSV promoter, derived from VCL1005, which has been modified back to the wild-type RSV sequence (TAC AAT AAA CG (SEQ ID NO:83)). The wild-type RSV promoter is fused to the "R" region plus the first 39 nucleotides of the U5 region from Human T-Cell Leukemia Virus I (HTLV-I), hereinafter referred to as the RU5 element. The R and U5 regions are portions of the long terminal repeat region (LTR) of HTLV-I which control expression of the HTLV-I transcript and is duplicated at either end of the integrated viral genome as a result of the retroviral integration mechanism. The LTR of HTLV-1 and most retroviruses are divided into three regions, U3, R and U5. Transcription from the intigrated viral genome commences at the U3-R boundary of the 5' LTR and the transcript is polyadenylated at the R-U5 boundary of the 3' LTR. (See Goff, S. P. Retroviridae, *Field's Virology* $4^{th}$ ed. 2:1871-1939 (2001). This RU5 HTLV-I element has been shown to be a potent stimulator of translation when fused to the SV40 early gene promoter. See Takebe et al., *Mol. Cell. Biol.* 8:466-472 (1988). It has been proposed that the stimulation of translation by the HTLV-I RU5 element is due to its function, in part, as a translational enhancing internal ribosome entry site (IRES). See Attal et al. *FEBS Letters* 392: 220-224 (1996). Additionally the HTLV-I RU5 element provides the 5'-splice donor site. Immediately downstream of the RU5 element is the 3'-end of the HCMV intron A sequence containing the splice acceptor sequence. The VR10686 and VR6430 expression vectors contain a hybrid intron composed of the 5'-HTLV I intron sequence fused to the 3'-end of the HCMV intron A, a bovine growth hormone poly-adenylation site, a polylinker for insertion of forign genes and a kanamycin resistance gene. The VR6430 vector expresses the prM and E West Nile Virus antigens (Genebank Accession No. AF202541).

The vector backbones described above may by used to create expression vectors which express multiple influenza proteins, fragments, variants or derivatives thereof. An expression vector as described herein may contain an additional promoter. For example, construct VR4774 (described in Example 13), contains a CMV promoter and an RSV promoter. Thus, the vector backbones described herein may contain multiple expression cassettes which comprise a promoter and an influenza coding sequence including, inter alia, polynucleotides as described herein. The expression cassettes may encode the same or different influenza polypeptides. Additionally, the expression cassettes may be in the same or opposite orientation relative to each other. As such transcription from each cassette may be in the same or opposition direction (i.e. 5' to 3' in both expression cassettes or, alternatively, 5' to 3' in one expression cassette and 3' to 5' in the other expression cassette).

Plasmid DNA Purification

Plasmid DNA may be transformed into competent cells of an appropriate *Escherichia coli* strain (including but not limited to the DH5a strain) and highly purified covalently closed circular plasmid DNA was isolated by a modified lysis procedure (Horn, N. A., et al., *Hum. Gene Ther.* 6:565-573 (1995)) followed by standard double CsCl-ethidium bromide gradient ultracentrifugation (Sambrook, J., et al., *Molecular Cloning: A Laboratory Manual,* 2nd Ed., Cold Spring Harbor Laboratory Press, Plainview, N.Y. (1989)). Alternatively, plasmid DNAs are purified using Giga columns from Qiagen (Valencia, Calif.) according to the kit instructions. All plasmid preparations were free of detectable chromosomal DNA, RNA and protein impurities based on gel analysis and the bicinchoninic protein assay (Pierce Chem. Co., Rockford Ill.). Endotoxin levels were measured using *Limulus Amebocyte* Lysate assay (LAL, Associates of Cape Cod, Falmouth, Mass.) and were less than 0.6 Endotoxin Units/mg of plasmid DNA. The spectrophotometric $A_{260})/A_{280}$ ratios of the DNA solutions were typically above 1.8. Plasmids were ethanol precipitated and resuspended in an appropriate solution, e.g., 150 mM sodium phosphate (for other appropriate excipients and auxiliary agents, see U.S. Patent Application Publication 2002/0019358, published Feb. 14, 2002). DNA was stored at −20EC until use. DNA was diluted by mixing it with 300 mM salt solutions and by adding appropriate amount of USP water to obtain 1 mg/ml plasmid DNA in the desired salt at the desired molar concentration.

Plasmid Expression in Mammalian Cell Lines

The expression plasmids were analyzed in vitro by transfecting the plasmids into a well characterized mouse melanoma cell line (VM-92, also known as UM-449). See, e.g., Wheeler, C. J., Sukhu, L., Yang, G., Tsai, Y., Bustamente, C., Feigner, P. Norman, J & Manthorpe, M. "Converting an Alcohol to an Amine in a Cationic Lipid Dramatically Alters the Co-lipid Requirement, Cellular Transfection Activity and the Ultrastructure of DNA-Cytofectin Complexes," *Biochim. Biophys. Acta.* 1280:1-11 (1996). Other well-characterized human cell lines can also be used, e.g. MRC-5 cells, ATCC Accession No. CCL-171 or human rhabdomyosarcoma cell line RD (ATCC CCL-136). The transfection was performed using cationic lipid-based transfection procedures well known to those of skill in the art. Other transfection procedures are well known in the art and may be used, for example electroporation and calcium chloride-mediated transfection (Graham F. L. and A. J. van der Eb *Virology* 52:456-67 (1973)). Following transfection, cell lysates and culture supernatants of transfected cells were evaluated to compare relative levels of expression of IV antigen proteins. The samples were assayed by western blots and ELISAs, using commercially available polyclonal and/or monoclonal antibodies (available, e.g., from Research Diagnostics Inc., Flanders N.J.), so as to compare both the quality and the quantity of expressed antigen.

Injections of Plasmid DNA

The quadriceps muscles of restrained awake mice (e.g., female 6-12 week old BALB/c mice from Harlan Sprague Dawley, Indianapolis, Ind.) are injected bilaterally with 1-50 μg of DNA in 50 μl solution (100 μg in 100 μl total per mouse) using a disposable plastic insulin syringe and 28G1/2 needle (Becton-Dickinson, Franklin Lakes, N.J., Cat. No. 329430) fitted with a plastic collar cut from a micropipette tip, as previously described (Hartikka, J., et al., *Hum. Gene Ther.* 7:1205-1217 (1996).

Animal care throughout the study was in compliance with the "Guide for the Use and Care of Laboratory Animals", Institute of Laboratory Animal Resources, Commission on Life Sciences, National Research Council, National Academy Press, Washington, D.C., 1996 as well as with Vical's Institutional Animal Care and Use Committee.

Example 1

Construction of Expression Vectors

Plasmid constructs comprising the native coding regions encoding NP, M1, M2, HA, and eM2, IV proteins or fragments, variants or derivatives are constructed as follows. The NP, M1, and M2 genes from IV (A/PR/8/34) are isolated from viral RNA by RT PCR, or prepared by direct synthesis if the wildtype sequence is known, by standard methods and are inserted into the vector VR10551 via standard restriction sites, by standard methods.

Plasmid constructs comprising human codon-optimized coding regions encoding NP, M1, M2, HA, eM2, and/or an eM2-NP fusion; or other codon-optimized coding regions encoding other IV proteins or fragments, variants or derivatives either alone or as fusions with a carrier protein, e.g., HBcAg, are prepared as follows. The codon-optimized coding regions are generated using the full, minimal, or uniform codon optimization methods described herein. The codon optimized coding regions are constructed using standard PCR methods described herein, or are ordered commercially. Oligonucleotides representing about the first 23-24 aa extracellular region of M2 are constructed, and are used in an overlap PCR reaction with the NP coding regions described above, to create a coding region coding for an eM2/NP fusion protein, for example as shown in SEQ ID NOs 6 and 7. The codon-optimized coding regions are inserted into the vector VR10551 via standard restriction sites, by standard methods.

Plasmids constructed as above are propagated in *Escherichia coli* and purified by the alkaline lysis method (Sambrook, J., et al., *Molecular Cloning: A Laboratory Manual*, Cold Spring Harbor Laboratory Press, Cold Spring Harbor, N. Y., ed. 2 (1989)). CsCl-banded DNA are ethanol precipitated and resuspended in 0.9% saline or PBS to a final concentration of 2 mg/ml for injection. Alternately, plasmids are purified using any of a variety of commercial kits, or by other known procedures involving differential precipitation and/or chromatographic purification.

Expression is tested by formulating each of the plasmids in DMRIE/DOPE and transfecting VM92 cells. The supernatants are collected and the protein production tested by Western blot or ELISA. The relative expression of the wild type and codon optimized constructs are compared.

Examples of constructs made according to the above methods are listed in Table 13. The experimental procedure for generating the listed constructs is as described above, with particular parameters and materials employed as described herein.

TABLE 13

| Plasmid # | Description |
|---|---|
| VR4700 | TPA leader - NP (A/PR/34) in VR 1255 |
| VR4707 | TPA leader - M2 with transmembrane deletion, glycine linker inserted |
| VR4710 | TPA leader - 1st 24 amino acids of M2 from VR4707 fused to NP from VR4700 |
| VR4750 | full length HA from mouse adapted virus (H3, Hong Kong 68 ) |
| VR4752 | full length HA from mouse adapted virus (H1, Puerto Rico 34) |
| VR4755 | algorithm to codon optimize consensus amino acid sequence, direct fusion M2 to ATG of M1 |
| VR4756 | native sequence from A/Niigata/137/96 influenza strain (matches amino acid consensus sequence) |
| VR4757 | Contracted codon optimized - 1st 24 amino acids of M2 from consensus fused to full-length length NP consensus |
| VR4758 | Applicants' codon optimized - 1st 24 amino acids of M2 from consensus fused to full-length NP consensus |
| VR4759 | Full-length M2 derived from VR4755 |
| VR4760 | Full-length M1 derived from VR4755 |
| VR4761 | Full-length NP derived from VR4757 |
| VR4762 | Full-length NP derived from VR4758 |
| VR4763 | Selectively codon-optimized regions of segment 7 |

The pDNA expression vector VR4700 which encodes the influenza NP protein has been described in the art. See, e.g. Sankar, V., Baccaglilni, L., Sawddey, M., Wheeler, C. J., Pillemer, S. R., Baum, B. J. and Atkinson, J. C., "Salivary Gland Delivery of pDNA-Cationic Lipolplexes Elicits Systemic Immune Responses," *Oral Diseases* 8:275-281 (2002). The following is the open reading frame for TPA-NP (from VR4700), referred to herein as SEQ ID NO:46:

```
  1  atggatgcaa tgaagagagg gctctgctgt gtgctgctgc tgtgtggagc agtcttcgtt
 61  tcgcccagcg ctagaggatc gggaatggcg tcccaaggca ccaaacggtc ttacgaacag
121  atggagactg atggagaacg ccagaatgcc actgaaatca gagcatccgt cggaaaaatg
181  attggtggaa ttggacgatt ctacatccaa atgtgcaccg aactcaaact cagtgattat
241  gagggacggt tgatccaaaa cagcttaaca atagagagaa tggtgctctc tgcttttgac
301  gaaaggagaa ataaatacct ggaagaacat cccagtgcgg ggaaagatcc taagaaaact
361  ggaggaccta tatacaggag agtaaacgga aagtggatga gagaactcat cctttatgac
```

-continued

```
421   aaagaagaaa taaggcgaat ctggcgccaa gctaataatg gtgacgatgc aacggctggt

481   ctgactcaca tgatgatctg gcattccaat ttgaatgatg caacttatca gaggacaaga

541   gctcttgttc gcaccggaat ggatcccagg atgtgctctc tgatgcaagg ttcaactctc

601   cctaggaggt ctggagccgc aggtgctgca gtcaaaggag ttggaacaat ggtgatggaa

661   ttggtcagga tgatcaaacg tgggatcaat gatcggaact tctggagggg tgagaatgga

721   cgaaaaacaa gaattgctta tgaaagaatg tgcaacattc tcaaagggaa atttcaaact

781   gctgcacaaa aagcaatgat ggatcaagtg agagagagcc ggaacccagg gaatgctgag

841   ttcgaagatc tcacttttct agcacggtct gcactcatat tgagagggtc ggttgctcac

901   aagtcctgcc tgcctgcctg tgtgtatgga cctgccgtag ccagtgggta cgactttgaa

961   agagagggat actctctagt cggaatagac cctttcagac tgcttcaaaa cagccaagtg

1021  tacagcctaa tcagaccaaa tgagaatcca gcacacaaga gtcaactggt gtggatggca

1081  tgccattctg ccgcatttga agatctaaga gtattaagct tcatcaaagg gacgaaggtg

1141  ctcccaagag ggaagctttc cactagagga gttcaaattg cttccaatga aaatatggag

1201  actatggaat caagtacact tgaactgaga agcaggtact gggccataag gaccagaagt

1261  ggaggaaaca ccaatcaaca gagggcatct gcgggccaaa tcagcataca acctacgttc

1321  tcagtacaga gaaatctccc ttttgacaga acaaccatta tggcagcatt caatgggaat

1381  acagagggaa gaacatctga catgaggacc gaaatcataa ggatgatgga aagtgcaaga

1441  ccagaagatg tgtctttcca ggggcgggga gtcttcgagc tctcggacga aaaggcagcg

1501  agcccgatcg tgccttcctt tgacatgagt aatgaaggat cttatttctt cggagacaat

1561  gcagatgagt acgacaatta a
```

Purified VR4700DNA was used to transfect the murine cell line VM92 to determine expression of the NP protein. Expression of NP was confirmed with a Western Blot assay. Western blot analysis showed very low level expression of VR4700 in vitro as detected with mouse polyclonal anti-NP antibody. In vivo antibody response was detected by ELISA with an average titer of 62,578.

Plasmid VR4707 expresses a secreted form of M2, i.e., TPA-M2. The sequence was assembled using synthetic oligonucleotides in which the oligos were annealed amongst themselves, and then ligated and gel purified. The purified product was then ligated (cloned) into Eco RI/Sal I of VR10551. The M2 sequence lacks the transmembrane domain; the cloned sequence contains amino acids [TPA(1-23)]ARGSG[M2(1-25)]GGG[M2(44-97)]. Amino acid residues between TPA and M2 and between M2 domains were added as flexible linkers. The following mutations were introduced to generate appropriate T-cell epitopes: 74S->G and 78S->N. The following is the open reading frame for TPA-M20ΔTM (from VR4707), referred to herein as SEQ ID NO:47:

Purified VR4707DNA was used to transfect the murine cell line VM92 to determine expression of the M2 protein. Expression of M2 was confirmed with a Western Blot assay. Expression was visualized with a commercially available anti-M2 monoclonal antibody. In vivo M2 antibody response to VR4707, as assayed by ELISA, resulted in an average titer of 110, which is lower than the average titer of 9,240 for VR4756, encoding full-length M2 from segment 7. An IFNγ ELISPOT assay for M2-specific T cells resulted in an average of 61 SFU/$10^6$ cells versus an average of 121 SFU/$10^6$ cells for the segment 7 construct.

VR4710 was created by fusing the TPA leader and the first 24 amino acids of M2 from VR4707 to the full-length NP gene from VR4700. Primers 5'-GCCGAATCCATGGATGCAATGAAG-3' (SEQ ID NO:48) and 5'-GGTGCCTTGGGACGCCATATCACTTGAATCGTTGCA-3' (SEQ ID NO:49) were used to amplify the TPA-M2 fragment from VR4707. Primers 5'-TGCAACGATTCAAGTGATATGGCGTCCCAAGGCACC-3' (SEQ ID NO:50) and 5'-GCCGTCGACTTAATTGTCGTACTC-3' (SEQ ID NO:51)

```
1     atggatgcaa tgaagagagg gctctgctgt gtgctgctgc tgtgtggagc agtcttcgtt

61    tcgcccagcg ctagaggatc gggaatgagt cttctgaccg aggtcgaaac ccctatcaga

121   aacgaatggg ggtgcagatg caacgattca agtgatcctg gcggcggcga tcggcttttt

181   ttcaaatgca tttatcggcg ctttaaatac ggcttgaaaa gagggccttc taccgaagga

241   gtgccagagt ctatgaggga agaatatcgg aaggaacagc agaatgctgt ggatgttgac

301   gatagccatt ttgtcagcat cgagctggag taa
```

were used to amplify the NP gene from VR4700. Then the N-terminal and C-terminal primers were used to assemble the fusion, and the eM2NP fusion was cloned into VR10551 as an EcoRI-SalI fragment. The following is the open reading frame for TPA-M2-NP (from VR4710), referred to herein as SEQ ID NO:52:

```
   1  atggatgcaa tgaagagagg gctctgctgt gtgctgctgc tgtgtggagc agtcttcgtt
  61  tcgcccagcg ctagaggatc gggaatgagt cttctgaccg aggtcgaaac ccctatcaga
 121  aacgaatggg ggtgcagatg caacgattca agtgatatgg cgtcccaagg caccaaacgg
 181  tcttacgaac agatggagac tgatggagaa cgccagaatg ccactgaaat cagagcatcc
 241  gtcggaaaaa tgattggtgg aattggacga ttctacatcc aaatgtgcac cgaactcaaa
 301  ctcagtgatt atgagggacg gttgatccaa aacagcttaa caatagagag aatggtgctc
 361  tctgcttttg acgaaaggag aaataaatac ctggaagaac atcccagtgc ggggaaagat
 421  cctaagaaaa ctggaggacc tatatacagg agagtaaacg gaaagtggat gagagaactc
 481  atcctttatg acaaagaaga aataaggcga atctggcgcc aagctaataa tggtgacgat
 541  gcaacggctg gtctgactca catgatgatc tggcattcca atttgaatga tgcaacttat
 601  cagaggacaa gagctcttgt tcgcaccgga atggatccca ggatgtgctc tctgatgcaa
 661  ggttcaactc tccctaggag gtctggagcc gcaggtgctg cagtcaaagg agttggaaca
 721  atggtgatgg aattggtcag gatgatcaaa cgtgggatca atgatcggaa cttctggagg
 781  ggtgagaatg gacgaaaaac aagaattgct tatgaaagaa tgtgcaacat tctcaaaggg
 841  aaatttcaaa ctgctgcaca aaaagcaatg atggatcaag tgagagagag ccggaaccca
 901  gggaatgctg agttcgaaga tctcactttt ctagcacggt ctgcactcat attgagaggg
 961  tcggttgctc acaagtcctg cctgcctgcc tgtgtgtatg gacctgccgt agccagtggg
1021  tacgactttg aaagagaggg atactctcta gtcggaatag accctttcag actgcttcaa
1081  aacagccaag tgtacagcct aatcagacca aatgagaatc cagcacacaa gagtcaactg
1141  gtgtggatgg catgccattc tgccgcattt gaagatctaa gagtattaag cttcatcaaa
1201  gggacgaagg tgctcccaag agggaagctt tccactagag gagttcaaat tgcttccaat
1261  gaaaatatgg agactatgga atcaagtaca cttgaactga gaagcaggta ctgggccata
1321  aggaccagaa gtggaggaaa caccaatcaa cagagggcat ctgcgggcca aatcagcata
1381  caacctacgt tctcagtaca gagaaatctc ccttttgaca gaacaaccat tatggcagca
1441  ttcaatggga atacagaggg aagaacatct gacatgagga ccgaaatcat aaggatgatg
1501  gaaagtgcaa gaccagaaga tgtgtctttc caggggcggg gagtcttcga gctctcggac
1561  gaaaaggcag cgagcccgat cgtgccttcc tttgacatga gtaatgaagg atcttatttc
1621  ttcggagaca atgcagatga gtacgacaat taa
```

Purified VR4710DNA was used to transfect the murine cell line VM92 to determine expression of the eM2-NP fusion protein. Expression of eM2-NP was confirmed with a Western Blot assay. Expression was visualized with a commercially available monoclonal antibody to M2 and with mouse polyclonal antibody to NP. ELISA assay results following 2 injections of pDNA into mice revealed little antibody response to M2, but an average titer of 66,560 for anti-NP antibody.

VR4750 was created by first reverse transcribing RNA from the mouse-adapted A/Hong Kong/1/68 virus stock using random hexamer to create a cDNA library. Then primers 5' GGGCTAGCGCCGCCACCATGAAGACCATCATTGCT 3' (SEQ ID NO:53) and 5' CCGTCGACTCAAATGCAAATGTTGCA 3' (SEQ ID NO:54) were employed to PCR the HA gene. The gene was inserted into the Invitrogen TOPO-TA vector first, and then sub-cloned into VR10551 using restriction enzymes NheI and SalI. The following is the open reading frame for HA (H3N2) from mouse-adapted A/Hong Kong/68 (from VR4750), referred to herein as SEQ ID NO:55:

```
   1  atgaagacca tcattgcttt gagctacatt ttctgtctgg ctctcggcca agaccttcca
  61  ggaaatgaca acaacacagc aacgctgtgc ctgggacatc atgcaatgcc aaacggaaca
 121  ctagtgaaaa caatcacaga tgatcagatt gaagtgacta atgctactga gctagttcag
 181  agctcctcaa cggggaaaat atgcaacaat cctcatcgaa tccttgatgg aatagactgc
 241  acactgatag atgctctatt gggggaccct cattgtgatg tttttcaaaa tgagacatgg
 301  gaccttttcg ttgaacgcag caaagctttc agcaactgtt acccttatga tgtgccagat
 361  tatgcccccc ttaggtcact agttgcctcg tcaggcactc tggagtttat cactgagggt
 421  ttcacttgga ctggggtcac tcagaatggg ggaagcagtg cttgcaaaag gggacctggt
 481  agcggttttt tcagtagact gaactggttg accaaatcag gaagcacata tccagtgctg
 541  aacgtgacta tgccaaacaa tgacaatttt gacaaactat acatttgggg ggttcaccac
 601  ccgagcacga accaagaaca aaccagcctg tatgttcaag catcagggag agtcacagtc
 661  tctaccagga gaagccagca aactataatc ccgaatatcg agtccagacc ctgggtaagg
 721  ggtctgtcta gtagaataag catctattgg acaatagtta agccgggaga cgtactggta
 781  attaatagta atgggaacct aatcgctcct cggggttatt tcaagatgcg cactgggaaa
 841  agctcaataa tgaggtcaga tgcacctatt gatacctgta tttctgaatg catcactcca
 901  aatggaagca ttcccaatga caagcccttt caaaacgtaa acaaaatcac gtatggagca
 961  tgccccaagt atgttaagca aaacaccctg aagttggcaa cagggatgcg gaatgtacca
1021  gagaaacaaa ctagaggcct attcggcgca atagcaggtt tcatagaaaa tggttgggag
1081  ggaatgatag acggttggta cggtttcagg catcaaaatt ctgagggcac aggacaagca
1141  gcagatctta aaagcactca agcagccatc gaccaaatca atgggaaatt gaacaggata
1201  atcaagaaga cgaacgagaa attccatcaa atcgaaaagg aattctcaga agtagaaggg
1261  agaattcagg acctcgagaa atacgttgaa gacactaaaa tagatctctg gtcttacaat
1321  gcggagcttc ttgtcgctct ggagaatcaa catacaattg acctgactga ctcggaaatg
1381  aacaagctgt ttgaaaaaac aaggaggcaa ctgagggaaa atgctgaaga catgggcaat
1441  ggttgcttca aaatatacca caaatgtgac aacgcttgca tagagtcaat cagaactggg
1501  acttatgacc atgatgtata cagagacgaa gcattaaaca accggtttca gatcaaaggt
1561  gttgaactga agtctggata caaagactgg atcctgtgga tttcctttgc catatcatgc
1621  tttttgcttt gtgttgtttt gctggggttc atcatgtggg cctgccagaa aggcaacatt
1681  aggtgcaaca tttgcatttg a
```

While VR4750 expression was not clearly detected in vitro by Western blot assay, two 100 μg vaccinations of VR4750 have been shown to protect mice from intranasal challenge with mouse-adapted A/Hong Kong/68 virus.

VR4752 was created by first reverse transcribing RNA from the mouse-adapted A/Puerto Rico/8/34 virus stock using random hexamer to create a cDNA library. Then primers 5' GGGCTAGCGCCGCCACCATGAAGGCAAACC TACTG 3' (SEQ ID NO:56) and 5' CCGTCGACTCAGATGCATATTCTGCA 3' (SEQ ID NO:57) were employed to PCR the HA gene. The gene was then cloned into the TOPO-TA vector first, and then sub-cloned into VR10551 using restriction enzymes NheI and SalI. The following is the open reading frame for HA (H1N1) cloned from mouse-adapted A/Puerto Rico/34 (from VR4752), referred to herein as SEQ ID NO:58:

```
1     atgaaggcaa acctactggt cctgttatgt gcacttgcag ctgcagatgc agacacaata
61    tgtataggct accatgcgaa caattcaacc gacactgttg acacagtgct cgagaagaat
121   gtgacagtga cacactctgt taacctgctc gaagacagcc acaacggaaa actatgtaga
181   ttaaaaggaa tagccccact acaattgggg aaatgtaaca tcgccggatg gctcttggga
241   aacccagaat gcgacccact gcttccagtg agatcatggt cctacattgt agaaacacca
301   aactctgaga atggaatatg ttatccagga gatttcatcg actatgagga gctgagggag
361   caattgagct cagtgtcatc attcgaaaga ttcgaaatat ttcccaaaga aagctcatgg
421   cccaaccaca acacaaccaa aggagtaacg gcagcatgct cccatgcggg gaaaagcagt
481   ttttacagaa atttgctatg gctgacggag aaggagggct catacccaaa gctgaaaaat
541   tcttatgtga acaagaaagg gaaagaagtc cttgtactgt ggggtattca tcacccgtct
601   aacagtaagg atcaacagaa tatctatcag aatgaaaatg cttatgtctc tgtagtgact
661   tcaaattata acaggagatt taccccggaa atagcagaaa gacccaaagt aagagatcaa
721   gctgggagga tgaactatta ctggaccttg ctaaaacccg gagacacaat aatatttgag
781   gcaaatggaa atctaatagc accaaggtat gctttcgcac tgagtagagg ctttgggtcc
841   ggcatcatca cctcaaacgc atcaatgcat gagtgtaaca cgaagtgtca aacaccccctg
901   ggagctataa acagcagtct ccctttccag aatatacacc cagtcacaat aggagagtgc
961   ccaaaatacg tcaggagtgc caaattgagg atggttacag gactaaggaa cattccgtcc
1021  attcaatcca gaggtctatt tggagccatt gccggtttta ttgaaggggg atggactgga
1081  atgatagatg gatggtacgg ttatcatcat cagaatgaac agggatcagg ctatgcagcg
1141  gatcaaaaaa gcacacaaaa tgccattaac gggattacaa acaaggtgaa ctctgttatc
1201  gagaaaatga acattcaatt cacagctgtg ggtaaagaat tcaacaaatt agaaaaaagg
1261  atggaaaatt taaataaaaa agttgatgat ggatttctgg acatttggac atataatgca
1321  gaattgttag ttctactgga aaatgaaagg actctggatt tccatgactc aaatgtgaag
1381  aatctgtatg agaaagtaaa aagccaatta aagaataatg ccaaagaaat cggaaatgga
1441  tgttttgagt tctaccacaa gtgtgacaat gaatgcatgg aaagtgtaag aaatgggact
1501  tatgattatc ccaaatattc agaagagtca aagttgaaca gggaaaaggt agatggagtg
1561  aaattggaat caatggggat ctatcagatt ctggcgatct actcaactgt cgccagttca
1621  ctggtgcttt tggtctccct gggggcaatc agtttctgga tgtgttctaa tggatctttg
1681  cagtgcagaa tatgcatctg a
```

Purified VR4752DNA was used to transfect the murine cell line VM92 to determine expression of the HA protein. Expression of HA was confirmed with a Western Blot assay. Expression was visualized with a commercially available goat anti-influenza A (H1N1) antibody.

A direct fusion of the M2 gene to the M1 gene was synthesized based on a codon-optimized sequence derived from methods described in Example 4 using the "universal" optimization strategy. The synthesized gene was received in the pUC119 vector and then sub-cloned into VR10551 as an EcoRI-SalI fragment. The following is the open reading frame for the M2M1 fusion (from VR4755), referred to herein as SEQ ID NO:59:

```
1     atgagcctgc tgaccgaggt ggagaccccc atcagaaacg agtggggctg cagatgcaac
61    gacagcagcg accccctggt ggtggccgcc agcatcatcg gcatcctgca cctgatcctg
121   tggatcctgg acagactgtt cttcaagtgc atctacagac tgttcaagca cggcctgaag
181   agaggcccca gcaccgaggg cgtgcccgag agcatgagag aggagtacag aaaggagcag
241   cagaacgccg tggacgccga cgacagccac ttcgtgagca tcgagctgga gatgtccctg
301   ctgacagaag tggaaacata cgtgctgagc atcgtgccca gcggcccccct gaaggccgag
```

-continued

```
361   atcgcccaga gactggagga cgtgttcgcc ggcaagaaca ccgacctgga ggccctgatg

421   gagtggctga agaccagacc catcctgagc cccctgacca agggcatcct gggcttcgtg

481   ttcaccctga ccgtgcccag cgagagaggc ctgcagagaa gaagattcgt gcagaacgcc

541   ctgaacggca acggcgaccc caacaacatg gaccgggccg tgaagctgta ccggaagctg

601   aagagagaga tcaccttcca cggcgccaag gagatcgccc tgagctacag cgccggcgcc

661   ctggccagct gcatgggcct gatctacaac agaatgggcg ccgtgaccac cgaggtggcc

721   ttcggcctgg tgtgcgccac ctgcgagcag atcgccgaca gccagcacag aagccacaga

781   cagatggtgg ccaccaccaa ccccctgatc agacacgaga acagaatggt gctggccagc

841   accaccgcca aggccatgga gcagatggcc ggcagcagcg agcaggccgc cgaggccatg

901   gagatcgcca gccaggccag acagatggtg caggccatga gagccatcgg cacccacccc

961   agcagcagcg ccggcctgaa ggacgacctg ctggagaacc tgcagaccta ccagaagaga

1021  atgggcgtgc agatgcagag attcaagtga
```

Purified VR4755DNA was used to transfect the murine cell line VM92 to determine expression of the M2M1 fusion protein. Expression of M2M1 was confirmed with a Western Blot assay. Expression of the M2M1 fusion was visualized with commercially available anti-M1 and anti-M2 monoclonal antibodies.

The segment 7 RNA of influenza A encodes both the M1 and M2 genes. A consensus amino acid sequence for M1 and M2 was derived according to methods described herein. The consensus sequences for both proteins, however, are identical to the M1 and M2 amino acid sequences derived from the IV strain A/Niigata/137/96, represented herein as SEQ ID NO:77 and SEQ ID NO:78, respectively. Accordingly, the native sequence for segment 7, A/Niigata/137/96, was synthesized and received as an insert in pUC119. The segment 7 insert was sub-cloned into VR10551 as an EcoRI-Sail fragment. The following is the open reading frame for segment 7 (from VR4756), referred to herein as SEQ ID NO:60:

```
  1   atgagccttc taaccgaggt cgaaacgtat gttctctcta tcgttccatc aggccccctc

 61   aaagccgaaa tcgcgcagag acttgaagat gtctttgctg ggaaaaacac agatcttgag

121   gctctcatgg aatggctaaa gacaagacca atcctgtcac ctctgactaa ggggattttg

181   gggtttgtgt tcacgctcac cgtgcccagt gagcgaggac tgcagcgtag acgctttgtc

241   caaaatgccc tcaatgggaa tggggatcca aataacatgg acagagcagt taaactatat

301   agaaaactta agagggagat tacattccat ggggccaaag aaatagcact cagttattct

361   gctggtgcac ttgccagttg catgggcctc atatacaaca gaatgggggc tgtaaccact

421   gaagtggcct ttggcctggt atgtgcaaca tgtgaacaga ttgctgactc ccagcacagg

481   tctcataggc aaatggtggc aacaaccaat ccattaataa ggcatgagaa cagaatggtt

541   ttggccagca ctacagctaa ggctatggag caaatggctg gatcaagtga gcaggcagcg

601   gaggccatgg aaattgctag tcaggccagg caaatggtgc aggcaatgag agccattggg

661   actcatccta gctccagtgc tggtctaaaa gatgatcttc ttgaaaattt gcagacctat

721   cagaaacgaa tgggggtgca gatgcaacga ttcaagtgac ccgcttgttg ttgctgcgag

781   tatcattggg atcttgcact tgatattgtg gattcttgat cgtctttttt tcaaatgcat

841   ctatcgactc ttcaaacacg gtctgaaaag agggccttct acggaaggag tacctgagtc

901   tatgagggaa gaatatcgaa aggaacagca gaatgctgtg gatgctgacg acagtcattt

961   tgtcagcata gagctggagt aa
```

SEQ ID NO:77 ("consensus" (A/Niigata/137/96) M1):

MSLLTEVETYVLSIVPSGPLKAEIAQRLEDVFAGKNTDLEALMEWLKTRP

ILSPLTKGILGFVFTLTVPSERGLQRRRFVQNALNGNGDPNNMDRAVKLY

RKLKREITFHGAKEIALSYSAGALASCMGLIYNRMGAVITEVAFGLVCAT

CEQIADSQHRSHRQMVATTNPLIRHENRMVLASTTAKAMEQMAGSSEQAA

EAMEIASQARQMVQAMRAIGTHPSSSAGLKDDLLENLQTYQKRMGVQMQR

FK

SEQ ID NO:78 ("consensus" (A/Niigata/137/96) M2):

MSLLTEVETPIRNEWGCRCNDSSDPLVVAASIIGILHLILWILDRLFFKC

IYRLFICHGLKRGPSTEGVPESMREEYRICEQQNAVDADDSHFVSIELE encoded by bp 1 through 759 of the segment 7 RNA, while M2 is encoded by a spliced messenger RNA which includes nucleotides 1 to 26 of segment 7 spliced to nucleotides 715 to 982 of segment 7. Optimization of the region from 715 to 759 is avoided because the M1 and M2 coding sequences (in different reading frames) overlap in that region. Due to the splicing that occurs to join by 26 to an alternate frame at by 715 of the segment 7 sequence, optimization in these splicing regions is also avoided; adjacent regions that arguably could also participate in splicing are likewise avoided. Optimization is done in a manner to insure that no new splicing sites are inadvertently introduced. The areas that are optimized are done so using "universal" strategy, e.g. inserting the most frequently used codon for each amino acid. The following is the nucleotide sequence for codon-optimized segment 7 (from VR4763), referred to herein as SEQ ID NO:61:

```
1   atgagcctgc tgaccgaggt cgaaacgtat gttctctcta tcgtgcccag cggcccccctg
61  aaggccgaga tcgcccagag actggaggac gtgttcgccg gcaagaacac cgacctggag
121 gccctgatgg agtggctgaa gaccagaccc atcctgagcc ccctgaccaa gggcatcctg
181 ggcttcgtgt tcaccctgac cgtgcccagc gagagaggcc tgcagagaag aagattcgtg
241 cagaacgccc tgaacggcaa cggcgacccc aacaacatgg acagagccgt gaagctgtac
301 agaaagctga agagagagat caccttccac ggcgccaagg agatcgccct gagctacagc
361 gccggcgccc tggccagctg catgggcctg atctacaaca gaatgggcgc cgtgaccacc
421 gaggtggcct tcggcctggt gtgcgccacc tgcgagcaga tcgccgacag ccagcacaga
481 agccacagac agatggtggc caccaccaac cccctgatca gacacgagaa cagaatggtg
541 ctggccagca ccaccgccaa ggccatggag cagatggccg gcagcagcga gcaggccgcc
601 gaggccatgg agatcgccag ccaggccaga cagatggtgc aggccatgag agccatcggc
661 acccacccca gcagcagcgc cggcctgaaa gatgatcttc ttgaaaattt gcagacctat
721 cagaaacgaa tgggggtgca gatgcaacga ttcaagtgac cccctggtgg tggccgccag
781 catcatcggc atcctgcacc tgatcctgtg gatcctggac agactgttct tcaagtgcat
841 ctacagactg ttcaagcacg gcctgaagag aggccccagc accgagggcg tgcccgagag
901 catgagagag gagtacagaa aggagcagca gaacgccgtg gacgccgacg acagccactt
961 cgtgagcatc gagctggagt ga
```

Purified VR4756DNA was used to transfect the murine cell line VM92 to determine expression of the proteins encoded by segment 7. Expression of both M1 and M2 was confirmed with a Western blot assay using commercially available anti-M1 and anti-M2 monoclonal antibodies. ELISA assay results following 2 injections of pDNA into mice revealed an average anti-M2 antibody titer of 9,240 versus a 110 average titer for VR4707. An IFNγ ELISPOT assay for M2-specific T cells resulted in an average of 121 SFU/106 cells for VR4756 injected mice versus an average of 61 SFU/106 cells for the VR4707 construct.

An additional segment 7 sequence is created, VR4763, which contains selectively codon-optimized regions of segment 7. Optimization of the coding regions in segment 7 is selective, because segment 7 contains two overlapping coding regions (i.e., encoding M1 and M2,) and these coding regions are partially in different reading frames. From the AUG encoded by nucleotides 1 to 3 of segment 7, M1 is The codon optimized coding region for M1 extends from nucleotide 1 to nucleotide 759 of SEQ ID NO:61 including the stop codon, and is represented herein as SEQ ID NO:79. The codon-optimized coding region for M2 extends from nucleotide 1 to nucleotide 26 of SEQ ID NO:61 spliced to nucleotide 715 through nucleotide 959 of SEQ ID NO:61, including the stop codon, and is represented herein as SEQ ID NO:80.

Optimized M1 Coding Region (SEQ ID NO:79):

ATGAGCCTGCTGACCGAGGTCGAAACGTATGTTCTCTCTATCGTGCCCAGC

GGCCCCCTGAAGGCCGAGATCGCCCAGAGACTGGAGGACGTGTTCGCCGGC

AAGAACACCGACCTGGAGGCCCTGATGGAGTGGCTGAAGACCAGACCCATC

CTGAGCCCCCTGACCAAGGGCATCCTGGGCTTCGTGTTCACCCTGACCGTG

CCCAGCGAGAGAGGCCTGCAGAGAAGAAGATTCGTGCAGAACGCCCTGAAC

-continued

```
GGCAACGGCGACCCCAACAACATGGACAGAGCCGTGAAGCTGTACAGAAAG
CTGAAGAGAGAGATCACCTTCCACGGCGCCAAGGAGATCGCCCTGAGCTAC
AGCGCCGGCGCCCTGGCCAGCTGCATGGGCCTGATCTACAACAGAATGGGC
GCCGTGACCACCGAGGTGGCCTTCGGCCTGGTGTGCGCCACCTGCGAGCAG
ATCGCCGACAGCCAGCACAGAAGCCACAGACAGATGGTGGCCACCACCAAC
CCCCTGATCAGACACGAGAACAGAATGGTGCTGGCCAGCACCACCGCCAAG
GCCATGGAGCAGATGGCCGGCAGCAGCGAGCAGGCCGCCGAGGCCATGGAG
ATCGCCAGCCAGGCCAGACAGATGGTGCAGGCCATGAGAGCCATCGGCACC
CACCCCAGCAGCAGCGCCGGCCTGAAAGATGATCTTCTTGAAAATTTGCAG
ACCTATCAGAAACGAATGGGGGTGCAGATGCAACGATTCAAGTGA
```

Optimized M2 Coding Region (SEQ ID NO:80):

```
ATGAGCCTGCTGACCGAGGTCGAAACACCTATCAGAAACGAATGGGGGTGC
AGATGCAACGATTCAAGTGACCCCCTGGTGGTGGCCGCCAGCATCATCGGC
ATCCTGCACCTGATCCTGTGGATCCTGGACAGACTGTTCTTCAAGTGCATC
TACAGACTGTTCAAGCACGGCCTGAAGAGAGGCCCCAGCACCGAGGGCGTG
CCCGAGAGCATGAGAGAGGAGTACAGAAAGGAGCAGCAGAACGCCGTGGAC
GCCGACGACAGCCACTTCGTGAGCATCGAGCTGGAGTGA
```

The eM2-NP fusion was codon-optimized, inserted in pUC119 and sub-cloned into VR10551 as an EcoRI-SalI fragment. The following is the open reading frame for eM2-NP: codon-optimized by Contract (from VR4757), referred to herein as SEQ ID NO:62:

```
   1 atgagcttgc tcactgaagt cgagacacca atcagaaacg aatggggatg tagatgcaac
  61 gatagctcag acatggcctc ccagggaacc aaaagaagct atgaacagat ggagactgac
 121 ggagagagac agaacgccac agagatcaga gctagtgtag gaaagatgat agacggtatc
 181 gggcgatttt acattcaaat gtgtacggaa ttgaaactca gcgactatga aggcagactt
 241 acccagaact cactcacaat tgagcgcatg gtactcagtg catttgatga aagaaggaat
 301 aggtacctcg aagaacaccc cagcgccggc aaagatccca agaagactgg cggcccaatt
 361 tacagaagag tggacggtaa gtggatgaga gagctggtat tgtacgataa agaagaaatt
 421 agaagaatct ggaggcaagc aaacaatgga gaggatgcta cagctggcct gacccacatg
 481 atgacttggc atagtaacct gaatgatacc acctaccagc ggacaagggc tctcgttcga
 541 accgggatgg atccccgcat gtgctcattg atgcagggta gtacactccc gaggaggtca
 601 ggcgcggccg gtgcagccgt gaaaggaatc ggcactatgg taatggaatc gataagaatg
 661 attaaaaggg ggatcaatga caggaacttt tggagaggag aaaatggacg caaaacaagg
 721 agtgcgtatg aacggatgtg caatatcttg aaaggaaaat tccaaactgc agcacagcgc
 781 gccatgatgg atcaggtacg agaaagtcgc aacccaggta atgctgaaat agaggacctt
 841 atatttctcg cccggagtgc tctcatactt agaggaagcg tggcccataa aagttgcctc
 901 cccgcatgcg tatacggtcc cgctgtgtct tccggatacg atctcgaaaa agagggatat
 961 tcactggtgg gaatcgaccc ttttaagctg cttcagaact cacaggttta cagtttgatt
1021 agaccaaacg agaacccagc ccacaaatca caactcgtgt ggatggcatg ccactctgcc
1081 gctttcgaag atctgagact gctctcattt attagaggca ctaaagtgag cccgagggga
1141 aaactgagca cacgaggagt acagatagca tctaacgaaa atatggacaa tatgggatct
1201 agcacactcg aattgaggtc acgatactgg gctattagaa cacggagcgg agggaacacc
1261 aaccagcaga gagcacccgc cggtcagata agcgttcagc ctacattttc agtacaacga
1321 aacctgccac ttgaaaagag tacagtgatg gccgcattta ccggcaacac cgagggacga
1381 acaagcgaca tgagagcaga gattattaga atgatggaag gagctaaacc agaggaggtt
1441 tcatttagag gaaggggagt cttcgaattg tccgatgaga aagccacaaa tcccatagta
1501 cctagcttcg acatgtccaa cgaaggctct tactttttg gtgacaatgc cgaagagtac
1561 gacaattga
```

Purified VR4757DNA was used to transfect the murine cell line VM92 to determine expression of the eM2-NP fusion protein. Expression of eM2-NP was confirmed with a Western Blot assay. Expression was visualized with a commercially available monoclonal antibody to M2 and with mouse polyclonal antibody to NP. In vivo antibody response to NP was detected by ELISA with an average titer of 51,200.

The eM2-NP fusion gene in VR4758 was codon-optimized and synthesized. The gene was inserted into pUC119 and sub-cloned into VR10551 as an EcoRI-SalI fragment. The following is the open reading frame for eM2-NP: codon-optimized by Applicants (from VR4758), referred to herein as SEQ ID NO:63:

```
   1 atgagcctgc tgaccgaggt ggagaccccc atcagaaacg agtggggccg cagatgcaac
  61 gacagcagcg acatggccag ccagggcacc aagagaagct acgagcagat ggagaccgac
 121 ggcgagagac agaacgccac cgagatcaga gccagcgtgg gcaagatgat cgacggcatc
 181 ggcagattct acatccagat gtgcaccgag ctgaagctga gcgactacga gggcagactg
 241 atccagaaca gcctgaccat cgagagaatg gtgctgagcg ccttcgacga gagaagaaac
 301 agatacctgg aggagcaccc cagcgccggc aaggacccca agaagaccgg cggccccatc
 361 tacagaagag tggacggcaa gtggatgaga gagctggtgc tgtacgacaa ggaggagatc
 421 agaagaatct ggagacaggc caacaacggc gaggacgcca ccgccggcct gacccacatg
 481 atgatctggc acagcaacct gaacgacacc acctaccaga gaaccagagc cctggtgcgg
 541 accggcatgg accccagaat gtgcagcctg atgcagggca gcaccctgcc cagaagaagc
 601 ggcgccgccg gcgccgccgt gaagggcatc ggcaccatgg tgatggagct gatcagaatg
 661 atcaagagag gcatcaacga cagaaacttc tggagaggcg agaacggcag aaagaccaga
 721 agcgcctacg agagaatgtg caacatcctg aagggcaagt tccagaccgc cgcccagaga
 781 gccatgatgg accaggtccg ggagagcaga aaccccggca acgccgagat cgaggacctg
 841 atcttcctgg ccagaagcgc cctgatcctg agaggcagcg tggcccacaa gagctgcctg
 901 cccgcctgcg tgtacggccc cgccgtgagc agcggctacg acttcgagaa ggagggctac
 961 agcctggtgg gcatcgaccc cttcaagctg ctgcagaaca gccaggtgta cagcctgatc
1021 agacccaacg agaaccccgc ccacaagagc cagctggtgt ggatggcctg ccacagcgcc
1081 gccttcgagg acctgagact gctgagcttc atcagaggca ccaaggtgtc ccccagaggc
1141 aagctgagca ccagaggcgt gcagatcgcc agcaacgaga acatggacaa catgggcagc
1201 agcaccccgg agctgagaag cagatactgg gccatcagaa ccagaagcgg cggcaacacc
1261 aaccagcaga gagccagcgc cggccagatc agcgtgcagc ccaccttcag cgtgcagaga
1321 aacctgccct tcgagaagag caccgtgatg gccgccttca ccggcaacac cgagggcaga
1381 accagcgaca tgagagccga gatcatcaga atgatggagg gcgccaagcc cgaggaggtg
1441 tccttcagag gcagaggcgt gttcgagctg agcgacgaga aggccaccaa ccccatcgtg
1501 cctagcttcg acatgagcaa cgagggcagc tacttcttcg gcgacaacgc cgaggagtac
1561 gacaactga
```

Purified VR4758DNA was used to transfect the murine cell line VM92 to determine expression of the eM2-NP protein. Expression of eM2-NP was confirmed with a Western Blot assay. Expression was visualized with a commercially available monoclonal antibody to M2 and with mouse polyclonal antibody to NP. In vivo antibody response to NP was detected by ELISA with an average titer of 48,640.

The M2 gene was PCR-amplified from VR4755 using the primers 5'-GCCGAATTCGCCACCATGAGCCTGCTGACC-3' (SEQ ID NO:64) and 5'-GCCGTCGACTGATCACTCCAGCTCGATGCTCAC-3' (SEQ ID NO:65) and sub-cloned into VR10551 as an EcoRI-SalI fragment. The following is the open reading frame for M2 (from VR4759), referred to herein as SEQ ID NO:66:

```
  1 atgagcctgc tgaccgaggt ggagaccccc atcagaaacg agtggggctg cagatgcaac
 61 gacagcagcg accccctggt ggtggccgcc agcatcatcg gcatcctgca cctgatcctg
121 tggatcctgg acagactgtt cttcaagtgc atctacagac tgttcaagca cggcctgaag
181 agaggcccca gcaccgaggg cgtgcccgag agcatgagag aggagtacag aaaggagcag
241 cagaacgccg tggacgccga cgacagccac ttcgtgagca tcgagctgga gtga
```

Purified VR4759DNA was used to transfect the murine cell line VM92 to determine expression of the M2 protein. Expression of M2 was confirmed with a Western Blot assay. Expression was visualized with a commercially available anti-M2 monoclonal antibody.

The M1 gene was PCR-amplified from VR4755 using the primers 5'-GCCGAATTCGCCACCATGTCCCTGCTGA-CAGAAGTG-3' (SEQ ID NO:67) and 5'-GCCGTCGACT-GATCACTTGAATCTCTGCATC-3' (SEQ ID NO:68) and sub-cloned into VR10551 as an EcoRI-SalI fragment. The following is the open reading frame for M1 (from VR4760), referred to herein as SEQ ID NO:69:

```
  1 atgtccctgc tgacagaagt ggaaacatac gtgctgagca tcgtgcccag cggcccccctg
 61 aaggccgaga tcgcccagag actggaggac gtgttcgccg gcaagaacac cgacctggag
121 gccctgatgg agtggctgaa gaccagaccc atcctgagcc ccctgaccaa gggcatcctg
181 ggcttcgtgt tcaccctgac cgtgcccagc gagagaggcc tgcagagaag aagattcgtg
241 cagaacgccc tgaacggcaa cggcgacccc aacaacatgg accgggccgt gaagctgtac
301 cggaagctga agagagagat caccttccac ggcgccaagg agatcgccct gagctacagc
361 gccggcgccc tggccagctg catgggcctg atctacaaca gaatgggcgc cgtgaccacc
421 gaggtggcct tcggcctggt gtgcgccacc tgcgagcaga tcgccgacag ccagcacaga
481 agccacagac agatggtggc caccaccaac cccctgatca gacacgagaa cagaatggtg
541 ctggccagca ccaccgccaa ggccatggag cagatggccg gcagcagcga gcaggccgcc
601 gaggccatgg agatcgccag ccaggccaga cagatggtgc aggccatgag agccatcggc
661 acccacccca gcagcagcgc cggcctgaag gacgacctgc tggagaacct gcagacctac
721 cagaagagaa tgggcgtgca gatgcagaga ttcaagtga
```

Purified VR4760DNA was used to transfect the murine cell line VM92 to determine expression of the M1 protein. Expression of M1 was confirmed with a Western Blot assay. Expression was visualized with a commercially available anti-M1 monoclonal antibody.

The NP gene was PCR-amplified from VR4757 using primers 5'-GCCGAATTCGCCACCATGGCCTCCCAGG-GAACCAAAAG-3' (SEQ ID NO:70) and 5'-GCCGTC-GACTGATCAATTGTCGTACTCTTC-3' (SEQ ID NO:71) and sub-cloned into VR10551 as an EcoRI-SalI fragment. The following is the open reading frame for NP: codon-optimized by Contract (from VR4761), referred to herein as SEQ ID NO:72:

```
  1  atg gcc tcc cag gga acc aaa aga agc-
 tat gaa cag atg gag act gac

  49  gga gag aga cag aac gcc aca gag atc a-
ga gct agt gta gga aag atg

  97  ata gac ggt atc ggg cga ttt tac at-
t caa atg tgt acg gaa ttg aaa

 145  ctc agc gac tat gaa ggc aga ctt atc-
 cag aac tca ctc aca att gag

 193  cgc atg gta ctc agt gca ttt gat gaa a-
ga agg aat agg tac ctc gaa
```

-continued

```
241  gaa cac ccc agc gcc ggc aaa gat c-
cc aag aag act ggc ggc cca att

289  tac aga aga gtg gac ggt aag tgg at-
g aga gag ctg gta ttg tac gat

337  aaa gaa gaa att aga aga atc tgg ag-
g caa gca aac aat gga gag gat

385  gct aca gct ggc ctg acc cac atg at-
g att tgg cat agt aac ctg aat

433  gat acc acc tac cag cgg a-
ca agg gct ctc gtt cga acc ggg atg gat

481  ccc cgc atg tgc tca ttg atg-
 cag ggc agt aca ctc ccg agg agg tca

529  ggc gcg gcc ggt gca gcc gtg aaa g-
ga atc ggc act atg gta atg gaa

577  ttg ata aga atg att aaa agg ggg at-
t aat gac agg aac ttt tgg aga

625  gga gaa aat gga cgc aaa aca agg agt-
 gcg tat gaa cgg atg tgc aat

673  att ttg aaa gga aaa ttc caa act gca g-
ca cag cgc gcc atg atg gat

721  cag gta cga gaa agt cgc aac cca gg-
t aat gct gaa ata gag gac ctt

769  ata ttt ctc gcc cgg agt gct ctc at-
a ctt aga gga agc gtg gcc cat

817  aaa agt tgt ctc ccc gca tgc gta tac g-
gt ccc gct gtg tct tcc gga

865  tac gat ttt gaa aaa gag gga tat tca t-
tg gtg gga atc gac cct ttt

913  aag ctg ctt cag aac tca cag gtt ta-
c agt ttg att aga cca aac gag

961  aac cca gcc cac aaa tca caa ctc gt-
g tgg atg gca tgc cac tct gcc
```

-continued

```
1009  gct ttc gaa gat ctg aga ctg ctc t-
ca ttt att aga ggc act aaa gtg

1057  agc ccg agg gga aaa ctg agc aca cga g-
ga gta cag ata gca tct aac

1105  gaa aat atg gat aat atg gga tct agc a-
ca ctc gaa ttg agg tca cga

1153  tac tgg gct att aga aca cgg agc g-
ga ggg aac acc aac cag cag aga

1201  gca tcc gcc ggt cag ata agc gtt cag c-
ct aca ttt tca gta caa cga

1249  aac ctg cca ttt gaa aag agt aca gt-
g atg gcc gca ttt act ggc aac

1297  acc gag gga cga aca agc gac atg aga g-
ca gag att att aga atg atg

1345  gaa gga gct aaa cca gag gag-
 gtt tca ttt aga gga agg gga gtc ttc

1393  gaa ttg tcc gat gag aaa gcc aca aat c-
cc ata gta cct agc ttc gac

1441  atg tcc aac gaa ggc tct tac ttt ttt g-
gt gac aat gcc gaa gag tac

1489  gac aat tga
```

Purified VR4761DNA was used to transfect the murine cell line VM92 to determine expression of the NP protein. Expression of NP was confirmed with a Western Blot assay. Expression was visualized with a mouse polyclonal anti-NP antibody. In vitro expression of VR4761 was significantly higher than VR4700 and comparable to VR4762.

The NP gene was PCR-amplified from VR4758 using primers 5'-GCCGAATTCGCCACCATGGCCAGCCAGGGCACCAAG-3' (SEQ ID NO:73) and 5'-GCCGTCGACTGATCAGTTGTCGTACTCC-3' (SEQ ID NO:74) and sub-cloned into VR10551 as an EcoRI-SalI fragment. The following is the open reading frame for NP: codon-optimized by Applicants (from VR4762), referred to herein as SEQ ID NO:75:

```
  1  atggccagcc agggcaccaa gagaagctac gagcagatgg agaccgacgg cgagagacag
 61  aacgccaccg agatcagagc cagcgtgggc aagatgatcg acggcatcgg cagattctac
121  atccagatgt gcaccgagct gaagctgagc gactacgagg gcagactgat ccagaacagc
181  ctgaccatcg agagaatggt gctgagcgcc ttcgacgaga gaagaaacag atacctggag
241  gagcacccca gcgccggcaa ggaccccaag aagaccggcg gccccatcta cagaagagtg
301  gacggcaagt ggatgagaga gctggtgctg tacgacaagg aggagatcag aagaatctgg
361  agacaggcca acaacggcga ggacgccacc gccggcctga cccacatgat gatctggcac
421  agcaacctga acgacaccac ctaccagaga accagagccc tggtgcggac cggcatggac
481  cccagaatgt gcagcctgat gcagggcagc accctgccca gaagaagcgg cgccgccggc
541  gccgccgtga agggcatcgg caccatggtg atggagctga tcagaatgat caagagaggc
601  atcaacgaca gaaacttctg gagaggcgag aacggcagaa agaccagaag cgcctacgag
661  agaatgtgca acatcctgaa gggcaagttc cagaccgccg cccagagagc catgatggac
721  caggtccggg agagcagaaa ccccggcaac gccgagatcg aggacctgat cttcctggcc
781  agaagcgccc tgatcctgag aggcagcgtg gcccacaaga gctgcctgcc cgcctgcgtg
841  tacggccccg ccgtgagcag cggctacgac ttcgagaagg agggctacag cctggtgggc
901  atcgacccct tcaagctgct gcagaacagc caggtgtaca gcctgatcag acccaacgag
```

-continued

```
961   aaccccgccc acaagagcca gctggtgtgg atggcctgcc acagcgccgc cttcgaggac

1021  ctgagactgc tgagcttcat cagaggcacc aaggtgtccc ccagaggcaa gctgagcacc

1081  agaggcgtgc agatcgccag caacgagaac atggacaaca tgggcagcag caccctggag

1141  ctgagaagca gatactgggc catcagaacc agaagcggcg gcaacaccaa ccagcagaga

1201  gccagcgccg gccagatcag cgtgcagccc accttcagcg tgcagagaaa cctgcccttc

1261  gagaagagca ccgtgatggc cgccttcacc ggcaacaccg agggcagaac cagcgacatg

1321  agagccgaga tcatcagaat gatggagggc gccaagcccg aggaggtgtc cttcagaggc

1381  agaggcgtgt tcgagctgag cgacgagaag gccaccaacc ccatcgtgcc tagcttcgac

1441  atgagcaacg agggcagcta cttcttcggc gacaacgccg aggagtacga caactga
```

Purified VR4762 DNA was used to transfect the murine cell line VM92 to determine expression of the NP protein. Expression of NP was confirmed with a Western Blot assay. Expression was visualized with a mouse polyclonal anti-NP antibody. In vitro expression of VR4762 was significantly higher than VR4700 and comparable to VR4761.

In addition to plasmids encoding single IV proteins, single plasmids which contain two or more IV coding regions are constructed according to standard methods. For example, a polycistronic construct, where two or more IV coding regions are transcribed as a single transcript in eukaryotic cells may be constructed by separating the various coding regions with IRES sequences. Alternatively, two or more coding regions may be inserted into a single plasmid, each with their own promoter sequence.

Example 2

Preparation of Recombinant NP DNA and Protein

Recombinant NP DNA and protein may be prepared using the following procedure. Eukaryotic cells may be used to express the NP protein from a transfected expression plasmid. Alternatively, a baculovirus system can be used wherein insect cells such as, but not limited to, Sf9, Sf21, or D.MeI-2 cells are infected with a recombinant baculovirus which can expresses the NP protein. Cells which have been infected with recombinant baculoviruses, or contain expression plasmids, encoding recombinant NP are collected by knocking and scraping cells off the bottom of the flask in which they are grown. Cells infected for 24 or 48 hours are less easy to detach from flask and may lyse, thus care must be taken with their removal. The flask containing the cells is then rinsed with PBS and the cells are transferred to 250 ml conical tubes. The tubes are spun at 1000 rpm in J-6 centrifuge (300×g) for about 5-10 minutes. The cell pellets are washed two times with PBS and then resuspended in about 10-20 ml of PBS in order to count. The cells are finally resuspended at a concentration of about $2\times10^7$ cells/ml in RSB (10 mM Tris pH=7.5, 1.5 mM $MgCl_2$, 10 mM KCl).

Approximately $10^6$ cells are used per lane of a standard SDS-PAGE mini-protein gel which is equivalent to the whole cell fraction for gel analysis purposes. 10% NP40 is added to the cells for a final concentration of 0.5%. The cell-NP40 mixture is vortexed and placed on ice for 10 minutes, vortexing occasionally. After ice incubation, the cells are spun at 1500 rpm in a J-6 centrifuge (600×1) for 10 minutes. The supernatant is removed which is the cytoplasmic fraction. The remaining pellet, containing the nuclei, is washed two times with buffer C (20 mM HEPES pH=7.9, 1.5 mM $MgCl_2$, 0.2 mM EDTA, 0.5 mM PMSF, 0.5 mM DTT) to remove cytoplasmic proteins. The nuclei are resuspended in buffer C to $5\times10^7$ nuclei/ml. The nuclei are vortexed vigorously to break up particles and an aliquot is removed for the mini-protein gel which is the nuclei fraction.

To the remaining nuclei a quarter of the volume of 5M NaCl is added and the mixture is sonicated for 5 minutes at a maximum output in a bath-type sonicator at 4° C., in 1-2 minute bursts, resting 30 seconds between bursts. The sonicated mixture is stirred at 4° C., then spun at 12000×g for 10 minutes. A sample is removed for the protein mini-gel equivalent to approximately $10^6$ nuclei. The sample for the gel is centrifuged and the supernatant is the nuclear extract and the pellet is the nuclear pellet for gel analysis.

For gel analysis, a small amount (about $10^6$ nuclear equivalents) of the nuclear pellet is resuspended directly in gel sample buffer and run with equivalent amounts of whole cells, cytoplasm, nuclei, nuclear extract and nuclear pellet. The above method gives relatively crude NP. To recover NP of a higher purity, 2.1M NaCl can be added to the nuclear pellet instead of 5M NaCl. This will bring the salt content to 0.42M NaCl. The supernatant will then contain about 60-70% of the total NP plus nuclear proteins. The resulting pellet is then extracted with 1M NaCl and centrifuged as above. The supernatant will contain NP at more than 95% purity.

Example 3

Consensus Amino Acid Sequences of NP, M1 and M2

By analyzing amino acid sequences from influenza strains sequenced since 1990, consensus amino acid sequences were derived for influenza NP, M1 and M2 antigens.

NP Consensus Amino Acid Sequence

The method by which amino acid sequences for influenza NP (strain A) was chosen is as follows. The www.flulanl.gov database containing influenza sequences for each segment was searched for influenza A strains, human, NP, amino acids. Results gave about 400 sequences, the majority of which were only partial sequences. The sequences were subsequently narrowed down to 85 approximately full length sequences. If different passages of the same strain were found, the earliest passage was chosen. The sequences were further narrowed down to 28 full length NP sequences isolated from 1990 to 2000 (no full-length sequences from 2001-2003). Five additional sequences were eliminated which were identical to another sequence isolated from the same year based on the assumption that sequences with the same year and identical amino acid sequences were likely to be the same virus strain (in order to avoid double weighting). If there were sequences from the same year with different amino acid sequences, both sequences were kept.

Sequences were aligned to the A/PR/8/34 strain in descending order by most recent, and the consensus sequence was determined by utilizing the amino acid with the majority (FIG. 12). There are 32 amino acid changes between the A/PR/8/34 and the consensus sequence, and all amino acid changes are also present in the two year 2000 NP sequences. For one additional amino acid (aa 275) 15/23 have changed from E (in A/PR/34) to G/D or V (7G, 7D, 1V). Since the two 2000 strains both contain a G at this position, G was chosen. The changes total 33 amino acids, which is about a 7% difference from the A/PR/8/34 strain.

The dominant Balb/c epitope TYQRTRALV (SEQ ID NO:81) is still maintained in the new consensus; changes to other theoretical human epitopes have not been determined as yet.

The A strains used in the last 8 years of flu vaccines (USA) are as follows (no full length sequences are available on any of the these strains' NP genes):

| | |
|---|---|
| a. | 2002-2003 A/Moscow/10/99, A/New Caledonia/20/99 |
| b. | 2001-2002 A/Moscow/10/99, A/New Caledonia/20/99 |
| c. | 2000-2001 A/Panama/2007/99, A/New Caledonia/20/99 |
| d. | 1999-2000 A/Sydney/05/97, A/Beijing/262/95 |
| e. | 1998-1999 A/Sydney/05/97, A/Beijing/262/95 |
| f. | 1997-1998 A/Nanchang/933/95, A/Johannesburg/82/96 |
| g. | 1996-1997 A/Nanchang/933/95, A/Texas/36/91 |
| h. | 1995-1996 A/Johannesburg/33/94, A/Texas/36/91 |

The final NP consensus amino acid sequence derived using this method is referred to herein as SEQ ID NO:76:

```
  1  masqgtkrsy eqmetdgerq nateiras-
vg kmidgigrfy iqmctelkls dyegrliqns

 61  ltiermvlsa fderrnryle ehpsagkdpk kcggpiyrrv dgkwmrelvl ydkeeirriw

121  rqanngedat aglthmmiwh snlndctyqr tralvrtgmd prmcslmqgs tlprrsgaag

181  aavkgigtmv melirmikrg indrnfwrge ngrktrsaye rmcnilkgkf qtaaqrammd

241  qvresrnpgn aeiedlifla rsalilrgsv ahksclpacv ygpavssgyd fekegyslvg

301  idpfkllqns qvyslirpne npahksqlvw machsaafed lrllsfirgt kvsprgklst

361  rgvqiasnen mdnmgsstle lrsrywairc rsggntnqqr asagqisvqp tfsvqrnlpf

421  ekstvmaaft gntegrtsdm raeiirm-
meg akpeevsfrg rgvfelsdek atnpivpsfd

481  msnegsyffg dnaeeydn
```

M1 and M2 Consensus Amino Acid Sequences

Consensus sequences for M1 and M2 were determined in a similar fashion, as follows. The search parameters on the www.flu.lan1.gov/ website were: influenza A strains, human, segment 7, nucleotide (both M1 and M2 are derived from segment 7). Full-length sequences from 1990-1999 (no 2000+sequences were available) were chosen. For sequences with the same year and city, only the earliest passage was used. For entries for the same year, sequences were eliminated that were identical to another sequence isolated from the same year (even if different city). Twenty one sequences, full-length for both M1 and M2 from 1993-1999, were compared. At each position, the amino acid with the simple majority was used.

The M1 amino acid consensus sequence is identical to the M1 amino acid sequences derived from the influenza virus strain A/Niigata/137/96, and is referred to herein as SEQ ID NO:77:

1 mslltevety vlsivpsgpl kaeiaqrled vfagkntdle almewlktrp ilspltkgil 61 gfvftltvps erglqrrrfv qnalngngdp nnmdravkly rklkreitfh gakeialsys 121 agalascmgl iynrmgavtt evafglvcat ceqiadsqhr shrqmvattn plirhenrmv 181 lasttakame qmagsseqaa eameiasqar qmvqamraig thpsssaglk ddllenlqty 241 qkrmgvqmqr fk The M2 amino acid consensus sequence is identical to the M2 amino acid sequences derived from the influenza virus strain A/Niigata/137/96, and is referred to herein as SEQ ID NO:78:

1 mslltevetp irnewgcrcn dssdplvvaa siigilhlil wildrlffkc iyrlfkhglk 61 rgpstegvpe smreeyrkeq qnavdaddsh fvsiele Example 4

Codon Optimization Algorithm

The following is an outline of the algorithm used to derive human codon-optimized sequences of influenza antigens.

Back Translation

Starting with the amino acid sequence, one can either (a) manually backtranslate using the human codon usage table from www.kazusa.or.jp/codon/

*Homo sapiens* [gbpri]: 55194 CDS's (24298072 codons)

Fields: [triplet] [frequency: per thousand] ([number])

| | | | |
|---|---|---|---|
| UUU 17.1(415589) | UCU 14.7(357770) | UAU 12.1(294182) | UGU 10.0(243198) |
| UUC 20.6(500964) | UCC 17.6(427664) | UAC 15.5(377811) | UGC 12.2(297010) |
| UUA 7.5(182466) | UCA 12.0(291788) | UAA 0.7(17545) | UGA 1.5(36163) |
| UUG 12.6(306793) | UCG 4.4(107809) | UAG 0.6(13416) | UGG 12.7(309683) |
| CUU 13.0(315804) | CCU 17.3(419521) | CAU 10.5(255135) | CGU 4.6(112673) |
| CUC 19.8(480790) | CCC 20.1(489224) | CAC 15.0(364828) | CGC 10.7(259950) |
| CUA 7.8(189383) | CCA 16.7(405320) | CAA 12.0(292745) | CGA 6.3(152905) |
| CUG 39.8(967277) | CCG 6.9(168542) | CAG 34.1(827754) | CGG 11.6(281493) |
| AUU 16.1(390571) | ACU 13.0(315736) | AAU 16.7(404867) | AGU 11.9(289294) |
| AUC 21.6(525478) | ACC 19.4(471273) | AAC 19.5(473208) | AGC 19.3(467869) |
| AUA 7.7(186138) | ACA 15.1(366753) | AAA 24.1(585243) | AGA 11.5(278843) |
| AUG 22.2(538917) | ACG 6.1(148277) | AAG 32.2(781752) | AGG 11.4(277693) |
| GUU 11.0(266493) | GCU 18.6(451517) | GAU 21.9(533009) | GGU 10.8(261467) |
| GUC 14.6(354537) | GCC 28.4(690382) | GAC 25.6(621290) | GGC 22.5(547729) |
| GUA 7.2(174572) | GCA 16.1(390964) | GAA 29.0(703852) | GGA 16.4(397574) |
| GUG 28.4(690428) | GCG 7.5(181803) | GAG 39.9(970417) | GGG 16.3(396931) |

*Coding GC 52.45% 1st letter GC 56.04% 2nd letter GC 42.37% 3rd letter GC 58.93%
(Table as of Nov. 6, 2003)

Or (b) log on to www.syntheticgenes.com and use the backtranslation tool, as follows:

(1) Under Protein tab, paste amino acid sequence;

(2) Under download codon usage tab, highlight *homo sapiens* and then download CUT.

| | | | |
|---|---|---|---|
| UUU 17.1(415589) | UCU 14.7(357770) | UAU 12.1(294182) | UGU 10.0(243198) |
| UUC 20.6(500964) | UCC 17.6(427664) | UAC 15.5(377811) | UGC 12.2(297010) |
| UUA 7.5(182466) | UCA 12.0(291788) | UAA 0.7(17545) | UGA 1.5(36163) |
| UUG 12.6(306793) | UCG 4.4(107809) | UAG 0.6(13416) | UGG 12.7(309683) |
| CUU 13.0(315804) | CCU 17.3(419521) | CAU 10.5(255135) | CGU 4.6(112673) |
| CUC 19.8(480790) | CCC 20.1(489224) | CAC 15.0(364828) | CGC 10.7(259950) |
| CUA 7.8(189383) | CCA 16.7(405320) | CAA 12.0(292745) | CGA 6.3(152905) |
| CUG 39.8(967277) | CCG 6.9(168542) | CAG 34.1(827754) | CGG 11.6(281493) |
| AUU 16.1(390571) | ACU 13.0(315736) | AAU 16.7(404867) | AGU 11.9(289294) |
| AUC 21.6(525478) | ACC 19.4(471273) | AAC 19.5(473208) | AGC 19.3(467869) |
| AUA 7.7(186138) | ACA 15.1(366753) | AAA 24.1(585243) | AGA 11.5(278843) |
| AUG 22.2(538917) | ACG 6.1(148277) | AAG 32.2(781752) | AGG 11.4(277693) |
| GUU 11.0(266493) | GCU 18.6(451517) | GAU 21.9(533009) | GGU 10.8(261467) |
| GUC 14.6(354537) | GCC 28.4(690382) | GAC 25.6(621290) | GGC 22.5(547729) |
| GUA 7.2(174572) | GCA 16.1(390964) | GAA 29.0(703852) | GGA 16.4(397574) |
| GUG 28.4(690428) | GCG 7.5(181803) | GAG 39.9(970417) | GGG 16.3(396931) |

(Table as of Nov. 6, 2003)

(3) Hit Apply button.

(4) Under Optimize TAB, open General TAB.

(5) Check use only most frequent codon box.

(6) Hit Apply button.

(7) Under Optimize TAB, open Motif TAB.

(8) Load desired cloning restriction sites into bad motifs; load any undesirable sequences, such as Pribnow Box sequences (TATAA), Chi sequences (GCTGGCGG), and restriction sites into bad motifs.

(9) Under Output TAB, click on Start box. Output will include sequence, motif search results (under Report TAB), and codon usage report.

The program did not always use the most frequent codon for amino acids such as cysteine proline, and arginine. To change this, go back to the Edit CUT TAB and manually drag the rainbow colored bar to 100% for the desired codon. Then re-do start under the Output TAB.

The use of CGG for arginine can lead to very high GC content, so AGA can be used for arginine as an alternative. The difference in codon usage is 11.6 per thousand for CGG vs. 11.5 per thousand for AGA.

Splice Donor and Acceptor Site Search (1) Log on to Berkeley *Drosophila* Genome Project Website at www.fruitfly.org/seq_tools/splice.html\

(2) Check boxes for Human or other and both splice sites.

(3) Select minimum scores for 5' and 3' splice sites between 0 and 1.

Used the default setting at 0.4 where:

Default minimum score is 0.4, where:

| | % splice sites recognized | % false positives |
|---|---|---|
| Human 5' Splice sites | 93.2% | 5.2% |
| Human 3' Splice sites | 83.8% | 3.1% |

(4) Paste in sequence.

(5) Submit.

(6) Based on predicted donors or acceptors, change the individual codons until the sites are no longer predicted. Add in 5' and 3' sequences.

On the 5' end of the gene sequence, the restriction enzyme site and Kozak sequence (gccacc) was added before ATG. On 3' end of the sequence, tca was added following the stop codon (tga on opposite strand) and then a restriction enzyme site. The GC content and Open Reading Frames were then checked in SEC Central.

Example 5

Preparation of Vaccine Formulations

Plasmid constructs comprising codon-optimized and non-codon-optimized coding regions encoding NP, M1, M2, HA, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are formulated with the poloxamer CRL 1005 and BAK (Benzalkonium chloride 50% solution, available from Ruger Chemical Co. Inc.) by the following methods. Specific final concentrations of each component of the formulae are described in the following methods, but for any of these methods, the concentrations of each component may be varied by basic stoichiometric calculations known by those of ordinary skill in the art to make a final solution having the desired concentrations.

For example, the concentration of CRL 1005 is adjusted depending on, for example, transfection efficiency, expression efficiency, or immunogenicity, to achieve a final concentration of between about 1 mg/ml to about 75 mg/ml, for example, about 1 mg/ml, about 2 mg/ml, about 3 mg/ml, about 4 mg/ml, about 5 mg/ml, about 6.5 mg/ml, about 7 mg/ml, about 7.5 mg/ml, about 8 mg/ml, about 9 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of CRL 1005.

Similarly the concentration of DNA is adjusted depending on many factors, including the amount of a formulation to be delivered, the age and weight of the subject, the delivery method and route and the immunogenicity of the antigen being delivered. In general, formulations of the present invention are adjusted to have a final concentration from about 1 ng/ml to about 30 mg/ml of plasmid (or other polynucleotide). For example, a formulation of the present invention may have a final concentration of about 1 ng/ml, about 5 ng/ml, about 10 ng/ml, about 50 ng/ml, about 100 ng/ml, about 500 ng/ml, about 1 μg/ml, about 5 μg/ml, about 10 μg/ml, about 50 μg/ml, about 200 μg/ml, about 400 μg/ml, about 600 μg/ml, about 800 μg/ml, about 1 mg/ml, about 2 mg/ml, about 2.5, about 3 mg/ml, about 3.5, about 4 mg/ml, about 4.5, about 5 mg/ml, about 5.5 mg/ml, about 6 mg/ml, about 7 mg/ml, about 8 mg/ml, about 9 mg/ml, about 10 mg/ml, about 20 mg/ml, or about 30 mg mg/ml of a plasmid.

Certain formulations of the present invention include a cocktail of plasmids (see, e.g., Example 2 supra) of the present invention, e.g., comprising coding regions encoding IV proteins NP, M1 and/or M2 and optionally, plasmids encoding immunity enhancing proteins, e.g., cytokines. Various plasmids desired in a cocktail are combined together in PBS or other diluent prior to the addition to the other ingredients. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportion, or up to twice or three times as much of one plasmid may be included relative to other plasmids in the cocktail.

Additionally, the concentration of BAK may be adjusted depending on, for example, a desired particle size and improved stability. Indeed, in certain embodiments, formulations of the present invention include CRL 1005 and DNA, but are free of BAK. In general BAK-containing formulations of the present invention are adjusted to have a final concentration of BAK from about 0.05 mM to about 0.5 mM. For example, a formulation of the present invention may have a final BAK concentration of about 0.05 mM, 0.1 mM, 0.2 mM, 0.3 mM, 0.4 mM or 0.5 mM.

The total volume of the formulations produced by the methods below may be scaled up or down, by choosing apparatus of proportional size. Finally, in carrying out any of the methods described below, the three components of the formulation, BAK, CRL 1005, and plasmid DNA, may be added in any order. In each of these methods described below the term "cloud point" refers to the point in a temperature shift, or other titration, at which a clear solution becomes cloudy, i.e., when a component dissolved in a solution begins to precipitate out of solution.

Thermal Cycling of a Pre-Mixed Formulation

This example describes the preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is thermally cycled to room temperature (above the cloud point) several times, according to the protocol outlined in FIG. 2.

A 1.28 mM solution of BAK is prepared in PBS, 846 μl of the solution is placed into a 15 ml round bottom flask fitted with a magnetic stirring bar, and the solution is stirred with moderate speed, in an ice bath on top of a stirrer/hotplate (hotplate off) for 10 minutes. CRL 1005 (27 μl) is then added using a 100 μl positive displacement pipette and the solution is stirred for a further 60 minutes on ice. Plasmids comprising codon-optimized coding regions encoding, for example, NP, M1, and M2 as described herein, and optionally, additional plasmids comprising codon-optimized or non-codin-optimized coding regions encoding, e.g., additional IV proteins, and or other proteins, e.g., cytokines, are mixed together at desired proportions in PBS to achieve 6.4 mg/ml total DNA. This plasmid cocktail is added drop wise, slowly, to the stirring solution over 1 min using a 5 ml pipette. The solution at this point (on ice) is clear since it is below the cloud point of the poloxamer and is further stirred on ice for 15 min. The ice bath is then removed, and the solution is stirred at ambient temperature for 15 minutes to produce a cloudy solution as the poloxamer passes through the cloud point.

The flask is then placed back into the ice bath and stirred for a further 15 minutes to produce a clear solution as the mixture is cooled below the poloxamer cloud point. The ice bath is again removed and the solution stirred at ambient temperature for a further 15 minutes. Stirring for 15 minutes above and below the cloud point (total of 30 minutes), is defined as one thermal cycle. The mixture is cycled six more times. The resulting formulation may be used immediately, or may be placed in a glass vial, cooled below the cloud point, and frozen at −80° C. for use at a later time.

Thermal Cycling, Dilution and Filtration of a Pre-mixed Formulation, Using Increased Concentrations of CRL 1005

Figure 3:
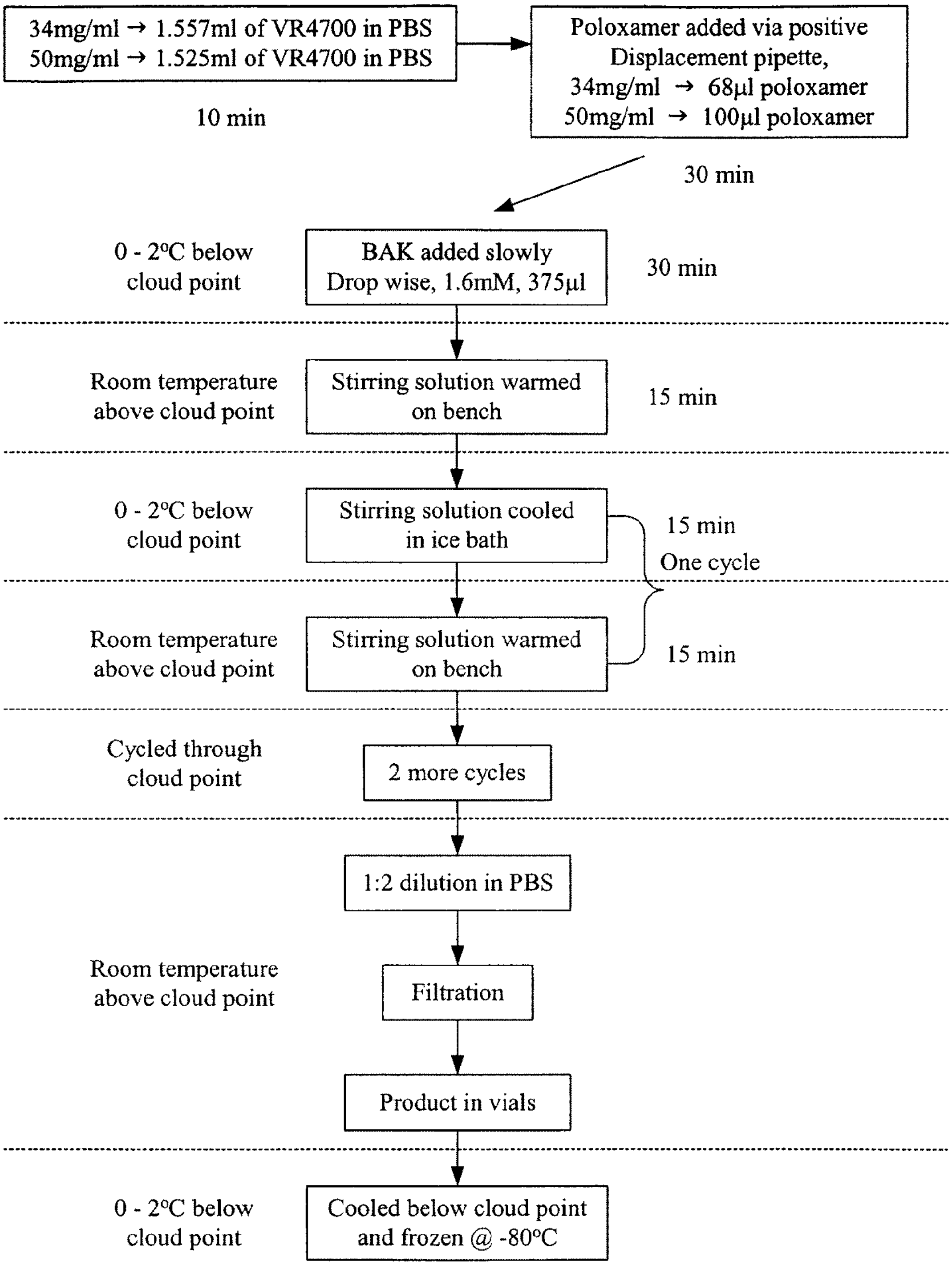
FIG. 3 shows the protocol for the preparation of a formulation comprising 0.3 mM BAK, 34 mg/ml or 50 mg/ml CRL 1005 and 2.5 mg/ml DNA in a final volume of 4.0 ml, through the use of thermal cycling.

This example describes the preparation of a formulation comprising 0.3 mM BAK, 34 mg/ml or 50 mg/ml CRL 1005, and 5.0 mg/ml of DNA in a final volume of 4.0 ml. The ingredients are combined together at a temperature below the cloud point, then the formulation is thermally cycled to room temperature (above the cloud point) several times, diluted, and filtered according to the protocol outlined in FIG. 3.

Plasmids comprising codon-optimized coding regions encoding, for example, NP, M1, and M2 as described herein, and optionally, additional plasmids comprising codon-optimized or non-codin-optimized coding regions encoding, e.g., additional IV proteins, and or other proteins, e.g., cytokines, are mixed together at desired proportions in PBS to achieve 6.4 mg/ml total DNA. This plasmid cocktail is placed into the 15 ml round bottom flask fitted with a magnetic stirring bar, and for the formulation containing 50 mg/ml CRL 1005, 3.13 ml of a solution containing about 3.2 mg/ml of NP encoding plasmid and about 3.2 mg/ml M2 encoding plasmid (about 6.4 mg/ml total DNA) is placed into the 15 ml round bottom flask fitted with a magnetic stirring bar, and the solutions are stirred with moderate speed, in an ice bath on top of a stirrer/hotplate (hotplate off) for 10 minutes. CRL 1005 (136 μl for 34 mg/ml final concentration, and 200 μl for 50 mg/ml final concentration) is then added using a 200 μl positive displacement pipette and the solution is stirred for a further 30 minutes on ice. Solutions of 1.6 mM and 1.8 mM BAK are prepared in PBS, and 734 μl of 1.6 mM and 670 μl of 1.8 mM are then added drop wise, slowly, to the stirring poloxamer solutions with concentrations of 34 mg/ml or 50 mg/ml mixtures, respectively, over 1 min using a 1 ml pipette. The solutions at this point are clear since they are below the cloud point of the poloxamer and are stirred on ice for 30 min. The ice baths are then removed; the solutions stirred at ambient temperature for 15 minutes to produce cloudy solutions as the poloxamer passes through the cloud point.

The flasks are then placed back into the ice baths and stirred for a further 15 minutes to produce clear solutions as the mixtures cooled below the poloxamer cloud point. The ice baths are again removed and the solutions stirred for a further 15 minutes. Stirring for 15 minutes above and below the cloud point (total of 30 minutes), is defined as one thermal cycle. The mixtures are cycled two more times.

In the meantime, two Steriflip® 50 ml disposable vacuum filtration devices, each with a 0.22 μm Millipore Express® membrane (available from Millipore, cat #SCGP00525) are placed in an ice bucket, with a vacuum line attached and left for 1 hour to allow the devices to equilibrate to the temperature of the ice. The poloxamer formulations are then diluted to 2.5 mg/ml DNA with PBS and filtered under vacuum.

The resulting formulations may be used immediately, or may be transferred to glass vials, cooled below the cloud point, and frozen at −80° C. for use at a later time.

A Simplified Method Without Thermal Cycling

Figure 4:
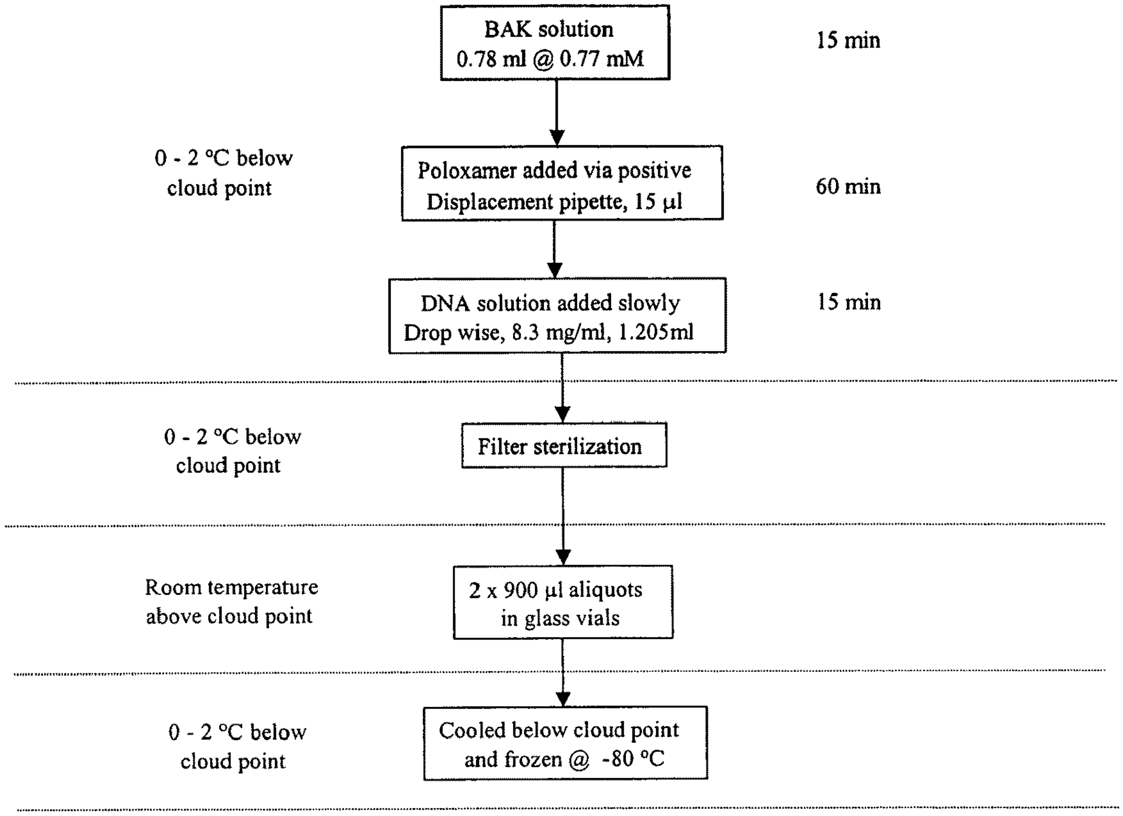
FIG. 4 shows the protocol for the simplified preparation (without thermal cycling) of a formulation comprising 0.3 mM BAK, 7.5 mg/ml CRL 1005 and 5 mg/ml DNA.

This example describes a simplified preparation of a formulation comprising 0.3 mM BAK, 7.5 mg/ml CRL 1005, and 5 mg/ml of DNA in a total volume of 2.0 ml. The ingredients are combined together at a temperature below the cloud point and then the formulation is simply filtered and then used or stored, according to the protocol outlined in FIG. 4.

A 0.77 mM solution of BAK is prepared in PBS, and 780 μl of the solution is placed into a 15 ml round bottom flask fitted with a magnetic stirring bar, and the solution is stirred with moderate speed, in an ice bath on top of a stirrer/hotplate (hotplate off) for 15 minutes. CRL 1005 (15 μl) is then added using a 100 μl positive displacement pipette and the solution is stirred for a further 60 minutes on ice. Plasmids comprising codon-optimized coding regions encoding, for example, NP, M1, and M2 as described herein, and optionally, additional plasmids comprising codon-optimized or non-codin-optimized coding regions encoding, e.g., additional IV proteins, and or other proteins, e.g., cytokines, are mixed together at desired proportions in PBS to achieve a final concentration of about 8.3 mg/ml total DNA. This plasmid cocktail is added drop wise, slowly, to the stirring solution over 1 min using a 5 ml pipette. The solution at this point (on ice) is clear since it is below the cloud point of the poloxamer and is further stirred on ice for 15 min.

In the meantime, one Steriflip® 50 ml disposable vacuum filtration devices, with a 0.22 μm Millipore Express® membrane (available from Millipore, cat #SCGP00525) is placed in an ice bucket, with a vacuum line attached and left for 1 hour to allow the device to equilibrate to the temperature of the ice. The poloxamer formulation is then filtered under vacuum, below the cloud point and then allowed to warm above the cloud point. The resulting formulations may be used immediately, or may be transferred to glass vials, cooled below the cloud point and then frozen at −80° C. for use at a later time.

Example 6

Animal Immunizations

The immunogenicity of the various IV expression products encoded by the codon-optimized polynucleotides described herein are initially evaluated based on each plasmid's ability to mount an immune response in vivo. Plasmids are tested individually and in combinations by injecting single constructs as well as multiple constructs. Immunizations are initially carried out in animals, such as mice, rabbits, goats, sheep, non-human primates, or other suitable animal, by intramuscular (IM) injections. Serum is collected from immunized animals, and the antigen specific antibody response is quantified by ELISA assay using purified immobilized antigen proteins in a protein—immunized subject antibody—anti-species antibody type assay, according to standard protocols. The tests of immunogenicity further include measuring antibody titer, neutralizing antibody titer, T-cell proliferation, T-cell secretion of cytokines, cytolytic T cell responses, and by direct enumeration of antigen specific CD4+ and CD8+ T-cells. Correlation to protective levels of the immune responses in humans are made according to methods well known by those of ordinary skill in the art. See above.

A. DNA Formulations

Plasmid DNA is formulated with a poloxamer by any of the methods described in Example 3. Alternatively, plasmid DNA is prepared as described above and dissolved at a concentration of about 0.1 mg/ml to about 10 mg/ml, preferably about 1 mg/ml, in PBS with or without transfection-facilitating cationic lipids, e.g., DMRIE/DOPE at a 4:1 DNA:lipid mass ratio. Alternative DNA formulations include 150 mM sodium phosphate instead of PBS, adjuvants, e.g., Vaxfectin™ at a 4:1 DNA:Vaxfectin™ mass ratio, mono-phosphoryl lipid A (detoxified endotoxin) from *S. minnesota* (MPL) and trehalosedicorynomycolateAF (TDM), in 2% oil (squalene)-Tween 80-water (MPL+TDM, available from Sigma/Aldrich, St. Louis, Mo., (catalog #M6536)), a solubilized mono-phosphoryl lipid A formulation (AF, available from Corixa), or (±)-N-(3-Acetoxypropyl)-N,N-dimethyl-2,3-bis(octyloxy)-1-propanaminium chloride (compound # VC1240) (see Shriver, J. W. et al., Nature 415:331-335 (2002), and P.C.T. Publication No. WO 02/00844 A2, each of which is incorporated herein by reference in its entirety).

B. Animal Immunizations

Plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are injected into BALB/c mice as single plasmids or as cocktails of two or more plasmids, as either DNA in PBS or formulated with the poloxamer-based delivery system: 2 mg/ml DNA, 3 mg/ml CRL 1005, and 0.1 mM BAK. Groups of 10 mice are immunized three times, at biweekly intervals, and serum is obtained to determine antibody titers to each of the antigens. Groups are also included in which mice are immunized with a trivalent preparation, containing each of the three plasmid constructs in equal mass.

The immunization schedule is as follows:

| | |
|---|---|
| Day −3 | Pre-bleed |
| Day 0 | Plasmid injections, intramuscular, bilateral in rectus femoris, 5-50 μg/leg |
| Day 21 | Plasmid injections, intramuscular, bilateral in rectus femoris, 5-50 μg/leg |
| Day 49 | Plasmid injections, intramuscular, bilateral in rectus femoris, 5-50 μg/leg |
| Day 59 | Serum collection |

Serum antibody titers are determined by ELISA with recombinant proteins, peptides or transfection supernatants and lysates from transfected VM-92 cells live, inactivated, or lysed virus.

C. Immunization of Mice with Vaccine Formulations Using a Vaxfectin™ Adjuvant

Vaxfectin™ (a 1:1 molar ratio of the cationic lipid VC1052 and the neutral co-lipid DPyPE) is a synthetic cationic lipid formulation which has shown promise for its ability to enhance antibody titers against when administered with DNA intramuscularly to mice.

In mice, intramuscular injection of Vaxfectin™ formulated with NP DNA increased antibody titers up to 20-fold to levels that could not be reached with DNA alone. In rabbits, complexing DNA with Vaxfectin™ enhanced antibody titers up to 50-fold. Thus, Vaxfectin™ shows promise as a delivery system and as an adjuvant in a DNA vaccine.

Vaxfectin™ mixtures are prepared by mixing chloroform solutions of VC1052 cationic lipid with chloroform solutions of DpyPE neutral co-lipid. Dried films are prepared in 2 ml sterile glass vials by evaporating the chloroform under a stream of nitrogen, and placing the vials under vacuum overnight to remove solvent traces. Each vial contains 1.5 μmole each of VC1052 and DPyPE. Liposomes are prepared by adding sterile water followed by vortexing. The resulting liposome solution is mixed with DNA at a phosphate mole: cationic lipid mole ratio of 4:1.

Plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are mixed together at desired proportions in PBS to achieve a final concentration of 1.0 mg/ml. The plasmid cocktail, as well as the controls, are formulated with Vaxfectin™. Groups of 5 BALB/c female mice are injected bilaterally in the rectus femoris muscle with 50 μl of DNA solution (100 μl total/mouse), on days 1 and 21 and 49 with each formulation. Mice are bled for serum on days 0 (prebleed), 20 (bleed 1), and 41 (bleed 2), and 62 (bleed 3), and up to 40 weeks post-injection. Antibody titers to the various IV proteins encoded by the plasmid DNAs are measured by ELISA as described elsewhere herein.

Cytolytic T-cell responses are measured as described in Hartikka et al. "Vaxfectin Enhances the Humoral Response to Plasmid DNA-encoded Antigens," *Vaccine* 19:1911-1923 (2001) and is incorporated herein in its entirety by reference. Standard ELISPOT technology is used for the CD4+ and CD8+ T-cell assays as described in Example 6, part A.

D. Production of NP, M1 or M2 Antisera in Animals

Plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are prepared according to the immunization scheme described above and injected into a suitable animal for generating polyclonal antibodies. Serum is collected and the antibody titered as above.

Monoclonal antibodies are also produced using hybridoma technology (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in *Monoclonal Antibodies and T-Cell Hybridomas*, Elsevier, N.Y., (1981), pp. 563-681, each of which is incorporated herein by reference in its entirety). In general, such procedures involve immunizing an animal (preferably a mouse) as described above. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al., *Gastroenterology* 80:225-232 (1981), incorporated herein by reference in its entirety. The hybridoma cells obtained through such a selection are then assayed to identify clones which secrete antibodies capable of binding the various IV proteins.

Alternatively, additional antibodies capable of binding to IV proteins described herein may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, various IV-specific antibodies are used to immunize an animal, preferably a mouse. The splenocytes of such an animal are then used to produce hybridoma cells, and the hybridoma cells are screened to identify clones which produce an antibody whose ability to bind to the IV protein-specific antibody can be blocked by the cognate IV protein. Such antibodies comprise anti-idiotypic antibodies to the IV protein-specific antibody and can be used to immunize an animal to induce formation of further IV-specific antibodies.

It will be appreciated that Fab and $F(ab')_2$ and other fragments of the antibodies of the present invention may be used according to the methods disclosed herein. Such fragments are typically produced by proteolytic cleavage, using enzymes such as papain (to produce Fab fragments) or pepsin (to produce $F(ab')_2$ fragments). Alternatively, NP, M1, M2, HA and eM2 binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

These antibodies are used, for example, in diagnostic assays, as a research reagent, or to further immunize animals to generate IV-specific anti-idiotypic antibodies. Non-limiting examples of uses for anti-IV antibodies include use in Western blots, ELISA (competitive, sandwich, and direct), immunofluorescence, immunoelectron microscopy, radioimmunoassay, immunoprecipitation, agglutination assays, immunodiffusion, immunoelectrophoresis, and epitope mapping (Weir, D. Ed. *Handbook of Experimental Immunology*, $4^{th}$ ed. Vols. I and H, Blackwell Scientific Publications (1986)).

Example 7

Mucosal Vaccination and Electrically Assisted Plasmid Delivery

A. Mucosal DNA Vaccination

Plasmid constructs comprising codon-optimized and non-codon-optimized coding regions encoding NP, M1, M2, HA, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, (100 μg/50 μl total DNA) are delivered to BALB/c mice at 0, 2 and 4 weeks via i.m., intranasal (i.n.), intravenous (i.v.), intravaginal (i.vag.), intrarectal (i.r.) or oral routes. The DNA is delivered unformulated or formulated with the cationic lipids DMRIE/DOPE (DD) or GAP-DLRIE/DOPE (GD). As endpoints, serum IgG titers against the various IV antigens are measured by ELISA and splenic T-cell responses are measured by antigen-specific production of IFN-gamma and IL-4 in ELISPOT assays. Standard chromium release assays are used to measure specific cytotoxic T lymphocyte (CTL) activity against the various IV antigens. Tetramer assays are used to detect and quantify antigen specific T-cells, with quantification being confirmed and phenotypic characterization accomplished by intracellular cytokine staining. In addition, IgG and IgA responses against the various IV antigens are analyzed by ELISA of vaginal washes.

B. Electrically-Assisted Plasmid Delivery

In vivo gene delivery may be enhanced through the application of brief electrical pulses to injected tissues, a procedure referred to herein as electrically-assisted plasmid delivery. See, e.g., Aihara, H. & Miyazaki, J. *Nat. Biotechnol.* 16:867-70 (1998); Mir, L. M. et al., *Proc. Natl. Acad. Sci. USA* 96:4262-67 (1999); Hartikka, J. et al., *Mol. Ther.* 4:407-15 (2001); and Mir, L. M. et al.; Rizzuto, G. et al., *Hum Gene Ther* 11:1891-900 (2000); Widera, G. et al, *J. of Immuno.* 164: 4635-4640 (2000). The use of electrical pulses for cell electropermeabilization has been used to introduce foreign DNA into prokaryotic and eukaryotic cells in vitro. Cell permeabilization can also be achieved locally, in vivo, using electrodes and optimal electrical parameters that are compatible with cell survival.

The electroporation procedure can be performed with various electroporation devices. These devices include external plate type electrodes or invasive needle/rod electrodes and can possess two electrodes or multiple electrodes placed in an array. Distances between the plate or needle electrodes can vary depending upon the number of electrodes, size of target area and treatment subject.

The TriGrid needle array, used in examples described herein, is a three electrode array comprising three elongate electrodes in the approximate shape of a geometric triangle. Needle arrays may include single, double, three, four, five, six or more needles arranged in various array formations. The electrodes are connected through conductive cables to a high voltage switching device that is connected to a power supply.

The electrode array is placed into the muscle tissue, around the site of nucleic acid injection, to a depth of approximately 3 mm to 3 cm. The depth of insertion varys depending upon the target tissue and size of patient receiving electroporation. After injection of foreign nucleic acid, such as plasmid DNA, and a period of time sufficient for distribution of the nucleic acid, square wave electrical pulses are applied to the tissue. The amplitude of each pulse ranges from about 100 volts to about 1500 volts, e.g., about 100 volts, about 200 volts, about 300 volts, about 400 volts, about 500 volts, about 600 volts, about 700 volts, about 800 volts, about 900 volts, about 1000 volts, about 1100 volts, about 1200 volts, about 1300 volts, about 1400 volts, or about 1500 volts or about 1-1.5 kV/cm, based on the spacing between electrodes. Each pulse has a duration of about 1 μs to about 1000 μs, e.g., about 1 μs, about 10 μs, about 50 μs, about 100 μs, about 200 μs, about 300 μs, about 400 μs, about 500 μs, about 600 μs, about 700 μs, about 800 μs, about 900 μs, or about 1000 μs, and a pulse frequency on the order of about 1-10 Hz. The polarity of the pulses may be reversed during the electroporation procedure by switching the connectors to the pulse generator. Pulses are repeated multiple times. The electroporation parameters (e.g. voltage amplitude, duration of pulse, number of pulses, depth of electrode insertion and frequency) will vary based on target tissue type, number of electrodes used and distance of electrode spacing, as would be understood by one of ordinary skill in the art.

Immediately after completion of the pulse regimen, subjects receiving electroporation can be optionally treated with membrane stabilizing agents to prolong cell membrane permeability as a result of the electroporation. Examples of membrane stabilizing agents include, but are not limited to, steroids (e.g. dexamethasone, methylprednisone and progesterone), angiotensin II and vitamin E. A single dose of dexamethasone, approximately 0.1 mg per kilogram of body weight, should be sufficient to achieve a beneficial affect.

EAPD techniques such as electroporation can also be used for plasmids contained in liposome formulations. The liposome—plasmid suspension is administered to the animal or patient and the site of injection is treated with a safe but effective electrical field generated, for example, by a TriGrid needle array. The electroporation may aid in plasmid delivery to the cell by destabilizing the liposome bilayer so that membrane fusion between the liposome and the target cellular structure occurs. Electroporation may also aid in plasmid delivery to the cell by triggering the release of the plasmid, in high concentrations, from the liposome at the surface of the target cell so that the plasmid is driven across the cell membrane by a concentration gradient via the pores created in the cell membrane as a result of the electroporation.

Female BALB/c mice aged 8-10 weeks are anesthetized with inhalant isoflurane and maintained under anesthesia for the duration of the electroporation procedure. The legs are shaved prior to treatment. Plasmid constructs comprising codon-optimized and non-codon-optimized coding regions encoding NP, M1, M2, HA, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are administered to BALB/c mice (n=10) via unilateral injection in the quadriceps with 25 μg total of a plasmid DNA per mouse using an 0.3 cc insulin syringe and a 26 gauge, 1/2 length needle fitted with a plastic collar to regulate injection depth. Approximately one minute after injection, electrodes are applied. Modified caliper electrodes are used to apply the electrical pulse. See Hartikka J. et al. *Mol Ther* 188:407-415 (2001). The caliper electrode plates are coated with conductivity gel and applied to the sides of the injected muscle before closing to a gap of 3 mm for administration of pulses. EAPD is applied using a square pulse type at 1-10 Hz with a field strength of 100-500 V/cm, 1-10 pulses, of 10-100 ms each.

Mice are vaccinated ±EAPD at 0, 2 and 4 weeks. As endpoints, serum IgG titers against the various IV antigens are measured by ELISA and splenic T-cell responses are measured by antigen-specific production of IFN-gamma and IL-4 in ELISPOT assays. Standard chromium release assays are used to measure specific cytotoxic T lymphocyte (CTL) activity against the various IV antigens.

Rabbits (n=3) are given bilateral injections in the quadriceps muscle with plasmid constructs comprising codon-optimized and non-codon-optimized coding regions encoding NP, HA, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector. The implantation area is shaved and the TriGrid electrode array is implanted into the target region of the muscle. 3.0 mg of plasmid DNA is administered per dose through the injection port of the electrode array. An injection collet is used to control the depth of injection.

Electroporation begins approximately one minute after injection of the plasmid DNA is complete. Electroporation is administered with a TriGrid needle array, with electrodes evenly spaced 7 mm apart, using an Ichor TGP-2 pulse generator. The array is inserted into the target muscle to a depth of about 1 to 2 cm. 4-8 pulses are administered. Each pulse has a duration of about 50-100 μs, an amplitude of about 1-1.2 kV/cm and a pulse frequency of 1 Hz. The injection and electroporation may be repeated.

Sera are collected from vaccinated rabbits at various time point. As endpoints, serum IgG titers against the various IV antigens are measured by ELISA and PBMC T-cell proliferative responses.

To test the effect of electroporation on therapeutic protein expression in non-human primates, male or female rhesus monkeys are given either 2 or 6 i.m. injections of plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, (0.1 to 10 mg DNA total per animal). Target muscle groups include, but are not limited to, bilateral rectus fermoris, cranial tibialis, biceps, gastrocenemius or deltoid muscles. The target area is shaved and a needle array, comprising between 4 and 10 electrodes, spaced between 0.5-1.5 cm apart, is implanted into the target muscle. Once injections are complete, a sequence of brief electrical pulses are applied to the electrodes implanted in the target muscle using an Ichor TGP-2 pulse generator. The pulses have an amplitude of approximately 120-200V. The pulse sequence is completed within one second. During this time, the target muscle may make brief contractions or twitches. The injection and electroporation may be repeated.

Sera are collected from vaccinated monkeys at various time points. As endpoints, serum IgG titers against the various IV antigens are measured by ELISA and PBMC T-cell proliferative responses are measured by antigen-specific production of IFN-gamma and IL-4 in ELISPOT assays or by tetramer assays to detect and quantify antigen specific T-cells, with quantification being confirmed and phenotypic characterization accomplished by intracellular cytokine staining. Standard chromium release assays are used to measure specific cytotoxic T lymphocyte (CTL) activity against the various IV antigens.

Example 8

Combinatorial DNA Vaccine Using Heterologous Prime-Boost Vaccination

This Example describes vaccination with a combinatorial formulation including one or more polynucleotides comprising one codon-optimized coding regions encoding an IV protein or fragment, variant, or derivative thereof prepared with an adjuvant and/or transfection facilitating agent; and also an isolated IV protein or fragment, variant, or derivative thereof. Thus, antigen is provided in two forms. The exogenous isolated protein stimulates antigen specific antibody and CD4+

T-cell responses, while the polynucleotide-encoded protein, produced as a result of cellular uptake and expression of the coding region, stimulates a CD8+ T-cell response. Unlike conventional "prime-boost" vaccination strategies, this approach provides different forms of antigen in the same formulation. Because antigen expression from the DNA vaccine doesn't peak until 7-10 days after injection, the DNA vaccine provides a boost for the protein component. Furthermore, the formulation takes advantage of the immunostimulatory properties of the bacterial plasmid DNA.

A. Non-Codon Optimized NP Gene

This example demonstrates the efficacy of this procedure using a non-codon-optimized polynucleotide encoding NP, however, the methods described herein are applicable to any IV polynucleotide vaccine formulation. Because only a small amount of protein is needed in this method, it is conceivable that the approach could be used to reduce the dose of conventional vaccines, thus increasing the availability of scarce or expensive vaccines. This feature would be particularly important for vaccines against pandemic influenza or biological warfare agents.

An injection dose of 10 μg influenza A/PR/8/34 nucleoprotein (NP) DNA per mouse, prepared essentially as described in Ulmer, J. B., et al., *Science* 259:1745-49 (1993) and Ulmer, J. B. et al., *J. Virol.* 72:5648-53 (1998) was pre-determined in dose response studies to induce T cell and antibody responses in the linear range of the dose response and results in a response rate of greater than 95% of mice injected. Each formulation, NP DNA alone, or NP DNA+/−NP protein formulated with Ribi I or the cationic lipids, DMRIE:DOPE or Vaxfectin™, was prepared in the recommended buffer for that vaccine modality. For injections with NP DNA formulated with cationic lipid, the DNA was diluted in 2×PBS to 0.2 mg/ml+/−purified recombinant NP protein (produced in baculovirus as described in Example 2) at 0.08 mg/ml. Each cationic lipid was reconstituted from a dried film by adding 1 ml of sterile water for injection (SWFI) to each vial and vortexing continuously for 2 min., then diluted with SWFI to a final concentration of 0.15 mM. Equal volumes of NP DNA (+/−NP protein) and cationic lipid were mixed to obtain a DNA to cationic lipid molar ratio of 4:1. For injections with DNA containing Ribi I adjuvant (Sigma), Ribi I was reconstituted with saline to twice the final concentration. Ribi I (2×) was mixed with an equal volume of NP DNA at 0.2 mg/ml in saline+/−NP protein at 0.08 mg/ml. For immunizations without cationic lipid or Ribi, NP DNA was prepared in 150 mM sodium phosphate buffer, pH 7.2. For each experiment, groups of 9 BALB/c female mice at 7-9 weeks of age were injected with 50 μl of NP DNA+/−NP protein, cationic lipid or Ribi I. Injections were given bilaterally in each rectus femoris at day 0 and day 21. The mice were bled by OSP on day 20 and day 33 and serum titers of individual mice were measured.

NP specific serum antibody titers were determined by indirect binding ELISA using 96 well ELISA plates coated overnight at 4° C. with purified recombinant NP protein at 0.5 μg per well in BBS buffer pH 8.3. NP coated wells were blocked with 1% bovine serum albumin in BBS for 1 h at room temperature. Two-fold serial dilutions of sera in blocking buffer were incubated for 2 h at room temperature and detected by incubating with alkaline phosphatase conjugated (AP) goat anti-mouse IgG-Fc (Jackson Immunoresearch, West Grove, Pa.) at 1:5000 for 2 h at room temperature. Color was developed with 1 mg/ml para-nitrophenyl phosphate (Calbiochem, La Jolla, Calif.) in 50 mM sodium bicarbonate buffer, pH 9.8 and 1 mM $MgCl_2$ and the absorbance read at 405 nm. The titer is the reciprocal of the last dilution exhibiting an absorbance value 2 times that of pre-bleed samples.

Standard ELISPOT technology, used to identify the number of interferon gamma (IFN-γ) secreting cells after stimulation with specific antigen (spot forming cells per million splenocytes, expressed as SFU/million), was used for the CD4+ and CD8+ T-cell assays. For the screening assays, 3 mice from each group were sacrificed on day 34, 35, and 36. At the time of collection, spleens from each group were pooled, and single cell suspensions made in cell culture media using a dounce homogenizer. Red blood cells were lysed, and cells washed and counted. For the CD4+ and CD8+ assays, cells were serially diluted 3-fold, starting at $10^6$ cells per well and transferred to 96 well ELISPOT plates pre-coated with anti-murine IFN-γ monoclonal antibody. Spleen cells were stimulated with the H-$2K^d$ binding peptide, TYQRTRALV (SEQ ID NO:81), at 1 μg/ml and recombinant murine IL-2 at 1 U/ml for the CD8+ assay and with purified recombinant NP protein at 20 μg/ml for the CD4+ assay. Cells were stimulated for 20-24 hours at 37° C. in 5% $CO_2$, then the cells were washed out and biotin labeled anti-IFN-γ monoclonal antibody added for a 2 hour incubation at room temperature. Plates were washed and horseradish peroxidase-labeled avidin was added. After a 1-hour incubation at room temperature, AEC substrate was added and "spots" developed for 15 mM. Spots were counted using the Immunospot automated spot counter (C.T.L. Inc., Cleveland Ohio). Thus, CD4+ and CD8+responses were measured in three separate assays, using spleens collected on each of three consecutive days.

Figure 5:
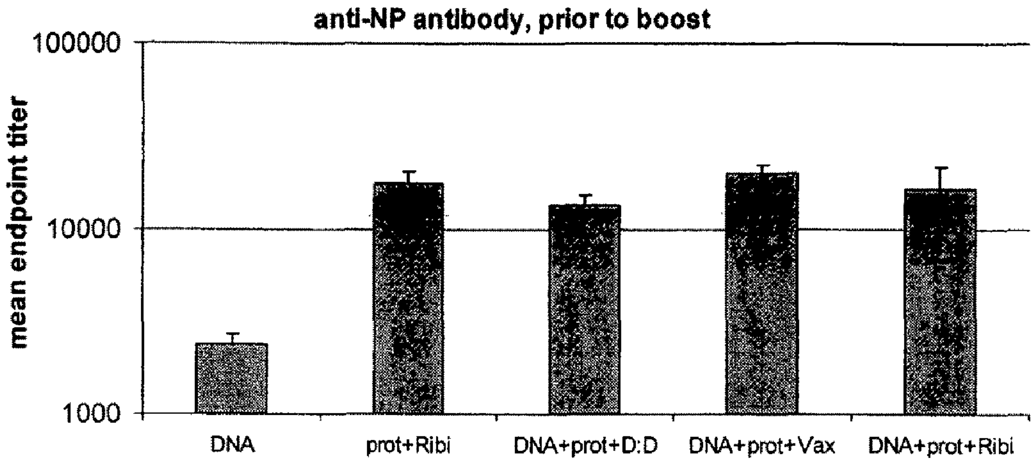
FIG. 5 shows the anti-NP antibody response three weeks after a single administration of a combinatorial prime-boost vaccine formulation against the influenza virus NP protein.

Three weeks after a single injection, antibody responses in mice receiving vaccine formulations containing purified protein were 6 to 8-fold higher than for mice receiving NP DNA only (FIG. 5, Table 15). The titers for mice receiving DNA and protein formulated with a cationic lipid were similar to those for mice receiving protein in Ribi adjuvant or DNA and protein in Ribi adjuvant. These data indicate that the levels of antibody seen when protein is injected with an adjuvant can be obtained with DNA vaccines containing DNA and protein formulated with a cationic lipid, without the addition of conventional adjuvant.

Figure 6:
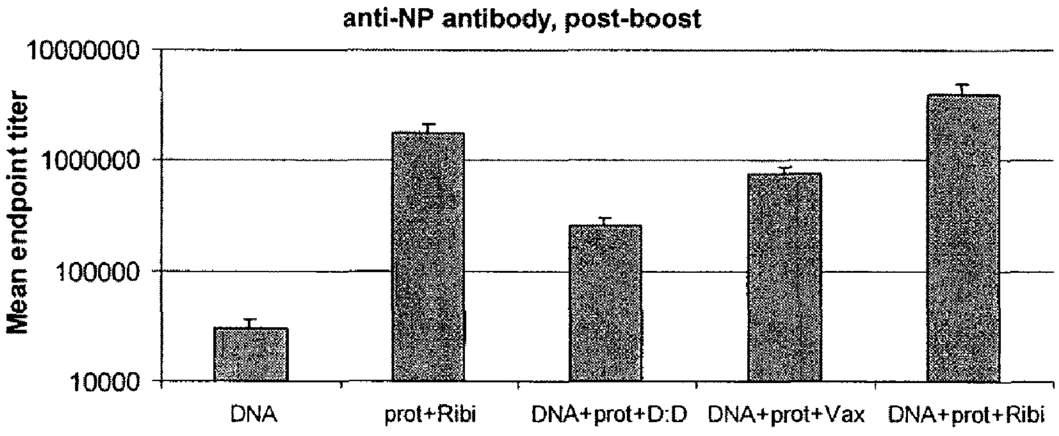
FIG. 6 shows the anti-NP antibody response twelve days after a second administration of a combinatorial prime-boost vaccine formulation against the influenza virus NP protein.

Twelve days after a second injection, antibody responses in mice receiving vaccine formulations containing purified protein were 9 to 129-fold higher than for mice receiving NP DNA only (FIG. 6, Table 15). With a mean anti-NP antibody titer of 750,933 at day 33, the titers for mice receiving DNA and protein formulated with Vaxfectin™ were 25-fold higher than for mice receiving DNA alone (mean titer=30,578), and nearly as high as those for mice injected with protein in Ribi adjuvant (mean titer=1,748,133).

TABLE 15

| Fold increase in antibody response over DNA alone | | |
|---|---|---|
| Formulation | 20 days after one injection | 12 days after second injection |
| protein + Ribi | 7X (p = 0.0002) | 57X (p = 0.002) |
| DNA + protein + DMRIE: DOPE | 6X (p = 0.00005) | 9X (p = 0.0002) |
| DNA + protein + Vaxfectin ™ | 8X (p = 0.00003) | 25X (p = 0.0004) |
| DNA + protein + Ribi | 7X (p = 0.01) | 129X (p = 0.003) |

*protein = purified recombinant NP protein

Figure 7:
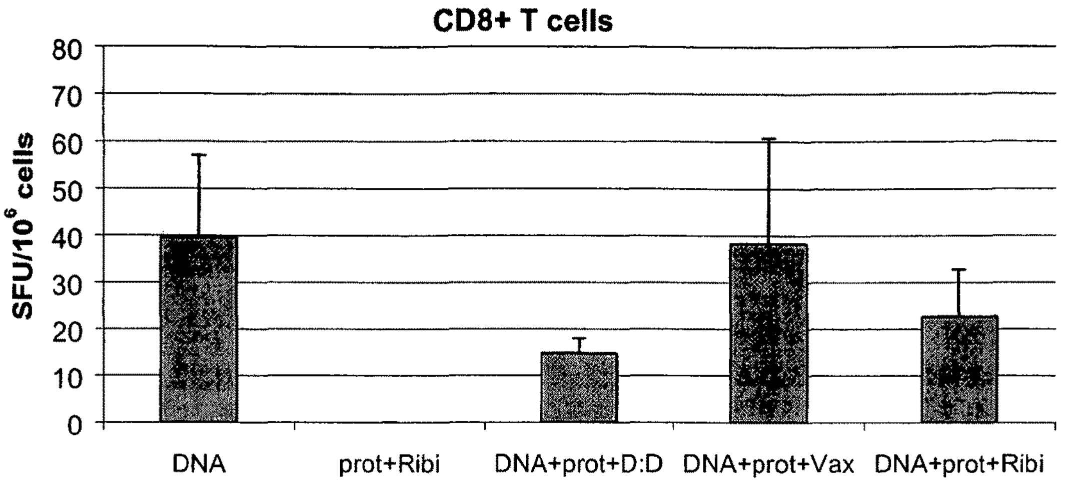
FIG. 7 shows the CD8+ T Cell response to a combinatorial prime-boost vaccine formulation against the influenza virus NP protein.

As expected, an NP specific CD8+ T-cell IFN-γ response was not detected in spleens of mice injected with NP protein in Ribi (FIG. 7). All of the other groups had detectable NP specific CD8+ T-cell responses. The CD8+ T-cell responses for all groups receiving vaccine formulations containing NP DNA were not statistically different from each other.

Figure 8:
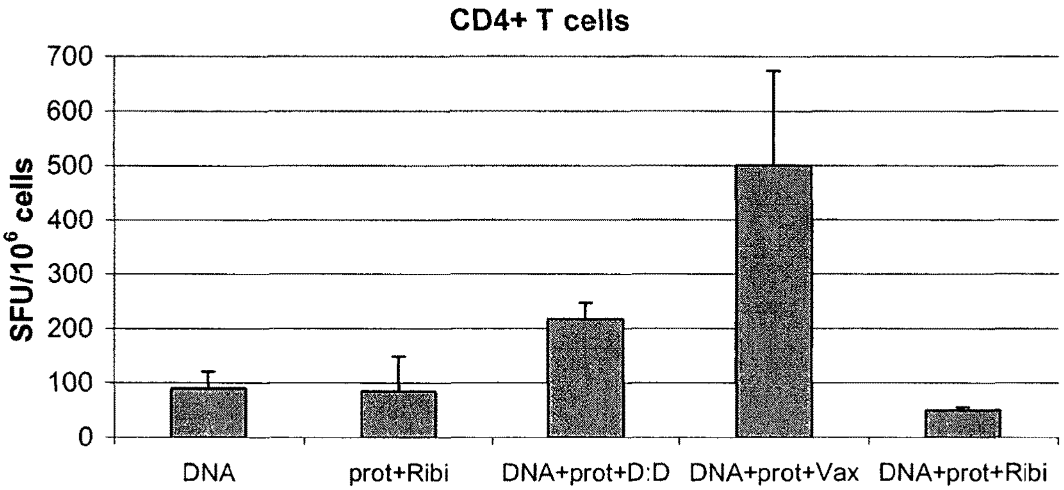
FIG. 8 shows the CD4+ T Cell response to a combinatorial prime-boost vaccine formulation against the influenza virus NP protein.

Mice from all of the groups had detectable NP specific CD4+ T-cell responses (FIG. 8). The CD4+ T-cell responses of splenocytes from groups receiving vaccine formulations containing NP DNA and NP protein formulated with cationic lipid were 2-6 fold higher than the group injected with DNA alone.

B. Codon-Optimized IV Constructs

Plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are used in the prime-boost compositions described herein. For the prime-boost modalities, the same protein may be used for the boost, e.g., DNA encoding NP with NP protein, or a heterologous boost may be used, e.g., DNA encoding NP with an M1 protein boost. Each formulation, the plasmid comprising a coding region for the IV protein alone, or the plasmid comprising a coding region for the IV protein plus the isolated protein are formulated with Ribi I or the cationic lipids, DMRIE:DOPE or Vaxfectin™. The formulations are prepared in the recommended buffer for that vaccine modality. Exemplary formulations, using NP as an example, are described herein. Other plasmid/protein formulations, including multivalent formulations, can be easily prepared by one of ordinary skill in the art by following this example. For injections with DNA formulated with cationic lipid, the DNA is diluted in 2×PBS to 0.2 mg/ml+/−purified recombinant NP protein at 0.08 mg/ml. Each cationic lipid is reconstituted from a dried film by adding 1 ml of sterile water for injection (SWFI) to each vial and vortexing continuously for 2 min., then diluted with SWFI to a final concentration of 0.15 mM. Equal volumes of NP DNA (+/−NP protein) and cationic lipid are mixed to obtain a DNA to cationic lipid molar ratio of 4:1. For injections with DNA containing Ribi I adjuvant (Sigma), Ribi I is reconstituted with saline to twice the final concentration. Ribi I (2×) is mixed with an equal volume of NP DNA at 0.2 mg/ml in saline+/−NP protein at 0.08 mg/ml. For immunizations without cationic lipid or Ribi, NP DNA is prepared in 150 mM sodium phosphate buffer, pH 7.2. For each experiment, groups of 9 BALB/c female mice at 7-9 weeks of age are injected with 50 μl of NP DNA+/−NP protein, cationic lipid or Ribi I. The formulations are administered to BALB/c mice (n=10) via bilateral injection in each rectus femoris at day 0 and day 21.

The mice are bled on day 20 and day 33 and serum titers of individual mice to the various IV antigens are measured. Serum antibody titers specific for the various IV antigens are determined by ELISA. Standard ELISPOT technology, used to identify the number of interferon gamma (IFN-γ) secreting cells after stimulation with specific antigen (spot forming cells per million splenocytes, expressed as SFU/million), is used for the CD4+ and CD8+ T-cell assays using 3 mice from each group vaccinated above, sacrificed on day 34, 35 and 36, post vaccination.

Example 9

Murine Challenge Model of Influenza

General Experimental Procedure

A murine challenge model with influenza A virus is used to test the efficacy of the immunotherapies. The model used is based on that described in Ulmer, J. B., et al., *Science* 259: 1745-49 (1993) and Ulmer, J. B. et al., *J Viral.* 72:5648-53 (1998), both of which are incorporated herein by reference in their entireties. This model utilizes a mouse-adapted strain of influenza A/HK/8/68 which replicates in mouse lungs and is titered in tissue culture in Madin Darby Canine Kidney cells. The $LD_{90}$ of this mouse-adapted influenza virus is determined in female BALB/c mice age 13-15 weeks. In this model, two types of challenge study can be conducted: lethal challenge, where the virus is administered intranasally to heavily sedated mice under ketamine anesthesia; and a sub-lethal challenge, where mice are not anesthetized when the viral inoculum is administered (also intranasally). The endpoint for lethal challenge is survival, but loss in body mass and body temperature can also be monitored. The read-outs for the sublethal challenge include lung virus titer and loss in body mass and body temperature.

In the studies described here, mice are subjected to lethal challenge.

Mice that are previously vaccinated with DNA encoding IV antigens are anesthetized and challenged intranasally with 0.02 mL of mouse-adapted influenza A/HK/8/68 (mouse passage #6), diluted 1 to 10,000 (500 PFU) in PBS containing 0.2% wt/vol BSA.

These challenge studies utilize groups of 10 mice. The route of administration is intramuscular in rectus femoris (quadriceps), using 0.1 μg up to 1 mg total plasmid DNA. Plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are tested singly and in multivalent cocktails for the ability to protect against challenge. The plasmids are formulated with an adjuvant and/or a transfection facilitating agent, e.g., Vaxfectin™ by methods described elsewhere herein. Mice are vaccinated on days 0 and 21 using amounts of plasmids as described in Example 6. Subsequent injections can be administered. Nasal challenge of mice takes place 3 weeks after the final immunization, and animals are monitored daily for body mass, hypothermia, general appearance and then death.

For each group of mice that are studied, blood is taken at 2 weeks following the second injection, and/or any subsequent injection, and the animals are terminally bled two weeks following the last injection. Antibody titers are determined for M2, M1, and NP using ELISAs as previously described.

Plasmids

As described above, constructs of the present invention were inserted into the expression vector VR10551. VR10551 is an expression vector without any transgene insert.

VR4750 contains the coding sequence for hemagglutinin (HA) ($H_3N_2$) from mouse adapted A/Hong Kong/68. The DNA was prepared using Qiagen plasmid purification kits.

Experimental Procedure

The experimental procedure for the following example is as described above, with particular parameters and materials employed as described herein. In order to provide a pDNA control for protection in the mouse influenza challenge model, the hemagglutinin (HA) gene was cloned from the influenza A/HK/8/68 challenge virus stock, which was passaged 6 times in mice.

Mice were vaccinated twice at 3 week intervals with either 100 μg pDNA VR4750 encoding the HA gene cloned directly from the mouse-adapted influenza A/HK/8/68 strain, or with 100 μg blank vector pDNA (VR10551). An additional control group was immunized intranasally with live A/HK/8/68 virus (500 PFU). Three weeks after the last injection, mice were challenged intranasally with mouse-adapted influenza A/HK/8/68 with one of 3 doses (50, 500 and 5,000 PFU). Following viral challenge, mice were monitored daily for symptoms of disease, loss in body mass and survival.

Figure 9A:
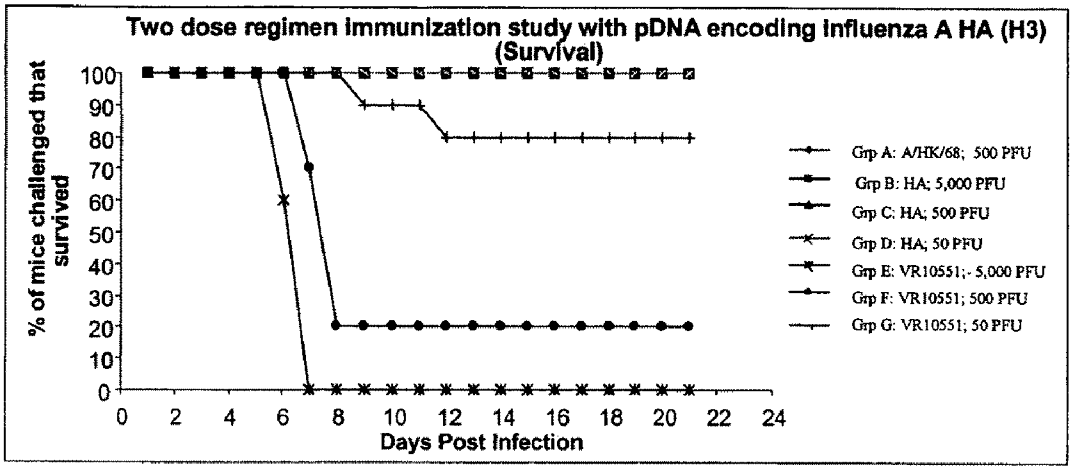
FIGS. 9A and 9B show the results of a two dose mouse immunization regimen study with plasmid DNA encoding IAV HA (H3).
Figure 9B:
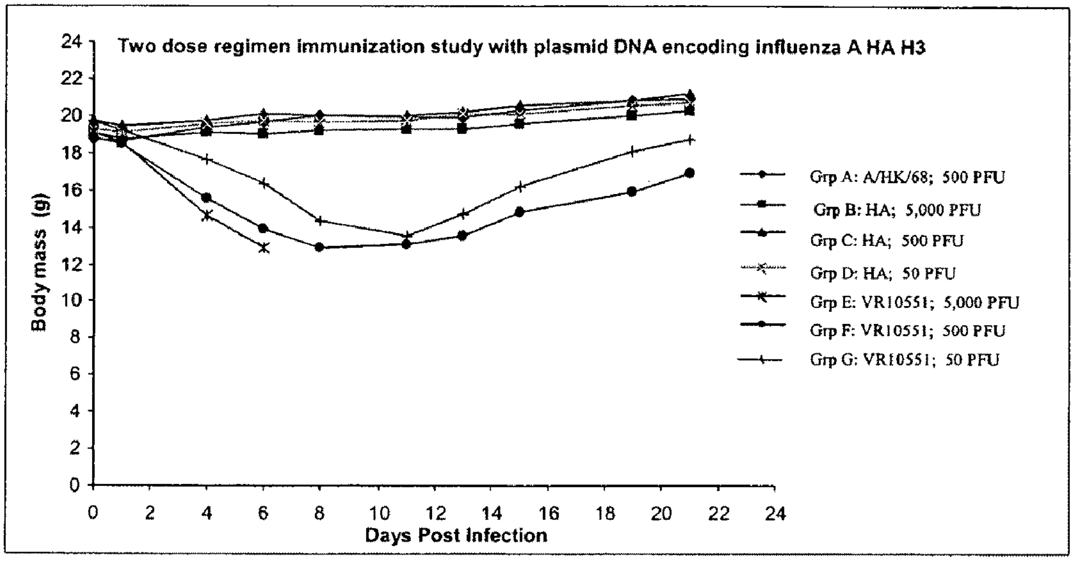

FIG. 9 shows that homologous HA-pDNA vaccinated mice are completely protected over a range of viral challenge doses (FIG. 9A) and did not suffer significant weight loss (FIG. 9B) during the 3 week period following challenge.

Based on these results, future mouse flu challenge studies can include VR4750 (HA) pDNA as a positive control for protection and utilize 500 PFU, which is the LD90 for this mouse-adapted virus, as the challenge dose.

Example 10

Challenge in Non-Human Primates

The purpose of these studies is to evaluate three or more of the optimal plasmid DNA vaccine formulations for immunogenicity in non-human primates. Rhesus or cynomolgus monkeys (6/group) are vaccinated with plasmid constructs comprising codon-optimized and non-codon-optimized coding regions encoding NP, HA, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, intramuscularly 0.1 to 2 mg DNA combined with cationic lipid, and/or poloxamer and/or aluminum phosphate based or other adjuvants at 0, 1 and 4 months.

Blood is drawn twice at baseline and then again at the time of and two weeks following each vaccination, and then again 4 months following the last vaccination. At 2 weeks post-vaccination, plasma is analyzed for humoral response, and PBMCs are monitored for cellular responses, by standard methods described herein. Animals are monitored for 4 months following the final vaccination to determine the durability of the immune response.

Animals are challenged within 2-4 weeks following the final vaccination. Animals are challenged intratracheally with the suitable dose of virus based on preliminary challenge studies. Nasal swabs, pharyngeal swabs and lung lavages are collected at days 0, 2, 4, 6, 8 and 11 post-challenge and will be assayed for cell-free virus titers on monkey kidney cells. After challenge, animals are monitored for clinical symptoms, e.g., rectal temperature, body weight, leukocyte counts, and in addition, hematocrit and respiratory rate. Oropharyngeal swab samples are taken to allow determination of the length of viral shedding. Illness is scored using the system developed by Berendt & Hall (*Infect Immun* 16:476-479 (1977)), and will be analyzed by analysis of variance and the method of least significant difference.

Example 11

Challenge in Birds

In this example, various vaccine formulations of the present invention are tested in the chicken influenza model. For these studies an IV H5N1 virus, known to infect birds, is used. Plasmid constructs comprising codon-optimized and non-codon-optimized coding regions encoding NP, M1, M2, eM2, and/or an eM2-NP fusion; or alternatively coding regions (either codon-optimized or non-codon optimized) encoding various IV proteins or fragments, variants or derivatives either alone or as fusions with a carrier protein, e.g., HBcAg, as well as various controls, e.g., empty vector, are formulated with cationic lipid, and/or poloxamer and/or aluminum phosphate based or other adjuvants. The vaccine formulations are delivered at a dose of about 1-10 μg, delivered 1M into the defeathered breast area, at 0 and 1 month. The animals are bled for antibody results 3 weeks following the second vaccine. Antibody titers against the various IV antigens are determined using techniques described in the literature. See, e.g., Kodihalli S. et al., Vaccine 18:2592-9 (2000). The birds are challenged intranasally with 0.1 mL containing 100 $LD_{50}$ 3 weeks post second vaccination. The birds are monitored daily for 10 days for disease symptoms, which include loss of appetite, diarrhea, swollen faces, cyanosis, paralysis and death. Tracheal and cloacal swabs are taken 4 days following challenge for virus titration.

Example 12

Formulation Selection Studies

The potency of different vaccine formulations was evaluated in different experimental studies using the NP protein of Influenza A/PR/8/34.

Vaccination Regimen

Groups of nine, six- to eight-week old BALB/c mice (Harlan-Sprague-Dawley) received bilateral (50 μL/leg) intramuscular (rectus femoris) injections of plasmid DNA. Control mice received DNA in PBS alone. Mice received injections on days 0, 20 and 49. Mice were bled by OSP on day 62, and NP-specific antibodies analyzed by ELISA. Splenocytes were harvested from 3 mice/group/day for three sequential days beginning day 63, and NP-specific T cells were analyzed by IFNγ ELISPOT using overlapping peptide stimulation.

Cell Culture Media

Splenocyte cultures were grown in RPMI-1640 medium containing 25 mM HEPES buffer and L-glutamine and supplemented with 10% (v/v) FBS, 55 μM β-mercaptoethanol, 100 U/mL of penicillin G sodium salt, and 100 μg/mL of streptomycin sulfate.

Standard Influenza NP Indirect Binding Assay

NP specific serum antibody titers were determined by indirect binding ELISA using 96 well ELISA plates coated overnight at 4° C. with purified recombinant NP protein at 0.5 μg per well in BBS buffer, pH 8.3. NP coated wells were blocked with 1% bovine serum albumin in BBS for 1 hour at room temperature. Two-fold serial dilutions of sera in blocking buffer were incubated for 2 hours at room temperature and detected by incubating with alkaline phosphatase conjugated (AP) goat anti-mouse IgG-Fc (Jackson Immunoresearch, West Grove, Pa.) at 1:5000 for 2 hours at room temperature. Color was developed with 1 mg/ml para-nitrophenyl phosphate (Calbiochem, La Jolla, Calif.) in 50 mM sodium bicarbonate buffer, pH 9.8 and 1 mM $MgCl_2$ and the absorbance read at 405 nm. The titer is the reciprocal of the last dilution exhibiting an absorbance value 2 times that of pre-bleed samples.

Standard NP CD8+ and CD4+ T-Cell ELISPOT Assay

Standard ELISPOT technology, used to identify the number of interferon gamma (IFN-γ) secreting cells after stimulation with specific antigen (spot forming cells per million splenocytes, expressed as SFU/million), was used for the CD4+ and CD8+ T-cell assays. Three mice from each group were sacrificed on each of three consecutive days. At the time of collection, spleens from each group were pooled, and single cell suspensions were made in cell culture media using a dounce homogenizer. Red blood cells were lysed, and cells were washed and counted. For the CD4+ and CD8+ assays, cells were serially diluted 3-fold, starting at $10^6$ cells per well and transferred to 96 well ELISPOT plates pre-coated with anti-murine IFN-γ monoclonal antibody. Spleen cells were stimulated with the H-$2K^d$ binding peptide, TYQRTRALV, at 1 μg/ml and recombinant murine IL-2 at 1 U/ml for the CD8+ assay and with purified recombinant NP protein at 20 μg/ml for the CD4+ assay. Cells were stimulated for 20-24 hours at 3TC in 5% $CO_2$, and then the cells were washed out and biotin labeled anti-IFN-γ monoclonal antibody added for a 2 hour incubation at room temperature. Plates were washed and horseradish peroxidase-labeled avidin was added. After a 1-hour incubation at room temperature, AEC substrate was added and "spots" developed for 15 minutes. Spots were counted using the Immunospot automated spot counter (C.T.L. Inc., Cleveland Ohio).

Experiment 1

The purpose of this experiment was to determine a dose response to naked pDNA (VR4700) and for pDNA formulated with W—P1205-02A. VR4700 is a plasmid encoding influenza A/PR/8/34 nucleoprotein (NP) in a VR10551 backbone. VR10551 is an expression vector without any transgene insert. VF-P1205-02A is a formulation containing a poloxamer with a POP molecular weight of 12 KDa and POE of 5% (CRL1005) at a DNA:poloxamer:BAK ratio of 5 mg/ml:7.5 mg/ml:0.3 mM. The results of this experiment are shown in the following Table:

TABLE 16

| DNA dose (μg) | CRL1005 dose (μg) | BAK conc. (μM) | Serum Ab titers (total IgG, n = 9) | $CD8^+T$ cells ($SFU/10^6$) | $CD4^+T$ cells ($SFU/10^6$) |
|---|---|---|---|---|---|
| 1 | | | 11,206 | 28 | 24 |
| 10 | | | 31,289 | 77 | 99 |
| 100 | | | 65,422 | 243 | 304 |
| 1 | 1.5 | 0.06 | 9,956 | 48 | 57 |
| 10 | 15 | 0.6 | 45,511 | 174 | 220 |
| 100 | 150 | 6 | 79,644 | 397 | 382 |

The results of this experiment indicate that increasing the dose of DNA increases both the humoral and cell mediated immune responses. When the DNA is formulated with poloxamer and BAK, increasing the dose also increases both the humoral and cell mediated immune responses.

Experiment 2

The purpose of this experiment was to determine a dose response to CRL1005, with a fixed pDNA (VR4700) dose and no BAK. The results of this experiment are shown in the following Table:

TABLE 17

| DNA dose (μg) | CRL1005 dose (μg) | Serum Ab titers (total IgG, n = 9) | $CD8^+T$ cells ($SFU/10^6$) | $CD4^+T$ cells ($SFU/10^6$) |
|---|---|---|---|---|
| 10 | | 27,733 | 45 | 46 |
| 10 | 15 | 38,400 | 69 | 86 |
| 10 | 50 | 46,933 | 66 | 73 |
| 10 | 150 | 54,044 | 90 | 97 |
| 10 | 450 | 76,800 | 90 | 92 |
| 10 | 750 | 119,467 | 83 | 60 |

The results of this experiment indicate that increasing the dose of CRL1005 increases both the humoral and cell mediated immune responses.

Experiment 3

The purpose of this experiment was to compare immune responses of DMRIE:DOPE (1:1, mol:mol) and Vaxfectin™ cationic lipid formulations at different pDNA/cationic lipid molar ratios. The results of this experiment are shown in the following Table:

TABLE 18

| DNA dose (μg) | DMRIE:DOPE pDNA/ cationic lipid molar ratios | Vaxfectin ™ pDNA/ cationic lipid molar ratios | Serum Ab titers (total IgG, n = 9) | $CD8^+T$ cells ($SFU/10^6$) | $CD4^+T$ cells ($SFU/10^6$) |
|---|---|---|---|---|---|
| 10 | | | 17,778 | 57 | 54 |
| 10 | 4:1 | | 48,356 | 47 | 112 |
| 10 | 2:1 | | 49,778 | 44 | 133 |
| 10 | | 4:1 | 88,178 | 68 | 464 |
| 10 | | 2:1 | 150,756 | 46 | 363 |

The results of this experiment indicate that formulating the plasmid with DMRIE:DOPE or Vaxfectin™ increases both the humoral and cell mediated immune responses.

Experiment 4

The purpose of this experiment was first to compare immune responses of DMRIE:DOPE (1:1, mol:mol) at pDNA/cationic lipid molar ratios of 4:1 as an MLV (multi lamellar vesicle formulation—multi-vial) or SUV (small unilamellar vesicles—single-vial) formulation. Second, it was to compare sucrose (lyophilized and frozen) and PBS based formulations. The results of this experiment are shown in the following Table:

TABLE 19

| DNA dose (μg) | Formulation | Buffer | Serum Ab titers (total IgG, n = 9) | $CD8^+T$ cells ($SFU/10^6$) | $CD4^+T$ cells ($SFU/10^6$) |
|---|---|---|---|---|---|
| 10 | | PBS, pH 7.2 | 21,333 | 107 | 118 |
| 10 | SUV | PBS, pH 7.2 | 15,644 | 144 | 169 |
| 10 | SUV | PBS, pH 7.8 | 13,511 | 114 | 173 |
| 10 | SUV Frozen/thawed | Sucrose pH 7.8 | 15,644 | 103 | 119 |
| 10 | SUV Lyophilized | Sucrose pH 7.8 | 10,311 | ND | 246 |
| 10 | MLV | PBS, pH 7.2 | 29,867 | 170 | 259 |

* ND - could not be counted due to high background

The results of this experiment indicate that formulating the plasmid with DMRIE:DOPE stimulates both the humoral and cell mediated immune responses.

Experiment 5

The purpose of this experiment was first to determine what effect changing the ratio of DMRIE to DOPE has on immune response at pDNA/cationic lipid molar ratios of 4:1 as an MLV (multi-vial, in PBS) or SUV (single-vial in PBS) formulation. Second, it was to compare the effect of changing the co-lipid from DOPE to cholesterol. The results of this experiment are shown in the following Table:

TABLE 20

| DNA dose (μg) | Formulation | DMRIE:DOPE | Serum Ab titers (total IgG, n = 9) | $CD8^+T$ cells (SFU/$10^6$) | $CD4^+T$ cells (SFU/$10^6$) |
|---|---|---|---|---|---|
| 10 | | | 19,342 | 65 | 98 |
| 10 | MLV, DM:DP | 1:0 | 38,684 | 70 | 126 |
| 10 | MLV, DM:DP | 3:1 | 75,093 | 82 | 162 |
| 10 | MLV, DM:DP | 1:1 | 53,476 | 78 | 186 |
| 10 | SUV, DM:DP | 1:1 | 36,409 | 96 | 106 |
| 10 | MLV, DM:Chol | 1:1 | 52,338 | 65 | 154 |

The results of this experiment indicate that formulating the plasmid with DMRIE:DOPE stimulates both the humoral and cell mediated immune responses. Changing the co-lipid from DOPE to cholesterol also stimulates both the humoral and cell mediated immune responses.

Experiment 6

The purpose of this experiment was to obtain a dose response to pDNA formulated with DMRIE:DOPE (1:1, mol:mol) at a 4:1 pDNA/cationic lipid molar ratio. The results of this experiment are shown in the following Table:

TABLE 21

| DNA dose (μg) | Formulation | Serum Ab titers (total IgG, n = 9) | $CD8^+T$ cells (SFU/$10^6$) | $CD4^+T$ cells (SFU/$10^6$) |
|---|---|---|---|---|
| 10 | | 22,044 | 119 | 154 |
| 1 | MLV | 5,600 | 22 | 67 |
| 3 | MLV | 22,756 | 46 | 97 |
| 10 | MLV | 45,511 | 199 | 250 |
| 30 | MLV | 60,444 | 274 | 473 |
| 100 | MLV | 91,022 | 277 | 262 |

The results of this experiment indicate that when the plasmid is formulated with DMRIE:DOPE, increasing the dose also increases both the humoral and cell mediated immune responses.

Example 13

In vitro expression of influenza antigens

Plasmid Vector

Polynucleotides of the present invention were inserted into eukaryotic expression vector backbones VR10551, VR10682 and VR6430 all of which are described previously. The VR10551 vector is built on a modified pUC18 background (see Yanisch-Perron, C., et al. *Gene* 33:103-119 (1985)), and contains a kanamycin resistance gene, the human cytomegalovirus immediate early 1 promoter/enhancer and intron A, and the bovine growth hormone transcription termination signal, and a polylinker for inserting foreign genes. See Hartikka, J., et al., *Hum. Gene Ther.* 7:1205-1217 (1996). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.).

Various plasmids were generated by cloning the nucleotide sequence for the following influenza A antigens: segment 7 (encodes both M1 and M2 proteins via differential splicing), M2 and NP into expression constructions as described below and pictured in FIG. 13.

Plasmids VR4756 (SEQ ID NO:91), VR4759 (SEQ ID NO:92) and VR4762 (SEQ ID NO:93) were created by cloning the nucleotide sequence encoding the consensus sequence for the following influenza A antigens respectively: segment 7 (encoding both the M1 and M2 proteins by differential splicing), M2 and NP into the VR10551 backbone. The VR4756, VR4759 and VR4762 plasmids are also described in Table 13.

The VR4764 (SEQ ID NO:95) and VR4765 (SEQ ID NO:96) plasmids were constructed by ligating the segment 7 and NP coding regions from VR4756 and VR4762 respectively into the VR10682 vector. Specifically, the VR4756 vector was digested with EcoRV and SalI restriction endonucleases and the blunted fragment was ligated into the VR10682 backbone, which had been digested with the EcoRV restriction endonuclease. The VR4765 vector was constructed by digesting the VR4762 vector with EcoRV and NotI and ligating the NP coding region into the VR10682 backbone digested with the same restriction endonucleases.

VR4766 (SEQ ID NO:97) and VR4767 (SEQ ID NO:98) contain a CMV promoter/intron A-NP expression cassette and a RSV promoter (from VCL1005)-segment 7 expression cassette in the same orientation (VR4766) or opposite orientation (VR4767). These plasmids were generated by digesting VR4762 with the DraIII restriction endonuclease and cutting the RSV-segment 7-mRBG cassette from VR4764 with EcoRV and BamHI restriction endonucleases. After exonuclease digestion with the Klenow fragment of DNA polymerase I, the EcoRV/BamHI fragment was cloned into the Drain digested VR4762 vector. Both insert orientations were obtained by this blunt end cloning method.

VR4768 (SEQ ID NO:99) and VR4769 (SEQ ID NO:100), containing a CMV promoter/intron A-segment 7 expression cassette and a RSV promoter-NP expression cassette, were similarly derived. VR4756 was digested with the DraIII restriction endonuclease and blunted by treatment with the Klenow fragment of DNA Polymerase I. The cassette containing the RSV promoter, NP coding region and mRBG terminator was removed from VR4765 by digesting with KpnI and NdeI restriction endonucleases. The fragment was also blunted with the Klenow fragment of DNA polymerase I and ligated into the DraIII-digested VR4756 vector in both gene orientations.

VR4770 (SEQ ID NO:101), VR4771 (SEQ ID NO:102) and VR4772 (SEQ ID NO:103) were constructed by cloning the coding regions from VR4756, VR4762 and VR4759 respectively into the VR6430 vector backbone. Specifically, the segment 7 gene from VR4756 was removed using Sail and EcoRV restriction endonucleases and blunted with the Klenow fragment of DNA polymerase I. The VR6430 plasmid was digested with EcoRV and BamHI and the vector backbone fragment was blunted with the Klenow fragment of DNA polymerase I. The segment 7 gene fragment was then ligated into the VR6430 vector backbone. VR4771 was derived by removing the NP insert from VR4762 following EcoRV and BglII restriction endonuclease digestion and the fragment was ligated into the VR6430 vector backbone which had been digested the same restriction endonucleases. VR4772 was derived by subcloning the M2 coding region from VR4759 as a blunted SalI-EcoRV fragment and ligating into the VR6430 vector backbone from a blunted EcoRV-BamHI digest.

VR4773 (SEQ ID NO:104) and VR4774 (SEQ ID NO:105) contain a CMV promoter/intron A-segment 7 expression cassette and a RSV/R-NP expression cassette with the genes in the same or opposite orientation. These plasmids were generated by digesting VR4756 with the DraIII restriction endonuclease, blunting, and ligating to the RSV/R-NP-BGH fragment from VR4771 (VR4771 digested with NdeI and SfiI and then blunted).

VR4775 (SEQ ID NO:106) and VR4776 (SEQ ID NO:107) contain a CMV promoter/intron A-NP expression cassette and a RSV/R-segment 7 expression cassette with the genes in the same or opposite orientation. These plasmids were generated by digesting VR4762 with the Drain restriction enzyme and blunting with the Klenow fragment of DNA polymerase. The RSV/R-segment 7-BGH fragment was generated by digesting VR4770 with NdeI and SfiI restriction endonucleases and ligating the blunted fragment with the DraIII restriction endonuclease digested VR4762.

VR4777 (SEQ ID NO:108) and VR4778 (SEQ ID NO:109) contain a CMV promoter/intron A-NP expression cassette and a RSV/R-M2 expression cassette in the same or opposite orientation. These plasmids were generated by digesting VR4762 with the MscI restriction endonuclease, digesting VR4772 with NdeI and SfiI restriction endonucleases and treating the RSV/R-M2-BGH with the Klenow fragment of DNA polymerase, followed by ligation of these two gel purified fragments.

VR4779 and VR4780 contain a CMV promoter/intron A-M2 expression cassette and a RSV/R-NP expression cassette in the same or opposite orientation. These plasmids were generated by digesting VR4759 with the MscI restriction endonuclease, digesting VR4771 with NdeI and SfiI restriction endonucleases and treating the RSV/R—NP-BGH segment with the Klenow fragment of DNA polymerase, followed by ligation of these two gel purified fragments.

Plasmid DNA purification

Plasmid DNA was transformed into *Escherichia coli* DH5a competent cells, and highly purified covalently closed circular plasmid DNA was isolated by a modified lysis procedure (Horn, N. A., et al., *Hum. Gene Ther.* 6:565-573 (1995)) followed by standard double CsCl-ethidium bromide gradient ultracentrifugation (Sambrook, J., et al., *Molecular Cloning: A Laboratory Manual,* 2nd Ed., Cold Spring Harbor Laboratory Press, Plainview, N.Y. (1989)). All plasmid preparations were free of detectable chromosomal DNA, RNA and protein impurities based on gel analysis and the bicinchoninic protein assay (Pierce Chem. Co., Rockford Ill.). Endotoxin levels were measured using *Limulus Amebocyte* Lysate assay (LAL, Associates of Cape Cod, Falmouth, Mass.) and were less than 0.6 Endotoxin Units/mg of plasmid DNA. The spectrophotometric $A_{260}/A_{280}$ ratios of the DNA solutions were typically above 1.8. Plasmids were ethanol precipitated and resuspended in an appropriate solution, e.g., 150 mM sodium phosphate (for other appropriate excipients and auxiliary agents, see U.S. Patent Application Publication 2002/0019358, published Feb. 14, 2002). DNA was stored at −20° C. until use. DNA was diluted by mixing it with 300 mM salt solutions and by adding appropriate amount of USP water to obtain 1 mg/ml plasmid DNA in the desired salt at the desired molar concentration.

Plasmid Expression in Mammalian Cell Lines

The expression plasmids were analyzed in vitro by transfecting the plasmids into a well characterized mouse melanoma cell line (VM-92, also known as UM-449) and the human rhabdomyosarcoma cell line RD (ATCC CCL-136) both available from the American Type Culture Collection, Manassas, Va. Other well-characterized human cell lines may also be used, e.g. MRC-5 cells, ATCC Accession No. CCL-171. The transfection was performed using cationic lipid-based transfection procedures well known to those of skill in the art. Other transfection procedures are well known in the art and may be used, for example electroporation and calcium chloride-mediated transfection (Graham F. L. and A. J. van der Eb Virology 52:456-67 (1973)). Following transfection, cell lysates and culture supernatants of transfected cells were evaluated to compare relative levels of expression of IV antigen proteins. The samples were assayed by western blots and ELISAs, using commercially available monoclonal antibodies (available, e.g., from Research Diagnostics Inc., Flanders, N.J.), so as to compare both the quality and the quantity of expressed antigen.

Genes encoding the consensus amino acid sequences (described above) derived for NP, M1 and M2 antigens were cloned in several configurations into several plasmid vector backbones. The pDNAs were tested for in vitro expression and are being assessed in vivo for immunogenicity, as well as for the ability to protect mice from influenza challenge.

Experiment I

Following the derivation of an amino acid consensus for M1 and M2, a native segment 7 isolate was found to encode this consensus, and this nucleotide sequence was synthesized according to methods described above. An M2-M1 fusion gene was also created and the nucleotide sequence was human codon-optimized using the above described codon optimization algorithm of Example 4. The individual full-length M2 and M1 genes were also cloned via PCR from this fusion.

Figure 10A:
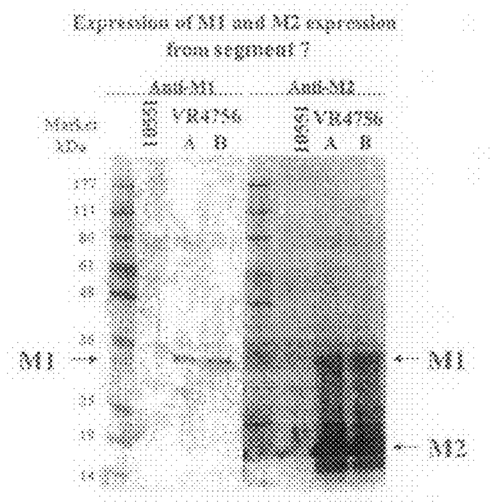
FIGS. 10A and 10B show the in vitro expression of M1 and M2 from segment 7 and an M1M2 fusion.
Figure 10B:
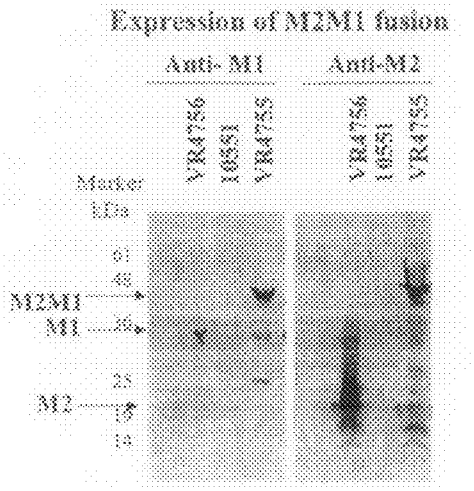

In vitro expression of influenza antigens in cell lysates was assessed 48 hours after transfection into a mouse melanoma cell line. M2 expression was detected following transfection of VR4756 (segment 7), VR4755 (M2-M1 fusion) and VR4759 (full-length M2) using the anti-M2 monoclonal antibody (14C2) from Affinity BioReagents. The data are shown in FIG. 10 for VR4756 and VR4755. Expression of M1 was detected from transfected VR4756, VR4755 and VR4760 (full-length M1) pDNAs, as detected by anti-M1 monoclonal (Serotec) in FIG. 10 for VR4756 and VR4755, or by anti-M1 goat polyclonal (Virostat, data not shown). VR10551 is the empty cloning vector.

Experiment 2

In order to compare alternative human codon-optimization methods, two versions of a fusion of the first 24 amino acids of M2 to full-length NP ("eM2-NP") were constructed. One nucleotide sequence was derived from the above codon optimization algorithm, while the other was done by an outside vendor. Comparison of expression levels from the two eM2-NP pDNAs was measured in vitro, and comparison of immunogenicity in vivo is on-going. Additionally, the full-length NP genes for both codon-optimized versions were sub-cloned from the eM2-NP pDNAs and analyzed for expression in vitro.

Figure 11A:
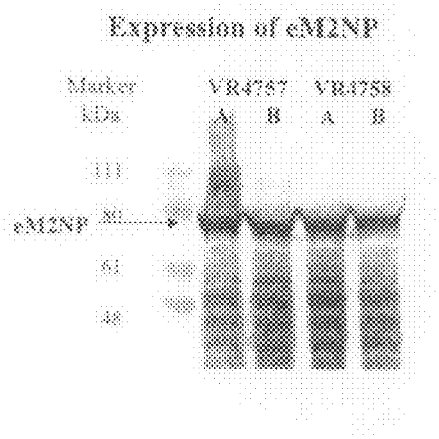
FIGS. 11A and 11B show the in vitro expression of eM2-NP and codon-optimized influenza virus NP protein.
Figure 11B:
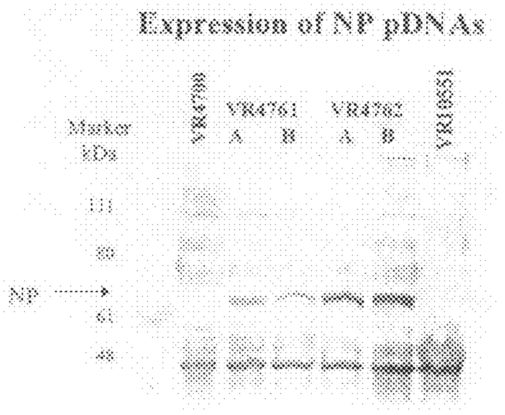

In vitro expression was tested to compare eM2-NP and NP pDNAs derived from the above described codon-optimization algorithm and an outside vendor algorithm. The data are shown in FIG. 11. Expression levels were approximately the same for VR4757 (eM2-NP vendor optimization) vs. VR4758 (eM2-NP Applicant optimization), as detected by anti-M2 monoclonal (FIG. 11A) or anti-NP mouse polyclonal (data not shown). Similarly, NP expression was approximately equal for VR4761 (vendor optimization) vs. VR4762 (Applicant optimization), detected by anti-NP mouse polyclonal generated by Applicants (FIG. 11B). NP consensus protein expression in vitro was also detected using a goat polyclonal antibody (Fitzgerald) generated against whole H1N1 or H3N2 virus (data not shown). Expression levels of both of these NP constructs were much higher than a pDNA containing A/PR/34 NP (VR4700).

Experiment 3

Influenza antigen-encoding plasmids were transfected into VM92 cells using methods described above. Cell lysates and media were collected 48 hours after transfection. Cells were lysed in 200 μl of Laemmli buffer, cell debris removed by microcentrifuge spin, and 20 μl was heated and loaded on a 4-12% Bis-Tris gel. To determine expression of those vectors encoding secreted NP protein, 15 μl of media was mixed with 5 μl of loading buffer, heated, and loaded on a gel. Western blots were processed as described above. Primary antibodies were as follows: monoclonal antibody MAI-082 (ABR) to detect M2 protein, monoclonal antibody MCA401 (Serotec) to detect M1 protein, and a polyclonal antibody against VR4762-injected rabbits generated in-house. All primary antibodies were used at a 1:500 dilution.

Figure 14:
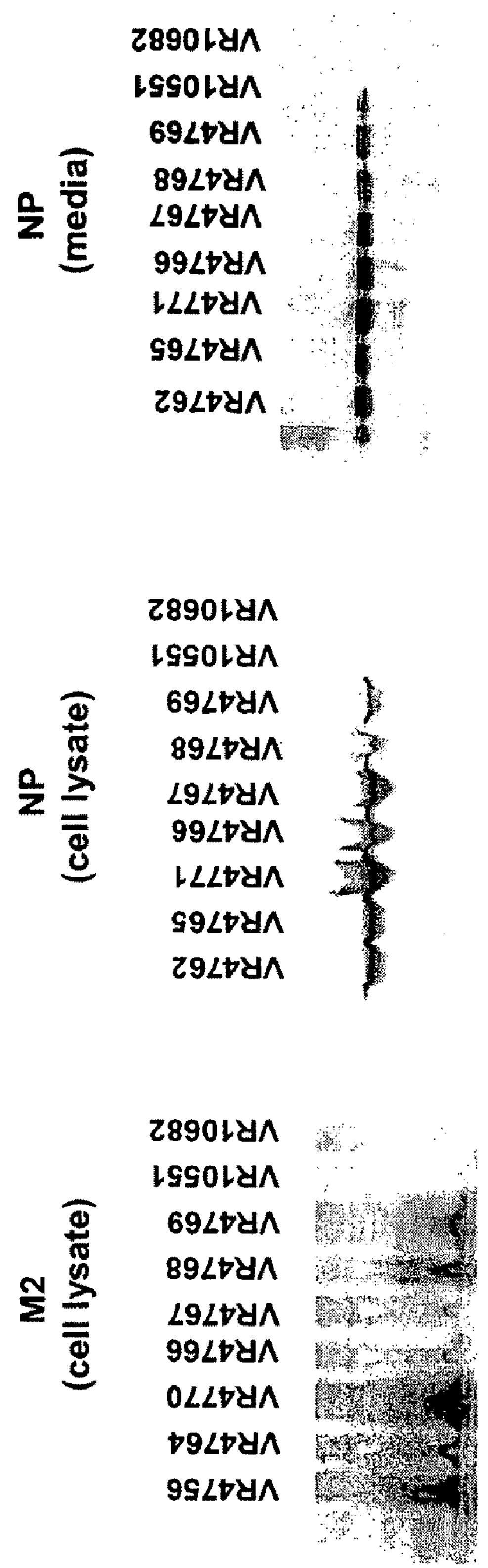
FIG. 14 are the results of western blot experiments as described in Example 13, Experiment 3. The blots show lysates of VM92 cells transfected with plasmids which express M2 or NP to compare expression of the influenza protein from different expression vectors.

FIG. 14 shows Western blot results wherein M2 protein expression from segment 7-encoding plasmids are higher in CMV promoter/intron A-segment 7 (VR4756) and RSV/R-segment 7 (VR4770) than VR4764 (RSV promoter). NP expression appeared highest from the RSV/R-NP plasmid (VR4771), followed by CMV/intron A-NP (VR4762) and then RSV-NP (VR4765). Similar results were seen in Western blots from human RD-transfected cells.

For dual promoter plasmids, containing RSV-segment 7 and CMV/intron A-NP (VR4766 and VR4767), M2 expression from segment 7 is very low, independent of orientation. The CMV/intron A-NP expression in these dual promoter plasmids does not differ significantly compared to VR4762. RSV-NP expression in dual promoter plasmids (VR4768 and VR4769), where segment 7 is expressed from CMV/intron A, NP expression decreases somewhat, but not as drastically as M2 expression in the dual promoter VR4766 and VR4767.

Figure 15:
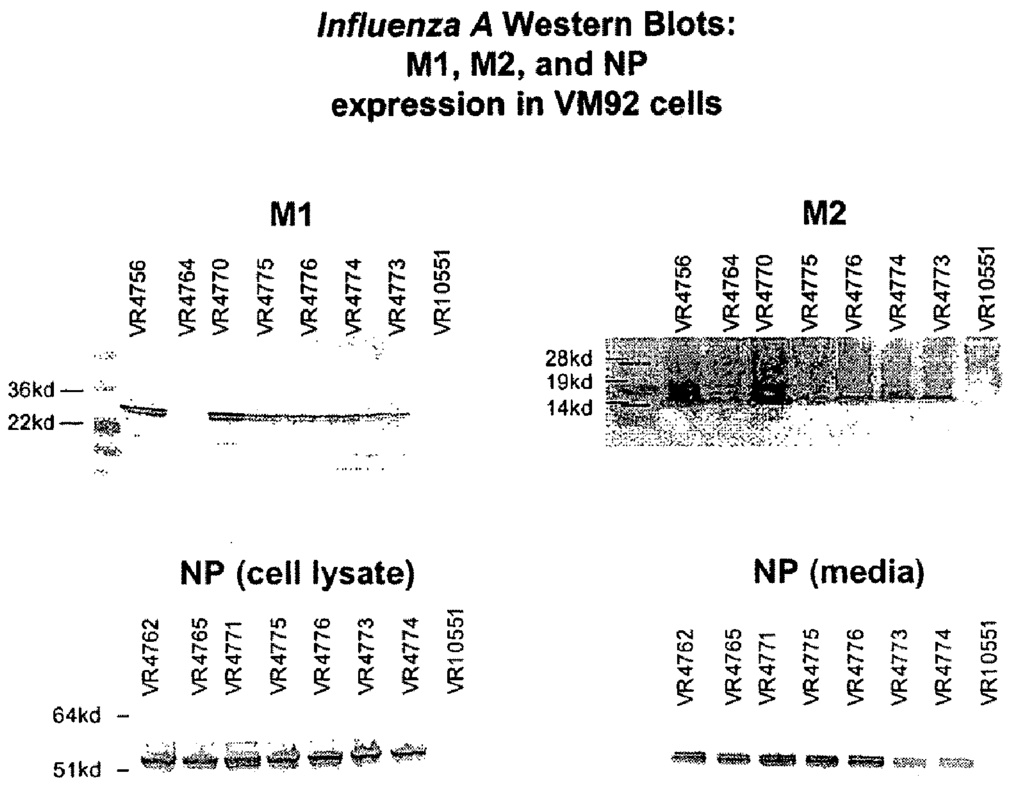
FIG. 15 are the results of western blot experiments as described in Example 13, Experiment 3. The blots show lysates of VM92 cells transfected with plasmids which express M1, M2 or NP to compare expression of the influenza protein from expression vectors.

FIG. 15 shows expression of the M1 and M2 proteins from segment 7, as well as NP, from CMV promoter/intron A, RSV promoter, and RSV/R-containing plasmids. For these Western blots, dual promoter plasmids contain the CMV promoter/intron A and RSV/R driving either NP or segment 7. Similar results were seen in Western blots from human RD-transfected cells.

Western blot results confirm that the M1 and M2 protein expression from both CMV promoter/intron A-segment 7 (VR4756) and RSV/R-segment 7 (VR4770) is superior to RSV-segment 7 (VR4764). M1 and M2 expression decrease slightly when RSV/R-segment 7 or CMV/intron A-segment 7 is combined with CMV/intron A-NP or RSV/R-NP in a dual promoter plasmid (VR4773, VR4774, VR4775, and VR4776). Results were similar in Western blots from human RD transfected cells. Human RD cells transfected with M2 antigen encoding plasmids, RSV/R-M2 (VR4772) and CMV/intron A-M2 (VR4759), showed a similar level of M2 expression, which was decreased in dual promoter plasmids (VR4777, VR4778, VR4779, and VR4780). Human RD cells transfected with NP antigen-encoding plasmids, VR4762, VR4771, VR4777, VR4778, VR4779, and VR4780, all showed similar NP expression levels.

Example 14

Murine Influenza A Challenge Model

A challenge model for influenza A has been established utilizing a mouse-adapted A/BK/8/68 strain. Positive and negative control Hemaglutinin (HA)-containing plasmids were generated by PCR of the HA genes directly from mouse-adapted A/Hong Kong/68 (H3N2) and A/Puerto Rico/34 (H1N1) viruses, respectively.

For all experiments, plasmid DNA vaccinations are given as bilateral, rectus femoris injections at 0 and 3 weeks, followed by orbital sinus puncture (OSP) bleed at 5 weeks and intranasal viral challenge at 6 weeks with 500 pfu (1 $LD_{90}$) of virus. Mice are monitored for morbidity and weight loss for about 3 weeks following viral challenge. Endpoint antibody titers for NP and M2 were determined by ELISA. For study GSJ08, 5 additional mice per test group were vaccinated and interferon-γ ELISPOT assays were performed at week number 5.

Study CL88:

A mouse influenza challenge study was initiated to test the M1, M2, Segment 7, and NP-encoding plasmids alone, or in combination. In addition to HA pDNAs, sub-lethal infection and naïve mice serve as additional positive and negative controls, respectively. Mice received 100 μg of each plasmid formulated in poloxamer CRL1005, 02A formulation. The test groups and 21 day post-challenge survival are shown in Table 21:

TABLE 21

| Group | Construct(s) | Total pDNA per vaccination | # mice/ group | 21 day Survival (%) |
|---|---|---|---|---|
| A | VR4762 (NP) | 100 μg | 12 | 17 |
| B | VR4759 (M2) | 100 μg | 12 | 25 |
| C | VR4760 (M1) | 100 μg | 12 | 0 |
| D | VR4756 (S7) | 100 μg | 12 | 50 |
| E | VR4762 (NP) + VR4759 (M2) | 200 μg | 12 | 100 |
| F | VR4762 (NP) + VR4760 (M1) | 200 μg | 12 | 17 |
| G | VR4762 (NP) + VR4756 (S7) | 200 μg | 12 | 75 |
| H | VR4750 (HA, H3N2, + control) | 100 μg | 12 | 100 |
| I | VR4752 (HA, H1N1, − control) | 100 μg | 12 | 8 |
| J | Naïve mice (− control) | N/A | 12 | 8 |
| K | Sub-lethal (+ control) | N/A | 12 | 100 |

CL88 Results:

The performance criteria for this study was survival of >90% for the positive controls, <10% for the negative controls, and >75% for the experimental groups. Table 21 shows that all of the control groups, as well as two experimental groups met the performance criteria. The M2+NP and S7+NP plamsid DNA combinations resulted in 100% and 75% survival, respectively. There was no statistically significant difference ($p<0.05$) between the two lead plasmid combinations, but there was statistical significance in the S7, S7+NP, and M2+NP groups vs. the negative controls.

Weight loss data showed that the positive control groups did not exhibit any weight loss following viral challenge, as opposed to the weight loss seen in all of the experimental groups. Mice that survived the viral challenge recovered to their starting weight by the end of the study. Tables 22 and 23 show endpoint antibody titers for test groups containing M2, Segment 7, and NP antigens. Shaded boxes represent mice that died following viral challenge.

TABLE 22: CL88 M2 Antibody Titers

| mouse | Group D (seg 7) | Group G (NP + seg 7) | Group B (M2) | Group E (NP + M2) |
|---|---|---|---|---|
| 1 | 800 | 1600 | 25600 | 1600 |
| 2 | 3200 | 1600 | 200 | 6400 |
| 3 | 3200 | 6400 | 3200 | 200 |
| 4 | 6400 | 800 | 12800 | 6400 |
| 5 | 12800 | 0 | 3200 | 3200 |
| 6 | 800 | 12800 | 12800 | 3200 |
| 7 | 12800 | 0 | 3200 | 3200 |
| 8 | 6400 | 0 | 3200 | 6400 |
| 9 | 800 | 3200 | 400 | 1600 |
| 10 | 12800 | 3200 | 6400 | 800 |
| 11 | 12800 | 1600 | 200 | 3200 |
| 12 | 6400 | 12800 | 12800 | 400 |

TABLE 23: CL88 NP Antibody Titers

| mouse | Group A NP | Group E (NP + M2) | Group F (NP + M1) | Group G (NP + seg7) |
|---|---|---|---|---|
| 1 | 204800 | 51200 | 102400 | 25600 |
| 2 | 204800 | 51200 | 204800 | 51200 |
| 3 | 204800 | 51200 | 102400 | 51200 |
| 4 | 204800 | 25600 | 512001 | 25600 |
| 5 | 102400 | 102400 | 102400 | 25600 |
| 6 | 102400 | 51200 | 102400 | 102400 |
| 7 | 204800 | 204800 | 51200 | 102400 |
| 8 | 409600 | 102400 | 51200 | 102400 |
| 9 | <6400 | 102400 | 102400 | 51200 |
| 10 | 409600 | 102400 | 25600 | 102400 |
| 11 | 204800 | 51200 | 204800 | 25600 |
| 12 | 204800 | 51200 | 102400 | 25600 |

Study GSJ05:

In order to attempt to distinguish between the two antigen combinations, S7+NP and M2+NP, a dose ranging challenge experiment was undertaken with these two plasmid combinations. Mice were injected with 100 μg, 30 μg, or 10 μg per plasmid in the 02A poloxamer formulation at 0 and 3 weeks, followed by bleed at 5 weeks and viral challenge at 6 weeks. Sixteen mice per group were vaccinated for test groups A-H, while 12 mice per group were vaccinated for the controls. Poloxamer 02A-formulated HA plasmids, VR4750 (HA H3) and VR4752 (HA H1), were included as positive and negative controls, respectively. The test groups and 21 day survival post-challenge are shown in Table 24:

TABLE 24

| Group | Construct(s) | Total pDNA per vaccination | # mice/ group | 21 day Survival (%) |
|---|---|---|---|---|
| A | VR4756 (Seg 7) + VR4762 (NP) | 200 μg | 16 | 73 |
| B | VR4756 (Seg 7) + VR4762 (NP) | 60 μg | 16 | 81 |
| C | VR4756 (Seg 7) + VR4762 (NP) | 20 μg | 16 | 69 |
| D | VR4759 (M2) + VR4762 (NP) | 200 μg | 16 | 94 |
| E | VR4759 (M2) + VR4762 (NP) | 60 μg | 16 | 81 |
| F | VR4759 (M2) + VR4762 (NP) | 20 μg | 16 | 75 |
| G | VR4750 (Positive DNA control) | 100 μg | 12 | 100 |
| H | VR4752 (Negative DNA control) | 100 μg | 12 | 8 |

Results

The performance criteria of >90% survival with the HA positive control and ≦10% for the HA negative control plasmid again were met. The performance criteria for the experimental groups, >75% survival at the 30 μg per plasmid dose, was met by both M2+NP and S7+NP (Table 24). In fact, at a dose of 10 μg per plasmid, S7+NP and M2+NP resulted in 69% and 75% survival, respectively. There was no statistical significance ($p<0.05$) between the three doses of M2+NP or between the 3 doses of S7+NP, nor was there statistical significance when comparing M2+NP to S7+NP at the 200 μg, 60 μg, or 20 μg doses. However, there was a statistical difference for the HA positive control vs. S7+NP at 200 μg and 20 μg. Body mass data shows weight loss and recovery by all surviving experimental plasmid DNA-vaccinated groups, while the HA positive control mice did not experience weight loss. Antibody data for M2 and NP are shown in Tables 25 and 26.

TABLE 25: GSJ05 M2 Antibody Titers

| mouse # | Group A | Group B | Group C | Group D | Group E | Group F |
|---|---|---|---|---|---|---|
| 1 | 800 | 400 | 3200 | 6400 | 800 | 3200 |
| 2 | 200 | 0 | 0 | 25600 | 1600 | 0 |
| 3 | 0 | 0 | 0 | 3200 | 3200 | 3200 |
| 4 | 100 | 0 | 0 | 6400 | 1600 | 400 |
| 5 | 0 | 0 | 0 | 3200 | 800 | 1600 |
| 6 | 3200 | 400 | 0 | 6400 | 200 | 100 |
| 7 | 25600 | 800 | 0 | 6400 | 0 | 0 |
| 8 | 0 | 100 | 0 | 1600 | 0 | 400 |
| 9 | 0 | 0 | 800 | 3200 | 12800 | 0 |
| 10 | 0 | 800 | 0 | 1600 | 800 | 1600 |
| 11 | 100 | 1600 | 0 | 3200 | 200 | 1600 |
| 12 | 3200 | 0 | 100 | 6400 | 800 | 1600 |
| 13 | 800 | 0 | 400 | 3200 | 400 | 800 |
| 14 | 0 | 0 | 1600 | 3200 | 400 | 100 |
| 15 | 0 | 1600 | 800 | 1600 | 3200 | 200 |
| 16 | 0 | 0 | 800 | 800 | 3200 | 800 |

TABLE 26: GSJ05 NP Antibody Titers

| mouse # | Group A | Group B | Group C | Group D | Group E | Group F |
|---|---|---|---|---|---|---|
| 1 | 25600 | 51200 | 51200 | 51200 | 25600 | 25600 |
| 2 | 25600 | 51200 | 12800 | 51200 | 25600 | 6400 |
| 3 | 102400 | 25600 | 51200 | 12800 | 51200 | 25600 |
| 4 | 25600 | 12800 | 25600 | 25600 | 12800 | 12800 |
| 5 | 51200 | 102400 | 6400 | 25600 | 12800 | 12800 |
| 6 | 25600 | 51200 | 25600 | 25600 | 12800 | 6400 |
| 7 | 102400 | 51200 | 6400 | 6400 | 3200 | 800 |
| 8 | 54200 | 25600 | 12800 | 12800 | 51200 | 6400 |
| 9 | 12800 | 51200 | 25600 | 102400 | 12800 | 12800 |
| 10 | 25600 | 25600 | 25600 | 25600 | 12800 | 25600 |
| 11 | 51200 | 25600 | 51200 | 25600 | 25600 | 3200 |
| 12 | 51200 | 51200 | 3200 | 25600 | 12800 | 12800 |
| 13 | 51200 | 51200 | 25600 | 51200 | 25600 | 12800 |
| 14 | 51200 | 12800 | 25600 | 51200 | 6400 | 12800 |
| 15 | 25600 | 6400 | 25600 | 25600 | 25600 | 12800 |
| 16 | 51200 | 51200 | 25600 | 12800 | 12800 | 6400 |

Study GSJ06

The plasmid combination VR4759 (M2) and VR4762 (NP) was utilized in further mouse influenza challenge studies to examine additional formulations.

Using the experimental protocol described above, 12 mice per group were vaccinated with equal weight VR4759 (M2) and VR4762 (NP) in the following formulations:

- Poloxamer 02A used in the previous two challenge experiments.
- DMRIE+Cholesterol (DM:Chol) at a 4:1 molar ratio of DNA to DMRIE, the molar ratio of DM:Chol is 3:1.
- Vaxfectin™ (VC1052+DPyPE) at a 4:1 molar ratio of DNA:VC1052, the molar ratio of VC1052:DpyPE is 1:1.

GSJ06 study design and 21 day survival post-challenge is found in Table 27.

TABLE 27

| Group | pDNA | Total pDNA | 21 day Survival (%) |
|---|---|---|---|
| A | Poloxamer 02A | 20 µg | 92 |
| B | Poloxamer 02A | 2 µg | 58 |
| C | DMRIE:Cholesterol | 20 µg | 58 |
| D | DMRIE:Cholesterol | 2 µg | 17 |
| E | Vaxfectin | 20 µg | 100 |
| F | Vaxfectin | 2 µg | 75 |
| G | VR4750 (HA, positive) | 100 µg | 100 |
| H | VR4752 (HA, negative) | 100 µg | 0 |

Results

Poloxamer 02A and Vaxfectin™-formulated plasmid DNA led to 92% and 100% survival at the 20 µg pDNA dose, and 58% and 75% at the 2 µg dose, respectively (Table 27).

Average weights were tracked for each group of mice starting at the day of challenge. As shown in Table 28, it was noted in this experiment that the weight recovery for group E (Vaxfectin™-formulated pDNA, 20 µg total) began after day 4, as opposed to the other groups' recovery beginning at day 7. Antibody titers, Tables 29 and 30, were determined for M2 and NP and shaded boxes represent mice that died following viral challenge.

| Group | pDNA | Total pDNA | Avg Body Weights (g)- Days post-challenge | | | | | | | | | |
|---|---|---|---|---|---|---|---|---|---|---|---|---|
| | | | 0 | 2 | 4 | 7 | 9 | 11 | 14 | 16 | 18 | 21 |
| A | Poloxamer 02A | 20 ug | 20.73 | 19.98 | 17.98 | 16.14 | 17.36 | 18.74 | 19.94 | 20.45 | 20.60 | 21.08 |
| B | Poloxamer 02A | 2 ug | 21.08 | 19.91 | 17.96 | 15.17 | 15.16 | 16.03 | 16.77 | 17.41 | 18.10 | 19.52 |
| C | DMRE-Cholesterol | 20 ug | 21.43 | 20.24 | 18.14 | 16.41 | 18.68 | 19.24 | 20.14 | 20.50 | 20.90 | 21.42 |
| D | DMRE-Cholesterol | 2 ug | 21.28 | 20.24 | 17.58 | 14.83 | 16.18 | 17.45 | 18.80 | 19.84 | 20.13 | 20.98 |
| E | Vaxfectin | 20 ug | 21.41 | 19.97 | 17.83 | 18.10 | 19.12 | 19.82 | 20.39 | 20.87 | 20.93 | 21.34 |
| F | Vaxfectin | 2 ug | 20.47 | 18.97 | 16.86 | 15.10 | 16.22 | 16.84 | 17.87 | 18.60 | 19.08 | 20.02 |
| G | VR4750 (HA positive) | 100 ug | 21.30 | 20.97 | 21.60 | 21.21 | 21.57 | 21.79 | 21.84 | 22.13 | 21.94 | 22.13 |
| H | VR4750 (HA positive) | 100 ug | 20.89 | 20.25 | 17.57 | 14.67 | | | | | | |

Shading represents the lowest group average post-challenge for each test group. Group H (negative control) weight averages are not recorded once the percentage survival has dropped below 50%

TABLE 29: GSJ06 M2 Antibody Titers

| mouse # | Group A | Group B | Group C | Group D | Group E | Group F |
|---|---|---|---|---|---|---|
| 1 | 800 | 400 | 200 | 0 | 1600 | 6400 |
| 2 | 6400 | 800 | 1600 | 0 | 400 | 800 |
| 3 | 6400 | 0 | 400 | 0 | 12800 | 3200 |
| 4 | 1600 | 0 | 400 | 0 | 25600 | 1600 |
| 5 | 6400 | 3200 | 1600 | 400 | 100 | 400 |
| 6 | 3200 | 100 | 100 | 0 | 12800 | 1600 |
| 7 | 800 | 1600 | 1600 | 0 | 800 | 3200 |
| 8 | 400 | 100 | 3200 | 200 | 6400 | 100 |
| 9 | 1600 | 0 | 100 | 0 | 6400 | 100 |
| 10 | 100 | 400 | 1600 | 100 | 3200 | 400 |
| 11 | 3200 | 0 | 800 | 0 | 1600 | 1600 |
| 12 | 6400 | 0 | 0 | 0 | 6400 | 1600 |

TABLE 30: GSJ06 NP Antibody Titers

| mouse # | Group A | Group B | Group C | Group D | Group E | Group F |
|---|---|---|---|---|---|---|
| 1 | 6400 | 6400 | 12800 | 1600 | 51200 | 51200 |
| 2 | 51200 | 6400 | 6400 | 3200 | 102400 | 102400 |
| 3 | 12800 | 1600 | 6400 | 200 | 51200 | 25600 |
| 4 | 25600 | 1600 | 6400 | 3200 | 204800 | 102400 |
| 5 | 25600 | 6400 | 25600 | 3200 | 51200 | 51200 |
| 6 | 51200 | 12800 | 25600 | 12800 | 102400 | 51200 |
| 7 | 25600 | 25600 | 12800 | 100 | 51200 | 51200 |
| 8 | 25600 | 3200 | 12800 | 6400 | 25600 | 25600 |
| 9 | 25600 | 6400 | 51200 | 400 | 51200 | 25600 |
| 10 | 51200 | 6400 | 12800 | 3200 | 51200 | 51200 |
| 11 | 25600 | 12800 | 25600 | 6400 | 102400 | 51200 |
| 12 | 51200 | 6400 | 12800 | 400 | 51200 | 51200 |

Study GSJ08

Further formulation comparisons were done with utilizing VR4759 (M2) and VR4762 (NP). Seventeen mice per test group (A-G) were vaccinated with equal weight VR4759 (M2) and VR4762 (NP) vectors in the following formulations:

Poloxamer 02A

Vaxfectin™ (preparations A and B represent different purifications)

DMRIE:DOPE at a 4:1 molar ratio of DNA to DMRIE

DMRIE:DOPE at a 2.5:1 molar ratio of DNA to DMRIE

PBS (unformulated pDNA)

Twelve mice per test group were challenged with influenza virus at week number 6. Five mice per test group were sacrificed at days 36-38 for T cell assays (IFN-γ ELISPOT). The test groups and 21 day survival post-challenge are shown in Table 31. Groups A-D, and F-G were vaccinated with 20 μg total plasmid DNA per injection to further explore the weight loss/recovery phenomena seen in study GSJ06 with the Vaxfectin™-formulated pDNA.

TABLE 31

| Group | Construct(s) | Total pDNA per vaccination | 21 Day Survival (%) |
|---|---|---|---|
| A | Poloxamer 02A | 20 μg | 50 |
| B | DMRIE:DOPE 4:1 | 20 μg | 92 |
| C | DMRIE:DOPE 2.5:1 | 20 μg | 92 |
| D | Vaxfectin - prep A | 20 μg | 92 |
| E | Vaxfectin - prep A | 2 μg | 75 |
| F | Vaxfectin - prep B | 20 μg | 100 |
| G | PBS | 20 μg | 42 |

TABLE 31-continued

| Group | Construct(s) | Total pDNA per vaccination | 21 Day Survival (%) |
|---|---|---|---|
| H | VR4750 (HA, H3N2, + control) | 100 μg | 100 |
| I | VR4752 (HA, H1N1, − control) | 100 μg | 17 |

Results

The DMRIE:DOPE and Vaxfectin™ formulated groups resulted in 92-100% survival at a 20 μg pDNA dose. Group A (Poloxamer 02A) and Group G (PBS) survival results were not statistically different than the negative control (as measured by Fisher exact p, one-tailed), while the Vaxfectin™ and DMIRE:DOPE Groups (Groups B-F) were shown to be statistically superior ($p<0.05$) as compared to the negative control. Therefore, the plasmid DNA formulated with lipids appear to provide superior protection in the mouse influenza model challenge.

A repeated measures ANOVA mixed model analysis of weight data for groups B, C, and D of the weight loss and recovery data showed that Group B and Group D were not statistically different, while Group C and Group D were statistically different.

T cell responses, as measured by IFN-γ ELISPOT assay, were conducted on the last 5 mice per group using an M2 peptide encompassing the first 24 amino acids of M2 (TABLE 33), an NP protein expressed in baculovirus (TABLE 34), and an NP CD8+ Balb/c immunodominant peptide (TABLE 35).

Antibody titers, Tables 36 and 37, were determined for M2 and NP proteins. The first 12 mice listed for each group were challenge at day 42 and the last 5 mice per group were sacrificed for IFN-γ ELISPOT. The shaded boxes represent mice that died following viral challenge.

TABLE 32: GSJ06 Average Body Weights Post-Challenge

| Group | Construct(s) | Total pDNA per vaccination | Avg Body Weights (g)- Days post-challenge | | | | | | | | | | | |
|---|---|---|---|---|---|---|---|---|---|---|---|---|---|---|
| | | | 0 | 2 | 4 | 5 | 6 | 7 | 9 | 11 | 14 | 16 | 18 | 22 |
| A | Poloxamer 02A | 20 μg | 20.47 | 18.97 | 16.30 | 15.43 | 14.75 | 14.31 | 14.35 | 14.44 | 16.63 | 17.64 | 18.36 | 20.53 |
| B | DMRE-DOPE 4:1 | 20 μg | 21.56 | 19.94 | 17.43 | 16.75 | 16.17 | 15.86 | 16.43 | 17.28 | 18.45 | 19.50 | 20.22 | 20.89 |
| C | DMRE-DOPE 2.5:1 | 20 μg | 19.95 | 18.56 | 16.44 | 15.77 | 15.46 | 15.56 | 15.75 | 16.22 | 16.78 | 17.16 | 17.31 | 18.04 |
| D | Vaxfectin - prep A | 20 μg | 20.87 | 19.22 | 16.81 | 16.47 | 16.40 | 16.92 | 17.94 | 19.48 | 20.06 | 20.19 | 20.64 | 21.17 |
| E | Vaxfectin - prep A | 2 μg | 20.40 | 19.59 | 17.97 | 17.47 | 17.27 | 17.23 | 18.96 | 19.83 | 20.24 | 20.49 | 20.57 | 21.05 |
| F | Vaxfectin - prep B | 20 μg | 21.33 | 20.01 | 17.88 | 17.61 | 17.74 | 18.21 | 18.85 | 19.85 | 20.29 | 20.77 | 20.88 | 21.39 |
| G | PHS | 20 μg | 20.84 | 19.46 | 16.97 | 16.00 | 15.38 | 14.79 | 15.80 | 16.39 | 17.35 | | | |
| H | VR4750 (HA, H3N2 + control | 100 μg | 21.25 | 21.15 | 21.27 | 20.77 | 20.92 | 21.24 | 20.74 | 21.16 | 21.33 | 21.40 | 21.64 | 21.64 |
| I | VR4750 (HA, H3N2 - control | 100 μg | 21.26 | 20.65 | 17.87 | 16.77 | 16.05 | 15.17 | 15.09 | | | | | |

Shading represents the lowest group average post-challenge for each test group. Group G and I weight averages are not recoreded once the percentage survival has dropped below 50%.

TABLE 33

M2 peptide Interferon-γ ELISPOT
M2 peptide IFN gamma ELISPOT (SFU/10E6 cells)

| Mouse | A | B | C | D | E | F | G |
|---|---|---|---|---|---|---|---|
| 1 | 66 | 88 | 145 | 189 | 283 | 253 | 31 |
| 2 | 11 | 115 | 150 | 269 | 62 | 282 | 47 |
| 3 | 115 | 247 | 190 | 233 | 99 | 283 | 112 |
| 4 | 20 | 6 | 51 | 67 | 73 | 93 | 45 |
| 5 | 93 | 277 | 397 | 248 | 202 | 399 | 93 |
| AVG | 61 | 147 | 187 | 201 | 144 | 262 | 66 |

TABLE 34

NP CD4 peptide Interferon-γ ELISPOT
NP CD4 peptide IFN gamma ELISPOT (SFU/10E6 cells)

| Mouse | A | B | C | D | E | F | G |
|---|---|---|---|---|---|---|---|
| 1 | 7 | 32 | 3 | 52 | 72 | 108 | 18 |
| 2 | 8 | 83 | 34 | 125 | 8 | 34 | 8 |
| 3 | 22 | 91 | 106 | 293 | 26 | 51 | 73 |
| 4 | 9 | 15 | 80 | 39 | 53 | 10 | 12 |

TABLE 34-continued

NP CD4 peptide Interferon-γ ELISPOT
NP CD4 peptide IFN gamma ELISPOT (SFU/10E6 cells)

| Mouse | A | B | C | D | E | F | G |
|---|---|---|---|---|---|---|---|
| 5 | 37 | 150 | 374 | 117 | 40 | 217 | 43 |
| AVG | 17 | 74 | 119 | 125 | 40 | 84 | 31 |

TABLE 35

NP CD8 peptide Interferon-γ ELISPOT
NP CD8 peptide IFN gamma ELISPOT (SFU/10E6 cells)

| Mouse | A | B | C | D | E | F | G |
|---|---|---|---|---|---|---|---|
| 1 | 11 | 37 | 4 | 14 | 20 | 67 | 8 |
| 2 | 0 | 3 | 4 | 6 | 1 | 0 | 2 |
| 3 | 31 | 19 | 15 | 26 | 23 | 51 | 34 |
| 4 | 1 | 0 | 0 | 12 | 1 | 38 | 3 |
| 5 | 46 | 36 | 39 | 21 | 13 | 15 | 18 |
| AVG | 18 | 19 | 12 | 16 | 12 | 34 | 13 |

TABLE 36: GSJ08 M2 Antibody Titers

| mouse # | Group A | Group B | Group C | Group D | Group E | Group F | Group G | Group H | ELISPOT # |
|---|---|---|---|---|---|---|---|---|---|
| 1 | 1600 | 3200 | 3200 | 6400 | 400 | 12800 | 800 | 6400 | |
| 2 | 12800 | 12800 | 6400 | 1600 | 3200 | 800 | 1600 | 800 | |
| 3 | 100 | 3200 | 6400 | 25600 | 800 | 3200 | 1600 | 800 | |
| 4 | 800 | 0 | 6400 | 1600 | 400 | 800 | 1600 | 0 | |
| 5 | 1600 | 0 | 800 | 12800 | 1600 | 800 | 800 | 200 | |
| 6 | 6400 | 3200 | 1600 | 6400 | 200 | 12800 | 400 | 800 | |
| 7 | 12800 | 3200 | 12800 | 800 | 1600 | 3200 | 1600 | 6400 | |
| 8 | 12800 | 6400 | 3200 | 12800 | 12800 | 12800 | 12800 | 400 | |
| 9 | 1600 | 1600 | 0 | 12800 | 6400 | 12800 | 100 | 200 | |
| 10 | 3200 | 1600 | 12800 | 12800 | 1600 | 800 | 100 | 12800 | |
| 11 | 1600 | 6400 | 3200 | 3200 | 0 | 6400 | 800 | 400 | |
| 12 | 200 | 800 | 6400 | 25600 | 1600 | 800 | 6400 | 6400 | |
| 13 | 1600 | 800 | 6400 | 12800 | 3200 | 6400 | 6400 | 6400 | 1 |
| 14 | 3200 | 6400 | 1600 | 1600 | 800 | 12800 | 3200 | 12800 | 2 |
| 15 | 0 | 1600 | 3200 | 3200 | 12800 | 12800 | 6400 | 12800 | 3 |
| 16 | 3200 | 3200 | 1600 | 12800 | 0 | 12800 | 200 | 6400 | 4 |
| 17 | 3200 | 200 | 400 | 6400 | 800 | 400 | 1600 | 3200 | 5 |

TABLE 37: GSJ08 NP Antibody Titers

| mouse # | Group A | Group B | Group C | Group D | Group E | Group F | Group G | Group H | ELISPOT # |
|---|---|---|---|---|---|---|---|---|---|
| 1 | 51200 | 25600 | 6400 | 51200 | 12800 | 51200 | 51200 | 25600 | |
| 2 | 6400 | 25600 | 51200 | 51200 | 25600 | 102400 | 12800 | 25600 | |
| 3 | <3200 | 51200 | 12800 | 25600 | 6400 | 102400 | 25600 | 12800 | |
| 4 | 3200 | 25600 | 51200 | 102400 | 12800 | 25600 | 25600 | 25600 | |
| 5 | 25600 | 12800 | 12800 | 51200 | 51200 | 102400 | 25600 | 3200 | |
| 6 | 25600 | 12800 | 51200 | 102400 | 25600 | 51200 | 25600 | 12800 | |
| 7 | 51200 | 51200 | 51200 | 51200 | 25600 | 204800 | 102400 | 51200 | |
| 8 | 25600 | 51200 | 25600 | 51200 | 12800 | 51200 | 25600 | 51200 | |
| 9 | 25600 | 12800 | 25600 | 51200 | 51200 | 51200 | 12800 | 3200 | |
| 10 | 6400 | 12800 | 51200 | 51200 | 25600 | 204800 | 6400 | 25600 | |
| 11 | 12800 | 51200 | 25600 | 204800 | 12800 | 102400 | 51200 | 25600 | |
| 12 | 102400 | 102400 | 51200 | 102400 | 25600 | 204800 | 12800 | 51200 | |
| 13 | 25600 | 25600 | 12800 | 51200 | 51200 | 102400 | 25600 | 25600 | 1 |
| 14 | 51200 | 25600 | 12800 | 51200 | 25600 | 102400 | 25600 | 51200 | 2 |
| 15 | 51200 | 51200 | 51200 | 51200 | 25600 | 25600 | 102400 | 12800 | 3 |
| 16 | 25600 | 6400 | 25600 | 51200 | 25600 | 102400 | 25600 | 51200 | 4 |
| 17 | 25600 | 25600 | 51200 | 51200 | 12800 | 51200 | 25600 | 25600 | 5 |

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method for treating or preventing influenza infection in a vertebrate comprising administering to a vertebrate in need thereof a composition comprising: a carrier and an isolated polynucleotide comprising a nucleic acid fragment which encodes an amino acid sequence consisting of SEQ ID NO:76, wherein the codons of said nucleic acid fragment are optimized for expression in humans.

2. The method of claim 1, wherein said nucleotide sequence is SEQ ID NO:75.

3. The method of claim 1, wherein said composition comprises a vector comprising said nucleic acid fragment, and wherein said vector, upon uptake by a suitable host cell, expresses said amino acid sequence.

4. The method of claim 1, wherein said polynucleotide further comprises a heterologous nucleic acid ligated to said nucleic acid fragment.

5. The method of claim 1, wherein said composition further comprises a component selected from the group consisting of an adjuvant, a transfection facilitating compound and a combination thereof.

6. The method of claim 5, wherein said component is a cationic lipid.

7. The method of claim 5, wherein said component comprises (±)-N-(3-aminopropyl)-N,N-dimethyl-2,3-bis(syn-9-tetradeceneyloxy)-1-propanaminium bromide (GAP-DMORIE) and a neutral lipid, wherein said neutral lipid is selected from the group consisting of:

(a) 1,2-dioleoyl-sn-glycero-3-phosphoethanolamine (DOPE);

(b) 1,2-diphytanoyl-sn-glycero-3-phosphoethanolamine (DPyPE); and (c) 1,2-dimyristoyl-glycer-3-phosphoethanolamine (DMPE).

8. The method of claim 5, wherein said component comprises (±)-N-(2-hydroxyethyl)-N,N-dimethyl-2,3-bis(tetradecyloxy)-1-propanaminium bromide (DMRIE).

9. The method of claim 8, wherein said component further comprises a neutral lipid.

10. The method of claim 9, wherein said neutral lipid is DOPE.

11. The method of claim 7 wherein said component comprises a 1:1 molar ratio of GAP-DMORIE and DPyPE.

12. A method for eliciting an immune response to influenza virus in a vertebrate comprising administering to a vertebrate in need thereof a composition comprising a carrier and a polynucleotide comprising a nucleic acid fragment which encodes an amino acid sequence of SEQ ID NO:76, wherein the codons of said nucleic acid fragment are optimized for expression in humans.

13. The method of claim 12, wherein said nucleotide sequence is SEQ ID NO:75.

14. The method of claim 12, wherein said composition comprises a vector comprising said nucleic acid fragment, and wherein said vector, upon uptake by a suitable host cell, expresses said amino acid sequence.

15. The method of claim 12, wherein said polynucleotide further comprises a heterologous nucleic acid ligated to said nucleic acid fragment.

16. The method of claim 12, wherein said composition further comprises a component selected from the group consisting of an adjuvant, a transfection facilitating compound and a combination thereof.

17. The method of claim 16, wherein said component is a cationic lipid.

18. The method of claim 16, wherein said component comprises (±)-N-(3-aminopropyl)-N,N-dimethyl-2,3-bis(syn-9-tetradeceneyloxy)-1-propanaminium bromide (GAP-DMORIE) and a neutral lipid, wherein said neutral lipid is selected from the group consisting of:

(a) 1,2-dioleoyl-sn-glycero-3-phosphoethanolamine (DOPE);

(b) 1,2-diphytanoyl-sn-glycero-3-phosphoethanolamine (DPyPE); and (c) 1,2-dimyristoyl-glycer-3-phosphoethanolamine (DMPE).

19. The method of claim 16, wherein said component comprises (±)-N-(2-hydroxyethyl)-N,N-dimethyl-2,3-bis(tetradecyloxy)-1-propanaminium bromide (DMRIE).

20. The method of claim 19, wherein said component further comprises a neutral lipid.

21. The method of claim 20, wherein said neutral lipid is DOPE.

22. The method of claim 18 wherein said component comprises a 1:1 molar ratio of GAP-DMORIE and DPyPE.

23. An isolated polynucleotide comprising a nucleic acid fragment which encodes an amino acid sequence comprising SEQ ID NO: 76, wherein said nucleic fragment is codon optimized for expression in humans.

24. The isolated polynucleotide of claim 23, wherein said nucleic acid fragment is SEQ ID NO: 75.

* * * * *